(12) United States Patent
Ito et al.

(10) Patent No.: US 10,435,399 B2
(45) Date of Patent: Oct. 8, 2019

(54) HDAC6 INHIBITORY HETEROCYCLIC COMPOUND

(71) Applicant: TAKEDA PHARMACEUTICAL COMPANY LIMITED, Osaka-shi, Osaka (JP)

(72) Inventors: Masahiro Ito, Kanagawa (JP); Hideyuki Sugiyama, Kanagawa (JP); Osamu Kubo, Kanagawa (JP); Fumiaki Kikuchi, Kanagawa (JP); Takeshi Yasui, Kanagawa (JP); Keiko Kakegawa, Kanagawa (JP); Zenichi Ikeda, Kanagawa (JP); Tohru Miyazaki, Kanagawa (JP); Yasuyoshi Arikawa, Kanagawa (JP); Tomohiro Okawa, Kanagawa (JP); Jinichi Yonemori, Kanagawa (JP); Akinori Toita, Kanagawa (JP); Takuto Kojima, Kanagawa (JP); Yasutomi Asano, Kanagawa (JP); Ayumu Sato, Kanagawa (JP); Hironobu Maezaki, Kanagawa (JP); Shinobu Sasaki, Kanagawa (JP); Hironori Kokubo, Kanagawa (JP); Misaki Homma, Kanagawa (JP); Minoru Sasaki, Kanagawa (JP); Yasuhiro Imaeda, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/049,359

(22) Filed: Jul. 30, 2018

(65) Prior Publication Data
US 2019/0135799 A1 May 9, 2019

(30) Foreign Application Priority Data

Jul. 31, 2017 (JP) .................................. 2017-148649
Nov. 17, 2017 (JP) .................................. 2017-222301

(51) Int. Cl.
| | |
|---|---|
| *C07D 413/14* | (2006.01) |
| *C07D 413/04* | (2006.01) |
| *C07D 417/14* | (2006.01) |
| *C07D 487/04* | (2006.01) |
| *A61P 25/28* | (2006.01) |
| *C07D 471/04* | (2006.01) |

(52) U.S. Cl.
CPC ............ *C07D 413/14* (2013.01); *A61P 25/28* (2018.01); *C07D 413/04* (2013.01); *C07D 417/14* (2013.01); *C07D 471/04* (2013.01); *C07D 487/04* (2013.01)

(58) Field of Classification Search
CPC .. C07D 413/04; C07D 413/14; C07D 417/14; C07D 471/04; C07D 487/04
See application file for complete search history.

(56) References Cited

U.S. PATENT DOCUMENTS

| | | | |
|---|---|---|---|
| 8,026,260 | B2 | 9/2011 | Close et al. |
| 8,389,553 | B2 | 3/2013 | Harrington et al. |
| 8,901,156 | B2 | 12/2014 | Baloglu et al. |
| 8,981,084 | B2 | 3/2015 | Baloglu et al. |
| 9,056,843 | B2 | 6/2015 | Hebach et al. |
| 9,096,559 | B2 | 8/2015 | Harrington et al. |
| 9,365,498 | B2 | 6/2016 | Holson et al. |
| 9,447,030 | B2 | 9/2016 | Holson et al. |
| 9,512,083 | B2 | 12/2016 | Raje et al. |
| 9,670,193 | B2 | 6/2017 | Hebach et al. |
| 9,890,172 | B2 | 2/2018 | Holson et al. |
| 2012/0289495 | A1 | 11/2012 | Baloglu et al. |
| 2013/0059883 | A1 | 3/2013 | Baloglu et al. |
| 2014/0080800 | A1 | 3/2014 | Holson et al. |
| 2014/0080802 | A1 | 3/2014 | Holson et al. |
| 2014/0329825 | A1 | 11/2014 | Hebach et al. |
| 2014/0378385 | A1 | 12/2014 | Raje et al. |
| 2015/0038534 | A1 | 2/2015 | Baloglu et al. |
| 2016/0251351 | A1 | 9/2016 | Holson et al. |
| 2016/0347761 | A1 | 12/2016 | Holson et al. |

(Continued)

FOREIGN PATENT DOCUMENTS

| | | |
|---|---|---|
| EP | 3 187 497 | 7/2017 |
| EP | 3 327 019 | 5/2018 |

(Continued)

OTHER PUBLICATIONS

Dubey, et al., "Neurodegeneration and microtubule dynamics: death by a thousands cuts", Frontiers in Cellular Neuroscience, 9, Article 343, Sep. 2015, pp. 1-15.

(Continued)

*Primary Examiner* — Valerie Rodriguez-Garcia
(74) *Attorney, Agent, or Firm* — Hamre, Schumann, Mueller & Larson, P.C.

(57) ABSTRACT

The present invention provides a heterocyclic compound having a HDAC inhibitory action, and useful for the treatment of central nervous system diseases including neurodegenerative disease, and the like, and a medicament comprising the compound.
The present invention relates to a compound represented by the formula (I):

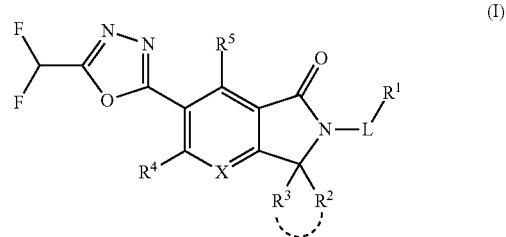

wherein each symbol is as defined in the specification, or a salt thereof.

17 Claims, 3 Drawing Sheets

(56) References Cited

U.S. PATENT DOCUMENTS

| | | | |
|---|---|---|---|
| 2017/0015655 A1* | 1/2017 | Kaieda | C07D 413/14 |
| 2017/0217955 A9 | 8/2017 | Holson et al. | |
| 2017/0305866 A1 | 10/2017 | Raje et al. | |
| 2018/0016282 A9 | 1/2018 | Holson et al. | |
| 2018/0099977 A1 | 4/2018 | Holson et al. | |

FOREIGN PATENT DOCUMENTS

| | | |
|---|---|---|
| JP | 2009-514858 | 4/2009 |
| JP | 2010-531359 | 9/2010 |
| JP | 2013-517278 | 5/2013 |
| JP | 2013-517281 | 5/2013 |
| JP | 2014-523857 | 9/2014 |
| JP | 2014-524922 | 9/2014 |
| JP | 2014-533721 | 12/2014 |
| WO | 2011/088181 | 7/2011 |
| WO | 2013/006408 | 1/2013 |
| WO | 2013/008162 | 1/2013 |
| WO | 2013/009810 | 1/2013 |
| WO | 2013009827 | 1/2013 |
| WO | 2013009830 | 1/2013 |
| WO | 2013/066831 | 5/2013 |
| WO | 2013/066833 | 5/2013 |
| WO | 2013/066835 | 5/2013 |
| WO | 2013/066838 | 5/2013 |
| WO | 2013/066839 | 5/2013 |
| WO | 2013/080120 | 6/2013 |
| WO | 2016/031815 | 3/2016 |
| WO | 2016/039398 | 3/2016 |
| WO | 2017/014321 | 1/2017 |
| WO | 2017/018803 | 2/2017 |
| WO | 2017/018804 | 2/2017 |
| WO | 2017/018805 | 2/2017 |
| WO | 2017/023133 | 2/2017 |
| WO | WO 2017/018805 A1 * | 2/2017 |
| WO | 2017/033946 | 3/2017 |
| WO | 2017/014170 | 10/2017 |

OTHER PUBLICATIONS

Morfini, et al., "Fast Axonal Transport Misregulation and Alzheimer's Disease", NeuroMolecular Medicine, 2, 2002, pp. 89-99.
Goedert, et al., "Frontotemporal Dementia: Implications for Understanding Alzheimer Disease" Cold Spring Harbor Perspectives in Medicine, 2:a006254, 2002, pp. 1-21.
Hubbert, et al., "HDAC6 is a minrotubule-associated deacetylase" Nature, 417, May 23, 2002, pp. 455-458.
Leroux, "Tubulin acetyltransferase discovered: Ciliary role in the ancestral eukaryote expanded to neurons in metazoans", PNAS, 107 (50), Dec. 14, 2010, pp. 21238-21239.
Selenica, et al., "Histone deacetylase 6 inhibition improves memory and reduces total tau levels in a mouse model of tau deposition", Alzheimer's Research & Therapy, 6:12, 2014, pp. 1-12.
Haberland, et al., "The many roles of histone deacetylases in development and physiology: implications for disease and therapy", Nature Reviews Genetics, 10, Jan. 2009, pp. 32-42.

Shakespear, et al., "Histone deacetylases as regulators of inflammation and immunity", Trends in Immunology, 32 (7), Jul. 2011, pp. 335-343.
West, et al., "New and emerging HDAC Inhibitors for cancer treatment", The Journal of Clinical Investigation, 124 (1), Jan. 2014, pp. 30-39.
Chung, et al., "A Therapeutic Strategy Uses Histone Deacetylase Inhibitors to Modulate the Expression of Genes Involved in the Pathogenesis of Rheumatoid Arthritis", Molecular Therapy, 8 (5), Nov. 2003, pp. 707-717.
Glauben, et al., "Histone Hyperacetylation is Associated with Amelioration of Experimental Colitis in Mice", The Journal of Immunology, 176, 2006, pp. 5015-5022.
Lin, et al., "Anti-rheumatic activities of histone deacetylase (HDAC) inhibitors in vivo in collagen-induced arthritis in rodents", British Journal of Pharmacology, 150, 2017, pp. 862-872.
Li et al "HDAC inhibitor reduces cytokine storm and facilitates induction of chimerism that reverses lupus in anti-CD3 conditioning regimen", PNAS, 105 (12), Mar. 25, 2008, pp. 4796-4801.
Zoeten, et al., Histone Deacetylase 6 and heat Shock Protein 90 Control the Functions of Foxp3+ T-Regulatory Cells, Molecular and Cellular Biology, 31 (10), May 2011, pp. 2066-2078.
Hancock, et al., "HDAC Inhibitor therapy in autoimmunity and transplantation", Ann Rheum Dis 2012; 71 (Supp II): i46-i54.
Azad, et al., "The future of epigenetic therapy i solid tumours—lessons fro the past", Nature Reviews Clinical Oncology, 10, May 2013, pp. 256-266.
Santo, et al., "Preclinical activity, pharmacodynamic, and pharmacokinetic properties of a selective HDAC6 inhibitor, ACY-1215, in combination with bortezomib in multiple myeloma", Blood, 119 (11), Mar. 2012, pp. 2579-2589.
Chuang, et al., Multiple roles of HDAC inhibition in neurodegenerative conditions, Trends in Neurosciences, 32 (11), 2009, pp. 591-601.
Jochems, et al. "Antidepressant-Like Properties of Novel HDAC6-Selective Inhibitors with Improved Brain Bioavailability", Neuropsychopharmacology, 39, 2014, pp. 389-400.
Govindarajan, et al., "Reducing HDAC6 ameliorates cognitive deficits in a mouse model for Alzheimer's disease", EMBO Mol Med, 5, 2013, pp. 52-63.
Kalin, et al., "Develoment and Therapeutic Implications of Selective Histone Deacetylase 6 Inhibitors", Journal of Medicinal Chemistry, 56, 2013, pp. 6297-6313.
Jin, et al., "Design, synthesis and preliminary biological evaluation of indoline-2,3-dione derivatives as novel HDAC Inhibitors", Bioorganic & Medicinal Chemistry, 23, 2015, pp. 4728-4736.
Editor H. Kubinyi, 3D Qsar in Drug Design—Ligand-Protein Interactions and Molecular Similarity, Springer, 1998, vol. 2-3, 800 pages, pp. 243-244 provided.
Terfloth, et al., "Electronic Screening: Lead Finding from Database Mining", The Practice of Medicinal Chemistry, 2d, Ed, 2003, 768 pages, chs, 9-10.
International Search Report issued in International Application No. PCT/JP2018/029321, dated Nov. 13, 2018, 4 pages.

* cited by examiner

**:p<0.01 as compared to vehicle control (Dunnett's Test)
a) from single culture due to mechanical error
MMS= Methyl methanesulfonate (positive control)

HDAC6 INHIBITORY HETEROCYCLIC COMPOUND

TECHNICAL FIELD

The present invention relates to a heterocyclic compound having a histone deacetylase (hereinafter sometimes to be referred to as "HDAC") inhibitory activity, preferably a class II HDAC inhibitory activity, more preferably a HDAC6 inhibitory activity, which may be useful for the treatment of central nervous system diseases including neurodegenerative diseases (Alzheimer's disease, progressive supranuclear palsy, etc.) and the like, and a medicament comprising the compound and the like.

BACKGROUND OF THE INVENTION

Nerve axon is known to play an important role in transport of nutritional factor, neurotransmitter, organelle and the like in nerve cell, and axon function disorder, axonal degeneration and intracellular accumulation of axon binding protein tau are observed in various neurodegenerative diseases (Non-Patent Document 1 and Non-Patent Document 2). Diseases characterized by intracellular tau accumulation are collectively called pathologically as tauopathy, and they encompass Alzheimer's disease, progressive supranuclear palsy and the like (Non-Patent Document 3). HDAC6 is an enzyme which plays a role in deacetylation of axon component, tubulin (Non-Patent Document 4), and microtubule containing acetylated tubulin is known to contribute to stability (Non-Patent Document 5). In addition, it is reported that Tubastatin A having a HDAC6 inhibitory activity increases acetylation of tubulin in tauopathy mouse model, and shows therapeutic effectiveness (Non-Patent Document 6). Therefore, the above-mentioned reports suggest that HDAC6 inhibitor has the potential to be a therapeutic drug for Alzheimer's disease and progressive supranuclear palsy via stabilization of axon.

As heterocyclic compounds, for example, the following compound are known.

(1) Patent Document 1 discloses a compound represented by the following formula:

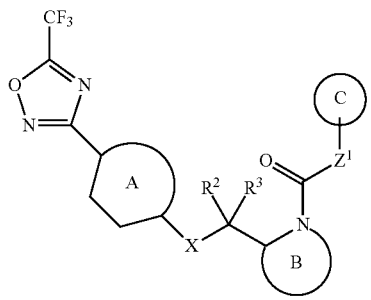

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(2) Patent Document 2 discloses a compound represented by the following formula:

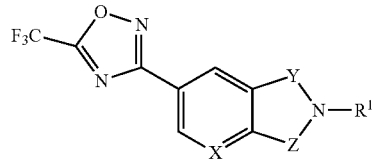

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(3) Patent Document 3 discloses a compound represented by the following formula:

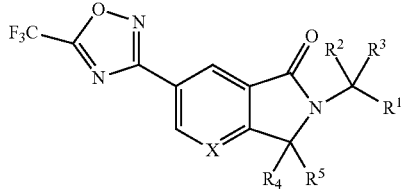

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(4) Patent Document 4 discloses a compound represented by the following formula:

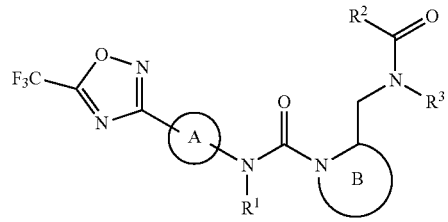

wherein each symbol is as defined in the document, which is a HDAC inhibitor, and is effective for the treatment of autoimmune diseases, inflammatory diseases, metabolic/osteoarticular degenerative diseases, neurodegenerative diseases/central diseases (e.g., schizophrenia, Alzheimer's disease (dementia of Alzheimer type), Parkinson's disease, Huntington's disease, Rubinstein-Taybi syndrome, muscular dystrophy, Rett syndrome, Charcot-Marie-Tooth disease, depression), neoplastic diseases and the like.

(5) Patent Document 5 discloses a compound represented by the following formula:

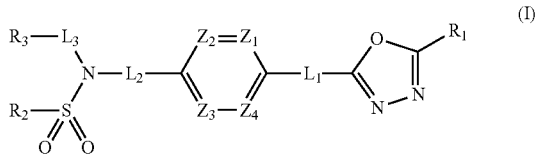

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(6) Patent Document 6 discloses a compound represented by the following formula:

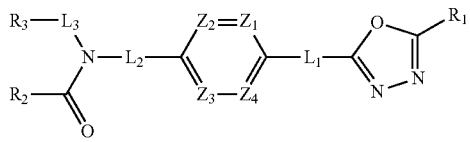

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(7) Patent Document 7 discloses a compound represented by the following formula:

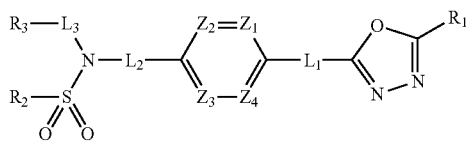

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

(8) Patent Document 8 discloses a compound represented by the following formula:

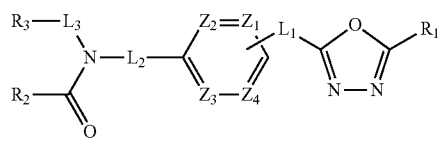

wherein each symbol is as defined in the document, which is a HDAC6 inhibitor, and is effective for the treatment of HDAC6-mediated diseases (e.g., infections, tumor, endocrine/nutritional/metabolic diseases, mental and behavioral disorders, neurological diseases, diseases of the eye and adnexa, cardiovascular diseases, respiratory diseases, digestive diseases, diseases of the skin and subcutaneous tissue, diseases of the musculoskeletal system and connective tissue, or congenital malformations, deformations and chromosomal abnormalities).

DOCUMENT LIST

Patent Document

[Patent Document 1] WO 2016/031815
[Patent Document 2] WO 2017/014321
[Patent Document 3] WO 2017/014170
[Patent Document 4] WO 2017/033946
[Patent Document 5] WO 2017/018803
[Patent Document 6] WO 2017/018804
[Patent Document 7] WO 2017/018805
[Patent Document 8] WO 2017/023133

Non-Patent Document

[Non-Patent Document 1] Front Cell Neurosci. 9, 343, (2015).
[Non-Patent Document 2] Neuromolecular Med. 2: 89-99, (2002).
[Non-Patent Document 3] Cold Spring Harb Perspect Med. 2: a006254 (2012)
[Non-Patent Document 4] Nature. 417: 455-458, (2002).
[Non-Patent Document 5] Proc Natl Acad Sci USA. 107: 21238-21239, (2010).
[Non-Patent Document 6] Alzheimers Res Ther. 6: 12, (2014).

SUMMARY OF THE INVENTION

Problems to be Solved by the Invention

The present invention aims to provide a heterocyclic compound having a HDAC inhibitory action, and useful for the treatment of central nervous system diseases including neurodegenerative diseases (Alzheimer's disease, progressive supranuclear palsy, etc.) and the like, and a medicament comprising the compound.

Means of Solving the Problems

The present inventors have conducted intensive studies to solve the above-mentioned problems, and have found that a compound represented by the following formula (I) has a superior HDAC inhibitory action, and completed the present invention based on these findings.

Accordingly, the present invention provides the following.

[1] A compound represented by the formula (I):

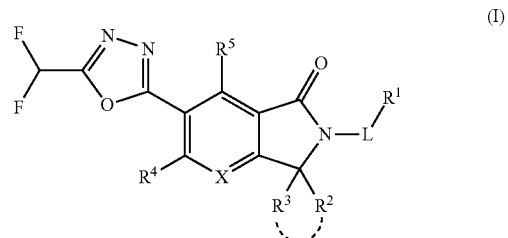

wherein

R$^1$ is an optionally substituted C$_{1-6}$ alkyl group or an optionally substituted cyclic group, R$^2$ and R$^3$ are each independently a hydrogen atom, a halogen atom or an optionally substituted C$_{1-6}$ alkyl group, or R$^2$ and R$^3$ in combination form an oxo group, or R$^2$ and R$^3$ are bonded to each other to form an optionally substituted ring together with the adjacent carbon atom, R$^4$ and R$^5$ are each independently a hydrogen atom or a halogen atom, X is CR$^6$ or N, R$^6$ is a hydrogen atom or a halogen atom, L is a bond or an optionally substituted C$_{1-6}$ alkylene group, or a salt thereof (hereinafter sometimes to be referred to as compound (I)).

[2] The compound or salt of the above-mentioned [1], wherein R$^1$ is (1) a C$_{3-10}$ cycloalkyl group optionally substituted by 1 to 3 substituents selected from
 (a) an amino group,
 (b) a halogen atom,
 (c) a hydroxy group,
 (d) a C$_{1-6}$ alkyl group optionally substituted by 1 to 3 substituents selected from
  (i) a C$_{1-6}$ alkoxy-carbonylamino group, and
  (ii) a C$_{1-6}$ alkylsulfonylamino group optionally substituted by 1 to 3 halogen atoms,
 (e) a C$_{1-6}$ alkoxy group,
 (f) a C$_{1-6}$ alkyl-carbonylamino group optionally substituted by 1 to 6 substituents selected from
  (i) a halogen atom,
  (ii) a cyano group,
  (iii) a hydroxy group,
  (iv) a C$_{1-6}$ alkoxy group,
  (v) a C$_{3-10}$ cycloalkyl group optionally substituted by 1 to 3 substituents selected from a hydroxy group and a cyano group, and
  (vi) a C$_{6-14}$ aryl group,
 (g) a C$_{1-6}$ alkoxy-carbonylamino group optionally substituted by 1 to 3 halogen atoms,
 (h) a mono- or di-C$_{1-6}$ alkyl-carbamoyl group optionally substituted by 1 to 3 halogen atoms,
 (i) a mono- or di-C$_{1-6}$ alkyl-carbamoyloxy group,
 (j) a C$_{3-10}$ cycloalkyl-carbonylamino group optionally substituted by 1 to 3 substituents selected from
  (i) a halogen atom,
  (ii) a cyano group,
  (iii) a hydroxy group,
  (iv) an optionally halogenated C$_{1-6}$ alkyl group,
  (v) a C$_{1-6}$ alkoxy group, and
  (vi) a C$_{6-14}$ aryl group optionally substituted by 1 to 3 halogen atoms,
 (k) a C$_{3-10}$ cycloalkoxy-carbonylamino group,
 (l) a N-5- or 6-membered monocyclic aromatic heterocyclyl-N—C$_{1-6}$ alkyl-carbonyl-amino group optionally substituted by 1 to 3 halogen atoms,
 (m) a C$_{1-6}$ alkylsulfonylamino group optionally substituted by 1 to 3 halogen atoms,
 (n) a C$_{3-10}$ cycloalkylsulfonylamino group,
 (o) a C$_{1-6}$ alkylamino group optionally substituted by 1 to 3 halogen atoms,
 (p) a C$_{6-14}$ aryl group optionally substituted by 1 to 3 halogen atoms,
 (q) a C$_{6-14}$ aryl-carbonylamino group optionally substituted by 1 to 3 substituents selected from
  (i) a halogen atom,
  (ii) a cyano group, and
  (iii) an optionally halogenated C$_{1-6}$ alkyl group,
 (r) a C$_{7-16}$ aralkyl-carbonylamino group,
 (s) a C$_{7-16}$ aralkyl-oxycarbonylamino group,
 (t) a 5- to 14-membered aromatic heterocyclic group optionally substituted by 1 to 3 substituents selected from
  (i) a C$_{1-6}$ alkyl group, and
  (ii) a C$_{3-10}$ cycloalkyl group,
 (u) a 3- to 14-membered non-aromatic heterocyclic group optionally substituted by 1 to 6 substituents selected from
  (i) an oxo group,
  (ii) a C$_{1-6}$ alkyl group, and
  (iii) a halogen atom,
 (v) a 5- to 14-membered aromatic heterocylylcarbonylamino group optionally substituted by 1 to 3 C$_{1-6}$ alkyl groups,
 (w) a 3- to 14-membered non-aromatic heterocyclylcarbonylamino group optionally substituted by 1 to 3 substituents selected from
  (i) a C$_{1-6}$ alkyl group, and
  (ii) a C$_{6-14}$ aryl group,
 (x) a 3- to 14-membered non-aromatic heterocyclylcarbonyloxy group,
 (y) a 5- to 14-membered aromatic heterocyclylamino group,
 (z) a C$_{6-14}$ aryloxy group optionally substituted by 1 to 3 halogen atoms,
 (aa) a cyano group, and
 (bb) a 5- to 14-membered aromatic heterocyclyloxy group optionally substituted by 1 to 3 halogen atoms, (2) a C$_{6-14}$ aryl group optionally substituted by 1 to 3 substituents selected from
 (a) a halogen atom,
 (b) a cyano group,
 (c) an optionally halogenated C$_{1-6}$ alkyl group,
 (d) an optionally halogenated C$_{1-6}$ alkoxy group,
 (e) a C$_{1-6}$ alkylsulfonyl group,
 (f) a C$_{6-14}$ aryl group optionally substituted by 1 to 3 substituents selected from
  (i) a cyano group,
  (ii) an optionally halogenated C$_{1-6}$ alkyl group,
  (iii) a C$_{1-6}$ alkoxy group optionally substituted by 1 to 3 substituents selected from a halogen atom, a C$_{1-6}$ alkoxy group and a cyano group,
  (iv) a C$_{1-6}$ alkylsulfonyl group,
  (v) a halogen atom,
  (vi) a C$_{3-10}$ cycloalkyl group optionally substituted by 1 to 3 cyano groups, and
  (vii) a 3- to 14-membered non-aromatic heterocyclylcarbonyl group,
 (g) a C$_{7-16}$ aralkyl group,
 (h) a 5- to 14-membered aromatic heterocyclic group optionally substituted by 1 to 3 substituents selected from
  (i) a halogen atom,
  (ii) a C$_{1-6}$ alkyl group optionally substituted by 1 to 3 substituents selected from a halogen atom and a pyridyl group,
  (iii) an optionally halogenated C$_{1-6}$ alkoxy group,
  (iv) a C$_{3-10}$ cycloalkyl group,
  (v) a C$_{1-6}$ alkylsulfonyl group, and
  (vi) a 3- to 14-membered non-aromatic heterocyclic group,
 (i) a 3- to 14-membered non-aromatic heterocyclic group optionally substituted by 1 to 3 substituents selected from
  (i) an oxo group,
  (ii) a C$_{1-6}$ alkoxy-carbonyl group, and
  (iii) an optionally halogenated C$_{1-6}$ alkyl-carbonyl group, (j) a 4,4,5,5-tetramethyl-1,3,2-dioxaborolan-2-yl group,
(k) a $C_{3-10}$ cycloalkenyl group optionally substituted by 1 to 3 $C_{1-6}$ alkoxy-carbonylamino groups, and
(l) a $C_{3-10}$ cycloalkyl group optionally substituted by 1 to 3 substituents selected from
   (i) a $C_{1-6}$ alkyl-carbonylamino group optionally substituted by 1 to 5 halogen atoms, and
   (ii) a $C_{1-6}$ alkoxy-carbonylamino group,
(3) a 5- to 14-membered aromatic heterocyclic group optionally substituted by 1 to 3 substituents selected from
(a) a halogen atom,
(b) a $C_{1-6}$ alkyl group optionally substituted by 1 to 3 substituents selected from
   (i) a halogen atom, and
   (ii) a hydroxy group,
(c) a $C_{3-10}$ cycloalkyl group optionally substituted by 1 to 3 substituents selected from
   (i) a halogen atom,
   (ii) a $C_{1-6}$ alkoxy-carbonylamino group,
   (iii) a $C_{1-6}$ alkyl-carbonylamino group optionally substituted by 1 to 5 halogen atoms, and
   (iv) a mono- or di-$C_{1-6}$ alkylamino group optionally substituted by 1 to 5 halogen atoms,
(d) a $C_{4-10}$ cycloalkenyl group optionally substituted by 1 to 3 substituents selected from
   (i) a halogen atom, and
   (ii) a $C_{1-6}$ alkoxy-carbonylamino group,
(e) a $C_{6-14}$ aryl group optionally substituted by 1 to 3 substituents selected from
   (i) a cyano group,
   (ii) a halogen atom, and
   (iii) a $C_{1-6}$ alkoxy group,
(f) a 5- to 14-membered aromatic heterocyclic group optionally substituted by 1 to 3 substituents selected from
   (i) a halogen atom, and
   (ii) an optionally halogenated $C_{1-6}$ alkyl group,
(g) a 3- to 14-membered non-aromatic heterocyclic group optionally substituted by 1 to 3 substituents selected from
   (i) a $C_{1-6}$ alkoxy-carbonyl group,
   (ii) an optionally halogenated $C_{1-6}$ alkyl-carbonyl group, and
   (iii) an optionally halogenated $C_{1-6}$ alkyl group,
(h) a mono- or di-$C_{1-6}$ alkyl-carbamoyl group optionally substituted by 1 to 3 substituents selected from
   (i) a halogen atom, and
   (ii) a $C_{3-10}$ cycloalkyl group,
(i) a 3- to 14-membered non-aromatic heterocyclylcarbonyl group optionally substituted by 1 to 3 halogen atoms, and
(j) a $C_{6-14}$ aryl-carbonyl group,
(4) a 3- to 14-membered non-aromatic heterocyclic group optionally substituted by 1 to 3 substituents selected from
(a) a halogen atom,
(b) an oxo group,
(c) an amino group,
(d) an optionally halogenated $C_{1-6}$ alkyl group, (e) a $C_{1-6}$ alkylamino group optionally substituted by 1 to 7 halogen atoms,
(f) an optionally halogenated $C_{1-6}$ alkyl-carbonyl group,
(g) a $C_{1-6}$ alkyl-carbonylamino group optionally substituted by 1 to 5 halogen atoms,
(h) a $C_{1-6}$ alkoxy-carbonyl group,
(i) a $C_{1-6}$ alkoxy-carbonylamino group optionally substituted by 1 to 3 halogen atoms,
(j) a $C_{1-6}$ alkylsulfonyl group optionally substituted by 1 to 3 halogen atoms,
(k) a $C_{3-10}$ cycloalkyl-carbonyl group optionally substituted by 1 to 3 substituents selected from
   (i) a halogen atom, and
   (ii) an optionally halogenated $C_{1-6}$ alkyl group,
(l) a $C_{3-10}$ cycloalkyl-carbonylamino group optionally substituted by 1 to 3 optionally halogenated $C_{1-6}$ alkyl groups,
(m) a $C_{3-10}$ cycloalkylsulfonyl group,
(n) a $C_{6-14}$ aryl group optionally substituted by 1 to 3 halogen atoms,
(o) a $C_{7-16}$ aralkyl group,
(p) a $C_{6-14}$ aryl-carbonyl group,
(q) a $C_{6-14}$ aryl-carbonylamino group optionally substituted by 1 to 3 halogen atoms,
(r) a $C_{6-14}$ arylsulfonyl group optionally substituted by 1 to 3 substituents selected from
   (i) a $C_{1-6}$ alkyl group, and
   (ii) a halogen atom,
(s) a 3- to 14-membered non-aromatic heterocyclic group optionally substituted by 1 to 3 substituents selected from
   (i) an oxo group, and
   (ii) a $C_{1-6}$ alkyl-carbonyl group,
(t) a 5- to 14-membered aromatic heterocyclic group optionally substituted by 1 to 3 substituents selected from
   (i) a halogen atom, and
   (ii) a $C_{1-6}$ alkyl group,
(u) a mono- or di-$C_{1-6}$ alkyl-carbamoyl group optionally substituted by 1 to 5 halogen atoms,
(v) a $C_{7-16}$ aralkyloxy-carbonyl group, and
(w) a $C_{6-14}$ aryloxy group optionally substituted by 1 to 3 halogen atoms, or
(5) a $C_{1-6}$ alkyl group optionally substituted by 1 to 3 substituents selected from
(a) a $C_{6-14}$ aryloxy group, and
(b) a $C_{7-16}$ aralkyloxy group.
[3] The compound or salt of the above-mentioned [1], wherein $R^1$ is a cyclohexyl group optionally substituted by 1 to 3 substituents selected from
(a) a halogen atom,
(b) a $C_{1-6}$ alkyl-carbonylamino group optionally substituted by 1 to 5 halogen atoms,
(c) a $C_{1-6}$ alkoxy-carbonylamino group optionally substituted by 1 to 3 halogen atoms, and
(d) a $C_{3-10}$ cycloalkyl-carbonylamino group optionally substituted by 1 to 3 halogen atoms.
[4] The compound or salt of the above-mentioned [1], wherein $R^2$ and $R^3$ are both hydrogen atoms, or $R^2$ and $R^3$ in combination form an oxo group.
[5] The compound or salt of the above-mentioned [1], wherein $R^2$ and $R^3$ are both hydrogen atoms.
[6] The compound or salt of the above-mentioned [1], wherein $R^4$ and $R^5$ are both hydrogen atoms.
[7] The compound or salt of the above-mentioned [1], wherein X is CH, CF or N.
[8] The compound or salt of the above-mentioned [1], wherein X is CH or N.
[9] The compound or salt of the above-mentioned [1], wherein L is
(1) a bond, or
(2) a $C_{1-6}$ alkylene group optionally substituted by 1 to 3 $C_{6-14}$ aryl groups.
[10] The compound or salt of the above-mentioned [1], wherein L is a bond.

[11] The compound or salt of the above-mentioned [1], wherein $R^1$ is
(1) a $C_{3-10}$ cycloalkyl group optionally substituted by 1 to 3 substituents selected from
  (a) an amino group,
  (b) a halogen atom,
  (c) a hydroxy group,
  (d) a $C_{1-6}$ alkyl group optionally substituted by 1 to 3 substituents selected from
    (i) a $C_{1-6}$ alkoxy-carbonylamino group, and
    (ii) a $C_{1-6}$ alkylsulfonylamino group optionally substituted by 1 to 3 halogen atoms,
  (e) a $C_{1-6}$ alkoxy group,
  (f) a $C_{1-6}$ alkyl-carbonylamino group optionally substituted by 1 to 6 substituents selected from
    (i) a halogen atom,
    (ii) a cyano group,
    (iii) a hydroxy group,
    (iv) a $C_{1-6}$ alkoxy group,
    (v) a $C_{3-10}$ cycloalkyl group optionally substituted by 1 to 3 substituents selected from a hydroxy group and a cyano group, and
    (vi) a $C_{6-14}$ aryl group,
  (g) a $C_{1-6}$ alkoxy-carbonylamino group optionally substituted by 1 to 3 halogen atoms,
  (h) a mono- or di-$C_{1-6}$ alkyl-carbamoyl group optionally substituted by 1 to 3 halogen atoms,
  (i) a mono- or di-$C_{1-6}$ alkyl-carbamoyloxy group,
  (j) a $C_{3-10}$ cycloalkyl-carbonylamino group optionally substituted by 1 to 3 substituents selected from
    (i) a halogen atom,
    (ii) a cyano group,
    (iii) a hydroxy group,
    (iv) an optionally halogenated $C_{1-6}$ alkyl group,
    (v) a $C_{1-6}$ alkoxy group, and
    (vi) a $C_{6-14}$ aryl group optionally substituted by 1 to 3 halogen atoms,
  (k) a $C_{3-10}$ cycloalkoxy-carbonylamino group,
  (l) a N-5- or 6-membered monocyclic aromatic heterocyclyl-N—$C_{1-6}$ alkyl-carbonyl-amino group optionally substituted by 1 to 3 halogen atoms,
  (m) a $C_{1-6}$ alkylsulfonylamino group optionally substituted by 1 to 3 halogen atoms,
  (n) a $C_{3-10}$ cycloalkylsulfonylamino group,
  (o) a $C_{1-6}$ alkylamino group optionally substituted by 1 to 3 halogen atoms,
  (p) a $C_{6-14}$ aryl group optionally substituted by 1 to 3 halogen atoms,
  (q) a $C_{6-14}$ aryl-carbonylamino group optionally substituted by 1 to 3 substituents selected from
    (i) a halogen atom,
    (ii) a cyano group, and
    (iii) an optionally halogenated $C_{1-6}$ alkyl group,
  (r) a $C_{7-16}$ aralkyl-carbonylamino group,
  (s) a $C_{7-16}$ aralkyl-oxycarbonylamino group,
  (t) a 5- to 14-membered aromatic heterocyclic group optionally substituted by 1 to 3 substituents selected from
    (i) a $C_{1-6}$ alkyl group, and
    (ii) a $C_{3-10}$ cycloalkyl group,
  (u) a 3- to 14-membered non-aromatic heterocyclic group optionally substituted by 1 to 6 substituents selected from
    (i) an oxo group,
    (ii) a $C_{1-6}$ alkyl group, and
    (iii) a halogen atom,
  (v) a 5- to 14-membered aromatic heterocyclylcarbonylamino group optionally substituted by 1 to 3 $C_{1-6}$ alkyl groups,
  (w) a 3- to 14-membered non-aromatic heterocyclylcarbonylamino group optionally substituted by 1 is to 3 substituents selected from
    (i) a $C_{1-6}$ alkyl group, and
    (ii) a $C_{6-14}$ aryl group,
  (x) a 3- to 14-membered non-aromatic heterocyclylcarbonyloxy group,
  (y) a 5- to 14-membered aromatic heterocyclylamino group,
  (z) a $C_{6-14}$ aryloxy group optionally substituted by 1 to 3 halogen atoms,
  (aa) a cyano group, and
  (bb) a 5- to 14-membered aromatic heterocyclyloxy group optionally substituted by 1 to 3 halogen atoms,
(2) a $C_{6-14}$ aryl group optionally substituted by 1 to 3 substituents selected from
  (a) a halogen atom,
  (b) a cyano group,
  (c) an optionally halogenated $C_{1-6}$ alkyl group,
  (d) an optionally halogenated $C_{1-6}$ alkoxy group,
  (e) a $C_{1-6}$ alkylsulfonyl group,
  (f) a $C_{6-14}$ aryl group optionally substituted by 1 to 3 substituents selected from
    (i) a cyano group,
    (ii) an optionally halogenated $C_{1-6}$ alkyl group,
    (iii) a $C_{1-6}$ alkoxy group optionally substituted by 1 to 3 substituents selected from a halogen atom, a $C_{1-6}$ alkoxy group and a cyano group,
    (iv) a $C_{1-6}$ alkylsulfonyl group,
    (v) a halogen atom,
    (vi) a $C_{3-10}$ cycloalkyl group optionally substituted by 1 to 3 cyano groups, and
    (vii) a 3- to 14-membered non-aromatic heterocyclylcarbonyl group,
  (g) a $C_{7-16}$ aralkyl group,
  (h) a 5- to 14-membered aromatic heterocyclic group optionally substituted by 1 to 3 substituents selected from
    (i) a halogen atom,
    (ii) a $C_{1-6}$ alkyl group optionally substituted by 1 to 3 substituents selected from a halogen atom and a pyridyl group,
    (iii) an optionally halogenated $C_{1-6}$ alkoxy group, (iv) a $C_{3-10}$ cycloalkyl group,
    (v) a $C_{1-6}$ alkylsulfonyl group, and
    (vi) a 3- to 14-membered non-aromatic heterocyclic group,
  (i) a 3- to 14-membered non-aromatic heterocyclic group optionally substituted by 1 to 3 substituents selected from
    (i) an oxo group,
    (ii) a $C_{1-6}$ alkoxy-carbonyl group, and
    (iii) an optionally halogenated $C_{1-6}$ alkyl-carbonyl group,
  (j) a 4,4,5,5-tetramethyl-1,3,2-dioxaborolan-2-yl group,
  (k) a $C_{3-10}$ cycloalkenyl group optionally substituted by 1 to 3 $C_{1-6}$ alkoxy-carbonylamino groups, and
  (l) a $C_{3-10}$ cycloalkyl group optionally substituted by 1 to 3 substituents selected from
    (i) a $C_{1-6}$ alkyl-carbonylamino group optionally substituted by 1 to 5 halogen atoms, and
    (ii) a $C_{1-6}$ alkoxy-carbonylamino group, (3) a 5- to 14-membered aromatic heterocyclic group optionally substituted by 1 to 3 substituents selected from
(a) a halogen atom,
(b) a $C_{1-6}$ alkyl group optionally substituted by 1 to 3 substituents selected from
  (i) a halogen atom, and
  (ii) a hydroxy group,
(c) a $C_{3-10}$ cycloalkyl group optionally substituted by 1 to 3 substituents selected from
  (i) a halogen atom,
  (ii) a $C_{1-6}$ alkoxy-carbonylamino group,
  (iii) a $C_{1-6}$ alkyl-carbonylamino group optionally substituted by 1 to 5 halogen atoms, and
  (iv) a mono- or di-$C_{1-6}$ alkylamino group optionally substituted by 1 to 5 halogen atoms,
(d) a $C_{4-10}$ cycloalkenyl group optionally substituted by 1 to 3 substituents selected from
  (i) a halogen atom, and
  (ii) a $C_{1-6}$ alkoxy-carbonylamino group,
(e) a $C_{6-14}$ aryl group optionally substituted by 1 to 3 substituents selected from
  (i) a cyano group,
  (ii) a halogen atom, and
  (iii) a $C_{1-6}$ alkoxy group,
(f) a 5- to 14-membered aromatic heterocyclic group optionally substituted by 1 to 3 substituents selected from
  (i) a halogen atom, and
  (ii) an optionally halogenated $C_{1-6}$ alkyl group,
(g) a 3- to 14-membered non-aromatic heterocyclic group optionally substituted by 1 to 3 substituents selected from
  (i) a $C_{1-6}$ alkoxy-carbonyl group,
  (ii) an optionally halogenated $C_{1-6}$ alkyl-carbonyl group, and
  (iii) an optionally halogenated $C_{1-6}$ alkyl group,
(h) a mono- or di-$C_{1-6}$ alkyl-carbamoyl group optionally substituted by 1 to 3 substituents selected from
  (i) a halogen atom, and
  (ii) a $C_{3-10}$ cycloalkyl group,
(i) a 3- to 14-membered non-aromatic heterocyclylcarbonyl group optionally substituted by 1 to 3 halogen atoms, and
(j) a $C_{6-14}$ aryl-carbonyl group,
(4) a 3- to 14-membered non-aromatic heterocyclic group optionally substituted by 1 to 3 substituents selected from
(a) a halogen atom,
(b) an oxo group,
(c) an amino group,
(d) an optionally halogenated $C_{1-6}$ alkyl group,
(e) a $C_{1-6}$ alkylamino group optionally substituted by 1 to 7 halogen atoms,
(f) an optionally halogenated $C_{1-6}$ alkyl-carbonyl group,
(g) a $C_{1-6}$ alkyl-carbonylamino group optionally substituted by 1 to 5 halogen atoms,
(h) a $C_{1-6}$ alkoxy-carbonyl group,
(i) a $C_{1-6}$ alkoxy-carbonylamino group optionally substituted by 1 to 3 halogen atoms,
(j) a $C_{1-6}$ alkylsulfonyl group optionally substituted by 1 to 3 halogen atoms,
(k) a $C_{3-10}$ cycloalkyl-carbonyl group optionally substituted by 1 to 3 substituents selected from
  (i) a halogen atom, and
  (ii) an optionally halogenated $C_{1-6}$ alkyl group,
(l) a $C_{3-10}$ cycloalkyl-carbonylamino group optionally substituted by 1 to 3 optionally halogenated $C_{1-6}$ alkyl groups,
(m) a $C_{3-10}$ cycloalkylsulfonyl group,
(n) a $C_{6-14}$ aryl group optionally substituted by 1 to 3 halogen atoms,
(o) a $C_{7-16}$ aralkyl group,
(p) a $C_{6-14}$ aryl-carbonyl group,
(q) a $C_{6-14}$ aryl-carbonylamino group optionally substituted by 1 to 3 halogen atoms,
(r) a $C_{6-14}$ arylsulfonyl group optionally substituted by 1 to 3 substituents selected from
  (i) a $C_{1-6}$ alkyl group, and
  (ii) a halogen atom,
(s) a 3- to 14-membered non-aromatic heterocyclic group optionally substituted by 1 to 3 substituents selected from
  (i) an oxo group, and
  (ii) a $C_{1-6}$ alkyl-carbonyl group,
(t) a 5- to 14-membered aromatic heterocyclic group optionally substituted by 1 to 3 substituents selected from
  (i) a halogen atom, and
  (ii) a $C_{1-6}$ alkyl group,
(u) a mono- or di-$C_{1-6}$ alkyl-carbamoyl group optionally substituted by 1 to 5 halogen atoms,
(v) a $C_{7-16}$ aralkyloxy-carbonyl group, and
(w) a $C_{6-14}$ aryloxy group optionally substituted by 1 to 3 halogen atoms, or
(5) a $C_{1-6}$ alkyl group optionally substituted by 1 to 3 substituents selected from
(a) a $C_{6-14}$ aryloxy group, and
(b) a $C_{7-16}$ aralkyloxy group;
$R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom; and
L is
(1) a bond, or
(2) a $C_{1-6}$ alkylene group optionally substituted by 1 to 3 $C_{6-14}$ aryl groups.

[12] The compound or salt of the above-mentioned [1], wherein
$R^1$ is a cyclohexyl group optionally substituted by 1 to 3 substituents selected from
(a) a halogen atom,
(b) a $C_{1-6}$ alkyl-carbonylamino group optionally substituted by 1 to 5 halogen atoms,
(c) a $C_{1-6}$ alkoxy-carbonylamino group optionally substituted by 1 to 3 halogen atoms, and
(d) a $C_{3-10}$ cycloalkyl-carbonylamino group optionally substituted by 1 to 3 halogen atoms;
$R^2$ and $R^3$ are both hydrogen atoms;
$R^4$ and $R^5$ are both hydrogen atoms;
X is CH or N; and
L is a bond.

[13] N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2,3,3,3-pentafluoropropanamide or a salt thereof.

[14] N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2-difluoropropanamide or a salt thereof.

[15] N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2-difluoropropanamide or a salt thereof.

[16] A medicament comprising the compound or salt of the above-mentioned [1].

[17] The medicament of the above-mentioned [16], which is a histone deacetylase inhibitor.
[18] The medicament of the above-mentioned [16], which is an agent for the prophylaxis or treatment of Alzheimer's disease or progressive supranuclear palsy.
[19] The compound or salt of the above-mentioned [1] for use in the prophylaxis or treatment of Alzheimer's disease or progressive supranuclear palsy.
[20] A method of inhibiting histone deacetylase in a mammal, which comprises administering an effective amount of the compound or salt of the above-mentioned [1] to the mammal.
[21] A method for the prophylaxis or treatment of Alzheimer's disease or progressive supranuclear palsy in a mammal, which comprises administering an effective amount of the compound or salt of the above-mentioned [1] to the mammal.
[22] Use of the compound or salt of the above-mentioned [1] for the production of an agent for the prophylaxis or treatment of Alzheimer's disease or progressive supranuclear palsy.

EFFECT OF THE INVENTION

Compound (I) has a HDAC inhibitory activity, and may be useful for the treatment of central nervous system diseases including neurodegenerative diseases (Alzheimer's disease, progressive supranuclear palsy, etc.) and the like.

DETAILED DESCRIPTION OF THE INVENTION

Figure 1:
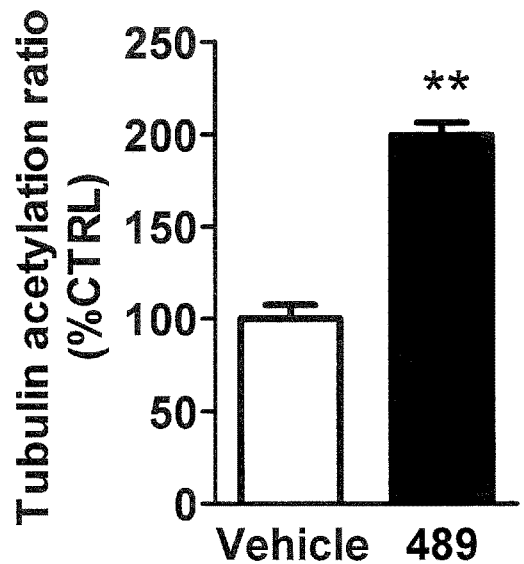
FIG. 1 shows relative tubulin acetylation level by the compound of Example 489.

The present invention is explained in detail in the following.
The definition of each substituent used in the present specification is described in detail in the following. Unless otherwise specified, each substituent has the following definition.
In the present specification, examples of the "halogen atom" include fluorine, chlorine, bromine and iodine.
In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.
In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.
In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.
In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.
In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.
In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.
In the present specification, examples of the "$C_{3-10}$ cycloalkenyl group" include cyclopropenyl, cyclobutenyl, cyclopentenyl, cyclohexenyl, cycloheptenyl and cyclooctenyl.
In the present specification, examples of the "$C_{6-14}$ aryl group" include phenyl, 1-naphthyl, 2-naphthyl, 1-anthryl, 2-anthryl and 9-anthryl.
In the present specification, examples of the "$C_{7-16}$ aralkyl group" include benzyl, phenethyl, naphthylmethyl and phenylpropyl.
In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.
In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.
In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.
In the present specification, examples of the "$C_{1-6}$ alkylthio group" include methylthio, ethylthio, propylthio, isopropylthio, butylthio, sec-butylthio, tert-butylthio, pentylthio and hexylthio.
In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.
In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.
In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,

(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkyl-sulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—$CH_2$—, —$CH_2$—$CH_2$—$CH_2$—$C(CH_3)_2$— and —$C(CH_3)_2$—$CH_2$—$CH_2$—$CH_2$—.

In the present specification, examples of the "$C_{2-6}$ alkenylene group" include —CH=CH—, —$CH_2$—CH=CH—, —CH=CH—$CH_2$—, —$C(CH_3)_2$—CH=CH—, —CH=CH—$C(CH_3)_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$— and —$CH_2$—$CH_2$—$CH_2$—CH=CH—.

In the present specification, examples of the "$C_{2-6}$ alkynylene group" include —C≡C—, —$CH_2$—C≡C—, —C≡C—$CH_2$—, —$C(CH_3)_2$—C≡C—, —C≡C—$C(CH_3)_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$— and —$CH_2$—$CH_2$—$CH_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a heterocycle containing at least one nitrogen atom as a ring-constituting atom, from among the "heterocycle".

The definition of each symbol in the formula (I) is explained in detail in the following.

$R^1$ is an optionally substituted $C_{1-6}$ alkyl group or an optionally substituted cyclic group.

The "$C_{1-6}$ alkyl group" of the "optionally substituted $C_{1-6}$ alkyl group" represented by $R^1$ is optionally substituted, at substitutable position(s), by substituent(s) selected from the above-mentioned Substituent Group A. The number of the substituents is, for example, 1 to 3. When the number of the substituents is 2 or more, the respective substituents may be the same or different.

Examples of the "cyclic group" of the "optionally substituted cyclic group" represented by $R^1$ include a $C_{3-10}$ cycloalkyl group, a $C_{3-10}$ cycloalkenyl group, a $C_{6-14}$ aryl group, a 5- to 14-membered aromatic heterocyclic group and a 3- to 14-membered non-aromatic heterocyclic group, and preferred are a $C_{3-10}$ cycloalkyl group, a $C_{6-14}$ aryl group, a 5- to 14-membered aromatic heterocyclic group (preferably a 5- or 6-membered monocyclic aromatic heterocyclic group) and a 3- to 14-membered non-aromatic heterocyclic group (preferably a 3- to 8-membered monocyclic non-aromatic heterocyclic group).

The "cyclic group" of the "optionally substituted cyclic group" represented by $R^1$ is optionally substituted, at substitutable position(s), by substituent(s) selected from the above-mentioned Substituent Group A. The number of the substituents is, for example, 1 to 3. When the number of the substituents is 2 or more, the respective substituents may be the same or different. In addition, the Substituent Group A is optionally substituted by substituent(s) selected from the above-mentioned Substituent Group A. The number of the substituents is, for example, 1 to 3. When the number of the substituents is 2 or more, the respective substituents may be the same or different.

$R^1$ is preferably
(1) an optionally substituted $C_{3-10}$ cycloalkyl group (e.g., cyclopropyl, cyclohexyl),
(2) an optionally substituted $C_{6-14}$ aryl group (e.g., phenyl),
(3) an optionally substituted 5- to 14-membered aromatic heterocyclic group (preferably a 5- or 6-membered monocyclic aromatic heterocyclic group (e.g., pyridyl, isoxazolyl, pyrazolyl)), or
(4) an optionally substituted 3- to 14-membered non-aromatic heterocyclic group (preferably a 3- to 8-membered monocyclic non-aromatic heterocyclic group, more preferably a 5- or 6-membered monocyclic non-aromatic heterocyclic group (including a 6-membered monocyclic non-aromatic heterocyclic group and a 5- or 6-membered monocyclic nitrogen-containing non-aromatic heterocyclic group) (e.g., tetrahydropyranyl, piperidyl, morpholinyl)).

$R^1$ is more preferably
(1) a $C_{3-10}$ cycloalkyl group (e.g., cyclopropyl, cyclohexyl) optionally substituted by 1 to 3 substituents selected from
  (a) an amino group,
  (b) a $C_{1-6}$ alkoxy group (e.g., butoxy),
  (c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
  (i) a halogen atom (e.g., a fluorine atom),
  (ii) a cyano group,
  (iii) a hydroxy group,
  (iv) a $C_{1-6}$ alkoxy group (e.g., methoxy),
  (v) a $C_{3-10}$ cycloalkyl group (e.g., cyclopropyl, cyclobutyl, cyclopentyl) optionally substituted by 1 to 3 substituents selected from a hydroxy group and a cyano group, and
  (vi) a $C_{6-14}$ aryl group (e.g., phenyl),
(d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(e) a mono- or di-$C_{1-6}$ alkyl-carbamoyl group (e.g., ethylcarbamoyl) optionally substituted by 1 to 3 halogen atoms (e.g., a fluorine atom),
(f) a mono- or di-$C_{1-6}$ alkyl-carbamoyloxy group (e.g., methylcarbamoyloxy),
(g) a $C_{3-10}$ cycloalkyl-carbonylamino group (the $C_{3-10}$ cycloalkyl in the $C_{3-10}$ cycloalkyl-carbonylamino group may be a bridged group or a spiro ring group. e.g., cyclopropylcarbonylamino, cyclobutylcarbonylamino, cyclohexylcarbonylamino, spiro[2.3]hexylcarbonylamino, spiro[3.3]heptylcarbonylamino, bicyclo[1.1.1]pentylcarbonylamino) optionally substituted by 1 to 3 substituents selected from
  (i) a halogen atom (e.g., a fluorine atom),
  (ii) a cyano group,
  (iii) a hydroxy group,
  (iv) an optionally halogenated $C_{1-6}$ alkyl group (e.g., methyl, difluoromethyl, trifluoromethyl),
  (v) a $C_{1-6}$ alkoxy group (e.g., methoxy), and
  (vi) a $C_{6-14}$ aryl group (e.g., phenyl) optionally substituted by 1 to 3 halogen atoms (e.g., a fluorine atom),
(h) a $C_{3-10}$ cycloalkoxy-carbonylamino group (e.g., cyclopropoxycarbonylamino),
(i) a $C_{6-14}$ aryl-carbonylamino group (e.g., phenylcarbonylamino) optionally substituted by 1 to 3 halogen atoms (e.g., a chlorine atom),
(j) a $C_{7-16}$ aralkyl-oxycarbonylamino group (e.g., benzyloxycarbonylamino),
(k) a 5- to 14-membered aromatic heterocyclic group (preferably a 5- or 6-membered monocyclic aromatic heterocyclic group (e.g., pyrazolyl, triazolyl) or a 8- to 14-membered fused polycyclic (preferably bi- or tricyclic) aromatic heterocyclic group (e.g., indazolyl)) optionally substituted by 1 to 3 $C_{1-6}$ alkyl groups (e.g., methyl, ethyl),
(l) a 3- to 14-membered non-aromatic heterocyclic group (preferably a 3- to 8-membered monocyclic non-aromatic heterocyclic group (e.g., pyrrolidinyl, piperidyl, morpholinyl, tetrahydrooxazinyl, hexahydropyrimidinyl, oxazolidinyl, imidazolidinyl, 1,1-dioxido-1,2-thiazolidinyl) or a 9- to 14-membered fused polycyclic (preferably bi- or tri-cyclic) non-aromatic heterocyclic group (e.g., dihydroisoindolyl, 5-azaspiro[2.4]heptyl)) optionally substituted by 1 to 3 substituents selected from
  (i) an oxo group, and
  (ii) a $C_{1-6}$ alkyl group (e.g., methyl),
(m) a 5- to 14-membered aromatic heterocyclylcarbonylamino group (preferably a 5- or 6-membered monocyclic aromatic heterocyclylcarbonylamino group (e.g., oxazolylcarbonylamino, imidazolylcarbonylamino, pyrazolylcarbonylamino, pyridylcarbonylamino)) optionally substituted by 1 to 3 $C_{1-6}$ alkyl groups (e.g., methyl), and
(n) a 3- to 14-membered non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino, tetrahydropyranylcarbonylamino)) optionally substituted by 1 to 3 substituents selected from
  (i) a $C_{1-6}$ alkyl group (e.g., methyl, ethyl), and
  (ii) a $C_{6-14}$ aryl group (e.g., phenyl),
(2) a $C_{6-14}$ aryl group (e.g., phenyl) optionally substituted by 1 to 3 substituents selected from
  (a) a halogen atom (e.g., a fluorine atom, a bromine atom),
  (b) an optionally halogenated $C_{1-6}$ alkyl group (e.g., trifluoromethyl),
  (c) a $C_{1-6}$ alkylsulfonyl group (e.g., methylsulfonyl),
  (d) a $C_{6-14}$ aryl group (e.g., phenyl) optionally substituted by 1 to 3 substituents selected from
    (i) a cyano group,
    (ii) an optionally halogenated $C_{1-6}$ alkyl group (e.g., trifluoromethyl),
    (iii) a $C_{1-6}$ alkoxy group (e.g., methoxy), and
    (iv) a $C_{1-6}$ alkylsulfonyl group (e.g., methylsulfonyl),
  (e) a 5- to 14-membered aromatic heterocyclic group (preferably a 5- or 6-membered monocyclic aromatic heterocyclic group (e.g., pyrazolyl)) optionally substituted by 1 to 3 $C_{1-6}$ alkyl groups (e.g., methyl),
  (f) a 3- to 14-membered non-aromatic heterocyclic group (preferably a 3- to 8-membered monocyclic non-aromatic heterocyclic group (e.g., pyrrolidinyl)) optionally substituted by 1 to 3 oxo groups, and
  (g) a 4,4,5,5-tetramethyl-1,3,2-dioxaborolan-2-yl group,
(3) a 5- to 14-membered aromatic heterocyclic group (preferably a 5- or 6-membered monocyclic aromatic heterocyclic group (e.g., pyridyl, isoxazolyl, pyrazolyl)) optionally substituted by 1 to 3 substituents selected from
  (a) a halogen atom (e.g., a fluorine atom, a chlorine atom),
  (b) an optionally halogenated $C_{1-6}$ alkyl group (e.g., methyl, trifluoromethyl),
  (c) a $C_{3-10}$ cycloalkyl group (e.g., cyclopropyl), and
  (d) a $C_{6-14}$ aryl group (e.g., phenyl), or
(4) a 3- to 14-membered non-aromatic heterocyclic group (preferably a 3- to 8-membered monocyclic non-aromatic heterocyclic group, more preferably a 5- or 6-membered monocyclic non-aromatic heterocyclic group (including a 6-membered monocyclic non-aromatic heterocyclic group and a 5- or 6-membered monocyclic nitrogen-containing non-aromatic heterocyclic group) (e.g., tetrahydropyranyl, piperidyl, morpholinyl)) optionally substituted by 1 to 3 substituents selected from
  (a) a $C_{1-6}$ alkyl-carbonyl group (e.g., acetyl),
  (b) a $C_{1-6}$ alkyl-carbonylamino group (e.g., propanoylamino, pivaloylamino) optionally substituted by 1 to 5 halogen atoms (e.g., a fluorine atom),
  (c) a $C_{1-6}$ alkoxy-carbonyl group (e.g., methoxycarbonyl, ethoxycarbonyl, isopropoxycarbonyl, tert-butoxycarbonyl),
  (d) a $C_{1-6}$ alkoxy-carbonylamino group (e.g., tert-butoxycarbonylamino),
  (e) a $C_{3-10}$ cycloalkyl-carbonyl group (e.g., cyclopropylcarbonyl, cyclopentylcarbonyl),
  (f) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl), (g) a $C_{3-10}$ cycloalkylsulfonyl group (e.g., cyclopropylsulfonyl),
(h) a $C_{6-14}$ aryl group (e.g., phenyl),
(i) a $C_{6-14}$ aryl-carbonylamino group (e.g., phenylcarbonylamino) optionally substituted by 1 to 3 halogen atoms (e.g., a chlorine atom),
(j) a $C_{6-14}$ arylsulfonyl group (e.g., phenylsulfonyl) optionally substituted by 1 to 3 $C_{1-6}$ alkyl groups (e.g., methyl), and
(k) a 3- to 14-membered non-aromatic heterocyclic group (preferably a 3- to 8-membered monocyclic non-aromatic heterocyclic group (e.g., pyrrolidinyl, piperidyl)) optionally substituted by 1 to 3 oxo groups.

$R^1$ is further more preferably
(1) a cyclohexyl group optionally substituted by 1 to 3 substituents selected from
  (a) an amino group,
  (b) a $C_{1-6}$ alkoxy group (e.g., butoxy),
  (c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
    (i) a halogen atom (e.g., a fluorine atom),
    (ii) a cyano group,
    (iii) a hydroxy group,
    (iv) a $C_{1-6}$ alkoxy group (e.g., methoxy),
    (v) a $C_{3-10}$ cycloalkyl group (e.g., cyclopropyl, cyclobutyl, cyclopentyl) optionally substituted by 1 to 3 substituents selected from a hydroxy group and a cyano group, and
    (vi) a $C_{6-14}$ aryl group (e.g., phenyl),
  (d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
  (e) a mono- or di-$C_{1-6}$ alkyl-carbamoyloxy group (e.g., methylcarbamoyloxy),
  (f) a $C_{3-10}$ cycloalkyl-carbonylamino group (the $C_{3-10}$ cycloalkyl in the $C_{3-10}$ cycloalkyl-carbonylamino group may be a bridged group or a spiro ring group. e.g., cyclopropylcarbonylamino, cyclobutylcarbonylamino, cyclohexylcarbonylamino, spiro[2.3]hexylcarbonylamino, spiro[3.3]heptylcarbonylamino, bicyclo[1.1.1]pentylcarbonylamino) optionally substituted by 1 to 3 substituents selected from
    (i) a halogen atom (e.g., a fluorine atom),
    (ii) a cyano group,
    (iii) a hydroxy group,
    (iv) an optionally halogenated $C_{1-6}$ alkyl group (e.g., methyl, difluoromethyl, trifluoromethyl),
    (v) a $C_{1-6}$ alkoxy group (e.g., methoxy), and
    (vi) a $C_{6-14}$ aryl group (e.g., phenyl) optionally substituted by 1 to 3 halogen atoms (e.g., a fluorine atom),
  (g) a $C_{3-10}$ cycloalkoxy-carbonylamino group (e.g., cyclopropoxycarbonylamino),
  (h) a $C_{6-14}$ aryl-carbonylamino group (e.g., phenylcarbonylamino) optionally substituted by 1 to 3 halogen atoms (e.g., a chlorine atom),
  (i) a $C_{7-16}$ aralkyl-oxycarbonylamino group (e.g., benzyloxycarbonylamino),
  (j) a 5- to 14-membered aromatic heterocyclic group (preferably a 5- or 6-membered monocyclic aromatic heterocyclic group (e.g., pyrazolyl, triazolyl) or a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl, ethyl),
  (k) a 3- to 14-membered non-aromatic heterocyclic group (preferably a 3- to 8-membered monocyclic non-aromatic heterocyclic group (e.g., pyrrolidinyl, piperidyl, morpholinyl, tetrahydrooxazinyl, hexahydropyrimidinyl, oxazolidinyl, imidazolidinyl, 1,1-dioxido-1,2-thiazolidinyl) or a 9- to 14-membered fused polycyclic (preferably bi- or tri-cyclic) non-aromatic heterocyclic group (e.g., dihydroisoindolyl, 5-azaspiro[2.4]heptyl)) optionally substituted by 1 to 3 substituents selected from
    (i) an oxo group, and
    (ii) a $C_{1-6}$ alkyl group (e.g., methyl),
  (l) a 5- to 14-membered aromatic heterocyclylcarbonylamino group (preferably a 5- or 6-membered monocyclic aromatic heterocyclylcarbonylamino group (e.g., oxazolylcarbonylamino, imidazolylcarbonylamino, pyrazolylcarbonylamino, pyridylcarbonylamino)) optionally substituted by 1 to 3 $C_{1-6}$ alkyl groups (e.g., methyl), and
  (m) a 3- to 14-membered non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino, tetrahydropyranylcarbonylamino)) optionally substituted by 1 to 3 substituents selected from
    (i) a $C_{1-6}$ alkyl group (e.g., methyl, ethyl), and
    (ii) a $C_{6-14}$ aryl group (e.g., phenyl),
(2) a cyclopropyl group optionally substituted by 1 to 3 of mono- or di-$C_{1-6}$ alkyl-carbamoyl groups (e.g., ethylcarbamoyl) optionally substituted by 1 to 3 halogen atoms (e.g., a fluorine atom),
(3) a phenyl group optionally substituted by 1 to 3 substituents selected from
  (a) a halogen atom (e.g., a fluorine atom, a bromine atom),
  (b) an optionally halogenated $C_{1-6}$ alkyl group (e.g., trifluoromethyl),
  (c) a $C_{1-6}$ alkylsulfonyl group (e.g., methylsulfonyl),
  (d) a $C_{6-14}$ aryl group (e.g., phenyl) optionally substituted by 1 to 3 substituents selected from
    (i) a cyano group,
    (ii) an optionally halogenated $C_{1-6}$ alkyl group (e.g., trifluoromethyl),
    (iii) a $C_{1-6}$ alkoxy group (e.g., methoxy), and
    (iv) a $C_{1-6}$ alkylsulfonyl group (e.g., methylsulfonyl),
  (e) a 5- to 14-membered aromatic heterocyclic group (preferably a 5- or 6-membered monocyclic aromatic heterocyclic group (e.g., pyrazolyl)) optionally substituted by 1 to 3 $C_{1-6}$ alkyl groups (e.g., methyl),
  (f) a 3- to 14-membered non-aromatic heterocyclic group (preferably a 3- to 8-membered monocyclic non-aromatic heterocyclic group (e.g., pyrrolidinyl)) optionally substituted by 1 to 3 oxo groups, and
  (g) a 4,4,5,5-tetramethyl-1,3,2-dioxaborolan-2-yl group,
(4) a pyridyl group optionally substituted by 1 to 3 substituents selected from
  (a) a halogen atom (e.g., a fluorine atom, a chlorine atom), and
  (b) an optionally halogenated $C_{1-6}$ alkyl group (e.g., trifluoromethyl),
(5) an isoxazolyl group optionally substituted by 1 to 3 $C_{3-10}$ cycloalkyl groups (e.g., cyclopropyl), (6) a pyrazolyl group optionally substituted by 1 to 3 substituents selected from
  (a) a $C_{1-6}$ alkyl group (e.g., methyl), and
  (b) a $C_{6-14}$ aryl group (e.g., phenyl),
(7) a tetrahydropyranyl group optionally substituted by 1 to 3 substituents selected from
  (a) a $C_{1-6}$ alkyl-carbonylamino group (e.g., propanoylamino, pivaloylamino) optionally substituted by 1 to 5 halogen atoms (e.g., a fluorine atom),
  (b) a $C_{1-6}$ alkoxy-carbonylamino group (e.g., tert-butoxycarbonylamino),
  (c) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl),
  (d) a $C_{6-14}$ aryl-carbonylamino group (e.g., phenylcarbonylamino) optionally substituted by 1 to 3 halogen atoms (e.g., a chlorine atom), and
  (e) a 3- to 14-membered non-aromatic heterocyclic group (preferably a 3- to 8-membered monocyclic non-aromatic heterocyclic group (e.g., pyrrolidinyl, piperidyl)) optionally substituted by 1 to 3 oxo groups,
(8) a piperidyl group optionally substituted by 1 to 3 substituents selected from
  (a) a $C_{1-6}$ alkyl-carbonyl group (e.g., acetyl),
  (b) a $C_{1-6}$ alkoxy-carbonyl group (e.g., methoxycarbonyl, ethoxycarbonyl, isopropoxycarbonyl, tert-butoxycarbonyl),
  (c) a $C_{3-10}$ cycloalkyl-carbonyl group (e.g., cyclopropylcarbonyl),
  (d) a $C_{3-10}$ cycloalkylsulfonyl group (e.g., cyclopropylsulfonyl), and
  (e) a $C_{6-14}$ aryl group (e.g., phenyl), or
(9) a morpholinyl group optionally substituted by 1 to 3 substituents selected from
  (a) a $C_{1-6}$ alkoxy-carbonyl group (e.g., methoxycarbonyl, isopropoxycarbonyl, tert-butoxycarbonyl),
  (b) a $C_{3-10}$ cycloalkyl-carbonyl group (e.g., cyclopropylcarbonyl, cyclopentylcarbonyl),
  (c) a $C_{3-10}$ cycloalkylsulfonyl group (e.g., cyclopropylsulfonyl), and
  (d) a $C_{6-14}$ arylsulfonyl group (e.g., phenylsulfonyl) optionally substituted by 1 to 3 $C_{1-6}$ alkyl groups (e.g., methyl).

$R^1$ is still more preferably
(1) a cyclohexyl group optionally substituted by 1 to 3 substituents selected from
  (a) an amino group,
  (b) a $C_{1-6}$ alkoxy group (e.g., butoxy),
  (c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
    (i) a halogen atom (e.g., a fluorine atom),
    (ii) a cyano group,
    (iii) a hydroxy group,
    (iv) a $C_{1-6}$ alkoxy group (e.g., methoxy),
    (v) a $C_{3-10}$ cycloalkyl group (e.g., cyclopropyl, cyclobutyl, cyclopentyl) optionally substituted by 1 to 3 substituents selected from a hydroxy group and a cyano group, and
    (vi) a phenyl group,
  (d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
  (e) a mono- or di-$C_{1-6}$ alkyl-carbamoyloxy group (e.g., methylcarbamoyloxy),
  (f) a $C_{3-10}$ cycloalkyl-carbonylamino group (e.g., cyclopropylcarbonylamino, cyclobutylcarbonylamino, cyclohexylcarbonylamino) optionally substituted by 1 to 3 substituents selected from
    (i) a halogen atom (e.g., a fluorine atom),
    (ii) a cyano group,
    (iii) a hydroxy group,
    (iv) an optionally halogenated $C_{1-6}$ alkyl group (e.g., methyl, difluoromethyl, trifluoromethyl),
    (v) a $C_{1-6}$ alkoxy group (e.g., methoxy), and
    (vi) a phenyl group optionally substituted by 1 to 3 halogen atoms (e.g., a fluorine atom),
  (g) a spiro[2.3]hexylcarbonylamino group,
  (h) a spiro[3.3]heptylcarbonylamino group,
  (i) a bicyclo[1.1.1]pentylcarbonylamino group optionally substituted by 1 to 3 optionally halogenated $C_{1-6}$ alkyl groups (e.g., trifluoromethyl),
  (j) a $C_{3-10}$ cycloalkoxy-carbonylamino group (e.g., cyclopropoxycarbonylamino),
  (k) a phenylcarbonylamino group optionally substituted by 1 to 3 halogen atoms (e.g., a chlorine atom),
  (l) a benzyloxycarbonylamino group,
  (m) a pyrazolyl group optionally substituted by 1 to 3 $C_{1-6}$ alkyl groups (e.g., methyl, ethyl),
  (n) a triazolyl group,
  (o) an indazolyl group
  (p) a pyrrolidinyl group optionally substituted by 1 to 3 oxo groups,
  (q) a piperidyl group optionally substituted by 1 to 3 oxo groups,
  (r) a morpholinyl group optionally substituted by 1 to 3 oxo groups,
  (s) a tetrahydrooxazinyl group optionally substituted by 1 to 3 oxo groups,
  (t) a hexahydropyrimidinyl group optionally substituted by 1 to 3 oxo groups,
  (u) an oxazolidinyl group optionally substituted by 1 to 3 oxo groups,
  (v) an imidazolidinyl group optionally substituted by 1 to 3 substituents selected from
    (i) an oxo group, and
    (ii) a $C_{1-6}$ alkyl group (e.g., methyl),
  (w) a 1,1-dioxido-1,2-thiazolidinyl group,
  (x) a dihydroisoindolyl group optionally substituted by 1 to 3 oxo groups,
  (y) a 5-azaspiro[2.4]heptyl group optionally substituted by 1 to 3 oxo groups,
  (z) an oxazolylcarbonylamino group,
  (aa) an imidazolylcarbonylamino group optionally substituted by 1 to 3 $C_{1-6}$ alkyl groups (e.g., methyl),
  (bb) a pyrazolylcarbonylamino group optionally substituted by 1 to 3 $C_{1-6}$ alkyl groups (e.g., methyl),
  (cc) a pyridylcarbonylamino group,
  (dd) an oxetanylcarbonylamino group optionally substituted by 1 to 3 substituents selected from
    (i) a $C_{1-6}$ alkyl group (e.g., methyl, ethyl), and
    (ii) a phenyl group,
  (ee) a tetrahydrofurylcarbonylamino group, and
  (ff) a tetrahydropyranylcarbonylamino group,
(2) a cyclopropyl group optionally substituted by 1 to 3 of mono- or di-$C_{1-6}$ alkyl-carbamoyl groups (e.g., ethylcarbamoyl) optionally substituted by 1 to 3 halogen atoms (e.g., a fluorine atom), (3) a phenyl group optionally substituted by 1 to 3 substituents selected from
  (a) a halogen atom (e.g., a fluorine atom, a bromine atom),
  (b) an optionally halogenated $C_{1-6}$ alkyl group (e.g., trifluoromethyl),
  (c) a $C_{1-6}$ alkylsulfonyl group (e.g., methylsulfonyl),
  (d) a phenyl group optionally substituted by 1 to 3 substituents selected from
    (i) a cyano group,
    (ii) an optionally halogenated $C_{1-6}$ alkyl group (e.g., trifluoromethyl),
    (iii) a $C_{1-6}$ alkoxy group (e.g., methoxy), and
    (iv) a $C_{1-6}$ alkylsulfonyl group (e.g., methylsulfonyl),
  (e) a pyrazolyl group optionally substituted by 1 to 3 $C_{1-6}$ alkyl groups (e.g., methyl),
  (f) a pyrrolidinyl group optionally substituted by 1 to 3 oxo groups, and
  (g) a 4,4,5,5-tetramethyl-1,3,2-dioxaborolan-2-yl group,
(4) a pyridyl group optionally substituted by 1 to 3 substituents selected from
  (a) a halogen atom (e.g., a fluorine atom, a chlorine atom), and
  (b) an optionally halogenated $C_{1-6}$ alkyl group (e.g., trifluoromethyl),
(5) an isoxazolyl group optionally substituted by 1 to 3 $C_{3-10}$ cycloalkyl groups (e.g., cyclopropyl),
(6) a pyrazolyl group optionally substituted by 1 to 3 substituents selected from
  (a) a $C_{1-6}$ alkyl group (e.g., methyl), and
  (b) a phenyl group,
(7) a tetrahydropyranyl group optionally substituted by 1 to 3 substituents selected from
  (a) a $C_{1-6}$ alkyl-carbonylamino group (e.g., propanoylamino, pivaloylamino) optionally substituted by 1 to 5 halogen atoms (e.g., a fluorine atom),
  (b) a $C_{1-6}$ alkoxy-carbonylamino group (e.g., tert-butoxycarbonylamino),
  (c) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl),
  (d) a phenylcarbonylamino group optionally substituted by 1 to 3 halogen atoms (e.g., a chlorine atom),
  (e) a pyrrolidinyl group optionally substituted by 1 to 3 oxo groups, and
  (f) a piperidyl group optionally substituted by 1 to 3 oxo groups,
(8) a piperidyl group optionally substituted by 1 to 3 substituents selected from
  (a) a $C_{1-6}$ alkyl-carbonyl group (e.g., acetyl),
  (b) a $C_{1-6}$ alkoxy-carbonyl group (e.g., methoxycarbonyl, ethoxycarbonyl, isopropoxycarbonyl, tert-butoxycarbonyl),
  (c) a $C_{3-10}$ cycloalkyl-carbonyl group (e.g., cyclopropylcarbonyl),
  (d) a $C_{3-10}$ cycloalkylsulfonyl group (e.g., cyclopropylsulfonyl), and
  (e) a phenyl group, or
(9) a morpholinyl group optionally substituted by 1 to 3 substituents selected from
  (a) a $C_{1-6}$ alkoxy-carbonyl group (e.g., methoxycarbonyl, isopropoxycarbonyl, tert-butoxycarbonyl),
  (b) a $C_{3-10}$ cycloalkyl-carbonyl group (e.g., cyclopropylcarbonyl, cyclopentylcarbonyl),
  (c) a $C_{3-10}$ cycloalkylsulfonyl group (e.g., cyclopropylsulfonyl), and
  (d) a phenylsulfonyl group optionally substituted by 1 to 3 $C_{1-6}$ alkyl groups (e.g., methyl).

$R^1$ is particularly preferably
(1) a cyclohexyl group optionally substituted by 1 to 3 substituents selected from
  (a) a $C_{1-6}$ alkyl-carbonylamino group (e.g., acetylamino, propanoylamino) optionally substituted by 1 to 3 halogen atoms (e.g., a fluorine atom),
  (b) a $C_{1-6}$ alkoxy-carbonylamino group (e.g., methoxycarbonylamino), and
  (c) a $C_{3-10}$ cycloalkyl-carbonylamino group (e.g., cyclopropylcarbonylamino) optionally substituted by 1 to 3 halogen atoms (e.g., a fluorine atom), or
(2) a phenyl group.

As another embodiment, $R^1$ is preferably
(1) an optionally substituted $C_{3-10}$ cycloalkyl group (e.g., cyclopropyl, cyclohexyl),
(2) an optionally substituted $C_{6-14}$ aryl group (e.g., phenyl),
(3) an optionally substituted 5- to 14-membered aromatic heterocyclic group (preferably a 5- or 6-membered monocyclic aromatic heterocyclic group (e.g., pyridyl, isoxazolyl, pyrazolyl, pyrrolyl, thiazolyl, thienyl) or a 8- to 14-membered fused polycyclic (preferably bi- or tricyclic) aromatic heterocyclic group (e.g., pyrazolopyridyl (e.g., pyrazolo[1,5-a]pyridyl)),
(4) an optionally substituted 3- to 14-membered non-aromatic heterocyclic group (preferably a 3- to 8-membered monocyclic non-aromatic heterocyclic group, more preferably a 5- or 6-membered monocyclic non-aromatic heterocyclic group (including a 6-membered monocyclic non-aromatic heterocyclic group and a 5- or 6-membered monocyclic nitrogen-containing non-aromatic heterocyclic group) (e.g., tetrahydropyranyl, piperidyl, morpholinyl, pyrrolidinyl)), or
(5) an optionally substituted $C_{1-6}$ alkyl group (e.g., ethyl).

In this embodiment, $R^1$ is more preferably
(1) a $C_{3-10}$ cycloalkyl group (e.g., cyclopropyl, cyclohexyl) optionally substituted by 1 to 3 substituents selected from
  (a) an amino group,
  (b) a halogen atom (e.g., a fluorine atom),
  (c) a hydroxy group,
  (d) a $C_{1-6}$ alkyl group (e.g., methyl) optionally substituted by 1 to 3 substituents selected from
    (i) a $C_{1-6}$ alkoxy-carbonylamino group (e.g., tert-butoxycarbonylamino), and
    (ii) a $C_{1-6}$ alkylsulfonylamino group (e.g., ethylsulfonylamino) optionally substituted by 1 to 3 halogen atoms (e.g., a fluorine atom),
  (e) a $C_{1-6}$ alkoxy group (e.g., butoxy),
  (f) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 6 substituents selected from
    (i) a halogen atom (e.g., a fluorine atom),
    (ii) a cyano group,
    (iii) a hydroxy group,
    (iv) a $C_{1-6}$ alkoxy group (e.g., methoxy),
    (v) a $C_{3-10}$ cycloalkyl group (e.g., cyclopropyl, cyclobutyl, cyclopentyl) optionally substituted by 1 to 3 substituents selected from a hydroxy group and a cyano group, and
    (vi) a $C_{6-14}$ aryl group (e.g., phenyl),
  (g) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(h) a mono- or di-$C_{1-6}$ alkyl-carbamoyl group (e.g., ethylcarbamoyl) optionally substituted by 1 to 3 halogen atoms (e.g., a fluorine atom),
(i) a mono- or di-$C_{1-6}$ alkyl-carbamoyloxy group (e.g., methylcarbamoyloxy),
(j) a $C_{3-10}$ cycloalkyl-carbonylamino group (the $C_{3-10}$ cycloalkyl in the $C_{3-10}$ cycloalkyl-carbonylamino group may be a bridged group or a spiro ring group. e.g., cyclopropylcarbonylamino, cyclobutylcarbonylamino, cyclohexylcarbonylamino, spiro[2.3]hexylcarbonylamino, spiro[3.3]heptylcarbonylamino, bicyclo[1.1.1]pentylcarbonylamino) optionally substituted by 1 to 3 substituents selected from
  (i) a halogen atom (e.g., a fluorine atom),
  (ii) a cyano group,
  (iii) a hydroxy group,
  (iv) an optionally halogenated $C_{1-6}$ alkyl group (e.g., methyl, difluoromethyl, trifluoromethyl),
  (v) a $C_{1-6}$ alkoxy group (e.g., methoxy), and
  (vi) a $C_{6-14}$ aryl group (e.g., phenyl) optionally substituted by 1 to 3 halogen atoms (e.g., a fluorine atom),
(k) a $C_{3-10}$ cycloalkoxy-carbonylamino group (e.g., cyclopropoxycarbonylamino),
(l) a N-5- or 6-membered monocyclic aromatic heterocyclyl-N—$C_{1-6}$ alkyl-carbonyl-amino group (e.g., N-pyridyl-N-acetylamino) optionally substituted by 1 to 3 halogen atoms (e.g., a fluorine atom),
(m) a $C_{1-6}$ alkylsulfonylamino group (e.g., ethylsulfonylamino) optionally substituted by 1 to 3 halogen atoms (e.g., a fluorine atom),
(n) a $C_{3-10}$ cycloalkylsulfonylamino group (e.g., cyclopropylsulfonylamino),
(o) a $C_{1-6}$ alkylamino group (e.g., ethylamino) optionally substituted by 1 to 3 halogen atoms (e.g., a fluorine atom),
(p) a $C_{6-14}$ aryl group (e.g., phenyl) optionally substituted by 1 to 3 halogen atoms (e.g., a fluorine atom),
(q) a $C_{6-14}$ aryl-carbonylamino group (e.g., phenylcarbonylamino) optionally substituted by 1 to 3 substituents selected from
  (i) a halogen atom (e.g., a fluorine atom, a chlorine atom),
  (ii) a cyano group, and
  (iii) an optionally halogenated $C_{1-6}$ alkyl group (e.g., trifluoromethyl),
(r) a $C_{7-16}$ aralkyl-carbonylamino group (e.g., benzylcarbonylamino),
(s) a $C_{7-16}$ aralkyl-oxycarbonylamino group (e.g., benzyloxycarbonylamino),
(t) a 5- to 14-membered aromatic heterocyclic group (preferably a 5- or 6-membered monocyclic aromatic heterocyclic group (e.g., pyrazolyl, triazolyl, oxazolyl, oxadiazolyl, pyridyl) or a 8- to 14-membered fused polycyclic (preferably bi- or tri-cyclic) aromatic heterocyclic group (e.g., indazolyl, benzimidazolyl, benzotriazolyl, triazolopyridyl (e.g., [1,2,4]triazolo[4,3-a]pyridyl))) optionally substituted by 1 to 3 substituents selected from
  (i) a $C_{1-6}$ alkyl group (e.g., methyl, ethyl), and
  (ii) a $C_{3-10}$ cycloalkyl group (e.g., cyclopropyl),
(u) a 3- to 14-membered non-aromatic heterocyclic group (preferably a 3- to 8-membered monocyclic non-aromatic heterocyclic group (e.g., pyrrolidinyl, piperidyl, morpholinyl, tetrahydrooxazinyl, hexahydropyrimidinyl, oxazolidinyl, imidazolidinyl, 1,1-dioxido-1,2-thiazolidinyl) or a 9- to 14-membered fused polycyclic (preferably bi- or tri-cyclic) non-aromatic heterocyclic group (e.g., dihydroisoindolyl, 5-azaspiro[2.4]heptyl)) optionally substituted by 1 to 6 substituents selected from
  (i) an oxo group,
  (ii) a $C_{1-6}$ alkyl group (e.g., methyl), and
  (iii) a halogen atom (e.g., a fluorine atom),
(v) a 5- to 14-membered aromatic heterocyclylcarbonylamino group (preferably a 5- or 6-membered monocyclic aromatic heterocyclylcarbonylamino group (e.g., oxazolylcarbonylamino, imidazolylcarbonylamino, pyrazolylcarbonylamino, pyridylcarbonylamino)) optionally substituted by 1 to 3 $C_{1-6}$ alkyl groups (e.g., methyl),
(w) a 3- to 14-membered non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino, tetrahydropyranylcarbonylamino)) optionally substituted by 1 to 3 substituents selected from
  (i) a $C_{1-6}$ alkyl group (e.g., methyl, ethyl), and
  (ii) a $C_{6-14}$ aryl group (e.g., phenyl),
(x) a 3- to 14-membered non-aromatic heterocyclylcarbonyloxy group (preferably a 3- to 8-membered monocyclic non-aromatic heterocyclylcarbonyloxy group (e.g., azetidinylcarbonyloxy, pyrrolidinylcarbonyloxy, piperidylcarbonyloxy)),
(y) a 5- to 14-membered aromatic heterocyclylamino group (preferably a 5- or 6-membered monocyclic aromatic heterocyclylamino group (e.g., pyridylamino)),
(z) a $C_{6-14}$ aryloxy group (e.g., phenyloxy) optionally substituted by 1 to 3 halogen atoms (e.g., a fluorine atom),
(aa) a cyano group, and
(bb) a 5- to 14-membered aromatic heterocyclyloxy group (preferably a 5- or 6-membered monocyclic aromatic heterocyclyloxy group (e.g., pyridyloxy)) optionally substituted by 1 to 3 halogen atoms (e.g., a fluorine atom),
(2) a $C_{6-14}$ aryl group (e.g., phenyl) optionally substituted by 1 to 3 substituents selected from
(a) a halogen atom (e.g., a fluorine atom, a chlorine atom, a bromine atom),
(b) a cyano group,
(c) an optionally halogenated $C_{1-6}$ alkyl group (e.g., trifluoromethyl, difluoromethyl),
(d) an optionally halogenated $C_{1-6}$ alkoxy group (e.g., methoxy, ethoxy, difluoromethoxy, trifluoromethoxy, difluoroethoxy),
(e) a $C_{1-6}$ alkylsulfonyl group (e.g., methylsulfonyl),
(f) a $C_{6-14}$ aryl group (e.g., phenyl) optionally substituted by 1 to 3 substituents selected from
  (i) a cyano group,
  (ii) an optionally halogenated $C_{1-6}$ alkyl group (e.g., methyl, trifluoromethyl, difluoromethyl),
  (iii) a $C_{1-6}$ alkoxy group (e.g., methoxy, ethoxy) optionally substituted by 1 to 3 substituents selected from a halogen atom (e.g., a fluorine atom), a $C_{1-6}$ alkoxy group (e.g., methoxy) and a cyano group,
  (iv) a $C_{1-6}$ alkylsulfonyl group (e.g., methylsulfonyl),
  (v) a halogen atom (e.g., a fluorine atom, a chlorine atom),
  (vi) a $C_{3-10}$ cycloalkyl group (e.g., cyclopropyl) optionally substituted by 1 to 3 cyano groups, and (vii) a 3- to 14-membered non-aromatic heterocyclyl-carbonyl group (preferably a 3- to 8-membered monocyclic non-aromatic heterocyclylcarbonyl group (e.g., pyrrolidinylcarbonyl)),
(g) a $C_{7-16}$ aralkyl group (e.g., benzyl),
(h) a 5- to 14-membered aromatic heterocyclic group (preferably a 5- or 6-membered monocyclic aromatic heterocyclic group (e.g., pyrazolyl, pyridyl, pyrimidinyl) or a 8- to 14-membered fused polycyclic (preferably bi- or tri-cyclic) aromatic heterocyclic group (e.g., furopyridyl (e.g., furo[2,3-b]pyridyl), imidazopyridyl (e.g., imidazo[1,2-a]pyridyl))) optionally substituted by 1 to 3 substituents selected from
  (i) a halogen atom (e.g., a fluorine atom, a chlorine atom, a bromine atom),
  (ii) a $C_{1-6}$ alkyl group (e.g., methyl, ethyl) optionally substituted by 1 to 3 substituents selected from a halogen atom (e.g., a fluorine atom) and a pyridyl group,
  (iii) an optionally halogenated $C_{1-6}$ alkoxy group (e.g., methoxy, ethoxy, isopropoxy, trifluoroethoxy),
  (iv) a $C_{3-10}$ cycloalkyl group (e.g., cyclopropyl),
  (v) a $C_{1-6}$ alkylsulfonyl group (e.g., methylsulfonyl), and
  (vi) a 3- to 14-membered non-aromatic heterocyclic group (preferably a 3- to 8-membered monocyclic non-aromatic heterocyclic group (e.g., tetrahydropyranyl)),
(i) a 3- to 14-membered non-aromatic heterocyclic group (preferably a 3- to 8-membered monocyclic non-aromatic heterocyclic group (e.g., pyrrolidinyl, piperidyl) or a 9- to 14-membered fused polycyclic (preferably bi- or tri-cyclic) non-aromatic heterocyclic group (e.g., dihydrobenzofuryl)) optionally substituted by 1 to 3 substituents selected from
  (i) an oxo group,
  (ii) a $C_{1-6}$ alkoxy-carbonyl group (e.g., tert-butoxycarbonyl), and
  (iii) an optionally halogenated $C_{1-6}$ alkyl-carbonyl group (e.g., pentafluoropropionyl),
(j) a 4,4,5,5-tetramethyl-1,3,2-dioxaborolan-2-yl group,
(k) a $C_{3-10}$ cycloalkenyl group (e.g., cyclohexenyl) optionally substituted by 1 to 3 $C_{1-6}$ alkoxy-carbonylamino groups (e.g., tert-butoxycarbonylamino), and
(l) a $C_{3-10}$ cycloalkyl group (e.g., cyclohexyl) optionally substituted by 1 to 3 substituents selected from
  (i) a $C_{1-6}$ alkyl-carbonylamino group (e.g., propanoylamino) optionally substituted by 1 to 5 halogen atoms (e.g., a fluorine atom), and
  (ii) a $C_{1-6}$ alkoxy-carbonylamino group (e.g., tert-butoxycarbonylamino),
(3) a 5- to 14-membered aromatic heterocyclic group (preferably a 5- or 6-membered monocyclic aromatic heterocyclic group (e.g., pyridyl, isoxazolyl, pyrazolyl, pyrrolyl, thiazolyl, thienyl) or a 8- to 14-membered fused polycyclic (preferably bi- or tri-cyclic) aromatic heterocyclic group (e.g., pyrazolopyridyl (e.g., pyrazolo[1,5-a]pyridyl), imidazopyridyl (e.g., imidazo[1,2-a]pyridyl))) optionally substituted by 1 to 3 substituents selected from
  (a) a halogen atom (e.g., a fluorine atom, a chlorine atom, a bromine atom),
  (b) a $C_{1-6}$ alkyl group (e.g., methyl, isopropyl) optionally substituted by 1 to 3 substituents selected from
    (i) a halogen atom (e.g., a fluorine atom), and
    (ii) a hydroxy group,
  (c) a $C_{3-10}$ cycloalkyl group (e.g., cyclopropyl, cyclohexyl) optionally substituted by 1 to 3 substituents selected from
    (i) a halogen atom (e.g., a fluorine atom),
    (ii) a $C_{1-6}$ alkoxy-carbonylamino group (e.g., tert-butoxycarbonylamino),
    (iii) a $C_{1-6}$ alkyl-carbonylamino group (e.g., propanoylamino) optionally substituted by 1 to 5 halogen atoms (e.g., a fluorine atom), and
    (iv) a mono- or di-$C_{1-6}$ alkylamino group (e.g., propylamino) optionally substituted by 1 to 5 halogen atoms (e.g., a fluorine atom),
  (d) a $C_{4-10}$ cycloalkenyl group (e.g., cyclohexenyl) optionally substituted by 1 to 3 substituents selected from
    (i) a halogen atom (e.g., a fluorine atom), and
    (ii) a $C_{1-6}$ alkoxy-carbonylamino group (e.g., tert-butoxycarbonylamino),
  (e) a $C_{6-14}$ aryl group (e.g., phenyl) optionally substituted by 1 to 3 substituents selected from
    (i) a cyano group,
    (ii) a halogen atom (e.g., a fluorine atom, a chlorine atom), and
    (iii) a $C_{1-6}$ alkoxy group (e.g., methoxy),
  (f) a 5- to 14-membered aromatic heterocyclic group (preferably a 5- or 6-membered monocyclic aromatic heterocyclic group (e.g., pyridyl, pyrazolyl) or a 8- to 14-membered fused polycyclic (preferably bi- or tri-cyclic) aromatic heterocyclic group (e.g., pyrazolopyridyl (e.g., pyrazolo[1,5-a]pyridyl))) optionally substituted by 1 to 3 substituents selected from
    (i) a halogen atom (e.g., a fluorine atom), and
    (ii) an optionally halogenated $C_{1-6}$ alkyl group (e.g., methyl, difluoromethyl),
  (g) a 3- to 14-membered non-aromatic heterocyclic group (preferably a 3- to 8-membered monocyclic non-aromatic heterocyclic group (e.g., tetrahydropyranyl, dihydropyranyl, tetrahydropyridyl, piperidyl)) optionally substituted by 1 to 3 substituents selected from
    (i) a $C_{1-6}$ alkoxy-carbonyl group (e.g., tert-butoxycarbonyl),
    (ii) an optionally halogenated $C_{1-6}$ alkyl-carbonyl group (e.g., pentafluoropropanoyl), and
    (iii) an optionally halogenated $C_{1-6}$ alkyl group (e.g., pentafluoropropyl),
  (h) a mono- or di-$C_{1-6}$ alkyl-carbamoyl group (e.g., methylcarbamoyl, ethylcarbamoyl) optionally substituted by 1 to 3 substituents selected from
    (i) a halogen atom (e.g., a fluorine atom), and
    (ii) a $C_{3-10}$ cycloalkyl group (e.g., cyclopropyl),
  (i) a 3- to 14-membered non-aromatic heterocyclylcarbonyl group (preferably a 3- to 8-membered monocyclic non-aromatic heterocyclylcarbonyl group (e.g., piperidylcarbonyl)) optionally substituted by 1 to 3 halogen atoms (e.g., a fluorine atom), and
  (j) a $C_{6-14}$ aryl-carbonyl group (e.g., benzoyl),
(4) a 3- to 14-membered non-aromatic heterocyclic group (preferably a 3- to 8-membered monocyclic non-aromatic heterocyclic group, more preferably a 5- or 6-membered monocyclic non-aromatic heterocyclic group (including a 6-membered monocyclic non-aromatic heterocyclic group and a 5- or 6-membered monocyclic nitrogen-containing non-aromatic heterocyclic group) (e.g., tetrahydropyranyl, piperidyl, morpholinyl, pyrrolidinyl)) optionally substituted by 1 to 3 substituents selected from
  (a) a halogen atom (e.g., a fluorine atom),
  (b) an oxo group, (c) an amino group,
(d) an optionally halogenated $C_{1-6}$ alkyl group (e.g., tetrafluoropropyl, pentafluoropropyl, heptafluorobutyl),
(e) a $C_{1-6}$ alkylamino group (e.g., ethylamino, propylamino, butylamino) optionally substituted by 1 to 7 halogen atoms (e.g., a fluorine atom),
(f) an optionally halogenated $C_{1-6}$ alkyl-carbonyl group (e.g., acetyl, propanoyl, difluoroacetyl, difluoropropanoyl, pentafluoropropanoyl),
(g) a $C_{1-6}$ alkyl-carbonylamino group (e.g., propanoylamino, butanoylamino, pivaloylamino) optionally substituted by 1 to 5 halogen atoms (e.g., a fluorine atom),
(h) a $C_{1-6}$ alkoxy-carbonyl group (e.g., methoxycarbonyl, ethoxycarbonyl, isopropoxycarbonyl, tert-butoxycarbonyl),
(i) a $C_{1-6}$ alkoxy-carbonylamino group (e.g., tert-butoxycarbonylamino) optionally substituted by 1 to 3 halogen atoms (e.g., a fluorine atom),
(j) a $C_{1-6}$ alkylsulfonyl group (e.g., ethylsulfonyl) optionally substituted by 1 to 3 halogen atoms (e.g., a fluorine atom),
(k) a $C_{3-10}$ cycloalkyl-carbonyl group (e.g., cyclopropylcarbonyl, cyclopentylcarbonyl) optionally substituted by 1 to 3 substituents selected from
  (i) a halogen atom (e.g., a fluorine atom), and
  (ii) an optionally halogenated $C_{1-6}$ alkyl group (e.g., trifluoromethyl),
(l) a $C_{3-10}$ cycloalkyl-carbonylamino group (e.g., cyclopropylcarbonylamino, cyclobutylcarbonylamino) optionally substituted by 1 to 3 optionally halogenated $C_{1-6}$ alkyl groups (e.g., trifluoromethyl),
(m) a $C_{3-10}$ cycloalkylsulfonyl group (e.g., cyclopropylsulfonyl),
(n) a $C_{6-14}$ aryl group (e.g., phenyl) optionally substituted by 1 to 3 halogen atoms (e.g., a fluorine atom),
(o) a $C_{7-16}$ aralkyl group (e.g., benzyl),
(p) a $C_{6-14}$ aryl-carbonyl group (e.g., benzoyl),
(q) a $C_{6-14}$ aryl-carbonylamino group (e.g., phenylcarbonylamino) optionally substituted by 1 to 3 halogen atoms (e.g., a chlorine atom),
(r) a $C_{6-14}$ arylsulfonyl group (e.g., phenylsulfonyl) optionally substituted by 1 to 3 substituents selected from
  (i) a $C_{1-6}$ alkyl group (e.g., methyl), and
  (ii) a halogen atom (e.g., a fluorine atom),
(s) a 3- to 14-membered non-aromatic heterocyclic group (preferably a 3- to 8-membered monocyclic non-aromatic heterocyclic group (e.g., pyrrolidinyl, piperidyl)) optionally substituted by 1 to 3 substituents selected from
  (i) an oxo group, and
  (ii) a $C_{1-6}$ alkyl-carbonyl group (e.g., acetyl),
(t) a 5- to 14-membered aromatic heterocyclic group (preferably a 5- or 6-membered monocyclic aromatic heterocyclic group (e.g., pyrazolyl, pyridyl) or a 8- to 14-membered fused polycyclic (preferably bi- or tricyclic) aromatic heterocyclic group (e.g., benzotriazolyl)) optionally substituted by 1 to 3 substituents selected from
  (i) a halogen atom (e.g., a chlorine atom, a fluorine atom), and
  (ii) a $C_{1-6}$ alkyl group (e.g., methyl),
(u) a mono- or di-$C_{1-6}$ alkyl-carbamoyl group (e.g., ethylcarbamoyl, propylcarbamoyl, diethylcarbamoyl) optionally substituted by 1 to 5 halogen atoms (e.g., a fluorine atom),
(v) a $C_{7-16}$ aralkyloxy-carbonyl group (e.g., benzyloxycarbonyl), and
(w) a $C_{6-14}$ aryloxy group (e.g., phenyloxy) optionally substituted by 1 to 3 halogen atoms (e.g., a fluorine atom), or
(5) a $C_{1-6}$ alkyl group (e.g., ethyl) optionally substituted by 1 to 3 substituents selected from
(a) a $C_{6-14}$ aryloxy group (e.g., phenyloxy), and
(b) a $C_{7-16}$ aralkyloxy group (e.g., benzyloxy).
In this embodiment, $R^1$ is further more preferably
(1) a cyclohexyl group optionally substituted by 1 to 3 substituents selected from
(a) an amino group,
(b) a halogen atom (e.g., a fluorine atom),
(c) a hydroxy group,
(d) a $C_{1-6}$ alkyl group (e.g., methyl) optionally substituted by 1 to 3 substituents selected from
  (i) a $C_{1-6}$ alkoxy-carbonylamino group (e.g., tert-butoxycarbonylamino), and
  (ii) a $C_{1-6}$ alkylsulfonylamino group (e.g., ethylsulfonylamino) optionally substituted by 1 to 3 halogen atoms (e.g., a fluorine atom),
(e) a $C_{1-6}$ alkoxy group (e.g., butoxy),
(f) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
  (i) a halogen atom (e.g., a fluorine atom),
  (ii) a cyano group,
  (iii) a hydroxy group,
  (iv) a $C_{1-6}$ alkoxy group (e.g., methoxy),
  (v) a $C_{3-10}$ cycloalkyl group (e.g., cyclopropyl, cyclobutyl, cyclopentyl) optionally substituted by 1 to 3 substituents selected from a hydroxy group and a cyano group, and
  (vi) a $C_{6-14}$ aryl group (e.g., phenyl),
(g) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(h) a mono- or di-$C_{1-6}$ alkyl-carbamoyloxy group (e.g., methylcarbamoyloxy),
(i) a $C_{3-10}$ cycloalkyl-carbonylamino group (the $C_{3-10}$ cycloalkyl in the $C_{3-10}$ cycloalkyl-carbonylamino group may be a bridged group or a spiro ring group. e.g., cyclopropylcarbonylamino, cyclobutylcarbonylamino, cyclohexylcarbonylamino, spiro[2.3]hexylcarbonylamino, spiro[3.3]heptylcarbonylamino, bicyclo[1.1.1]pentylcarbonylamino) optionally substituted by 1 to 3 substituents selected from
  (i) a halogen atom (e.g., a fluorine atom),
  (ii) a cyano group,
  (iii) a hydroxy group,
  (iv) an optionally halogenated $C_{1-6}$ alkyl group (e.g., methyl, difluoromethyl, trifluoromethyl),
  (v) a $C_{1-6}$ alkoxy group (e.g., methoxy), and
  (vi) a $C_{6-14}$ aryl group (e.g., phenyl) optionally substituted by 1 to 3 halogen atoms (e.g., a fluorine atom),
(j) a $C_{3-10}$ cycloalkoxy-carbonylamino group (e.g., cyclopropoxycarbonylamino),
(k) a N-5- or 6-membered monocyclic aromatic heterocyclyl-N—$C_{1-6}$ alkyl-carbonyl-amino group (e.g., N-pyridyl-N-acetylamino) optionally substituted by 1 to 3 halogen atoms (e.g., a fluorine atom), (l) a $C_{1-6}$ alkylsulfonylamino group (e.g., ethylsulfonylamino) optionally substituted by 1 to 3 halogen atoms (e.g., a fluorine atom),
(m) a $C_{3-10}$ cycloalkylsulfonylamino group (e.g., cyclopropylsulfonylamino),
(n) a $C_{1-6}$ alkylamino group (e.g., ethylamino) optionally substituted by 1 to 3 halogen atoms (e.g., a fluorine atom),
(o) a $C_{6-14}$ aryl-carbonylamino group (e.g., phenylcarbonylamino) optionally substituted by 1 to 3 substituents selected from
  (i) a halogen atom (e.g., a fluorine atom, a chlorine atom),
  (ii) a cyano group, and
  (iii) an optionally halogenated $C_{1-6}$ alkyl group (e.g., trifluoromethyl),
(p) a $C_{7-16}$ aralkyl-carbonylamino group (e.g., benzylcarbonylamino),
(q) a $C_{7-16}$ aralkyl-oxycarbonylamino group (e.g., benzyloxycarbonylamino),
(r) a 5- to 14-membered aromatic heterocyclic group (preferably a 5- or 6-membered monocyclic aromatic heterocyclic group (e.g., pyrazolyl, triazolyl) or a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl, ethyl),
(s) a 3- to 14-membered non-aromatic heterocyclic group (preferably a 3- to 8-membered monocyclic non-aromatic heterocyclic group (e.g., pyrrolidinyl, piperidyl, morpholinyl, tetrahydrooxazinyl, hexahydropyrimidinyl, oxazolidinyl, imidazolidinyl, 1,1-dioxido-1,2-thiazolidinyl) or a 9- to 14-membered fused polycyclic (preferably bi- or tri-cyclic) non-aromatic heterocyclic group (e.g., dihydroisoindolyl, 5-azaspiro[2.4]heptyl)) optionally substituted by 1 to 3 substituents selected from
  (i) an oxo group, and
  (ii) a $C_{1-6}$ alkyl group (e.g., methyl),
(t) a 5- to 14-membered aromatic heterocyclylcarbonylamino group (preferably a 5- or 6-membered monocyclic aromatic heterocyclylcarbonylamino group (e.g., oxazolylcarbonylamino, imidazolylcarbonylamino, pyrazolylcarbonylamino, pyridylcarbonylamino)) optionally substituted by 1 to 3 $C_{1-6}$ alkyl groups (e.g., methyl),
(u) a 3- to 14-membered non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino, tetrahydropyranylcarbonylamino)) optionally substituted by 1 to 3 substituents selected from
  (i) a $C_{1-6}$ alkyl group (e.g., methyl, ethyl), and
  (ii) a $C_{6-14}$ aryl group (e.g., phenyl), and
(v) a 3- to 14-membered non-aromatic heterocyclylcarbonyloxy group (preferably a 3- to 8-membered monocyclic non-aromatic heterocyclylcarbonyloxy group (e.g., azetidinylcarbonyloxy, pyrrolidinylcarbonyloxy, piperidylcarbonyloxy)),
(2) a cyclopropyl group optionally substituted by 1 to 3 substituents selected from
  (a) a mono- or di-$C_{1-6}$ alkyl-carbamoyl group (e.g., ethylcarbamoyl) optionally substituted by 1 to 3 halogen atoms (e.g., a fluorine atom), and
  (b) a $C_{6-14}$ aryl group (e.g., phenyl) optionally substituted by 1 to 3 halogen atoms (e.g., a fluorine atom),
(3) a phenyl group optionally substituted by 1 to 3 substituents selected from
  (a) a halogen atom (e.g., a fluorine atom, a chlorine atom, a bromine atom),
  (b) a cyano group,
  (c) an optionally halogenated $C_{1-6}$ alkyl group (e.g., trifluoromethyl, difluoromethyl),
  (d) an optionally halogenated $C_{1-6}$ alkoxy group (e.g., methoxy, ethoxy, difluoromethoxy, trifluoromethoxy, difluoroethoxy),
  (e) a $C_{1-6}$ alkylsulfonyl group (e.g., methylsulfonyl),
  (f) a $C_{6-14}$ aryl group (e.g., phenyl) optionally substituted by 1 to 3 substituents selected from
    (i) a cyano group,
    (ii) an optionally halogenated $C_{1-6}$ alkyl group (e.g., methyl, trifluoromethyl, difluoromethyl),
    (iii) a $C_{1-6}$ alkoxy group (e.g., methoxy, ethoxy) optionally substituted by 1 to 3 substituents selected from a halogen atom (e.g., a fluorine atom), a $C_{1-6}$ alkoxy group (e.g., methoxy) and a cyano group,
    (iv) a $C_{1-6}$ alkylsulfonyl group (e.g., methylsulfonyl),
    (v) a halogen atom (e.g., a fluorine atom, a chlorine atom),
    (vi) a $C_{3-10}$ cycloalkyl group (e.g., cyclopropyl) optionally substituted by 1 to 3 cyano groups, and
    (vii) a 3- to 14-membered non-aromatic heterocyclylcarbonyl group (preferably a 3- to 8-membered monocyclic non-aromatic heterocyclylcarbonyl group (e.g., pyrrolidinylcarbonyl)),
  (g) a $C_{7-16}$ aralkyl group (e.g., benzyl),
  (h) a 5- to 14-membered aromatic heterocyclic group (preferably a 5- or 6-membered monocyclic aromatic heterocyclic group (e.g., pyrazolyl, pyridyl, pyrimidinyl) or a 8- to 14-membered fused polycyclic (preferably bi- or tri-cyclic) aromatic heterocyclic group (e.g., furopyridyl (e.g., furo[2,3-b]pyridyl), imidazopyridyl (e.g., imidazo[1,2-a]pyridyl))) optionally substituted by 1 to 3 substituents selected from
    (i) a halogen atom (e.g., a fluorine atom, a chlorine atom, a bromine atom),
    (ii) a $C_{1-6}$ alkyl group (e.g., methyl, ethyl) optionally substituted by 1 to 3 substituents selected from a halogen atom (e.g., a fluorine atom) and a pyridyl group,
    (iii) an optionally halogenated $C_{1-6}$ alkoxy group (e.g., methoxy, ethoxy, isopropoxy, trifluoroethoxy),
    (iv) a $C_{3-10}$ cycloalkyl group (e.g., cyclopropyl),
    (v) a $C_{1-6}$ alkylsulfonyl group (e.g., methylsulfonyl), and
    (vi) a 3- to 14-membered non-aromatic heterocyclic group (preferably a 3- to 8-membered monocyclic non-aromatic heterocyclic group (e.g., tetrahydropyranyl)),
  (i) a 3- to 14-membered non-aromatic heterocyclic group (preferably a 3- to 8-membered monocyclic non-aromatic heterocyclic group (e.g., pyrrolidinyl) or a 9- to 14-membered fused polycyclic (preferably bi- or tri-cyclic) non-aromatic heterocyclic group (e.g., dihydrobenzofuryl)) optionally substituted by 1 to 3 oxo groups, and
  (j) a 4,4,5,5-tetramethyl-1,3,2-dioxaborolan-2-yl group,
(4) a pyridyl group optionally substituted by 1 to 3 substituents selected from
  (a) a halogen atom (e.g., a fluorine atom, a chlorine atom),
  (b) an optionally halogenated $C_{1-6}$ alkyl group (e.g., trifluoromethyl), (c) a $C_{6-14}$ aryl group (e.g., phenyl) optionally substituted by 1 to 3 cyano groups, and
(d) a 5- to 14-membered aromatic heterocyclic group (preferably a 5- or 6-membered monocyclic aromatic heterocyclic group (e.g., pyrazolyl)) optionally substituted by 1 to 3 optionally halogenated $C_{1-6}$ alkyl groups (e.g., difluoromethyl),
(5) an isoxazolyl group optionally substituted by 1 to 3 substituents selected from
(a) a $C_{3-10}$ cycloalkyl group (e.g., cyclopropyl), and
(b) a $C_{1-6}$ alkyl group (e.g., methyl),
(6) a pyrazolyl group optionally substituted by 1 to 3 substituents selected from
(a) a $C_{1-6}$ alkyl group (e.g., methyl),
(b) a halogen atom (e.g., a bromine atom),
(c) a $C_{6-14}$ aryl group (e.g., phenyl) optionally substituted by 1 to 3 substituents selected from
(i) a cyano group,
(ii) a halogen atom (e.g., a fluorine atom, a chlorine atom), and
(iii) a $C_{1-6}$ alkoxy group (e.g., methoxy),
(d) a $C_{3-10}$ cycloalkyl group (e.g., cyclohexyl) optionally substituted by 1 to 3 halogen atoms (e.g., a fluorine atom),
(e) a $C_{4-10}$ cycloalkenyl group (e.g., cyclohexenyl) optionally substituted by 1 to 3 halogen atoms (e.g., a fluorine atom),
(f) a 5- to 14-membered aromatic heterocyclic group (preferably a 5- or 6-membered monocyclic aromatic heterocyclic group (e.g., pyridyl, pyrazolyl) or a 8- to 14-membered fused polycyclic (preferably bi- or tricyclic) aromatic heterocyclic group (e.g., pyrazolopyridyl (e.g., pyrazolo[1,5-a]pyridyl))) optionally substituted by 1 to 3 substituents selected from
(i) a halogen atom (e.g., a fluorine atom), and
(ii) a $C_{1-6}$ alkyl group (e.g., methyl), and
(g) a 3- to 14-membered non-aromatic heterocyclic group (preferably a 3- to 8-membered monocyclic non-aromatic heterocyclic group (e.g., tetrahydropyranyl, dihydropyranyl)),
(7) a pyrrolyl group optionally substituted by 1 to 3 $C_{1-6}$ alkyl groups (e.g., methyl),
(8) a thiazolyl group,
(9) a thienyl group optionally substituted by 1 to 3 halogen atoms (e.g., a chlorine atom),
(10) a pyrazolopyridyl group (e.g., pyrazolo[1,5-a]pyridyl),
(11) a tetrahydropyranyl group optionally substituted by 1 to 3 substituents selected from
(a) an amino group,
(b) a $C_{1-6}$ alkylamino group (e.g., ethylamino, propylamino, butylamino) optionally substituted by 1 to 7 halogen atoms (e.g., a fluorine atom),
(c) a $C_{1-6}$ alkyl-carbonylamino group (e.g., propanoylamino, butanoylamino, pivaloylamino) optionally substituted by 1 to 5 halogen atoms (e.g., a fluorine atom),
(d) a $C_{1-6}$ alkoxy-carbonylamino group (e.g., tert-butoxycarbonylamino) optionally substituted by 1 to 3 halogen atoms (e.g., a fluorine atom),
(e) a $C_{3-10}$ cycloalkyl-carbonylamino group (e.g., cyclopropylcarbonylamino, cyclobutylcarbonylamino) optionally substituted by 1 to 3 optionally halogenated $C_{1-6}$ alkyl groups (e.g., trifluoromethyl),
(f) a $C_{6-14}$ aryl-carbonylamino group (e.g., phenylcarbonylamino) optionally substituted by 1 to 3 halogen atoms (e.g., a chlorine atom),
(g) a 3- to 14-membered non-aromatic heterocyclic group (preferably a 3- to 8-membered monocyclic non-aromatic heterocyclic group (e.g., pyrrolidinyl, piperidyl)) optionally substituted by 1 to 3 oxo groups, and
(h) a $C_{7-16}$ aralkyl group (e.g., benzyl),
(12) a piperidyl group optionally substituted by 1 to 3 substituents selected from
(a) a $C_{1-6}$ alkyl-carbonyl group (e.g., acetyl),
(b) a $C_{1-6}$ alkoxy-carbonyl group (e.g., methoxycarbonyl, ethoxycarbonyl, isopropoxycarbonyl, tert-butoxycarbonyl),
(c) a $C_{3-10}$ cycloalkyl-carbonyl group (e.g., cyclopropylcarbonyl),
(d) a $C_{3-10}$ cycloalkylsulfonyl group (e.g., cyclopropylsulfonyl), and
(e) a $C_{6-14}$ aryl group (e.g., phenyl),
(13) a morpholinyl group optionally substituted by 1 to 3 substituents selected from
(a) an optionally halogenated $C_{1-6}$ alkyl group (e.g., tetrafluoropropyl, pentafluoropropyl, heptafluorobutyl),
(b) a $C_{1-6}$ alkoxy-carbonyl group (e.g., methoxycarbonyl, isopropoxycarbonyl, tert-butoxycarbonyl),
(c) a $C_{3-10}$ cycloalkyl-carbonyl group (e.g., cyclopropylcarbonyl, cyclopentylcarbonyl),
(d) a $C_{3-10}$ cycloalkylsulfonyl group (e.g., cyclopropylsulfonyl),
(e) a $C_{6-14}$ arylsulfonyl group (e.g., phenylsulfonyl) optionally substituted by 1 to 3 substituents selected from
(i) a $C_{1-6}$ alkyl group (e.g., methyl), and
(ii) a halogen atom (e.g., a fluorine atom), and
(f) a $C_{1-6}$ alkylsulfonyl group (e.g., ethylsulfonyl) optionally substituted by 1 to 3 halogen atoms (e.g., a fluorine atom),
(14) a pyrrolidinyl group optionally substituted by 1 to 3 substituents selected from
(a) a halogen atom (e.g., a fluorine atom),
(b) an oxo group,
(c) a $C_{1-6}$ alkoxy-carbonyl group (e.g., tert-butoxycarbonyl),
(d) a $C_{6-14}$ aryl-carbonyl group (e.g., benzoyl),
(e) a $C_{3-10}$ cycloalkyl-carbonyl group (e.g., cyclopropylcarbonyl),
(f) a $C_{1-6}$ alkylsulfonyl group (e.g., ethylsulfonyl) optionally substituted by 1 to 3 halogen atoms (e.g., a fluorine atom),
(g) a $C_{6-14}$ arylsulfonyl group (e.g., phenylsulfonyl) optionally substituted by 1 to 3 halogen atoms (e.g., a fluorine atom), and
(h) a $C_{3-10}$ cycloalkylsulfonyl group (e.g., cyclopropylsulfonyl), or
(15) a $C_{1-6}$ alkyl group (e.g., ethyl) optionally substituted by 1 to 3 substituents selected from
(a) a $C_{6-14}$ aryloxy group (e.g., phenyloxy), and
(b) a $C_{7-16}$ aralkyloxy group (e.g., benzyloxy).
In this embodiment, $R^1$ is still more preferably
(1) a cyclohexyl group optionally substituted by 1 to 3 substituents selected from
(a) an amino group,
(b) a halogen atom (e.g., a fluorine atom),
(c) a hydroxy group,
(d) a $C_{1-6}$ alkyl group (e.g., methyl) optionally substituted by 1 to 3 substituents selected from
(i) a $C_{1-6}$ alkoxy-carbonylamino group (e.g., tert-butoxycarbonylamino), and
(ii) a $C_{1-6}$ alkylsulfonylamino group (e.g., ethylsulfonylamino) optionally substituted by 1 to 3 halogen atoms (e.g., a fluorine atom), (e) a $C_{1-6}$ alkoxy group (e.g., butoxy),
(f) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
  (i) a halogen atom (e.g., a fluorine atom),
  (ii) a cyano group,
  (iii) a hydroxy group,
  (iv) a $C_{1-6}$ alkoxy group (e.g., methoxy),
  (v) a $C_{3-10}$ cycloalkyl group (e.g., cyclopropyl, cyclobutyl, cyclopentyl) optionally substituted by 1 to 3 substituents selected from a hydroxy group and a cyano group, and
  (vi) a phenyl group,
(g) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(h) a mono- or di-$C_{1-6}$ alkyl-carbamoyloxy group (e.g., methylcarbamoyloxy),
(i) a $C_{3-10}$ cycloalkyl-carbonylamino group (e.g., cyclopropylcarbonylamino, cyclobutylcarbonylamino, cyclohexylcarbonylamino) optionally substituted by 1 to 3 substituents selected from
  (i) a halogen atom (e.g., a fluorine atom),
  (ii) a cyano group,
  (iii) a hydroxy group,
  (iv) an optionally halogenated $C_{1-6}$ alkyl group (e.g., methyl, difluoromethyl, trifluoromethyl),
  (v) a $C_{1-6}$ alkoxy group (e.g., methoxy), and
  (vi) a phenyl group optionally substituted by 1 to 3 halogen atoms (e.g., a fluorine atom),
(j) a spiro[2.3]hexylcarbonylamino group,
(k) a spiro[3.3]heptylcarbonylamino group,
(l) a bicyclo[1.1.1]pentylcarbonylamino group optionally substituted by 1 to 3 optionally halogenated $C_{1-6}$ alkyl groups (e.g., trifluoromethyl),
(m) a $C_{3-10}$ cycloalkoxy-carbonylamino group (e.g., cyclopropoxycarbonylamino),
(n) a N-pyridyl-N—$C_{1-6}$ alkyl-carbonyl-amino group (e.g., N-pyridyl-N-acetylamino) optionally substituted by 1 to 3 halogen atoms (e.g., a fluorine atom),
(o) a $C_{1-6}$ alkylsulfonylamino group (e.g., ethylsulfonylamino) optionally substituted by 1 to 3 halogen atoms (e.g., a fluorine atom),
(p) a $C_{3-10}$ cycloalkylsulfonylamino group (e.g., cyclopropylsulfonylamino),
(q) a $C_{1-6}$ alkylamino group (e.g., ethylamino) optionally substituted by 1 to 3 halogen atoms (e.g., a fluorine atom),
(r) a phenylcarbonylamino group optionally substituted by 1 to 3 substituents selected from
  (i) a halogen atom (e.g., a fluorine atom, a chlorine atom),
  (ii) a cyano group, and
  (iii) an optionally halogenated $C_{1-6}$ alkyl group (e.g., trifluoromethyl),
(s) a benzylcarbonylamino group,
(t) a benzyloxycarbonylamino group,
(u) a pyrazolyl group optionally substituted by 1 to 3 $C_{1-6}$ alkyl groups (e.g., methyl, ethyl),
(v) a triazolyl group,
(w) an indazolyl group
(x) a pyrrolidinyl group optionally substituted by 1 to 3 oxo groups,
(y) a piperidyl group optionally substituted by 1 to 3 oxo groups,
(z) a morpholinyl group optionally substituted by 1 to 3 oxo groups,
(aa) a tetrahydrooxazinyl group optionally substituted by 1 to 3 oxo groups,
(bb) a hexahydropyrimidinyl group optionally substituted by 1 to 3 oxo groups,
(cc) an oxazolidinyl group optionally substituted by 1 to 3 oxo groups,
(dd) an imidazolidinyl group optionally substituted by 1 to 3 substituents selected from
  (i) an oxo group, and
  (ii) a $C_{1-6}$ alkyl group (e.g., methyl),
(ee) a 1,1-dioxido-1,2-thiazolidinyl group,
(ff) a dihydroisoindolyl group optionally substituted by 1 to 3 oxo groups,
(gg) a 5-azaspiro[2.4]heptyl group optionally substituted by 1 to 3 oxo groups,
(hh) an oxazolylcarbonylamino group,
(ii) an imidazolylcarbonylamino group optionally substituted by 1 to 3 $C_{1-6}$ alkyl groups (e.g., methyl),
(jj) a pyrazolylcarbonylamino group optionally substituted by 1 to 3 $C_{1-6}$ alkyl groups (e.g., methyl),
(kk) a pyridylcarbonylamino group,
(ll) an oxetanylcarbonylamino group optionally substituted by 1 to 3 substituents selected from
  (i) a $C_{1-6}$ alkyl group (e.g., methyl, ethyl), and
  (ii) a phenyl group,
(mm) a tetrahydrofurylcarbonylamino group,
(nn) a tetrahydropyranylcarbonylamino group,
(oo) an azetidinylcarbonyloxy group,
(pp) a pyrrolidinylcarbonyloxy group, and
(qq) a piperidylcarbonyloxy group,
(2) a cyclopropyl group optionally substituted by 1 to 3 substituents selected from
  (a) a mono- or di-$C_{1-6}$ alkyl-carbamoyl group (e.g., ethylcarbamoyl) optionally substituted by 1 to 3 halogen atoms (e.g., a fluorine atom), and
  (b) a phenyl group optionally substituted by 1 to 3 halogen atoms (e.g., a fluorine atom),
(3) a phenyl group optionally substituted by 1 to 3 substituents selected from
  (a) a halogen atom (e.g., a fluorine atom, a chlorine atom, a bromine atom),
  (b) a cyano group,
  (c) an optionally halogenated $C_{1-6}$ alkyl group (e.g., trifluoromethyl, difluoromethyl),
  (d) an optionally halogenated $C_{1-6}$ alkoxy group (e.g., methoxy, ethoxy, difluoromethoxy, trifluoromethoxy, difluoroethoxy),
  (e) a $C_{1-6}$ alkylsulfonyl group (e.g., methylsulfonyl),
  (f) a phenyl group optionally substituted by 1 to 3 substituents selected from
    (i) a cyano group,
    (ii) an optionally halogenated $C_{1-6}$ alkyl group (e.g., methyl, trifluoromethyl, difluoromethyl),
    (iii) a $C_{1-6}$ alkoxy group (e.g., methoxy, ethoxy) optionally substituted by 1 to 3 substituents selected from a halogen atom (e.g., a fluorine atom), a $C_{1-6}$ alkoxy group (e.g., methoxy) and a cyano group,
    (iv) a $C_{1-6}$ alkylsulfonyl group (e.g., methylsulfonyl),
    (v) a halogen atom (e.g., a fluorine atom, a chlorine atom),
    (vi) a $C_{3-10}$ cycloalkyl group (e.g., cyclopropyl) optionally substituted by 1 to 3 cyano groups, and
    (vii) a pyrrolidinylcarbonyl group, (g) a benzyl group,
(h) a pyrazolyl group optionally substituted by 1 to 3 substituents selected from
  (i) a halogen atom (e.g., a fluorine atom, a chlorine atom, a bromine atom),
  (ii) a $C_{1-6}$ alkyl group (e.g., methyl, ethyl) optionally substituted by 1 to 3 substituents selected from a halogen atom (e.g., a fluorine atom) and a pyridyl group,
  (iii) a $C_{3-10}$ cycloalkyl group (e.g., cyclopropyl), and
  (iv) a tetrahydropyranyl group,
(i) a pyridyl group optionally substituted by 1 to 3 substituents selected from
  (i) a halogen atom (e.g., a fluorine atom, a chlorine atom),
  (ii) an optionally halogenated $C_{1-6}$ alkyl group (e.g., ethyl, trifluoromethyl),
  (iii) a $C_{1-6}$ alkoxy group (e.g., methoxy, ethoxy, isopropoxy), and
  (iv) a $C_{1-6}$ alkylsulfonyl group (e.g., methylsulfonyl),
(j) a pyrimidinyl group optionally substituted by 1 to 3 optionally halogenated $C_{1-6}$ alkoxy groups (e.g., trifluoroethoxy),
(k) a furopyridyl group (e.g., furo[2,3-b]pyridyl),
(l) an imidazopyridyl group (e.g., imidazo[1,2-a]pyridyl) optionally substituted by 1 to 3 $C_{1-6}$ alkyl groups (e.g., methyl),
(m) a pyrrolidinyl group optionally substituted by 1 to 3 oxo groups,
(n) a dihydrobenzofuryl group, and
(o) a 4,4,5,5-tetramethyl-1,3,2-dioxaborolan-2-yl group,
(4) a pyridyl group optionally substituted by 1 to 3 substituents selected from
(a) a halogen atom (e.g., a fluorine atom, a chlorine atom),
(b) an optionally halogenated $C_{1-6}$ alkyl group (e.g., trifluoromethyl),
(c) a phenyl group optionally substituted by 1 to 3 cyano groups, and
(d) a pyrazolyl group optionally substituted by 1 to 3 optionally halogenated $C_{1-6}$ alkyl groups (e.g., difluoromethyl),
(5) an isoxazolyl group optionally substituted by 1 to 3 substituents selected from
(a) a $C_{3-10}$ cycloalkyl group (e.g., cyclopropyl), and
(b) a $C_{1-6}$ alkyl group (e.g., methyl),
(6) a pyrazolyl group optionally substituted by 1 to 3 substituents selected from
(a) a $C_{1-6}$ alkyl group (e.g., methyl),
(b) a halogen atom (e.g., a bromine atom),
(c) a phenyl group optionally substituted by 1 to 3 substituents selected from
  (i) a cyano group,
  (ii) a halogen atom (e.g., a fluorine atom, a chlorine atom), and
  (iii) a $C_{1-6}$ alkoxy group (e.g., methoxy),
(d) a $C_{3-10}$ cycloalkyl group (e.g., cyclohexyl) optionally substituted by 1 to 3 halogen atoms (e.g., a fluorine atom),
(e) a $C_{4-10}$ cycloalkenyl group (e.g., cyclohexenyl) optionally substituted by 1 to 3 halogen atoms (e.g., a fluorine atom),
(f) a pyridyl group optionally substituted by 1 to 3 halogen atoms (e.g., a fluorine atom),
(g) a pyrazolyl group optionally substituted by 1 to 3 $C_{1-6}$ alkyl groups (e.g., methyl),
(h) a pyrazolopyridyl group (e.g., pyrazolo[1,5-a]pyridyl),
(i) a tetrahydropyranyl group, and
(j) a dihydropyranyl group,
(7) a pyrrolyl group optionally substituted by 1 to 3 $C_{1-6}$ alkyl groups (e.g., methyl),
(8) a thiazolyl group,
(9) a thienyl group optionally substituted by 1 to 3 halogen atoms (e.g., a chlorine atom),
(10) a pyrazolopyridyl group (e.g., pyrazolo[1,5-a]pyridyl),
(11) a tetrahydropyranyl group optionally substituted by 1 to 3 substituents selected from
(a) an amino group,
(b) a $C_{1-6}$ alkylamino group (e.g., ethylamino, propylamino, butylamino) optionally substituted by 1 to 7 halogen atoms (e.g., a fluorine atom),
(c) a $C_{1-6}$ alkyl-carbonylamino group (e.g., propanoylamino, butanoylamino, pivaloylamino) optionally substituted by 1 to 5 halogen atoms (e.g., a fluorine atom),
(d) a $C_{1-6}$ alkoxy-carbonylamino group (e.g., tert-butoxycarbonylamino) optionally substituted by 1 to 3 halogen atoms (e.g., a fluorine atom),
(e) a $C_{3-10}$ cycloalkyl-carbonylamino group (e.g., cyclopropylcarbonylamino, cyclobutylcarbonylamino) optionally substituted by 1 to 3 optionally halogenated $C_{1-6}$ alkyl groups (e.g., trifluoromethyl),
(f) a phenylcarbonylamino group optionally substituted by 1 to 3 halogen atoms (e.g., a chlorine atom),
(g) a pyrrolidinyl group optionally substituted by 1 to 3 oxo groups,
(h) a piperidyl group optionally substituted by 1 to 3 oxo groups, and
(i) a benzyl group,
(12) a piperidyl group optionally substituted by 1 to 3 substituents selected from
(a) a $C_{1-6}$ alkyl-carbonyl group (e.g., acetyl),
(b) a $C_{1-6}$ alkoxy-carbonyl group (e.g., methoxycarbonyl, ethoxycarbonyl, isopropoxycarbonyl, tert-butoxycarbonyl),
(c) a $C_{3-10}$ cycloalkyl-carbonyl group (e.g., cyclopropylcarbonyl),
(d) a $C_{3-10}$ cycloalkylsulfonyl group (e.g., cyclopropylsulfonyl), and
(e) a phenyl group,
(13) a morpholinyl group optionally substituted by 1 to 3 substituents selected from
(a) an optionally halogenated $C_{1-6}$ alkyl group (e.g., tetrafluoropropyl, pentafluoropropyl, heptafluorobutyl),
(b) a $C_{1-6}$ alkoxy-carbonyl group (e.g., methoxycarbonyl, isopropoxycarbonyl, tert-butoxycarbonyl),
(c) a $C_{3-10}$ cycloalkyl-carbonyl group (e.g., cyclopropylcarbonyl, cyclopentylcarbonyl),
(d) a $C_{3-10}$ cycloalkylsulfonyl group (e.g., cyclopropylsulfonyl),
(e) a phenylsulfonyl group optionally substituted by 1 to 3 substituents selected from
  (i) a $C_{1-6}$ alkyl group (e.g., methyl), and
  (ii) a halogen atom (e.g., a fluorine atom), and
(f) a $C_{1-6}$ alkylsulfonyl group (e.g., ethylsulfonyl) optionally substituted by 1 to 3 halogen atoms (e.g., a fluorine atom),
(14) a pyrrolidinyl group optionally substituted by 1 to 3 substituents selected from
(a) a halogen atom (e.g., a fluorine atom),
(b) an oxo group,
(c) a $C_{1-6}$ alkoxy-carbonyl group (e.g., tert-butoxycarbonyl),
(d) a benzoyl group, (e) a $C_{3-10}$ cycloalkyl-carbonyl group (e.g., cyclopropylcarbonyl),
(f) a $C_{1-6}$ alkylsulfonyl group (e.g., ethylsulfonyl) optionally substituted by 1 to 3 halogen atoms (e.g., a fluorine atom),
(g) a phenylsulfonyl group optionally substituted by 1 to 3 halogen atoms (e.g., a fluorine atom), and
(h) a $C_{3-10}$ cycloalkylsulfonyl group (e.g., cyclopropylsulfonyl), or
(15) a $C_{1-6}$ alkyl group (e.g., ethyl) optionally substituted by 1 to 3 substituents selected from
(a) a phenyloxy group, and
(b) a benzyloxy group.

In this embodiment, $R^1$ is even more preferably
(1) a cyclohexyl group optionally substituted by 1 to 3 substituents selected from
(a) a $C_{1-6}$ alkyl-carbonylamino group (e.g., acetylamino, propanoylamino) optionally substituted by 1 to 5 halogen atoms (e.g., a fluorine atom),
(b) a $C_{1-6}$ alkoxy-carbonylamino group (e.g., methoxycarbonylamino, tert-butoxycarbonylamino) optionally substituted by 1 to 3 halogen atoms (e.g., a fluorine atom), and
(c) a $C_{3-10}$ cycloalkyl-carbonylamino group (e.g., cyclopropylcarbonylamino) optionally substituted by 1 to 3 halogen atoms (e.g., a fluorine atom),
(2) a tetrahydropyranyl group optionally substituted by 1 to 3 $C_{1-6}$ alkylamino groups (e.g., ethylamino) optionally substituted by 1 to 3 halogen atoms (e.g., a fluorine atom), or
(3) a pyrazolyl group optionally substituted by 1 to 3 substituents selected from
(a) a $C_{1-6}$ alkyl group (e.g., methyl), and
(b) a phenyl group.

As another embodiment, $R^1$ is even more preferably a cyclohexyl group optionally substituted by 1 to 3 substituents selected from
(a) a halogen atom (e.g., a fluorine atom),
(b) a $C_{1-6}$ alkyl-carbonylamino group (e.g., acetylamino, propanoylamino) optionally substituted by 1 to 5 halogen atoms (e.g., a fluorine atom),
(c) a $C_{1-6}$ alkoxy-carbonylamino group (e.g., tert-butoxycarbonylamino) optionally substituted by 1 to 3 halogen atoms (e.g., a fluorine atom), and
(d) a $C_{3-10}$ cycloalkyl-carbonylamino group (e.g., cyclopropylcarbonylamino) optionally substituted by 1 to 3 halogen atoms (e.g., a fluorine atom).

$R^2$ and $R^3$ are each independently a hydrogen atom, a halogen atom or an optionally substituted $C_{1-6}$ alkyl group, or $R^2$ and $R^3$ in combination form an oxo group, or $R^2$ and $R^3$ are bonded to each other to form an optionally substituted ring together with the adjacent carbon atom.

The "$C_{1-6}$ alkyl group" of the "optionally substituted $C_{1-6}$ alkyl group" represented by $R^2$ or $R^3$ is optionally substituted, at substitutable position(s), by substituent(s) selected from the above-mentioned Substituent Group A. The number of the substituents is, for example, 1 to 3. When the number of the substituents is 2 or more, the respective substituents may be the same or different.

Examples of the "ring" of the "optionally substituted ring" formed by $R^2$ or $R^3$ bonded to each other together with the adjacent carbon atom include a hydrocarbon ring and a heterocycle.

The "ring" of the "optionally substituted ring" formed by $R^2$ or $R^3$ bonded to each other together with the adjacent carbon atom is optionally substituted, at substitutable position(s), by substituent(s) selected from the above-mentioned Substituent Group A. The number of the substituents is, for example, 1 to 3. When the number of the substituents is 2 or more, the respective substituents may be the same or different.

$R^2$ and $R^3$ are preferably both hydrogen atoms, or $R^2$ and $R^3$ in combination form an oxo group.

$R^2$ and $R^3$ are particularly preferably both hydrogen atoms.

$R^4$ and $R^5$ are each independently a hydrogen atom or a halogen atom $R^4$ and $R^5$ are preferably both hydrogen atoms.

X is $CR^6$ or N.

$R^6$ is a hydrogen atom or a halogen atom.

X is preferably CH, CF or N.

X is more preferably CH or N.

L is a bond or an optionally substituted $C_{1-6}$ alkylene group.

The "$C_{1-6}$ alkylene group" of the "optionally substituted $C_{1-6}$ alkylene group" represented by L is optionally substituted, at substitutable position(s), by substituent(s) selected from the above-mentioned Substituent Group A. The number of the substituents is, for example, 1 to 3. When the number of the substituents is 2 or more, the respective substituents may be the same or different.

L is preferably a bond, —$CH_2$— or —$CH(CH_3)$—.

L is more preferably a bond, or —$CH_2$—.

L is particularly preferably —$CH_2$—.

As another embodiment, L is preferably
(1) a bond, or
(2) a $C_{1-6}$ alkylene group (e.g., —$CH_2$—, —$CH(CH_3)$—, —$CH_2CH_2$—) optionally substituted by 1 to 3 $C_{6-14}$ aryl groups (e.g., phenyl).

In this embodiment, L is more preferably
(1) a bond, or
(2) a $C_{1-6}$ alkylene group (e.g., —$CH_2$—, —$CH(CH_3)$—, —$CH_2CH_2$—) optionally substituted by 1 to 3 phenyl groups.

In this embodiment, L is particularly preferably a bond.

Preferable combination of $R^1$ and L are as follows.
(a) a combination of that L is a bond, and $R^1$ is an optionally substituted cyclohexyl group or an optionally substituted 6-membered monocyclic non-aromatic heterocyclic group (e.g., tetrahydropyranyl, piperidyl);
(b) a combination of that L is a bond, and $R^1$ is an optionally substituted phenyl group or an optionally substituted 5- or 6-membered monocyclic aromatic heterocyclic group (e.g., pyrazolyl);
(c) a combination of that L is —$CH_2$— or —$CH(CH_3)$—, and $R^1$ is an optionally substituted phenyl group or an optionally substituted 5- or 6-membered monocyclic aromatic heterocyclic group (e.g., pyridyl, isoxazolyl); or
(d) a combination of that L is —$CH_2$—, and $R^1$ is an optionally substituted 5- or 6-membered monocyclic nitrogen-containing non-aromatic heterocyclic group (e.g., piperidyl, morpholinyl).

In (a) of the preferable combination of $R^1$ and L, the combination is preferably
L is a bond, and
$R^1$ is
(1) a cyclohexyl group optionally substituted by 1 to 3 substituents selected from
(a) an amino group,
(b) a $C_{1-6}$ alkoxy group (e.g., butoxy),
(c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
(i) a halogen atom (e.g., a fluorine atom),
(ii) a cyano group,
(iii) a hydroxy group,
(iv) a $C_{1-6}$ alkoxy group (e.g., methoxy),
(v) a $C_{3-10}$ cycloalkyl group (e.g., cyclopropyl, cyclobutyl, cyclopentyl) optionally substituted by 1 to 3 substituents selected from a hydroxy group and a cyano group, and
(vi) a $C_{6-14}$ aryl group (e.g., phenyl),
(d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(e) a mono- or di-$C_{1-6}$ alkyl-carbamoyloxy group (e.g., methylcarbamoyloxy),
(f) a $C_{3-10}$ cycloalkyl-carbonylamino group (the $C_{3-10}$ cycloalkyl in the $C_{3-10}$ cycloalkyl-carbonylamino group may be a bridged group or a spiro ring group. e.g., cyclopropylcarbonylamino, cyclobutylcarbonylamino, cyclohexylcarbonylamino, spiro[2.3]hexylcarbonylamino, spiro[3.3]heptylcarbonylamino, bicyclo[1.1.1]pentylcarbonylamino) optionally substituted by 1 to 3 substituents selected from
(i) a halogen atom (e.g., a fluorine atom),
(ii) a cyano group,
(iii) a hydroxy group,
(iv) an optionally halogenated $C_{1-6}$ alkyl group (e.g., methyl, difluoromethyl, trifluoromethyl),
(v) a $C_{1-6}$ alkoxy group (e.g., methoxy), and
(vi) a $C_{6-14}$ aryl group (e.g., phenyl) optionally substituted by 1 to 3 halogen atoms (e.g., a fluorine atom),
(g) a $C_{3-10}$ cycloalkoxy-carbonylamino group (e.g., cyclopropoxycarbonylamino),
(h) a $C_{6-14}$ aryl-carbonylamino group (e.g., phenylcarbonylamino) optionally substituted by 1 to 3 halogen atoms (e.g., a chlorine atom),
(i) a $C_{7-16}$ aralkyl-oxycarbonylamino group (e.g., benzyloxycarbonylamino),
(j) a 5- to 14-membered aromatic heterocyclic group (preferably a 5- or 6-membered monocyclic aromatic heterocyclic group (e.g., pyrazolyl, triazolyl) or a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl, ethyl),
(k) a 3- to 14-membered non-aromatic heterocyclic group (preferably a 3- to 8-membered monocyclic non-aromatic heterocyclic group (e.g., pyrrolidinyl, piperidyl, morpholinyl, tetrahydrooxazinyl, hexahydropyrimidinyl, oxazolidinyl, imidazolidinyl, 1,1-dioxido-1,2-thiazolidinyl) or a 9- to 14-membered fused polycyclic (preferably bi- or tri-cyclic) non-aromatic heterocyclic group (e.g., dihydroisoindolyl, 5-azaspiro[2.4]heptyl)) optionally substituted by 1 to 3 substituents selected from
(i) an oxo group, and
(ii) a $C_{1-6}$ alkyl group (e.g., methyl),
(l) a 5- to 14-membered aromatic heterocyclylcarbonylamino group (preferably a 5- or 6-membered monocyclic aromatic heterocyclylcarbonylamino group (e.g., oxazolylcarbonylamino, imidazolylcarbonylamino, pyrazolylcarbonylamino, pyridylcarbonylamino)) optionally substituted by 1 to 3 $C_{1-6}$ alkyl groups (e.g., methyl), and (m) a 3- to 14-membered non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino, tetrahydropyranylcarbonylamino)) optionally substituted by 1 to 3 substituents selected from
(i) a $C_{1-6}$ alkyl group (e.g., methyl, ethyl), and
(ii) a $C_{6-14}$ aryl group (e.g., phenyl),
(2) a tetrahydropyranyl group optionally substituted by 1 to 3 substituents selected from
(a) a $C_{1-6}$ alkyl-carbonylamino group (e.g., propanoylamino, pivaloylamino) optionally substituted by 1 to 5 halogen atoms (e.g., a fluorine atom),
(b) a $C_{1-6}$ alkoxy-carbonylamino group (e.g., tert-butoxycarbonylamino),
(c) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl),
(d) a $C_{6-14}$ aryl-carbonylamino group (e.g., phenylcarbonylamino) optionally substituted by 1 to 3 halogen atoms (e.g., a chlorine atom), and
(e) a 3- to 14-membered non-aromatic heterocyclic group (preferably a 3- to 8-membered monocyclic non-aromatic heterocyclic group (e.g., pyrrolidinyl, piperidyl)) optionally substituted by 1 to 3 oxo groups, or
(3) a piperidyl group optionally substituted by 1 to 3 substituents selected from
(a) a $C_{1-6}$ alkyl-carbonyl group (e.g., acetyl),
(b) a $C_{1-6}$ alkoxy-carbonyl group (e.g., methoxycarbonyl, ethoxycarbonyl, tert-butoxycarbonyl), and
(c) a $C_{6-14}$ aryl group (e.g., phenyl).
In (a) of the preferable combination of $R^1$ and L, the combination is more preferably
L is a bond, and
$R^1$ is
(1) a cyclohexyl group optionally substituted by 1 to 3 substituents selected from
(a) an amino group,
(b) a $C_{1-6}$ alkoxy group (e.g., butoxy),
(c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
(i) a halogen atom (e.g., a fluorine atom),
(ii) a cyano group,
(iii) a hydroxy group,
(iv) a $C_{1-6}$ alkoxy group (e.g., methoxy),
(v) a $C_{3-10}$ cycloalkyl group (e.g., cyclopropyl, cyclobutyl, cyclopentyl) optionally substituted by 1 to 3 substituents selected from a hydroxy group and a cyano group, and
(vi) a phenyl group,
(d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(e) a mono- or di-$C_{1-6}$ alkyl-carbamoyloxy group (e.g., methylcarbamoyloxy),
(f) a $C_{3-10}$ cycloalkyl-carbonylamino group (e.g., cyclopropylcarbonylamino, cyclobutylcarbonylamino, cyclohexylcarbonylamino) optionally substituted by 1 to 3 substituents selected from
(i) a halogen atom (e.g., a fluorine atom),
(ii) a cyano group,
(iii) a hydroxy group, (iv) an optionally halogenated $C_{1-6}$ alkyl group (e.g., methyl, difluoromethyl, trifluoromethyl),
(v) a $C_{1-6}$ alkoxy group (e.g., methoxy), and
(vi) a phenyl group optionally substituted by 1 to 3 halogen atoms (e.g., a fluorine atom),
(g) a spiro[2.3]hexylcarbonylamino group,
(h) a spiro[3.3]heptylcarbonylamino group,
(i) a bicyclo[1.1.1]pentylcarbonylamino group optionally substituted by 1 to 3 optionally halogenated $C_{1-6}$ alkyl groups (e.g., trifluoromethyl),
(j) a $C_{3-10}$ cycloalkoxy-carbonylamino group (e.g., cyclopropoxycarbonylamino),
(k) a $C_{6-14}$ aryl-carbonylamino group (e.g., phenylcarbonylamino) optionally substituted by 1 to 3 halogen atoms (e.g., a chlorine atom),
(l) a benzyloxycarbonylamino group,
(m) a pyrazolyl group optionally substituted by 1 to 3 $C_{1-6}$ alkyl groups (e.g., methyl, ethyl),
(n) a triazolyl group,
(o) an indazolyl group
(p) a pyrrolidinyl group optionally substituted by 1 to 3 oxo groups,
(q) a piperidyl group optionally substituted by 1 to 3 oxo groups,
(r) a morpholinyl group optionally substituted by 1 to 3 oxo groups,
(s) a tetrahydrooxazinyl group optionally substituted by 1 to 3 oxo groups,
(t) a hexahydropyrimidinyl group optionally substituted by 1 to 3 oxo groups,
(u) an oxazolidinyl group optionally substituted by 1 to 3 oxo groups,
(v) an imidazolidinyl group optionally substituted by 1 to 3 substituents selected from
  (i) an oxo group, and
  (ii) a $C_{1-6}$ alkyl group (e.g., methyl),
(w) a 1,1-dioxido-1,2-thiazolidinyl group,
(x) a dihydroisoindolyl group optionally substituted by 1 to 3 oxo groups,
(y) a 5-azaspiro[2.4]heptyl group optionally substituted by 1 to 3 oxo groups,
(z) an oxazolylcarbonylamino group,
(aa) an imidazolylcarbonylamino group optionally substituted by 1 to 3 $C_{1-6}$ alkyl groups (e.g., methyl),
(bb) a pyrazolylcarbonylamino group optionally substituted by 1 to 3 $C_{1-6}$ alkyl groups (e.g., methyl),
(cc) a pyridylcarbonylamino group,
(dd) an oxetanylcarbonylamino group optionally substituted by 1 to 3 substituents selected from
  (i) a $C_{1-6}$ alkyl group (e.g., methyl, ethyl), and
  (ii) a phenyl group,
(ee) a tetrahydrofurylcarbonylamino group, and
(ff) a tetrahydropyranylcarbonylamino group,
(2) a tetrahydropyranyl group optionally substituted by 1 to 3 substituents selected from
(a) a $C_{1-6}$ alkyl-carbonylamino group (e.g., propanoylamino, pivaloylamino) optionally substituted by 1 to 5 halogen atoms (e.g., a fluorine atom),
(b) a $C_{1-6}$ alkoxy-carbonylamino group (e.g., tert-butoxycarbonylamino),
(c) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl),
(d) a phenylcarbonylamino group optionally substituted by 1 to 3 halogen atoms (e.g., a chlorine atom),
(e) a pyrrolidinyl group optionally substituted by 1 to 3 oxo groups, and
(f) a piperidyl group optionally substituted by 1 to 3 oxo groups, or
(3) a piperidyl group optionally substituted by 1 to 3 substituents selected from
(a) a $C_{1-6}$ alkyl-carbonyl group (e.g., acetyl),
(b) a $C_{1-6}$ alkoxy-carbonyl group (e.g., methoxycarbonyl, ethoxycarbonyl, tert-butoxycarbonyl), and
(c) a phenyl group.

In (a) of the preferable combination of $R^1$ and L, the combination is further more preferably
L is a bond, and
$R^1$ is
(1) a cyclohexyl group optionally substituted by 1 to 3 substituents selected from
  (a) a $C_{1-6}$ alkyl-carbonylamino group (e.g., acetylamino, propanoylamino) optionally substituted by 1 to 3 halogen atoms (e.g., a fluorine atom),
  (b) a $C_{1-6}$ alkoxy-carbonylamino group (e.g., methoxycarbonylamino), and
  (c) a $C_{3-10}$ cycloalkyl-carbonylamino group (e.g., cyclopropylcarbonylamino) optionally substituted by 1 to 3 halogen atoms (e.g., a fluorine atom),
(2) a tetrahydropyranyl group optionally substituted by 1 to 3 $C_{1-6}$ alkoxy-carbonylamino groups (e.g., tert-butoxycarbonylamino), or
(3) a piperidyl group optionally substituted by 1 to 3 substituents selected from
  (a) a $C_{1-6}$ alkoxy-carbonyl group (e.g., methoxycarbonyl), and
  (b) a phenyl group.

In (a) of the preferable combination of $R^1$ and L, the combination is particularly preferably
L is a bond, and
$R^1$ is a cyclohexyl group optionally substituted by 1 to 3 substituents selected from
  (a) a $C_{1-6}$ alkyl-carbonylamino group (e.g., acetylamino, propanoylamino) optionally substituted by 1 to 3 halogen atoms (e.g., a fluorine atom),
  (b) a $C_{1-6}$ alkoxy-carbonylamino group (e.g., methoxycarbonylamino), and
  (c) a $C_{3-10}$ cycloalkyl-carbonylamino group (e.g., cyclopropylcarbonylamino) optionally substituted by 1 to 3 halogen atoms (e.g., a fluorine atom).

In (b) of the preferable combination of $R^1$ and L, the combination is preferably
L is a bond, and
$R^1$ is
(1) a phenyl group optionally substituted by 1 to 3 substituents selected from
  (a) a halogen atom (e.g., a bromine atom),
  (b) a $C_{6-14}$ aryl group (e.g., phenyl) optionally substituted by 1 to 3 substituents selected from
    (i) a cyano group,
    (ii) an optionally halogenated $C_{1-6}$ alkyl group (e.g., trifluoromethyl),
    (iii) a $C_{1-6}$ alkoxy group (e.g., methoxy), and
    (iv) a $C_{1-6}$ alkylsulfonyl group (e.g., methylsulfonyl),
  (c) a 5- to 14-membered aromatic heterocyclic group (preferably a 5- or 6-membered monocyclic aromatic heterocyclic group (e.g., pyrazolyl)) optionally substituted by 1 to 3 $C_{1-6}$ alkyl groups (e.g., methyl),
  (d) a 3- to 14-membered non-aromatic heterocyclic group (preferably a 3- to 8-membered monocyclic non-aromatic heterocyclic group (e.g., pyrrolidinyl)) optionally substituted by 1 to 3 oxo groups, and (e) a 4,4,5,5-tetramethyl-1,3,2-dioxaborolan-2-yl group, or
(2) a pyrazolyl group optionally substituted by 1 to 3 substituents selected from
   (a) a $C_{1-6}$ alkyl group (e.g., methyl), and
   (b) a $C_{6-14}$ aryl group (e.g., phenyl).

In (b) of the preferable combination of $R^1$ and L, the combination is more preferably
L is a bond, and
$R^1$ is
(1) a phenyl group optionally substituted by 1 to 3 substituents selected from
   (a) a halogen atom (e.g., a bromine atom),
   (b) a phenyl group optionally substituted by 1 to 3 substituents selected from
      (i) a cyano group,
      (ii) an optionally halogenated $C_{1-6}$ alkyl group (e.g., trifluoromethyl),
      (iii) a $C_{1-6}$ alkoxy group (e.g., methoxy), and
      (iv) a $C_{1-6}$ alkylsulfonyl group (e.g., methylsulfonyl),
   (c) a pyrazolyl group optionally substituted by 1 to 3 $C_{1-6}$ alkyl groups (e.g., methyl),
   (d) a pyrrolidinyl group optionally substituted by 1 to 3 oxo groups, and
   (e) a 4,4,5,5-tetramethyl-1,3,2-dioxaborolan-2-yl group, or
(2) a pyrazolyl group optionally substituted by 1 to 3 substituents selected from
   (a) a $C_{1-6}$ alkyl group (e.g., methyl), and
   (b) a phenyl group.

In (b) of the preferable combination of $R^1$ and L, the combination is particularly preferably
L is a bond, and
$R^1$ is
(1) a phenyl group optionally substituted by 1 to 3 substituents selected from
   (a) a phenyl group optionally substituted by 1 to 3 cyano groups,
   (b) a pyrazolyl group optionally substituted by 1 to 3 $C_{1-6}$ alkyl groups (e.g., methyl), and
   (c) a $C_{1-6}$ alkyl group (e.g., methyl), or
(2) a pyrazolyl group optionally substituted by 1 to 3 substituents selected from
   (a) a $C_{1-6}$ alkyl group (e.g., methyl), and
   (b) a phenyl group.

In (c) of the preferable combination of $R^1$ and L, the combination is preferably
L is —$CH_2$— or —$CH(CH_3)$—, and
$R^1$ is
(1) a phenyl group optionally substituted by 1 to 3 substituents selected from
   (a) a halogen atom (e.g., a fluorine atom),
   (b) an optionally halogenated $C_{1-6}$ alkyl group (e.g., trifluoromethyl), and
   (c) a $C_{1-6}$ alkylsulfonyl group (e.g., methylsulfonyl),
(2) a pyridyl group optionally substituted by 1 to 3 substituents selected from
   (a) a halogen atom (e.g., a fluorine atom, a chlorine atom), and
   (b) an optionally halogenated $C_{1-6}$ alkyl group (e.g., trifluoromethyl), or
(3) an isoxazolyl group optionally substituted by 1 to 3 $C_{3-10}$ cycloalkyl groups (e.g., cyclopropyl).

In (c) of the preferable combination of $R^1$ and L, the combination is particularly preferably
L is —$CH_2$— or —$CH(CH_3)$—, and
$R^1$ is
(1) a phenyl group optionally substituted by 1 to 3 halogen atoms (e.g., a fluorine atom),
(2) a pyridyl group optionally substituted by 1 to 3 optionally halogenated $C_{1-6}$ alkyl groups (e.g., trifluoromethyl), or
(3) an isoxazolyl group optionally substituted by 1 to 3 $C_{3-10}$ cycloalkyl groups (e.g., cyclopropyl).

In (d) of the preferable combination of $R^1$ and L, the combination is preferably
L is —$CH_2$—, and
$R^1$ is
(1) a piperidyl group optionally substituted by 1 to 3 substituents selected from
   (a) a $C_{1-6}$ alkoxy-carbonyl group (e.g., isopropoxycarbonyl, tert-butoxycarbonyl),
   (b) a $C_{3-10}$ cycloalkyl-carbonyl group (e.g., cyclopropylcarbonyl), and
   (c) a $C_{3-10}$ cycloalkylsulfonyl group (e.g., cyclopropylsulfonyl), or
(2) a morpholinyl group optionally substituted by 1 to 3 substituents selected from
   (a) a $C_{1-6}$ alkoxy-carbonyl group (e.g., methoxycarbonyl, isopropoxycarbonyl, tert-butoxycarbonyl),
   (b) a $C_{3-10}$ cycloalkyl-carbonyl group (e.g., cyclopropylcarbonyl, cyclopentylcarbonyl),
   (c) a $C_{3-10}$ cycloalkylsulfonyl group (e.g., cyclopropylsulfonyl), and
   (d) a $C_{6-14}$ arylsulfonyl group (e.g., phenylsulfonyl) optionally substituted by 1 to 3 $C_{1-6}$ alkyl groups (e.g., methyl).

In (d) of the preferable combination of $R^1$ and L, the combination is more preferably
L is —$CH_2$—, and
$R^1$ is
(1) a piperidyl group optionally substituted by 1 to 3 substituents selected from
   (a) a $C_{1-6}$ alkoxy-carbonyl group (e.g., isopropoxycarbonyl, tert-butoxycarbonyl),
   (b) a $C_{3-10}$ cycloalkyl-carbonyl group (e.g., cyclopropylcarbonyl), and
   (c) a $C_{3-10}$ cycloalkylsulfonyl group (e.g., cyclopropylsulfonyl), or
(2) a morpholinyl group optionally substituted by 1 to 3 substituents selected from
   (a) a $C_{1-6}$ alkoxy-carbonyl group (e.g., methoxycarbonyl, isopropoxycarbonyl, tert-butoxycarbonyl),
   (b) a $C_{3-10}$ cycloalkyl-carbonyl group (e.g., cyclopropylcarbonyl, cyclopentylcarbonyl),
   (c) a $C_{3-10}$ cycloalkylsulfonyl group (e.g., cyclopropylsulfonyl), and
   (d) a phenylsulfonyl group optionally substituted by 1 to 3 $C_{1-6}$ alkyl groups (e.g., methyl).

In (d) of the preferable combination of $R^1$ and L, the combination is particularly preferably
L is —$CH_2$—, and
$R^1$ is
(1) a piperidyl group optionally substituted by 1 to 3 $C_{3-10}$ cycloalkylsulfonyl groups (e.g., cyclopropylsulfonyl), or
(2) a morpholinyl group optionally substituted by 1 to 3 substituents selected from
   (a) a $C_{3-10}$ cycloalkyl-carbonyl group (e.g., cyclopentylcarbonyl),
   (b) a $C_{3-10}$ cycloalkylsulfonyl group (e.g., cyclopropylsulfonyl), and
   (c) a phenylsulfonyl group optionally substituted by 1 to 3 $C_{1-6}$ alkyl groups (e.g., methyl).

Another embodiment of combination of $R^1$ and L are as follows.

L is a bond, and
$R^1$ is
(1) a cyclohexyl group optionally substituted by 1 to 3 substituents selected from
  (a) a $C_{1-6}$ alkyl-carbonylamino group (e.g., acetylamino, propanoylamino) optionally substituted by 1 to 5 halogen atoms (e.g., a fluorine atom),
  (b) a $C_{1-6}$ alkoxy-carbonylamino group (e.g., methoxycarbonylamino, tert-butoxycarbonylamino) optionally substituted by 1 to 3 halogen atoms (e.g., a fluorine atom), and
  (c) a $C_{3-10}$ cycloalkyl-carbonylamino group (e.g., cyclopropylcarbonylamino) optionally substituted by 1 to 3 halogen atoms (e.g., a fluorine atom),
(2) a tetrahydropyranyl group optionally substituted by 1 to 3 $C_{1-6}$ alkylamino groups (e.g., ethylamino) optionally substituted by 1 to 3 halogen atoms (e.g., a fluorine atom), or
(3) a pyrazolyl group optionally substituted by 1 to 3 substituents selected from
  (a) a $C_{1-6}$ alkyl group (e.g., methyl), and
  (b) a phenyl group.

Preferable examples of compound (I) include the following compounds.

[Compound A-1]
Compound (I) wherein
$R^1$ is
(1) an optionally substituted $C_{3-10}$ cycloalkyl group (e.g., cyclopropyl, cyclohexyl),
(2) an optionally substituted $C_{6-14}$ aryl group (e.g., phenyl),
(3) an optionally substituted 5- to 14-membered aromatic heterocyclic group (preferably a 5- or 6-membered monocyclic aromatic heterocyclic group (e.g., pyridyl, isoxazolyl, pyrazolyl)), or
(4) an optionally substituted 3- to 14-membered non-aromatic heterocyclic group (preferably a 3- to 8-membered monocyclic non-aromatic heterocyclic group, more preferably a 5- or 6-membered monocyclic non-aromatic heterocyclic group (including a 6-membered monocyclic non-aromatic heterocyclic group and a 5- or 6-membered monocyclic nitrogen-containing non-aromatic heterocyclic group) (e.g., tetrahydropyranyl, piperidyl, morpholinyl));
$R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom (e.g., a fluorine atom); and
L is a bond or an optionally substituted $C_{1-6}$ alkylene group.

[Compound B-1]
Compound (I) wherein
$R^1$ is
(1) a $C_{3-10}$ cycloalkyl group (e.g., cyclopropyl, cyclohexyl) optionally substituted by 1 to 3 substituents selected from
  (a) an amino group,
  (b) a $C_{1-6}$ alkoxy group (e.g., butoxy),
  (c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
    (i) a halogen atom (e.g., a fluorine atom),
    (ii) a cyano group,
    (iii) a hydroxy group,
    (iv) a $C_{1-6}$ alkoxy group (e.g., methoxy),
    (v) a $C_{3-10}$ cycloalkyl group (e.g., cyclopropyl, cyclobutyl, cyclopentyl) optionally substituted by 1 to 3 substituents selected from a hydroxy group and a cyano group, and
    (vi) a $C_{6-14}$ aryl group (e.g., phenyl),
  (d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
  (e) a mono- or di-$C_{1-6}$ alkyl-carbamoyl group (e.g., ethylcarbamoyl) optionally substituted by 1 to 3 halogen atoms (e.g., a fluorine atom),
  (f) a mono- or di-$C_{1-6}$ alkyl-carbamoyloxy group (e.g., methylcarbamoyloxy),
  (g) a $C_{3-10}$ cycloalkyl-carbonylamino group (the $C_{3-10}$ cycloalkyl in the $C_{3-10}$ cycloalkyl-carbonylamino group may be a bridged group or a spiro ring group. e.g., cyclopropylcarbonylamino, cyclobutylcarbonylamino, cyclohexylcarbonylamino, spiro[2.3]hexylcarbonylamino, spiro[3.3]heptylcarbonylamino, bicyclo[1.1.1]pentylcarbonylamino) optionally substituted by 1 to 3 substituents selected from
    (i) a halogen atom (e.g., a fluorine atom),
    (ii) a cyano group,
    (iii) a hydroxy group,
    (iv) an optionally halogenated $C_{1-6}$ alkyl group (e.g., methyl, difluoromethyl, trifluoromethyl),
    (v) a $C_{1-6}$ alkoxy group (e.g., methoxy), and
    (vi) a $C_{6-14}$ aryl group (e.g., phenyl) optionally substituted by 1 to 3 halogen atoms (e.g., a fluorine atom),
  (h) a $C_{3-10}$ cycloalkoxy-carbonylamino group (e.g., cyclopropoxycarbonylamino),
  (i) a $C_{6-14}$ aryl-carbonylamino group (e.g., phenylcarbonylamino) optionally substituted by 1 to 3 halogen atoms (e.g., a chlorine atom),
  (j) a $C_{7-16}$ aralkyl-oxycarbonylamino group (e.g., benzyloxycarbonylamino),
  (k) a 5- to 14-membered aromatic heterocyclic group (preferably a 5- or 6-membered monocyclic aromatic heterocyclic group (e.g., pyrazolyl, triazolyl) or a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl, ethyl),
  (l) a 3- to 14-membered non-aromatic heterocyclic group (preferably a 3- to 8-membered monocyclic non-aromatic heterocyclic group (e.g., pyrrolidinyl, piperidyl, morpholinyl, tetrahydrooxazinyl, hexahydropyrimidinyl, oxazolidinyl, imidazolidinyl, 1,1-dioxido-1,2-thiazolidinyl) or a 9- to 14-membered fused polycyclic (preferably bi- or tri-cyclic) non-aromatic heterocyclic group (e.g., dihydroisoindolyl, 5-azaspiro[2.4]heptyl)) optionally substituted by 1 to 3 substituents selected from
    (i) an oxo group, and
    (ii) a $C_{1-6}$ alkyl group (e.g., methyl),
  (m) a 5- to 14-membered aromatic heterocyclylcarbonylamino group (preferably a 5- or 6-membered monocyclic aromatic heterocyclylcarbonylamino group (e.g., oxazolylcarbonylamino, imidazolylcarbonylamino, pyrazolylcarbonylamino, pyridylcarbonylamino)) optionally substituted by 1 to 3 $C_{1-6}$ alkyl groups (e.g., methyl), and
  (n) a 3- to 14-membered non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino, tetrahydropyranylcarbonylamino)) optionally substituted by 1 to 3 substituents selected from
(i) a $C_{1-6}$ alkyl group (e.g., methyl, ethyl), and
(ii) a $C_{6-14}$ aryl group (e.g., phenyl),
(2) a $C_{6-14}$ aryl group (e.g., phenyl) optionally substituted by 1 to 3 substituents selected from
(a) a halogen atom (e.g., a fluorine atom, a bromine atom),
(b) an optionally halogenated $C_{1-6}$ alkyl group (e.g., trifluoromethyl),
(c) a $C_{1-6}$ alkylsulfonyl group (e.g., methylsulfonyl),
(d) a $C_{6-14}$ aryl group (e.g., phenyl) optionally substituted by 1 to 3 substituents selected from
(i) a cyano group,
(ii) an optionally halogenated $C_{1-6}$ alkyl group (e.g., trifluoromethyl),
(iii) a $C_{1-6}$ alkoxy group (e.g., methoxy), and
(iv) a $C_{1-6}$ alkylsulfonyl group (e.g., methylsulfonyl),
(e) a 5- to 14-membered aromatic heterocyclic group (preferably a 5- or 6-membered monocyclic aromatic heterocyclic group (e.g., pyrazolyl)) optionally substituted by 1 to 3 $C_{1-6}$ alkyl groups (e.g., methyl),
(f) a 3- to 14-membered non-aromatic heterocyclic group (preferably a 3- to 8-membered monocyclic non-aromatic heterocyclic group (e.g., pyrrolidinyl)) optionally substituted by 1 to 3 oxo groups, and
(g) a 4,4,5,5-tetramethyl-1,3,2-dioxaborolan-2-yl group,
(3) a 5- to 14-membered aromatic heterocyclic group (preferably a 5- or 6-membered monocyclic aromatic heterocyclic group (e.g., pyridyl, isoxazolyl, pyrazolyl)) optionally substituted by 1 to 3 substituents selected from
(a) a halogen atom (e.g., a fluorine atom, a chlorine atom),
(b) an optionally halogenated $C_{1-6}$ alkyl group (e.g., methyl, trifluoromethyl),
(c) a $C_{3-10}$ cycloalkyl group (e.g., cyclopropyl), and
(d) a $C_{6-14}$ aryl group (e.g., phenyl), or
(4) a 3- to 14-membered non-aromatic heterocyclic group (preferably a 3- to 8-membered monocyclic non-aromatic heterocyclic group, more preferably a 5- or 6-membered monocyclic non-aromatic heterocyclic group (including a 6-membered monocyclic non-aromatic heterocyclic group and a 5- or 6-membered monocyclic nitrogen-containing non-aromatic heterocyclic group) (e.g., tetrahydropyranyl, piperidyl, morpholinyl)) optionally substituted by 1 to 3 substituents selected from
(a) a $C_{1-6}$ alkyl-carbonyl group (e.g., acetyl),
(b) a $C_{1-6}$ alkyl-carbonylamino group (e.g., propanoylamino, pivaloylamino) optionally substituted by 1 to 5 halogen atoms (e.g., a fluorine atom),
(c) a $C_{1-6}$ alkoxy-carbonyl group (e.g., methoxycarbonyl, ethoxycarbonyl, isopropoxycarbonyl, tert-butoxycarbonyl),
(d) a $C_{1-6}$ alkoxy-carbonylamino group (e.g., tert-butoxycarbonylamino),
(e) a $C_{3-10}$ cycloalkyl-carbonyl group (e.g., cyclopropylcarbonyl, cyclopentylcarbonyl),
(f) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl),
(g) a $C_{3-10}$ cycloalkylsulfonyl group (e.g., cyclopropylsulfonyl),
(h) a $C_{6-14}$ aryl group (e.g., phenyl),
(i) a $C_{6-14}$ aryl-carbonylamino group (e.g., phenylcarbonylamino) optionally substituted by 1 to 3 halogen atoms (e.g., a chlorine atom),
(j) a $C_{6-14}$ arylsulfonyl group (e.g., phenylsulfonyl) optionally substituted by 1 to 3 $C_{1-6}$ alkyl groups (e.g., methyl), and
(k) a 3- to 14-membered non-aromatic heterocyclic group (preferably a 3- to 8-membered monocyclic non-aromatic heterocyclic group (e.g., pyrrolidinyl, piperidyl)) optionally substituted by 1 to 3 oxo groups;
$R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom (e.g., a fluorine atom); and
L is a bond, —$CH_2$— or —$CH(CH_3)$—.
[Compound C-1]
Compound (I) wherein
$R^1$ is
(1) a cyclohexyl group optionally substituted by 1 to 3 substituents selected from
(a) an amino group,
(b) a $C_{1-6}$ alkoxy group (e.g., butoxy),
(c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
(i) a halogen atom (e.g., a fluorine atom),
(ii) a cyano group,
(iii) a hydroxy group,
(iv) a $C_{1-6}$ alkoxy group (e.g., methoxy),
(v) a $C_{3-10}$ cycloalkyl group (e.g., cyclopropyl, cyclobutyl, cyclopentyl) optionally substituted by 1 to 3 substituents selected from a hydroxy group and a cyano group, and
(vi) a $C_{6-14}$ aryl group (e.g., phenyl),
(d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(e) a mono- or di-$C_{1-6}$ alkyl-carbamoyloxy group (e.g., methylcarbamoyloxy),
(f) a $C_{3-10}$ cycloalkyl-carbonylamino group (the $C_{3-10}$ cycloalkyl in the $C_{3-10}$ cycloalkyl-carbonylamino group may be a bridged group or a spiro ring group. e.g., cyclopropylcarbonylamino, cyclobutylcarbonylamino, cyclohexylcarbonylamino, spiro[2.3]hexylcarbonylamino, spiro[3.3]heptylcarbonylamino, bicyclo[1.1.1]pentylcarbonylamino) optionally substituted by 1 to 3 substituents selected from
(i) a halogen atom (e.g., a fluorine atom),
(ii) a cyano group,
(iii) a hydroxy group,
(iv) an optionally halogenated $C_{1-6}$ alkyl group (e.g., methyl, difluoromethyl, trifluoromethyl),
(v) a $C_{1-6}$ alkoxy group (e.g., methoxy), and
(vi) a $C_{6-14}$ aryl group (e.g., phenyl) optionally substituted by 1 to 3 halogen atoms (e.g., a fluorine atom),
(g) a $C_{3-10}$ cycloalkoxy-carbonylamino group (e.g., cyclopropoxycarbonylamino),
(h) a $C_{6-14}$ aryl-carbonylamino group (e.g., phenylcarbonylamino) optionally substituted by 1 to 3 halogen atoms (e.g., a chlorine atom), (i) a $C_{7-16}$ aralkyl-oxycarbonylamino group (e.g., benzyloxycarbonylamino), (j) a 5- to 14-membered aromatic heterocyclic group (preferably a 5- or 6-membered monocyclic aromatic heterocyclic group (e.g., pyrazolyl, triazolyl) or a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl, ethyl), (k) a 3- to 14-membered non-aromatic heterocyclic group (preferably a 3- to 8-membered monocyclic non-aromatic heterocyclic group (e.g., pyrrolidinyl, piperidyl, morpholinyl, tetrahydrooxazinyl, hexahydropyrimidinyl, oxazolidinyl, imidazolidinyl, 1,1-dioxido-1,2-thiazolidinyl) or a 9- to 14-membered fused polycyclic (preferably bi- or tri-cyclic) non-aromatic heterocyclic group (e.g., dihydroisoindolyl, 5-azaspiro[2.4]heptyl)) optionally substituted by 1 to 3 substituents selected from
  (i) an oxo group, and
  (ii) a $C_{1-6}$ alkyl group (e.g., methyl), (l) a 5- to 14-membered aromatic heterocyclylcarbonylamino group (preferably a 5- or 6-membered monocyclic aromatic heterocyclylcarbonylamino group (e.g., oxazolylcarbonylamino, imidazolylcarbonylamino, pyrazolylcarbonylamino, pyridylcarbonylamino)) optionally substituted by 1 to 3 $C_{1-6}$ alkyl groups (e.g., methyl), and (m) a 3- to 14-membered non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino, tetrahydropyranylcarbonylamino)) optionally substituted by 1 to 3 substituents selected from
  (i) a $C_{1-6}$ alkyl group (e.g., methyl, ethyl), and
  (ii) a $C_{6-14}$ aryl group (e.g., phenyl), (2) a cyclopropyl group optionally substituted by 1 to 3 of mono- or di-$C_{1-6}$ alkyl-carbamoyl groups (e.g., ethylcarbamoyl) optionally substituted by 1 to 3 halogen atoms (e.g., a fluorine atom), (3) a phenyl group optionally substituted by 1 to 3 substituents selected from
  (a) a halogen atom (e.g., a fluorine atom, a bromine atom),
  (b) an optionally halogenated $C_{1-6}$ alkyl group (e.g., trifluoromethyl),
  (c) a $C_{1-6}$ alkylsulfonyl group (e.g., methylsulfonyl),
  (d) a $C_{6-14}$ aryl group (e.g., phenyl) optionally substituted by 1 to 3 substituents selected from
    (i) a cyano group,
    (ii) an optionally halogenated $C_{1-6}$ alkyl group (e.g., trifluoromethyl),
    (iii) a $C_{1-6}$ alkoxy group (e.g., methoxy), and
    (iv) a $C_{1-6}$ alkylsulfonyl group (e.g., methylsulfonyl),
  (e) a 5- to 14-membered aromatic heterocyclic group (preferably a 5- or 6-membered monocyclic aromatic heterocyclic group (e.g., pyrazolyl)) optionally substituted by 1 to 3 $C_{1-6}$ alkyl groups (e.g., methyl),
  (f) a 3- to 14-membered non-aromatic heterocyclic group (preferably a 3- to 8-membered monocyclic non-aromatic heterocyclic group (e.g., pyrrolidinyl)) optionally substituted by 1 to 3 oxo groups, and
  (g) a 4,4,5,5-tetramethyl-1,3,2-dioxaborolan-2-yl group, (4) a pyridyl group optionally substituted by 1 to 3 substituents selected from
  (a) a halogen atom (e.g., a fluorine atom, a chlorine atom), and
  (b) an optionally halogenated $C_{1-6}$ alkyl group (e.g., trifluoromethyl), (5) an isoxazolyl group optionally substituted by 1 to 3 $C_{3-10}$ cycloalkyl groups (e.g., cyclopropyl), (6) a pyrazolyl group optionally substituted by 1 to 3 substituents selected from
  (a) a $C_{1-6}$ alkyl group (e.g., methyl), and
  (b) a $C_{6-14}$ aryl group (e.g., phenyl), (7) a tetrahydropyranyl group optionally substituted by 1 to 3 substituents selected from
  (a) a $C_{1-6}$ alkyl-carbonylamino group (e.g., propanoylamino, pivaloylamino) optionally substituted by 1 to 5 halogen atoms (e.g., a fluorine atom),
  (b) a $C_{1-6}$ alkoxy-carbonylamino group (e.g., tert-butoxycarbonylamino),
  (c) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl),
  (d) a $C_{6-14}$ aryl-carbonylamino group (e.g., phenylcarbonylamino) optionally substituted by 1 to 3 halogen atoms (e.g., a chlorine atom), and
  (e) a 3- to 14-membered non-aromatic heterocyclic group (preferably a 3- to 8-membered monocyclic non-aromatic heterocyclic group (e.g., pyrrolidinyl, piperidyl)) optionally substituted by 1 to 3 oxo groups, (8) a piperidyl group optionally substituted by 1 to 3 substituents selected from
  (a) a $C_{1-6}$ alkyl-carbonyl group (e.g., acetyl),
  (b) a $C_{1-6}$ alkoxy-carbonyl group (e.g., methoxycarbonyl, ethoxycarbonyl, isopropoxycarbonyl, tert-butoxycarbonyl),
  (c) a $C_{3-10}$ cycloalkyl-carbonyl group (e.g., cyclopropylcarbonyl),
  (d) a $C_{3-10}$ cycloalkylsulfonyl group (e.g., cyclopropylsulfonyl), and
  (e) a $C_{6-14}$ aryl group (e.g., phenyl), or (9) a morpholinyl group optionally substituted by 1 to 3 substituents selected from
  (a) a $C_{1-6}$ alkoxy-carbonyl group (e.g., methoxycarbonyl, isopropoxycarbonyl, tert-butoxycarbonyl),
  (b) a $C_{3-10}$ cycloalkyl-carbonyl group (e.g., cyclopropylcarbonyl, cyclopentylcarbonyl),
  (c) a $C_{3-10}$ cycloalkylsulfonyl group (e.g., cyclopropylsulfonyl), and
  (d) a $C_{6-14}$ arylsulfonyl group (e.g., phenylsulfonyl) optionally substituted by 1 to 3 $C_{1-6}$ alkyl groups (e.g., methyl);

$R^2$ and $R^3$ are both hydrogen atoms, or $R^2$ and $R^3$ in combination form an oxo group;

$R^4$ and $R^5$ are both hydrogen atoms;

X is $CR^6$ or N;

$R^6$ is a hydrogen atom or a halogen atom (e.g., a fluorine atom); and

L is a bond, —$CH_2$— or —$CH(CH_3)$—.

[Compound C-a]

Compound (I) wherein $R^1$ is (1) a cyclohexyl group optionally substituted by 1 to 3 substituents selected from
  (a) an amino group,
  (b) a $C_{1-6}$ alkoxy group (e.g., butoxy),
  (c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
  (i) a halogen atom (e.g., a fluorine atom),
  (ii) a cyano group,
  (iii) a hydroxy group,
  (iv) a $C_{1-6}$ alkoxy group (e.g., methoxy),
  (v) a $C_{3-10}$ cycloalkyl group (e.g., cyclopropyl, cyclobutyl, cyclopentyl) optionally substituted by 1 to 3 substituents selected from a hydroxy group and a cyano group, and
  (vi) a $C_{6-14}$ aryl group (e.g., phenyl),
(d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(e) a mono- or di-$C_{1-6}$ alkyl-carbamoyloxy group (e.g., methylcarbamoyloxy),
(f) a $C_{3-10}$ cycloalkyl-carbonylamino group (the $C_{3-10}$ cycloalkyl in the $C_{3-10}$ cycloalkyl-carbonylamino group may be a bridged group or a spiro ring group. e.g., cyclopropylcarbonylamino, cyclobutylcarbonylamino, cyclohexylcarbonylamino, spiro[2.3]hexylcarbonylamino, spiro[3.3]heptylcarbonylamino, bicyclo[1.1.1]pentylcarbonylamino) optionally substituted by 1 to 3 substituents selected from
  (i) a halogen atom (e.g., a fluorine atom),
  (ii) a cyano group,
  (iii) a hydroxy group,
  (iv) an optionally halogenated $C_{1-6}$ alkyl group (e.g., methyl, difluoromethyl, trifluoromethyl),
  (v) a $C_{1-6}$ alkoxy group (e.g., methoxy), and
  (vi) a $C_{6-14}$ aryl group (e.g., phenyl) optionally substituted by 1 to 3 halogen atoms (e.g., a fluorine atom),
(g) a $C_{3-10}$ cycloalkoxy-carbonylamino group (e.g., cyclopropoxycarbonylamino),
(h) a $C_{6-14}$ aryl-carbonylamino group (e.g., phenylcarbonylamino) optionally substituted by 1 to 3 halogen atoms (e.g., a chlorine atom),
(i) a $C_{7-16}$ aralkyl-oxycarbonylamino group (e.g., benzyloxycarbonylamino),
(j) a 5- to 14-membered aromatic heterocyclic group (preferably a 5- or 6-membered monocyclic aromatic heterocyclic group (e.g., pyrazolyl, triazolyl) or a 8- to 14-membered fused polycyclic (preferably bi- or tricyclic) aromatic heterocyclic group (e.g., indazolyl)) optionally substituted by 1 to 3 $C_{1-6}$ alkyl groups (e.g., methyl, ethyl),
(k) a 3- to 14-membered non-aromatic heterocyclic group (preferably a 3- to 8-membered monocyclic non-aromatic heterocyclic group (e.g., pyrrolidinyl, piperidyl, morpholinyl, tetrahydrooxazinyl, hexahydropyrimidinyl, oxazolidinyl, imidazolidinyl, 1,1-dioxido-1,2-thiazolidinyl) or a 9- to 14-membered fused polycyclic (preferably bi- or tri-cyclic) non-aromatic heterocyclic group (e.g., dihydroisoindolyl, 5-azaspiro[2.4]heptyl)) optionally substituted by 1 to 3 substituents selected from
  (i) an oxo group, and
  (ii) a $C_{1-6}$ alkyl group (e.g., methyl),
(l) a 5- to 14-membered aromatic heterocyclylcarbonylamino group (preferably a 5- or 6-membered monocyclic aromatic heterocyclylcarbonylamino group (e.g., oxazolylcarbonylamino, imidazolylcarbonylamino, pyrazolylcarbonylamino, pyridylcarbonylamino)) optionally substituted by 1 to 3 $C_{1-6}$ alkyl groups (e.g., methyl), and
(m) a 3- to 14-membered non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino, tetrahydropyranylcarbonylamino)) optionally substituted by 1 to 3 substituents selected from
  (i) a $C_{1-6}$ alkyl group (e.g., methyl, ethyl), and
  (ii) a $C_{6-14}$ aryl group (e.g., phenyl),
(2) a tetrahydropyranyl group optionally substituted by 1 to 3 substituents selected from
  (a) a $C_{1-6}$ alkyl-carbonylamino group (e.g., propanoylamino, pivaloylamino) optionally substituted by 1 to 5 halogen atoms (e.g., a fluorine atom),
  (b) a $C_{1-6}$ alkoxy-carbonylamino group (e.g., tert-butoxycarbonylamino),
  (c) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl),
  (d) a $C_{6-14}$ aryl-carbonylamino group (e.g., phenylcarbonylamino) optionally substituted by 1 to 3 halogen atoms (e.g., a chlorine atom), and
  (e) a 3- to 14-membered non-aromatic heterocyclic group (preferably a 3- to 8-membered monocyclic non-aromatic heterocyclic group (e.g., pyrrolidinyl, piperidyl)) optionally substituted by 1 to 3 oxo groups, or
(3) a piperidyl group optionally substituted by 1 to 3 substituents selected from
  (a) a $C_{1-6}$ alkyl-carbonyl group (e.g., acetyl),
  (b) a $C_{1-6}$ alkoxy-carbonyl group (e.g., methoxycarbonyl, ethoxycarbonyl, tert-butoxycarbonyl), and
  (c) a $C_{6-14}$ aryl group (e.g., phenyl);
$R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom (e.g., a fluorine atom); and
L is a bond.
[Compound C-b]
Compound (I) wherein
$R^1$ is
(1) a phenyl group optionally substituted by 1 to 3 substituents selected from
  (a) a halogen atom (e.g., a bromine atom),
  (b) a $C_{6-14}$ aryl group (e.g., phenyl) optionally substituted by 1 to 3 substituents selected from
    (i) a cyano group,
    (ii) an optionally halogenated $C_{1-6}$ alkyl group (e.g., trifluoromethyl),
    (iii) a $C_{1-6}$ alkoxy group (e.g., methoxy), and
    (iv) a $C_{1-6}$ alkylsulfonyl group (e.g., methylsulfonyl),
  (c) a 5- to 14-membered aromatic heterocyclic group (preferably a 5- or 6-membered monocyclic aromatic heterocyclic group (e.g., pyrazolyl)) optionally substituted by 1 to 3 $C_{1-6}$ alkyl groups (e.g., methyl),
  (d) a 3- to 14-membered non-aromatic heterocyclic group (preferably a 3- to 8-membered monocyclic non-aromatic heterocyclic group (e.g., pyrrolidinyl)) optionally substituted by 1 to 3 oxo groups, and
  (e) a 4,4,5,5-tetramethyl-1,3,2-dioxaborolan-2-yl group, or
(2) a pyrazolyl group optionally substituted by 1 to 3 substituents selected from
  (a) a $C_{1-6}$ alkyl group (e.g., methyl), and
  (b) a $C_{6-14}$ aryl group (e.g., phenyl);
$R^2$ and $R^3$ are both hydrogen atoms;
$R^4$ and $R^5$ are both hydrogen atoms;
X is CH; and
L is a bond.

[Compound C-c]
Compound (I) wherein
R¹ is
(1) a phenyl group optionally substituted by 1 to 3 substituents selected from
    (a) a halogen atom (e.g., a fluorine atom),
    (b) an optionally halogenated $C_{1-6}$ alkyl group (e.g., trifluoromethyl), and
    (c) a $C_{1-6}$ alkylsulfonyl group (e.g., methylsulfonyl),
(2) a pyridyl group optionally substituted by 1 to 3 substituents selected from
    (a) a halogen atom (e.g., a fluorine atom, a chlorine atom), and
    (b) an optionally halogenated $C_{1-6}$ alkyl group (e.g., trifluoromethyl), or
(3) an isoxazolyl group optionally substituted by 1 to 3 $C_{3-10}$ cycloalkyl groups (e.g., cyclopropyl);
R² and R³ are both hydrogen atoms;
R⁴ and R⁵ are both hydrogen atoms;
X is CR⁶ or N;
R⁶ is a hydrogen atom or a halogen atom (e.g., a fluorine atom); and
L is —CH₂— or —CH(CH₃)—.

[Compound C-d]
Compound (I) wherein
R¹ is
(1) a piperidyl group optionally substituted by 1 to 3 substituents selected from
    (a) a $C_{1-6}$ alkoxy-carbonyl group (e.g., isopropoxycarbonyl, tert-butoxycarbonyl),
    (b) a $C_{3-10}$ cycloalkyl-carbonyl group (e.g., cyclopropylcarbonyl), and
    (c) a $C_{3-10}$ cycloalkylsulfonyl group (e.g., cyclopropylsulfonyl), or
(2) a morpholinyl group optionally substituted by 1 to 3 substituents selected from
    (a) a $C_{1-6}$ alkoxy-carbonyl group (e.g., methoxycarbonyl, isopropoxycarbonyl, tert-butoxycarbonyl),
    (b) a $C_{3-10}$ cycloalkyl-carbonyl group (e.g., cyclopropylcarbonyl, cyclopentylcarbonyl),
    (c) a $C_{3-10}$ cycloalkylsulfonyl group (e.g., cyclopropylsulfonyl), and
    (d) a $C_{6-14}$ arylsulfonyl group (e.g., phenylsulfonyl) optionally substituted by 1 to 3 $C_{1-6}$ alkyl groups (e.g., methyl);
R² and R³ are both hydrogen atoms;
R⁴ and R⁵ are both hydrogen atoms;
X is CR⁶;
R⁶ is a hydrogen atom or a halogen atom (e.g., a fluorine atom); and
L is —CH₂—.

[Compound D-1]
Compound (I) wherein
R¹ is
(1) a cyclohexyl group optionally substituted by 1 to 3 substituents selected from
    (a) an amino group,
    (b) a $C_{1-6}$ alkoxy group (e.g., butoxy),
    (c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
        (i) a halogen atom (e.g., a fluorine atom),
        (ii) a cyano group,
        (iii) a hydroxy group,
        (iv) a $C_{1-6}$ alkoxy group (e.g., methoxy),
        (v) a $C_{3-10}$ cycloalkyl group (e.g., cyclopropyl, cyclobutyl, cyclopentyl) optionally substituted by 1 to 3 substituents selected from a hydroxy group and a cyano group, and
        (vi) a phenyl group,
    (d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
    (e) a mono- or di-$C_{1-6}$ alkyl-carbamoyloxy group (e.g., methylcarbamoyloxy),
    (f) a $C_{3-10}$ cycloalkyl-carbonylamino group (e.g., cyclopropylcarbonylamino, cyclobutylcarbonylamino, cyclohexylcarbonylamino) optionally substituted by 1 to 3 substituents selected from
        (i) a halogen atom (e.g., a fluorine atom),
        (ii) a cyano group,
        (iii) a hydroxy group,
        (iv) an optionally halogenated $C_{1-6}$ alkyl group (e.g., methyl, difluoromethyl, trifluoromethyl),
        (v) a $C_{1-6}$ alkoxy group (e.g., methoxy), and
        (vi) a phenyl group optionally substituted by 1 to 3 halogen atoms (e.g., a fluorine atom),
    (g) a spiro[2.3]hexylcarbonylamino group,
    (h) a spiro[3.3]heptylcarbonylamino group,
    (i) a bicyclo[1.1.1]pentylcarbonylamino group optionally is substituted by 1 to 3 optionally halogenated $C_{1-6}$ alkyl groups (e.g., trifluoromethyl),
    (j) a $C_{3-10}$ cycloalkoxy-carbonylamino group (e.g., cyclopropoxycarbonylamino),
    (k) a phenylcarbonylamino group optionally substituted by 1 to 3 halogen atoms (e.g., a chlorine atom),
    (l) a benzyloxycarbonylamino group,
    (m) a pyrazolyl group optionally substituted by 1 to 3 $C_{1-6}$ alkyl groups (e.g., methyl, ethyl),
    (n) a triazolyl group,
    (o) an indazolyl group
    (p) a pyrrolidinyl group optionally substituted by 1 to 3 oxo groups,
    (q) a piperidyl group optionally substituted by 1 to 3 oxo groups,
    (r) a morpholinyl group optionally substituted by 1 to 3 oxo groups,
    (s) a tetrahydrooxazinyl group optionally substituted by 1 to 3 oxo groups,
    (t) a hexahydropyrimidinyl group optionally substituted by 1 to 3 oxo groups,
    (u) an oxazolidinyl group optionally substituted by 1 to 3 oxo groups,
    (v) an imidazolidinyl group optionally substituted by 1 to 3 substituents selected from
        (i) an oxo group, and
        (ii) a $C_{1-6}$ alkyl group (e.g., methyl),
    (w) a 1,1-dioxido-1,2-thiazolidinyl group,
    (x) a dihydroisoindolyl group optionally substituted by 1 to 3 oxo groups,
    (y) a 5-azaspiro[2.4]heptyl group optionally substituted by 1 to 3 oxo groups,
    (z) an oxazolylcarbonylamino group,
    (aa) an imidazolylcarbonylamino group optionally substituted by 1 to 3 $C_{1-6}$ alkyl groups (e.g., methyl),
    (bb) a pyrazolylcarbonylamino group optionally substituted by 1 to 3 $C_{1-6}$ alkyl groups (e.g., methyl),
    (cc) a pyridylcarbonylamino group,
    (dd) an oxetanylcarbonylamino group optionally substituted by 1 to 3 substituents selected from (i) a $C_{1-6}$ alkyl group (e.g., methyl, ethyl), and
(ii) a phenyl group,
(ee) a tetrahydrofurylcarbonylamino group, and
(ff) a tetrahydropyranylcarbonylamino group,
(2) a cyclopropyl group optionally substituted by 1 to 3 of mono- or di-$C_{1-6}$ alkyl-carbamoyl groups (e.g., ethylcarbamoyl) optionally substituted by 1 to 3 halogen atoms (e.g., a fluorine atom),
(3) a phenyl group optionally substituted by 1 to 3 substituents selected from
  (a) a halogen atom (e.g., a fluorine atom, a bromine atom),
  (b) an optionally halogenated $C_{1-6}$ alkyl group (e.g., trifluoromethyl),
  (c) a $C_{1-6}$ alkylsulfonyl group (e.g., methylsulfonyl),
  (d) a phenyl group optionally substituted by 1 to 3 substituents selected from
    (i) a cyano group,
    (ii) an optionally halogenated $C_{1-6}$ alkyl group (e.g., trifluoromethyl),
    (iii) a $C_{1-6}$ alkoxy group (e.g., methoxy), and
    (iv) a $C_{1-6}$ alkylsulfonyl group (e.g., methylsulfonyl),
  (e) a pyrazolyl group optionally substituted by 1 to 3 $C_{1-6}$ alkyl groups (e.g., methyl),
  (f) a pyrrolidinyl group optionally substituted by 1 to 3 oxo groups, and
  (g) a 4,4,5,5-tetramethyl-1,3,2-dioxaborolan-2-yl group,
(4) a pyridyl group optionally substituted by 1 to 3 substituents selected from
  (a) a halogen atom (e.g., a fluorine atom, a chlorine atom), and
  (b) an optionally halogenated $C_{1-6}$ alkyl group (e.g., trifluoromethyl),
(5) an isoxazolyl group optionally substituted by 1 to 3 $C_{3-10}$ cycloalkyl groups (e.g., cyclopropyl),
(6) a pyrazolyl group optionally substituted by 1 to 3 substituents selected from
  (a) a $C_{1-6}$ alkyl group (e.g., methyl), and
  (b) a phenyl group,
(7) a tetrahydropyranyl group optionally substituted by 1 to 3 substituents selected from
  (a) a $C_{1-6}$ alkyl-carbonylamino group (e.g., propanoylamino, pivaloylamino) optionally substituted by 1 to 5 halogen atoms (e.g., a fluorine atom),
  (b) a $C_{1-6}$ alkoxy-carbonylamino group (e.g., tert-butoxycarbonylamino),
  (c) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl),
  (d) a phenylcarbonylamino group optionally substituted by 1 to 3 halogen atoms (e.g., a chlorine atom),
  (e) a pyrrolidinyl group optionally substituted by 1 to 3 oxo groups, and
  (f) a piperidyl group optionally substituted by 1 to 3 oxo groups,
(8) a piperidyl group optionally substituted by 1 to 3 substituents selected from
  (a) a $C_{1-6}$ alkyl-carbonyl group (e.g., acetyl),
  (b) a $C_{1-6}$ alkoxy-carbonyl group (e.g., methoxycarbonyl, ethoxycarbonyl, isopropoxycarbonyl, tert-butoxycarbonyl),
  (c) a $C_{3-10}$ cycloalkyl-carbonyl group (e.g., cyclopropylcarbonyl),
  (d) a $C_{3-10}$ cycloalkylsulfonyl group (e.g., cyclopropylsulfonyl), and
  (e) a phenyl group, or
(9) a morpholinyl group optionally substituted by 1 to 3 substituents selected from
  (a) a $C_{1-6}$ alkoxy-carbonyl group (e.g., methoxycarbonyl, isopropoxycarbonyl, tert-butoxycarbonyl),
  (b) a $C_{3-10}$ cycloalkyl-carbonyl group (e.g., cyclopropylcarbonyl, cyclopentylcarbonyl),
  (c) a $C_{3-10}$ cycloalkylsulfonyl group (e.g., cyclopropylsulfonyl), and
  (d) a phenylsulfonyl group optionally substituted by 1 to 3 $C_{1-6}$ alkyl groups (e.g., methyl);
$R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom (e.g., a fluorine atom); and
L is a bond, —$CH_2$— or —$CH(CH_3)$—.
[Compound D-a']
Compound (I) wherein
$R^1$ is
(1) a cyclohexyl group optionally substituted by 1 to 3 substituents selected from
  (a) an amino group,
  (b) a $C_{1-6}$ alkoxy group (e.g., butoxy),
  (c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
    (i) a halogen atom (e.g., a fluorine atom),
    (ii) a cyano group,
    (iii) a hydroxy group,
    (iv) a $C_{1-6}$ alkoxy group (e.g., methoxy),
    (v) a $C_{3-10}$ cycloalkyl group (e.g., cyclopropyl, cyclobutyl, cyclopentyl) optionally substituted by 1 to 3 substituents selected from a hydroxy group and a cyano group, and
    (vi) a phenyl group,
  (d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
  (e) a mono- or di-$C_{1-6}$ alkyl-carbamoyloxy group (e.g., methylcarbamoyloxy),
  (f) a $C_{3-10}$ cycloalkyl-carbonylamino group (e.g., cyclopropylcarbonylamino, cyclobutylcarbonylamino, cyclohexylcarbonylamino) optionally substituted by 1 to 3 substituents selected from
    (i) a halogen atom (e.g., a fluorine atom),
    (ii) a cyano group,
    (iii) a hydroxy group,
    (iv) an optionally halogenated $C_{1-6}$ alkyl group (e.g., methyl, difluoromethyl, trifluoromethyl),
    (v) a $C_{1-6}$ alkoxy group (e.g., methoxy), and
    (vi) a phenyl group optionally substituted by 1 to 3 halogen atoms (e.g., a fluorine atom),
  (g) a spiro[2.3]hexylcarbonylamino group,
  (h) a spiro[3.3]heptylcarbonylamino group,
  (i) a bicyclo[1.1.1]pentylcarbonylamino group optionally substituted by 1 to 3 optionally halogenated $C_{1-6}$ alkyl groups (e.g., trifluoromethyl),
  (j) a $C_{3-10}$ cycloalkoxy-carbonylamino group (e.g., cyclopropoxycarbonylamino),
  (k) a $C_{6-14}$ aryl-carbonylamino group (e.g., phenylcarbonylamino) optionally substituted by 1 to 3 halogen atoms (e.g., a chlorine atom), (l) a benzyloxycarbonylamino group,
(m) a pyrazolyl group optionally substituted by 1 to 3 $C_{1-6}$ alkyl groups (e.g., methyl, ethyl),
(n) a triazolyl group,
(o) an indazolyl group
(p) a pyrrolidinyl group optionally substituted by 1 to 3 oxo groups,
(q) a piperidyl group optionally substituted by 1 to 3 oxo groups,
(r) a morpholinyl group optionally substituted by 1 to 3 oxo groups,
(s) a tetrahydrooxazinyl group optionally substituted by 1 to 3 oxo groups,
(t) a hexahydropyrimidinyl group optionally substituted by 1 to 3 oxo groups,
(u) an oxazolidinyl group optionally substituted by 1 to 3 oxo groups,
(v) an imidazolidinyl group optionally substituted by 1 to 3 substituents selected from
  (i) an oxo group, and
  (ii) a $C_{1-6}$ alkyl group (e.g., methyl),
(w) a 1,1-dioxido-1,2-thiazolidinyl group,
(x) a dihydroisoindolyl group optionally substituted by 1 to 3 oxo groups,
(y) a 5-azaspiro[2.4]heptyl group optionally substituted by 1 to 3 oxo groups,
(z) an oxazolylcarbonylamino group,
(aa) an imidazolylcarbonylamino group optionally substituted by 1 to 3 $C_{1-6}$ alkyl groups (e.g., methyl),
(bb) a pyrazolylcarbonylamino group optionally substituted by 1 to 3 $C_{1-6}$ alkyl groups (e.g., methyl),
(cc) a pyridylcarbonylamino group,
(dd) an oxetanylcarbonylamino group optionally substituted by 1 to 3 substituents selected from
  (i) a $C_{1-6}$ alkyl group (e.g., methyl, ethyl), and
  (ii) a phenyl group,
(ee) a tetrahydrofurylcarbonylamino group, and
(ff) a tetrahydropyranylcarbonylamino group,
(2) a tetrahydropyranyl group optionally substituted by 1 to 3 substituents selected from
  (a) a $C_{1-6}$ alkyl-carbonylamino group (e.g., propanoylamino, pivaloylamino) optionally substituted by 1 to 5 halogen atoms (e.g., a fluorine atom),
  (b) a $C_{1-6}$ alkoxy-carbonylamino group (e.g., tert-butoxycarbonylamino),
  (c) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl),
  (d) a phenylcarbonylamino group optionally substituted by 1 to 3 halogen atoms (e.g., a chlorine atom),
  (e) a pyrrolidinyl group optionally substituted by 1 to 3 oxo groups,
  (f) a piperidyl group optionally substituted by 1 to 3 oxo groups, and
  (g) a $C_{1-6}$ alkylamino group (e.g., ethylamino, propylamino, butylamino) optionally substituted by 1 to 7 halogen atoms (e.g., a fluorine atom), or
(3) a piperidyl group optionally substituted by 1 to 3 substituents selected from
  (a) a $C_{1-6}$ alkyl-carbonyl group (e.g., acetyl),
  (b) a $C_{1-6}$ alkoxy-carbonyl group (e.g., methoxycarbonyl, ethoxycarbonyl, tert-butoxycarbonyl), and
  (c) a phenyl group;
$R^2$ and $R^3$ are both hydrogen atoms, or $R^2$ and $R^3$ in combination form an oxo group;
$R^4$ and $R^5$ are both hydrogen atoms;

X is $CR^6$ or N;
$R^6$ is a hydrogen atom or a halogen atom (e.g., a fluorine atom); and
L is a bond.
[Compound D-a]
Compound (I) wherein
$R^1$ is
(1) a cyclohexyl group optionally substituted by 1 to 3 substituents selected from
  (a) an amino group,
  (b) a $C_{1-6}$ alkoxy group (e.g., butoxy),
  (c) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
    (i) a halogen atom (e.g., a fluorine atom),
    (ii) a cyano group,
    (iii) a hydroxy group,
    (iv) a $C_{1-6}$ alkoxy group (e.g., methoxy),
    (v) a $C_{3-10}$ cycloalkyl group (e.g., cyclopropyl, cyclobutyl, cyclopentyl) optionally substituted by 1 to 3 substituents selected from a hydroxy group and a cyano group, and
    (vi) a phenyl group,
  (d) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
  (e) a mono- or di-$C_{1-6}$ alkyl-carbamoyloxy group (e.g., methylcarbamoyloxy),
  (f) a $C_{3-10}$ cycloalkyl-carbonylamino group (e.g., cyclopropylcarbonylamino, cyclobutylcarbonylamino, cyclohexylcarbonylamino) optionally substituted by 1 to 3 substituents selected from
    (i) a halogen atom (e.g., a fluorine atom),
    (ii) a cyano group,
    (iii) a hydroxy group,
    (iv) an optionally halogenated $C_{1-6}$ alkyl group (e.g., methyl, difluoromethyl, trifluoromethyl),
    (v) a $C_{1-6}$ alkoxy group (e.g., methoxy), and
    (vi) a phenyl group optionally substituted by 1 to 3 halogen atoms (e.g., a fluorine atom),
  (g) a spiro[2.3]hexylcarbonylamino group,
  (h) a spiro[3.3]heptylcarbonylamino group,
  (i) a bicyclo[1.1.1]pentylcarbonylamino group optionally substituted by 1 to 3 optionally halogenated $C_{1-6}$ alkyl groups (e.g., trifluoromethyl),
  (j) a $C_{3-10}$ cycloalkoxy-carbonylamino group (e.g., cyclopropoxycarbonylamino),
  (k) a $C_{6-14}$ aryl-carbonylamino group (e.g., phenylcarbonylamino) optionally substituted by 1 to 3 halogen atoms (e.g., a chlorine atom),
  (l) a benzyloxycarbonylamino group,
  (m) a pyrazolyl group optionally substituted by 1 to 3 $C_{1-6}$ alkyl groups (e.g., methyl, ethyl),
  (n) a triazolyl group,
  (o) an indazolyl group
  (p) a pyrrolidinyl group optionally substituted by 1 to 3 oxo groups,
  (q) a piperidyl group optionally substituted by 1 to 3 oxo groups,
  (r) a morpholinyl group optionally substituted by 1 to 3 oxo groups,
  (s) a tetrahydrooxazinyl group optionally substituted by 1 to 3 oxo groups, (t) a hexahydropyrimidinyl group optionally substituted by 1 to 3 oxo groups,
(u) an oxazolidinyl group optionally substituted by 1 to 3 oxo groups,
(v) an imidazolidinyl group optionally substituted by 1 to 3 substituents selected from
  (i) an oxo group, and
  (ii) a $C_{1-6}$ alkyl group (e.g., methyl),
(w) a 1,1-dioxido-1,2-thiazolidinyl group,
(x) a dihydroisoindolyl group optionally substituted by 1 to 3 oxo groups,
(y) a 5-azaspiro[2.4]heptyl group optionally substituted by 1 to 3 oxo groups,
(z) an oxazolylcarbonylamino group,
(aa) an imidazolylcarbonylamino group optionally substituted by 1 to 3 $C_{1-6}$ alkyl groups (e.g., methyl),
(bb) a pyrazolylcarbonylamino group optionally substituted by 1 to 3 $C_{1-6}$ alkyl groups (e.g., methyl),
(cc) a pyridylcarbonylamino group,
(dd) an oxetanylcarbonylamino group optionally substituted by 1 to 3 substituents selected from
  (i) a $C_{1-6}$ alkyl group (e.g., methyl, ethyl), and
  (ii) a phenyl group,
(ee) a tetrahydrofurylcarbonylamino group, and
(ff) a tetrahydropyranylcarbonylamino group,
(2) a tetrahydropyranyl group optionally substituted by 1 to 3 substituents selected from
  (a) a $C_{1-6}$ alkyl-carbonylamino group (e.g., propanoylamino, pivaloylamino) optionally substituted by 1 to 5 halogen atoms (e.g., a fluorine atom),
  (b) a $C_{1-6}$ alkoxy-carbonylamino group (e.g., tert-butoxycarbonylamino),
  (c) a $C_{3-10}$ cycloalkyl-carbonylamino group (e.g., cyclopropylcarbonylamino) optionally substituted by 1 to 3 optionally halogenated $C_{1-6}$ alkyl groups (e.g., trifluoromethyl),
  (d) a phenylcarbonylamino group optionally substituted by 1 to 3 halogen atoms (e.g., a chlorine atom),
  (e) a pyrrolidinyl group optionally substituted by 1 to 3 oxo groups, and
  (f) a piperidyl group optionally substituted by 1 to 3 oxo groups, or
(3) a piperidyl group optionally substituted by 1 to 3 substituents selected from
  (a) a $C_{1-6}$ alkyl-carbonyl group (e.g., acetyl),
  (b) a $C_{1-6}$ alkoxy-carbonyl group (e.g., methoxycarbonyl, ethoxycarbonyl, tert-butoxycarbonyl), and
  (c) a phenyl group;
$R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom (e.g., a fluorine atom); and
L is a bond.
[Compound D-b]
Compound (I) wherein
$R^1$ is
(1) a phenyl group optionally substituted by 1 to 3 substituents selected from
  (a) a halogen atom (e.g., a bromine atom),
  (b) a phenyl group optionally substituted by 1 to 3 substituents selected from
    (i) a cyano group,
    (ii) an optionally halogenated $C_{1-6}$ alkyl group (e.g., trifluoromethyl),
    (iii) a $C_{1-6}$ alkoxy group (e.g., methoxy), and
    (iv) a $C_{1-6}$ alkylsulfonyl group (e.g., methylsulfonyl),
  (c) a pyrazolyl group optionally substituted by 1 to 3 $C_{1-6}$ alkyl groups (e.g., methyl),
  (d) a pyrrolidinyl group optionally substituted by 1 to 3 oxo groups, and
  (e) a 4,4,5,5-tetramethyl-1,3,2-dioxaborolan-2-yl group, or
(2) a pyrazolyl group optionally substituted by 1 to 3 substituents selected from
  (a) a $C_{1-6}$ alkyl group (e.g., methyl), and
  (b) a phenyl group;
$R^2$ and $R^3$ are both hydrogen atoms;
$R^4$ and $R^5$ are both hydrogen atoms;
X is CH; and
L is a bond.
[Compound D-c]
Compound (I) wherein
$R^1$ is
(1) a phenyl group optionally substituted by 1 to 3 substituents selected from
  (a) a halogen atom (e.g., a fluorine atom),
  (b) an optionally halogenated $C_{1-6}$ alkyl group (e.g., trifluoromethyl), and
  (c) a $C_{1-6}$ alkylsulfonyl group (e.g., methylsulfonyl),
(2) a pyridyl group optionally substituted by 1 to 3 substituents selected from
  (a) a halogen atom (e.g., a fluorine atom, a chlorine atom), and
  (b) an optionally halogenated $C_{1-6}$ alkyl group (e.g., trifluoromethyl), or
(3) an isoxazolyl group optionally substituted by 1 to 3 $C_3$-10 cycloalkyl groups (e.g., cyclopropyl);
$R^2$ and $R^3$ are both hydrogen atoms;
$R^4$ and $R^5$ are both hydrogen atoms;
X is $CR^6$ or N;
$R^6$ is a hydrogen atom or a halogen atom (e.g., a fluorine atom); and
L is —$CH_2$— or —$CH(CH_3)$—.
[Compound D-d]
Compound (I) wherein
$R^1$ is
(1) a piperidyl group optionally substituted by 1 to 3 substituents selected from
  (a) a $C_{1-6}$ alkoxy-carbonyl group (e.g., isopropoxycarbonyl, tert-butoxycarbonyl),
  (b) a $C_{3-10}$ cycloalkyl-carbonyl group (e.g., cyclopropylcarbonyl), and
  (c) a $C_{3-10}$ cycloalkylsulfonyl group (e.g., cyclopropylsulfonyl), or
(2) a morpholinyl group optionally substituted by 1 to 3 substituents selected from
  (a) a $C_{1-6}$ alkoxy-carbonyl group (e.g., methoxycarbonyl, isopropoxycarbonyl, tert-butoxycarbonyl),
  (b) a $C_{3-10}$ cycloalkyl-carbonyl group (e.g., cyclopropylcarbonyl, cyclopentylcarbonyl),
  (c) a $C_{3-10}$ cycloalkylsulfonyl group (e.g., cyclopropylsulfonyl), and
  (d) a phenylsulfonyl group optionally substituted by 1 to 3 $C_{1-6}$ alkyl groups (e.g., methyl);
$R^2$ and $R^3$ are both hydrogen atoms;
$R^4$ and $R^5$ are both hydrogen atoms;
X is $CR^6$;
$R^6$ is a hydrogen atom or a halogen atom (e.g., a fluorine atom); and
L is —$CH_2$—.
[Compound E-a]
Compound (I) wherein
$R^1$ is
(1) a cyclohexyl group optionally substituted by 1 to 3 substituents selected from
  (a) a $C_{1-6}$ alkyl-carbonylamino group (e.g., acetylamino, propanoylamino) optionally substituted by 1 to 3 halogen atoms (e.g., a fluorine atom), (b) a $C_{1-6}$ alkoxy-carbonylamino group (e.g., methoxycarbonylamino), and
(c) a $C_{3-10}$ cycloalkyl-carbonylamino group (e.g., cyclopropylcarbonylamino) optionally substituted by 1 to 3 halogen atoms (e.g., a fluorine atom),
(2) a tetrahydropyranyl group optionally substituted by 1 to 3 $C_{1-6}$ alkoxy-carbonylamino groups (e.g., tert-butoxycarbonylamino), or
(3) a piperidyl group optionally substituted by 1 to 3 substituents selected from
(a) a $C_{1-6}$ alkoxy-carbonyl group (e.g., methoxycarbonyl), and
(b) a phenyl group;
$R^2$ and $R^3$ are both hydrogen atoms;
$R^4$ and $R^5$ are both hydrogen atoms;
X is $CR^6$;
$R^6$ is a hydrogen atom or a halogen atom (e.g., a fluorine atom); and
L is a bond.

[Compound E-b]
Compound (I) wherein
$R^1$ is
(1) a phenyl group optionally substituted by 1 to 3 substituents selected from
(a) a phenyl group optionally substituted by 1 to 3 cyano groups,
(b) a pyrazolyl group optionally substituted by 1 to 3 $C_{1-6}$ alkyl groups (e.g., methyl), and
(c) a $C_{1-6}$ alkyl group (e.g., methyl), or
(2) a pyrazolyl group optionally substituted by 1 to 3 substituents selected from
(a) a $C_{1-6}$ alkyl group (e.g., methyl), and
(b) a phenyl group;
$R^2$ and $R^3$ are both hydrogen atoms;
$R^4$ and $R^5$ are both hydrogen atoms;
X is CH; and
L is a bond.

[Compound E-c]
Compound (I) wherein
$R^1$ is
(1) a phenyl group optionally substituted by 1 to 3 halogen atoms (e.g., a fluorine atom),
(2) a pyridyl group optionally substituted by 1 to 3 optionally halogenated $C_{1-6}$ alkyl groups (e.g., trifluoromethyl), or
(3) an isoxazolyl group optionally substituted by 1 to 3 $C_{3-10}$ cycloalkyl groups (e.g., cyclopropyl);
$R^2$ and $R^3$ are both hydrogen atoms;
$R^4$ and $R^5$ are both hydrogen atoms;
X is CH or N; and
L is —$CH_2$— or —$CH(CH_3)$—.

[Compound E-d]
Compound (I) wherein
$R^1$ is
(1) a piperidyl group optionally substituted by 1 to 3 $C_{3-10}$ cycloalkylsulfonyl groups (e.g., cyclopropylsulfonyl), or
(2) a morpholinyl group optionally substituted by 1 to 3 substituents selected from
(a) a $C_{3-10}$ cycloalkyl-carbonyl group (e.g., cyclopentylcarbonyl),
(b) a $C_{3-10}$ cycloalkylsulfonyl group (e.g., cyclopropylsulfonyl), and
(c) a phenylsulfonyl group optionally substituted by 1 to 3 $C_{1-6}$ alkyl groups (e.g., methyl);
$R^2$ and $R^3$ are both hydrogen atoms;
$R^4$ and $R^5$ are both hydrogen atoms;
X is CH; and
L is —$CH_2$—.

[Compound F-1]
Compound (I) wherein
$R^1$ is
(1) a cyclohexyl group optionally substituted by 1 to 3 substituents selected from
(a) a $C_{1-6}$ alkyl-carbonylamino group (e.g., acetylamino, propanoylamino) optionally substituted by 1 to 3 halogen atoms (e.g., a fluorine atom),
(b) a $C_{1-6}$ alkoxy-carbonylamino group (e.g., methoxycarbonylamino), and
(c) a $C_{3-10}$ cycloalkyl-carbonylamino group (e.g., cyclopropylcarbonylamino) optionally substituted by 1 to 3 halogen atoms (e.g., a fluorine atom), or
(2) a phenyl group;
$R^2$ and $R^3$ are both hydrogen atoms;
$R^4$ and $R^5$ are both hydrogen atoms;
X is CH or N; and
L is a bond or —$CH_2$—.

[Compound A-2]
Compound (I) wherein
$R^1$ is
(1) an optionally substituted $C_{3-10}$ cycloalkyl group (e.g., cyclopropyl, cyclohexyl),
(2) an optionally substituted $C_{6-14}$ aryl group (e.g., phenyl),
(3) an optionally substituted 5- to 14-membered aromatic heterocyclic group (preferably a 5- or 6-membered monocyclic aromatic heterocyclic group (e.g., pyridyl, isoxazolyl, pyrazolyl, pyrrolyl, thiazolyl, thienyl) or a 8- to 14-membered fused polycyclic (preferably bi- or tricyclic) aromatic heterocyclic group (e.g., pyrazolopyridyl (e.g., pyrazolo[1,5-a]pyridyl)),
(4) an optionally substituted 3- to 14-membered non-aromatic heterocyclic group (preferably a 3- to 8-membered monocyclic non-aromatic heterocyclic group, more preferably a 5- or 6-membered monocyclic non-aromatic heterocyclic group (including a 6-membered monocyclic non-aromatic heterocyclic group and a 5- or 6-membered monocyclic nitrogen-containing non-aromatic heterocyclic group) (e.g., tetrahydropyranyl, piperidyl, morpholinyl, pyrrolidinyl)), or
(5) an optionally substituted $C_{1-6}$ alkyl group (e.g., ethyl); $R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom (e.g., a fluorine atom); and
L is a bond or an optionally substituted $C_{1-6}$ alkylene group (e.g., —$CH_2$—, —$CH(CH_3)$—, —$CH_2CH_2$—).

[Compound B-2]
Compound (I) wherein
$R^1$ is
(1) a $C_{3-10}$ cycloalkyl group (e.g., cyclopropyl, cyclohexyl) optionally substituted by 1 to 3 substituents selected from
(a) an amino group,
(b) a halogen atom (e.g., a fluorine atom),
(c) a hydroxy group,
(d) a $C_{1-6}$ alkyl group (e.g., methyl) optionally substituted by 1 to 3 substituents selected from
(i) a $C_{1-6}$ alkoxy-carbonylamino group (e.g., tert-butoxycarbonylamino), and
(ii) a $C_{1-6}$ alkylsulfonylamino group (e.g., ethylsulfonylamino) optionally substituted by 1 to 3 halogen atoms (e.g., a fluorine atom),
(e) a $C_{1-6}$ alkoxy group (e.g., butoxy),
(f) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 6 substituents selected from
  (i) a halogen atom (e.g., a fluorine atom),
  (ii) a cyano group,
  (iii) a hydroxy group,
  (iv) a $C_{1-6}$ alkoxy group (e.g., methoxy),
  (v) a $C_{3-10}$ cycloalkyl group (e.g., cyclopropyl, cyclobutyl, cyclopentyl) optionally substituted by 1 to 3 substituents selected from a hydroxy group and a cyano group, and
  (vi) a $C_{6-14}$ aryl group (e.g., phenyl),
(g) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(h) a mono- or di-$C_{1-6}$ alkyl-carbamoyl group (e.g., ethylcarbamoyl) optionally substituted by 1 to 3 halogen atoms (e.g., a fluorine atom),
(i) a mono- or di-$C_{1-6}$ alkyl-carbamoyloxy group (e.g., methylcarbamoyloxy),
(j) a $C_{3-10}$ cycloalkyl-carbonylamino group (the $C_{3-10}$ cycloalkyl in the $C_{3-10}$ cycloalkyl-carbonylamino group may be a bridged group or a spiro ring group. e.g., cyclopropylcarbonylamino, cyclobutylcarbonylamino, cyclohexylcarbonylamino, spiro[2.3]hexylcarbonylamino, spiro[3.3]heptylcarbonylamino, bicyclo[1.1.1]pentylcarbonylamino) optionally substituted by 1 to 3 substituents selected from
  (i) a halogen atom (e.g., a fluorine atom),
  (ii) a cyano group,
  (iii) a hydroxy group,
  (iv) an optionally halogenated $C_{1-6}$ alkyl group (e.g., methyl, difluoromethyl, trifluoromethyl),
  (v) a $C_{1-6}$ alkoxy group (e.g., methoxy), and
  (vi) a $C_{6-14}$ aryl group (e.g., phenyl) optionally substituted by 1 to 3 halogen atoms (e.g., a fluorine atom),
(k) a $C_{3-10}$ cycloalkoxy-carbonylamino group (e.g., cyclopropoxycarbonylamino),
(l) a N-5- or 6-membered monocyclic aromatic heterocyclyl-N—$C_{1-6}$ alkyl-carbonyl-amino group (e.g., N-pyridyl-N-acetylamino) optionally substituted by 1 to 3 halogen atoms (e.g., a fluorine atom),
(m) a $C_{1-6}$ alkylsulfonylamino group (e.g., ethylsulfonylamino) optionally substituted by 1 to 3 halogen atoms (e.g., a fluorine atom),
(n) a $C_{3-10}$ cycloalkylsulfonylamino group (e.g., cyclopropylsulfonylamino),
(o) a $C_{1-6}$ alkylamino group (e.g., ethylamino) optionally substituted by 1 to 3 halogen atoms (e.g., a fluorine atom),
(p) a $C_{6-14}$ aryl group (e.g., phenyl) optionally substituted by 1 to 3 halogen atoms (e.g., a fluorine atom),
(q) a $C_{6-14}$ aryl-carbonylamino group (e.g., phenylcarbonylamino) optionally substituted by 1 to 3 substituents selected from
  (i) a halogen atom (e.g., a fluorine atom, a chlorine atom),
  (ii) a cyano group, and
  (iii) an optionally halogenated $C_{1-6}$ alkyl group (e.g., trifluoromethyl),
(r) a $C_{7-16}$ aralkyl-carbonylamino group (e.g., benzylcarbonylamino),
(s) a $C_{7-16}$ aralkyl-oxycarbonylamino group (e.g., benzyloxycarbonylamino),
(t) a 5- to 14-membered aromatic heterocyclic group (preferably a 5- or 6-membered monocyclic aromatic heterocyclic group (e.g., pyrazolyl, triazolyl, oxazolyl, oxadiazolyl, pyridyl) or a 8- to 14-membered fused polycyclic (preferably bi- or tri-cyclic) aromatic heterocyclic group (e.g., indazolyl, benzimidazolyl, benzotriazolyl, triazolopyridyl (e.g., [1,2,4]triazolo[4,3-a]pyridyl))) optionally substituted by 1 to 3 substituents selected from
  (i) a $C_{1-6}$ alkyl group (e.g., methyl, ethyl), and
  (ii) a $C_{3-10}$ cycloalkyl group (e.g., cyclopropyl),
(u) a 3- to 14-membered non-aromatic heterocyclic group (preferably a 3- to 8-membered monocyclic non-aromatic heterocyclic group (e.g., pyrrolidinyl, piperidyl, morpholinyl, tetrahydrooxazinyl, hexahydropyrimidinyl, oxazolidinyl, imidazolidinyl, 1,1-dioxido-1,2-thiazolidinyl) or a 9- to 14-membered fused polycyclic (preferably bi- or tri-cyclic) non-aromatic heterocyclic group (e.g., dihydroisoindolyl, 5-azaspiro[2.4]heptyl)) optionally substituted by 1 to 6 substituents selected from
  (i) an oxo group,
  (ii) a $C_{1-6}$ alkyl group (e.g., methyl), and
  (iii) a halogen atom (e.g., a fluorine atom),
(v) a 5- to 14-membered aromatic heterocyclylcarbonylamino group (preferably a 5- or 6-membered monocyclic aromatic heterocyclylcarbonylamino group (e.g., oxazolylcarbonylamino, imidazolylcarbonylamino, pyrazolylcarbonylamino, pyridylcarbonylamino)) optionally substituted by 1 to 3 $C_{1-6}$ alkyl groups (e.g., methyl),
(w) a 3- to 14-membered non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino, tetrahydropyranylcarbonylamino)) optionally substituted by 1 to 3 substituents selected from
  (i) a $C_{1-6}$ alkyl group (e.g., methyl, ethyl), and
  (ii) a $C_{6-14}$ aryl group (e.g., phenyl),
(x) a 3- to 14-membered non-aromatic heterocyclylcarbonyloxy group (preferably a 3- to 8-membered monocyclic non-aromatic heterocyclylcarbonyloxy group (e.g., azetidinylcarbonyloxy, pyrrolidinylcarbonyloxy, piperidylcarbonyloxy)),
(y) a 5- to 14-membered aromatic heterocyclylamino group (preferably a 5- or 6-membered monocyclic aromatic heterocyclylamino group (e.g., pyridylamino)),
(z) a $C_{6-14}$ aryloxy group (e.g., phenyloxy) optionally substituted by 1 to 3 halogen atoms (e.g., a fluorine atom),
(aa) a cyano group, and
(bb) a 5- to 14-membered aromatic heterocyclyloxy group (preferably a 5- or 6-membered monocyclic aromatic heterocyclyloxy group (e.g., pyridyloxy)) optionally substituted by 1 to 3 halogen atoms (e.g., a fluorine atom),
(2) a $C_{6-14}$ aryl group (e.g., phenyl) optionally substituted by 1 to 3 substituents selected from
  (a) a halogen atom (e.g., a fluorine atom, a chlorine atom, a bromine atom),
  (b) a cyano group,
  (c) an optionally halogenated $C_{1-6}$ alkyl group (e.g., trifluoromethyl, difluoromethyl), (d) an optionally halogenated $C_{1-6}$ alkoxy group (e.g., methoxy, ethoxy, difluoromethoxy, trifluoromethoxy, difluoroethoxy),
(e) a $C_{1-6}$ alkylsulfonyl group (e.g., methylsulfonyl),
(f) a $C_{6-14}$ aryl group (e.g., phenyl) optionally substituted by 1 to 3 substituents selected from
  (i) a cyano group,
  (ii) an optionally halogenated $C_{1-6}$ alkyl group (e.g., methyl, trifluoromethyl, difluoromethyl),
  (iii) a $C_{1-6}$ alkoxy group (e.g., methoxy, ethoxy) optionally substituted by 1 to 3 substituents selected from a halogen atom (e.g., a fluorine atom), a $C_{1-6}$ alkoxy group (e.g., methoxy) and a cyano group,
  (iv) a $C_{1-6}$ alkylsulfonyl group (e.g., methylsulfonyl),
  (v) a halogen atom (e.g., a fluorine atom, a chlorine atom),
  (vi) a $C_{3-10}$ cycloalkyl group (e.g., cyclopropyl) optionally substituted by 1 to 3 cyano groups, and
  (vii) a 3- to 14-membered non-aromatic heterocyclylcarbonyl group (preferably a 3- to 8-membered monocyclic non-aromatic heterocyclylcarbonyl group (e.g., pyrrolidinylcarbonyl)),
(g) a $C_{7-16}$ aralkyl group (e.g., benzyl),
(h) a 5- to 14-membered aromatic heterocyclic group (preferably a 5- or 6-membered monocyclic aromatic heterocyclic group (e.g., pyrazolyl, pyridyl, pyrimidinyl) or a 8- to 14-membered fused polycyclic (preferably bi- or tri-cyclic) aromatic heterocyclic group (e.g., furopyridyl (e.g., furo[2,3-b]pyridyl), imidazopyridyl (e.g., imidazo[1,2-a]pyridyl))) optionally substituted by 1 to 3 substituents selected from
  (i) a halogen atom (e.g., a fluorine atom, a chlorine atom, a bromine atom),
  (ii) a $C_{1-6}$ alkyl group (e.g., methyl, ethyl) optionally substituted by 1 to 3 substituents selected from a halogen atom (e.g., a fluorine atom) and a pyridyl group,
  (iii) an optionally halogenated $C_{1-6}$ alkoxy group (e.g., methoxy, ethoxy, isopropoxy, trifluoroethoxy),
  (iv) a $C_{3-10}$ cycloalkyl group (e.g., cyclopropyl),
  (v) a $C_{1-6}$ alkylsulfonyl group (e.g., methylsulfonyl), and
  (vi) a 3- to 14-membered non-aromatic heterocyclic group (preferably a 3- to 8-membered monocyclic non-aromatic heterocyclic group (e.g., tetrahydropyranyl)),
(i) a 3- to 14-membered non-aromatic heterocyclic group (preferably a 3- to 8-membered monocyclic non-aromatic heterocyclic group (e.g., pyrrolidinyl, piperidyl) or a 9- to 14-membered fused polycyclic (preferably bi- or tri-cyclic) non-aromatic heterocyclic group (e.g., dihydrobenzofuryl)) optionally substituted by 1 to 3 substituents selected from
  (i) an oxo group,
  (ii) a $C_{1-6}$ alkoxy-carbonyl group (e.g., tert-butoxycarbonyl), and
  (iii) an optionally halogenated $C_{1-6}$ alkyl-carbonyl group (e.g., pentafluoropropionyl),
(j) a 4,4,5,5-tetramethyl-1,3,2-dioxaborolan-2-yl group,
(k) a $C_{3-10}$ cycloalkenyl group (e.g., cyclohexenyl) optionally substituted by 1 to 3 $C_{1-6}$ alkoxy-carbonylamino groups (e.g., tert-butoxycarbonylamino), and
(l) a $C_{3-10}$ cycloalkyl group (e.g., cyclohexyl) optionally substituted by 1 to 3 substituents selected from
  (i) a $C_{1-6}$ alkyl-carbonylamino group (e.g., propanoylamino) optionally substituted by 1 to 5 halogen atoms (e.g., a fluorine atom), and
  (ii) a $C_{1-6}$ alkoxy-carbonylamino group (e.g., tert-butoxycarbonylamino),
(3) a 5- to 14-membered aromatic heterocyclic group (preferably a 5- or 6-membered monocyclic aromatic heterocyclic group (e.g., pyridyl, isoxazolyl, pyrazolyl, pyrrolyl, thiazolyl, thienyl) or a 8- to 14-membered fused polycyclic (preferably bi- or tri-cyclic) aromatic heterocyclic group (e.g., pyrazolopyridyl (e.g., pyrazolo[1,5-a]pyridyl), imidazopyridyl (e.g., imidazo[1,2-a]pyridyl))) optionally substituted by 1 to 3 substituents selected from
  (a) a halogen atom (e.g., a fluorine atom, a chlorine atom, a bromine atom),
  (b) a $C_{1-6}$ alkyl group (e.g., methyl, isopropyl) optionally substituted by 1 to 3 substituents selected from
    (i) a halogen atom (e.g., a fluorine atom), and
    (ii) a hydroxy group,
  (c) a $C_{3-10}$ cycloalkyl group (e.g., cyclopropyl, cyclohexyl) optionally substituted by 1 to 3 substituents selected from
    (i) a halogen atom (e.g., a fluorine atom),
    (ii) a $C_{1-6}$ alkoxy-carbonylamino group (e.g., tert-butoxycarbonylamino),
    (iii) a $C_{1-6}$ alkyl-carbonylamino group (e.g., propanoylamino) optionally substituted by 1 to 5 halogen atoms (e.g., a fluorine atom), and
    (iv) a mono- or di-$C_{1-6}$ alkylamino group (e.g., propylamino) optionally substituted by 1 to 5 halogen atoms (e.g., a fluorine atom),
  (d) a $C_{4-10}$ cycloalkenyl group (e.g., cyclohexenyl) optionally substituted by 1 to 3 substituents selected from
    (i) a halogen atom (e.g., a fluorine atom), and
    (ii) a $C_{1-6}$ alkoxy-carbonylamino group (e.g., tert-butoxycarbonylamino),
  (e) a $C_{6-14}$ aryl group (e.g., phenyl) optionally substituted by 1 to 3 substituents selected from
    (i) a cyano group,
    (ii) a halogen atom (e.g., a fluorine atom, a chlorine atom), and
    (iii) a $C_{1-6}$ alkoxy group (e.g., methoxy),
  (f) a 5- to 14-membered aromatic heterocyclic group (preferably a 5- or 6-membered monocyclic aromatic heterocyclic group (e.g., pyridyl, pyrazolyl) or a 8- to 14-membered fused polycyclic (preferably bi- or tri-cyclic) aromatic heterocyclic group (e.g., pyrazolopyridyl (e.g., pyrazolo[1,5-a]pyridyl))) optionally substituted by 1 to 3 substituents selected from
    (i) a halogen atom (e.g., a fluorine atom), and
    (ii) an optionally halogenated $C_{1-6}$ alkyl group (e.g., methyl, difluoromethyl),
  (g) a 3- to 14-membered non-aromatic heterocyclic group (preferably a 3- to 8-membered monocyclic non-aromatic heterocyclic group (e.g., tetrahydropyranyl, dihydropyranyl, tetrahydropyridyl, piperidyl)) optionally substituted by 1 to 3 substituents selected from
    (i) a $C_{1-6}$ alkoxy-carbonyl group (e.g., tert-butoxycarbonyl),
    (ii) an optionally halogenated $C_{1-6}$ alkyl-carbonyl group (e.g., pentafluoropropanoyl), and
    (iii) an optionally halogenated $C_{1-6}$ alkyl group (e.g., pentafluoropropyl),
  (h) a mono- or di-$C_{1-6}$ alkyl-carbamoyl group (e.g., methylcarbamoyl, ethylcarbamoyl) optionally substituted by 1 to 3 substituents selected from
    (i) a halogen atom (e.g., a fluorine atom), and
    (ii) a $C_{3-10}$ cycloalkyl group (e.g., cyclopropyl),
  (i) a 3- to 14-membered non-aromatic heterocyclylcarbonyl group (preferably a 3- to 8-membered monocyclic non-aromatic heterocyclylcarbonyl group (e.g., piperidylcarbonyl)) optionally substituted by 1 to 3 halogen atoms (e.g., a fluorine atom), and
(j) a $C_{6-14}$ aryl-carbonyl group (e.g., benzoyl),
(4) a 3- to 14-membered non-aromatic heterocyclic group (preferably a 3- to 8-membered monocyclic non-aromatic heterocyclic group, more preferably a 5- or 6-membered monocyclic non-aromatic heterocyclic group (including a 6-membered monocyclic non-aromatic heterocyclic group and a 5- or 6-membered monocyclic nitrogen-containing non-aromatic heterocyclic group) (e.g., tetrahydropyranyl, piperidyl, morpholinyl, pyrrolidinyl)) optionally substituted by 1 to 3 substituents selected from
  (a) a halogen atom (e.g., a fluorine atom),
  (b) an oxo group,
  (c) an amino group,
  (d) an optionally halogenated $C_{1-6}$ alkyl group (e.g., tetrafluoropropyl, pentafluoropropyl, heptafluorobutyl),
  (e) a $C_{1-6}$ alkylamino group (e.g., ethylamino, propylamino, butylamino) optionally substituted by 1 to 7 halogen atoms (e.g., a fluorine atom),
  (f) an optionally halogenated $C_{1-6}$ alkyl-carbonyl group (e.g., acetyl, propanoyl, difluoroacetyl, difluoropropanoyl, pentafluoropropanoyl),
  (g) a $C_{1-6}$ alkyl-carbonylamino group (e.g., propanoylamino, butanoylamino, pivaloylamino) optionally substituted by 1 to 5 halogen atoms (e.g., a fluorine atom),
  (h) a $C_{1-6}$ alkoxy-carbonyl group (e.g., methoxycarbonyl, ethoxycarbonyl, isopropoxycarbonyl, tert-butoxycarbonyl),
  (i) a $C_{1-6}$ alkoxy-carbonylamino group (e.g., tert-butoxycarbonylamino) optionally substituted by 1 to 3 halogen atoms (e.g., a fluorine atom),
  (j) a $C_{1-6}$ alkylsulfonyl group (e.g., ethylsulfonyl) optionally substituted by 1 to 3 halogen atoms (e.g., a fluorine atom),
  (k) a $C_{3-10}$ cycloalkyl-carbonyl group (e.g., cyclopropylcarbonyl, cyclopentylcarbonyl) optionally substituted by 1 to 3 substituents selected from
    (i) a halogen atom (e.g., a fluorine atom), and
    (ii) an optionally halogenated $C_{1-6}$ alkyl group (e.g., trifluoromethyl),
  (l) a $C_{3-10}$ cycloalkyl-carbonylamino group (e.g., cyclopropylcarbonylamino, cyclobutylcarbonylamino) optionally substituted by 1 to 3 optionally halogenated $C_{1-6}$ alkyl groups (e.g., trifluoromethyl),
  (m) a $C_{3-10}$ cycloalkylsulfonyl group (e.g., cyclopropylsulfonyl),
  (n) a $C_{6-14}$ aryl group (e.g., phenyl) optionally substituted by 1 to 3 halogen atoms (e.g., a fluorine atom),
  (o) a $C_{7-16}$ aralkyl group (e.g., benzyl),
  (p) a $C_{6-14}$ aryl-carbonyl group (e.g., benzoyl),
  (q) a $C_{6-14}$ aryl-carbonylamino group (e.g., phenylcarbonylamino) optionally substituted by 1 to 3 halogen atoms (e.g., a chlorine atom),
  (r) a $C_{6-14}$ arylsulfonyl group (e.g., phenylsulfonyl) optionally substituted by 1 to 3 substituents selected from
    (i) a $C_{1-6}$ alkyl group (e.g., methyl), and
    (ii) a halogen atom (e.g., a fluorine atom),
  (s) a 3- to 14-membered non-aromatic heterocyclic group (preferably a 3- to 8-membered monocyclic non-aromatic heterocyclic group (e.g., pyrrolidinyl, piperidyl)) optionally substituted by 1 to 3 substituents selected from
    (i) an oxo group, and
    (ii) a $C_{1-6}$ alkyl-carbonyl group (e.g., acetyl),
  (t) a 5- to 14-membered aromatic heterocyclic group (preferably a 5- or 6-membered monocyclic aromatic heterocyclic group (e.g., pyrazolyl, pyridyl) or a 8- to 14-membered fused polycyclic (preferably bi- or tricyclic) aromatic heterocyclic group (e.g., benzotriazolyl)) optionally substituted by 1 to 3 substituents selected from
    (i) a halogen atom (e.g., a chlorine atom, a fluorine atom), and
    (ii) a $C_{1-6}$ alkyl group (e.g., methyl),
  (u) a mono- or di-$C_{1-6}$ alkyl-carbamoyl group (e.g., ethylcarbamoyl, propylcarbamoyl, diethylcarbamoyl) optionally substituted by 1 to 5 halogen atoms (e.g., a fluorine atom),
  (v) a $C_{7-16}$ aralkyloxy-carbonyl group (e.g., benzyloxycarbonyl), and
  (w) a $C_{6-14}$ aryloxy group (e.g., phenyloxy) optionally substituted by 1 to 3 halogen atoms (e.g., a fluorine atom), or
(5) a $C_{1-6}$ alkyl group (e.g., ethyl) optionally substituted by 1 to 3 substituents selected from
  (a) a $C_{6-14}$ aryloxy group (e.g., phenyloxy), and
  (b) a $C_{7-16}$ aralkyloxy group (e.g., benzyloxy);
$R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom (e.g., a fluorine atom); and
L is
(1) a bond, or
(2) a $C_{1-6}$ alkylene group (e.g., —CH$_2$—, —CH(CH$_3$)—, —CH$_2$CH$_2$—) optionally substituted by 1 to 3 $C_{6-14}$ aryl groups (e.g., phenyl).

[Compound C-2]
Compound (I) wherein
$R^1$ is
(1) a cyclohexyl group optionally substituted by 1 to 3 substituents selected from
  (a) an amino group,
  (b) a halogen atom (e.g., a fluorine atom),
  (c) a hydroxy group,
  (d) a $C_{1-6}$ alkyl group (e.g., methyl) optionally substituted by 1 to 3 substituents selected from
    (i) a $C_{1-6}$ alkoxy-carbonylamino group (e.g., tert-butoxycarbonylamino), and
    (ii) a $C_{1-6}$ alkylsulfonylamino group (e.g., ethylsulfonylamino) optionally substituted by 1 to 3 halogen atoms (e.g., a fluorine atom),
  (e) a $C_{1-6}$ alkoxy group (e.g., butoxy),
  (f) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
    (i) a halogen atom (e.g., a fluorine atom),
    (ii) a cyano group,
    (iii) a hydroxy group,
    (iv) a $C_{1-6}$ alkoxy group (e.g., methoxy),
    (v) a $C_{3-10}$ cycloalkyl group (e.g., cyclopropyl, cyclobutyl, cyclopentyl) optionally substituted by 1 to 3 substituents selected from a hydroxy group and a cyano group, and
    (vi) a $C_{6-14}$ aryl group (e.g., phenyl),
  (g) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(h) a mono- or di-$C_{1-6}$ alkyl-carbamoyloxy group (e.g., methylcarbamoyloxy),
(i) a $C_{3-10}$ cycloalkyl-carbonylamino group (the $C_{3-10}$ cycloalkyl in the $C_{3-10}$ cycloalkyl-carbonylamino group may be a bridged group or a spiro ring group. e.g., cyclopropylcarbonylamino, cyclobutylcarbonylamino, cyclohexylcarbonylamino, spiro[2.3]hexylcarbonylamino, spiro[3.3]heptylcarbonylamino, bicyclo[1.1.1]pentylcarbonylamino) optionally substituted by 1 to 3 substituents selected from
 (i) a halogen atom (e.g., a fluorine atom),
 (ii) a cyano group,
 (iii) a hydroxy group,
 (iv) an optionally halogenated $C_{1-6}$ alkyl group (e.g., methyl, difluoromethyl, trifluoromethyl),
 (v) a $C_{1-6}$ alkoxy group (e.g., methoxy), and
 (vi) a $C_{6-14}$ aryl group (e.g., phenyl) optionally substituted by 1 to 3 halogen atoms (e.g., a fluorine atom),
(j) a $C_{3-10}$ cycloalkoxy-carbonylamino group (e.g., cyclopropoxycarbonylamino),
(k) a N-5- or 6-membered monocyclic aromatic heterocyclyl-N—$C_{1-6}$ alkyl-carbonyl-amino group (e.g., N-pyridyl-N-acetylamino) optionally substituted by 1 to 3 halogen atoms (e.g., a fluorine atom),
(l) a $C_{1-6}$ alkylsulfonylamino group (e.g., ethylsulfonylamino) optionally substituted by 1 to 3 halogen atoms (e.g., a fluorine atom),
(m) a $C_{3-10}$ cycloalkylsulfonylamino group (e.g., cyclopropylsulfonylamino),
(n) a $C_{1-6}$ alkylamino group (e.g., ethylamino) optionally substituted by 1 to 3 halogen atoms (e.g., a fluorine atom),
(o) a $C_{6-14}$ aryl-carbonylamino group (e.g., phenylcarbonylamino) optionally substituted by 1 to 3 substituents selected from
 (i) a halogen atom (e.g., a fluorine atom, a chlorine atom),
 (ii) a cyano group, and
 (iii) an optionally halogenated $C_{1-6}$ alkyl group (e.g., trifluoromethyl),
(p) a $C_{7-16}$ aralkyl-carbonylamino group (e.g., benzylcarbonylamino),
(q) a $C_{7-16}$ aralkyl-oxycarbonylamino group (e.g., benzyloxycarbonylamino),
(r) a 5- to 14-membered aromatic heterocyclic group (preferably a 5- or 6-membered monocyclic aromatic heterocyclic group (e.g., pyrazolyl, triazolyl) or a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl, ethyl),
(s) a 3- to 14-membered non-aromatic heterocyclic group (preferably a 3- to 8-membered monocyclic non-aromatic heterocyclic group (e.g., pyrrolidinyl, piperidyl, morpholinyl, tetrahydrooxazinyl, hexahydropyrimidinyl, oxazolidinyl, imidazolidinyl, 1,1-dioxido-1,2-thiazolidinyl) or a 9- to 14-membered fused polycyclic (preferably bi- or tri-cyclic) non-aromatic heterocyclic group (e.g., dihydroisoindolyl, 5-azaspiro[2.4]heptyl)) optionally substituted by 1 to 3 substituents selected from
 (i) an oxo group, and
 (ii) a $C_{1-6}$ alkyl group (e.g., methyl),
(t) a 5- to 14-membered aromatic heterocyclylcarbonylamino group (preferably a 5- or 6-membered monocyclic aromatic heterocyclylcarbonylamino group (e.g., oxazolylcarbonylamino, imidazolylcarbonylamino, pyrazolylcarbonylamino, pyridylcarbonylamino)) optionally substituted by 1 to 3 $C_{1-6}$ alkyl groups (e.g., methyl),
(u) a 3- to 14-membered non-aromatic heterocyclylcarbonylamino group (preferably a 3- to 8-membered monocyclic non-aromatic heterocyclylcarbonylamino group (e.g., oxetanylcarbonylamino, tetrahydrofurylcarbonylamino, tetrahydropyranylcarbonylamino)) optionally substituted by 1 to 3 substituents selected from
 (i) a $C_{1-6}$ alkyl group (e.g., methyl, ethyl), and
 (ii) a $C_{6-14}$ aryl group (e.g., phenyl), and
(v) a 3- to 14-membered non-aromatic heterocyclylcarbonyloxy group (preferably a 3- to 8-membered monocyclic non-aromatic heterocyclylcarbonyloxy group (e.g., azetidinylcarbonyloxy, pyrrolidinylcarbonyloxy, piperidylcarbonyloxy)),
(2) a cyclopropyl group optionally substituted by 1 to 3 substituents selected from
 (a) a mono- or di-$C_{1-6}$ alkyl-carbamoyl group (e.g., ethylcarbamoyl) optionally substituted by 1 to 3 halogen atoms (e.g., a fluorine atom), and
 (b) a $C_{6-14}$ aryl group (e.g., phenyl) optionally substituted by 1 to 3 halogen atoms (e.g., a fluorine atom),
(3) a phenyl group optionally substituted by 1 to 3 substituents selected from
 (a) a halogen atom (e.g., a fluorine atom, a chlorine atom, a bromine atom),
 (b) a cyano group,
 (c) an optionally halogenated $C_{1-6}$ alkyl group (e.g., trifluoromethyl, difluoromethyl),
 (d) an optionally halogenated $C_{1-6}$ alkoxy group (e.g., methoxy, ethoxy, difluoromethoxy, trifluoromethoxy, difluoroethoxy),
 (e) a $C_{1-6}$ alkylsulfonyl group (e.g., methylsulfonyl),
 (f) a $C_{6-14}$ aryl group (e.g., phenyl) optionally substituted by 1 to 3 substituents selected from
  (i) a cyano group,
  (ii) an optionally halogenated $C_{1-6}$ alkyl group (e.g., methyl, trifluoromethyl, difluoromethyl),
  (iii) a $C_{1-6}$ alkoxy group (e.g., methoxy, ethoxy) optionally substituted by 1 to 3 substituents selected from a halogen atom (e.g., a fluorine atom), a $C_{1-6}$ alkoxy group (e.g., methoxy) and a cyano group,
  (iv) a $C_{1-6}$ alkylsulfonyl group (e.g., methylsulfonyl),
  (v) a halogen atom (e.g., a fluorine atom, a chlorine atom),
  (vi) a $C_{3-10}$ cycloalkyl group (e.g., cyclopropyl) optionally substituted by 1 to 3 cyano groups, and
  (vii) a 3- to 14-membered non-aromatic heterocyclylcarbonyl group (preferably a 3- to 8-membered monocyclic non-aromatic heterocyclylcarbonyl group (e.g., pyrrolidinylcarbonyl)),
 (g) a $C_{7-16}$ aralkyl group (e.g., benzyl),
 (h) a 5- to 14-membered aromatic heterocyclic group (preferably a 5- or 6-membered monocyclic aromatic heterocyclic group (e.g., pyrazolyl, pyridyl, pyrimidinyl) or a 8- to 14-membered fused polycyclic (preferably bi- or tri-cyclic) aromatic heterocyclic group (e.g., furopyridyl (e.g., furo[2,3-b]pyridyl), imidazopyridyl (e.g., imidazo[1,2-a]pyridyl))) optionally substituted by 1 to 3 substituents selected from
  (i) a halogen atom (e.g., a fluorine atom, a chlorine atom, a bromine atom), (ii) a $C_{1-6}$ alkyl group (e.g., methyl, ethyl) optionally substituted by 1 to 3 substituents selected from a halogen atom (e.g., a fluorine atom) and a pyridyl group,
(iii) an optionally halogenated $C_{1-6}$ alkoxy group (e.g., methoxy, ethoxy, isopropoxy, trifluoroethoxy),
(iv) a $C_{3-10}$ cycloalkyl group (e.g., cyclopropyl),
(v) a $C_{1-6}$ alkylsulfonyl group (e.g., methylsulfonyl), and
(vi) a 3- to 14-membered non-aromatic heterocyclic group (preferably a 3- to 8-membered monocyclic non-aromatic heterocyclic group (e.g., tetrahydropyranyl)),
(i) a 3- to 14-membered non-aromatic heterocyclic group (preferably a 3- to 8-membered monocyclic non-aromatic heterocyclic group (e.g., pyrrolidinyl) or a 9- to 14-membered fused polycyclic (preferably bi- or tricyclic) non-aromatic heterocyclic group (e.g., dihydrobenzofuryl)) optionally substituted by 1 to 3 oxo groups, and
(j) a 4,4,5,5-tetramethyl-1,3,2-dioxaborolan-2-yl group,
(4) a pyridyl group optionally substituted by 1 to 3 substituents selected from
(a) a halogen atom (e.g., a fluorine atom, a chlorine atom),
(b) an optionally halogenated $C_{1-6}$ alkyl group (e.g., trifluoromethyl),
(c) a $C_{6-14}$ aryl group (e.g., phenyl) optionally substituted by 1 to 3 cyano groups, and
(d) a 5- to 14-membered aromatic heterocyclic group (preferably a 5- or 6-membered monocyclic aromatic heterocyclic group (e.g., pyrazolyl)) optionally substituted by 1 to 3 optionally halogenated $C_{1-6}$ alkyl groups (e.g., difluoromethyl),
(5) an isoxazolyl group optionally substituted by 1 to 3 substituents selected from
(a) a $C_{3-10}$ cycloalkyl group (e.g., cyclopropyl), and
(b) a $C_{1-6}$ alkyl group (e.g., methyl),
(6) a pyrazolyl group optionally substituted by 1 to 3 substituents selected from
(a) a $C_{1-6}$ alkyl group (e.g., methyl),
(b) a halogen atom (e.g., a bromine atom),
(c) a $C_{6-14}$ aryl group (e.g., phenyl) optionally substituted by 1 to 3 substituents selected from
(i) a cyano group,
(ii) a halogen atom (e.g., a fluorine atom, a chlorine atom), and
(iii) a $C_{1-6}$ alkoxy group (e.g., methoxy),
(d) a $C_{3-10}$ cycloalkyl group (e.g., cyclohexyl) optionally substituted by 1 to 3 halogen atoms (e.g., a fluorine atom),
(e) a $C_{4-10}$ cycloalkenyl group (e.g., cyclohexenyl) optionally substituted by 1 to 3 halogen atoms (e.g., a fluorine atom),
(f) a 5- to 14-membered aromatic heterocyclic group (preferably a 5- or 6-membered monocyclic aromatic heterocyclic group (e.g., pyridyl, pyrazolyl) or a 8- to 14-membered fused polycyclic (preferably bi- or tricyclic) aromatic heterocyclic group (e.g., pyrazolopyridyl (e.g., pyrazolo[1,5-a]pyridyl))) optionally substituted by 1 to 3 substituents selected from
(i) a halogen atom (e.g., a fluorine atom), and
(ii) a $C_{1-6}$ alkyl group (e.g., methyl), and
(g) a 3- to 14-membered non-aromatic heterocyclic group (preferably a 3- to 8-membered monocyclic non-aromatic heterocyclic group (e.g., tetrahydropyranyl, dihydropyranyl)),
(7) a pyrrolyl group optionally substituted by 1 to 3 $C_{1-6}$ alkyl groups (e.g., methyl),
(8) a thiazolyl group,
(9) a thienyl group optionally substituted by 1 to 3 halogen atoms (e.g., a chlorine atom),
(10) a pyrazolopyridyl group (e.g., pyrazolo[1,5-a]pyridyl),
(11) a tetrahydropyranyl group optionally substituted by 1 to 3 substituents selected from
(a) an amino group,
(b) a $C_{1-6}$ alkylamino group (e.g., ethylamino, propylamino, butylamino) optionally substituted by 1 to 7 halogen atoms (e.g., a fluorine atom),
(c) a $C_{1-6}$ alkyl-carbonylamino group (e.g., propanoylamino, butanoylamino, pivaloylamino) optionally substituted by 1 to 5 halogen atoms (e.g., a fluorine atom),
(d) a $C_{1-6}$ alkoxy-carbonylamino group (e.g., tert-butoxycarbonylamino) optionally substituted by 1 to 3 halogen atoms (e.g., a fluorine atom),
(e) a $C_{3-10}$ cycloalkyl-carbonylamino group (e.g., cyclopropylcarbonylamino, cyclobutylcarbonylamino) optionally substituted by 1 to 3 optionally halogenated $C_{1-6}$ alkyl groups (e.g., trifluoromethyl),
(f) a $C_{6-14}$ aryl-carbonylamino group (e.g., phenylcarbonylamino) optionally substituted by 1 to 3 halogen atoms (e.g., a chlorine atom),
(g) a 3- to 14-membered non-aromatic heterocyclic group (preferably a 3- to 8-membered monocyclic non-aromatic heterocyclic group (e.g., pyrrolidinyl, piperidyl)) optionally substituted by 1 to 3 oxo groups, and
(h) a $C_{7-16}$ aralkyl group (e.g., benzyl),
(12) a piperidyl group optionally substituted by 1 to 3 substituents selected from
(a) a $C_{1-6}$ alkyl-carbonyl group (e.g., acetyl),
(b) a $C_{1-6}$ alkoxy-carbonyl group (e.g., methoxycarbonyl, ethoxycarbonyl, isopropoxycarbonyl, tert-butoxycarbonyl),
(c) a $C_{3-10}$ cycloalkyl-carbonyl group (e.g., cyclopropylcarbonyl),
(d) a $C_{3-10}$ cycloalkylsulfonyl group (e.g., cyclopropylsulfonyl), and
(e) a $C_{6-14}$ aryl group (e.g., phenyl),
(13) a morpholinyl group optionally substituted by 1 to 3 substituents selected from
(a) an optionally halogenated $C_{1-6}$ alkyl group (e.g., tetrafluoropropyl, pentafluoropropyl, heptafluorobutyl),
(b) a $C_{1-6}$ alkoxy-carbonyl group (e.g., methoxycarbonyl, isopropoxycarbonyl, tert-butoxycarbonyl),
(c) a $C_{3-10}$ cycloalkyl-carbonyl group (e.g., cyclopropylcarbonyl, cyclopentylcarbonyl),
(d) a $C_{3-10}$ cycloalkylsulfonyl group (e.g., cyclopropylsulfonyl),
(e) a $C_{6-14}$ arylsulfonyl group (e.g., phenylsulfonyl) optionally substituted by 1 to 3 substituents selected from
(i) a $C_{1-6}$ alkyl group (e.g., methyl), and
(ii) a halogen atom (e.g., a fluorine atom), and
(f) a $C_{1-6}$ alkylsulfonyl group (e.g., ethylsulfonyl) optionally substituted by 1 to 3 halogen atoms (e.g., a fluorine atom),
(14) a pyrrolidinyl group optionally substituted by 1 to 3 substituents selected from
(a) a halogen atom (e.g., a fluorine atom),
(b) an oxo group,
(c) a $C_{1-6}$ alkoxy-carbonyl group (e.g., tert-butoxycarbonyl),
(d) a $C_{6-14}$ aryl-carbonyl group (e.g., benzoyl), (e) a $C_{3-10}$ cycloalkyl-carbonyl group (e.g., cyclopropylcarbonyl),
(f) a $C_{1-6}$ alkylsulfonyl group (e.g., ethylsulfonyl) optionally substituted by 1 to 3 halogen atoms (e.g., a fluorine atom),
(g) a $C_{6-14}$ arylsulfonyl group (e.g., phenylsulfonyl) optionally substituted by 1 to 3 halogen atoms (e.g., a fluorine atom), and
(h) a $C_{3-10}$ cycloalkylsulfonyl group (e.g., cyclopropylsulfonyl), or
(15) a $C_{1-6}$ alkyl group (e.g., ethyl) optionally substituted by 1 to 3 substituents selected from
(a) a $C_{6-14}$ aryloxy group (e.g., phenyloxy), and
(b) a $C_{7-16}$ aralkyloxy group (e.g., benzyloxy);

$R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom (e.g., a fluorine atom); and
L is
(1) a bond, or
(2) a $C_{1-6}$ alkylene group (e.g., —$CH_2$—, —$CH(CH_3)$—, —$CH_2CH_2$—) optionally substituted by 1 to 3 $C_{6-14}$ aryl groups (e.g., phenyl).

[Compound D-2]
Compound (I) wherein
$R^1$ is
(1) a cyclohexyl group optionally substituted by 1 to 3 substituents selected from
(a) an amino group,
(b) a halogen atom (e.g., a fluorine atom),
(c) a hydroxy group,
(d) a $C_{1-6}$ alkyl group (e.g., methyl) optionally substituted by 1 to 3 substituents selected from
(i) a $C_{1-6}$ alkoxy-carbonylamino group (e.g., tert-butoxycarbonylamino), and
(ii) a $C_{1-6}$ alkylsulfonylamino group (e.g., ethylsulfonylamino) optionally substituted by 1 to 3 halogen atoms (e.g., a fluorine atom),
(e) a $C_{1-6}$ alkoxy group (e.g., butoxy),
(f) a $C_{1-6}$ alkyl-carbonylamino group (e.g., acetylamino, propanoylamino, 2-methylpropanoylamino, butanoylamino, 2,2-dimethylpropanoylamino, 3-methylbutanoylamino, pentanoylamino, hexanoylamino, heptanoylamino) optionally substituted by 1 to 5 substituents selected from
(i) a halogen atom (e.g., a fluorine atom),
(ii) a cyano group,
(iii) a hydroxy group,
(iv) a $C_{1-6}$ alkoxy group (e.g., methoxy),
(v) a $C_{3-10}$ cycloalkyl group (e.g., cyclopropyl, cyclobutyl, cyclopentyl) optionally substituted by 1 to 3 substituents selected from a hydroxy group and a cyano group, and
(vi) a phenyl group,
(g) a $C_{1-6}$ alkoxy-carbonylamino group (e.g., methoxycarbonylamino, ethoxycarbonylamino, propoxycarbonylamino, tert-butoxycarbonylamino) optionally substituted by 1 to 3 halogen atoms (e.g., a fluorine atom),
(h) a mono- or di-$C_{1-6}$ alkyl-carbamoyloxy group (e.g., methylcarbamoyloxy),
(i) a $C_{3-10}$ cycloalkyl-carbonylamino group (e.g., cyclopropylcarbonylamino, cyclobutylcarbonylamino, cyclohexylcarbonylamino) optionally substituted by 1 to 3 substituents selected from
(i) a halogen atom (e.g., a fluorine atom),
(ii) a cyano group,
(iii) a hydroxy group,
(iv) an optionally halogenated $C_{1-6}$ alkyl group (e.g., methyl, difluoromethyl, trifluoromethyl),
(v) a $C_{1-6}$ alkoxy group (e.g., methoxy), and
(vi) a phenyl group optionally substituted by 1 to 3 halogen atoms (e.g., a fluorine atom),
(j) a spiro[2.3]hexylcarbonylamino group,
(k) a spiro[3.3]heptylcarbonylamino group,
(l) a bicyclo[1.1.1]pentylcarbonylamino group optionally substituted by 1 to 3 optionally halogenated $C_{1-6}$ alkyl groups (e.g., trifluoromethyl),
(m) a $C_{3-10}$ cycloalkoxy-carbonylamino group (e.g., cyclopropoxycarbonylamino),
(n) a N-pyridyl-N—$C_{1-6}$ alkyl-carbonyl-amino group (e.g., N-pyridyl-N-acetylamino) optionally substituted by 1 to 3 halogen atoms (e.g., a fluorine atom),
(o) a $C_{1-6}$ alkylsulfonylamino group (e.g., ethylsulfonylamino) optionally substituted by 1 to 3 halogen atoms (e.g., a fluorine atom),
(p) a $C_{3-10}$ cycloalkylsulfonylamino group (e.g., cyclopropylsulfonylamino),
(q) a $C_{1-6}$ alkylamino group (e.g., ethylamino) optionally substituted by 1 to 3 halogen atoms (e.g., a fluorine atom),
(r) a phenylcarbonylamino group optionally substituted by 1 to 3 substituents selected from
(i) a halogen atom (e.g., a fluorine atom, a chlorine atom),
(ii) a cyano group, and
(iii) an optionally halogenated $C_{1-6}$ alkyl group (e.g., trifluoromethyl),
(s) a benzylcarbonylamino group,
(t) a benzyloxycarbonylamino group,
(u) a pyrazolyl group optionally substituted by 1 to 3 $C_{1-6}$ alkyl groups (e.g., methyl, ethyl),
(v) a triazolyl group,
(w) an indazolyl group
(x) a pyrrolidinyl group optionally substituted by 1 to 3 oxo groups,
(y) a piperidyl group optionally substituted by 1 to 3 oxo groups,
(z) a morpholinyl group optionally substituted by 1 to 3 oxo groups,
(aa) a tetrahydrooxazinyl group optionally substituted by 1 to 3 oxo groups,
(bb) a hexahydropyrimidinyl group optionally substituted by 1 to 3 oxo groups,
(cc) an oxazolidinyl group optionally substituted by 1 to 3 oxo groups,
(dd) an imidazolidinyl group optionally substituted by 1 to 3 substituents selected from
(i) an oxo group, and
(ii) a $C_{1-6}$ alkyl group (e.g., methyl),
(ee) a 1,1-dioxido-1,2-thiazolidinyl group,
(ff) a dihydroisoindolyl group optionally substituted by 1 to 3 oxo groups,
(gg) a 5-azaspiro[2.4]heptyl group optionally substituted by 1 to 3 oxo groups,
(hh) an oxazolylcarbonylamino group,
(ii) an imidazolylcarbonylamino group optionally substituted by 1 to 3 $C_{1-6}$ alkyl groups (e.g., methyl),
(jj) a pyrazolylcarbonylamino group optionally substituted by 1 to 3 $C_{1-6}$ alkyl groups (e.g., methyl),
(kk) a pyridylcarbonylamino group,
(ll) an oxetanylcarbonylamino group optionally substituted by 1 to 3 substituents selected from
(i) a $C_{1-6}$ alkyl group (e.g., methyl, ethyl), and
(ii) a phenyl group, (mm) a tetrahydrofurylcarbonylamino group,
(nn) a tetrahydropyranylcarbonylamino group,
(oo) an azetidinylcarbonyloxy group,
(pp) a pyrrolidinylcarbonyloxy group, and
(qq) a piperidylcarbonyloxy group,
(2) a cyclopropyl group optionally substituted by 1 to 3 substituents selected from
  (a) a mono- or di-$C_{1-6}$ alkyl-carbamoyl group (e.g., ethylcarbamoyl) optionally substituted by 1 to 3 halogen atoms (e.g., a fluorine atom), and
  (b) a phenyl group optionally substituted by 1 to 3 halogen atoms (e.g., a fluorine atom),
(3) a phenyl group optionally substituted by 1 to 3 substituents selected from
  (a) a halogen atom (e.g., a fluorine atom, a chlorine atom, a bromine atom),
  (b) a cyano group,
  (c) an optionally halogenated $C_{1-6}$ alkyl group (e.g., trifluoromethyl, difluoromethyl),
  (d) an optionally halogenated $C_{1-6}$ alkoxy group (e.g., methoxy, ethoxy, difluoromethoxy, trifluoromethoxy, difluoroethoxy),
  (e) a $C_{1-6}$ alkylsulfonyl group (e.g., methylsulfonyl),
  (f) a phenyl group optionally substituted by 1 to 3 substituents selected from
    (i) a cyano group,
    (ii) an optionally halogenated $C_{1-6}$ alkyl group (e.g., methyl, trifluoromethyl, difluoromethyl),
    (iii) a $C_{1-6}$ alkoxy group (e.g., methoxy, ethoxy) optionally substituted by 1 to 3 substituents selected from a halogen atom (e.g., a fluorine atom), a $C_{1-6}$ alkoxy group (e.g., methoxy) and a cyano group,
    (iv) a $C_{1-6}$ alkylsulfonyl group (e.g., methylsulfonyl),
    (v) a halogen atom (e.g., a fluorine atom, a chlorine atom),
    (vi) a $C_{3-10}$ cycloalkyl group (e.g., cyclopropyl) optionally substituted by 1 to 3 cyano groups, and
    (vii) a pyrrolidinylcarbonyl group,
  (g) a benzyl group,
  (h) a pyrazolyl group optionally substituted by 1 to 3 substituents selected from
    (i) a halogen atom (e.g., a fluorine atom, a chlorine atom, a bromine atom),
    (ii) a $C_{1-6}$ alkyl group (e.g., methyl, ethyl) optionally substituted by 1 to 3 substituents selected from a halogen atom (e.g., a fluorine atom) and a pyridyl group,
    (iii) a $C_{3-10}$ cycloalkyl group (e.g., cyclopropyl), and
    (iv) a tetrahydropyranyl group,
  (i) a pyridyl group optionally substituted by 1 to 3 substituents selected from
    (i) a halogen atom (e.g., a fluorine atom, a chlorine atom),
    (ii) an optionally halogenated $C_{1-6}$ alkyl group (e.g., ethyl, trifluoromethyl),
    (iii) a $C_{1-6}$ alkoxy group (e.g., methoxy, ethoxy, isopropoxy), and
    (iv) a $C_{1-6}$ alkylsulfonyl group (e.g., methylsulfonyl),
  (j) a pyrimidinyl group optionally substituted by 1 to 3 optionally halogenated $C_{1-6}$ alkoxy groups (e.g., trifluoroethoxy),
  (k) a furopyridyl group (e.g., furo[2,3-b]pyridyl),
  (l) an imidazopyridyl group (e.g., imidazo[1,2-a]pyridyl) optionally substituted by 1 to 3 $C_{1-6}$ alkyl groups (e.g., methyl),
  (m) a pyrrolidinyl group optionally substituted by 1 to 3 oxo groups,
  (n) a dihydrobenzofuryl group, and
  (o) a 4,4,5,5-tetramethyl-1,3,2-dioxaborolan-2-yl group,
(4) a pyridyl group optionally substituted by 1 to 3 substituents selected from
  (a) a halogen atom (e.g., a fluorine atom, a chlorine atom),
  (b) an optionally halogenated $C_{1-6}$ alkyl group (e.g., trifluoromethyl),
  (c) a phenyl group optionally substituted by 1 to 3 cyano groups, and
  (d) a pyrazolyl group optionally substituted by 1 to 3 optionally halogenated $C_{1-6}$ alkyl groups (e.g., difluoromethyl),
(5) an isoxazolyl group optionally substituted by 1 to 3 substituents selected from
  (a) a $C_{3-10}$ cycloalkyl group (e.g., cyclopropyl), and
  (b) a $C_{1-6}$ alkyl group (e.g., methyl),
(6) a pyrazolyl group optionally substituted by 1 to 3 substituents selected from
  (a) a $C_{1-6}$ alkyl group (e.g., methyl),
  (b) a halogen atom (e.g., a bromine atom),
  (c) a phenyl group optionally substituted by 1 to 3 substituents selected from
    (i) a cyano group,
    (ii) a halogen atom (e.g., a fluorine atom, a chlorine atom), and
    (iii) a $C_{1-6}$ alkoxy group (e.g., methoxy),
  (d) a $C_{3-10}$ cycloalkyl group (e.g., cyclohexyl) optionally substituted by 1 to 3 halogen atoms (e.g., a fluorine atom),
  (e) a $C_{4-10}$ cycloalkenyl group (e.g., cyclohexenyl) optionally substituted by 1 to 3 halogen atoms (e.g., a fluorine atom),
  (f) a pyridyl group optionally substituted by 1 to 3 halogen atoms (e.g., a fluorine atom),
  (g) a pyrazolyl group optionally substituted by 1 to 3 $C_{1-6}$ alkyl groups (e.g., methyl),
  (h) a pyrazolopyridyl group (e.g., pyrazolo[1,5-a]pyridyl),
  (i) a tetrahydropyranyl group, and
  (j) a dihydropyranyl group,
(7) a pyrrolyl group optionally substituted by 1 to 3 $C_{1-6}$ alkyl groups (e.g., methyl),
(8) a thiazolyl group,
(9) a thienyl group optionally substituted by 1 to 3 halogen atoms (e.g., a chlorine atom),
(10) a pyrazolopyridyl group (e.g., pyrazolo[1,5-a]pyridyl),
(11) a tetrahydropyranyl group optionally substituted by 1 to 3 substituents selected from
  (a) an amino group,
  (b) a $C_{1-6}$ alkylamino group (e.g., ethylamino, propylamino, butylamino) optionally substituted by 1 to 7 halogen atoms (e.g., a fluorine atom),
  (c) a $C_{1-6}$ alkyl-carbonylamino group (e.g., propanoylamino, butanoylamino, pivaloylamino) optionally substituted by 1 to 5 halogen atoms (e.g., a fluorine atom),
  (d) a $C_{1-6}$ alkoxy-carbonylamino group (e.g., tert-butoxycarbonylamino) optionally substituted by 1 to 3 halogen atoms (e.g., a fluorine atom),
  (e) a $C_{3-10}$ cycloalkyl-carbonylamino group (e.g., cyclopropylcarbonylamino, cyclobutylcarbonylamino) optionally substituted by 1 to 3 optionally halogenated $C_{1-6}$ alkyl groups (e.g., trifluoromethyl),
  (f) a phenylcarbonylamino group optionally substituted by 1 to 3 halogen atoms (e.g., a chlorine atom), (g) a pyrrolidinyl group optionally substituted by 1 to 3 oxo groups,
(h) a piperidyl group optionally substituted by 1 to 3 oxo groups, and
(i) a benzyl group,
(12) a piperidyl group optionally substituted by 1 to 3 substituents selected from
 (a) a $C_{1-6}$ alkyl-carbonyl group (e.g., acetyl),
 (b) a $C_{1-6}$ alkoxy-carbonyl group (e.g., methoxycarbonyl, ethoxycarbonyl, isopropoxycarbonyl, tert-butoxycarbonyl),
 (c) a $C_{3-10}$ cycloalkyl-carbonyl group (e.g., cyclopropylcarbonyl),
 (d) a $C_{3-10}$ cycloalkylsulfonyl group (e.g., cyclopropylsulfonyl), and
 (e) a phenyl group,
(13) a morpholinyl group optionally substituted by 1 to 3 substituents selected from
 (a) an optionally halogenated $C_{1-6}$ alkyl group (e.g., tetrafluoropropyl, pentafluoropropyl, heptafluorobutyl),
 (b) a $C_{1-6}$ alkoxy-carbonyl group (e.g., methoxycarbonyl, isopropoxycarbonyl, tert-butoxycarbonyl),
 (c) a $C_{3-10}$ cycloalkyl-carbonyl group (e.g., cyclopropylcarbonyl, cyclopentylcarbonyl),
 (d) a $C_{3-10}$ cycloalkylsulfonyl group (e.g., cyclopropylsulfonyl),
 (e) a phenylsulfonyl group optionally substituted by 1 to 3 substituents selected from
  (i) a $C_{1-6}$ alkyl group (e.g., methyl), and
  (ii) a halogen atom (e.g., a fluorine atom), and
 (f) a $C_{1-6}$ alkylsulfonyl group (e.g., ethylsulfonyl) optionally substituted by 1 to 3 halogen atoms (e.g., a fluorine atom),
(14) a pyrrolidinyl group optionally substituted by 1 to 3 substituents selected from
 (a) a halogen atom (e.g., a fluorine atom),
 (b) an oxo group,
 (c) a $C_{1-6}$ alkoxy-carbonyl group (e.g., tert-butoxycarbonyl),
 (d) a benzoyl group,
 (e) a $C_{3-10}$ cycloalkyl-carbonyl group (e.g., cyclopropylcarbonyl),
 (f) a $C_{1-6}$ alkylsulfonyl group (e.g., ethylsulfonyl) optionally substituted by 1 to 3 halogen atoms (e.g., a fluorine atom),
 (g) a phenylsulfonyl group optionally substituted by 1 to 3 halogen atoms (e.g., a fluorine atom), and
 (h) a $C_{3-10}$ cycloalkylsulfonyl group (e.g., cyclopropylsulfonyl), or
(15) a $C_{1-6}$ alkyl group (e.g., ethyl) optionally substituted by 1 to 3 substituents selected from
 (a) a phenyloxy group, and
 (b) a benzyloxy group;
$R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom (e.g., a fluorine atom); and
L is
(1) a bond, or
(2) a $C_{1-6}$ alkylene group (e.g., —$CH_2$—, —$CH(CH_3)$—, —$CH_2CH_2$—) optionally substituted by 1 to 3 phenyl groups.

[Compound F]
Compound (I) wherein
$R^1$ is
(1) a cyclohexyl group optionally substituted by 1 to 3 substituents selected from
 (a) a $C_{1-6}$ alkyl-carbonylamino group (e.g., acetylamino, propanoylamino) optionally substituted by 1 to 5 halogen atoms (e.g., a fluorine atom),
 (b) a $C_{1-6}$ alkoxy-carbonylamino group (e.g., methoxycarbonylamino, tert-butoxycarbonylamino) optionally substituted by 1 to 3 halogen atoms (e.g., a fluorine atom), and
 (c) a $C_{3-10}$ cycloalkyl-carbonylamino group (e.g., cyclopropylcarbonylamino) optionally substituted by 1 to 3 halogen atoms (e.g., a fluorine atom),
(2) a tetrahydropyranyl group optionally substituted by 1 to 3 $C_{1-6}$ alkylamino groups (e.g., ethylamino) optionally substituted by 1 to 3 halogen atoms (e.g., a fluorine atom), or
(3) a pyrazolyl group optionally substituted by 1 to 3 substituents selected from
 (a) a $C_{1-6}$ alkyl group (e.g., methyl), and
 (b) a phenyl group;
$R^2$ and $R^3$ are both hydrogen atoms;
$R^4$ and $R^5$ are both hydrogen atoms;
X is CH or N; and
L is a bond.
[Compound F']
Compound (I) wherein
$R^1$ is a cyclohexyl group optionally substituted by 1 to 3 substituents selected from
 (a) a halogen atom (e.g., a fluorine atom),
 (b) a $C_{1-6}$ alkyl-carbonylamino group (e.g., acetylamino, propanoylamino) optionally substituted by 1 to 5 halogen atoms (e.g., a fluorine atom),
 (c) a $C_{1-6}$ alkoxy-carbonylamino group (e.g., tert-butoxycarbonylamino) optionally substituted by 1 to 3 halogen atoms (e.g., a fluorine atom), and
 (d) a $C_{3-10}$ cycloalkyl-carbonylamino group (e.g., cyclopropylcarbonylamino) optionally substituted by 1 to 3 halogen atoms (e.g., a fluorine atom);
$R^2$ and $R^3$ are both hydrogen atoms;
$R^4$ and $R^5$ are both hydrogen atoms;
X is CH or N; and
L is a bond.

Specific examples of compound (I) include the compounds of Examples 1 to 56, 58 to 117, 119, 121 to 134 and 136 to 661.

Among them, compound (I) is preferably
(1S)—N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluorocyclopropanecarboxamide (Example 18);
N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluoroacetamide (Example 28);
N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluoropropanamide (Example 40);
N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2,3,3,3-pentafluoropropanamide (Examples 196, 489);
1,1,1-trifluoro-2-methylpropan-2-yl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate (Example 268);

N-((1R,2R)-2-(6-(5-(difluoromethyl)-1,3,4-oxadiazol-2-yl)-1-oxo-1,3-dihydro-2H-isoindol-2-yl)-5,5-difluorocyclohexyl)-2,2,3,3,3-pentafluoropropanamide (Example 469);

N-((1R,2R)-2-(6-(5-(difluoromethyl)-1,3,4-oxadiazol-2-yl)-1-oxo-1,3-dihydro-2H-isoindol-2-yl)-5,5-difluorocyclohexyl)-2,2-difluoropropanamide (Example 470);

N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2-difluoropropanamide (Example 512);

N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2,3,3,3-pentafluoropropanamide (Example 513);

N-((1S,2R)-2-(6-(5-(difluoromethyl)-1,3,4-oxadiazol-2-yl)-1-oxo-1,3-dihydro-2H-isoindol-2-yl)-5,5-difluorocyclohexyl)-2,2-difluoropropanamide (Example 516);

N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2,3,3-tetrafluoropropanamide (Example 581);

N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2-difluoropropanamide (Example 598);

N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2,3,3-tetrafluoropropanamide (Example 601);

or a salt thereof.

Compound (I) is particularly preferably
N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2,3,3,3-pentafluoropropanamide (Examples 196, 489);

N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2-difluoropropanamide (Example 512);

N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2-difluoropropanamide (Example 598);

or a salt thereof.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylarnine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The production method of compound (I) is explained below.

The raw material compound and reagent used and the compound obtained in each step in the following production method may be each in a form of a salt, and examples of such salt include those similar to the salts of compound (I) and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally —78° C.-300° C., preferably –78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature—300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogencarbonate, cesium carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminium chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminium hydride, sodium triacetoxyborohydride, sodium cyanoborohydride, diisobutylaluminium hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, examples of the reagent to be used include a combination of a Lewis acid and an acid chloride or a combination of a Lewis acid and an alkylating agent (e.g., an alkyl halide, an alcohol, an olefin etc.). Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as reagents.

When nucleophilic addition reaction by a carbo anion, nucleophilic 1,4-addition reaction (Michael addition reaction) by a carbo anion or nucleophilic substitution reaction by a carbo anion is carried out in each step, examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, a method using diphenylphosphorylazide, triphenylphosphine and azodicarboxylate, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSC HCl) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphorylazide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When halogenation reaction is carried out in each step, examples of the halogenating agent to be used include N-iodosuccinimide, N-bromosuccinimide (NBS), N-chlorosuccinimide (NCS), bromine, sulfuryl chloride, trichloroisocyanuric acid and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When alkylation reaction is carried out in each step, a electrophile (e.g., an alkyl halide etc.) and a base (e.g., an organic base, an inorganic base, a metal alkoxide, a metal amide etc.) are used as reagents.

Compound (I) can be produced according the production methods shown below. Each symbol in the formulas of the schemes is as defined above, unless otherwise specified. $P^1$ is a "protecting group for an amino group". Examples of the "protecting group for an amino group" include a tert-butoxycarbonyl group and the like, in addition to the protecting group for an amino group which is exemplified above. $R^7$ is an optionally substituted $C_{1-6}$ alkyl group (e.g., a methyl group, an ethyl group). LG is a leaving group (e.g., a chlorine atom, a bromine atom, an iodine atom).

Moreover, compound (I) can be produced by carrying out protection reaction, deprotection reaction, amidation reaction, sulfonamidation reaction, ureation reaction, carbamoylation reaction, alkylation reaction, Mitsunobu reaction, hydrogenation reaction, oxidation reaction, reduction reaction, halogenation reaction, coupling reaction, nucleophilic addition reaction by a carbo anion, Grignard reaction, deoxofluorination reaction, dehydration reaction and the like singly or two or more thereof in combination.

Production Method A

Among compound (I), compound (Ia) can be produced according to the following method.

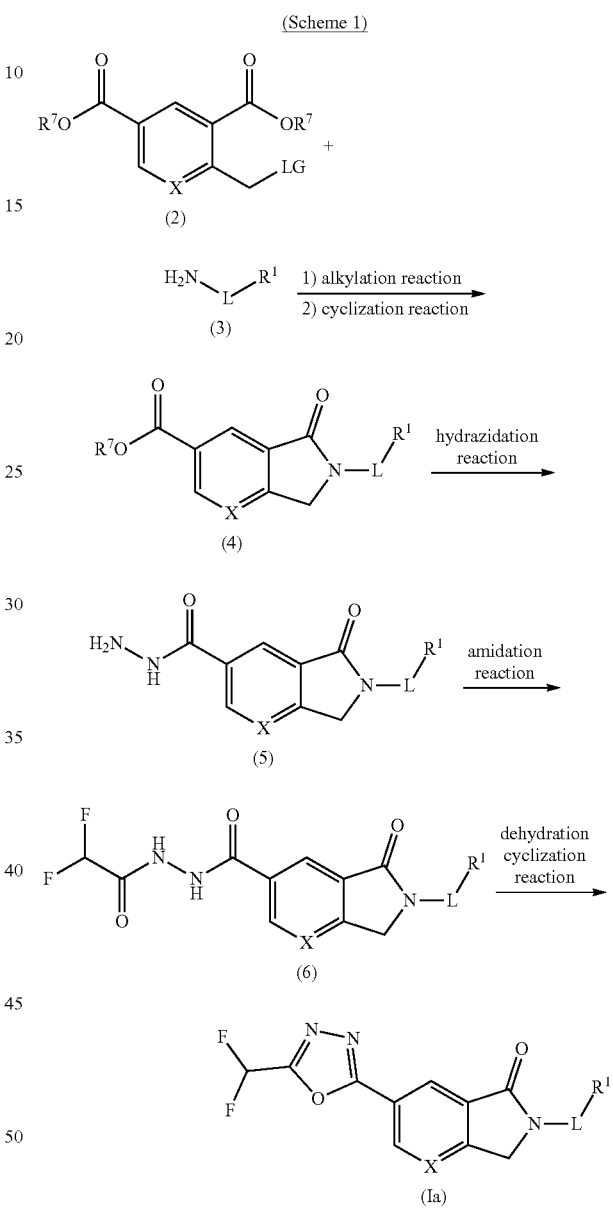

Compound (4) can be produced by subjecting compound (2) and compound (3) to an alkylation reaction, followed by a cyclization reaction. The cyclization reaction follows the alkylation reaction, or may be progressed step-by step. In latter case, the cyclization reaction can be progressed under a basic or acidic condition. Examples of the base include triethylamine, sodium methoxide and the like. Examples of the acid to be used include acetic acid and the like.

Compound (5) can be produced by subjecting compound (4) to a hydrazidation reaction. Examples of the hydraziding agent include hydrazine monohydrate and the like.

Compound (Ia) can be produced by subjecting compound (6) to a dehydration cyclization reaction. Examples of the reagent to be used include a combination of Burgess reagent or p-toluenesulfonyl chloride and a base. Examples of the base include the above-mentioned organic bases (e.g., N,N-diisopropylethylamine, triethylamine, etc.).

Production Method B

Among compound (I), compound (Ib) can be produced according to the following method.

(Scheme 2)

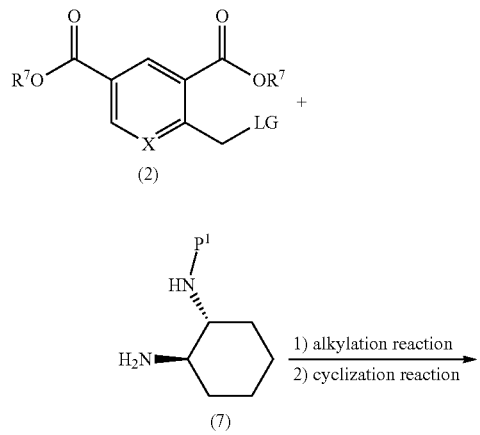

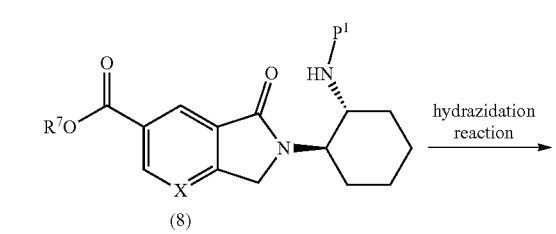

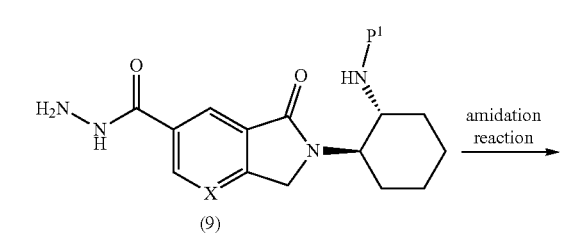

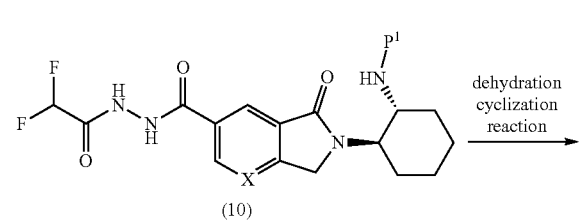

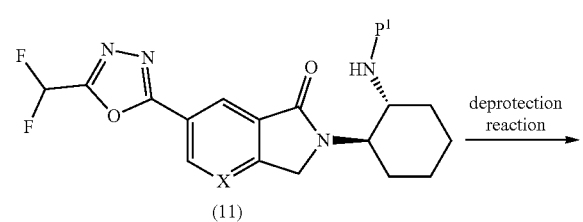

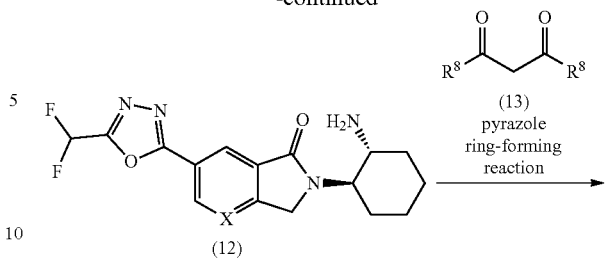

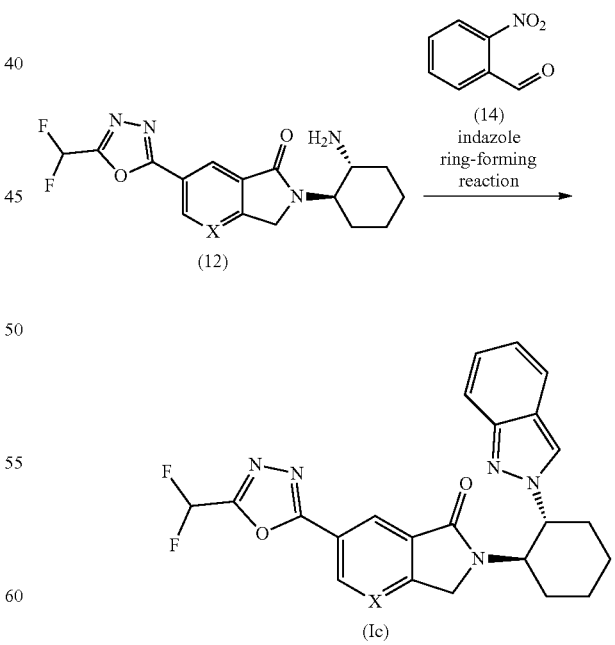

Compound (11) can be produced from compound (2) and compound (7) according to Production Method A.

Compound (Ib) can be produced by subjecting compound (12) and compound (13) to a pyrazole ring-forming reaction. Examples of the reagent to be used include O-(4-nitrobenzoyl)hydroxylamine and the like.

Production Method C

Among compound (I), compound (Ic) can be produced according to the following method.

(Scheme 3)

Compound (Ic) can be produced by subjecting compound (12) and compound (14) to an indazole ring-forming reaction. Examples of the reducing agent to be used include tributylphosphine and the like.

Production Method D

Among compound (I), compound (Id) can be produced according to the following method.

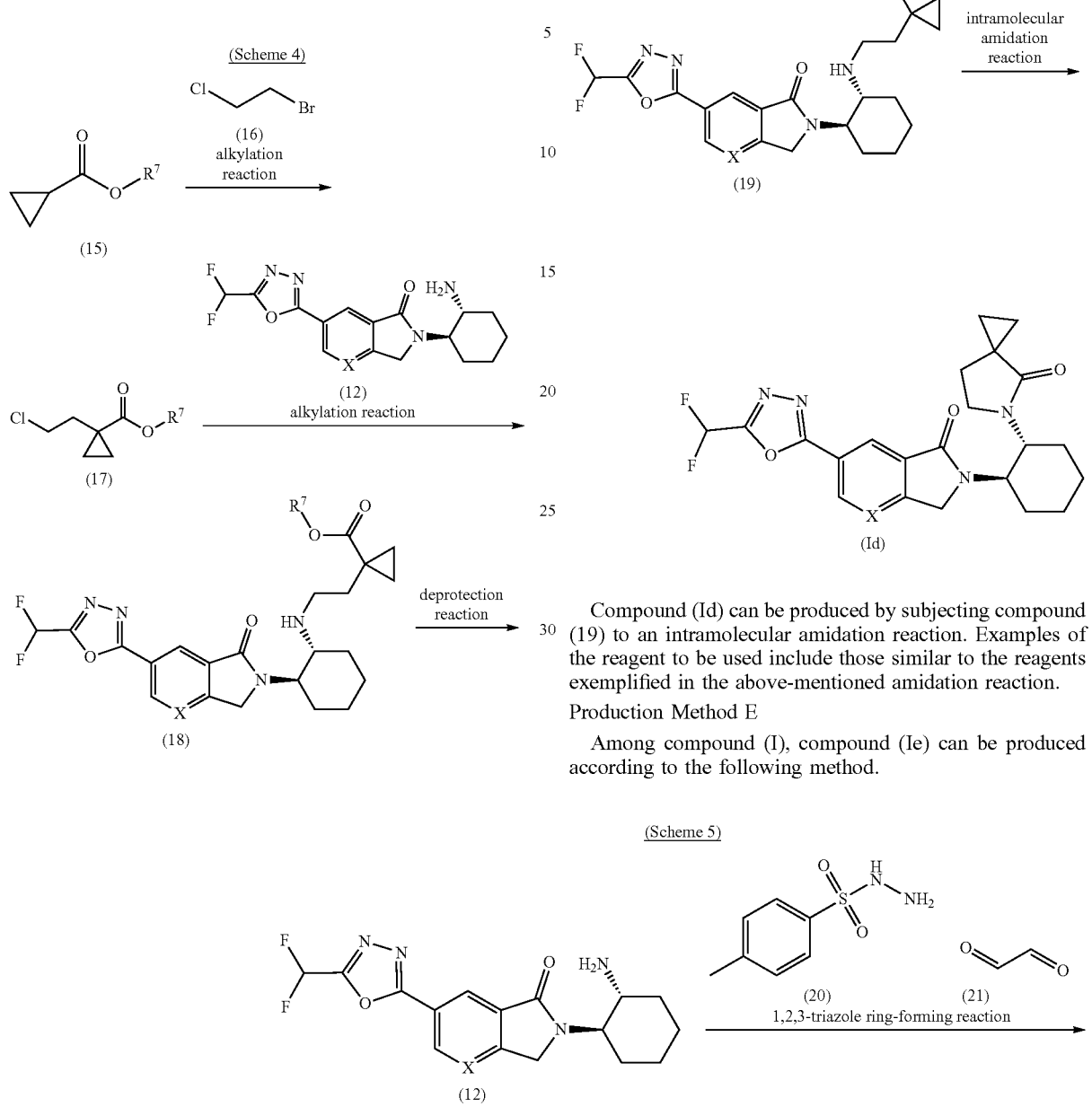

Compound (Id) can be produced by subjecting compound (19) to an intramolecular amidation reaction. Examples of the reagent to be used include those similar to the reagents exemplified in the above-mentioned amidation reaction.

Production Method E

Among compound (I), compound (Ie) can be produced according to the following method.

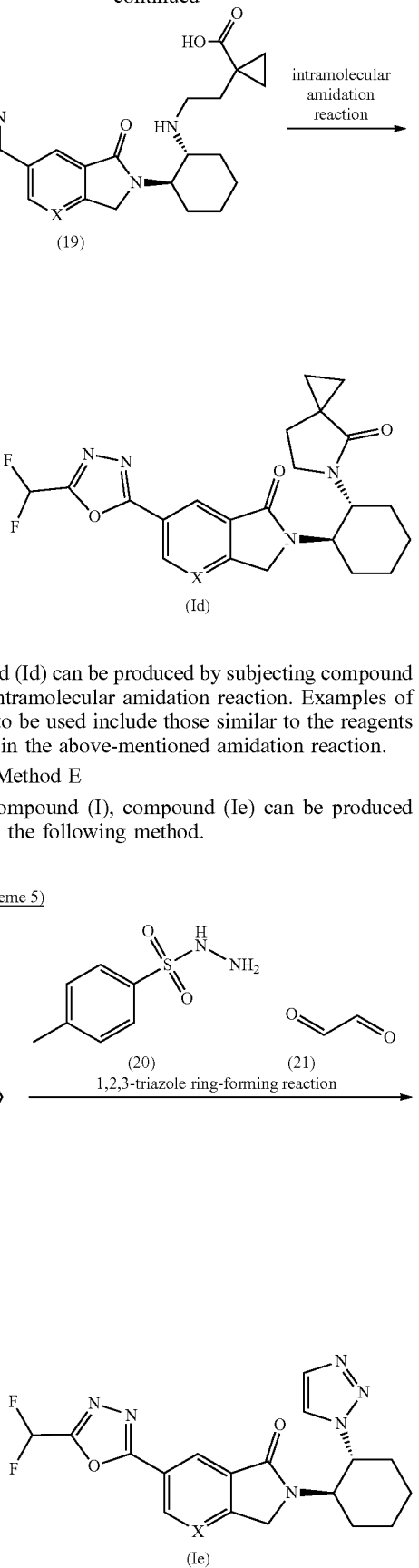

Compound (Ie) can be produced by subjecting compound (12) to a 1,2,3-triazole ring-forming reaction. Examples of the reagent to be used include a combination of p-toluenesulfonyl hydrazide (20) and glyoxal (21) and the like.

Production Method F

Among compound (I), compound (If) can be produced according to the following method.

(Scheme 6)

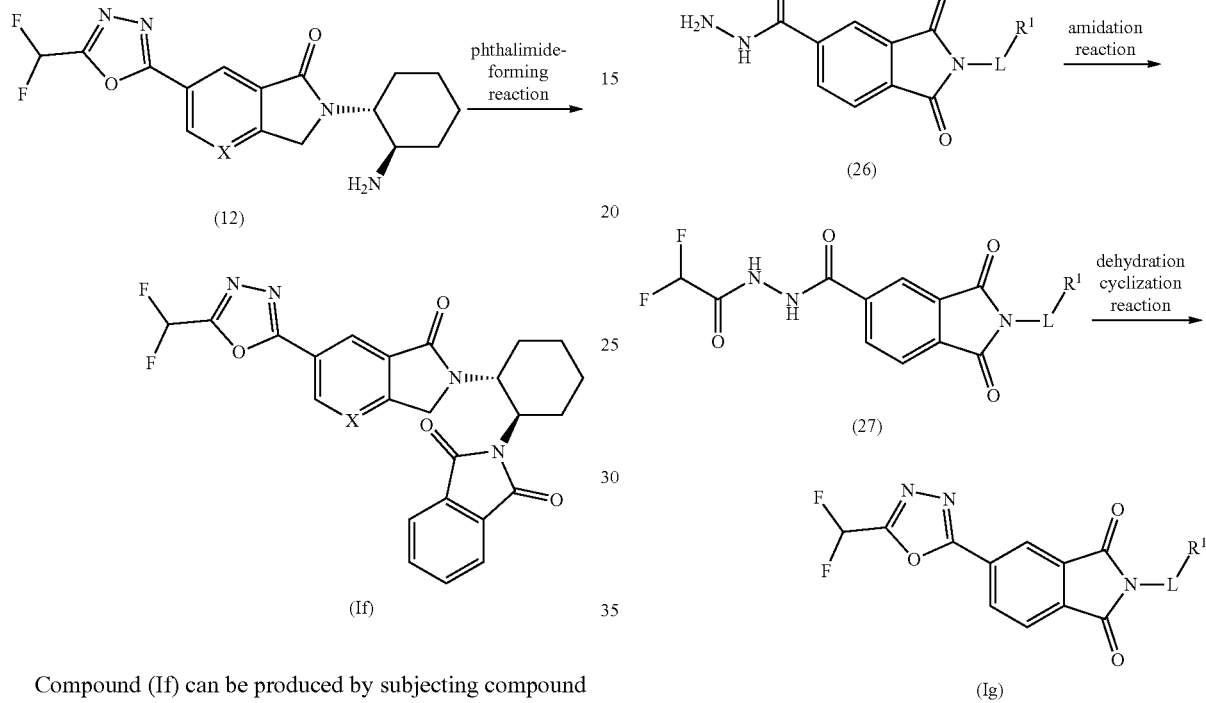

(12)

(If)

Compound (If) can be produced by subjecting compound (12) to a phthalimide-forming reaction. Examples of the reagent to be used include phthalic anhydride and the like.

Production Method G

Among compound (I), compound (Ig) can be produced according to the following method.

(Scheme 7)

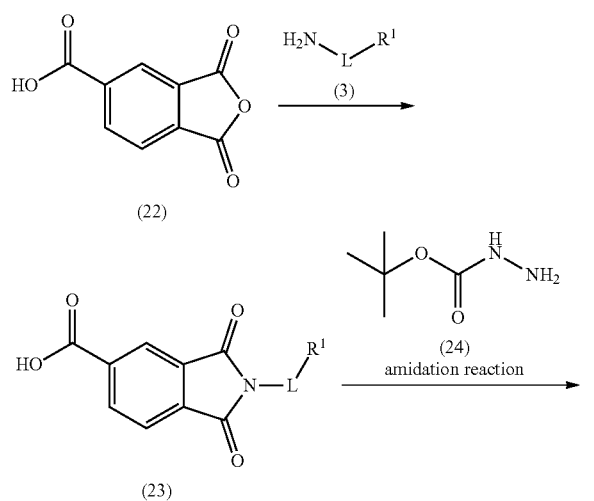

(22)

(23)

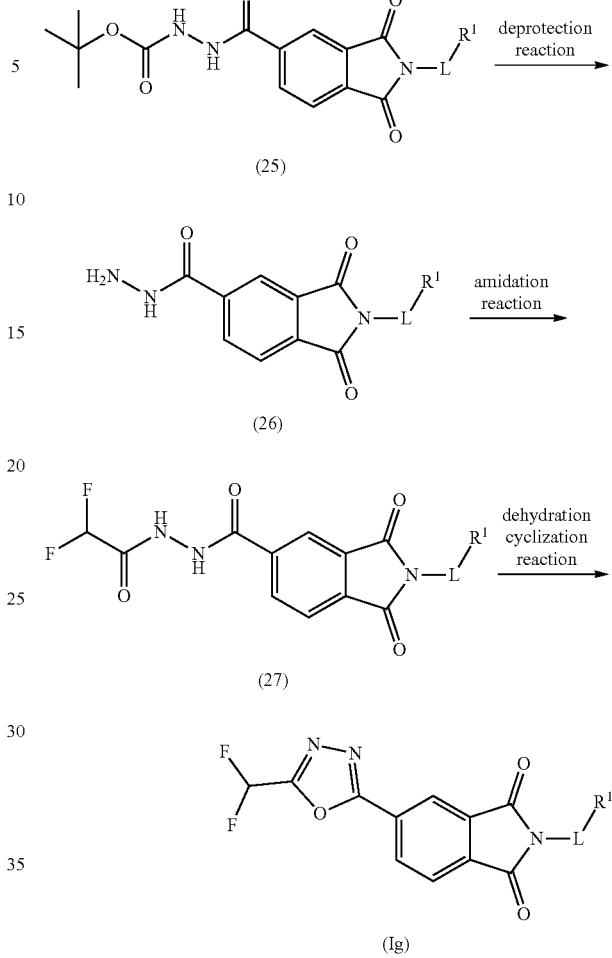

(25)

(26)

(27)

(Ig)

Compound (23) can be produced by subjecting compound (22) and compound (3) to a phthalimide-forming reaction. Examples of the acid include acetic acid and the like.

Among compound (2), compound (2a) can be produced according to the following method.

(Scheme 8)

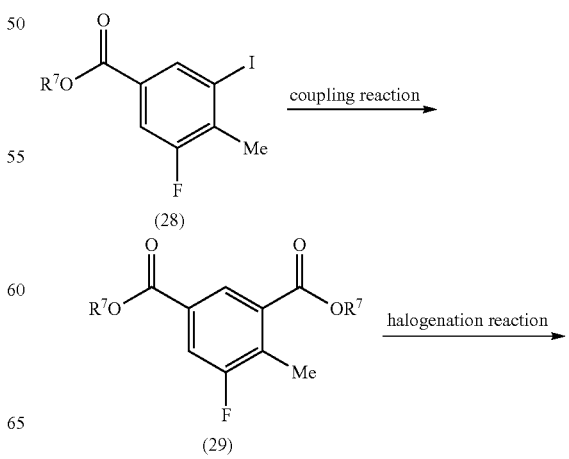

(28)

(29)

103

-continued

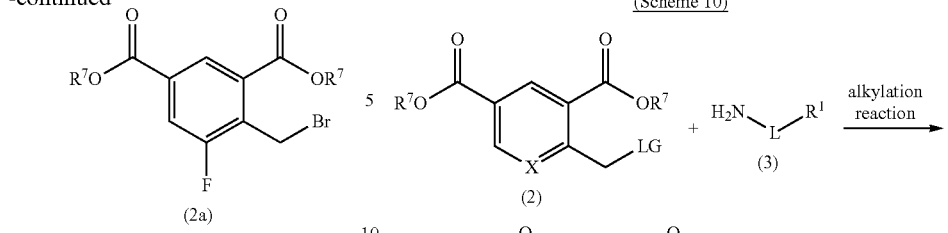

(2a)

Compound (29) can be produced by subjecting compound (28) to a coupling reaction with carbon monoxide. Compound (28) can be produced according to the method described in WO 2011/12191.

Among compound (4), compound (4a) can be produced according to the following method.

104

(Scheme 10)

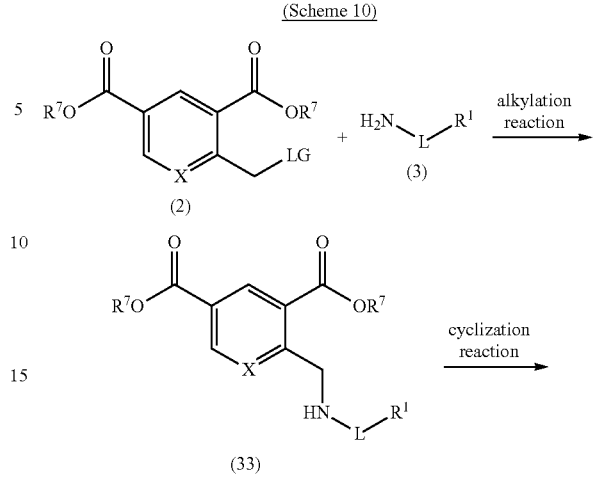

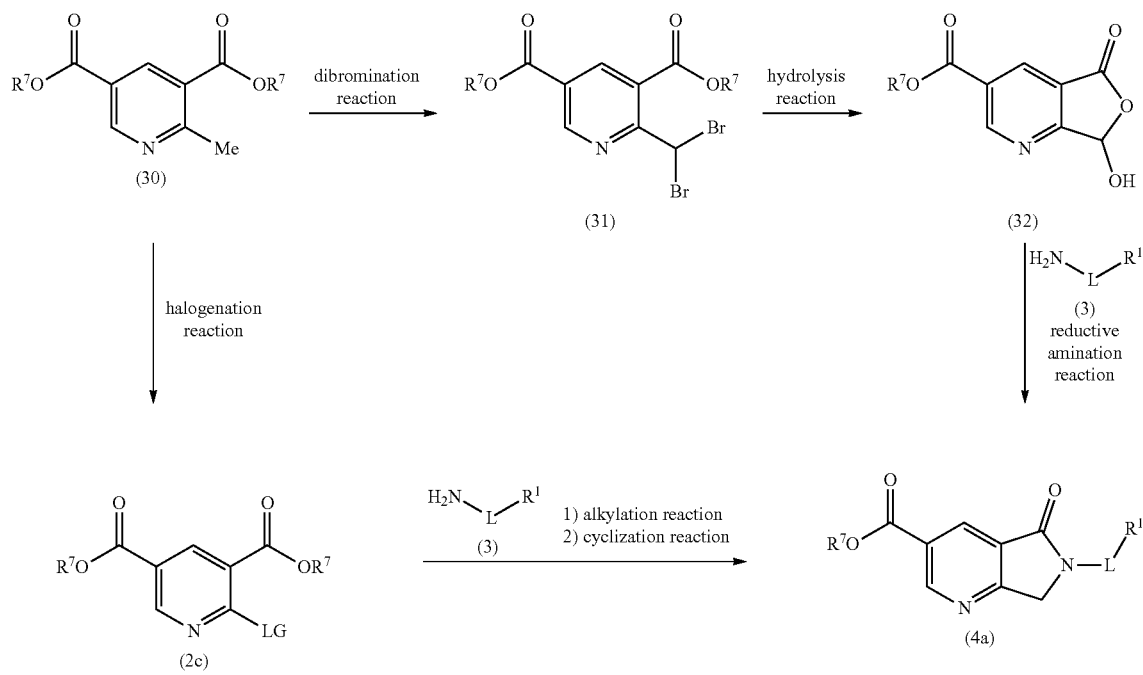

Compound (31) can be produced by subjecting compound (30) to a dibromination reaction. Examples of the reagent include those similar to the reagents (NBS, bromine) to be used in a halogenation reaction, and the like.

Compound (32) can be produced by subjecting compound (31) to a hydrolysis reaction. Examples of the reagent to be used include silver nitrate and the like.

Compound (6) can also be produced according to the following method.

-continued

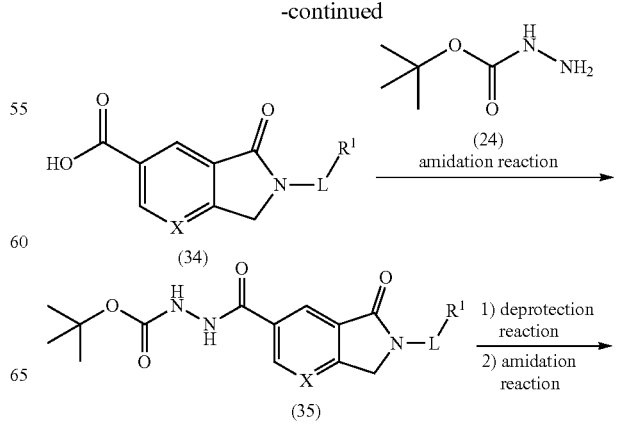

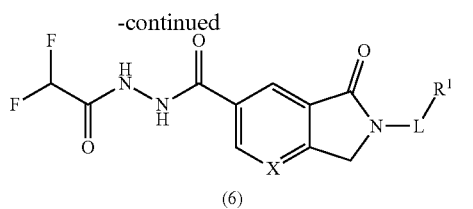

Compound (34) can be produced by subjecting compound (33) to a cyclization reaction. Examples of the acid to be used include hydrochloric acid and the like.

Compound (6) can also be produced according to the following method.

(Scheme 11)

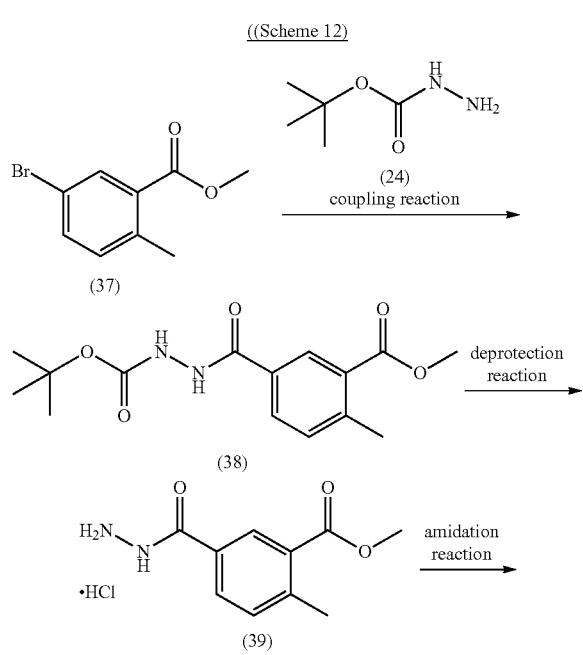

Among compound (1), compound (if) can be produced according to the following method.

((Scheme 12)

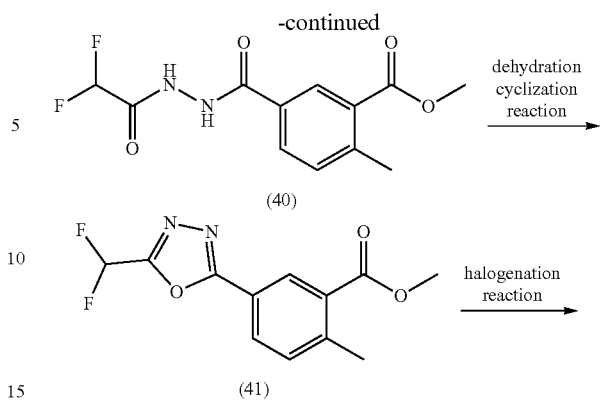

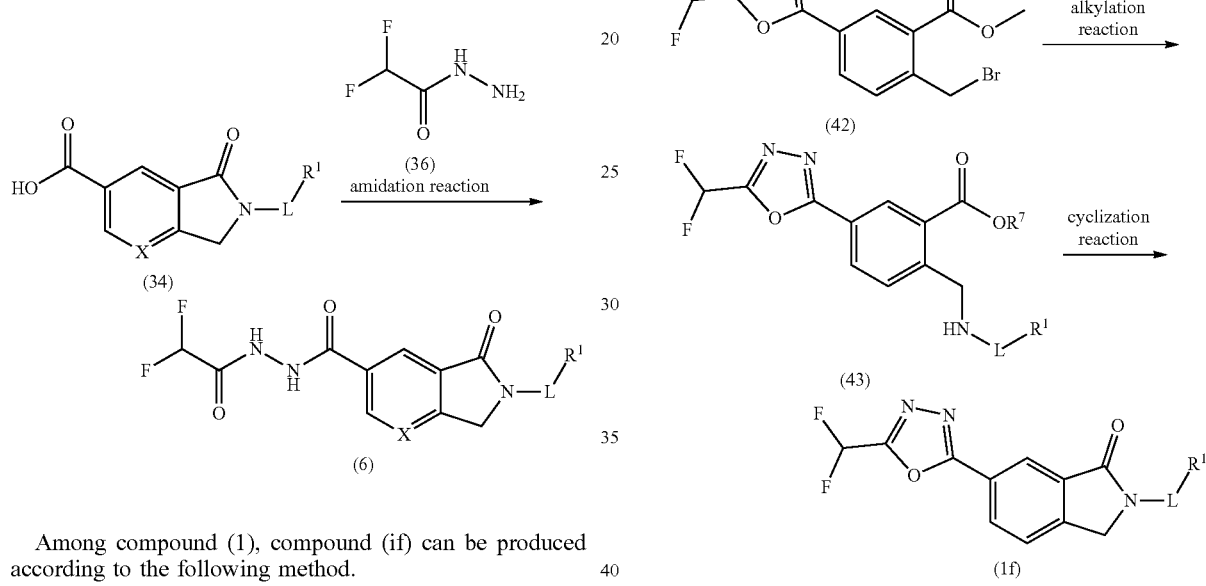

Compound (38) can be produced by coupling compound (37) and compound (24) using a palladium catalyst and a base, under carbon monoxide atmosphere (0.5 MPa). Examples of the palladium catalyst include a combination of 4,5-bis(diphenylphosphino)-9,9-dimethylxanthene (alias: Xantophos) and bis(dibenzylideneacetone)palladium (0), and the like. Examples of the base include N,N-dicyclohexylmethylamine.

Compounds (2), (3), (7), (13), (14), (15), (16), (20), (21), (22), (24), (28), (30), (36) and (37) which are used as raw materials in each production method can be produced according to a method known per se.

The starting compound and/or production intermediate for compound (I) may form a salt. While the salt is not particularly limited as long as the reaction can be performed, examples thereof include those similar to the salts which compound (I) optionally forms, and the like.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, or 4th Edition Jikken Kagaku Kouza 19 (The Chemical Society of Japan ed.), pages 273 to 274, or a method analogous thereto.

Compound (I) contains a stereoisomer depending on the kind of a substituent, and each stereoisomer and a mixture thereof are encompassed in the present invention.

Compound (I) may be a hydrate or a non-hydrate.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form can be isolated according to a conventional optical resolution such as preparative high performance liquid chromatography (preparative HPLC), supercritical fluid chromatography (preparative SFC) and the like.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

Compound (I) may be a crystal.

The crystal of compound (I) can be produced according to a crystallization method known per se.

Examples of the crystallization method include crystallization method from a solution, crystallization method from vapor, crystallization method from a melt, and the like.

The "crystallization method from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, isopropyl acetate, etc.), alcohols (e.g., methanol, ethanol, 2-propanol, etc.), water and the like. These solvents are used alone or in a combination of two or more at a suitable ratio (e.g., 1:1 to 1:100 (a volume ratio)). Where necessary, a seed crystal can be used.

The "crystallization method from vapor" is, for example, a vaporization method (a sealed tube method, a gas stream method), a gas phase reaction method, a chemical transportation method and the like.

The "crystallization method from a melt" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound (I) in a suitable solvent (e.g., alcohols such as methanol, ethanol etc.) at 20° C. to 120° C., and cooling the obtained solution to a temperature (e.g., 0 to 50° C., preferably 0 to 20° C.) not higher than the dissolution temperature, and the like.

The thus-obtained crystals of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound (I) obtained by the above-mentioned production method may have high purity, high quality, and low hygroscopicity, may not be denatured even after a long-term preservation under general conditions, and may be expected to be superior in the stability. In addition, it may be also superior in the biological properties (e.g., pharmacokinetics (absorption, distribution, metabolism, excretion), efficacy expression etc.) and may be extremely useful as a medicament.

Compound (I) may be a prodrug. The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like. Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation or tert-butylation); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and the prodrug of compound (I) are sometimes collectively abbreviated as "the compound of the present invention".

Compound (I) may be a hydrate, a non-hydrate, a solvate or a non-solvate.

In addition, compound (I) may be a compound labeled or substituted with an isotope (e.g., $^2H$, $^3H$, $^{11}C$, $^{14}C$, $^{18}F$, $^{35}S$, $^{125}I$) and the like. The compound labeled or substituted with an isotope may be used, for example, as a tracer (PET tracer) used in positron emission tomography (PET), and useful in the field of medical diagnosis and the like.

Compound (I) also encompasses a deuterium conversion form wherein $^1H$ is converted to $^2H(D)$.

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability). The cocrystal or a salt thereof can be produced according to a cocrystallization a method known per se.

Compound (I) may also be used as a PET tracer.

Since the compound of the present invention has a superior HDAC inhibitory action, preferably class II HDAC inhibitory action, more preferably HDAC6 inhibitory action, it may be also useful as safe medicaments based on such action.

For example, the medicament of the present invention containing the compound of the present invention may be expected to show low toxicity (e.g., acute toxicity, chronic toxicity, genetic toxicity, reproductive toxicity, cardiotoxicity, carcinogenicity), and used for a mammal (e.g., mouse, rat, hamster, rabbit, cat, dog, bovine, sheep, monkey, human) as a prophylactic or therapeutic agent for HDAC-associated diseases, preferably class II HDAC-associated diseases, more preferably HDAC6-associated diseases, more specifically, the diseases described in (1)-(7) below.

Particularly, the compound of the present invention may be expected to show low genetic toxicity, and therefore, the medicament of the present invention may be expected to show low genetic toxicity.

(1) inflammatory diseases (e.g., acute pancreatitis, chronic pancreatitis, asthma, adult respiratory distress syndrome, chronic obstructive pulmonary disease (COPD), idiopathic pulmonary fibrosis, inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis, diabetic nephropathy, uveitis, suppurative hidradenitis etc.), (2) autoimmune diseases (e.g., rheumatoid arthritis, psoriasis, inflammatory bowel disease (e.g., Crohn's disease, ulcerative colitis etc.), Sjogren's syndrome, Behcet's disease, multiple sclerosis, systemic lupus erythematosus, lupus nephritis, discoid lupus erythematosus, Castleman's disease, ankylopoietic spondylarthritis, polymyositis, dermatomyositis (DM), polyarteritis nodosa (PN), mixed connective tissue disease (MCTD), scleroderma, profundus lupus erythematosus, chronic thyroiditis, Graves' disease, autoimmune gastritis, type I diabetes, autoimmune hemolytic anemia, autoimmune neutropenia, thrombocytopenia, atopic dermatitis, pemphigus, chronic active hepatitis, myasthenia gravis, graft versus host disease, Addison's disease, abnormal immunoresponse, arthritis, dermatitis, radiodermatitis, primary biliary cirrhosis etc.), (3) osteoarticular degenerative disease (e.g., rheumatoid arthritis, osteoporosis, osteoarthritis etc.), (4) neoplastic diseases [e.g., malignant tumor, angiogenesis glaucoma, infantile hemangioma, multiple myeloma, chronic sarcoma, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., papillary adenocarcinoma, mucinous adenocarcinoma, adenosquamous carcinoma, etc.), breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, adult T cell leukemia, chronic bone marrow proliferative disease, pancreatic endocrine tumor fibrous histiocytoma, leiomyosarcoma, rhabdomyosarcoma, cancer of unknown primary), leukemia (e.g., acute leukemia (e.g., acute lymphatic leukemia, acute myelocytic leukemia etc.), chronic leukemia (e.g., chronic lymphatic leukemia, chronic myelocytic leukemia etc.), myelodysplastic syndrome), uterine sarcoma (e.g., mixed mesodermal tumor, uterine leiomyosarcoma, endometrial stromal tumor etc.), myelofibrosis etc.], (5) neurodegenerative diseases and/or central diseases (i) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autistic spectrum syndrome, fragile X syndrome, Rett syndrome, adjustment disorder, bipolar disorder, neurosis, schizophrenia (e.g., positive symptom, negative symptom, cognitive symptom), cognitive dysfunction associated with schizophrenia, chronic fatigue syndrome, anxiety neurosis, compulsive neurosis, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression, hreditary sastic praplegia], (ii) neurodegenerative diseases [e.g., Alzheimer's disease, dementia of Alzheimer type, Alzheimer-type senile dementia, Parkinson's disease, muscular dystrophy, Parkinson's disease associated with dementia, Huntington's disease, multi-infarct dementia, frontotemporal lobar degeneration [progressive supranuclear palsy, corticobasal degeneration, frontotemporal dementia and parkinsonism linked to MAPT mutation (FTDP-17), frontotemporal dementia, Pick's disease, argyrophilic grain dementia etc.], Parkinson's type dementia, Niemann-Pick syndrome, Down's disease, vascular dementia, postencephalitic parkinsonism, Lewy body dementia, Rubinstein-Taybi syndrome, Charcot-Marie-Tooth disease, HIV dementia, amyotrophic lateral sclerosis (ALS), motor neurogenesis disease (MND), Creutzfeldt-Jakob disease or prion disease, cerebral palsy, multiple sclerosis, Riley-Day syndrome], (iii) age-related cognition memory disorders [e.g., age-related memory disorders, senile dementia], (iv) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (v) respiratory depression caused by anesthetics, traumatic disease, or neurodegenerative disease and the like, (vi) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, peptic ulcer, diarrhea, constipation, postoperative ileus, (vii) pain, (6) chronic heart failure or acute heart failure, acute decompensated heart failure, ischemic heart disease, cardiomyopathy, myocarditis, valvular disease, (7) peripheral neuropathy and the like.

The medicament of the present invention may be preferably used as an agent for the prophylaxis or treatment of autoimmune disease, inflammatory disease, osteoarticular degenerative disease, neurodegenerative disease, central disease, neoplastic disease, or peripheral neuropathy, more preferably inflammatory bowel disease (preferably Crohn's disease or ulcerative colitis), systemic lupus erythematosus, rheumatoid arthritis, psoriasis, Sjogren's syndrome, Behcet's syndrome, multiple sclerosis, graft versus host disease, Alzheimer's disease (preferably dementia of Alzheimer type), schizophrenia, dementia with Lewy Bodies, frontotemporal lobar degeneration [progressive supranuclear palsy, corticobasal degeneration, frontotemporal dementia and parkisonism linked to MAPT mutation (FTDP-17), frontotemporal dementia, Pick's disease, argyrophilic grain dementia etc.], Parkinson's disease, Huntington's disease, Rubinstein-Taybi Syndrome, muscular dystrophy, Rett Syndrome, amyotrophic lateral sclerosis, Charcot-Marie-Tooth disease, depression, hereditary spastic praplegia, Riley-Day syndrome, Castleman's disease, leukemia, uterine leiomyosarcoma, prostate cancer, colon cancer, multiple myeloma, cachexia or myelofibrosis, chronic heart failure or acute heart failure, acute decompensated heart failure, ischemic heart disease, cardiomyopathy, myocarditis, valvular disease, peripheral neuropathy and the like.

The medicament of the present invention may be more preferably used as an agent for the prophylaxis or treatment of Alzheimer's disease, frontotemporal lobar degeneration [progressive supranuclear palsy, corticobasal degeneration, frontotemporal dementia and parkinsonism linked to MAPT mutation (FTDP-17), frontotemporal dementia, Pick's disease, argyrophilic grain dementia etc.] and the like, particularly Alzheimer's disease or progressive supranuclear palsy.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

A medicament containing the compound of the present invention may be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor and administration to the lesion).

The content of the compound of the present invention in the medicament of the present invention is about 0.01 to 100% by weight of the entire medicament. The dose of the medicament of the present invention may vary depending on administration subject, administration route, disease and the like. For example, for oral administration to patients (body weight about 60 kg) with neurodegenerative disease (for example Alzheimer's disease, progressive supranuclear palsy, etc.), about 0.01 mg/kg body weight-about 50 mg/kg body weight, preferably about 0.05 mg/kg body weight-about 25 mg/kg body weight, more preferably about 0.1 mg/kg body weight-about 2 mg/kg body weight of an active ingredient (compound (I)) may be administered once to several portions per day.

Examples of the pharmaceutically acceptable carrier include various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

The dose of the medicament of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Examples of the excipient include lactose, white sugar, D-mannitol, starch, corn starch, crystalline cellulose, and light anhydrous silicic acid.

Examples of the lubricant include magnesium stearate, calcium stearate, talc, and colloidal silica.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, and carboxymethylcellulose sodium.

Examples of the disintegrant include starch, carboxymethylcellulose, carboxymethylcellulose calcium, carboxymethylstarch sodium, and L-hydroxypropylcellulose.

Examples of the solvent include water for injection, alcohol, propylene glycol, Macrogol, sesame oil, corn oil, and olive oil.

Examples of the solubilizing agent include polyethylene glycol, propylene glycol, D-mannitol, benzyl benzoate, ethanol, trisaminomethane, cholesterol, triethanolamine, and sodium carbonate, sodium citrate.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; and hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like.

Examples of the isotonic agent include glucose, D-sorbitol, sodium chloride, glycerin, and D-mannitol.

Examples of the buffering agent include buffer solutions such as phosphates, acetates, carbonates, and citrates.

Examples of the soothing agent include benzyl alcohol.

Examples of the preservative include parahydroxybenzoates, chlorobutanol, benzyl alcohol, phenylethyl alcohol, dehydroacetic acid, and sorbic acid.

Examples of the antioxidant include sulfites, ascorbic acid, and α-tocopherol.

For the prophylaxis or treatment of various diseases, the compound of the present invention may also be used together with other drug (hereinafter, to be referred to as concomitant drug). In the following, a medicament to be used when the compound of the present invention is used together with other drug is referred to as "the combination agent of the present invention".

For example, when the compound of the present invention is used as a HDAC inhibitor, preferably a class II HDAC inhibitor, more preferably a HDAC6 inhibitor, it may be used together with the following drugs.

tranquilizer (diazepam, lorazepam, clorazepate dipotassium, oxazepam, chlordiazepoxide, medazepam, oxazolam, cloxazolam, clotiazepam, bromazepam, etizolam, fludiazepam, hydroxyzine, nitrazepam, triazolam, alprazolam etc.), antipsychotic (chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, clozapine, trifluoperazine dihydrochloride, fluphenazine hydrochloride, olanzapine, quetiapine fumarate, risperidone, aripiprazole, bromperidol, spiperone, reserpine, clocapramine hydrochloride, sulpiride, zotepine, tiotixene etc.), antiepileptic drug (phenytoin, ethosuximide, acetazolamide, chlordiazepoxide, trimethadione, carbamazepine, phenobarbital, primidone, sulthiame, sodium valproate, clonazepam, diazepam, nitrazepam etc.), antidepressant and therapeutic drug for manic psychosis [tricyclic or tetracyclic antidepressant drug (imipramine hydrochloride, clomipramine hydrochloride, desipramine hydrochloride, amitriptyline hydrochloride, nortriptyline hydrochloride, amoxapine, mianserin hydrochloride, maprotiline hydrochloride, etc.), noxiptiline, phenelzine, sulpiride, trazodone hydrochloride, lithium carbonate, selective serotonin reuptake inhibitor (fluvoxamine maleate, fluoxetine hydrochloride, citalopram hydrobromide, sertraline hydrochloride, paroxetine hydrochloride, paroxetine hydrochloride hydrate, escitalopram oxalate etc.), serotonin-noradrenalin reuptake inhibitor (venlafaxine hydrochloride, duloxetine hydrochloride, venlafaxine hydrochloride etc.), noradrenalin reuptake inhibitor (reboxetine mesylate etc.), noradrenalin-dopamine reuptake inhibitor (bupropion hydrochloride etc.), mirtazapine, trazodone hydrochloride, nefazodone hydrochloride, setiptiline maleate, 5-HT$_{1A}$ agonist (buspirone hydrochloride, tandospirone citrate, osemozotan hydrochloride) etc.]

benzodiazepine (clonazepam etc.), L-type calcium channel inhibitor (pregabalin etc.), 5-HT$_{1A}$ agonist (buspirone hydrochloride, tandospirone citrate, osemozotan hydrochloride etc.), 5-HT$_3$ antagonist (cyamemazine etc.), heart non-selective β inhibitor (propranolol hydrochloride, oxiprenolol hydrochloride etc.), histamine H$_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), drug that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, type II carbonic anhydrase inhibitor, NMDA glycine site agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioids antagonist, opioids agonist, uridine, nicotinic acid receptor agonists, thyroid hormone (T3, T4), TSH, TRH, MAO inhibitor (phenelzine sulfate, tranylcypromine sulfate, moclobemide etc.), 5-HT$_{2A}$ antagonist, 5-HT$_{2A}$ inverse agonist, COMT inhibitor (entacapone, etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for convulsion, therapeutic drug forfibromyalgia, therapeutic drug for headache, therapeutic drug for insomnia (etizolam, zopiclone, triazolam, xolpidem, ramelteon, indiplon etc.), therapeutic drug for quitting smoking, therapeutic drug for myasthenia gravis, therapeutic drug for cerebral infarction, therapeutic drug for manic psychosis, therapeutic drug for hypersomnia, therapeutic drug for pain, therapeutic drug for dysthymia, therapeutic drug for dysautonomia, therapeutic drug for male and female sexual dysfunction, therapeutic drug for migraine, therapeutic drug for pathological gambling, therapeutic drug for restless legs syndrome, therapeutic drug for substance dependence, therapeutic drug for alcohol-related disease, therapeutic drug for irritable bowel syndrome, therapeutic drug for Alzheimer's disease (donepezil, galanthamine, memantine, rivastigmine, etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, amantadine hydrochloride, bromocriptine mesilate, trihexyphenidyl hydrochloride, selegiline hydrochloride, combination thereof etc.), therapeutic drug for Parkinson's disease associated with dementia (rivastigmine), therapeutic drug for Lewy body dementia (donepezil), therapeutic drug for ALS (riluzole, neurotrophic factor, etc.), therapeutic drug for hyperlipidemia such as cholesterol-lowering drug (statin series (pravastatin sodium, atorvastatin, simvastatin, rosuvastatin, etc.), fibrate (clofibrate etc.), squalene synthase inhibitor), therapeutic drug for abnormal behavior or dementia-related wandering (sedative drug, antianxiety drug, etc.), apoptosis inhibitor, antiobesity drug, antidiabetic drug, therapeutic drug for hypertension, therapeutic drug for hypotension, therapeutic drug for rheumatism (DMARD), anticancer drug, therapeutic drug for hypoparathyroidism (PTH), calcium receptor antagonist, sex hormone or derivative thereof (progesterone, estradiol, estradiol benzoate etc.), neuron differentiation accelerator, neurogeneration promotor, non-steroidal anti-inflammatory drug (meloxicam, tenoxicam, indomethacin, ibuprofen, celecoxib, rofecoxib, aspirin etc.), steroid (dexamethasone, cortisone acetate, etc.), anti-cytokine drug (TNF inhibitor, MAP kinase inhibitor, etc.), antibody medicament, nucleic acid or nucleic acid derivative, aptamer and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as a developing solvent, and UV detector was used for the detection. In silica gel column chromatography, the indication of NH means use of aminopropylsilane-bonded silica gel, and the indication of Diol means use of 3-(2,3-dihydroxypropoxy) propylsilane-bonded silica gel. In preparative HPLC (high performance liquid chromatography), the indication of C18 means use of octadecyl-bonded silica gel. The ratio for elution solvent is, unless otherwise specified, a volume mixing ratio.

For the analysis of $^1$H NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

Elemental analysis value (Anal.) is described as calculated value (Calcd) and actual measured value (Found).

Powder X-RAY diffraction pattern was measured using Cu-Kα characteristic radiation from Rigaku Ultima IV, and characteristic peaks were described.

In Examples, the following abbreviations are used.
MS: mass spectrum
M: mol concentration
N: normality
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: electrospray ionization
APCI: atomospheric pressure chemical ionization
AIBN: 2,2'-azobis(isobutyronitrile)
Boc$_2$O: di-tert-butyl dicarbonate
CDI: 1,1'-carbonyldiimidazole
CPME: cyclopentyl methyl ether
DBU: 1,8-diazabicyclo[5.4.0]undec-7-ene
DME: 1,2-dimethoxyethane
DIPEA: N,N-diisopropylethylamine
DMF: N,N-dimethylformamide
DMSO: dimethyl sulfoxide
DPPA: diphenylphosphoryl azide
HATU: O-(7-azabenzotriazole-1-yl)-N,N,N',N'-tetramethyluronium hexafluorophosphorate
NBS: N-bromosuccinimide
n-BuLi: n-butyllithium
TEA: triethylamine
TFA: trifluoroacetic acid
THF: tetrahydrofuran
WSC.HCl: 1-ethyl-3-(3-dimethylaminopropyl)carbodiimide hydrochloride Example 1

6-(5-(difluoromethyl)-1,3,4-oxadiazol-2-yl)-2-((3S,4R)-3-(2-oxopyrrolidin-1-yl)tetrahydro-2H-pyran-4-yl)isoindolin-1-one A) tert-butyl ((3S,4R)-3-(2-oxopyrrolidin-1-yl)tetrahydro-2H-pyran-4-yl)carbamate To a mixture of tert-butyl ((3S,4R)-3-aminotetrahydro-2H-pyran-4-yl)carbamate (1.51 g), TEA (868.6 mg) and THF (30 mL) was slowly added 4-chlorobutanoyl chloride (1.11 g) at 0° C. The mixture was stirred at 0° C. for 30 min, to the mixture was slowly added potassium tert-butoxide (2.29 g, content 85%), and the mixture was stirred for 1 hr. To the mixture was added ice water, and the mixture was extracted twice with ethyl acetate. The organic layer was washed with 0.1N hydrochloric acid and saturated brine, dried over anhydrous sodium sulfate, and concentrated under reduced pressure to give the title compound (1.51 g).

MS, found: 185.2.

B) 1-((3S,4R)-4-aminotetrahydro-2H-pyran-3-yl)pyrrolidin-2-one hydrochloride

A mixture of tert-butyl ((3S,4R)-3-(2-oxopyrrolidin-1-yl)tetrahydro-2H-pyran-4-yl)carbamate (1.51 g) and 4M hydrogen chloride CPME solution (20 mL) was stirred at room temperature for 18 hr. The mixture was concentrated, and the residue was washed with ethyl acetate to give the title compound (1.01 g).
$^1$H NMR (300 MHz, DMSO-$d_6$) δ ppm 1.54-1.75 (1H, m) 1.80-2.08 (3H, m) 2.14-2.38 (2H, m) 3.12-3.26 (1H, m) 3.29-3.47 (3H, m) 3.49-3.62 (1H, m) 3.67 (1H, dd, J=11.1, 4.9 Hz) 3.77-3.96 (2H, m) 8.00 (3H, brs).

C) methyl 3-oxo-2-((3S,4R)-3-(2-oxopyrrolidin-1-yl)tetrahydro-2H-pyran-4-yl)isoindoline-5-carboxylate A mixture of dimethyl 4-(bromomethyl)isophthalate (141.7 mg), 1-((3S,4R)-4-aminotetrahydro-2H-pyran-3-yl)pyrrolidin-2-one hydrochloride (125.3 mg), DIPEA (0.332 mL) and DMF (2 mL) was stirred at 50° C. for 5 hr, and then at room temperature for 3 days. To the mixture was added 1N hydrochloric acid, and the mixture was extracted twice with ethyl acetate. The organic layer was washed with water, saturated aqueous sodium hydrogencarbonate solution and saturated brine, dried over anhydrous magnesium sulfate, and concentrated under reduced pressure. The residue was purified by silica gel column chromatography (methanol/ethyl acetate) to give the title compound (51.1 mg).
MS: [M+H]$^+$359.2.

D) 3-oxo-2-((3S,4R)-3-(2-oxopyrrolidin-1-yl)tetrahydro-2H-pyran-4-yl)isoindoline-5-carbohydrazide A mixture of methyl 3-oxo-2-((3S,4R)-3-(2-oxopyrrolidin-1-yl)tetrahydro-2H-pyran-4-yl)isoindoline-5-carboxylate (198.2 mg), hydrazine monohydrate (821.9 mg) and ethanol (2 mL) was stirred at 50° C. for 2 hr. The mixture was concentrated, to the residue was added saturated aqueous sodium hydrogencarbonate solution, and the mixture was extracted with ethyl acetate/THF. The organic layer was separated, washed with saturated brine, and concentrated under reduced pressure to give the title compound (172.5 mg).
MS: [M+H]$^+$359.2.

E) 6-(5-(difluoromethyl)-1,3,4-oxadiazol-2-yl)-2-((3S,4R)-3-(2-oxopyrrolidin-1-yl)tetrahydro-2H-pyran-4-yl)isoindolin-1-one A mixture of 3-oxo-2-((3S,4R)-3-(2-oxopyrrolidin-1-yl)tetrahydro-2H-pyran-4-yl)isoindoline-5-carbohydrazide (171.7 mg), difluoroacetic anhydride (282.1 mg), TEA (163.3 mg) and THF (10 mL) was stirred at 80° C. for 2 hr. The mixture was concentrated, and the residue was partitioned between ethyl acetate-water. The organic layer was washed with saturated brine, dried over anhydrous sodium sulfate, and concentrated. A mixture of a part (240.2 mg) of the obtained residue, (methoxycarbonylsulfamoyl)triethylammonium hydroxide inner salt (alias: Burgess reagent) (395.1 mg) and THF (5 mL) was stirred under microwave irradiation at 130° C. for 1 hr. To the mixture was added saturated aqueous sodium hydrogencarbonate solution, and the mixture was extracted twice with ethyl acetate. The organic layer was separated, washed with saturated brine, dried over anhydrous sodium sulfate, and concentrated under reduced pressure. The residue was purified by silica gel column chromatography (ethyl acetate), and the obtained solid was crystallized from ethyl acetate/hexane to give the title compound (30.3 mg).
$^1$H NMR (300 MHz, DMSO-$d_6$) δ ppm 1.64-1.92 (4H, m) 1.93-2.16 (2H, m) 3.16-3.30 (1H, m) 3.42-3.68 (3H, m) 3.81 (1H, dd, J=10.9, 4.7 Hz) 3.96 (1H, dd, J=11.4, 3.9 Hz) 4.12 (1H, td, J=10.9, 4.7 Hz) 4.46-4.69 (3H, m) 7.36-7.79 (1H, m) 7.88 (1H, d, J=8.1 Hz) 8.21 (1H, d, J=0.9 Hz) 8.28 (1H, dd, J=8.0, 1.6 Hz).

Example 3 tert-butyl ((1R,2R)-2-(6-(5-(difluoromethyl)-1,3,4-oxadiazol-2-yl)-1-oxo-1,3-dihydro-2H-isoindol-2-yl)cyclohexyl)carbamate A) methyl 2-((1R,2R)-2-((tert-butoxycarbonyl)amino)cyclohexyl)-3-oxoisoindoline-5-carboxylate To a mixture of dimethyl 4-(bromomethyl)isophthalate (13.4 g), tert-butyl ((1R,2R)-2-aminocyclohexyl)carbamate (10.00 g) and DMF (130 mL) was added DIPEA (19.51 mL) at room temperature, and the mixture was stirred overnight at room temperature, and then at 50° C. for 3 hr, and then at 80° C. for 3 hr. The reaction mixture was cooled to 0° C., water was added thereto, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (14.7 g).
MS, found: 411.3.

B) tert-butyl ((1R,2R)-2-(6-(hydrazinocarbonyl)-1-oxo-1,3-dihydro-2H-isoindol-2-yl)cyclohexyl)carbamate To a mixture of methyl 2-((1R,2R)-2-((tert-butoxycarbonyl)amino)cyclohexyl)-3-oxoisoindoline-5-carboxylate (12.2 g), THF (60 mL) and methanol (60 mL) was added hydrazine monohydrate (6.09 mL) at room temperature, and the mixture was stirred at 80° C. for 16 hr. The reaction mixture was cooled to room temperature, diisopropyl ether (300 mL) was added thereto, and the suspension was stirred at room temperature for 30 min. The solid was collected by filtration to give the title compound (11.2 g).
MS, found: 289.1.

C) tert-butyl ((1R,2R)-2-(6-((2-(difluoroacetyl)hydrazino)carbonyl)-1-oxo-1,3-dihydro-2H-isoindol-2-yl)cyclohexyl)carbamate To a mixture of tert-butyl ((1R,2R)-2-(6-(hydrazinocarbonyl)-1-oxo-1,3-dihydro-2H-isoindol-2-yl)cyclohexyl)carbamate (11.2 g), TEA (6.01 mL), and THF (110 mL) was added difluoroacetic anhydride (4.30 mL) at 0° C., and the mixture was stirred at room temperature for 1.5 hr. To the mixture were added TEA (4.01 mL) and difluoroacetic anhydride (2.87 mL) at room temperature, and the mixture was stirred for 30 min. The mixture was diluted with saturated aqueous sodium hydrogencarbonate solution/water, and the mixture was extracted twice with ethyl acetate. The extract was washed with water and saturated brine, dried over anhydrous sodium sulfate, and concentrated under reduced pressure to give the title compound (8.57 g).
MS, found: 367.1.

D) tert-butyl ((1R,2R)-2-(6-(5-(difluoromethyl)-1,3,4-oxadiazol-2-yl)-1-oxo-1,3-dihydro-2H-isoindol-2-yl)cyclohexyl)carbamate To a mixture of tert-butyl ((1R,2R)-2-(6-((2-(difluoroacetyl)hydrazino)carbonyl)-1-oxo-1,3-dihydro-2H-isoindol-2-yl)cyclohexyl)carbamate (8.56 g), TEA (3.83 mL) and acetonitrile (100 mL) was added 4-methylbenzenesulfonyl chloride (3.85 g) at room temperature, and the mixture was stirred at room temperature for 3 hr. The mixture was poured into water, and extracted with ethyl acetate. The extract was washed with water and saturated brine, dried over anhydrous sodium sulfate, and concentrated under reduced pressure. The residue was purified by silica gel column chromatography (ethyl acetate/hexane) to give the title compound (6.02 g).

$^1$H NMR (300 MHz, DMSO-$d_6$) δ1.00 (9H, s), 1.24-1.56 (3H, m), 1.59-1.90 (5H, m), 3.52 (1H, d, J=8.3 Hz), 3.84-4.02 (1H, m), 4.44-4.90 (2H, m), 6.85 (1H, d, J=9.4 Hz), 7.35-7.78 (1H, m), 7.88 (1H, d, J=7.5 Hz), 8.19 (1H, s), 8.25 (1H, d, J=7.7 Hz).

Example 4

6-(5-(difluoromethyl)-1,3,4-oxadiazol-2-yl)-2-((1R,2R)-2-(1,1-dioxido-1,2-thiazolidin-2-yl)cyclohexyl)isoindolin-1-one

A) tert-butyl ((1R,2R)-2-(1,1-dioxido-1,2-thiazolidin-2-yl)cyclohexyl)carbamate A mixture of 3-chloropropane-1-sulfonyl chloride (0.638 mL), tert-butyl ((1R,2R)-2-aminocyclohexyl)carbamate (1.072 g) and pyridine (10 mL) was stirred overnight at room temperature. The mixture was added to water at room temperature, and extracted with ethyl acetate. The organic layer was separated, washed with water and saturated brine, dried over anhydrous sodium sulfate, and concentrated under reduced pressure. To a mixture of the obtained residue and DMF (12 mL) was added 60% sodium hydride (0.279 g) at room temperature, and the mixture was stirred at room temperature for 1 hr. The mixture was added to saturated aqueous ammonium chloride solution at room temperature, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (0.62 g).

$^1$H NMR (300 MHz, DMSO-$d_6$) δ1.20-1.41 (12H, m), 1.42-1.56 (1H, m), 1.56-1.81 (4H, m), 2.02-2.25 (2H, m), 2.98-3.18 (4H, m), 3.23-3.31 (1H, m), 3.42 (1H, td, J=8.0, 3.3 Hz), 6.57 (1H, d, J=9.3 Hz).

B) (1R,2R)-2-(1,1-dioxido-1,2-thiazolidin-2-yl)cyclohexanamine hydrochloride To a mixture of tert-butyl ((1R,2R)-2-(1,1-dioxido-1,2-thiazolidin-2-yl)cyclohexyl)carbamate (0.62 g) and ethyl acetate (3 mL) was added 4M hydrogen chloride ethyl acetate solution (3.00 mL) at room temperature, and the mixture was stirred overnight at room temperature. The mixture was concentrated to give the title compound (0.47 g).

$^1$H NMR (300 MHz, DMSO-$d_6$) δ 1.12-1.31 (2H, m), 1.31-1.49 (1H, m), 1.51-1.85 (4H, m), 2.09 (1H, d, J=12.7 Hz), 2.15-2.28 (1H, m), 2.30-2.42 (1H, m), 3.01-3.20 (3H, m), 3.22-3.41 (3H, m), 7.98 (3H, brs).

C) methyl 2-((1R,2R)-2-(1,1-dioxido-1,2-thiazolidin-2-yl)cyclohexyl)-3-oxoisoindoline-5-carboxylate To a mixture of (1R,2R)-2-(1,1-dioxido-1,2-thiazolidin-2-yl)cyclohexanamine hydrochloride (98 mg) and DMF (1 mL) was added a mixture of DIPEA (0.200 mL), dimethyl 4-(bromomethyl)isophthalate (110 mg) and DMF (1 mL), and the mixture was stirred at room temperature for 4 hr, and then at 50° C. for 18 hr. To the mixture was added 1N hydrochloric acid at room temperature, and the mixture was extracted twice with ethyl acetate. The organic layer was washed with water, saturated aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (146 mg).

MS: [M+H]$^+$393.1.

D) 2-((1R,2R)-2-(1,1-dioxido-1,2-thiazolidin-2-yl)cyclohexyl)-3-oxoisoindoline-5-carbohydrazide A mixture of methyl 2-((1R,2R)-2-(1,1-dioxido-1,2-thiazolidin-2-yl)cyclohexyl)-3-oxoisoindoline-5-carboxylate (146 mg), hydrazine monohydrate (0.361 mL) and methanol (2 mL) was stirred at 50° C. for 2 hr. The mixture was concentrated, to the residue was added saturated aqueous sodium hydrogencarbonate solution, and the mixture was extracted twice with ethyl acetate-THF. The organic layer was washed with saturated brine, dried over anhydrous sodium sulfate, and concentrated under reduced pressure to give the title compound (146 mg).

MS: [M+H]$^+$393.2.

E) N'-(difluoroacetyl)-2-((1R,2R)-2-(1,1-dioxido-1,2-thiazolidin-2-yl)cyclohexyl)-3-oxoisoindoline-5-carbohydrazide To a mixture of 2-((1R,2R)-2-(1,1-dioxido-1,2-thiazolidin-2-yl)cyclohexyl)-3-oxoisoindoline-5-carbohydrazide (146 mg), TEA (0.078 mL) and THF (4 mL) was added difluoroacetic anhydride (0.055 mL) at room temperature. The mixture was stirred at room temperature for 30 min, and concentrated to give the title compound (81 mg).

MS: [M+H]$^+$471.2.

F) 6-(5-(difluoromethyl)-1,3,4-oxadiazol-2-yl)-2-((1R,2R)-2-(1,1-dioxido-1,2-thiazolidin-2-yl)cyclohexyl)isoindolin-1-one A mixture of N'-(difluoroacetyl)-2-((1R,2R)-2-(1,1-dioxido-1,2-thiazolidin-2-yl)cyclohexyl)-3-oxoisoindoline-5-carbohydrazide (81 mg), 4-methylbenzenesulfonyl chloride (98 mg), DIPEA (0.090 mL) and acetonitrile (2 mL) was stirred at room temperature for 2 hr. The mixture was added to saturated aqueous sodium hydrogencarbonate solution at room temperature, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (69 mg).

$^1$H NMR (300 MHz, DMSO-$d_6$) δ1.31-1.47 (2H, m), 1.55-1.91 (7H, m), 2.05-2.21 (1H, m), 2.84-3.04 (2H, m), 3.12-3.23 (1H, m), 3.35-3.48 (1H, m), 3.52-3.66 (1H, m), 4.11-4.29 (1H, m), 4.56 (2H, s), 7.36-7.77 (1H, m), 7.87 (1H, d, J=7.3 Hz), 8.21 (1H, s), 8.26 (1H, dd, J=7.9, 1.7 Hz).

Example 5

N-((1R,2R)-2-(6-(5-(difluoromethyl)-1,3,4-oxadiazol-2-yl)-1-oxo-1,3-dihydro-2H-isoindol-2-yl)cyclohexyl)acetamide A) 2-((1R,2R)-2-aminocyclohexyl)-6-(5-(difluoromethyl)-1,3,4-oxadiazol-2-yl)isoindolin-1-one A mixture of tert-butyl ((1R,2R)-2-(6-(5-(difluoromethyl)-1,3,4-oxadiazol-2-yl)-1-oxo-1,3-dihydro-2H-isoindol-2-yl)cyclohexyl)carbamate (6.02 g) and TFA (50 mL) was stirred at 0° C. for 1 hr. The mixture was concentrated under reduced pressure, and the residue was purified by silica gel column chromatography (NH, methanol/ethyl acetate), and crystallized from ethyl acetate/diisopropyl ether/hexane to give the title compound (3.70 g).

MS: [M+H]$^+$349.2.

B) N-((1R,2R)-2-(6-(5-(difluoromethyl)-1,3,4-oxadiazol-2-yl)-1-oxo-1,3-dihydro-2H-isoindol-2-yl) cyclohexyl) acetamide To a mixture of 2-((1R,2R)-2-aminocyclohexyl)-6-(5-(difluoromethyl)-1,3,4-oxadiazol-2-yl)isoindolin-1-one (60.0 mg), TEA (0.048 mL) and THF (1 mL) was added acetyl chloride (0.018 mL) at 0° C., and the mixture was stirred at room temperature for 20 min. The mixture was purified by silica gel column chromatography (ethyl acetate/hexane, followed by methanol/ethyl acetate), and washed with diethyl ether to give the title compound (19.7 mg).

$^1$H NMR (300 MHz, DMSO-d$_6$) δ1.24-1.52 (3H, m), 1.55 (3H, s), 1.60-1.91 (5H, m), 3.78-4.10 (2H, m), 4.46-4.75 (2H, m), 7.35-7.80 (1H, m), 7.87 (2H, d, J=7.9 Hz), 8.20 (1H, d, J=1.1 Hz), 8.26 (1H, dd, J=7.9, 1.7 Hz).

Example 6

N-((1R,2R)-2-(6-(5-(difluoromethyl)-1,3,4-oxadiazol-2-yl)-1-oxo-1,3-dihydro-2H-isoindol-2-yl)cyclohexyl)-2,2,2-trifluoroacetamide To a mixture of 2-((1R,2R)-2-aminocyclohexyl)-6-(5-(difluoromethyl)-1,3,4-oxadiazol-2-yl)isoindolin-1-one (80 mg), TEA (0.038 mL) and THF (1 mL) was added trifluoroacetic anhydride (0.034 mL) at 0° C., and the mixture was stirred at room temperature for 4 hr. The mixture was cooled to 0° C., TEA (0.038 mL) and trifluoroacetic anhydride (0.034 mL) were added thereto, and the mixture was stirred at room temperature for 30 min. The mixture was concentrated under reduced pressure without warming, and the residue was purified by silica gel column chromatography (ethyl acetate/hexane) to give the title compound (73.2 mg).

$^1$H NMR (300 MHz, DMSO-d$_6$) δ1.26-1.50 (2H, m), 1.63-1.91 (6H, m), 3.92-4.07 (1H, m), 4.08-4.22 (1H, m), 4.58 (2H, s), 7.35-7.78 (1H, m), 7.88 (1H, d, J=8.4 Hz), 8.19 (1H, d, J=0.9 Hz), 8.27 (1H, dd, J=8.0, 1.7 Hz), 9.46 (1H, d, J=8.9 Hz).

Example 10 methyl((1R,2R)-2-(6-(5-(difluoromethyl)-1,3,4-oxadiazol-2-yl)-1-oxo-1,3-dihydro-2H-isoindol-2-yl) cyclohexyl)carbamate To a mixture of 2-((1R,2R)-2-aminocyclohexyl)-6-(5-(difluoromethyl)-1,3,4-oxadiazol-2-yl)isoindolin-1-one (120.0 mg) and acetonitrile (5.0 mL) were successively added chloromethyl formate (0.032 mL) and TEA (0.096 mL) at room temperature, and the mixture was stirred overnight. The reaction mixture was poured into water, and extracted with ethyl acetate. The extract was washed with saturated brine, dried over anhydrous sodium sulfate, and concentrated under reduced pressure. The residue was purified by silica gel column chromatography (ethyl acetate/hexane) to give the title compound (140 mg).

$^1$H NMR (300 MHz, DMSO-d$_6$) δ1.31 (3H, brs), 1.59-1.94 (5H, m), 3.26 (3H, s), 3.61 (1H, d, J=7.7 Hz), 3.93-4.11 (1H, m), 4.60 (2H, s), 7.15 (1H, d, J=9.0 Hz), 7.38-7.79 (1H, m), 7.89 (1H, d, J=7.9 Hz), 8.20 (1H, s), 8.27 (1H, dd, J=7.9, 1.7 Hz).

Example 18

(1S)—N-((1R,2R)-2-(6-(5-(difluoromethyl)-1,3,4-oxadiazol-2-yl)-1-oxo-1,3-dihydro-2H-isoindol-2-yl) cyclohexyl)-2,2-difluorocyclopropanecarboxamide To a mixture of (1S)-2,2-difluorocyclopropanecarboxylic acid (42.1 mg) and THF (1 mL) was added oxalyl chloride (0.063 mL) at room temperature. Then, DMF (one drop) was added thereto, and the mixture was stirred under nitrogen atmosphere at room temperature for 10 min. The mixture was added to a mixture of 2-((1R,2R)-2-aminocyclohexyl)-6-(5-(difluoromethyl)-1,3,4-oxadiazol-2-yl)isoindolin-1-one (100 mg), TEA (0.240 mL) and THF (1 mL) at 0° C. Then, THF (1 mL) was added thereto, and the mixture was stirred overnight at room temperature. To the mixture was added saturated aqueous sodium hydrogencarbonate solution at 0° C., and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), followed by silica gel column chromatography (NH, ethyl acetate/hexane) to give the title compound (65.1 mg).

$^1$H NMR (300 MHz, DMSO-d$_6$) δ1.27-1.54 (3H, m), 1.56-1.93 (7H, m), 2.31-2.46 (1H, m), 3.89-4.07 (2H, m), 4.46-4.66 (2H, m), 7.33-7.76 (1H, m), 7.81 (1H, d, J=7.9 Hz), 8.18 (1H, d, J=0.9 Hz), 8.23 (1H, dd, J=7.9, 1.6 Hz), 8.42 (1H, d, J=8.9 Hz).

Example 20

6-(5-(difluoromethyl)-1,3,4-oxadiazol-2-yl)-2-((1R,2R)-2-(2-oxopiperidin-1-yl)cyclohexyl)isoindolin-1-one A) tert-butyl ((1R,2R)-2-(2-oxopiperidin-1-yl)cyclohexyl)carbamate To a mixture of tert-butyl ((1R,2R)-2-aminocyclohexyl) carbamate (1.00 g), 5-chloropentanoyl chloride (0.689 mL) and THF (20 mL) was added dropwise DIPEA (1.63 mL) at 0° C. The mixture was stirred at room temperature for 1 hr, to the mixture was added water, and the mixture was extracted with ethyl acetate. The organic layer was separated, washed with saturated brine, dried over anhydrous magnesium sulfate, and concentrated under reduced pressure. To a mixture of the obtained residue and DMF (20 mL) was added 60% sodium hydride (0.411 g) at 0° C. The mixture was stirred overnight at room temperature, to the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (1.28 g).
MS: [M+H]$^+$297.3.

B) 1-((1R,2R)-2-aminocyclohexyl)piperidin-2-one hydrochloride

To a mixture of tert-butyl ((1R,2R)-2-(2-oxopiperidin-1-yl)cyclohexyl)carbamate (415 mg) and ethyl acetate (4 mL) was added 4M hydrogen chloride ethyl acetate solution (10 mL) at room temperature. The mixture was stirred at room temperature for 3 hr, and concentrated to give the title compound (34 mg).
MS: [M+H]$^+$197.2.

C) methyl 3-oxo-2-((1R,2R)-2-(2-oxopiperidin-1-yl)cyclohexyl)isoindoline-5-carboxylate To a mixture of 1-((1R,2R)-2-aminocyclohexyl)piperidin-2-one hydrochloride (34 mg), DIPEA (0.076 mL) and DMF (1 mL) was added dimethyl 4-(bromomethyl)isophthalate (41.9 mg) at room temperature. The mixture was stirred overnight at room temperature, and then at 50° C. for 4 hr. To the mixture was added 1N hydrochloric acid, and the mixture was extracted with ethyl acetate. The organic layer was separated, washed with saturated aqueous sodium hydrogencarbonate solution and saturated brine, dried over anhydrous magnesium sulfate, and concentrated under reduced pressure. The residue was purified by silica gel column chromatography (ethyl acetate/hexane, followed by methanol/ethyl acetate) to give the title compound (27 mg).
MS: [M+H]$^+$371.1.

D) 3-oxo-2-((1R,2R)-2-(2-oxopiperidin-1-yl)cyclohexyl)isoindoline-5-carbohydrazide A mixture of methyl 3-oxo-2-((1R,2R)-2-(2-oxopiperidin-1-yl)cyclohexyl)isoindoline-5-carboxylate (27 mg), hydrazine monohydrate (365 mg) and methanol (1 mL) was stirred at 50° C. for 2 hr. The mixture was concentrated, to the residue was added saturated aqueous sodium hydrogencarbonate solution, and the mixture was extracted with ethyl acetate/THF. The aqueous layer was separated, saturated with potassium carbonate, and extracted with ethyl acetate/THF. The organic layer was dried over anhydrous magnesium sulfate, and concentrated under reduced pressure to give the title compound (25 mg).
MS: [M+H]$^+$371.2.

E) N'-(difluoroacetyl)-3-oxo-2-((1R,2R)-2-(2-oxopiperidin-1-yl)cyclohexyl)isoindoline-5-carbohydrazide To a mixture of 3-oxo-2-((1R,2R)-2-(2-oxopiperidin-1-yl)cyclohexyl)isoindoline-5-carbohydrazide (25 mg), TEA (0.014 mL) and THF (2 mL) was added difluoroacetic anhydride (0.010 mL) at room temperature. The mixture was stirred at room temperature for 2 hr, to the mixture was added saturated aqueous sodium hydrogencarbonate solution, and the mixture was extracted with ethyl acetate. The aqueous layer was saturated with potassium carbonate, and extracted with ethyl acetate/THF. The organic layer was dried over anhydrous sodium sulfate, and concentrated under reduced pressure to give the title compound (30 mg).
MS: [M+H]$^+$449.2.

F) 6-(5-(difluoromethyl)-1,3,4-oxadiazol-2-yl)-2-((1R,2R)-2-(2-oxopiperidin-1-yl)cyclohexyl)isoindolin-1-one To a mixture of N'-(difluoroacetyl)-3-oxo-2-((1R,2R)-2-(2-oxopiperidin-1-yl)cyclohexyl) isoindoline-5-carbohydrazide (30 mg), DIPEA (0.035 mL) and THF (5 mL) was added 4-methylbenzenesulfonyl chloride (38.3 mg) at room temperature, and the mixture was stirred at room temperature for 2 hr, and then at 50° C. for 1 hr. The mixture was poured into saturated aqueous sodium hydrogencarbonate solution, and extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane, followed by methanol/ethyl acetate) to give the title compound (17 mg).
$^1$H NMR (300 MHz, CDCl$_3$) δ1.16-2.04 (13H, m), 2.15-2.28 (1H, m), 3.06-3.27 (1H, m), 3.39-3.55 (1H, m), 4.30-4.55 (2H, m), 4.70-4.92 (2H, m), 6.64-7.16 (1H, m), 7.63 (1H, d, J=7.9 Hz), 8.31 (1H, dd, J=7.9, 1.6 Hz), 8.44-8.60 (1H, m).

Example 21

6-(5-(difluoromethyl)-1,3,4-oxadiazol-2-yl)-2-((1R,2R)-2-(2-oxo-1,3-oxazinan-3-yl)cyclohexyl)isoindolin-1-one

A) tert-butyl ((1R,2R)-2-(2-oxo-1,3-oxazinan-3-yl)cyclohexyl)carbamate

A mixture of tert-butyl ((1R,2R)-2-aminocyclohexyl)carbamate (1.072 g), 3-chloropropyl chloroformate (0.603 mL) and toluene (10 mL) was stirred overnight at 100° C. The mixture was added to water at room temperature, and extracted with ethyl acetate. The organic layer was separated, washed with saturated aqueous sodium hydrogencarbonate solution and saturated brine, dried over anhydrous sodium sulfate, and concentrated under reduced pressure. To a mixture of the residue and DMF (13 mL) was added 60% sodium hydride (0.323 g) at room temperature. The mixture was stirred at room temperature for 1 hr, added to saturated aqueous ammonium chloride solution at room temperature, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (0.73 g).
$^1$H NMR (300 MHz, DMSO-d$_6$) δ1.06-1.31 (3H, m), 1.37 (9H, s), 1.48-1.79 (5H, m), 1.80-1.95 (2H, m), 3.13 (1H, dt, J=11.5, 6.0 Hz), 3.23-3.31 (1H, m), 3.37-3.54 (1H, m), 3.85 (1H, brs), 3.95-4.18 (2H, m), 6.63 (1H, d, J=9.3 Hz).

B) methyl 3-oxo-2-((1R,2R)-2-(2-oxo-1,3-oxazinan-3-yl)cyclohexyl) isoindoline-5-carboxylate To a mixture of tert-butyl ((1R,2R)-2-(2-oxo-1,3-oxazinan-3-yl)cyclohexyl)carbamate (0.73 g) and ethyl acetate (4 mL) was added 4M hydrogen chloride ethyl acetate solution (4.00 mL) at room temperature. The mixture was stirred overnight at room temperature. The mixture was concentrated to give 3-((1R,2R)-2-aminocyclohexyl)-1,3-oxazinan-2-one hydrochloride (0.60 g). To a mixture of the obtained 3-((1R,2R)-2-aminocyclohexyl)-1,3-oxazinan-2-one hydrochloride (90 mg) and DMF (1 mL) was added a mixture of DIPEA (0.200 mL), dimethyl 4-(bromomethyl)isophthalate (110 mg) and DMF (1 mL) at room temperature, and the mixture was stirred overnight at room temperature. The mixture was purified by silica gel column chromatography (ethyl acetate/hexane) to give the title compound (66 mg).

MS: [M+H]$^+$373.2.

C) 3-oxo-2-((1R,2R)-2-(2-oxo-1,3-oxazinan-3-yl)cyclohexyl)isoindoline-5-carbohydrazide A mixture of methyl 3-oxo-2-((1R,2R)-2-(2-oxo-1,3-oxazinan-3-yl)cyclohexyl)isoindoline-5-carboxylate (142 mg), hydrazine monohydrate (0.370 mL) and methanol (4 mL) was stirred at 50° C. overnight. The mixture was concentrated to give the title compound (142 mg).

MS: [M+H]$^+$373.2.

D) N'-(difluoroacetyl)-3-oxo-2-((1R,2R)-2-(2-oxo-1,3-oxazinan-3-yl)cyclohexyl)isoindoline-5-carbohydrazide A mixture of 3-oxo-2-((1R,2R)-2-(2-oxo-1,3-oxazinan-3-yl)cyclohexyl)isoindoline-5-carbohydrazide (142 mg), difluoroacetic anhydride (0.095 mL), TEA (0.159 mL) and THF (4 mL) was stirred at room temperature for 1 hr, and concentrated to give the title compound (172 mg).

MS: [M+H]$^+$451.2.

E) 6-(5-(difluoromethyl)-1,3,4-oxadiazol-2-yl)-2-((1R,2R)-2-(2-oxo-1,3-oxazinan-3-yl)cyclohexyl)isoindolin-1-one A mixture of N'-(difluoroacetyl)-3-oxo-2-((1R,2R)-2-(2-oxo-1,3-oxazinan-3-yl)cyclohexyl)isoindoline-5-carbohydrazide (172 mg), 4-methylbenzenesulfonyl chloride (218 mg), DIPEA (0.200 mL) and acetonitrile (4 mL) was stirred at room temperature for 1 hr, and concentrated. The residue was purified by silica gel column chromatography (ethyl acetate/hexane) to give the title compound (122 mg).

$^1$H NMR (300 MHz, DMSO-d$_6$) δ 1.33-1.92 (10H, m), 3.09-3.26 (2H, m), 3.34-3.41 (1H, m), 3.83-4.12 (3H, m), 4.49-4.70 (2H, m), 7.38-7.76 (1H, m), 7.87 (1H, d, J=7.9 Hz), 8.21 (1H, d, J=0.9 Hz), 8.27 (1H, dd, J=7.9, 1.7 Hz).

Example 22

6-(5-(difluoromethyl)-1,3,4-oxadiazol-2-yl)-2-((1R,2R)-2-(2-oxo-1,3-oxazolidin-3-yl)cyclohexyl)isoindolin-1-one

A) tert-butyl ((1R,2R)-2-(2-oxo-1,3-oxazolidin-3-yl)cyclohexyl)carbamate

A mixture of 2-chloroethyl chloroformate (0.619 mL), tert-butyl ((1R,2R)-2-aminocyclohexyl)carbamate (1.072 g) and toluene (10 mL) was stirred overnight at 100° C. The mixture was added to water at room temperature, and extracted with ethyl acetate. The organic layer was separated, washed with saturated aqueous sodium hydrogencarbonate solution and saturated brine, dried over anhydrous sodium sulfate, and concentrated under reduced pressure. To a mixture of the obtained residue and DMF (15 mL) was added 60% sodium hydride (0.386 g) at room temperature, and the mixture was stirred at room temperature for 1 hr. The mixture was added to saturated aqueous ammonium chloride solution at room temperature, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (0.55 g).

$^1$H NMR (300 MHz, DMSO-d$_6$) δ1.11-1.52 (14H, m), 1.56-1.77 (4H, m), 3.33-3.48 (2H, m), 3.65 (1H, td, J=8.6, 5.3 Hz), 3.97-4.09 (1H, m), 4.25 (1H, td, J=8.8, 5.1 Hz), 6.76 (1H, d, J=8.5 Hz).

B) 3-((1R,2R)-2-aminocyclohexyl)-1,3-oxazolidin-2-one hydrochloride

To a mixture of tert-butyl ((1R,2R)-2-(2-oxo-1,3-oxazolidin-3-yl)cyclohexyl)carbamate (0.55 g) and ethyl acetate (4 mL) was added 4M hydrogen chloride ethyl acetate solution (4.00 mL) at room temperature. The mixture was stirred overnight at room temperature. The mixture was concentrated to give the title compound (0.48 g).

$^1$H NMR (300 MHz, DMSO-d$_6$) δ1.14-1.30 (2H, m), 1.32-1.46 (1H, m), 1.47-1.60 (1H, m), 1.62-1.78 (3H, m), 2.08 (1H, d, J=12.7 Hz), 3.20 (1H, td, J=11.1, 4.1 Hz), 3.38-3.62 (3H, m), 4.23-4.35 (2H, m), 8.12 (3H, brs).

C) methyl 3-oxo-2-((1R,2R)-2-(2-oxo-1,3-oxazolidin-3-yl)cyclohexyl)isoindoline-5-carboxylate To a mixture of 3-((1R,2R)-2-aminocyclohexyl)-1,3-oxazolidin-2-one hydrochloride (110 mg) and DMF (1 mL) was added a mixture of DIPEA (0.261 mL), dimethyl 4-(bromomethyl)isophthalate (144 mg) and DMF (1 mL), and the mixture was stirred overnight at room temperature. The reaction mixture was purified by silica gel column chromatography (ethyl acetate/hexane) to give the title compound (148 mg).

MS: [M+H]$^+$359.2.

D) N'-(difluoroacetyl)-3-oxo-2-((1R,2R)-2-(2-oxo-1,3-oxazolidin-3-yl)cyclohexyl)isoindoline-5-carbohydrazide A mixture of methyl 3-oxo-2-((1R,2R)-2-(2-oxo-1,3-oxazolidin-3-yl)cyclohexyl)isoindoline-5-carboxylate (148 mg), hydrazine monohydrate (0.401 mL) and methanol (4 mL) was stirred overnight at 50° C. The mixture was concentrated. A mixture of the residue, difluoroacetic anhydride (0.103 mL), TEA (0.172 mL) and THF (4 mL) was stirred at room temperature for 1 hr. The mixture was concentrated to give the title compound (180 mg).

MS: [M+H]$^+$437.2.

E) 6-(5-(difluoromethyl)-1,3,4-oxadiazol-2-yl)-2-((1R,2R)-2-(2-oxo-1,3-oxazolidin-3-yl)cyclohexyl)isoindolin-1-one A mixture of N'-(difluoroacetyl)-3-oxo-2-((1R,2R)-2-(2-oxo-1,3-oxazolidin-3-yl)cyclohexyl)isoindoline-5-carbohydrazide (180 mg), 4-methylbenzenesulfonyl chloride (236 mg), DIPEA (0.216 mL) and acetonitrile (4 mL) was stirred at room temperature for 2 hr, and the mixture was added to saturated aqueous sodium hydrogencarbonate solution at room temperature, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (120 mg).
$^1$H NMR (300 MHz, DMSO-$d_6$) δ1.35-1.49 (2H, m), 1.61-1.90 (6H, m), 3.44-3.56 (1H, m), 3.62-3.83 (2H, m), 4.00-4.11 (1H, m), 4.12-4.30 (2H, m), 4.57 (2H, s), 7.36-7.76 (1H, m), 7.88 (1H, d, J=8.0 Hz), 8.21 (1H, d, J=0.9 Hz), 8.28 (1H, dd, J=7.9, 1.7 Hz).

Example 28

N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluoroacetamide To a mixture of 2-((1R,2R)-2-aminocyclohexyl)-6-(5-(difluoromethyl)-1,3,4-oxadiazol-2-yl)isoindolin-1-one (100 mg), TEA (0.048 mL) and THF (1 mL) was added difluoroacetic anhydride (0.037 mL) at 0° C., and the mixture was stirred at room temperature for 4 hr. The mixture was concentrated under reduced pressure without warming, and the residue was purified by silica gel column chromatography (ethyl acetate/hexane) to give the title compound (102 mg).
$^1$H NMR (300 MHz, DMSO-$d_6$) δ1.26-1.47 (2H, m), 1.50-1.91 (6H, m), 3.92-4.17 (2H, m), 4.58 (2H, s), 5.73-6.19 (1H, m), 7.37-7.78 (1H, m), 7.88 (1H, d, J=8.4 Hz), 8.19 (1H, d, J=0.9 Hz), 8.26 (1H, dd, J=7.9, 1.6 Hz), 8.86 (1H, d, J=9.0 Hz).

Example 30

6-(5-(difluoromethyl)-1,3,4-oxadiazol-2-yl)-2-((1R, 2R)-2-(3-oxomorpholin-4-yl)cyclohexyl) isoindolin-1-one A) tert-butyl ((1R,2R)-2-(3-oxomorpholin-4-yl)cyclohexyl)carbamate To a mixture of tert-butyl ((1R,2R)-2-aminocyclohexyl)carbamate (200 mg), DIPEA (0.326 mL) and THF (10 mL) was added (2-chloroethoxy)acetyl chloride (0.140 mL) at 0° C. The mixture was stirred at 0° C. for 1 hr, to the mixture was added saturated aqueous sodium hydrogencarbonate solution at 0° C., and the mixture was extracted with ethyl acetate. The organic layer was separated, washed with water and saturated brine, dried over anhydrous magnesium sulfate, and concentrated under reduced pressure. To a mixture of the residue and DMF (10 mL) was added 60% sodium hydride (74.7 mg) at room temperature. The mixture was stirred at room temperature for 1 hr, and the mixture was poured into saturated aqueous ammonium chloride solution at room temperature, and extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (178 mg).
MS, found: 199.1.

B) 4-((1R,2R)-2-aminocyclohexyl)morpholin-3-one hydrochloride

To a mixture of tert-butyl ((1R,2R)-2-(3-oxomorpholin-4-yl)cyclohexyl)carbamate (175 mg) and ethyl acetate (2 mL) was added 4M hydrogen chloride ethyl acetate solution (6 mL) at room temperature. The mixture was stirred at room temperature for 3 hr, and the mixture was concentrated to give the title compound (109 mg).
MS: [M+H]$^+$199.3.

C) methyl 3-oxo-2-((1R,2R)-2-(3-oxomorpholin-4-yl)cyclohexyl)isoindoline-5-carboxylate To a mixture of 4-((1R,2R)-2-aminocyclohexyl)morpholin-3-one hydrochloride (109 mg), DIPEA (0.243 mL) and DMF (1 mL) was added dimethyl 4-(bromomethyl)isophthalate (133 mg) at room temperature. The mixture was stirred overnight at room temperature, and then at 50° C. for 4 hr. To the mixture was added 1N hydrochloric acid, and the mixture was extracted with ethyl acetate. The organic layer was separated, washed with saturated aqueous sodium hydrogencarbonate solution and saturated brine, dried over anhydrous magnesium sulfate, and concentrated under reduced pressure. The residue was purified by silica gel column chromatography (ethyl acetate/hexane, followed by methanol/ethyl acetate) to give the title compound (132 mg).
MS: [M+H]$^+$373.2.

D) 6-(5-(difluoromethyl)-1,3,4-oxadiazol-2-yl)-2-((1R,2R)-2-(3-oxomorpholin-4-yl)cyclohexyl)isoindolin-1-one A mixture of methyl 3-oxo-2-((1R,2R)-2-(3-oxomorpholin-4-yl)cyclohexyl)isoindoline-5-carboxylate (132 mg), hydrazine monohydrate (355 mg) and methanol (5 mL) was stirred overnight at 50° C., and concentrated under reduced pressure. A mixture of the residue, DIPEA (0.185 mL), difluoroacetic anhydride (0.088 mL) and THF (2 mL) was stirred at room temperature for 5 min. Then, DIPEA (0.185 mL) and 4-methylbenzenesulfonyl chloride (203 mg) were added thereto at room temperature. The mixture was stirred at 50° C. for 3 hr, and the reaction mixture was poured into saturated aqueous sodium hydrogencarbonate solution, and extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), followed by silica gel column chromatography (NH, ethyl acetate/hexane) to give the title compound (90 mg).
$^1$H NMR (300 MHz, DMSO-$d_6$) δ1.32-1.51 (2H, m), 1.64-1.95 (6H, m), 3.22-3.44 (2H, m), 3.47-3.60 (2H, m), 3.77-3.93 (2H, m), 4.22-4.37 (1H, m), 4.48-4.70 (3H, m), 7.36-7.80 (1H, m), 7.86 (1H, d, J=7.9 Hz), 8.18-8.33 (2H, m).

Example 31

6-(5-(difluoromethyl)-1,3,4-oxadiazol-2-yl)-2-((1R, 2R)-2-(2-oxotetrahydropyrimidin-1(2H)-yl)cyclohexyl) isoindolin-1-one A) tert-butyl ((1R,2R)-2-(2-oxotetrahydropyrimidin-1(2H)-yl)cyclohexyl)carbamate To a mixture of tert-butyl ((1R,2R)-2-aminocyclohexyl)carbamate (500 mg) and DMF (10 mL) was added 1-chloro-3-isocyanatopropane (0.262 mL) at 0° C. The mixture was stirred at room temperature for 1 hr, and a mixture of 60% sodium hydride (112 mg) and DMF (1 mL) at 0° C. was added thereto. The mixture was stirred at room temperature

131 for 1 hr, and the mixture was poured into saturated aqueous ammonium chloride solution at room temperature, and extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (680 mg).

MS: [M+H]$^+$298.3.

B) 1-((1R,2R)-2-aminocyclohexyl)tetrahydropyrimidin-2(1H)-one hydrochloride

To a mixture of tert-butyl ((1R,2R)-2-(2-oxotetrahydropyrimidin-1(2H)-yl)cyclohexyl)carbamate (680 mg) and ethyl acetate (4 mL) was added 4M hydrogen chloride ethyl acetate solution (10 mL), and the mixture was stirred overnight at room temperature. The mixture was concentrated, and the residue was washed with ethyl acetate and hexane to give the title compound (344 mg).

MS: [M+H]$^+$198.2.

C) methyl 3-oxo-2-((1R,2R)-2-(2-oxotetrahydropyrimidin-1(2H)-yl)cyclohexyl)isoindoline-5-carboxylate To a mixture of 1-((1R,2R)-2-aminocyclohexyl)tetrahydropyrimidin-2(1H)-one hydrochloride (167 mg) and DMF (1 mL) was added a mixture of DIPEA (0.373 mL), dimethyl 4-(bromomethyl)isophthalate (205 mg) and DMF (1 mL) at room temperature. The mixture was stirred overnight at room temperature, and then at 50° C. for 4 hr. To the mixture was added 1N hydrochloric acid, and the mixture was extracted twice with ethyl acetate. The organic layer was separated, washed with water, saturated aqueous sodium hydrogencarbonate solution and saturated brine, dried over anhydrous magnesium sulfate, and concentrated under reduced pressure. The residue was purified by silica gel column chromatography (ethyl acetate/hexane, followed by methanol/ethyl acetate) to give the title compound (182 mg).

MS: [M+H]$^+$372.2.

D) 6-(5-(difluoromethyl)-1,3,4-oxadiazol-2-yl)-2-((1R,2R)-2-(2-oxotetrahydropyrimidin-1 (2H)-yl) cyclohexyl) isoindolin-1-one A mixture of methyl 3-oxo-2-((1R,2R)-2-(2-oxotetrahydropyrimidin-1(2H)-yl)cyclohexyl)isoindoline-5-carboxylate (96 mg), hydrazine monohydrate (259 mg) and methanol (5 mL) was stirred overnight at 50° C., and the mixture was concentrated. To a mixture of the residue, DIPEA (0.135 mL) and THF (2 mL) was added difluoroacetic anhydride (0.064 mL) at room temperature. The reaction mixture was stirred at room temperature for 5 min, and DIPEA (0.135 mL) and 4-methylbenzenesulfonyl chloride (148 mg) were added thereto at room temperature. The mixture was stirred at 50° C. for 3 hr, and saturated aqueous sodium hydrogencarbonate solution was added thereto at room temperature. The mixture was stirred for 1 hr, and extracted with ethyl acetate. The organic layer was separated, washed with water and saturated brine, dried over anhydrous magnesium sulfate, and concentrated under reduced pressure. The residue was purified by silica gel column chromatography (ethyl acetate/methanol), followed by silica gel column chromatography (NH, methanol/ethyl acetate) to give the title compound (62 mg).

132

$^1$H NMR (300 MHz, DMSO-d$_6$) δ1.30-1.57 (2H, m), 1.61-1.90 (8H, m), 2.76-2.97 (2H, m), 3.00-3.14 (1H, m), 3.19-3.30 (1H, m), 4.17-4.34 (1H, m), 4.37-4.59 (2H, m), 4.69-4.83 (1H, m), 6.00 (1H, brs), 7.27-7.77 (1H, m), 7.85 (1H, d, J=7.7 Hz), 8.18-8.31 (2H, m).

Example 40

N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluoropropanamide To a mixture of 2,2-difluoropropanoic acid (47.4 mg) and THF (2.0 mL) was added dropwise oxalyl chloride (0.038 mL) at room temperature, DMF (one drop) was added thereto, and the reaction mixture was stirred at room temperature for 30 min. This mixture was added dropwise to a mixture of 2-((1R,2R)-2-aminocyclohexyl)-6-(5-(difluoromethyl)-1,3,4-oxadiazol-2-yl)isoindolin-1-one (100.0 mg), TEA (0.12 mL) and THF (4.0 mL) at 0° C., and the mixture was stirred overnight at room temperature. The mixture was poured into water, and extracted with ethyl acetate. The extract was washed with water and saturated brine, dried over anhydrous sodium sulfate, and concentrated under reduced pressure. The residue was purified by silica gel column chromatography (ethyl acetate/hexane) to give the title compound (126 mg).

$^1$H NMR (300 MHz, DMSO-d$_6$) δ1.27-1.49 (5H, m), 1.78 (6H, brs), 3.94 (1H, d, J=9.6 Hz), 4.09-4.25 (1H, m), 4.48-4.69 (2H, m), 7.32-7.77 (1H, m), 7.88 (1H, d, J=7.9 Hz), 8.18 (1H, d, J=0.9 Hz), 8.27 (1H, dd, J=7.9, 1.7 Hz), 8.67 (1H, d, J=9.1 Hz).

Example 53

6-(5-(difluoromethyl)-1,3,4-oxadiazol-2-yl)-2-((1R, 2R)-2-(4-oxo-5-azaspiro[2.4]hept-5-yl)cyclohexyl) isoindolin-1-one A) tert-butyl 1-(2-(((1R,2R)-2-(6-(5-(difluoromethyl)-1,3,4-oxadiazol-2-yl)-1-oxo-1,3-dihydro-2H-isoindol-2-yl)cyclohexyl)amino)ethyl)cyclopropanecarboxylate Under nitrogen atmosphere, to a mixture of diisopropylamine (1.067 g) and THF (10 mL) was added n-BuLi (1.6M hexane solution, 5.71 mL) at −78° C. The mixture was stirred at −78° C. for 20 min, and a mixture of tert-butyl cyclopropanecarboxylate (1.00 g) and THF (10 mL) was added dropwise thereto. The mixture was stirred at −78° C. for 30 min under nitrogen atmosphere, and 1-bromo-2-chloroethane (1.166 mL) was added thereto. The mixture was warmed to room temperature, and stirred overnight at room temperature. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane). A mixture of a part (150 mg) of the residue, 2-((1R,2R)-2-aminocyclohexyl)-6-(5-(difluoromethyl)-1,3,4-oxadiazol-2-yl)isoindolin-1-one (128 mg), tetrabutylammonium iodide (13.53 mg), DIPEA (0.064 mL), sodium iodide (54.9 mg) and DMF (1 mL) was stirred at room temperature for 30 min, and then at 80° C. overnight. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane) to give the title compound (24.5 mg).

MS: [M+H]+517.3.

B) 6-(5-(difluoromethyl)-1,3,4-oxadiazol-2-yl)-2-((1R,2R)-2-(4-oxo-5-azaspiro[2.4]hept-5-yl)cyclohexyl) isoindolin-1-one A mixture of tert-butyl 1-(2-(((1R,2R)-2-(6-(5-(difluoromethyl)-1,3,4-oxadiazol-2-yl)-1-oxo-1,3-dihydro-2H-isoindol-2-yl)cyclohexyl)amino)ethyl)cyclopropanecarboxylate (24.5 mg) and TFA (0.25 mL) was stirred at room temperature for 30 min, and the mixture was concentrated under reduced pressure.

To a mixture of a half of the residue and pyridine (1 mL) was added WSC.HCl (9.59 mg) at 0° C., and the mixture was stirred overnight at room temperature. Then, WSC.HCl (9.59 mg) was added thereto, and the mixture was stirred at room temperature for 4 hr.

Similarly, To a mixture of a half of the residue and pyridine (1 mL) was added 1-(chloro-1-pyrrolidinyl methylene)pyrrolidinium hexafluorophosphate (16.63 mg) at 0° C., and the mixture was stirred overnight at room temperature.

To each mixture was added 1N hydrochloric acid, and the mixtures were combined, and extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and washed with diethyl ether to give the title compound (6.7 mg).

$^1$H NMR (300 MHz, DMSO-$d_6$) δ-0.10 (1H, ddd, J=9.9, 6.6, 3.3 Hz), 0.26-0.37 (1H, m), 0.46-0.65 (2H, m), 1.40 (2H, d, J=14.8 Hz), 1.65-1.98 (8H, m), 3.24-3.44 (2H, m), 3.53-3.66 (1H, m), 4.14-4.36 (1H, m), 4.44-4.69 (2H, m), 7.37-7.75 (1H, m), 7.84 (1H, d, J=7.9 Hz), 8.19-8.22 (1H, m), 8.25 (1H, dd, J=7.9, 1.6 Hz).

Example 54

2-((1R,2R)-2-(3,5-diethyl-1H-pyrazol-1-yl)cyclohexyl)-6-(5-(difluoromethyl)-1,3,4-oxadiazol-2-yl) isoindolin-1-one Under nitrogen atmosphere, to a mixture of 2-((1R,2R)-2-aminocyclohexyl)-6-(5-(difluoromethyl)-1,3,4-oxadiazol-2-yl)isoindolin-1-one (50.0 mg) and DMF (1 mL) were added heptane-3,5-dione (0.021 mL) and O-(4-nitrobenzoyl) hydroxylamine (39.2 mg) at −40° C., and the mixture was stirred at 80° C. for 3 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (29.4 mg).

$^1$H NMR (300 MHz, DMSO-$d_6$) δ0.94-1.09 (6H, m), 1.36-1.56 (2H, m), 1.72-1.98 (5H, m), 2.20-2.31 (1H, m), 2.37-2.57 (3H, m), 3.90-4.01 (1H, m), 4.08-4.19 (1H, m), 4.47 (1H, d, J=18.8 Hz), 4.73 (1H, td, J=10.6, 5.3 Hz), 5.64 (1H, s), 7.37-7.72 (1H, m), 7.74 (1H, d, J=8.3 Hz), 8.09-8.33 (3H, m).

Example 55

6-(5-(difluoromethyl)-1,3,4-oxadiazol-2-yl)-2-((1R,2R)-2-(2H-indazol-2-yl)cyclohexyl)isoindolin-1-one A mixture of 2-((1R,2R)-2-aminocyclohexyl)-6-(5-(difluoromethyl)-1,3,4-oxadiazol-2-yl)isoindolin-1-one (50.0 mg), 2-nitrobenzaldehyde (21.69 mg) and 2-propanol (1 mL) was stirred at 80° C. for 4.5 hr. The mixture was cooled to room temperature, tributylphosphine (0.107 mL) was added thereto, and the mixture was stirred overnight at 80° C. Tributylphosphine (0.215 mL) was added thereto again, and the mixture was stirred at 80° C. for 5 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/ hexane) to give the title compound (35.7 mg).

$^1$H NMR (300 MHz, DMSO-$d_6$) δ1.25-2.36 (8H, m), 4.37-4.52 (1H, m), 4.57-4.76 (2H, m), 4.91-5.09 (1H, m), 6.91 (1H, ddd, J=8.3, 6.6, 0.8 Hz), 7.11 (1H, ddd, J=8.7, 6.6, 1.1 Hz), 7.31-7.74 (3H, m), 7.79 (1H, d, J=8.1 Hz), 7.99 (1H, d, J=1.0 Hz), 8.18 (1H, dd, J=7.9, 1.6 Hz), 8.39 (1H, d, J=0.8 Hz).

Example 62 tert-butyl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate A) diethyl 2-(bromomethyl)pyridine-3,5-dicarboxylate A mixture of diethyl 2-methylpyridine-3,5-dicarboxylate (1.10 g), NBS (2.476 g), AIBN (0.114 g) and (trifluoromethyl)benzene (15 mL) was heated under reflux for 6 hr. To the mixture were added water and saturated aqueous sodium hydrogencarbonate solution at room temperature, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (748.0 mg).

$^1$H NMR (300 MHz, DMSO-$d_6$) δ 1.36 (6H, q, J=7.1 Hz), 4.40 (4H, qd, J=7.1, 4.5 Hz), 5.03 (2H, s), 8.64 (1H, d, J=2.2 Hz), 9.19 (1H, d, J=2.1 Hz).

B) ethyl 6-((1R,2R)-2-((tert-butoxycarbonyl)amino) cyclohexyl)-5-oxo-6,7-dihydro-5H-pyrrolo[3,4-b] pyridine-3-carboxylate To a mixture of tert-butyl ((1R,2R)-2-aminocyclohexyl) carbamate (92 mg), DIPEA (0.124 mL) and DMF (1 mL) was added a mixture of diethyl 2-(bromomethyl)pyridine-3,5-dicarboxylate (90.3 mg) and DMF (1.5 mL) at 0° C. The mixture was stirred overnight at room temperature, and then at 80° C. for 4 hr. To the mixture was added water at 0° C., and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (48.8 mg).

MS: [M+H]+404.2.

C) tert-butyl ((1R,2R)-2-(3-(5-(difluoromethyl)-1,3, 4-oxadiazol-2-yl)-5-oxo-5,7-dihydro-6H-pyrrolo[3, 4-b]pyridin-6-yl)cyclohexyl)carbamate To a mixture of ethyl 6-((1R,2R)-2-((tert-butoxycarbonyl) amino)cyclohexyl)-5-oxo-6,7-dihydro-5H-pyrrolo[3,4-b] pyridine-3-carboxylate (2.18 g), THF (10 mL) and methanol (10 mL) was added hydrazine monohydrate (1.048 mL) at room temperature, and the mixture was stirred at 80° C. for 5 hr. The mixture was concentrated by azeotropic evaporation with toluene, the obtained residue was mixed with TEA (1.130 mL) and THF (15 mL), and difluoroacetic anhydride (0.806 mL) at 0° C. was added thereto. The mixture was stirred at room temperature for 30 min. The mixture was diluted with ethyl acetate, and washed with saturated brine. The organic layer was separated, dried over anhydrous magnesium sulfate, and concentrated under reduced pressure. To a mixture of the obtained residue and THF (30 mL) were added 4-methylbenzenesulfonyl chloride (3.38 g) and DIPEA (3.09 mL) at 0° C., and the mixture was stirred overnight at room temperature. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (2.07 g).
$^1$H NMR (300 MHz, DMSO-$d_6$) δ1.00 (9H, s), 1.24-1.61 (3H, m), 1.64-1.89 (5H, m), 3.44-3.63 (1H, m), 3.96-4.04 (1H, m), 4.50-4.94 (2H, m), 6.90 (1H, d, J=9.4 Hz), 7.32-7.84 (1H, m), 8.50 (1H, d, J=2.0 Hz), 9.37 (1H, d, J=2.0 Hz).

Example 112

2-(2-bromophenyl)-6-(5-(difluoromethyl)-1,3,4-oxadiazol-2-yl)isoindolin-1-one

A) methyl 2-(2-bromophenyl)-3-oxoisoindoline-5-carboxylate

A mixture of 2-bromoaniline (0.172 g), dimethyl 4-(bromomethyl)isophthalate (0.287 g), DIPEA (0.174 mL) and DMF (1 mL) was stirred overnight at room temperature. The mixture was added to water at room temperature, and extracted with ethyl acetate. The organic layer was separated, washed with water and saturated brine, dried over anhydrous sodium sulfate, and concentrated under reduced pressure. The residue was dissolved in acetic acid (1 mL), and the solution was stirred overnight at 80° C. The mixture was concentrated, and the residue was purified by silica gel column chromatography (ethyl acetate/hexane) to give the title compound (0.346 g).
$^1$H NMR (300 MHz, DMSO-$d_6$) δ3.92 (3H, s), 4.94 (2H, s), 7.36-7.45 (1H, m), 7.54 (1H, td, J=7.6, 1.5 Hz), 7.60-7.66 (1H, m), 7.78-7.89 (2H, m), 8.24-8.31 (2H, m).

B) 2-(2-bromophenyl)-N'-(difluoroacetyl)-3-oxoisoindoline-5-carbohydrazide

A mixture of methyl 2-(2-bromophenyl)-3-oxoisoindoline-5-carboxylate (0.346 g), hydrazine monohydrate (0.485 mL) and methanol (2 mL) was stirred overnight at 50° C. The mixture was concentrated, and a mixture of the obtained residue, difluoroacetic anhydride (0.249 mL), TEA (0.417 mL) and THF (4 mL) was stirred at room temperature for 1 hr. The mixture was concentrated to give the title compound (0.424 g).
MS: [M+H]$^+$424.0, 426.0.

C) 2-(2-bromophenyl)-6-(5-(difluoromethyl)-1,3,4-oxadiazol-2-yl)isoindolin-1-one A mixture of 2-(2-bromophenyl)-N'-(difluoroacetyl)-3-oxoisoindoline-5-carbohydrazide (7.60 g), 4-methylbenzenesulfonyl chloride (10.25 g), DIPEA (9.39 mL) and acetonitrile (80 mL) was stirred at room temperature for 1 hr. The mixture was concentrated, and the residue was purified by silica gel column chromatography (ethyl acetate/hexane) to give the title compound (6.26 g).
$^1$H NMR (300 MHz, DMSO-$d_6$) δ4.99 (2H, s), 7.38-7.78 (4H, m), 7.80-7.85 (1H, m), 7.97 (1H, dd, J=7.9, 0.7 Hz), 8.33 (1H, d, J=0.9 Hz), 8.39 (1H, dd, J=7.9, 1.7 Hz).

Example 123

6-(5-(difluoromethyl)-1,3,4-oxadiazol-2-yl)-2-(1R, 2R)-2-(1H-1,2,3-triazol-1-yl)cyclohexyl)isoindolin-1-one To a mixture of glyoxal (0.082 mL), acetic acid (0.01 mL) and methanol (0.8 mL) was added 4-methylbenzenesulfonylhydrazide (56.1 mg) at room temperature, and the mixture was stirred at room temperature for 1 hr. To the resulting suspension was added 2-((1R,2R)-2-aminocyclohexyl)-6-(5-(difluoromethyl)-1,3,4-oxadiazol-2-yl)isoindolin-1-one (100 mg) at 0° C., and the mixture was stirred at room temperature for 10 days. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and washed with diisopropyl ether to give the title compound (26.5 mg).
$^1$H NMR (300 MHz, DMSO-$d_6$) δ1.46-1.69 (2H, m), 1.81-2.24 (6H, m), 4.45-4.75 (3H, m), 4.91-5.11 (1H, m), 7.37-7.75 (2H, m), 7.85 (1H, d, J=7.9 Hz), 8.05 (1H, d, J=1.0 Hz), 8.21 (1H, d, J=1.0 Hz), 8.24 (1H, dd, J=8.0, 1.7 Hz).

Example 124

6-(5-(difluoromethyl)-1,3,4-oxadiazol-2-yl)-4-fluoro-2-((1R,2R)-2-(2-oxopyrrolidin-1-yl)cyclohexyl)isoindolin-1-one

A) 1-((1R,2R)-2-aminocyclohexyl)pyrrolidin-2-one hydrochloride

To a mixture of tert-butyl ((1R,2R)-2-aminocyclohexyl) carbamate (1 g), DIPEA (1.63 mL) and THF (10 mL) was added 4-chlorobutanoyl chloride (0.627 mL) at 0° C. The mixture was stirred at 0° C. for 1 hr, saturated aqueous sodium hydrogencarbonate solution was added thereto at 0° C., and the mixture was extracted with ethyl acetate. The organic layer was separated, washed with water and saturated brine, dried over anhydrous magnesium sulfate, and concentrated under reduced pressure. To a mixture of the obtained residue and DMF (10 mL) was added 60% sodium hydride (0.373 g) at room temperature. The mixture was stirred at room temperature for 1 hr, and the mixture was poured into saturated aqueous ammonium chloride solution at room temperature, and extracted with ethyl acetate. The organic layer was separated, washed with saturated brine, dried over anhydrous magnesium sulfate, and concentrated under reduced pressure. The residue was purified by silica gel column chromatography (ethyl acetate/hexane). To a mixture of the obtained tert-butyl ((1R,2R)-2-(2-oxopyrrolidin-1-yl)cyclohexyl)carbamate (1.318 g) and ethyl acetate (4 mL) was added 4M hydrogen chloride ethyl acetate solution (10 mL), and the mixture was stirred at room temperature for 3 hr. The mixture was concentrated, and the residue was washed with ethyl acetate/hexane to give the title compound (906 mg).
MS: [M+H]$^+$183.2.

B) dimethyl 5-fluoro-4-methylisophthalate

A mixture of methyl 3-fluoro-5-iodo-4-methylbenzoate (11.58 g), [1,1'-bis(diphenylphosphino)ferrocene]palladium (II) dichloride (2.88 g), TEA (10.95 mL) and methanol (160 mL) was stirred under 0.5 MPa of carbon monoxide atmosphere at 80° C. for 6 hr. The mixture was filtered, and the filtrate was concentrated under reduced pressure. To the residue were added ethyl acetate/methanol, and the mixture was filtered through silica gel pad, and the filtrate was concentrated under reduced pressure. The residue was purified by silica gel column chromatography (ethyl acetate/hexane) to give the title compound (8.86 g).
MS: [M+H]$^+$227.2.

C) dimethyl 4-(bromomethyl)-5-fluoroisophthalate

To a mixture of dimethyl 5-fluoro-4-methylisophthalate (17.0 g), NBS (14.1 g) and (trifluoromethyl)benzene (200 mL) was added AIBN (1.23 g) at room temperature, and the mixture was stirred at 80° C. for 2 hr. The reaction mixture was cooled to 0° C., and saturated aqueous sodium thiosulfate solution was added thereto. The solvent was evaporated under reduced pressure to a half volume, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/hexane) to give the title compound (22.1 g).
$^1$H NMR (300 MHz, DMSO-d$_6$) δ 3.90 (3H, s), 3.93 (3H, s), 4.99 (2H, d, J=1.9 Hz), 8.00 (1H, dd, J=10.0, 1.7 Hz), 8.26 (1H, dd, J=1.6, 0.8 Hz).

D) methyl 7-fluoro-3-oxo-2-((1R,2R)-2-(2-oxopyrrolidin-1-yl)cyclohexyl)isoindoline-5-carboxylate To a mixture of dimethyl 4-(bromomethyl)-5-fluoroisophthalate (150 mg), 1-((1R,2R)-2-aminocyclohexyl)pyrrolidin-2-one hydrochloride (108 mg) and DMF (2 mL) was added dropwise DIPEA (0.257 mL) at room temperature, and the mixture was stirred overnight at same temperature, and then at 50° C. for 2 hr, and then at 70° C. for 6 hr. The reaction mixture was cooled to 0° C., water was added thereto, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (171 mg).
MS: [M+H]$^+$375.2.

E) 6-(5-(difluoromethyl)-1,3,4-oxadiazol-2-yl)-4-fluoro-2-((1R,2R)-2-(2-oxopyrrolidin-1-yl)cyclohexyl)isoindolin-1-one To a mixture of methyl 7-fluoro-3-oxo-2-((1R,2R)-2-(2-oxopyrrolidin-1-yl)cyclohexyl)isoindoline-5-carboxylate (171 mg) and methanol (2 mL) was added hydrazine monohydrate (0.222 mL) at room temperature, and the mixture was stirred overnight at 60° C. The reaction mixture was concentrated under reduced pressure. To a mixture of the obtained residue, DIPEA (0.240 mL) and THF (2 mL) was added difluoroacetic anhydride (0.114 mL) at 0° C., and the mixture was stirred at room temperature for 30 min. DIPEA (0.241 mL) and 4-methylbenzenesulfonyl chloride (263 mg) were added thereto at 0° C., and the mixture was stirred at 50° C. for 1 hr. The reaction mixture was purified by silica gel column chromatography (NH, ethyl acetate/hexane) to give the title compound (100 mg).
$^1$H NMR (300 MHz, DMSO-d$_6$) δ 1.41 (2H, brs), 1.57-1.92 (9H, m), 1.97-2.10 (1H, m), 3.21-3.32 (1H, m), 3.36-3.49 (1H, m), 3.96-4.10 (1H, m), 4.13-4.26 (1H, m), 4.66 (2H, s), 7.58 (1H, t, J=51.2 Hz), 8.06 (1H, d, J=1.1 Hz), 8.11 (1H, dd, J=9.0, 1.1 Hz).

Example 125 tert-butyl (3S,4R)-4-(6-(5-(difluoromethyl)-1,3,4-oxadiazol-2-yl)-1-oxo-1,3-dihydro-2H-isoindol-2-yl)-3-phenylpiperidine-1-carboxylate A) methyl 2-((3S,4R)-1-(tert-butoxycarbonyl)-3-phenylpiperidin-4-yl)-3-oxoisoindoline-5-carboxylate To a mixture of dimethyl 4-(bromomethyl)isophthalate (1.143 g), tert-butyl (3S,4R)-4-amino-3-phenylpiperidine-1-carboxylate (1.10 g) and DMF (10 mL) was added dropwise DIPEA (1.664 mL) at room temperature, and the mixture was stirred overnight at room temperature, and then overnight at 80° C. The mixture was cooled to 0° C., water was added thereto, and the mixture was extracted with ethyl acetate. The organic layer was separated, washed with saturated brine, dried over anhydrous magnesium sulfate, and concentrated under reduced pressure to give the title compound (1.67 g).
MS, found: 473.3.

B) tert-butyl (3S,4R)-4-(6-(hydrazinocarbonyl)-1-oxo-1,3-dihydro-2H-isoindol-2-yl)-3-phenylpiperidine-1-carboxylate To a mixture of methyl 2-((3S,4R)-1-(tert-butoxycarbonyl)-3-phenylpiperidin-4-yl)-3-oxoisoindoline-5-carboxylate (1.67 g), methanol (20 mL) and THF (10 mL) was added hydrazine monohydrate (0.719 mL) at room temperature, and the mixture was stirred at 70° C. for 3 hr. Then, hydrazine monohydrate (0.719 mL) was added thereto, and the mixture was stirred at 80° C. for 1 hr. Then, ethanol (10 mL) was added thereto, and the mixture was stirred at 100° C. for 3 hr. The reaction mixture was concentrated under reduced pressure, and the residue was washed with diethyl ether to give the title compound (1.67 g).
MS, found: 473.2.

C) tert-butyl (3S,4R)-4-(6-(5-(difluoromethyl)-1,3,4-oxadiazol-2-yl)-1-oxo-1,3-dihydro-2H-isoindol-2-yl)-3-phenylpiperidine-1-carboxylate To a mixture of tert-butyl (3S,4R)-4-(6-(hydrazinocarbonyl)-1-oxo-1,3-dihydro-2H-isoindol-2-yl)-3-phenylpiperidine-1-carboxylate (1.67 g), difluoroacetic anhydride (0.553 mL) and THF (20 mL) was added dropwise TEA (0.775 mL) at 0° C., and the mixture was stirred at room temperature for 30 min. Difluoroacetic anhydride (0.553 mL) and TEA (0.775 mL) were added thereto at 0° C., and the mixture was stirred at room temperature for 20 min. Difluoroacetic anhydride (0.553 mL) and TEA (0.775 mL) were added thereto at 0° C., and the mixture was stirred at room temperature for 10 min. The mixture was cooled to 0° C., 4-methylbenzenesulfonyl chloride (3.53 g) and DIPEA (3.24 mL) were added thereto, and the mixture was stirred overnight at room temperature. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (1.42 g).
$^1$H NMR (300 MHz, DMSO-$d_6$) δ1.42 (9H, brs), 1.80-2.10 (2H, m), 2.88-3.29 (2H, m), 3.33-3.52 (2H, m), 4.14-4.38 (3H, m), 4.54-4.65 (1H, m), 7.07-7.23 (5H, m), 7.39-7.78 (2H, m), 8.19 (1H, dd, J=7.9, 1.7 Hz), 8.24 (1H, d, J=0.8 Hz).

Example 139

6-benzyl-3-(5-(difluoromethyl)-1,3,4-oxadiazol-2-yl)-6,7-dihydro-5H-pyrrolo[3,4-b]pyridin-5-one A) diethyl 2-(dibromomethyl)pyridine-3,5-dicarboxylate To a mixture of diethyl 2-methylpyridine-3,5-dicarboxylate (1.02 g), sodium acetate (1.76 g) and acetic acid (10 mL) was added bromine (0.551 mL) at room temperature. The mixture was stirred at 100° C. for 30 min. The insoluble material was removed by filtration, and the filtrate was concentrated under reduced pressure. To the residue were added ethyl acetate and saturated aqueous sodium hydrogencarbonate solution at 0° C., and the mixture was extracted with ethyl acetate. The organic layer was separated, washed with saturated aqueous sodium hydrogencarbonate solution and saturated brine, dried over anhydrous sodium sulfate, and concentrated under reduced pressure. The residue was purified by silica gel column chromatography (ethyl acetate/hexane) to give the title compound (1.74 g).
$^1$H NMR (300 MHz, DMSO-$d_6$) δ 1.36 (6H, td, J=7.1, 4.7 Hz), 4.41 (4H, qd, J=7.1, 1.6 Hz), 7.83 (1H, s), 8.60 (1H, d, J=2.1 Hz), 9.33 (1H, d, J=2.2 Hz).

B) ethyl 6-benzyl-5-oxo-6,7-dihydro-5H-pyrrolo[3,4-b]pyridine-3-carboxylate

A mixture of diethyl 2-(dibromomethyl)pyridine-3,5-dicarboxylate (1.004 g), silver nitrate (1.295 g), ethanol (7.5 mL) and water (2.5 mL) was heated under reflux overnight. The insoluble material was removed by filtration, and the filtrate was concentrated under reduced pressure, and concentrated by azeotropic evaporation with ethanol and toluene. To the residue was added ethyl acetate (14 mL), and the mixture was stirred at room temperature for 30 min. The insoluble substance was removed by filtration, and the filtrate was concentrated under reduced pressure, and concentrated by azeotropic evaporation three times with water and toluene. To a mixture of the obtained residue (800.8 mg, content 80%), benzylamine (0.291 mL), acetic acid (1 mL) and acetonitrile (10 mL) was added sodium triacetoxyborohydride (1009 mg) at 0° C. The mixture was stirred at room temperature for 64 hr. To the mixture were added ethanol and saturated aqueous sodium hydrogencarbonate solution at 0° C., and the mixture was extracted with ethyl acetate. The organic layer was separated, washed with saturated aqueous sodium hydrogencarbonate solution and saturated brine, dried over anhydrous sodium sulfate, and concentrated under reduced pressure. The residue was purified by silica gel column chromatography (ethyl acetate/hexane) to give the title compound (290.0 mg).
MS: [M+H]$^+$297.1.

C) 6-benzyl-3-(5-(difluoromethyl)-1,3,4-oxadiazol-2-yl)-6,7-dihydro-5H-pyrrolo[3,4-b]pyridin-5-one To a mixture of ethyl 6-benzyl-5-oxo-6,7-dihydro-5H-pyrrolo[3,4-b]pyridine-3-carboxylate (150.0 mg), THF (1.5 mL) and methanol (1.5 mL) was added hydrazine monohydrate (0.491 mL) at room temperature. The mixture was heated under reflux for 1 hr. The mixture was concentrated under reduced pressure, and concentrated by azeotropic evaporation with methanol and toluene. To a mixture of the residue, DIPEA (0.265 mL) and THF (3 mL) was added difluoroacetic anhydride (0.126 mL) at 0° C. The mixture was stirred at room temperature for 1 hr. To the mixture were added DIPEA (0.265 mL) and 4-methylbenzenesulfonyl chloride (290 mg) at room temperature, and the mixture was stirred at 50° C. for 1 hr. To the mixture was added saturated aqueous sodium hydrogencarbonate solution at 0° C., and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane), followed by silica gel column chromatography (NH, ethyl acetate/hexane) to give the title compound (39.3 mg).
$^1$H NMR (300 MHz, DMSO-$d_6$) δ 4.61 (2H, s), 4.81 (2H, s), 7.25-7.42 (5H, m), 7.43-7.83 (1H, m), 8.58 (1H, d, J=2.0 Hz), 9.39 (1H, d, J=2.1 Hz).

Example 142 benzyl ((1R,2R)-2-(5-(5-(difluoromethyl)-1,3,4-oxadiazol-2-yl)-1,3-dioxo-1,3-dihydro-2H-isoindol-2-yl)cyclohexyl)carbamate A) 2-((1R,2R)-2-(((benzyloxy)carbonyl)amino)cyclohexyl)-1,3-dioxoisoindoline-5-carboxylic acid A mixture of benzyl ((1R,2R)-2-aminocyclohexyl)carbamate hydrochloride (285 mg), 1,3-dioxo-1,3-dihydro-2-benzofuran-5-carboxylic acid (192 mg) and acetic acid (2 mL) was stirred at 100° C. for 1 day. The reaction mixture was concentrated, and the residue was purified by silica gel column chromatography (ethyl acetate/hexane) to give the title compound (275 mg).
MS: [M+H]$^+$423.1.

B) tert-butyl 2-((2-((1R,2R)-2-(((benzyloxy)carbonyl)amino)cyclohexyl)-1,3-dioxo-2,3-dihydro-1H-isoindol-5-yl)carbonyl)hydrazinecarboxylate A mixture of tert-butyl hydrazinecarboxylate (172 mg), 2-((1R,2R)-2-(((benzyloxy)carbonyl)amino)cyclohexyl)-1,3-dioxoisoindoline-5-carboxylic acid (275 mg), HATU (743 mg), TEA (0.272 mL) and DMF (3 mL) was stirred overnight at room temperature, and then at 80° C. for 2 hr. The mixture was concentrated, and the residue was purified by silica gel column chromatography (NH, ethyl acetate/hexane) to give the title compound (340 mg).
MS, found: 437.2.

C) benzyl ((1R,2R)-2-(5-(hydrazinocarbonyl)-1,3-dioxo-1,3-dihydro-2H-isoindol-2-yl)cyclohexyl)carbamate hydrochloride To a mixture of tert-butyl 2-((2-(((1R,2R)-2-(((benzyloxy)carbonyl)amino)cyclohexyl)-1,3-dioxo-2,3-dihydro-1H-isoindol-5-yl)carbonyl)hydrazinecarboxylate (0.34 g) and ethyl acetate (3 mL) was added 4M hydrogen chloride ethyl acetate solution (3.00 mL) at room temperature. The mixture was stirred at room temperature for 3 hr, and concentrated to give the title compound (0.299 g).
MS: [M+H]$^+$437.2.

D) benzyl ((1R,2R)-2-(5-((2-(difluoroacetyl)hydrazino)carbonyl)-1,3-dioxo-1,3-dihydro-2H-isoindol-2-yl)cyclohexyl)carbamate A mixture of benzyl ((1R,2R)-2-(5-(hydrazinocarbonyl)-1,3-dioxo-1,3-dihydro-2H-isoindol-2-yl)cyclohexyl)carbamate hydrochloride (0.299 g), difluoroacetic anhydride (0.235 mL), TEA (0.439 mL) and THF (2 mL) was stirred overnight at room temperature, and the mixture was concentrated to give the title compound (0.325 g).
MS: [M+H]$^+$515.2.

E) benzyl ((1R,2R)-2-(5-(5-(difluoromethyl)-1,3,4-oxadiazol-2-yl)-1,3-dioxo-1,3-dihydro-2H-isoindol-2-yl)cyclohexyl)carbamate A mixture of benzyl ((1R,2R)-2-(5-((2-(difluoroacetyl)hydrazino) carbonyl)-1,3-dioxo-1,3-dihydro-2H-isoindol-2-yl)cyclohexyl)carbamate (325 mg), 4-methylbenzenesulfonyl chloride (359 mg), DIPEA (0.33 mL) and acetonitrile (2 mL) was stirred at room temperature for 1 hr, and the reaction mixture was concentrated under reduced pressure. The residue was purified by silica gel column chromatography (ethyl acetate/hexane) to give the title compound (201 mg).
$^1$H NMR (300 MHz, DMSO-d$_6$) δ1.14-1.55 (3H, m), 1.67-1.94 (4H, m), 2.17-2.37 (1H, m), 3.88 (1H, td, J=11.4, 4.0 Hz), 4.03 (1H, d, J=7.2 Hz), 4.55-4.81 (2H, m), 6.94-7.08 (2H, m), 7.08-7.19 (3H, m), 7.31 (1H, d, J=8.6 Hz), 7.42-7.83 (1H, m), 8.05 (1H, d, J=7.7 Hz), 8.24 (1H, s), 8.45 (1H, dd, J=7.8, 1.5 Hz).

Example 149

N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-1-(trifluoromethyl)cyclopropanecarboxamide A) 6-((1R,2R)-2-aminocyclohexyl)-3-(5-(difluoromethyl)-1,3,4-oxadiazol-2-yl)-6,7-dihydro-5H-pyrrolo[3,4-b]pyridin-5-one A mixture of tert-butyl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate (2.07 g) and TFA (20 mL) was stirred at room temperature for 30 min. The mixture was concentrated under reduced pressure, and the residue was purified by silica gel column chromatography (NH, ethyl acetate/hexane) to give the title compound (1.52 g).
MS: [M+H]$^+$350.2.

B) N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-1-(trifluoromethyl)cyclopropanecarboxamide To a mixture of 1-(trifluoromethyl)cyclopropanecarboxylic acid (68.4 mg) and THF (1 mL) was added oxalyl chloride (0.058 mL) at room temperature. DMF (one drop) was added thereto, and the mixture was stirred under nitrogen atmosphere at room temperature for 10 min. The mixture was added dropwise to a mixture of 6-((1R,2R)-2-aminocyclohexyl)-3-(5-(difluoromethyl)-1,3,4-oxadiazol-2-yl)-6,7-dihydro-5H-pyrrolo[3,4-b]pyridin-5-one (77.5 mg), TEA (0.186 mL) and THF (1 mL) at 0° C., and the mixture was stirred at room temperature for 30 min. The mixture was purified by silica gel column chromatography (ethyl acetate/hexane), and washed with diisopropyl ether to give the title compound (50.0 mg).
$^1$H NMR (300 MHz, DMSO-d$_6$) δ0.80-1.46 (6H, m), 1.56-1.89 (6H, m), 3.86-4.21 (2H, m), 4.55-4.72 (2H, m), 7.41-7.77 (1H, m), 7.79 (1H, d, J=8.9 Hz), 8.51 (1H, d, J=2.0 Hz), 9.38 (1H, d, J=2.0 Hz).

Example 154

(1R,2R)-2-(6-(5-(difluoromethyl)-1,3,4-oxadiazol-2-yl)-1-oxo-1,3-dihydro-2H-isoindol-2-yl)cyclohexyl methylcarbamate A) tert-butyl ((1R,2R)-2-((methylcarbamoyl)oxy)cyclohexyl)carbamate To a mixture of tert-butyl ((1R,2R)-2-hydroxycyclohexyl)carbamate (300 mg) and THF (6.0 mL) was added CDI (249 mg) at 0° C., and the mixture was stirred overnight at room temperature. To the mixture was added methylamine (2M THF solution, 2.09 mL) at room temperature, and the mixture was stirred for 3 hr. The mixture was concentrated under reduced pressure, and the residue was partitioned between 0.5N hydrochloric acid and ethyl acetate. The organic layer was washed with water and saturated brine, dried over anhydrous sodium sulfate, filtered through silica gel pad, and the filtrate was concentrated under reduced pressure to give the title compound (374 mg).
$^1$H NMR (300 MHz, DMSO-d$_6$) δ1.18 (4H, d, J=5.9 Hz), 1.36 (9H, s), 1.53-1.95 (4H, m), 2.53 (3H, s), 3.24-3.32 (1H, m), 4.34 (1H, d, J=4.2 Hz), 6.65 (1H, d, J=8.9 Hz), 6.89 (1H, d, J=4.0 Hz).

B) methyl 2-((1R,2R)-2-((methylcarbamoyl)oxy)cyclohexyl)-3-oxoisoindoline-5-carboxylate tert-Butyl ((1R,2R)-2-((methylcarbamoyl)oxy)cyclohexyl)carbamate (372 mg) was dissolved in TFA (4.0 mL) at room temperature, and the solution was stirred for 1 hr. The reaction mixture was concentrated under reduced pressure. To a mixture of the residue, dimethyl 4-(bromomethyl)isophthalate (392 mg) and DMF (4.00 mL) was added dropwise TEA (0.686 mL) at room temperature, and the mixture was stirred at room temperature for 2 hr, and heated overnight at 60° C. The reaction mixture was partitioned between water and ethyl acetate. The separated organic layer was washed with water and saturated brine, dried over anhydrous sodium sulfate, and concentrated under reduced pressure. The residue was dissolved in acetic acid (4.00 mL), and the solution was heated at 50° C. for 2 hr. The reaction mixture was concentrated under reduced pressure, and the residue was purified by column chromatography (ethyl acetate/hexane) to give the title compound (277 mg).
MS: [M+H]$^+$347.2.

C) (1R,2R)-2-(6-(5-(difluoromethyl)-1,3,4-oxadiazol-2-yl)-1-oxo-1,3-dihydro-2H-isoindol-2-yl)cyclohexyl methylcarbamate To a mixture of methyl 2-((1R,2R)-2-((methylcarbamoyl)oxy)cyclohexyl)-3-oxoisoindoline-5-carboxylate (272 mg) and methanol (4.0 mL) was added hydrazine monohydrate (0.762 mL) at room temperature, and the mixture was heated at 60° C. for 3 hr. The reaction mixture was concentrated under reduced pressure, and subjected to azeotropic evaporation with ethanol/toluene. To a mixture of the obtained residue, DIPEA (0.276 mL) and THF (4.0 mL) was added dropwise difluoroacetic anhydride (0.148 mL) at room temperature, and the mixture was stirred for 1 hr. To the reaction mixture were added DIPEA (0.276 mL) and 4-methylbenzenesulfonyl chloride (226 mg) at room temperature, and the mixture was stirred overnight. The reaction mixture was poured into water, and extracted with ethyl acetate. The extract was washed with saturated brine, dried over anhydrous sodium sulfate, and concentrated under reduced pressure. The residue was purified by silica gel column chromatography (NH, ethyl acetate/hexane) to give the title compound (260 mg).
$^1$H NMR (300 MHz, DMSO-d$_6$) δ1.39 (3H, d, J=6.4 Hz), 1.76 (4H, brs), 2.02 (1H, brs), 2.32 (3H, d, J=4.5 Hz), 4.14 (1H, td, J=10.5, 5.1 Hz), 4.43-4.69 (2H, m), 4.74-4.89 (1H, m), 6.88 (1H, q, J=4.3 Hz), 7.38-7.79 (1H, m), 7.89 (1H, d, J=7.9 Hz), 8.20 (1H, d, J=0.9 Hz), 8.27 (1H, dd, J=7.9, 1.5 Hz).

Example 157

6-(5-(difluoromethyl)-1,3,4-oxadiazol-2-yl)-2-((1R,2R)-2-(3-methyl-2-oxoimidazolidin-1-yl)cyclohexyl)isoindolin-1-one A) benzyl tert-butyl (1R,2R)-cyclohexane-1,2-diylbiscarbamate To a mixture of tert-butyl ((1R,2R)-2-aminocyclohexyl)carbamate (3.00 g), sodium carbonate (2.97 g), THF (90 mL) and water (30 mL) was added benzyl chloroformate (2.40 mL) at 0° C., and the mixture was stirred overnight at room temperature. The mixture was poured into water, and extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (4.24 g).
MS, found: 249.2.

B) benzyl ((1R,2R)-2-aminocyclohexyl)carbamate hydrochloride

To a mixture of benzyl tert-butyl (1R,2R)-cyclohexane-1,2-diylbiscarbamate (1.40 g) and ethyl acetate (4 mL) was added 4M hydrogen chloride ethyl acetate solution (4.00 mL) at room temperature. The mixture was stirred at room temperature for 5 hr, and concentrated to give the title compound (0.99 g).
MS: [M+H]$^+$249.2.

C) benzyl ((1R,2R)-2-((2-((tert-butoxycarbonyl)(methyl)amino)ethyl)amino)cyclohexyl)carbamate A mixture of tert-butyl methyl(2-oxoethyl)carbamate (191 mg), benzyl ((1R,2R)-2-aminocyclohexyl)carbamate hydrochloride (285 mg), sodium triacetoxyborohydride (636 mg), acetic acid (0.172 mL) and methanol (3 mL) was stirred overnight at room temperature. The mixture was added to saturated aqueous sodium hydrogencarbonate solution at room temperature, and extracted with ethyl acetate. The organic layer was separated, washed with water and saturated brine, dried over anhydrous sodium sulfate, and concentrated under reduced pressure. The residue was purified by silica gel column chromatography (NH, ethyl acetate/hexane) to give the title compound (269 mg).
MS: [M+H]$^+$406.3.

D) benzyl ((1R,2R)-2-((2-(methylamino)ethyl)amino)cyclohexyl)carbamate dihydrochloride To a mixture of benzyl ((1R,2R)-2-((2-((tert-butoxycarbonyl)(methyl)amino)ethyl)amino)cyclohexyl) carbamate (230 mg) and ethyl acetate (2 mL) was added 4M hydrogen chloride ethyl acetate solution (4 mL) at room temperature. The mixture was stirred at room temperature for 2 hr, and concentrated to give the title compound (221 mg).
MS: [M+H]$^+$306.2.

E) benzyl ((1R,2R)-2-(3-methyl-2-oxoimidazolidin-1-yl)cyclohexyl)carbamate

A mixture of benzyl ((1R,2R)-2-((2-(methylamino)ethyl)amino)cyclohexyl)carbamate dihydrochloride (188 mg), CDI (242 mg), DBU (0.374 mL) and THF (3 mL) was stirred overnight at room temperature, and heated under reflux for 1 hr. The mixture was concentrated, and the residue was purified by silica gel column chromatography (ethyl acetate/hexane) to give the title compound (169 mg).
MS: [M+H]$^+$332.2.

F) 1-((1R,2R)-2-aminocyclohexyl)-3-methylimidazolidin-2-one

A mixture of benzyl ((1R,2R)-2-(3-methyl-2-oxoimidazolidin-1-yl)cyclohexyl)carbamate (169 mg), 10% palladium on carbon (50% hydrous product, 15 mg) and THF (5 mL) was hydrogenated under balloon pressure overnight at room temperature. The catalyst was removed by filtration, and the filtrate was concentrated under reduced pressure to give the title compound (78 mg). The product was used in the next reaction without further purification.
$^1$H NMR (300 MHz, DMSO-d$_6$) δ0.97-1.47 (7H, m), 1.54-1.70 (2H, m), 1.76-1.88 (1H, m), 2.62 (3H, s), 3.09-3.27 (6H, m).

G) methyl 2-((1R,2R)-2-(3-methyl-2-oxoimidazolidin-1-yl)cyclohexyl)-3-oxoisoindoline-5-carboxylate A mixture of 1-((1R,2R)-2-aminocyclohexyl)-3-methylimidazolidin-2-one (78 mg), DIPEA (0.069 mL), dimethyl 4-(bromomethyl)isophthalate (114 mg) and DMF (4 mL) was stirred overnight at room temperature. The mixture was concentrated, and the residue was purified by silica gel column chromatography (ethyl acetate/hexane) to give the title compound (82 mg).
MS: [M+H]$^+$372.2.

H) 2-((1R,2R)-2-(3-methyl-2-oxoimidazolidin-1-yl)cyclohexyl)-3-oxoisoindoline-5-carbohydrazide A mixture of methyl 2-((1R,2R)-2-(3-methyl-2-oxoimidazolidin-1-yl)cyclohexyl)-3-oxoisoindoline-5-carboxylate (56.7 mg), hydrazine monohydrate (0.074 mL) and methanol (2 mL) was stirred overnight at 50° C. The reaction mixture was concentrated under reduced pressure to give the title compound (56.7 mg).
MS: [M+H]$^+$372.2.

I) 6-(5-(difluoromethyl)-1,3,4-oxadiazol-2-yl)-2-((1R,2R)-2-(3-methyl-2-oxoimidazolidin-1-yl)cyclohexyl)isoindolin-1-one A mixture of 2-((1R,2R)-2-(3-methyl-2-oxoimidazolidin-1-yl)cyclohexyl)-3-oxoisoindoline-5-carbohydrazide (56.7 mg), difluoroacetic anhydride (0.038 mL), TEA (0.064 mL) and THF (2 mL) was stirred at room temperature for 1 hr, and the mixture was concentrated. A mixture of the residue, 4-methylbenzenesulfonyl chloride (195 mg), DIPEA (0.178 mL) and acetonitrile (3 mL) was stirred at room temperature for 3 hr, and concentrated under reduced pressure. The residue was purified by silica gel column chromatography (NH, ethyl acetate/hexane) to give the title compound (26 mg).
$^1$H NMR (300 MHz, DMSO-d$_6$) δ1.39 (2H, brs), 1.56-1.90 (6H, m), 2.32 (3H, s), 2.94-3.18 (2H, m), 3.19-3.30 (1H, m), 3.35-3.52 (1H, m), 3.81 (1H, td, J=10.9, 4.8 Hz), 4.14-4.28 (1H, m), 4.48-4.66 (2H, m), 7.38-7.75 (1H, m), 7.87 (1H, d, J=7.9 Hz), 8.19 (1H, d, J=0.9 Hz), 8.26 (1H, dd, J=7.9, 1.6 Hz).

Example 167 tert-butyl ((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)carbamate A) benzyl ((3S,4R)-4-aminotetrahydro-2H-pyran-3-yl)carbamate hydrochloride To a mixture of benzyl tert-butyl (3S,4R)-tetrahydro-2H-pyran-3,4-diylbiscarbamate (3.45 g) and ethyl acetate (20 ml) was added 4M hydrogen chloride ethyl acetate solution (20 mL) at room temperature. The mixture was stirred at room temperature for 5 hr. The mixture was concentrated under reduced pressure to give the title compound (2.77 g).
MS: [M+H]$^+$251.2.

B) methyl 2-((3S,4R)-3-(((benzyloxy)carbonyl)amino)tetrahydro-2H-pyran-4-yl)-7-fluoro-3-oxoisoindoline-5-carboxylate To a mixture of dimethyl 4-(bromomethyl)-5-fluoroisophthalate (2.95 g), benzyl ((3S,4R)-4-aminotetrahydro-2H-pyran-3-yl)carbamate hydrochloride (2.77 g) and DMF (30 mL) was added dropwise DIPEA (4.04 mL) at room temperature. The mixture was stirred overnight at room temperature. The mixture was cooled to 0° C., water was added thereto, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (3.25 g).
MS: [M+H]$^+$443.2.

C) methyl 2-((3S,4R)-3-((tert-butoxycarbonyl)amino)tetrahydro-2H-pyran-4-yl)-7-fluoro-3-oxoisoindoline-5-carboxylate A mixture of methyl 2-((3S,4R)-3-(((benzyloxy)carbonyl)amino)tetrahydro-2H-pyran-4-yl)-7-fluoro-3-oxoisoindoline-5-carboxylate (2.22 g), 20% palladium hydroxide on carbon (about 50% hydrous product, 0.2 g), Boc$_2$O (1.398 mL) and THF (50 mL) was hydrogenated under balloon pressure overnight at room temperature. The catalyst was removed by filtration, and the filtrate was concentrated under reduced pressure to give the title compound (2.049 g).
MS, found: 309.2.

D) tert-butyl ((3S,4R)-4-(4-fluoro-6-(hydrazinocarbonyl)-1-oxo-1,3-dihydro-2H-isoindol-2-yl)tetrahydro-2H-pyran-3-yl)carbamate A mixture of hydrazine monohydrate (6.06 mL), methyl 2-((3S,4R)-3-((tert-butoxycarbonyl)amino)tetrahydro-2H-pyran-4-yl)-7-fluoro-3-oxoisoindoline-5-carboxylate (2.55 g) and methanol (30 mL) was stirred at 50° C. for 4 hr. The mixture was concentrated to give the title compound (2.55 g).
MS, found: 309.2.

E) tert-butyl ((3S,4R)-4-(6-((2-(difluoroacetyl)hydrazino)carbonyl)-4-fluoro-1-oxo-1,3-dihydro-2H-isoindol-2-yl)tetrahydro-2H-pyran-3-yl)carbamate A mixture of tert-butyl ((3S,4R)-4-(4-fluoro-6-(hydrazinocarbonyl)-1-oxo-1,3-dihydro-2H-isoindol-2-yl)tetrahydro-2H-pyran-3-yl)carbamate (2.55 g), difluoroacetic anhydride (1.552 mL), TEA (2.60 mL) and THF (30 mL) was stirred at room temperature for 1 hr. The mixture was concentrated to give the title compound (3.04 g).
MS, found: 387.1.

F) tert-butyl ((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)carbamate A mixture of tert-butyl ((3S,4R)-4-(6-((2-(difluoroacetyl)hydrazino)carbonyl)-4-fluoro-1-oxo-1,3-dihydro-2H-isoindol-2-yl)tetrahydro-2H-pyran-3-yl)carbamate (3.04 g), 4-methylbenzenesulfonyl chloride (3.57 g), DIPEA (3.27 mL) and acetonitrile (30 mL) was stirred at room temperature for 1 hr. The mixture was concentrated under reduced pressure. The residue was purified by silica gel column chromatography (NH, ethyl acetate/hexane) to give the title compound (1.96 g).
$^1$H NMR (300 MHz, DMSO-d$_6$) δ1.01-1.19 (9H, m), 1.76 (1H, dd, J=12.8, 3.7 Hz), 1.92-2.10 (1H, m), 3.26 (1H, t, J=10.6 Hz), 3.38 (1H, t, J=11.1 Hz), 3.60-3.77 (1H, m), 3.82 (1H, dd, J=10.8, 4.8 Hz), 3.95 (1H, dd, J=11.6, 3.6 Hz), 4.12-4.27 (1H, m), 4.66-4.85 (2H, m), 6.95 (1H, d, J=9.4 Hz), 7.38-7.77 (1H, m), 8.08 (1H, s), 8.10-8.16 (1H, m).

Example 174

N-((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-4-yl)-2,2,3,3,3-pentafluoropropanamide A) methyl 2-((3S,4R)-4-((tert-butoxycarbonyl)amino)tetrahydro-2H-pyran-3-yl)-7-fluoro-3-oxoisoindoline-5-carboxylate To a mixture of dimethyl 4-(bromomethyl)-5-fluoroisophthalate (2.65 g), tert-butyl ((3S,4R)-3-aminotetrahydro-2H-pyran-4-yl)carbamate (1.879 g) and DMF (20.0 mL) was added dropwise DIPEA (3.63 mL) at 0° C., and the mixture was stirred at room temperature for 2 hr. The reaction mixture was partitioned between water and ethyl acetate. The separated organic layer was washed with water and saturated brine, dried over anhydrous sodium sulfate, and concentrated under reduced pressure. The residue was dissolved in acetic acid (20.0 mL), and the solution was stirred at 50° C. for 3 hr. The mixture was concentrated under reduced pressure, and the residue was purified by silica gel column chromatography (ethyl acetate/hexane) to give the title compound (3.55 g).

MS, found: 309.1.

B) tert-butyl ((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-4-yl)carbamate To a mixture of methyl 2-((3S,4R)-4-((tert-butoxycarbonyl)amino)tetrahydro-2H-pyran-3-yl)-7-fluoro-3-oxoisoindoline-5-carboxylate (3.60 g) and methanol (25.0 mL) was added hydrazine monohydrate (4.28 mL) at room temperature, and the mixture was stirred at 60° C. for 4 hr. The mixture was concentrated under reduced pressure. To a mixture of the obtained residue, DIPEA (3.07 mL) and THF (25.0 mL) was added dropwise difluoroacetic anhydride (1.75 mL) at room temperature, and the mixture was stirred overnight. To this mixture were added DIPEA (3.07 mL) and 4-methylbenzenesulfonyl chloride (2.52 g) at room temperature, and the mixture was stirred at room temperature for 1 hr, and then at 60° C. for 2 hr. To this mixture were added DIPEA (3.07 mL) and 4-methylbenzenesulfonyl chloride (2.52 g) at room temperature, and the mixture was heated at 60° C. for 1 hr. The mixture was poured into water, and extracted with ethyl acetate. The extract was washed with saturated brine, dried over anhydrous sodium sulfate, and concentrated under reduced pressure. The residue was purified by silica gel column chromatography (NH, ethyl acetate/hexane) to give the title compound (1.80 g).

MS, found: 369.2.

C) 2-((3S,4R)-4-aminotetrahydro-2H-pyran-3-yl)-6-(5-(difluoromethyl)-1,3,4-oxadiazol-2-yl)-4-fluoroisoindolin-1-one tert-Butyl ((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-4-yl)carbamate (1.76 g) was dissolved in TFA (10.0 mL) at room temperature, and the mixture was stirred at room temperature for 3 hr. The mixture was concentrated under reduced pressure, and the residue was purified by silica gel column chromatography (NH, methanol/ethyl acetate) to give the title compound (1.019 g).

MS: [M+H]$^+$ 369.1.

D) N-((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-4-yl)-2,2,3,3,3-pentafluoropropanamide To a mixture of 2-((3S,4R)-4-aminotetrahydro-2H-pyran-3-yl)-6-(5-(difluoromethyl)-1,3,4-oxadiazol-2-yl)-4-fluoroisoindolin-1-one (55.0 mg), TEA (0.052 mL) and THF (3.0 mL) was added dropwise pentafluoropropanoic anhydride (0.044 mL) at 0° C., and the mixture was stirred at room temperature for 3 hr. The mixture was poured into water, and extracted with ethyl acetate. The extract was washed with saturated brine, dried over anhydrous sodium sulfate, and concentrated under reduced pressure. The residue was purified by silica gel column chromatography (ethyl acetate/hexane), and crystallized from ethyl acetate/hexane to give the title compound (66.1 mg).

$^1$H NMR (300 MHz, DMSO-d$_6$) δ1.80-2.09 (2H, m), 3.50 (1H, t, J=11.0 Hz), 3.63-3.77 (1H, m), 3.80-4.01 (2H, m), 4.28 (1H, td, J=10.7, 4.4 Hz), 4.43 (1H, d, J=7.7 Hz), 4.69 (2H, s), 7.33-7.82 (1H, m), 8.08 (1H, s), 8.15 (1H, d, J=9.0 Hz), 9.71 (1H, d, J=8.5 Hz).

Example 178

6-(5-(difluoromethyl)-1,3,4-oxadiazol-2-yl)-2-(2-(4,4,5,5-tetramethyl-1,3,2-dioxaborolan-2-yl)phenyl)isoindolin-1-one A mixture of 2-(2-bromophenyl)-6-(5-(difluoromethyl)-1,3,4-oxadiazol-2-yl)isoindolin-1-one (406 mg), 4,4,4',4',5,5,5',5'-octamethyl-2,2'-bi-1,3,2-dioxaborolane (305 mg), [1,1'-bis(diphenylphosphino)ferrocene]palladium(II) dichloride dichloromethane adduct (40.8 mg), potassium acetate (294 mg) and DMSO (4 mL) was stirred under nitrogen atmosphere at 90° C. for 2 hr. The reaction mixture was purified by silica gel column chromatography (ethyl acetate/hexane) to give the title compound (50 mg).

$^1$H NMR (300 MHz, DMSO-d$_6$) δ1.19 (12H, s), 5.27 (2H, s), 7.29-7.41 (2H, m), 7.41-7.79 (3H, m), 8.01 (1H, d, J=7.9 Hz), 8.31 (1H, d, J=0.9 Hz), 8.42 (1H, dd, J=8.0, 1.6 Hz).

Example 186

2-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-H-isoindole-1,3(2H)-dione A mixture of 6-((1R,2R)-2-aminocyclohexyl)-3-(5-(difluoromethyl)-1,3,4-oxadiazol-2-yl)-6,7-dihydro-5H-pyrrolo[3,4-b]pyridin-5-one (49.0 mg), phthalic anhydride (21.5 mg) and acetic acid (2 mL) was stirred overnight at 100° C. The mixture was concentrated, and ethyl acetate was added thereto. The mixture was washed with saturated aqueous sodium hydrogencarbonate solution and saturated brine, dried over anhydrous sodium sulfate, and concentrated under reduced pressure. The residue was purified by silica gel column chromatography (NH, ethyl acetate/hexane) to give the title compound (10.7 mg).

$^1$H NMR (300 MHz, DMSO-d$_6$) δ 1.45 (2H, brs), 1.72-2.10 (6H, m), 4.24-4.41 (1H, m), 4.52-4.76 (2H, m), 4.76-4.89 (1H, m), 7.32-7.93 (5H, m), 8.26 (1H, d, J=2.0 Hz), 9.34 (1H, d, J=2.1 Hz).

Example 187

1-(6-(5-(difluoromethyl)-1,3,4-oxadiazol-2-yl)-1-oxo-1,3-dihydro-2H-isoindol-2-yl)-N-(2,2,2-trifluoroethyl)cyclopropanecarboxamide A) tert-butyl (1-((2,2,2-trifluoroethyl)carbamoyl)cyclopropyl)carbamate A mixture of 1-((tert-butoxycarbonyl)amino)cyclopropanecarboxylic acid (88.0 mg), 2,2,2-trifluoroethanamine (0.052 mL), HATU (249 mg), DIPEA (0.153 mL) and DMF (2 mL) was stirred overnight at room temperature. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (106 mg).
MS, found: 183.2.

B) 1-amino-N-(2,2,2-trifluoroethyl)cyclopropanecarboxamide hydrochloride

A mixture of tert-butyl (1-((2,2,2-trifluoroethyl)carbamoyl)cyclopropyl)carbamate (106 mg) and 4M hydrogen chloride ethyl acetate solution (2 mL) was stirred overnight at room temperature. The mixture was concentrated under reduced pressure to give the title compound (82.0 mg).
$^1$H NMR (300 MHz, DMSO-$d_6$) δ1.31-1.41 (2H, m), 1.41-1.49 (2H, m), 3.85-4.00 (2H, m), 8.43 (1H, t, J=5.8 Hz), 8.69 (3H, brs).

C) methyl 3-oxo-2-(1-((2,2,2-trifluoroethyl)carbamoyl)cyclopropyl)isoindoline-5-carboxylate To a mixture of dimethyl 4-(bromomethyl)isophthalate (108 mg), 1-amino-N-(2,2,2-trifluoroethyl)cyclopropanecarboxamide hydrochloride (82.0 mg) and DMF (1 mL) was added dropwise DIPEA (0.157 mL) at room temperature, and the mixture was stirred overnight at room temperature, and then overnight at 90° C. The mixture was cooled to 0° C., water was added thereto, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (53.0 mg).
MS: [M+H]$^+$357.2.

D) 1-(6-((2-(difluoroacetyl)hydrazino) carbonyl)-1-oxo-1,3-dihydro-2H-isoindol-2-yl)-N-(2,2,2-trifluoroethyl)cyclopropanecarboxamide To a mixture of methyl 3-oxo-2-(1-((2,2,2-trifluoroethyl)carbamoyl)cyclopropyl)isoindoline-5-carboxylate (53.0 mg), methanol (1 mL) and THF (1 mL) was added hydrazine monohydrate (0.216 mL) at room temperature, and the mixture was stirred at 80° C. for 5 hr. The mixture was concentrated by azeotropic evaporation with toluene, and the residue was mixed with TEA (0.031 mL) and THF (1 mL), difluoroacetic anhydride (0.022 mL) was added dropwise thereto at 0° C., and the mixture was stirred at room temperature for 30 min. The mixture was diluted with ethyl acetate, and washed with saturated brine. The organic layer was separated, dried over anhydrous magnesium sulfate, and concentrated under reduced pressure to give the title compound (61.0 mg).
MS: [M+H]$^+$435.2.

E) 1-(6-(5-(difluoromethyl)-1,3,4-oxadiazol-2-yl)-1-oxo-1,3-dihydro-2H-isoindol-2-yl)-N-(2,2,2-trifluoroethyl)cyclopropanecarboxamide To a mixture of 1-(6-((2-(difluoroacetyl)hydrazino)carbonyl)-1-oxo-1,3-dihydro-2H-isoindol-2-yl)-N-(2,2,2-trifluoroethyl)cyclopropanecarboxamide (61.0 mg) and THF (1 mL) were added 4-methylbenzenesulfonyl chloride (80 mg) and DIPEA (0.074 mL) at 0° C., and the mixture was stirred overnight at 40° C. The mixture was purified by silica gel column chromatography (ethyl acetate/hexane). The obtained product was crystallized from diisopropyl ether/ethyl acetate, collected by filtration, and washed with diisopropyl ether to give the title compound (34.4 mg).
$^1$H NMR (300 MHz, DMSO-$d_6$) δ1.34-1.44 (2H, m), 1.47-1.55 (2H, m), 3.74-3.93 (2H, m), 4.58 (2H, s), 7.35-7.78 (1H, m), 7.87 (1H, d, J=7.8 Hz), 8.23 (1H, d, J=0.9 Hz), 8.31 (1H, dd, J=8.0, 1.7 Hz), 8.60 (1H, t, J=6.3 Hz)

Example 188

6-(5-(difluoromethyl)-1,3,4-oxadiazol-2-yl)-2-(1-methyl-4-phenyl-1H-pyrazol-3-yl)isoindolin-1-one

A) methyl 2-(4-bromo-1-methyl-1H-pyrazol-3-yl)-3-oxoisoindoline-5-carboxylate To a mixture of dimethyl 4-(bromomethyl)isophthalate (28.3 g), DIPEA (34.4 mL) and DMF (280 mL) was added 4-bromo-1-methyl-1H-pyrazol-3-amine (26.0 g) at room temperature. The mixture was stirred overnight at room temperature. The reaction mixture was concentrated under reduced pressure, and to the obtained crude product was added acetic acid (280 mL) at room temperature. The mixture was stirred at 80° C. for 3 hr, and the reaction mixture was concentrated under reduced pressure. The residue was diluted with ethyl acetate (25 mL), and to the obtained suspension was added diisopropyl ether (50 mL). The suspension was stirred for 30 min, and the solid was collected by filtration. The obtained solid was dissolved in ethyl acetate/THF (8:2), and the solution was washed with saturated aqueous sodium hydrogencarbonate solution and saturated brine, dried over anhydrous sodium sulfate, and concentrated under reduced pressure. The residue was dried under reduced pressure to give the title compound (27.3 g).
MS: [M+H]$^+$349.9, 351.9.

B) methyl 2-(1-methyl-4-phenyl-1H-pyrazol-3-yl)-3-oxoisoindoline-5-carboxylate To a mixture of methyl 2-(4-bromo-1-methyl-1H-pyrazol-3-yl)-3-oxoisoindoline-5-carboxylate (5.0 g), phenylboronic acid (2.61 g), cesium carbonate (14.0 g) and DME (50 mL)/water (5.0 mL) was added bis(di-tert-butyl(4-dimethylaminophenyl)phosphine)dichloropalladium(II) (0.672 g) at room temperature. The mixture was stirred under nitrogen atmosphere at 70° C. for 3 hr. The mixture was poured into water at room temperature, and extracted with ethyl acetate/THF (1:1). The organic layer was separated, washed with 10% aqueous ammonium hydroxide solution and saturated brine, dried over anhydrous sodium sulfate, and concentrated under reduced pressure. The residue was dissolved in THF at 50° C., NH silica gel (50 g) was added thereto, and the mixture was stirred at the same temperature for 30 min. The NH silica gel was removed by filtration, and washed with THF, and the filtrate was concentrated under reduced pressure. The residue was suspended in diisopropyl ether, and the solid was collected by filtration, and dried under reduced pressure to give the title compound (4.53 g).
MS: [M+H]$^+$348.0.

C) 2-(1-methyl-4-phenyl-1H-pyrazol-3-yl)-3-oxoisoindoline-5-carbohydrazide

A solution of methyl 2-(1-methyl-4-phenyl-1H-pyrazol-3-yl)-3-oxoisoindoline-5-carboxylate (6.8 g), hydrazine monohydrate (9.51 mL) and THF (68 mL)/methanol (68 mL) was stirred overnight at 70° C. The mixture was filtered, and the filtrate was concentrated under reduced pressure to about 50 mL. The obtained suspension was diluted with ethyl acetate (50 mL), and the resulting solid was collected by filtration. The solid was washed with ethyl acetate, and dried under reduced pressure to give the title compound (6.30 g). The product was used in the next reaction without further purification.

MS: [M+H]$^+$348.1.

D) 6-(5-(difluoromethyl)-1,3,4-oxadiazol-2-yl)-2-(1-methyl-4-phenyl-1H-pyrazol-3-yl)isoindolin-1-one To a mixture of 2-(1-methyl-4-phenyl-1H-pyrazol-3-yl)-3-oxoisoindoline-5-carbohydrazide (6.8 g), DIPEA (6.84 mL) and THF (44 mL) was added difluoroacetic anhydride (3.65 mL) at 0° C. The mixture was stirred at room temperature for 1 hr. To the mixture were added DIPEA (10.3 mL) and 4-methylbenzenesulfonyl chloride (11.2 g) at 0° C. The mixture was stirred at room temperature for 3 hr. To the mixture was added water at 0° C., and the mixture was extracted with ethyl acetate/THF. The organic layer was separated, washed with saturated aqueous sodium hydrogencarbonate solution and saturated brine, dried over anhydrous magnesium sulfate, and concentrated under reduced pressure. The residue was suspended in ethyl acetate, and the precipitate was collected by filtration. The solid was washed with ethyl acetate, and dried under reduced pressure to give a crude product (7.00 g). The obtained crude product (4.4 g) was dissolved in 10% hydrous acetone (80 mL) at 60° C. To the solution was added water (80 mL) at 60° C., and the mixture was stirred at the same temperature for 1 hr, and then at room temperature for 1 hr. The solid was collected by filtration, washed with acetone/water (1:2), and dried under reduced pressure. The obtained solid was dissolved in 10% hydrous acetone (80 mL) at 60° C. To the solution were added ethyl acetate/heptane (2:1, 80 mL) at 60° C., and the mixture was stirred at the same temperature for 1 hr, and then at room temperature for 1 hr. The solid was collected by filtration, washed with acetone/heptane (1:2), and dried under reduced pressure to give the title compound (2.5 g). The compound was combined with the title compound (1.2 g) obtained by the similar method, and suspended in isopropyl acetate, and the suspension was stirred for 30 min. The solid was collected by filtration, and dried under reduced pressure to give the title compound (3.6 g).

$^1$H NMR (300 MHz, DMSO-d$_6$) δ 3.91 (3H, s), 4.98 (2H, s), 7.13-7.37 (5H, m), 7.35-7.75 (1H, m), 7.92 (1H, d, J=8.3 Hz), 8.15 (1H, s), 8.28 (1H, d, J=1.1 Hz), 8.37 (1H, dd, J=7.9, 1.5 Hz).

Example 196

N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2,3,3,3-pentafluoropropanamide A) diethyl 2-methylpyridine-3,5-dicarboxylate To a mixture of ethyl 2-formyl-3-oxopropanoate (50.0 g) and diethyl ether (350 mL) was added dropwise TEA (38.5 g) at −10° C. The reaction mixture was stirred at 25° C. for 2 hr. The solvent was evaporated under reduced pressure, and a solution of 4-methylbenzenesulfonyl chloride (72.9 g) in DMF (200 mL) was added thereto with stirring at −20° C. The reaction mixture was warmed to 25° C., and stirred for 4 hr. To the mixture was added a solution of ethyl (2Z)-3-aminobuta-2-enoate (47.1 g) and pyridine (109 g) in DMF (150 mL) at 25° C. The reaction mixture was stirred at 80° C. for 10 hr. The reaction mixture was concentrated under reduced pressure, the residue was diluted with saturated aqueous sodium hydrogencarbonate solution (500 mL), and the mixture was extracted with ethyl acetate (600 mL×2). The combined organic layer was washed with saturated brine (1000 mL×2), dried over anhydrous sodium sulfate, and concentrated under reduced pressure. The crude product was purified by silica gel column chromatography (petroleum ether/ethyl acetate) to give the title compound (32.0 g).

MS: [M+H]$^+$237.9.

B) diethyl 2-(chloromethyl)pyridine-3,5-dicarboxylate

To a mixture of diethyl 2-methylpyridine-3,5-dicarboxylate (32.0 g) and benzotrifluoride (400 mL) was added 1,3,5-trichloro-1,3,5-triazinane-2,4,6-trione (41.0 g) at 25° C. The mixture was stirred at 25° C. for 0.5 hr, and then at 80° C. for 3 hr. The mixture was cooled to room temperature, and the insoluble material was removed by filtration. The filtrate was diluted with ethyl acetate (500 mL) and water (600 mL). To the mixture was added saturated aqueous sodium hydrogencarbonate solution until the pH became 10. The mixture was extracted with ethyl acetate (500 mL). The organic layer was washed with saturated aqueous sodium sulfite solution (800 mL) and saturated brine (800 mL), dried over anhydrous sodium sulfate, and concentrated under reduced pressure. The residue was purified by silica gel column chromatography (petroleum ether/ethyl acetate) to give the title compound (28.0 g).

MS: [M+H]$^+$272.0.

C) ethyl 6-((1R,2R)-2-aminocyclohexyl)-5-oxo-6,7-dihydro-5H-pyrrolo[3,4-b]pyridine-3-carboxylate To a mixture of diethyl 2-(chloromethyl)pyridine-3,5-dicarboxylate (10.0 g) and ethanol (50 mL) was added a solution of (1R,2R)-cyclohexane-1,2-diamine (8.41 g) and TEA (7.45 g) in ethanol (100 mL) dropwise at 25° C. The mixture was stirred at 25° C. for 5 hr, and concentrated under reduced pressure. The residue was purified by silica gel column chromatography (dichloromethane/methanol) to give the title compound (6.60 g).

MS, found: 304.1.

D) ethyl 6-((1R,2R)-2-((tert-butoxycarbonyl)amino) cyclohexyl)-5-oxo-6,7-dihydro-5H-pyrrolo[3,4-b] pyridine-3-carboxylate To a mixture of ethyl 6-((1R,2R)-2-aminocyclohexyl)-5-oxo-6,7-dihydro-5H-pyrrolo[3,4-b]pyridine-3-carboxylate (18 g) and dichloromethane (200 mL) were added TEA (12.0 g) and Boc$_2$O (15.5 g) at 0° C. The mixture was stirred at room temperature for 1.5 hr, and concentrated under reduced pressure. The residue was purified by silica gel column chromatography (petroleum ether/ethyl acetate) to give the title compound (22.0 g).

MS: [M+H]$^+$404.1.

E) tert-butyl ((1R,2R)-2-(3-(hydrazinocarbonyl)-5-oxo-5,7-dihydro-6H-pyrrolo[3,4-b]pyridin-6-yl)cyclohexyl)carbamate A mixture of ethyl 6-((1R,2R)-2-((tert-butoxycarbonyl) amino)cyclohexyl)-5-oxo-6,7-dihydro-5H-pyrrolo[3,4-b]

pyridine-3-carboxylate (14.8 g), hydrazine monohydrate (18 mL) and ethanol (150 mL) was stirred at 70° C. for 4 hr. The mixture was cooled, and the reaction was quenched with water (50 mL). The mixture was diluted with ethyl acetate (750 mL), washed with saturated brine (350 mL×2), dried over anhydrous sodium sulfate, and concentrated under reduced pressure to give the title compound (14.2 g).

MS, found: 290.0.

F) tert-butyl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate To a mixture of tert-butyl ((1R,2R)-2-(3-(hydrazinocarbonyl)-5-oxo-5,7-dihydro-6H-pyrrolo[3,4-b]pyridin-6-yl)cyclohexyl)carbamate (14.2 g), TEA (7.6 mL) and THF (150 mL) was added difluoroacetic anhydride (5.4 mL) at 0° C. The mixture was stirred at 0° C. for 1 hr. The mixture was diluted with ethyl acetate (450 mL), washed with saturated brine (300 mL), dried over anhydrous sodium sulfate, and concentrated under reduced pressure. The residue was dissolved in toluene, and the solution was concentrated under reduced pressure. To a mixture of the residue and THF (180 mL) were added DIPEA (19.1 mL) and 4-methylbenzenesulfonyl chloride (20.8 g) at 0° C. The mixture was stirred at room temperature for 3 hr. The reaction was quenched with saturated aqueous sodium hydrogencarbonate solution (180 mL) at 0° C., and the mixture was diluted with ethyl acetate (540 mL), washed with water (270 mL) and saturated brine, dried over anhydrous sodium sulfate, and concentrated under reduced pressure. The residue was purified by silica gel column chromatography (ethyl acetate/hexane) to give the title compound (12.7 g).

MS, found: 350.0.

G) 6-((1R,2R)-2-aminocyclohexyl)-3-(5-(difluoromethyl)-1,3,4-oxadiazol-2-yl)-6,7-dihydro-5H-pyrrolo[3,4-b]pyridin-5-one A mixture of tert-butyl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate (8.14 g) and TFA (80 mL) was stirred at room temperature for 10 min. The mixture was diluted with toluene (80 mL), and concentrated under reduced pressure. The residue was purified by silica gel column chromatography (NH, ethyl acetate), and the crude product was washed with hexane/ethyl acetate (1:1) to give the title compound (4.36 g).

MS: [M+H]$^+$350.0.

H) N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2,3,3,3-pentafluoropropanamide To a mixture of 6-((1R,2R)-2-aminocyclohexyl)-3-(5-(difluoromethyl)-1,3,4-oxadiazol-2-yl)-6,7-dihydro-5H-pyrrolo[3,4-b]pyridin-5-one (4.36 g), TEA (2.7 mL) and THF (74 mL) was added pentafluoropropionic anhydride (3.0 mL) at 0° C. The mixture was stirred at 0° C. for 30 min. The mixture was diluted with ethyl acetate (370 mL), washed with water (185 mL) and saturated brine, dried over anhydrous sodium sulfate, and concentrated under reduced pressure. The residue was purified by silica gel column chromatography (ethyl acetate/hexane) to give a crude product (6.00 g). The compound was combined with the crude product (3.50 g) obtained by the similar method, and the compound (total 9.50 g) was dissolved in ethyl acetate (23.5 mL). The solution was filtered, and washed with ethyl acetate (5.0 mL). The combined filtrate was added dropwise to diisopropyl ether (285 mL) at room temperature, and the mixture was stirred at 0° C. The precipitate was collected by filtration, washed with diisopropyl ether, and dried to give the title compound (8.48 g).

$^1$H NMR (300 MHz, CDCl$_3$) δ 1.35-1.66 (3H, m), 1.72-2.27 (5H, m), 4.02-4.19 (1H, m), 4.42 (1H, td, J=11.6, 3.6 Hz), 4.48-4.76 (2H, m), 6.77-7.15 (1H, m), 7.19 (1H, d, J=8.7 Hz), 8.72 (1H, d, J=1.9 Hz), 9.51 (1H, d, J=1.9 Hz).

Example 264

N-((1R,2R)-2-(6-(5-(difluoromethyl)-1,3,4-oxadiazol-2-yl)-1-oxo-1,3-dihydro-2H-isoindol-2-yl)cyclohexyl)-N-(pyridin-2-yl) acetamide A) tert-butyl ((1R,2R)-2-(pyridin-2-ylamino)cyclohexyl)carbamate To a mixture of tert-butyl ((1R,2R)-2-aminocyclohexyl)carbamate (520 mg), DIPEA (1.585 mL), pyridine 1-oxide (231 mg) and THF (10 mL) was added bromotri(pyrrolidino)phosphonium hexafluorophosphate (PyBrop, 1244 mg) at room temperature, and the mixture was stirred overnight at room temperature. The mixture was added to water, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (329 mg).

MS: [M+H]$^+$292.2.

B) (1R,2R)—N-(pyridin-2-yl)cyclohexane-1,2-diamine dihydrochloride

To a mixture of tert-butyl ((1R,2R)-2-(pyridin-2-ylamino)cyclohexyl)carbamate (409 mg) and ethyl acetate (10 mL) was added 4M hydrogen chloride ethyl acetate solution (8 mL) at room temperature, and the mixture was stirred at room temperature for 3 hr. The mixture was concentrated to give the title compound (370 mg).

MS: [M+H]$^+$192.1.

C) ethyl 3-oxo-2-((1R,2R)-2-(pyridin-2-ylamino)cyclohexyl)isoindoline-5-carboxylate To a mixture of (1R,2R)—N-(pyridin-2-yl)cyclohexane-1,2-diamine dihydrochloride (118 mg) and DMF (1 mL) were added DIPEA (0.233 mL) and diethyl 4-(bromomethyl)isophthalate (70.4 mg) at room temperature, and the mixture was stirred overnight at room temperature. The mixture was added to water at room temperature, and extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (69 mg).

MS: [M+H]$^+$380.1.

D) ethyl 2-((1R,2R)-2-(acetyl (pyridin-2-yl)amino) cyclohexyl)-3-oxoisoindoline-5-carboxylate To a mixture of ethyl 3-oxo-2-((1R,2R)-2-(pyridin-2-ylamino)cyclohexyl)isoindoline-5-carboxylate (69 mg), DIPEA (0.226 mL) and THF (2 mL) was added acetyl chloride (0.091 mL) at 0° C. The mixture was stirred at room temperature for 1 hr. To the mixture was added saturated aqueous sodium hydrogencarbonate solution at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (32 mg)

MS: [M+H]$^+$422.1.

E) N-((1R,2R)-2-(6-(5-(difluoromethyl)-1,3,4-oxadiazol-2-yl)-1-oxo-1,3-dihydro-2H-isoindol-2-yl)cyclohexyl)-N-(pyridin-2-yl) acetamide To a mixture of ethyl 2-((1R,2R)-2-(acetyl (pyridin-2-yl)amino)cyclohexyl)-3-oxoisoindoline-5-carboxylate (32 mg), ethanol (1 mL) and THF (1 mL) was added hydrazine monohydrate (0.074 mL) at room temperature, and the mixture was stirred under nitrogen atmosphere at 70° C. for 10 hr. The mixture was concentrated under reduced pressure. To a mixture of the residue, DIPEA (0.040 mL) and THF (1 mL) was added difluoroacetic anhydride (0.012 mL) at room temperature. The mixture was stirred at room temperature for 1 hr, to the mixture were added 4-methylbenzenesulfonyl chloride (43.5 mg) and DIPEA (0.040 mL) at room temperature, and the mixture was stirred at room temperature for 3 days. The mixture was added to water, and the mixture was extracted with ethyl acetate. The organic layer was separated, washed with saturated aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (24 mg).

$^1$H NMR (300 MHz, CDCl$_3$) δ0.94-2.13 (11H, m), 4.22-4.38 (1H, m), 4.51 (1H, d, J=17.7 Hz), 4.87-5.09 (2H, m), 6.66-7.14 (1H, m), 7.29-7.36 (1H, m), 7.64-7.81 (2H, m), 7.83-7.93 (1H, m), 8.35 (1H, dd, J=7.9, 1.5 Hz), 8.48-8.59 (2H, m).

Example 268

1,1,1-trifluoro-2-methylpropan-2-yl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl) carbamate To a mixture of 6-((1R,2R)-2-aminocyclohexyl)-3-(5-(difluoromethyl)-1,3,4-oxadiazol-2-yl)-6,7-dihydro-5H-pyrrolo[3,4-b]pyridin-5-one (61.5 mg), TEA (0.049 mL) and acetonitrile (1.5 mL) was added 4-nitrophenyl 1,1,1-trifluoro-2-methylpropan-2-yl carbonate (61.9 mg) at room temperature. The mixture was stirred at room temperature for 2 hr, and then at 60° C. for 2 hr. The mixture was purified by silica gel column chromatography (NH, ethyl acetate/hexane), and the crude product was washed with ethyl acetate/hexane to give the title compound (69.3 mg).

$^1$H NMR (300 MHz, DMSO-d$_6$) δ0.92 (3H, s), 1.20-1.34 (3H, m), 1.40 (3H, s), 1.67-1.88 (5H, m), 3.57 (1H, d, J=10.7 Hz), 4.03 (1H, d, J=7.2 Hz), 4.54-4.85 (2H, m), 7.38-7.79 (2H, m), 8.51 (1H, d, J=2.0 Hz), 9.38 (1H, d, J=2.0 Hz).

Example 399

6-(5-(difluoromethyl)-1,3,4-oxadiazol-2-yl)-2-((3S,4R)-3-((2,2,2-trifluoroethyl)amino)tetrahydro-2H-pyran-4-yl)isoindolin-1-one A) tert-butyl ((3S,4R)-3-((2,2,2-trifluoroethyl)amino)tetrahydro-2H-pyran-4-yl)carbamate A mixture of tert-butyl ((3S,4R)-3-aminotetrahydro-2H-pyran-4-yl)carbamate (2.00 g), DIPEA (3.23 mL), 2,2,2-trifluoroethyl trifluoromethanesulfonate (3.22 g) and DMF (20 mL) was stirred overnight at 50° C. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (2.44 g).

$^1$H NMR (300 MHz, DMSO-d$_6$) δ 1.39 (10H, s), 1.71 (1H, d, J=9.6 Hz), 2.18 (1H, q, J=7.1 Hz), 2.35-2.48 (1H, m), 2.91 (1H, t, J=10.7 Hz), 3.12-3.41 (4H, m), 3.66-3.86 (2H, m), 6.86 (1H, d, J=8.2 Hz).

B) (3S,4R)—N3-(2,2,2-trifluoroethyl)tetrahydro-2H-pyran-3,4-diamine hydrochloride A mixture of tert-butyl ((3S,4R)-3-((2,2,2-trifluoroethyl)amino)tetrahydro-2H-pyran-4-yl)carbamate (2.44 g) and 4M hydrogen chloride ethyl acetate solution (40 mL) was stirred at room temperature for 3 hr. The mixture was concentrated under reduced pressure. The residue was washed with diisopropyl ether to give the title compound (1.92 g).

$^1$H NMR (300 MHz, DMSO-d$_6$) δ 1.44-1.70 (1H, m), 1.88-2.01 (1H, m), 2.29-2.73 (2H, m), 2.96 (2H, t, J=10.7 Hz), 3.21-3.50 (3H, m), 3.71-3.99 (2H, m), 8.10 (3H, brs).

C) methyl 3-oxo-2-((3S,4R)-3-((2,2,2-trifluoroethyl)amino)tetrahydro-2H-pyran-4-yl) isoindoline-5-carboxylate To a mixture of dimethyl 4-(bromomethyl)isophthalate (333 mg) and DMF (4 mL) were added (3S,4R)—N3-(2,2,2-trifluoroethyl)tetrahydro-2H-pyran-3,4-diamine hydrochloride (272 mg) and DIPEA (0.485 mL) at 0° C. The mixture was stirred at room temperature for 4 days. The mixture was poured into water, and extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (248 mg).

MS: [M+H]$^+$373.1.

D) 6-(5-(difluoromethyl)-1,3,4-oxadiazol-2-yl)-2-((3S,4R)-3-((2,2,2-trifluoroethyl)amino)tetrahydro-2H-pyran-4-yl)isoindolin-1-one To a mixture of methyl 3-oxo-2-((3S,4R)-3-((2,2,2-trifluoroethyl)amino)tetrahydro-2H-pyran-4-yl)isoindoline-5-carboxylate (248 mg) and methanol (3 mL) was added hydrazine monohydrate (2.66 mL) at room temperature, and the mixture was heated at 70° C. for 5 hr. The mixture was concentrated under reduced pressure, and subjected to azeotropic evaporation with toluene. To the residue were added TEA (0.139 mL) and THF (3 mL). To the mixture was added dropwise difluoroacetic anhydride (0.099 mL) at 0° C. The mixture was stirred at room temperature for 30 min. The mixture was diluted with ethyl acetate, and washed with saturated brine. The organic layer was dried over anhydrous magnesium sulfate, and concentrated under reduced pressure. To a mixture of the residue and THF (3 mL) were added 4-methylbenzenesulfonyl chloride (406 mg) and DIPEA (0.372 mL) at 0° C. The mixture was stirred at 50° C. for 3 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (165 mg).

$^1$H NMR (300 MHz, DMSO-$d_6$) δ 1.73 (1H, dd, J=12.7, 4.3 Hz), 1.82-1.97 (1H, m), 2.45 (1H, brs), 2.85-3.01 (1H, m), 3.04-3.16 (1H, m), 3.17-3.29 (2H, m), 3.37-3.49 (1H, m), 3.90 (1H, dd, J=11.4, 4.1 Hz), 3.99-4.20 (2H, m), 4.50-4.76 (2H, m), 7.29-7.80 (1H, m), 7.89 (1H, d, J=8.5 Hz), 8.24 (1H, d, J=0.8 Hz), 8.29 (1H, dd, J=7.9, 1.7 Hz).

Example 406

6-(2-bromo-4-fluorophenyl)-3-(5-(difluoromethyl)-1,3,4-oxadiazol-2-yl)-6,7-dihydro-5H-pyrrolo[3,4-b]pyridin-5-one A) diethyl 2-(bromomethyl)pyridine-3,5-dicarboxylate A mixture of diethyl 2-methylpyridine-3,5-dicarboxylate (5 g), NBS (5.63 g), AIBN (0.519 g) and chlorobenzene (50 mL) was stirred at 100° C. for 2 hr. To the mixture were added water and saturated aqueous sodium hydrogencarbonate solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (3.19 g).

MS: [M+H]$^+$316.0, 317.9.

B) diethyl 2-(((2-bromo-4-fluorophenyl)amino)methyl)pyridine-3,5-dicarboxylate

A mixture of diethyl 2-(bromomethyl)pyridine-3,5-dicarboxylate (2.080 g) and 2-bromo-4-fluoroaniline (10.0 g) was stirred at room temperature for 4 days. To the mixture were added ethyl acetate, water and saturated aqueous sodium hydrogencarbonate solution, and the mixture was extracted with ethyl acetate. The extract was washed with water and saturated brine, dried over anhydrous magnesium sulfate, and concentrated under reduced pressure. The residue was suspended in hexane, and the solid was collected by filtration, washed with hexane, and dried to give the title compound (1.63 g).

MS: [M+H]$^+$425.0, 427.0.

C) 6-(2-bromo-4-fluorophenyl)-5-oxo-6,7-dihydro-5H-pyrrolo[3,4-b]pyridine-3-carboxylic acid hydrochloride A mixture of diethyl 2-(((2-bromo-4-fluorophenyl)amino)methyl)pyridine-3,5-dicarboxylate (1.63 g) and 6N hydrochloric acid (31.9 mL) was heated under reflux for 2.5 hr, and cooled to 0° C. The precipitated solid was collected by filtration, washed with a small amount of 6N hydrochloric acid and hexane, and dried to give the title compound (1.37 g).

MS: [M+H]$^+$350.9, 352.9

D) tert-butyl 2-((6-(2-bromo-4-fluorophenyl)-5-oxo-6,7-dihydro-5H-pyrrolo[3,4-b]pyridin-3-yl)carbonyl)hydrazinecarboxylate To a mixture of 6-(2-bromo-4-fluorophenyl)-5-oxo-6,7-dihydro-5H-pyrrolo[3,4-b]pyridine-3-carboxylic acid hydrochloride (1.37 g), tert-butyl hydrazinecarboxylate (0.934 g), DIPEA (1.85 mL) and DMF (15 mL) was added HATU (2.69 g) at 0° C. The mixture was stirred overnight at room temperature. The reaction was quenched with water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (1.75 g).

MS: [M+H]$^+$465.0, 467.0.

E) 6-(2-bromo-4-fluorophenyl)-N'-(difluoroacetyl)-5-oxo-6,7-dihydro-5H-pyrrolo[3,4-b]pyridine-3-carbohydrazide A mixture of tert-butyl 2-((6-(2-bromo-4-fluorophenyl)-5-oxo-6,7-dihydro-5H-pyrrolo[3,4-b]pyridin-3-yl)carbonyl)hydrazinecarboxylate (1.75 g) and 4M hydrogen chloride ethyl acetate solution (20 mL) was stirred at room temperature for 2 hr. The mixture was concentrated under reduced pressure. To the residue was added THF (20 mL) at room temperature. To the mixture were added TEA (1.57 mL) and difluoroacetic anhydride (0.561 mL) at 0° C. The mixture was stirred at room temperature for 1 hr. The mixture was diluted with ethyl acetate and water. The solid was collected by filtration, and washed with ethyl acetate to give the title compound (243 mg). The filtrate was extracted with ethyl acetate/THF (1:1). The organic layer was separated, dried over anhydrous magnesium sulfate, and concentrated under reduced pressure to give the title compound (1.08 g).

MS: [M+H]$^+$442.9, 444.9

F) 6-(2-bromo-4-fluorophenyl)-3-(5-(difluoromethyl)-1,3,4-oxadiazol-2-yl)-6,7-dihydro-5H-pyrrolo[3,4-b]pyridin-5-one To a mixture of 6-(2-bromo-4-fluorophenyl)-N'-(difluoroacetyl)-5-oxo-6,7-dihydro-5H-pyrrolo[3,4-b]pyridine-3-carbohydrazide (1.32 g) and THF (20 mL) were added 4-methylbenzenesulfonyl chloride (1.704 g) and DIPEA (1.56 mL) at 0° C. The mixture was stirred at 50° C. for 3 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (600 mg).

$^1$H NMR (300 MHz, DMSO-$d_6$) δ 5.05 (2H, s), 7.40-7.80 (3H, m), 7.83 (1H, dd, J=8.4, 2.8 Hz), 8.68 (1H, d, J=2.1 Hz), 9.50 (1H, d, J=2.0 Hz).

Example 452

6-(5-(difluoromethyl)-1,3,4-oxadiazol-2-yl)-2-(4-fluoro-2-(4-fluoro-1H-pyrazol-1-yl)phenyl)isoindolin-1-one

A) 4-fluoro-1-(5-fluoro-2-nitrophenyl)-1H-pyrazole

To a mixture of 60% sodium hydride (56 mg) and THF (15 mL) was added 4-fluoro-1H-pyrazole (103 mg) at 0° C. The mixture was stirred at 0° C. for 1 hr, and to the mixture was added 2,4-difluoro-1-nitrobenzene (0.110 mL). The mixture was stirred overnight at room temperature, to the mixture was added saturated aqueous ammonium chloride solution at 0° C., and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (155 mg).

MS: [M+H]$^+$226.1.

B) 4-fluoro-2-(4-fluoro-1H-pyrazol-1-yl)aniline

A mixture of 4-fluoro-1-(5-fluoro-2-nitrophenyl)-1H-pyrazole (155 mg), zinc powder (450 mg) and acetic acid (7 mL) was stirred overnight at room temperature. The mixture was filtered through Celite, and the obtained filtrate was concentrated. The residue was diluted with ethyl acetate, and the mixture was added to saturated aqueous sodium hydrogencarbonate solution at room temperature. The organic layer was separated, washed with water and saturated brine, dried over anhydrous sodium sulfate, and concentrated under reduced pressure to give the title compound (129 mg). The obtained product was used in the next reaction without further purification.

MS: [M+H]$^+$196.1.

C) methyl 2-(4-fluoro-2-(4-fluoro-1H-pyrazol-1-yl)phenyl)-3-oxoisoindoline-5-carboxylate A mixture of 4-fluoro-2-(4-fluoro-1H-pyrazol-1-yl)aniline (129 mg), dimethyl 4-(bromomethyl)isophthalate (190 mg), DIPEA (0.115 mL) and DMF (2 mL) was stirred overnight at room temperature. The mixture was added to water at room temperature, and extracted with ethyl acetate. The organic layer was separated, washed with water and saturated brine, dried over anhydrous sodium sulfate, and concentrated under reduced pressure. The residue was dissolved in acetic acid (2.0 mL), and the solution was stirred at 100° C. for 2 hr. The mixture was concentrated, and the residue was purified by silica gel column chromatography (ethyl acetate/hexane) to give the title compound (184 mg).

MS: [M+H]$^+$370.1.

D) 2-(4-fluoro-2-(4-fluoro-1H-pyrazol-1-yl)phenyl)-3-oxoisoindoline-5-carbohydrazide To a mixture of methyl 2-(4-fluoro-2-(4-fluoro-1H-pyrazol-1-yl)phenyl)-3-oxoisoindoline-5-carboxylate (184 mg), THF (3 mL) and methanol (2 mL) was added hydrazine monohydrate (0.483 mL) at room temperature, and the mixture was heated under reflux for 2 hr. The mixture was concentrated under reduced pressure, and subjected to azeotropic evaporation with toluene to give the title compound. The obtained product was used in the next reaction without further purification.

MS: [M+H]$^+$370.1.

E) 6-(5-(difluoromethyl)-1,3,4-oxadiazol-2-yl)-2-(4-fluoro-2-(4-fluoro-1H-pyrazol-1-yl)phenyl)isoindolin-1-one To a mixture of 2-(4-fluoro-2-(4-fluoro-1H-pyrazol-1-yl)phenyl)-3-oxoisoindoline-5-carbohydrazide (184 mg), DIPEA (0.174 mL) and THF (2 mL) was added difluoroacetic anhydride (0.124 mL) at 0° C., and the mixture was stirred at room temperature for 20 min. To the mixture were added ethyl acetate/THF and saturated brine. The organic layer was separated. The organic layer was dried over anhydrous sodium sulfate, and concentrated under reduced pressure. A mixture of the residue, 4-methylbenzenesulfonyl chloride (285 mg), DIPEA (0.261 mL) and acetonitrile (10 mL) was stirred at room temperature for 3 hr. The mixture was concentrated under reduced pressure, and the residue was purified by silica gel column chromatography (ethyl acetate/hexane) to give the title compound (112 mg).

$^1$H NMR (300 MHz, DMSO-d$_6$) δ 4.87 (2H, s), 7.37-7.75 (4H, m), 7.79 (1H, dd, J=8.8, 5.8 Hz), 7.93 (1H, d, J=8.0 Hz), 8.20 (1H, s), 8.27 (1H, d, J=4.4 Hz), 8.34 (1H, dd, J=7.9, 1.3 Hz).

Example 469

N-((1R,2R)-2-(6-(5-(difluoromethyl)-1,3,4-oxadiazol-2-yl)-1-oxo-1,3-dihydro-2H-isoindol-2-yl)-5,5-difluorocyclohexyl)-2,2,3,3,3-pentafluoropropanamide

A) ethyl (1R,2R)-2-(((benzyloxy)carbonyl)amino)-5,5-difluorocyclohexanecarboxylate A mixture of ethyl (1S,2R)-2-(((benzyloxy)carbonyl)amino)-5,5-difluorocyclohexanecarboxylate (9.40 g), DBU (6.18 mL) and ethanol (100 mL) was heated under reflux for 72 hr. The mixture was concentrated under reduced pressure, and the residue was diluted with water (40 mL). To the mixture was added dropwise 2N hydrochloric acid (20.7 mL), and the mixture was extracted with ethyl acetate. The extract was washed with water and saturated brine, dried over anhydrous sodium sulfate, and concentrated under reduced pressure. The residue was purified by silica gel column chromatography (ethyl acetate/hexane), and solidified from hexane/ethyl acetate to give the title compound (3.81 g).

MS: [M+H]$^+$342.1.

B) ethyl (1R,2R)-2-((tert-butoxycarbonyl)amino)-5,5-difluorocyclohexanecarboxylate A mixture of ethyl (1R,2R)-2-(((benzyloxy)carbonyl)amino)-5,5-difluorocyclohexanecarboxylate (4.41 g), 20% palladium hydroxide on carbon (about 50% hydrous product, 400 mg), Boc$_2$O (3.86 mL) and ethyl acetate (45.0 mL) was stirred under hydrogen atmosphere overnight at room temperature. The mixture was filtered, and the filtrate was concentrated under reduced pressure. The residue was solidified from ethyl acetate/hexane to give the title compound (3.26 g).

MS, found: 208.1.

C) (1R,2R)-2-((tert-butoxycarbonyl)amino)-5,5-difluorocyclohexanecarboxylic acid To a mixture of ethyl (1R,2R)-2-((tert-butoxycarbonyl)amino)-5,5-difluorocyclohexanecarboxylate (3.26 g) and THF (10 mL)/ethanol (20 mL) was added 1N aqueous sodium hydroxide solution (21.2 mL) at room temperature, and the mixture was stirred overnight. The mixture was acidified with 1N hydrochloric acid (22 mL) at 0° C., and the precipitate was collected by filtration, and washed with water to give the title compound (2.56 g).

MS, found: 180.1.

D) benzyl tert-butyl ((1R,2R)-4,4-difluorocyclohexane-1,2-diyl)biscarbamate

To a mixture of (1R,2R)-2-((tert-butoxycarbonyl)amino)-5,5-difluorocyclohexanecarboxylic acid (2.556 g), DPPA (2.36 mL) and toluene (25 mL) was added dropwise TEA (1.53 mL) at room temperature, and the mixture was stirred at room temperature for 30 min, and heated under reflux for 1 hr. To the mixture was added benzyl alcohol (1.42 mL) at room temperature, and the mixture was heated under reflux overnight. The mixture was poured into water/saturated aqueous sodium hydrogencarbonate solution (1:1), and extracted with ethyl acetate. The extract was washed with water and saturated brine, dried over anhydrous sodium sulfate, and concentrated under reduced pressure. The residue was purified by silica gel column chromatography (ethyl acetate/hexane) to give the title compound (1.52 g).

MS, found: 285.1.

E) benzyl ((1R,2R)-2-amino-5,5-difluorocyclohexyl)carbamate hydrochloride

A mixture of benzyl tert-butyl ((1R,2R)-4,4-difluorocyclohexane-1,2-diyl)biscarbamate (1.49 g) and TFA (12.0 mL) was stirred at room temperature for 2 hr, and concentrated under reduced pressure. The residue was dissolved in methanol (6.0 mL), and 2M hydrogen chloride methanol solution (3.88 mL) was added thereto. The mixture was stirred overnight at room temperature, and concentrated under reduced pressure. The residue was suspended in ethyl acetate, and the precipitate was collected by filtration, and washed with ethyl acetate to give the title compound (1.02 g).

MS: [M+H]$^+$285.1.

F) methyl 2-((1R,2R)-2-(((benzyloxy)carbonyl)amino)-4,4-difluorocyclohexyl)-3-oxoisoindoline-5-carboxylate To a mixture of dimethyl 4-(bromomethyl)isophthalate (470 mg), benzyl ((1R,2R)-2-amino-5,5-difluorocyclohexyl)carbamate hydrochloride (500 mg) and DMF (6.0 mL) was added dropwise TEA (0.65 mL) at 0° C., and the mixture was stirred overnight at room temperature. The mixture was partitioned between water and ethyl acetate. The separated organic layer was washed with water and saturated brine, dried over anhydrous sodium sulfate, and concentrated under reduced pressure. The residue was dissolved in acetic acid (6.0 mL), and the solution was heated at 50° C. for 3 hr. The mixture was concentrated under reduced pressure. The residue was purified by silica gel column chromatography (ethyl acetate/hexane) to give the title compound (455 mg).

MS: [M+H]$^+$459.1.

G) methyl 2-((1R,2R)-2-((tert-butoxycarbonyl)amino)-4,4-difluorocyclohexyl)-3-oxoisoindoline-5-carboxylate A mixture of methyl 2-((1R,2R)-2-(((benzyloxy)carbonyl)amino)-4,4-difluorocyclohexyl)-3-oxoisoindoline-5-carboxylate (453 mg), Boc$_2$O (0.272 mL), 20% palladium hydroxide on carbon (about 50% hydrous product, 50 mg) and THF (12 mL) was stirred under hydrogen atmosphere at room temperature for 3 days. The mixture was filtered through Celite, and the filtrate was concentrated under reduced pressure. The residue was purified by silica gel column chromatography (ethyl acetate/hexane) to give the title compound (419 mg).

MS, found: 325.1.

H) tert-butyl ((1R,2R)-2-(6-(5-(difluoromethyl)-1,3,4-oxadiazol-2-yl)-1-oxo-1,3-dihydro-2H-isoindol-2-yl)-5,5-difluorocyclohexyl)carbamate A mixture of methyl 2-((1R,2R)-2-((tert-butoxycarbonyl)amino)-4,4-difluorocyclohexyl)-3-oxoisoindoline-5-carboxylate (417 mg), hydrazine monohydrate (0.953 mL) and methanol (6.0 mL) was heated under reflux for 3 hr, and concentrated under reduced pressure. To a mixture of the residue, TEA (0.272 mL) and THF (6.0 mL) was added dropwise difluoroacetic anhydride (0.183 mL) at room temperature, and the mixture was stirred for 1 hr. To the mixture were added TEA (0.409 mL) and 4-methylbenzenesulfonyl chloride (374 mg) at room temperature, and the mixture was stirred overnight. The mixture was poured into water, and extracted with ethyl acetate. The extract was washed with saturated brine, dried over anhydrous sodium sulfate, and concentrated under reduced pressure. The residue was purified by silica gel column chromatography (ethyl acetate/hexane) to give the title compound (321 mg).

MS: [M+H]$^+$385.1.

I) 2-((1R,2R)-2-amino-4,4-difluorocyclohexyl)-6-(5-(difluoromethyl)-1,3,4-oxadiazol-2-yl)isoindolin-1-one trifluoroacetate A mixture of tert-butyl ((1R,2R)-2-(6-(5-(difluoromethyl)-1,3,4-oxadiazol-2-yl)-1-oxo-1,3-dihydro-2H-isoindol-2-yl)-5,5-difluorocyclohexyl)carbamate (320 mg) and TFA (4.0 mL) was stirred at room temperature for 2 hr. The mixture was concentrated under reduced pressure, and subjected to azeotropic evaporation with toluene. The residue was solidified from ethyl acetate/diisopropyl ether to give the title compound (288 mg).

MS: [M+H]$^+$385.1.

J) N-((1R,2R)-2-(6-(5-(difluoromethyl)-1,3,4-oxadiazol-2-yl)-1-oxo-1,3-dihydro-2H-isoindol-2-yl)-5,5-difluorocyclohexyl)-2,2,3,3,3-pentafluoropropanamide 2-((1R,2R)-2-Amino-4,4-difluorocyclohexyl)-6-(5-(difluoromethyl)-1,3,4-oxadiazol-2-yl)isoindolin-1-one trifluoroacetate (70 mg) was passed through NH silica gel using methanol/ethyl acetate as an eluting solvent. The filtrate was concentrated under reduced pressure to give the corresponding amine in a free form. The amine in a free form was dissolved in THF (3.0 mL), and TEA (0.078 mL) and pentafluoropropanoic anhydride (0.042 mL) were added thereto at 0° C. The mixture was stirred at room temperature for 1 hr, and pentafluoropropanoic anhydride (0.028 mL) was added thereto. The mixture was stirred for 30 min, and concentrated under reduced pressure. The residue was purified by silica gel column chromatography (ethyl acetate/hexane) to give the title compound (55.2 mg).

$^1$H NMR (300 MHz, DMSO-d$_6$) δ 1.82-2.48 (6H, m), 4.15-4.44 (2H, m), 4.46-4.72 (2H, m), 7.28-7.75 (1H, m), 7.88 (1H, d, J=8.5 Hz), 8.20 (1H, d, J=0.9 Hz), 8.28 (1H, dd, J=8.0, 1.6 Hz), 9.74 (1H, brs).

Example 470

N-((1R,2R)-2-(6-(5-(difluoromethyl)-1,3,4-oxadiazol-2-yl)-1-oxo-1,3-dihydro-2H-isoindol-2-yl)-5,5-difluorocyclohexyl)-2,2-difluoropropanamide To a mixture of 2,2-difluoropropanoic acid (34.0 mg) and THF (1.5 mL) was added dropwise oxalyl chloride (0.027 mL) at 0° C., and then DMF (one drop) was added thereto. The mixture was stirred at room temperature for 1 hr to prepare an acid chloride of 2,2-difluoropropanoic acid. 2-((1R,2R)-2-Amino-4,4-difluorocyclohexyl)-6-(5-(difluoromethyl)-1,3,4-oxadiazol-2-yl)isoindolin-1-one trifluoroacetate (70 mg) was passed through NH silica gel short pad using methanol/ethyl acetate (9/1), and the filtrate was concentrated under reduced pressure. To a mixture of the residue, TEA (0.078 mL) and THF (2.0 mL) was added dropwise the acid chloride solution prepared above at 0° C. The mixture was stirred at room temperature for 30 min. The mixture was filtered, and the filtrate was concentrated under reduced pressure. The residue was purified by silica gel column chromatography (ethyl acetate/hexane) to give the title compound (45.8 mg).

$^1$H NMR (300 MHz, DMSO-$d_6$) δ 1.39 (3H, t, J=19.5 Hz), 1.85-2.46 (6H, m), 4.09-4.25 (1H, m), 4.27-4.45 (1H, m), 4.59 (2H, s), 7.34-7.76 (1H, m), 7.88 (1H, d, J=7.9 Hz), 8.20 (1H, s), 8.29 (1H, br d, J=8.1 Hz), 8.87 (1H, br d, J=8.7 Hz).

Example 489

N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2,3,3,3-pentafluoropropanamide A) diethyl 2-methylpyridine-3,5-dicarboxylate Ethyl 2-formyl-3-oxopropanoate (500.0 g) was dissolved in DMF (1.50 L), and the solution was cooled to 0° C. To the solution were added TEA (702.0 g) and 4-methylbenzenesulfonyl chloride (728.0 g) at 0° C., and the mixture was stirred under nitrogen atmosphere at 15° C. for 1 hr. To the mixture were added molecular sieve 4A (500.0 g), pyridine (1.10 kg) and a solution of ethyl 3-aminobuta-2-enoate (448 g) in DMF (1 L) at 15° C., and the mixture was stirred at 80° C. under nitrogen atmosphere for 12 hr. The same procedure was carried out a total of ten times in parallel, all the mixtures were cooled to 15° C., the mixtures were combined, and the solid was removed by filtration. The filtrate was poured into saturated aqueous sodium hydrogencarbonate solution (50 L), and the mixture was extracted with tert-butyl methyl ether (20 L and 10 L). The combined organic layers were washed with saturated brine (10 L), dried over anhydrous sodium sulfate, and concentrated under reduced pressure. To the residue was added petroleum ether (5 L), the mixture was stirred, and the precipitated solid was collected by filtration. The obtained solid was purified by silica gel column chromatography (petroleum ether/ethyl acetate) to give the title compound (2.50 kg).

$^1$H NMR (400 MHz, DMSO-$d_6$) δ 1.32-1.36 (6H, m), 2.79 (3H, s), 4.33-4.39 (4H, m), 8.55 (1H, d, J=1.6 Hz), 9.08 (1H, d, J=2.0 Hz).

B) diethyl 2-(chloromethyl)pyridine-3,5-dicarboxylate

To a mixture of diethyl 2-methylpyridine-3,5-dicarboxylate (500.0 g) and benzotrifluoride (2.5 L) was added 1,3,5-trichloro-1,3,5-triazinane-2,4,6-trione (588 g) at 15° C. The mixture was stirred at 15° C. for 0.5 hr, and then at 80° C. for 3 hr. The same procedure was carried out a total of four times in parallel, all the mixtures were combined, and the solid was removed by filtration. To the filtrate was added saturated aqueous sodium hydrogencarbonate solution (10 L) below 20° C., and the mixture was extracted with ethyl acetate (2 L and 1 L). The combined organic layers were washed with saturated brine (2 L), dried over anhydrous sodium sulfate, and concentrated under reduced pressure to give the title compound (2.23 kg).

$^1$H NMR (400 MHz, DMSO-$d_6$) δ 1.33-1.38 (6H, m), 4.37-4.42 (4H, m), 5.12 (2H, s), 8.64 (1H, d, J=2.0 Hz), 9.20 (1H, d, J=1.6 Hz).

C) ethyl 6-((1R,2R)-2-aminocyclohexyl)-5-oxo-6,7-dihydro-5H-pyrrolo[3,4-b]pyridine-3-carboxylate To a mixture of diethyl 2-(chloromethyl)pyridine-3,5-dicarboxylate (557.0 g) and ethanol (1.6 L) was added TEA (444.0 g) at 15° C. To the mixture was added a solution of (1R,2R)-cyclohexane-1,2-diamine (468.0 g) in ethanol (1.1 L) dropwise at 15° C., and the mixture was stirred at 15° C. for 12 hr, and then at 60° C. for 5 hr. The same procedure was carried out a total of three times in parallel, all the mixtures were cooled to 15° C., the mixtures were combined, and filtered. The filtrate was concentrated under reduced pressure to give the title compound (1.34 kg). The obtained product was used in the next reaction without further purification.

D) ethyl 6-((1R,2R)-2-((tert-butoxycarbonyl)amino)cyclohexyl)-5-oxo-6,7-dihydro-5H-pyrrolo[3,4-b]pyridine-3-carboxylate To a mixture of ethyl 6-((1R,2R)-2-aminocyclohexyl)-5-oxo-6,7-dihydro-5H-pyrrolo[3,4-b]pyridine-3-carboxylate (360.0 g), TEA (180.0 g) and THF (2.4 L) was added Boc$_2$O (284.9 g) at 0° C. The mixture was stirred at 15° C. for 1 hr. The same procedure was carried out a total of four times in parallel, all the mixtures were combined, the mixture was added to water (10 L) below 20° C., and extracted with tert-butyl methyl ether (5 L). The separated organic layer was washed with saturated brine (2 L), dried over anhydrous sodium sulfate, filtered, and concentrated under reduced pressure. The residue was stirred in petroleum ether (3 L), and the precipitated solid was collected by filtration to give the title compound (1.70 kg).

$^1$H NMR (400 MHz, CDCl$_3$) δ 1.07 (9H, s), 1.34-1.44 (6H, m), 1.55-1.70 (1H, m), 1.76-1.96 (3H, m), 2.01-2.15 (1H, m), 3.62-3.67 (1H, m), 4.13-4.17 (1H, m), 4.35-4.50 (3H, m), 4.59 (1H, d, J=10.0 Hz), 4.81 (1H, d, J=18.0 Hz), 8.66 (1H, d, J=1.6 Hz), 9.32 (1H, d, J=1.6 Hz).

E) tert-butyl ((1R,2R)-2-(3-(hydrazinocarbonyl)-5-oxo-5,7-dihydro-6H-pyrrolo[3,4-b]pyridin-6-yl)cyclohexyl)carbamate To a mixture of ethyl 6-((1R,2R)-2-((tert-butoxycarbonyl)amino)cyclohexyl)-5-oxo-6,7-dihydro-5H-pyrrolo[3,4-b]pyridine-3-carboxylate (402.5 g) and ethanol (2.3 L) was added hydrazine monohydrate (515 g) dropwise at 15° C.

The mixture was stirred at 70° C. for 2 hr. The same procedure was carried out a total of four times in parallel, all the mixtures were combined, and concentrated under reduced pressure. To the residue was added water (2 L) with stirring below 20° C. The precipitated solid was collected by filtration, washed with tert-butyl methyl ether (2 L, 1 L and 500 mL), and dried under reduced pressure to give the title compound (1.62 kg).

$^1$H NMR (400 MHz, DMSO-$d_6$) δ 0.98 (9H, s), 1.29-1.47 (3H, m), 1.70-1.77 (5H, m), 3.47-3.55 (1H, m), 3.94-4.00 (1H, m), 4.49 (1H, d, J=18.0 Hz), 4.59 (2H, brs), 4.72 (1H, d, J=18.0 Hz), 6.83 (1H, d, J=9.6 Hz), 8.42 (1H, d, J=2.0 Hz), 9.12 (1H, d, J=2.0 Hz), 10.08 (1H, brs).

F) tert-butyl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate (Step 1)

To a mixture of tert-butyl ((1R,2R)-2-(3-(hydrazinocarbonyl)-5-oxo-5,7-dihydro-6H-pyrrolo[3,4-b]pyridin-6-yl)cyclohexyl)carbamate (467 g) and THF (2.34 L) was added TEA (182 g) dropwise at 0° C. Then, to the mixture was added difluoroacetic anhydride (250 g) dropwise below 0° C., and the reaction mixture was stirred at 0° C. for 1 hr. To the mixture was added difluoroacetic anhydride (62.6 g) dropwise at 0° C., and the reaction mixture was stirred at 0° C. for 1 hr. The same procedure was carried out a total of three times in parallel, all the mixtures were combined, the mixture was added to saturated brine (10 L) below 20° C., and the mixture was extracted with ethyl acetate (5 L and 2 L). The combined organic layers were dried over anhydrous sodium sulfate, and concentrated under reduced pressure to give tert-butyl ((1R,2R)-2-(3-((2-(difluoroacetyl)hydrazino)carbonyl)-5-oxo-5,7-dihydro-6H-pyrrolo[3,4-b]pyridin-6-yl)cyclohexyl)carbamate (1.9 kg).

(Step 2)

To a mixture of tert-butyl ((1R,2R)-2-(3-((2-(difluoroacetyl)hydrazino) carbonyl)-5-oxo-5,7-dihydro-6H-pyrrolo[3,4-b]pyridin-6-yl)cyclohexyl)carbamate (360.0 g) and THF (2.52 L) were added DIPEA (299.0 g) and 4-methylbenzenesulfonyl chloride (440.5 g) at 0° C. The mixture was stirred at 25° C. for 3 hr. To the mixture was added saturated aqueous sodium hydrogencarbonate solution (10 L) at 0° C., and the mixture was extracted with ethyl acetate (5 L). The separated organic layer was washed with water (5 L) and saturated brine (5 L), dried over anhydrous sodium sulfate, and concentrated under reduced pressure. The same procedure was carried out a total of five times in parallel, and all the residues were combined, and also combined with the residue separately obtained using tert-butyl ((1R,2R)-2-(3-((2-(difluoroacetyl)hydrazino)carbonyl)-5-oxo-5,7-dihydro-6H-pyrrolo[3,4-b]pyridin-6-yl)cyclohexyl)carbamate (140 g) by the similar method. The combined residues were purified by silica gel column chromatography (ethyl acetate/hexane) to give a crude product (1.05 kg). To a mixture of the obtained crude product (400 g) and toluene (4000 mL) was added hexane (4000 mL) dropwise at room temperature. The mixture was cooled to 0° C., and stirred at 0° C. for 2 hr. The precipitate was collected by filtration, and the obtained solid was washed with hexane to give the title compound (327 g).

$^1$H NMR (300 MHz, CDCl$_3$) δ 1.10 (9H, s), 1.30-1.55 (3H, m), 1.63-1.76 (1H, m), 1.82-2.01 (1H, m), 2.05-2.17 (1H, m), 3.58-3.78 (1H, m), 4.13-4.27 (1H, m), 4.47 (1H, d, J=18.5 Hz), 4.62 (1H, br d, J=9.8 Hz), 4.92 (1H, d, J=18.1 Hz), 6.96 (1H, t, J=52.1 Hz), 8.74 (1H, d, J=2.3 Hz), 9.47 (1H, d, J=2.3 Hz).

G) N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2,3,3,3-pentafluoropropanamide The following reaction was carried out by dividing the described scale reaction into two batches. To a mixture of N-hydroxysuccinimide (116.0 g) and THF (1600 mL) was added pentafluoropropionic anhydride (160 mL) dropwise below 10° C. The mixture was stirred overnight at room temperature to give a THF solution of N-hydroxysuccinimide activated ester of pentafluoropropionic acid. To a mixture of tert-butyl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate (300 g) and toluene (1500 mL) was added TFA (1500 mL) under ice-cooling. The mixture was stirred at room temperature for 1 hr, and concentrated under reduced pressure. The residue was dissolved in THF (1600 mL), TEA (930 mL) and the THF solution of N-hydroxysuccinimide activated ester of pentafluoropropionic acid (previously prepared) were added dropwise thereto at 10° C. or below, and the mixture was stirred at 10° C. or below for 20 min. To the mixture was added saturated aqueous sodium hydrogencarbonate solution (2000 mL) under ice-cooling, and the mixture was extracted with ethyl acetate (10000 mL). The separated organic layer was washed with water (1000 mL), saturated aqueous sodium hydrogencarbonate solution (3000 mL) and saturated brine (3000 mL), dried over anhydrous sodium sulfate, and concentrated under reduced pressure. The two residues obtained by separately performed reactions were combined. The combined residue was purified by silica gel column chromatography (ethyl acetate), and the obtained solid was dissolved in isopropyl acetate (900 mL) at 50° C. The insoluble material was removed by filtration, and washed with isopropyl acetate (600 mL). The combined filtrate was heated to 60° C., heptane (4500 mL) was added dropwise thereto, and the mixture was stirred at room temperature overnight. The mixture was cooled to 0° C., stirred for 1 hr, and the precipitate was collected by filtration. The obtained solid was washed with heptane, and dried to give a solid (276 g). The obtained solid (227 g) was sieved (16 mesh), and pulverized by using jet mill to give the title compound (173 g).

$^1$H NMR (300 MHz, CDCl$_3$) δ 1.37-1.65 (3H, m), 1.70-2.11 (4H, m), 2.14-2.25 (1H, m), 4.01-4.19 (1H, m), 4.42 (1H, td, J=11.5, 3.8 Hz), 4.52 (1H, d, J=18.1 Hz), 4.70 (1H, d, J=18.1 Hz), 6.96 (1H, t, J=51.7 Hz), 7.16 (1H, br d, J=9.1 Hz), 8.72 (1H, d, J=2.3 Hz), 9.50 (1H, d, J=1.9 Hz).

optical purity: >99.9% ee, >99.9% de (retention time: 13.489 min)

column: CHIRALPAK ID-3 (DAICEL), 4.6 mmID×150 mmL mobile phase: 50 mmol/L aqueous ammonium acetate solution/acetonitrile=70:30

Anal. Calcd for $C_{19}H_{16}F_7N_5O_3$: C, 46.07; H, 3.26; N, 14.14, Found: C, 46.15; H, 3.22; N, 14.12.

powder X-RAY crystal diffraction pattern (diffraction angle 2θ): 9.5°, 12.3°, 13.4°, 16.7°, 17.9°, 18.9°, 19.7°, 21.2°

Example 502

6-((1R,2R)-2-(1H-benzimidazol-1-yl)cyclohexyl)-3-(5-(difluoromethyl)-1,3,4-oxadiazol-2-yl)-6,7-dihydro-5H-pyrrolo[3,4-b]pyridin-5-one

A) tert-butyl ((1R,2R)-2-((2-nitrophenyl)amino)cyclohexyl)carbamate

To a mixture of tert-butyl ((1R,2R)-2-aminocyclohexyl)carbamate (3.0 g), 1-fluoro-2-nitrobenzene (1.48 mL) and DMF (50 mL) was added potassium carbonate (2.03 g) at room temperature, and the mixture was stirred overnight at 80° C. The mixture was poured into water at room temperature, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (3.71 g).
MS: [M+H]$^+$336.2.

B) tert-butyl ((1R,2R)-2-((2-aminophenyl)amino)cyclohexyl)carbamate

A mixture of tert-butyl ((1R,2R)-2-((2-nitrophenyl)amino)cyclohexyl)carbamate (1.20 g), 10% palladium on carbon (hydrous, 0.381 g) and methanol (20 mL) was hydrogenated under balloon pressure overnight at room temperature. The catalyst was removed by filtration, and the filtrate was concentrated under reduced pressure to give the title compound (1.09 g).
MS: [M+H]$^+$306.2.

C) tert-butyl ((1R,2R)-2-(1H-benzimidazol-1-yl)cyclohexyl)carbamate

A mixture of tert-butyl ((1R,2R)-2-((2-aminophenyl)amino)cyclohexyl)carbamate (1.09 g), trimethyl orthoformate (3.90 mL), pyridinium p-toluenesulfonate (0.090 g) and ethyl acetate (25 mL) was stirred at 60° C. for 1 hr. The mixture was poured into saturated aqueous sodium hydrogencarbonate solution at room temperature, and extracted with ethyl acetate. The organic layer was separated, washed with water and saturated brine, dried over anhydrous sodium sulfate, and concentrated under reduced pressure. The residue was purified by silica gel column chromatography (NH, ethyl acetate/hexane) to give the title compound (1.00 g).
MS: [M+H]$^+$316.3.

D) (1R,2R)-2-(1H-benzimidazol-1-yl)cyclohexanamine hydrochloride

A mixture of tert-butyl ((1R,2R)-2-(1H-benzimidazol-1-yl)cyclohexyl)carbamate (420 mg) and 4M hydrogen chloride ethyl acetate solution (10 mL) was stirred at room temperature for 3 hr. The mixture was concentrated under reduced pressure to give the title compound (334 mg).
MS: [M+H]$^+$216.1.

E) ethyl 6-((1R,2R)-2-(1H-benzimidazol-1-yl)cyclohexyl)-5-oxo-6,7-dihydro-5H-pyrrolo[3,4-b]pyridine-3-carboxylate To a mixture of (1R,2R)-2-(1H-benzimidazol-1-yl)cyclohexanamine hydrochloride (334 mg), DIPEA (0.962 mL) and DMF (10 mL) was added diethyl 2-(chloromethyl)pyridine-3,5-dicarboxylate (300 mg) at 0° C. The mixture was warmed to room temperature, and stirred at room temperature for 3 days. The mixture was poured into water, and extracted with ethyl acetate. The organic layer was separated, washed with water and saturated brine, dried over anhydrous sodium sulfate, and concentrated under reduced pressure. The residue was purified by silica gel column chromatography (NH, ethyl acetate/hexane) to give the title compound (120 mg).
MS: [M+H]$^+$405.1.

F) 6-((1R,2R)-2-(1H-benzimidazol-1-yl)cyclohexyl)-5-oxo-6,7-dihydro-5H-pyrrolo[3,4-b]pyridine-3-carbohydrazide To a mixture of ethyl 6-((1R,2R)-2-(1H-benzimidazol-1-yl)cyclohexyl)-5-oxo-6,7-dihydro-5H-pyrrolo[3,4-b]pyridine-3-carboxylate (120 mg) and methanol (10 mL) was added hydrazine monohydrate (0.144 mL) at room temperature, and the mixture was stirred at 60° C. for 4 hr. The mixture was concentrated under reduced pressure to give the title compound (116 mg).
MS: [M+H]$^+$391.1.

G) 6-((1R,2R)-2-(1H-benzimidazol-1-yl)cyclohexyl)-3-(5-(difluoromethyl)-1,3,4-oxadiazol-2-yl)-6,7-dihydro-5H-pyrrolo[3,4-b]pyridin-5-one To a mixture of 6-((1R,2R)-2-(1H-benzimidazol-1-yl)cyclohexyl)-5-oxo-6,7-dihydro-5H-pyrrolo[3,4-b]pyridine-3-carbohydrazide (116 mg), DIPEA (0.155 mL) and THF (3 mL) was added difluoroacetic anhydride (0.074 mL) at 0° C. The mixture was stirred at 0° C. to room temperature for 2 hr. The mixture was poured into saturated brine at room temperature, and extracted with ethyl acetate. The organic layer was separated, washed with saturated brine, dried over anhydrous sodium sulfate, and concentrated under reduced pressure. To a mixture of the obtained residue and THF (3 mL) were added DIPEA (0.207 mL) and 4-methylbenzenesulfonyl chloride (170 mg) at 0° C. The mixture was stirred overnight at 0° C. to room temperature. The mixture was poured into saturated aqueous sodium hydrogencarbonate solution at room temperature, and extracted with ethyl acetate. The separated organic layer was washed with water and saturated brine, dried over anhydrous sodium sulfate, and concentrated under reduced pressure. The residue was purified by silica gel column chromatography (ethyl acetate/hexane) and silica gel column chromatography (NH, ethyl acetate/hexane), and recrystallized from hexane/ethyl acetate to give the title compound (35.0 mg).
$^1$H NMR (300 MHz, CDCl$_3$) δ 1.61-1.73 (2H, m), 1.91-2.20 (5H, m), 2.36 (1H, d, J=12.3 Hz), 4.22 (2H, s), 4.57-4.90 (2H, m), 6.93 (1H, t, J=51.6 Hz), 7.14-7.26 (2H, m), 7.44 (1H, d, J=7.3 Hz), 7.67-7.74 (1H, m), 8.06 (1H, s), 8.60 (1H, d, J=2.0 Hz), 9.34 (1H, d, J=2.0 Hz).

Example 503

3-(5-(difluoromethyl)-1,3,4-oxadiazol-2-yl)-6-((1R,2R)-2-(2-methyl-1H-benzimidazol-1-yl)cyclohexyl)-6,7-dihydro-5H-pyrrolo[3,4-b]pyridin-5-one

A) tert-butyl ((1R,2R)-2-(2-methyl-1H-benzimidazol-1-yl)cyclohexyl)carbamate A mixture of tert-butyl ((1R,2R)-2-((2-aminophenyl)amino)cyclohexyl)carbamate (1.00 g), trimethyl orthoacetate (4.17 mL), pyridinium p-toluenesulfonate (0.082 g) and ethyl acetate (25 mL) was stirred overnight at 60° C. The mixture was poured into saturated aqueous sodium hydrogencarbonate solution at room temperature, and extracted with ethyl acetate. The organic layer was separated, washed with water and saturated brine, dried over anhydrous sodium sulfate, and concentrated under reduced pressure. The residue was purified by silica gel column chromatography (NH, ethyl acetate/methanol) to give the title compound (940 mg).
MS: [M+H]$^+$330.2.

B) (1R,2R)-2-(2-methyl-1H-benzimidazol-1-yl)cyclohexanamine hydrochloride

A mixture of tert-butyl ((1R,2R)-2-(2-methyl-1H-benzimidazol-1-yl)cyclohexyl)carbamate (400 mg) and 4M hydrogen chloride ethyl acetate solution (10 mL) was stirred at room temperature for 3 hr. The mixture was concentrated to give the title compound (323 mg).
MS: [M+H]$^+$230.1.

C) ethyl 6-((1R,2R)-2-(2-methyl-1H-benzimidazol-1-yl)cyclohexyl)-5-oxo-6,7-dihydro-5H-pyrrolo[3,4-b]pyridine-3-carboxylate To a mixture of (1R,2R)-2-(2-methyl-1H-benzimidazol-1-yl)cyclohexanamine hydrochloride (395 mg), DIPEA (1.30 mL) and DMF (10 mL) was added diethyl 2-(bromomethyl)pyridine-3,5-dicarboxylate (470 mg) at 0° C. The mixture was stirred at 0° C. to room temperature for 3 days. The mixture was poured into water at room temperature, and extracted with ethyl acetate. The organic layer was separated, washed with water and saturated brine, dried over anhydrous sodium sulfate, and concentrated under reduced pressure. The residue was dissolved in acetic acid (5 mL), and the mixture was stirred at 80° C. for 2 hr. The mixture was concentrated, the residue was neutralized with saturated aqueous sodium hydrogencarbonate solution at room temperature, and the mixture was extracted with ethyl acetate. The organic layer was separated, washed with water and saturated brine, dried over anhydrous sodium sulfate, and concentrated under reduced pressure. The residue was purified by silica gel column chromatography (NH, ethyl acetate/hexane) to give the title compound (123 mg).
MS: [M+H]$^+$419.2.

D) 6-((1R,2R)-2-(2-methyl-1H-benzimidazol-1-yl)cyclohexyl)-5-oxo-6,7-dihydro-5H-pyrrolo[3,4-b]pyridine-3-carbohydrazide To a mixture of ethyl 6-((1R,2R)-2-(2-methyl-1H-benzimidazol-1-yl)cyclohexyl)-5-oxo-6,7-dihydro-5H-pyrrolo[3,4-b]pyridine-3-carboxylate (115 mg) and methanol (5 mL) was added hydrazine monohydrate (0.267 mL) at room temperature. The mixture was stirred overnight at 70° C. The mixture was concentrated to give the title compound (111 mg).
MS: [M+H]$^+$405.1.

E) 3-(5-(difluoromethyl)-1,3,4-oxadiazol-2-yl)-6-((1R,2R)-2-(2-methyl-1H-benzimidazol-1-yl)cyclohexyl)-6,7-dihydro-5H-pyrrolo[3,4-b]pyridin-5-one To a mixture of 6-((1R,2R)-2-(2-methyl-1H-benzimidazol-1-yl)cyclohexyl)-5-oxo-6,7-dihydro-5H-pyrrolo[3,4-b]pyridine-3-carbohydrazide (111 mg), DIPEA (0.143 mL) and THF (5 mL) was added difluoroacetic anhydride (0.068 mL) at 0° C. The mixture was stirred at 0° C. for 2 hr. The mixture was poured into saturated brine at room temperature, and extracted with ethyl acetate. The organic layer was separated, washed with water and saturated brine, dried over anhydrous sodium sulfate, and concentrated under reduced pressure. The residue was dissolved in THF (5 mL), and to the solution were added DIPEA (0.574 mL) and 4-methylbenzenesulfonyl chloride (471 mg) at 0° C. The mixture was stirred overnight at 0° C. to room temperature. The mixture was poured into saturated aqueous sodium hydrogencarbonate solution at room temperature, and extracted with ethyl acetate. The organic layer was separated, washed with water and saturated brine, dried over anhydrous sodium sulfate, and concentrated under reduced pressure. The residue was purified by silica gel column chromatography (methanol/ethyl acetate) and silica gel column chromatography (NH, ethyl acetate/hexane) to give the title compound (20 mg).
$^1$H NMR (300 MHz, CDCl$_3$) δ 1.62-1.78 (3H, m), 2.09-2.94 (8H, m), 3.75 (1H, d, J=18.5 Hz), 4.29 (1H, d, J=18.5 Hz), 4.47-4.65 (1H, m), 4.99-5.25 (1H, m), 6.74-7.11 (1H, m), 7.16-7.26 (2H, m), 7.54-7.69 (2H, m), 8.53-8.69 (1H, m), 9.29-9.38 (1H, m).

Example 510 benzyl ((1S,6R)-6-(6-(5-(difluoromethyl)-1,3,4-oxadiazol-2-yl)-1-oxo-1,3-dihydro-2H-isoindol-2-yl)-2,2-difluorocyclohexyl)carbamate

A) benzyl ((1S,6R)-6-amino-2,2-difluorocyclohexyl)carbamate hydrochloride

To a mixture of tert-butyl ((1R,2S)-2-amino-3,3-difluorocyclohexyl)carbamate (2.503 g), potassium carbonate (4.15 g) and THF (100 mL) was added benzyl chloroformate (1.713 mL) at 0° C. The mixture was stirred overnight at room temperature. The precipitate was removed by filtration, and the filtrate was concentrated under reduced pressure. To the residue was added 4M hydrogen chloride ethyl acetate solution (10 mL) at room temperature. The mixture was stirred overnight at room temperature. The mixture was concentrated under reduced pressure, and the obtained solid was washed with hexane to give the title compound (3.21 g).
MS: [M+H]$^+$285.1.

B) methyl 2-((1R,2S)-2-(((benzyloxy)carbonyl)amino)-3,3-difluorocyclohexyl)-3-oxoisoindoline-5-carboxylate To a mixture of benzyl ((1S,6R)-6-amino-2,2-difluorocyclohexyl)carbamate hydrochloride (1.46 g) and DMF (45 mL) was added DIPEA (2.39 mL) at 0° C., and to the mixture was added dimethyl 4-(bromomethyl)isophthalate (1.57 g) at the same temperature. The mixture was stirred at room temperature for 2 days. The mixture was concentrated, and the obtained residue was partitioned between ethyl acetate/water. The organic layer was washed with water and saturated brine, dried over anhydrous magnesium sulfate, and concentrated under reduced pressure. The residue was purified by silica gel column chromatography (ethyl acetate/hexane) to give the title compound (1.52 g).
MS: [M+H]$^+$459.1.

C) benzyl ((1S,6R)-2,2-difluoro-6-(6-(hydrazinocarbonyl)-1-oxo-1,3-dihydro-2H-isoindol-2-yl)cyclohexyl)carbamate To a mixture of methyl 2-((1R,2S)-2-(((benzyloxy)carbonyl)amino)-3,3-difluorocyclohexyl)-3-oxoisoindoline-5- carboxylate (1.52 g) and methanol (15 mL) was added hydrazine monohydrate (3.22 mL) at room temperature. The mixture was stirred overnight at 60° C. The mixture was concentrated under reduced pressure, and azeotroped with toluene to give the title compound (1.52 g).

MS: [M+H]$^+$459.1.

D) benzyl ((1S,6R)-6-(6-(5-(difluoromethyl)-1,3,4-oxadiazol-2-yl)-1-oxo-1,3-dihydro-2H-isoindol-2-yl)-2,2-difluorocyclohexyl)carbamate To a mixture of benzyl ((1S,6R)-2,2-difluoro-6-(6-(hydrazinocarbonyl)-1-oxo-1,3-dihydro-2H-isoindol-2-yl)cyclohexyl)carbamate (1.52 g), DIPEA (1.74 mL) and THF (15 mL) was added difluoroacetic anhydride (0.618 mL) at 0° C. The mixture was stirred at room temperature for 1 hr, and DIPEA (1.74 mL) and 4-methylbenzenesulfonyl chloride (0.948 g) were added thereto at 0° C. The mixture was stirred overnight at room temperature. The mixture was concentrated, and the residue was purified by silica gel column chromatography (ethyl acetate/hexane) to give the title compound (1.40 g).

$^1$H NMR (300 MHz, DMSO-d$_6$) δ 1.40-1.61 (1H, m), 1.72-1.87 (2H, m), 1.90-2.05 (2H, m), 2.06-2.23 (1H, m), 4.16-4.45 (2H, m), 4.47-4.71 (2H, m), 4.75-5.02 (2H, m), 6.96-7.32 (5H, m), 7.40-7.78 (1H, m), 7.80-7.94 (2H, m), 8.20 (1H, d, J=1.0 Hz), 8.30 (1H, dd, J=8.0, 1.7 Hz).

Example 511

2-((1R,2S)-2-amino-3,3-difluorocyclohexyl)-6-(5-(difluoromethyl)-1,3,4-oxadiazol-2-yl)isoindolin-1-one A mixture of benzyl ((1S,6R)-6-(6-(5-(difluoromethyl)-1,3,4-oxadiazol-2-yl)-1-oxo-1,3-dihydro-2H-isoindol-2-yl)-2,2-difluorocyclohexyl)carbamate (1.40 g), 10% palladium on carbon (0.287 g) and methanol (25 mL) was hydrogenated under balloon pressure at room temperature for 2 hr. The catalyst was removed by filtration, and the filtrate was concentrated under reduced pressure to give the title compound (0.95 g).

$^1$H NMR (300 MHz, DMSO-d$_6$) δ1.40-1.62 (3H, m), 1.70-1.99 (4H, m), 2.13 (1H, brs), 3.17-3.31 (1H, m), 3.99 (1H, td, J=10.9, 5.6 Hz), 4.61 (2H, s), 7.37-7.78 (1H, m), 7.85-7.92 (1H, m), 8.23 (1H, d, J=0.9 Hz), 8.29 (1H, dd, J=7.9, 1.6 Hz).

Example 512

N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2-difluoropropanamide To a mixture of 2,2-difluoropropanoic acid (428 mg) and THF (15 mL) were added oxalyl chloride (0.341 mL) and DMF (one drop) at 0° C. The mixture was stirred at room temperature for 30 min. To the mixture was added a mixture of 2-((1R,2S)-2-amino-3,3-difluorocyclohexyl)-6-(5-(difluoromethyl)-1,3,4-oxadiazol-2-yl)isoindolin-1-one (650 mg), DIPEA (1.477 mL) and THF (1 mL) at room temperature. The mixture was stirred overnight at room temperature. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane). The obtained crude product was recrystallized from ethyl acetate/hexane to give the title compound (618 mg).

$^1$H NMR (300 MHz, DMSO-d$_6$) δ 1.34-1.62 (4H, m), 1.86 (2H, d, J=12.5 Hz), 1.92-2.25 (3H, m), 4.29-4.86 (4H, m), 7.56 (1H, t, J=51.0 Hz), 7.91 (1H, d, J=8.3 Hz), 8.20 (1H, d, J=0.9 Hz), 8.29 (1H, dd, J=8.0, 1.7 Hz), 8.94 (1H, d, J=9.5 Hz).

powder X-RAY crystal diffraction pattern (diffraction angle 2θ): 6.4°, 9.6°, 10.5°, 12.4°, 17.0°, 19.4°, 20.2°, 20.8°, 23.2°

Example 513

N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2,3,3,3-pentafluoropropanamide To a mixture of 2-((1R,2S)-2-amino-3,3-difluorocyclohexyl)-6-(5-(difluoromethyl)-1,3,4-oxadiazol-2-yl)isoindolin-1-one (50.1 mg), DIPEA (0.068 mL) and THF (3 mL) was added pentafluoropropanoic anhydride (0.031 mL) at 0° C. The mixture was stirred at room temperature for 2 hr. To the mixture was added saturated aqueous sodium hydrogencarbonate solution at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (29.6 mg).

$^1$H NMR (300 MHz, DMSO-d$_6$) δ 1.53 (1H, d, J=13.5 Hz), 1.86 (2H, d, J=12.7 Hz), 1.96-2.32 (3H, m), 4.25-4.53 (2H, m), 4.68 (1H, d, J=18.5 Hz), 4.77-5.08 (1H, m), 7.35-7.79 (1H, m), 7.91 (1H, d, J=8.0 Hz), 8.21 (1H, s), 8.29 (1H, dd, J=7.9, 1.6 Hz), 10.06 (1H, d, J=8.7 Hz).

Example 514

6-(5-(difluoromethyl)-1,3,4-oxadiazol-2-yl)-2-((1RS,2RS)-2-(1H-pyrazol-1-yl)cyclohexyl)isoindolin-1-one A) (1RS,2RS)-2-(1H-pyrazol-1-yl)cyclohexanol To a mixture of 7-oxabicyclo[4.1.0]heptane (24.2 g) and 1H-pyrazole (1.68 g) was added cesium carbonate (1.61 g) at room temperature, and the mixture was stirred at room temperature for 5 days. The mixture was concentrated, to the obtained residue was added water, and the mixture was extracted with a mixed solvent of ethyl acetate/THF. The organic layer was separated, washed with saturated brine, dried over anhydrous sodium sulfate, and concentrated under reduced pressure to give the title compound (3.95 g).

MS: [M+H]$^+$ 167.2.

B) (1SR,2RS)-2-(1H-pyrazol-1-yl)cyclohexyl 4-nitrobenzoate

To a mixture of (1RS,2RS)-2-(1H-pyrazol-1-yl)cyclohexanol (3.55 g), triphenylphosphine (19.6 g), 4-nitrobenzoic acid (10.7 g) and THF (100 mL) was added bis(2-methoxyethyl) azodicarboxylate (17.5 g) at room temperature. The mixture was stirred overnight at room temperature. The mixture was poured into water at room temperature, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (5.50 g).

MS: [M+H]$^+$ 316.1.

C) (1SR, 2RS)-2-(1H-pyrazol-1-yl)cyclohexanol

To a mixture of (1SR,2RS)-2-(1H-pyrazol-1-yl)cyclohexyl 4-nitrobenzoate (5.50 g), THF (100 mL) and methanol (50 mL) was added 2N aqueous sodium hydroxide solution (26.2 mL) at room temperature. The mixture was stirred at room temperature for 3 hr. The mixture was diluted with water, and extracted with a mixed solvent of ethyl acetate/THF. The organic layer was separated, washed with 1N aqueous sodium hydroxide solution, water and saturated brine, dried over anhydrous sodium sulfate, and concentrated under reduced pressure. The residue was purified by silica gel column chromatography (ethyl acetate/hexane) to give the title compound (2.40 g).

$^1$H NMR (300 MHz, CDCl$_3$) δ 1.29-1.61 (3H, m), 1.68-1.93 (3H, m), 1.94-2.09 (1H, m), 2.20-2.40 (1H, m), 4.12 (1H, ddd, J=12.3, 4.1, 2.3 Hz), 4.24-4.30 (1H, m), 4.39 (1H, t, J=1.7 Hz), 6.27 (1H, t, J=2.2 Hz), 7.45 (1H, d, J=1.9 Hz), 7.53 (1H, d, J=1.7 Hz).

D) (1RS,2RS)-2-(1H-pyrazol-1-yl)cyclohexanamine

A mixture of (1SR,2RS)-2-(1H-pyrazol-1-yl)cyclohexanol (500 mg), triphenylphosphine (1.97 g), bis(2-methoxyethyl) azodicarboxylate (1.76 g) and THF (25 mL) was stirred at 0° C. for 10 min. To the mixture was added DPPA (1.62 mL) at 0° C., and the mixture was stirred overnight at 0° C. to room temperature. The mixture was poured into water at room temperature, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give 1-((1RS,2RS)-2-azidocyclohexyl)-1H-pyrazole. 1-((1RS,2RS)-2-Azidocyclohexyl)-1H-pyrazole was dissolved in methanol (25 mL), and to the solution was added 10% palladium on carbon (hydrous, 160 mg). The mixture was hydrogenated under balloon pressure at room temperature for 3 hr. The catalyst was removed by filtration, and the filtrate was concentrated under reduced pressure. The residue was purified by silica gel column chromatography (ethyl acetate/methanol) to give the title compound (341 mg).

MS: [M+H]$^+$ 166.3.

E) methyl 3-oxo-2-((1RS,2RS)-2-(1H-pyrazol-1-yl)cyclohexyl)isoindoline-5-carboxylate To a mixture of (1RS,2RS)-2-(1H-pyrazol-1-yl)cyclohexanamine (173 mg), DIPEA (0.758 mL) and DMF (8 mL) was added dimethyl 4-(bromomethyl)isophthalate (250 mg) at 0° C. The mixture was stirred overnight at 0° C. to room temperature. The mixture was poured into water at room temperature, and extracted with ethyl acetate. The organic layer was separated, washed with water and saturated brine, dried over anhydrous sodium sulfate, and concentrated under reduced pressure. The residue was dissolved in acetic acid (8 mL), and the solution was stirred at 50° C. for 1 hr. The mixture was concentrated, the residue was basified with saturated aqueous sodium hydrogencarbonate solution at room temperature, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (257 mg).

$^1$H NMR (300 MHz, CDCl$_3$) δ 1.47-1.57 (2H, m), 1.88-2.10 (5H, m), 2.22-2.34 (1H, m), 3.93 (3H, s), 4.05 (1H, d, J=17.5 Hz), 4.23-4.38 (1H, m), 4.43 (1H, d, J=17.4 Hz), 4.73 (1H, td, J=11.4, 3.7 Hz), 6.09 (1H, t, J=2.1 Hz), 7.31 (1H, d, J=1.4 Hz), 7.39-7.45 (2H, m), 8.16 (1H, dd, J=7.9, 1.5 Hz), 8.38 (1H, d, J=0.9 Hz).

F) 3-oxo-2-((1RS,2RS)-2-(1H-pyrazol-1-yl)cyclohexyl) isoindoline-5-carbohydrazide To a mixture of methyl 3-oxo-2-((1RS,2RS)-2-(1H-pyrazol-1-yl)cyclohexyl)isoindoline-5-carboxylate (256 mg) and methanol (8 mL) was added hydrazine monohydrate (0.366 mL) at room temperature. The mixture was stirred at 70° C. for 4 hr. The mixture was concentrated under reduced pressure, and subjected to azeotropic evaporation with a mixed solvent of toluene/methanol to give the title compound (256 mg).

MS: [M+H]$^+$ 340.1.

G) 6-(5-(difluoromethyl)-1,3,4-oxadiazol-2-yl)-2-((1RS,2RS)-2-(1H-pyrazol-1-yl)cyclohexyl)isoindolin-1-one To a mixture of 3-oxo-2-((1RS,2RS)-2-(1H-pyrazol-1-yl)cyclohexyl)isoindoline-5-carbohydrazide (256 mg), DIPEA (0.657 mL) and THF (5 mL) was added difluoroacetic anhydride (0.375 mL) at 0° C. The mixture was stirred at 0° C. to room temperature for 1 hr. The mixture was poured into saturated brine at room temperature, and extracted with ethyl acetate. The organic layer was separated, washed with saturated brine, dried over anhydrous sodium sulfate, and concentrated under reduced pressure. The residue was dissolved in THF (5 mL), and to the solution were added DIPEA (1.58 mL) and 4-methylbenzenesulfonyl chloride (1.29 g) at 0° C. The mixture was stirred at 0° C. to room temperature for 4 hr. The mixture was added to saturated aqueous sodium hydrogencarbonate solution at room temperature, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) and preparative HPLC (column: C18, mobile phase: water (containing 0.1% (v/v) TFA)/acetonitrile (containing 0.1% (v/v) TFA)), and recrystallized from hexane/ethyl acetate to give the title compound (143 mg).

$^1$H NMR (300 MHz, CDCl$_3$) δ 1.47-1.58 (2H, m), 1.87-2.11 (5H, m), 2.24-2.34 (1H, m), 4.11 (1H, d, J=17.5 Hz), 4.23-4.41 (1H, m), 4.50 (1H, d, J=17.5 Hz), 4.73 (1H, td, J=11.5, 4.0 Hz), 6.10 (1H, t, J=2.1 Hz), 6.91 (1H, t, J=51.9 Hz), 7.31 (1H, d, J=1.6 Hz), 7.45 (1H, d, J=2.0 Hz), 7.54 (1H, dd, J=7.9, 0.7 Hz), 8.28 (1H, dd, J=7.9, 1.6 Hz), 8.42 (1H, d, J=1.0 Hz).

Example 516

N-((1S,2R)-2-(6-(5-(difluoromethyl)-1,3,4-oxadiazol-2-yl)-1-oxo-1,3-dihydro-2H-isoindol-2-yl)-5,5-difluorocyclohexyl)-2,2-difluoropropanamide A) 2-((1R,2S)-2-amino-4,4-difluorocyclohexyl)-6-(5-(difluoromethyl)-1,3,4-oxadiazol-2-yl)isoindolin-1-one A mixture of benzyl ((1S,2R)-2-(6-(5-(difluoromethyl)-1,3,4-oxadiazol-2-yl)-1-oxo-1,3-dihydro-2H-isoindol-2-yl)-5,5-difluorocyclohexyl)carbamate (264 mg), 10% palladium on carbon (about 55% hydrous product, 30 mg) and ethyl acetate (8.0 mL) was stirred under hydrogen atmosphere overnight at room temperature. The mixture was filtered through Celite, and the filtrate was concentrated under reduced pressure to give the title compound (184 mg).

MS: [M+H]$^+$ 385.1.

B) N-((1S,2R)-2-(6-(5-(difluoromethyl)-1,3,4-oxadiazol-2-yl)-1-oxo-1,3-dihydro-2H-isoindol-2-yl)-5,5-difluorocyclohexyl)-2,2-difluoropropanamide To a mixture of 2,2-difluoropropanoic acid (37.8 mg) and THF (1.0 mL) was added dropwise oxalyl chloride (0.030 mL) at 0° C., and then DMF (one drop) was added thereto. The mixture was stirred at room temperature for 1 hr. This mixture was added dropwise to a mixture of 2-((1R,2S)-2-amino-4,4-difluorocyclohexyl)-6-(5-(difluoromethyl)-1,3,4-oxadiazol-2-yl)isoindolin-1-one (60 mg), TEA (0.087 mL) and THF (2.0 mL) at 0° C., and the mixture was stirred at room temperature for 3 hr. The insoluble material was removed by filtration, and the filtrate was concentrated under reduced pressure. The residue was purified by silica gel column chromatography (ethyl acetate/hexane) to give the title compound (65.2 mg).

$^1$H NMR (300 MHz, DMSO-d$_6$) δ 1.66 (3H, t, J=19.6 Hz), 2.00-2.46 (6H, m), 4.39-4.63 (2H, m), 4.67-4.90 (2H, m), 7.36-7.76 (1H, m), 7.89 (1H, d, J=7.9 Hz), 8.22 (1H, d, J=0.9 Hz), 8.27-8.40 (2H, m).

Example 517 benzyl ((1S,2R)-2-(6-(5-(difluoromethyl)-1,3,4-oxadiazol-2-yl)-1-oxo-1,3-dihydro-2H-isoindol-2-yl)-5,5-difluorocyclohexyl) carbamate A) (1S,2R)-2-((tert-butoxycarbonyl)amino)-5,5-difluorocyclohexanecarboxylic acid A mixture of ethyl (1S,2R)-2-(((benzyloxy) carbonyl)amino)-5,5-difluorocyclohexanecarboxylate (5.00 g), palladium hydroxide on carbon (about 50% hydrous product, 0.50 g), Boc$_2$O (3.84 g) and ethyl acetate (50 mL) was stirred under hydrogen atmosphere overnight. The mixture was filtered through Celite, and the filtrate was concentrated under reduced pressure. The residue was dissolved in THF (15 mL)/ethanol (30 mL), and 2N aqueous sodium hydroxide solution (14.7 mL) was added thereto at room temperature. The mixture was stirred at room temperature for 2 hr, and neutralized with 2N hydrochloric acid (14.7 mL) at 0° C. The mixture was concentrated under reduced pressure, and the residue was partitioned between water and ethyl acetate. The separated organic layer was washed with saturated brine, dried over anhydrous sodium sulfate, and concentrated under reduced pressure to give the title compound (4.11 g).

MS, found: 180.1.

B) methyl 2-((1R,2S)-2-(((benzyloxy)carbonyl)amino)-4,4-difluorocyclohexyl)-3-oxoisoindoline-5-carboxylate To a mixture of (1S,2R)-2-((tert-butoxycarbonyl)amino)-5,5-difluorocyclohexanecarboxylic acid (4.11 g), DPPA (3.80 mL) and toluene (45 mL) was added dropwise TEA (2.46 mL) at room temperature, and the mixture was stirred for 2 hr. To this mixture was added benzyl alcohol (3.05 mL), and the mixture was stirred at 90° C. for 5 hr, and left stand for 3 days at room temperature. The mixture was poured into water/saturated aqueous sodium hydrogencarbonate solution, and extracted with ethyl acetate. The extract was washed with water and saturated brine, dried over anhydrous sodium sulfate, and concentrated under reduced pressure. The residue was purified by silica gel column chromatography (ethyl acetate/hexane) to give a mixture (3.33 g) of benzyl tert-butyl ((1R,2S)-4,4-difluorocyclohexane-1,2-diyl)biscarbamate and benzyl alcohol. To a mixture of the obtained mixture (3.33 g) of benzyl tert-butyl ((1R,2S)-4,4-difluorocyclohexane-1,2-diyl)biscarbamate and benzyl alcohol, 2-propanol (6.0 mL) and methanol (12.0 mL) was added 2N hydrogen chloride/2-propanol solution (17.3 mL) at room temperature, and the mixture was stirred for 3 days. The mixture was concentrated under reduced pressure, and the residue was diluted with ethyl acetate (20 mL). To this mixture was added TEA (4.82 mL), and the mixture was stirred at room temperature for 30 min. The precipitate was removed by filtration, and washed with ethyl acetate. The filtrate was concentrated under reduced pressure to give a mixture (3.2 g) of benzyl ((1S,2R)-2-amino-5,5-difluorocyclohexyl)carbamate and benzyl alcohol. To a mixture of the obtained mixture of benzyl ((1S,2R)-2-amino-5,5-difluorocyclohexyl)carbamate and benzyl alcohol, dimethyl 4-(bromomethyl)isophthalate (0.718 g) and DMF (10.0 mL) was added TEA (0.695 mL) at room temperature, and the mixture was stirred overnight. The mixture was poured into water, and extracted with ethyl acetate. The extract was washed with water and saturated brine, dried over anhydrous sodium sulfate, and concentrated under reduced pressure. The residue was dissolved in acetic acid (10 mL), and the solution was stirred at 50° C. for 5 hr. The mixture was concentrated under reduced pressure. The residue was purified by silica gel column chromatography (ethyl acetate/hexane) to give the title compound (315 mg).

MS: [M+H]$^+$ 459.1.

C) benzyl ((1S,2R)-2-(6-(5-(difluoromethyl)-1,3,4-oxadiazol-2-yl)-1-oxo-1,3-dihydro-2H-isoindol-2-yl)-5,5-difluorocyclohexyl)carbamate A mixture of methyl 2-((1R,2S)-2-(((benzyloxy)carbonyl)amino)-4,4-difluorocyclohexyl)-3-oxoisoindoline-5-carboxylate (314 mg), hydrazine monohydrate (0.664 mL) and methanol (6.0 mL) was stirred overnight at 60° C. The mixture was concentrated under reduced pressure. To a mixture of the obtained residue (312 mg), TEA (0.189 mL) and THF (6.0 mL) was added dropwise difluoroacetic anhydride (0.127 mL) at room temperature, and the mixture was stirred for 1 hr. The mixture was concentrated under reduced pressure, and the residue was dissolved in acetonitrile (6.00 mL). To this solution were added TEA (0.189 mL) and 4-methylbenzenesulfonyl chloride (194 mg) at room temperature, and the mixture was stirred for 3 days. To this mixture were added TEA (0.142 mL) and 4-methylbenzenesulfonyl chloride (130 mg) at room temperature, and the mixture was stirred for 1.5 hr. The mixture was poured into water, and extracted with ethyl acetate. The extract was washed with saturated brine, dried over anhydrous sodium sulfate, and concentrated under reduced pressure. The residue was purified by silica gel column chromatography (ethyl acetate/hexane) to give the title compound (280 mg).

$^1$H NMR (300 MHz, DMSO-$d_6$) δ1.90-2.00 (2H, m), 2.02-2.46 (5H, m), 4.36 (1H, br s), 4.42-4.57 (1H, m), 4.71 (2H, s), 4.84-5.07 (2H, m), 7.14-7.35 (5H, m), 7.39-7.77 (1H, m), 7.84 (1H, d, J=8.1 Hz), 8.23 (1H, s), 8.29 (1H, dd, J=7.9, 1.5 Hz).

Example 527

6-(5-(difluoromethyl)-1,3,4-oxadiazol-2-yl)-2-((1SR,2RS)-2-(1H-pyrazol-1-yl)cyclohexyl)isoindolin-1-one A) (1SR,2RS)-2-(1H-pyrazol-1-yl)cyclohexanamine To a mixture of (1RS,2RS)-2-(1H-pyrazol-1-yl)cyclohexanol (1.50 g), triphenylphosphine (8.28 g) and THF (60 mL) was added bis(2-methoxyethyl) azodicarboxylate (7.40 g) at 0° C. The mixture was stirred under nitrogen atmosphere at 0° C. for 10 min. To the mixture was added DPPA (7.40 g) at 0° C. The mixture was stirred under nitrogen atmosphere overnight at 0° C. to room temperature. The mixture was poured into water at room temperature, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give 1-((1RS,2SR)-2-azidocyclohexyl)-1H-pyrazole. 1-((1RS,2SR)-2-azidocyclohexyl)-1H-pyrazole was dissolved in methanol (80 mL), to the solution was added 10% palladium on carbon (about 50% hydrous product, 960 mg) at room temperature. The mixture was hydrogenated under balloon pressure at room temperature for 6 hr. The catalyst was removed by filtration, the filtrate was concentrated under reduced pressure, and the residue was purified by silica gel column chromatography (ethyl acetate/methanol) to give the title compound (730 mg).

MS: [M+H]$^+$ 166.3

B) methyl 3-oxo-2-((1SR,2RS)-2-(1H-pyrazol-1-yl)cyclohexyl)isoindoline-5-carboxylate To a mixture of (1SR,2RS)-2-(1H-pyrazol-1-yl)cyclohexanamine (190 mg), DIPEA (0.834 mL) and DMF (10 mL) was added dimethyl 4-(bromomethyl)isophthalate (275 mg) at 0° C. The mixture was stirred at 0° C. for 1.5 hr, and then overnight at room temperature. The mixture was diluted with ethyl acetate, washed with water and saturated brine, dried over anhydrous sodium sulfate, and concentrated under reduced pressure. The residue was dissolved in acetic acid (10 mL), and the solution was stirred at 65° C. for 2 hr. The mixture was concentrated, and the residue was diluted with ethyl acetate, and the mixture was basified with aqueous sodium hydrogencarbonate solution at room temperature. The organic layer was separated, washed with saturated brine, dried over anhydrous sodium sulfate, and concentrated under reduced pressure. The same procedure was performed using (1SR,2RS)-2-(1H-pyrazol-1-yl)cyclohexanamine (104 mg), and the two residues obtained in which the two reaction were carried out separately are combined, and recrystallized from ethyl acetate to give the title compound (297 mg).

MS: [M+H]$^+$ 340.0.

C) 3-oxo-2-((1SR,2RS)-2-(1H-pyrazol-1-yl)cyclohexyl)isoindoline-5-carbohydrazide To a mixture of methyl 3-oxo-2-((1SR,2RS)-2-(1H-pyrazol-1-yl)cyclohexyl)isoindoline-5-carboxylate (365 mg) and methanol (8 mL) was added hydrazine monohydrate (0.783 mL) at room temperature, and the mixture was stirred at 60° C. for 5 hr. The mixture was concentrated to give the title compound (365 mg).

MS: [M+H]$^+$ 340.1.

D) 6-(5-(difluoromethyl)-1,3,4-oxadiazol-2-yl)-2-((1SR,2RS)-2-(1H-pyrazol-1-yl)cyclohexyl) isoindolin-1-one To a mixture of 3-oxo-2-((1SR,2RS)-2-(1H-pyrazol-1-yl)cyclohexyl)isoindoline-5-carbohydrazide (365 mg), DIPEA (1.12 mL) and THF (10 mL) was added difluoroacetic anhydride (0.669 mL) at 0° C. The mixture was stirred at 0° C. for 1 hr. The mixture was poured into saturated brine at room temperature, and extracted with ethyl acetate. The organic layer was separated, washed with saturated brine, dried over anhydrous sodium sulfate, and concentrated under reduced pressure. The residue was dissolved in THF (10 mL), to the solution were added DIPEA (1.69 mL) and 4-methylbenzenesulfonyl chloride (1.64 g) at 0° C. The mixture was stirred at 0° C. to room temperature for 4 hr. The mixture was poured into saturated aqueous sodium hydrogencarbonate solution at room temperature, and extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) and preparative HPLC (column: C18, mobile phase: water (containing 0.1% (v/v) TFA)/acetonitrile (containing 0.1% (v/v) TFA)), and recrystallized from hexane/ethyl acetate to give the title compound (274 mg).

$^1$H NMR (300 MHz, CDCl$_3$) δ 1.59-1.82 (3H, m), 1.99-2.23 (3H, m), 2.29-2.64 (2H, m), 2.78 (1H, d, J=18.3 Hz), 4.13 (1H, d, J=18.5 Hz), 4.54-4.67 (1H, m), 4.80 (1H, brs), 6.08 (1H, s), 6.93 (1H, t, J=51.6 Hz), 7.14 (1H, s), 7.45 (1H, d, J=8.1 Hz), 7.53 (1H, s), 8.27 (1H, d, J=7.9 Hz), 8.54 (1H, s).

Example 535

3-(5-(difluoromethyl)-1,3,4-oxadiazol-2-yl)-6-((1RS,2RS)-2-(4-fluorophenoxy)cyclohexyl)-6,7-dihydro-5H-pyrrolo[3,4-b]pyridin-5-one A) tert-butyl 7-azabicyclo[4.1.0]heptane-7-carboxylate To a mixture of tert-butyl [(1RS,2RS)-2-hydroxycyclohexyl]carbamate (40.7 g), triphenylphosphine (64.5 g) and THF (900 mL) was added bis(2-methoxyethyl) azodicarboxylate (57.6 g) at 0° C., and the mixture was stirred under nitrogen atmosphere at room temperature for 3 hr. To the mixture was added water at room temperature, and the mixture was extracted with ethyl acetate. The organic layer was separated, washed with saturated brine, dried over anhydrous magnesium sulfate, and concentrated under reduced pressure. The residue was washed with diisopropyl ether, and the mother solution was concentrated under reduced pressure. The residue was purified by silica gel column chromatography (ethyl acetate/hexane) to give the title compound (28.1 g).

$^1$H NMR (300 MHz, DMSO-$d_6$) δ 1.11-1.32 (4H, m), 1.38 (9H, s), 1.69-1.80 (4H, m), 2.52-2.56 (2H, m).

B) tert-butyl [(1RS,2RS)-2-(4-fluorophenoxy)cyclohexyl]carbamate

A mixture of tert-butyl 7-azabicyclo[4.1.0]heptane-7-carboxylate (2.49 g), 4-fluorophenol (2.12 g), cesium carbonate (8.23 g) and DMSO (20 mL) was stirred at 100° C. for 1 hr. To the mixture was added water at room temperature, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane) to give the title compound (3.01 g).

$^1$H NMR (300 MHz, DMSO-$d_6$) δ 1.21-1.41 (13H, m), 1.65 (2H, brs), 1.77 (1H, brs), 1.99-2.09 (1H, m), 3.36-3.52 (1H, m), 3.92-4.01 (1H, m), 6.82 (1H, d, J=8.6 Hz), 6.90-6.97 (2H, m), 7.03-7.11 (2H, m).

C) (1RS,2RS)-2-(4-fluorophenoxy)cyclohexan-1-amine tert-Butyl [(1RS,2RS)-2-(4-fluorophenoxy)cyclohexyl]carbamate (2.70 g) was added to TFA (7 mL) at room temperature, and the mixture was stirred at room temperature for 20 min. The mixture was concentrated under reduced pressure, and the residue was neutralized with saturated aqueous sodium hydrogencarbonate solution at room temperature, and the mixture was extracted with ethyl acetate. The organic layer was separated, washed with saturated brine, dried over anhydrous magnesium sulfate, and concentrated under reduced pressure to give the title compound (1.29 g).

MS: [M+H]$^+$ 210.2.

D) ethyl 6-[(1RS,2RS)-2-(4-fluorophenoxy)cyclohexyl]-5-oxo-6,7-dihydro-5H-pyrrolo[3,4-b]pyridine-3-carboxylate To a mixture of (1RS,2RS)-2-(4-fluorophenoxy)cyclohexan-1-amine (1.19 g), diethyl 2-(chloromethyl)pyridine-3,5-dicarboxylate (1.54 g) and DMF (15 mL) was added DIPEA (2 mL) at room temperature, and the mixture was stirred at 60° C. for 2 hr. To the mixture was added water at room temperature, and the mixture was extracted with ethyl acetate. The organic layer was separated, washed with saturated brine, dried over anhydrous magnesium sulfate, and concentrated under reduced pressure. The residue was dissolved in acetic acid (15 mL), and the solution was stirred at 70° C. for 2 hr. The mixture was concentrated under reduced pressure, and the residue was neutralized with saturated aqueous sodium hydrogencarbonate solution at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (545 mg).

$^1$H NMR (300 MHz, DMSO-$d_6$) δ 1.29-1.45 (8H, m), 1.78-1.88 (2H, m), 2.14-2.23 (1H, m), 4.26-4.41 (4H, m), 4.55-4.72 (2H, m), 6.87-6.95 (4H, m), 8.36 (1H, d, J=1.9 Hz), 9.19 (1H, d, J=2.1 Hz).

E) 6-[(1RS,2RS)-2-(4-fluorophenoxy)cyclohexyl]-5-oxo-6,7-dihydro-5H-pyrrolo[3,4-b]pyridine-3-carbohydrazide To a mixture of ethyl 6-[(1RS,2RS)-2-(4-fluorophenoxy)cyclohexyl]-5-oxo-6,7-dihydro-5H-pyrrolo[3,4-b]pyridine-3-carboxylate (541 mg) and methanol (5 mL) was added hydrazine monohydrate (2 mL) at room temperature, and the mixture was stirred at 60° C. for 1 hr. The mixture was concentrated under reduced pressure to give the title compound (520 mg).

MS: [M+H]$^+$ 385.1.

F) 3-(5-(difluoromethyl)-1,3,4-oxadiazol-2-yl)-6-((1RS,2RS)-2-(4-fluorophenoxy)cyclohexyl)-6,7-dihydro-5H-pyrrolo[3,4-b]pyridin-5-one To a mixture of 6-[(1RS,2RS)-2-(4-fluorophenoxy)cyclohexyl]-5-oxo-6,7-dihydro-5H-pyrrolo[3,4-b]pyridine-3-carbohydrazide (520 mg), TEA (436 mg) and THF (5 mL) was added difluoroacetic anhydride (0.35 mL) at room temperature. The mixture was stirred at room temperature for 20 min, and the mixture was concentrated under reduced pressure. To the residue was added acetonitrile (5 mL), DIPEA (518 mg) and 4-methylbenzenesulfonyl chloride (774 mg) were added thereto at room temperature, and the mixture was stirred at room temperature for 1 hr. The mixture was neutralized with saturated aqueous sodium hydrogencarbonate solution at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and the obtained solid was washed with diisopropyl ether to give the title compound (71.2 mg).

$^1$H NMR (300 MHz, DMSO-$d_6$) δ 1.36-1.52 (3H, m), 1.70-1.93 (4H, m), 2.18 (1H, brs), 4.20-4.33 (1H, m), 4.39 (1H, d, J=19.0 Hz), 4.55-4.78 (2H, m), 6.85-7.01 (4H, m), 7.38-7.83 (1H, m), 8.48 (1H, d, J=2.1 Hz), 9.33 (1H, d, J=2.0 Hz).

Example 536

2-((1R,2R)-2-(1H-benzotriazol-1-yl)cyclohexyl)-6-(5-(difluoromethyl)-1,3,4-oxadiazol-2-yl)isoindolin-1-one A) benzyl tert-butyl (1R,2R)-cyclohexane-1,2-diylbiscarbamate To a mixture of sodium carbonate (3.96 g), tert-butyl ((1R,2R)-2-aminocyclohexyl)carbamate (4 g), water (10.00 mL) and THF (30 mL) was added benzyl chloroformate (3.20 mL) at 0° C. The mixture was stirred overnight at room temperature. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (6.07 g).
MS, found: 249.2.

B) benzyl ((1R,2R)-2-aminocyclohexyl)carbamate hydrochloride

To a mixture of benzyl tert-butyl (1R,2R)-cyclohexane-1,2-diylbiscarbamate (6.07 g) and ethyl acetate (30 mL) was added 4M hydrogen chloride ethyl acetate solution (30.0 mL) at room temperature. The mixture was stirred at room temperature for 3 hr. The reaction solution was concentrated under reduced pressure to give the title compound (4.67 g).
MS: [M+H]$^+$ 249.2.

C) benzyl ((1R,2R)-2-((2-nitrophenyl)amino)cyclohexyl)carbamate

A mixture of benzyl ((1R,2R)-2-aminocyclohexyl)carbamate hydrochloride (2.5 g), 1-fluoro-2-nitrobenzene (0.926 mL), potassium carbonate (2.427 g) and DMF (40 mL) was stirred overnight at 80° C. To the reaction solution was added water, and the precipitated solid was collected by filtration, and washed with water to give the title compound (2.92 g).
MS: [M+H]$^+$ 370.1.

D) benzyl ((1R,2R)-2-((2-aminophenyl)amino)cyclohexyl)carbamate

To a mixture of benzyl ((1R,2R)-2-((2-nitrophenyl)amino)cyclohexyl)carbamate (2.92 g) and acetic acid (79 mL) was slowly added zinc powder (5.17 g) at room temperature. The mixture was stirred overnight at room temperature. The mixture was filtered through Celite, and the filtrate was concentrated under reduced pressure. The residue was purified by silica gel column chromatography (NH, ethyl acetate/hexane) to give the title compound (2.55 g).
MS: [M+H]$^+$ 340.1.

E) benzyl ((1R,2R)-2-(1H-benzotriazol-1-yl)cyclohexyl)carbamate

To a mixture of benzyl ((1R,2R)-2-((2-aminophenyl)amino)cyclohexyl)carbamate (1 g) and 6 M hydrochloric acid (15 mL) was added a solution of sodium nitrite (0.407 g) in water (5 mL) at 0° C. The mixture was stirred overnight at room temperature. The reaction solution was diluted with ethyl acetate, and 8M aqueous sodium hydroxide solution (15.00 mL) was added thereto. The organic layer was separated, washed with water and saturated brine, dried over anhydrous sodium sulfate, and concentrated under reduced pressure. The residue was purified by silica gel column chromatography (ethyl acetate/hexane) to give the title compound (0.61 g).
MS: [M+H]$^+$ 351.2.

F) (1R,2R)-2-(1H-benzotriazol-1-yl)cyclohexanamine

A mixture of benzyl ((1R,2R)-2-(1H-benzotriazol-1-yl)cyclohexyl)carbamate (0.61 g), 10% palladium on carbon (0.185 g) and THF (15 mL) was stirred under hydrogen atmosphere at room temperature for 4 hr. The catalyst was removed by filtration, and the filtrate was concentrated under reduced pressure to give the title compound (360.9 mg).
MS: [M+H]$^+$ 217.1.

G) methyl 2-((1R,2R)-2-(1H-benzotriazol-1-yl)cyclohexyl)-3-oxoisoindoline-5-carboxylate A mixture of DIPEA (0.435 mL), dimethyl 4-(bromomethyl)isophthalate (239 mg), (1R,2R)-2-(1H-benzotriazol-1-yl)cyclohexanamine (180 mg) and DMF (2 mL) was stirred overnight at room temperature. To the mixture was added water at room temperature, and the mixture was extracted with ethyl acetate. The organic layer was separated, washed with water and saturated brine, dried over anhydrous sodium sulfate, and concentrated under reduced pressure. The residue was dissolved in acetic acid (2.00 mL), and the solution was stirred at 100° C. for 2 hr. The reaction mixture was concentrated under reduced pressure, and the residue was purified by silica gel column chromatography (ethyl acetate/hexane) to give the title compound (229 mg).
MS: [M+H]$^+$ 391.1.

H) 2-((1R,2R)-2-(1H-benzotriazol-1-yl)cyclohexyl)-3-oxoisoindoline-5-carbohydrazide A mixture of methyl 2-((1R,2R)-2-(1H-benzotriazol-1-yl)cyclohexyl)-3-oxoisoindoline-5-carboxylate (229 mg), hydrazine monohydrate (0.569 mL) and methanol (6 mL) was stirred at 60° C. for 1 day. The reaction mixture was concentrated under reduced pressure to give the title compound (229 mg). The obtained objective product was used in the next reaction without further purification.
MS: [M+H]$^+$ 391.2.

I) 2-((1R,2R)-2-(1H-benzotriazol-1-yl)cyclohexyl)-6-(5-(difluoromethyl)-1,3,4-oxadiazol-2-yl)isoindolin-1-one A mixture of 2-((1R,2R)-2-(1H-benzotriazol-1-yl)cyclohexyl)-3-oxoisoindoline-5-carbohydrazide (229 mg), difluoroacetic anhydride (0.109 mL), DIPEA (0.154 mL) and THF (5 mL) was stirred at room temperature for 2 hr, and 4-methylbenzenesulfonyl chloride (1118 mg) and DIPEA (1.024 mL) were added thereto. The reaction mixture was stirred overnight at room temperature. The reaction mixture was concentrated under reduced pressure, and the residue was purified by silica gel column chromatography (ethyl acetate/hexane) to give the title compound (210 mg).
$^1$H NMR (300 MHz, DMSO-d$_6$) δ 1.52-1.80 (2H, m), 1.84-2.26 (5H, m), 2.31-2.46 (1H, m), 4.33-4.50 (1H, m), 4.57-4.69 (1H, m), 4.75 (1H, td, J=10.9, 4.7 Hz), 5.42 (1H, td, J=11.3, 4.0 Hz), 7.24 (1H, td, J=7.6, 0.8 Hz), 7.32-7.71 (2H, m), 7.73-8.00 (4H, m), 8.16 (1H, dd, J=8.0, 1.7 Hz).

Example 547

6-(5-(difluoromethyl)-1,3,4-oxadiazol-2-yl)-2-((1R,2R)-2-([1,2,4]triazolo[4,3-a]pyridin-3-yl)cyclohexyl)isoindolin-1-one A) tert-butyl ((1R,2R)-2-((2-(pyridin-2-yl)hydrazino) carbonyl)cyclohexyl) carbamate A mixture of (1R,2R)-2-((tert-butoxycarbonyl)amino)cyclohexanecarboxylic acid (1.216 g), HATU (2.85 g), TEA (2.091 mL), 2-hydrazinopyridine (0.818 g) and DMF (12 mL) was stirred overnight at room temperature. Water was added thereto, and the resulting solid was collected by filtration to give the title compound (1.57 g).
MS: [M+H]$^+$ 335.2.

B) tert-butyl ((1R,2R)-2-([1,2,4]triazolo[4,3-a]pyridin-3-yl)cyclohexyl) carbamate A mixture of tert-butyl ((1R,2R)-2-((2-(pyridin-2-yl)hydrazino)carbonyl)cyclohexyl)carbamate (334 mg), Burgess reagent (methyl N-(triethylammonium-sulfonyl) carbamate) (715 mg) and THF (10 mL) was stirred at 60° C. for 2 hr. To the mixture was added water at room temperature, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (104.7 mg).
MS: [M+H]$^+$ 317.1.

C) (1R,2R)-2-([1,2,4]triazolo[4,3-a]pyridin-3-yl)cyclohexanamine hydrochloride

To a mixture of tert-butyl ((1R,2R)-2-([1,2,4]triazolo[4,3-a]pyridin-3-yl)cyclohexyl)carbamate (104 mg) and ethyl acetate (3 mL) was added 4M hydrogen chloride ethyl acetate (3.00 mL), and the mixture was stirred overnight at room temperature. The reaction mixture was concentrated under reduced pressure to give the title compound (94 mg).
MS: [M+H]$^+$ 217.2.

D) methyl 3-oxo-2-((1R,2R)-2-([1,2,4]triazolo[4,3-a]pyridin-3-yl)cyclohexyl) isoindoline-5-carboxylate A mixture of DIPEA (0.194 mL), dimethyl 4-(bromomethyl)isophthalate (107 mg), (1R,2R)-2-([1,2,4]triazolo[4,3-a]pyridin-3-yl)cyclohexanamine hydrochloride (94 mg) and DMF (2 mL) was stirred overnight at room temperature. To the mixture was added water at room temperature, and the mixture was extracted with ethyl acetate. The organic layer was separated, washed with water and saturated brine, dried over anhydrous sodium sulfate, and concentrated under reduced pressure. The residue was dissolved in acetic acid (2.000 mL), and the solution was stirred at 100° C. for 2 hr. The reaction mixture was concentrated under reduced pressure, and the residue was purified by silica gel column chromatography (ethyl acetate/hexane) to give the title compound (95.4 mg).
MS: [M+H]$^+$ 391.1.

E) 3-oxo-2-((1R,2R)-2-([1,2,4]triazolo[4,3-a]pyridin-3-yl)cyclohexyl)isoindoline-5-carbohydrazide A mixture of methyl 3-oxo-2-((1R,2R)-2-([1,2,4]triazolo[4,3-a]pyridin-3-yl)cyclohexyl)isoindoline-5-carboxylate (95 mg), hydrazine monohydrate (0.236 mL) and methanol (3 mL) was stirred at 60° C. for 1 day. The reaction mixture was concentrated under reduced pressure to give the title compound (95 mg). The obtained objective product was used in the next reaction without further purification.
MS: [M+H]$^+$ 391.2.

F) 6-(5-(difluoromethyl)-1,3,4-oxadiazol-2-yl)-2-((1R,2R)-2-([1,2,4]triazolo[4,3-a]pyridin-3-yl)cyclohexyl)isoindolin-1-one A mixture of difluoroacetic anhydride (0.045 mL), DIPEA (0.064 mL), 3-oxo-2-((1R,2R)-2-([1,2,4]triazolo[4,3-a]pyridin-3-yl)cyclohexyl)isoindoline-5-carbohydrazide (95 mg) and THF (3 mL) was stirred at room temperature for 2 hr. The reaction mixture was concentrated under reduced pressure. The residue was dissolved in acetonitrile (3 mL), 4-methylbenzenesulfonyl chloride (232 mg) and DIPEA (0.212 mL) were added thereto, and the mixture was stirred overnight at room temperature. The reaction mixture was concentrated under reduced pressure, and the residue was purified by silica gel column chromatography (ethyl acetate/hexane) to give the title compound (25 mg).
$^1$H NMR (300 MHz, DMSO-d$_6$) δ 1.41-1.74 (2H, m), 1.77-2.12 (6H, m), 3.92-4.09 (1H, m), 4.48-4.63 (3H, m), 6.78-6.88 (1H, m), 7.17-7.28 (1H, m), 7.32-7.72 (2H, m), 7.72-7.81 (1H, m), 7.97 (1H, d, J=0.9 Hz), 8.18 (1H, dd, J=7.9, 1.6 Hz), 8.61 (1H, d, J=7.1 Hz).

Example 549

6-(5-(difluoromethyl)-1,3,4-oxadiazol-2-yl)-2-((1RS,2RS)-2-(1,3-oxazol-2-yl)cyclohexyl)isoindolin-1-one A) tert-butyl {(1RS,2RS)-2-[(2,2-dimethoxyethyl)carbamoyl]cyclohexyl}carbamate To a mixture of (1RS,2RS)-2-[(tert-butoxycarbonyl)amino]cyclohexane-1-carboxylic acid (500 mg), 2,2-dimethoxyethanamine (0.267 mL) and DMF (10 mL) was added HATU (1.17 g) at 0° C. The mixture was stirred overnight at room temperature. To the mixture was added water at 0° C., and the precipitate was collected by filtration, and washed with diisopropyl ether to give the title compound (471 mg).
$^1$H NMR (300 MHz, DMSO-d$_6$) δ 0.94-1.27 (4H, m), 1.34 (9H, s), 1.52-1.70 (3H, m), 1.81 (1H, d, J=10.0 Hz), 2.04-2.21 (1H, m), 3.12 (2H, t, J=5.4 Hz), 3.26 (6H, d, J=4.9 Hz), 3.35-3.46 (1H, m), 4.28 (1H, t, J=5.5 Hz), 6.41 (1H, d, J=8.3 Hz), 7.48 (1H, brs).

B) tert-butyl [(1RS,2RS)-2-(1,3-oxazol-2-yl)cyclohexyl]carbamate

A mixture of tert-butyl {(1RS,2RS)-2-[(2,2-dimethoxyethyl)carbamoyl]cyclohexyl}carbamate (144 mg), 4-methylbenzenesulfonic acid monohydrate (8.29 mg) and acetone (4 mL) was refluxed for 2 hr. To the mixture was added saturated aqueous sodium hydrogencarbonate solution at room temperature, and the mixture was extracted with ethyl acetate. The organic layer was separated, washed with water and saturated brine, dried over anhydrous magnesium sulfate, and concentrated under reduced pressure. A mixture of the crude product, Burgess reagent (methyl N-(triethylammonium-sulfonyl) carbamate) (208 mg) and THF (4 mL) was refluxed for 30 min. The mixture was concentrated, and the residue was purified by silica gel column chromatography (NH, ethyl acetate/hexane) to give the title compound (36.5 mg).
MS, found: 167.1.

C) (1RS,2RS)-2-(1,3-oxazol-2-yl)cyclohexan-1-amine hydrochloride

To tert-butyl [(1RS,2RS)-2-(1,3-oxazol-2-yl)cyclohexyl]carbamate (36.5 mg) was added 4M hydrogen chloride ethyl acetate solution (1.0 mL) at room temperature. The mixture was stirred at room temperature for 30 min. The mixture was concentrated to give the title compound (27.0 mg).
MS: [M+H]$^+$ 167.2.

D) methyl 2-[(1RS,2RS)-2-(1,3-oxazol-2-yl)cyclohexyl]-3-oxo-2,3-dihydro-1H-isoindole-5-carboxylate To a mixture of (1RS,2RS)-2-(1,3-oxazol-2-yl)cyclohexan-1-amine hydrochloride (27.0 mg) and DMF (2 mL) was added DIPEA (0.116 mL) at room temperature. Then, to the reaction mixture was added dimethyl 4-(bromomethyl)isophthalate (42.1 mg) at room temperature. The mixture was stirred at 70° C. for 3 hr. The reaction solution was concentrated, and the obtained residue was partitioned between ethyl acetate-water. The organic layer was washed with water and saturated brine, dried over anhydrous magnesium sulfate, and concentrated under reduced pressure. The residue was purified by silica gel column chromatography (NH, ethyl acetate/hexane) to give the title compound (22.3 mg).

MS: [M+H]$^+$ 341.1.

E) 2-[(1RS,2RS)-2-(1,3-oxazol-2-yl)cyclohexyl]-3-oxo-2,3-dihydro-1H-isoindole-5-carbohydrazide To a mixture of methyl 2-[(1RS,2RS)-2-(1,3-oxazol-2-yl)cyclohexyl]-3-oxo-2,3-dihydro-1H-isoindole-5-carboxylate (22.3 mg) and THF (1 mL)/methanol (1 mL) was added hydrazine monohydrate (0.064 mL) at room temperature. The mixture was stirred at 80° C. for 3 hr. The reaction mixture was concentrated under reduced pressure to give the title compound (20.1 mg).

MS: [M+H]$^+$ 341.1.

F) 6-(5-(difluoromethyl)-1,3,4-oxadiazol-2-yl)-2-((1RS,2RS)-2-(1,3-oxazol-2-yl)cyclohexyl)isoindolin-1-one To a mixture of 2-[(1RS,2RS)-2-(1,3-oxazol-2-yl)cyclohexyl]-3-oxo-2,3-dihydro-1H-isoindole-5-carbohydrazide (20.1 mg), DIPEA (0.031 mL) and THF (1 mL) was added difluoroacetic anhydride (0.011 mL) at 0° C. The mixture was stirred at room temperature for 1 hr. Then, to the reaction mixture was added 4-methylbenzenesulfonyl chloride (16.9 mg) at 0° C. The mixture was stirred at 70° C. for 3 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (4.2 mg).

$^1$H NMR (300 MHz, DMSO-d$_6$) δ 1.05-1.60 (3H, m), 1.69-1.95 (5H, m), 1.99-2.18 (1H, m), 4.10-4.34 (1H, m), 4.49-4.70 (2H, m), 6.92 (1H, s), 7.32-7.76 (1H, m), 7.82-7.95 (2H, m), 8.10 (1H, s), 8.25 (1H, dd, J=7.9, 1.1 Hz).

Example 552

3-(5-(difluoromethyl)-1,3,4-oxadiazol-2-yl)-6-((1R*,2R*)-2-(4-fluorophenoxy)cyclohexyl)-6,7-dihydro-5H-pyrrolo[3,4-b]pyridin-5-one (optical isomer)

3-(5-(Difluoromethyl)-1,3,4-oxadiazol-2-yl)-6-(((1RS,2RS)-2-(4-fluorophenoxy)cyclohexyl)-6,7-dihydro-5H-pyrrolo[3,4-b]pyridin-5-one (racemate, 210 mg) was subjected to optical resolution using preparative SFC (column: CHIRALPAK IA (DAICEL), 50 mmID×250 mmL, mobile phase: carbon dioxide/methanol=700/300), and the obtained solid was washed with diisopropyl ether to give the title compound of Example 552 (46 mg, >99.9% ee, analysis SFC (column: CHIRALPAK IA (DAICEL), 4.6 mmID×150 mmL, mobile phase: carbon dioxide/methanol=700/300), retention time: 4.288 min) and the compound of Example 551 (49.7 mg, >99.9% ee, analysis SFC (column: CHIRALPAK IA (DAICEL), 4.6 mmID×150 mmL, mobile phase: carbon dioxide/methanol=700/300), retention time: 3.080 min).

$^1$H NMR (300 MHz, DMSO-d$_6$) δ 1.35-1.52 (3H, m), 1.72-1.93 (4H, m), 2.13-2.27 (1H, m), 4.21-4.32 (1H, m), 4.38 (1H, d, J=18.8 Hz), 4.57-4.66 (1H, m), 4.71 (1H, d, J=18.8 Hz), 6.89-6.99 (4H, m), 7.40-7.79 (1H, m), 8.48 (1H, d, J=1.9 Hz), 9.33 (1H, d, J=2.3 Hz).

Example 553

6-(5-(difluoromethyl)-1,3,4-oxadiazol-2-yl)-2-(2-(3-fluorophenyl)pyrrolidin-1-yl)isoindolin-1-one

A) 2-(3-fluorophenyl)-1-nitrosopyrrolidine

To a mixture of 2-(3-fluorophenyl)pyrrolidine (0.6 g), sodium nitrite (0.75 g) and water (20 mL) was added acetic acid (0.624 mL) at 0° C. The mixture was stirred overnight at room temperature. The reaction solution was partitioned between ethyl acetate and water. The organic layer was washed with saturated brine and water, dried over anhydrous magnesium sulfate, and concentrated under reduced pressure. The residue was purified by silica gel column chromatography (ethyl acetate/hexane) to give the title compound (459 mg).

MS: [M+H]$^+$ 195.2.

B) 2-(3-fluorophenyl)pyrrolidin-1-amine

A mixture of 2-(3-fluorophenyl)-1-nitrosopyrrolidine (0.459 g), zinc (0.773 g) and acetic acid (9.45 mL) was stirred at room temperature for 5 hr. The insoluble material was removed by filtration, and the filtrate was concentrated under reduced pressure. 2M ammonia 2-propanol solution was added thereto, and the mixture was concentrated under reduced pressure. The residue was purified by silica gel column chromatography (NH, ethyl acetate/hexane) to give the title compound (300 mg).

MS: [M+H]$^+$ 181.2.

C) methyl 2-(2-(3-fluorophenyl)pyrrolidin-1-yl)-3-oxoisoindoline-5-carboxylate To a mixture of dimethyl 4-(bromomethyl)isophthalate (580 mg), 2-(3-fluorophenyl)pyrrolidin-1-amine (300 mg) and DMF (10 mL) was added DIPEA (0.727 mL) at room temperature. The mixture was stirred overnight at room temperature. To the mixture was added saturated brine at room temperature, and the mixture was extracted with ethyl acetate. The organic layer was separated, washed with saturated brine, dried over anhydrous magnesium sulfate, and concentrated under reduced pressure. A mixture of the residue and acetic acid (10 mL) was stirred at 50° C. for 3 hr. To the mixture was added saturated aqueous sodium hydrogencarbonate solution at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (391 mg).

MS: [M+H]$^+$ 355.2.

D) 2-(2-(3-fluorophenyl)pyrrolidin-1-yl)-3-oxoisoindoline-5-carboxylic acid

A mixture of methyl 2-(2-(3-fluorophenyl)pyrrolidin-1-yl)-3-oxoisoindoline-5-carboxylate (391 mg), 4N aqueous lithium hydroxide solution (828 µL), THF (2.2 mL) and methanol (2.2 mL) was stirred at 50° C. for 1 hr. To the mixture was added 1N hydrochloric acid at room temperature, and the mixture was extracted with ethyl acetate. The organic layer was separated, washed with saturated brine, dried over anhydrous magnesium sulfate, and concentrated under reduced pressure to give the title compound (243 mg).
MS: [M+H]$^+$ 341.2.

E) N'-(difluoroacetyl)-2-(2-(3-fluorophenyl)pyrrolidin-1-yl)-3-oxoisoindoline-5-carbohydrazide A mixture of 2-(2-(3-fluorophenyl)pyrrolidin-1-yl)-3-oxoisoindoline-5-carboxylic acid (243 mg), 2,2-difluoroacetohydrazide (118 mg), HATU (326 mg), TEA (0.199 mL) and DMF (2.9 mL) was stirred at room temperature for 1 hr. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (290 mg).
MS: [M+H]$^+$ 433.2.

F) 6-(5-(difluoromethyl)-1,3,4-oxadiazol-2-yl)-2-(2-(3-fluorophenyl)pyrrolidin-1-yl)isoindolin-1-one A mixture of N'-(difluoroacetyl)-2-(2-(3-fluorophenyl)pyrrolidin-1-yl)-3-oxoisoindoline-5-carbohydrazide (280 mg), 4-methylbenzenesulfonyl chloride (370 mg), DIPEA (0.339 mL) and acetonitrile (5 mL) was stirred at 50° C. for 2 hr. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (141 mg).
$^1$H NMR (400 MHz, DMSO-d$_6$) δ 1.23-1.25 (1H, m), 1.61-1.76 (1H, m), 1.92-1.98 (1H, m), 2.23-2.39 (1H, m), 3.32-3.46 (2H, m), 4.37-4.70 (3H, m), 6.93-7.05 (1H, m), 7.22-7.37 (3H, m), 7.55 (1H, s), 7.71-7.80 (1H, m), 8.16 (1H, d, J=1.0 Hz), 8.24 (1H, dd, J=8.1, 1.7 Hz).

Example 558

2-((1RS,2RS)-2-(5-cyclopropyl-1,2,4-oxadiazol-3-yl)cyclohexyl)-6-(5-(difluoromethyl)-1,3,4-oxadiazol-2-yl)isoindolin-1-one

A) tert-butyl ((1RS,2RS)-2-(N'-hydroxycarbamimidoyl)cyclohexyl)carbamate

A mixture of tert-butyl ((1RS,2RS)-2-cyanocyclohexyl)carbamate (1.121 g), hydroxylamine (0.613 mL) and ethanol (10 mL) was stirred at 80° C. overnight. The reaction mixture was concentrated under reduced pressure to give the title compound (1.287 g). The obtained objective product was used in the next reaction without further purification.
$^1$H NMR (300 MHz, DMSO-d$_6$) δ 0.96-1.27 (3H, m), 1.35 (9H, s), 1.48-1.71 (4H, m), 1.82-1.97 (2H, m), 3.35-3.50 (1H, m), 5.17 (2H, s), 6.25 (1H, d, J=8.3 Hz), 8.71 (1H, s).

B) tert-butyl ((1RS,2RS)-2-(5-cyclopropyl-1,2,4-oxadiazol-3-yl)cyclohexyl)carbamate A mixture of cyclopropanecarbonitrile (0.736 mL), 1M zinc chloride diethyl ether solution (1.5 mL), 4-methylbenzenesulfonic acid monohydrate (190 mg), tert-butyl ((1RS,2RS)-2-(N'-hydroxycarbamimidoyl)cyclohexyl)carbamate (257 mg) and DMF (3 mL) was stirred overnight at 80° C. To the mixture was added water at room temperature, and the mixture was extracted with ethyl acetate. The organic layer was separated, washed with saturated aqueous sodium hydrogencarbonate solution and saturated brine, dried over anhydrous sodium sulfate, and concentrated under reduced pressure. The residue was purified by silica gel column chromatography (ethyl acetate/hexane) to give the title compound (90.3 mg).
MS, found: 208.1.

C) (1RS,2RS)-2-(5-cyclopropyl-1,2,4-oxadiazol-3-yl)cyclohexanamine hydrochloride To a mixture of tert-butyl ((1RS,2RS)-2-(5-cyclopropyl-1,2,4-oxadiazol-3-yl)cyclohexyl)carbamate (90 mg) and ethyl acetate (1 mL) was added 4M hydrogen chloride ethyl acetate solution (1.00 mL) at room temperature. The mixture was stirred overnight at room temperature. The mixture was concentrated under reduced pressure to give the title compound (71.4 mg).
MS: [M+H]$^+$ 208.1.

D) methyl 2-((1RS,2RS)-2-(5-cyclopropyl-1,2,4-oxadiazol-3-yl)cyclohexyl)-3-oxoisoindoline-5-carboxylate A mixture of DIPEA (0.150 mL), dimethyl 4-(bromomethyl)isophthalate (82 mg), (1RS,2RS)-2-(5-cyclopropyl-1,2,4-oxadiazol-3-yl)cyclohexanamine hydrochloride (70 mg) and DMF (2 mL) was stirred overnight at room temperature. To the mixture was added water at room temperature, and the mixture was extracted with ethyl acetate. The organic layer was separated, washed with water and saturated brine, dried over anhydrous sodium sulfate, and concentrated under reduced pressure. The residue was dissolved in acetic acid (2.000 mL), the solution was stirred at 100° C. for 2 hr, and the reaction solution was concentrated. The residue was purified by silica gel column chromatography (ethyl acetate/hexane) to give the title compound (76 mg).
MS: [M+H]$^+$ 382.1.

E) 2-((1RS,2RS)-2-(5-cyclopropyl-1,2,4-oxadiazol-3-yl)cyclohexyl)-3-oxoisoindoline-5-carbohydrazide A mixture of methyl 2-((1RS,2RS)-2-(5-cyclopropyl-1,2,4-oxadiazol-3-yl)cyclohexyl)-3-oxoisoindoline-5-carboxylate (76 mg), hydrazine monohydrate (0.193 mL) and methanol (2 mL) was stirred at 60° C. for 1 hr. The reaction mixture was concentrated to give the title compound (76 mg). The obtained objective product was used in the next reaction without further purification.
MS: [M+H]$^+$ 382.1.

F) 2-((1RS,2RS)-2-(5-cyclopropyl-1,2,4-oxadiazol-3-yl)cyclohexyl)-6-(5-(difluoromethyl)-1,3,4-oxadiazol-2-yl)isoindolin-1-one A mixture of 2-((1RS,2RS)-2-(5-cyclopropyl-1,2,4-oxadiazol-3-yl)cyclohexyl)-3-oxoisoindoline-5-carbohydrazide (76 mg), difluoroacetic anhydride (0.037 mL), DIPEA (0.052 mL), and THF (5 mL) was stirred at room temperature for 2 hr. To the reaction mixture were added 4-methylbenzenesulfonyl chloride (380 mg) and DIPEA (0.348 mL), and the mixture was stirred overnight. The mixture was concentrated, and the residue was purified by silica gel column chromatography (ethyl acetate/hexane) to give the title compound (75 mg).

$^1$H NMR (300 MHz, DMSO-d$_6$) δ 0.60-0.90 (2H, m), 1.02-1.11 (2H, m), 1.29-1.62 (2H, m), 1.67-1.89 (5H, m), 1.99 (1H, t, J=5.1 Hz), 2.08-2.19 (1H, m), 3.15-3.29 (1H, m), 4.10-4.30 (1H, m), 4.58 (2H, s), 7.35-7.75 (1H, m), 7.88 (1H, d, J=7.9 Hz), 8.12 (1H, d, J=1.0 Hz), 8.27 (1H, dd, J=8.0, 1.7 Hz).

Example 560

2-(4,4-difluoro-2-(3-fluorophenyl)piperidin-1-yl)-6-(5-(difluoromethyl)-1,3,4-oxadiazol-2-yl)isoindolin-1-one A) benzyl 2-(3-fluorophenyl)-4-oxo-3,4-dihydropyridine-1(2H)-carboxylate To 1M THF solution (33 mL) of (3-fluorophenyl)magnesium bromide was added dropwise a mixture of 4-methoxypyridine (3.02 g) and THF (10 mL) under nitrogen atmosphere at −65° C. Then, a mixture of benzyl chloroformate (4.8 mL) and THF (25 mL) was added thereto at −40° C. The mixture was stirred under nitrogen atmosphere at −40° C. for 3 hr. To the mixture was added 5% citric acid aqueous solution at the same temperature, and the mixture was warmed to room temperature, and extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (8.12 g).

MS: [M+H]$^+$ 326.2.

B) benzyl 2-(3-fluorophenyl)-4-oxopiperidine-1-carboxylate

To a mixture of benzyl 2-(3-fluorophenyl)-4-oxo-3,4-dihydropyridine-1(2H)-carboxylate (8.11 g) and acetic acid (210 mL) was added zinc (powder, 4.90 g) by a small amount at room temperature. The mixture was stirred at 90° C. for 1 hr, the reaction solution was filtered through Celite, and the filtrate was concentrated. The residue was purified by silica gel column chromatography (ethyl acetate/hexane) to give the title compound (5.62 g).

MS: [M+H]+ 328.2.

C) benzyl 4,4-difluoro-2-(3-fluorophenyl)piperidine-1-carboxylate

To a mixture of benzyl 2-(3-fluorophenyl)-4-oxopiperidine-1-carboxylate (2.79 g) and toluene (80 mL) was added bis(2-methoxyethyl)aminosulfur trifluoride (14 mL) at 0° C. The mixture was stirred under nitrogen atmosphere at room temperature for 17 hr, poured into aqueous sodium hydrogencarbonate solution at 0° C., and extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (2.03 g).

MS: [M+H]$^+$ 350.2.

D) 4,4-difluoro-2-(3-fluorophenyl)piperidine

A mixture of benzyl 4,4-difluoro-2-(3-fluorophenyl)piperidine-1-carboxylate (1.573 g), 10% palladium on carbon (55% hydrous product, 0.436 g) and ethanol (30 mL) was hydrogenated under balloon pressure at room temperature for hr. The catalyst was removed by filtration, and the filtrate was concentrated under reduced pressure to give the title compound (0.945 g).

MS: [M+H]$^+$ 216.1.

E) 4,4-difluoro-2-(3-fluorophenyl)-1-nitrosopiperidine

To a mixture of 4,4-difluoro-2-(3-fluorophenyl)piperidine (1.13 g), acetic acid (1.2 mL) and water (1.8 mL) was added dropwise a mixture of sodium nitrite (0.543 g) and water (0.6 mL) at 0° C. The mixture was stirred at room temperature for 1 hr. The mixture was partitioned between ethyl acetate and saturated aqueous sodium hydrogencarbonate solution. The organic layer was separated, washed with saturated aqueous sodium hydrogencarbonate solution and saturated brine, dried over anhydrous magnesium sulfate, and concentrated under reduced pressure to give the title compound (1.26 g).

MS: [M+H]$^+$ 245.2.

F) 4,4-difluoro-2-(3-fluorophenyl)piperidin-1-amine

To a mixture of 4,4-difluoro-2-(3-fluorophenyl)-1-nitrosopiperidine (0.630 g), zinc (powder, 0.854 g) and ethanol (16 mL) was added dropwise conc. hydrochloric acid (1.1 mL) at −20° C. The mixture was stirred at room temperature for 40 hr. The mixture was filtered through Celite, to the filtrate was added TEA (0.72 mL), and the mixture was concentrated. The obtained residue was supported on silica gel (NH), and purified by silica gel column chromatography (NH, ethyl acetate/hexane) to give the title compound (0.39 g).

MS: [M+H]$^+$ 231.1.

G) methyl 2-(4,4-difluoro-2-(3-fluorophenyl)piperidin-1-yl)-3-oxoisoindoline-5-carboxylate To a mixture of 4,4-difluoro-2-(3-fluorophenyl)piperidin-1-amine (0.186 g), DIPEA (0.30 mL) and DMF (5 mL) was added a mixture of dimethyl 4-(bromomethyl)isophthalate (0.164 g) and DMF (2 mL) at 0° C. The mixture was stirred at room temperature for 40 hr. The mixture was partitioned between water and ethyl acetate. The organic layer was separated, washed with water and saturated brine, dried over anhydrous magnesium sulfate, and concentrated under reduced pressure. To the residue was added acetic acid (5 mL), the mixture was stirred at 80° C. for 2 hr, and the reaction solution was concentrated. The obtained residue was partitioned between ethyl acetate and saturated aqueous sodium hydrogencarbonate solution. The organic layer was washed with saturated brine, dried over anhydrous magnesium sulfate, and concentrated under reduced pressure. The residue was purified by silica gel column chromatography (ethyl acetate/hexane) to give the title compound (0.153 g).
MS: [M+H]$^+$ 405.2.

H) 2-(4,4-difluoro-2-(3-fluorophenyl)piperidin-1-yl)-3-oxoisoindoline-5-carboxylic acid To a mixture of methyl 2-(4,4-difluoro-2-(3-fluorophenyl)piperidin-1-yl)-3-oxoisoindoline-5-carboxylate (0.296 g), THF (2 mL), methanol (2 mL) and water (1 mL) was added 4N aqueous lithium hydroxide solution (1 mL) at room temperature. The mixture was stirred at 50° C. for 1 hr. The mixture was neutralized with 1N hydrochloric acid, and extracted with ethyl acetate. The organic layer was separated, washed with water and saturated brine, dried over anhydrous magnesium sulfate, and concentrated under reduced pressure to give the title compound (0.286 g).
MS: [M–H]$^-$ 388.9.

I) N'-(difluoroacetyl)-2-(4,4-difluoro-2-(3-fluorophenyl)piperidin-1-yl)-3-oxoisoindoline-5-carbohydrazide To a mixture of 2-(4,4-difluoro-2-(3-fluorophenyl)piperidin-1-yl)-3-oxoisoindoline-5-carboxylic acid (0.235 g), 2,2-difluoroacetohydrazide (0.104 g), O-(7-azabenzotriazol-1-yl)-N,N,N',N'-tetramethyluronium hexafluorophosphate (0.275 g) and DMF (5 mL) was added TEA (0.101 mL) at room temperature. The mixture was stirred at room temperature for 1 hr. The mixture was partitioned between ethyl acetate and water. The organic layer was separated, washed with water, dried over anhydrous sodium sulfate, and concentrated under reduced pressure. The residue was purified by silica gel column chromatography (ethyl acetate/hexane) to give the title compound (0.279 g).
MS: [M–H]$^-$ 481.0.

J) 2-(4,4-difluoro-2-(3-fluorophenyl)piperidin-1-yl)-6-(5-(difluoromethyl)-1,3,4-oxadiazol-2-yl)isoindolin-1-one To a mixture of N'-(difluoroacetyl)-2-(4,4-difluoro-2-(3-fluorophenyl)piperidin-1-yl)-3-oxoisoindoline-5-carbohydrazide (0.278 g), 4-methylbenzenesulfonyl chloride (0.336 g) and acetonitrile (5 mL) was added DIPEA (305 μL) at 0° C. The mixture was stirred at room temperature 2.5 hr. To the mixture was added ethyl acetate, and the mixture was washed with water and saturated brine, dried over anhydrous magnesium sulfate, and concentrated under reduced pressure. The residue was purified by silica gel column chromatography (ethyl acetate/hexane) to give the title compound (0.084 g).
$^1$H NMR (400 MHz, CDCl$_3$) δ 2.11-2.39 (4H, m), 3.24 (1H, d, J=9.0 Hz), 3.74-4.52 (3H, m), 5.24 (1H, brs), 6.90 (1H, t, J=51.8 Hz), 6.85-6.90 (1H, m), 7.15-7.25 (3H, m), 7.37-7.50 (1H, m), 8.25 (1H, dd, J=7.3, 0.7 Hz), 8.41 (1H, s).

Example 561

2-((1RS,2RS)-2-(3-cyclopropyl-1,2,4-oxadiazol-5-yl)cyclohexyl)-6-(5-(difluoromethyl)-1,3,4-oxadiazol-2-yl)isoindolin-1-one

A) tert-butyl ((1RS,2RS)-2-(3-cyclopropyl-1,2,4-oxadiazol-5-yl)cyclohexyl)carbamate A mixture of N'-hydroxycyclopropanecarboximidamide (0.400 g), tert-butyl ((1RS,2RS)-2-cyanocyclohexyl)carbamate (0.449 g), 1M zinc chloride diethyl ether solution (3 mL), 4-methylbenzenesulfonic acid monohydrate (0.380 g) and DMF (5 mL) was stirred overnight at 80° C. To the mixture was added saturated aqueous sodium hydrogencarbonate solution at room temperature, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (0.41 g).
MS, found: 208.2.

B) (1RS,2RS)-2-(3-cyclopropyl-1,2,4-oxadiazol-5-yl)cyclohexanamine hydrochloride To a mixture of tert-butyl ((1RS,2RS)-2-(3-cyclopropyl-1,2,4-oxadiazol-5-yl)cyclohexyl)carbamate (206 mg) and ethyl acetate (5 mL) was added 4M hydrogen chloride ethyl acetate (5 mL). The mixture was stirred overnight at room temperature. The reaction mixture was concentrated under reduced pressure to give the title compound (163 mg). The obtained objective product was used in the next reaction without further purification.
MS: [M+H]$^+$ 208.2.

C) methyl 2-((1RS,2RS)-2-(3-cyclopropyl-1,2,4-oxadiazol-5-yl)cyclohexyl)-3-oxoisoindoline-5-carboxylate A mixture of DIPEA (0.349 mL), dimethyl 4-(bromomethyl)isophthalate (192 mg), (1RS,2RS)-2-(3-cyclopropyl-1,2,4-oxadiazol-5-yl)cyclohexanamine hydrochloride (163 mg) and DMF (2 mL) was stirred overnight at room temperature. To the mixture was added water at room temperature, and the mixture was extracted with ethyl acetate. The organic layer was separated, washed with water and saturated brine, dried over anhydrous sodium sulfate, and concentrated under reduced pressure. The residue was dissolved in acetic acid (2 mL), and the solution was stirred at 100° C. for 2 hr. The reaction mixture was concentrated under reduced pressure, and the residue was purified by silica gel column chromatography (ethyl acetate/hexane) to give the title compound (40.3 mg).
MS: [M+H]$^+$ 382.1.

D) 2-((1RS,2RS)-2-(3-cyclopropyl-1,2,4-oxadiazol-5-yl)cyclohexyl)-3-oxoisoindoline-5-carbohydrazide A mixture of hydrazine monohydrate (0.102 mL), methyl 2-((1RS,2RS)-2-(3-cyclopropyl-1,2,4-oxadiazol-5-yl)cyclohexyl)-3-oxoisoindoline-5-carboxylate (40 mg) and methanol (3 mL) was stirred at 60° C. for 1 day. The reaction mixture was concentrated under reduced pressure to give the title compound (40.0 mg). The obtained objective product was used in the next reaction without further purification.
MS: [M+H]$^+$ 382.1.

E) 2-((1RS,2RS)-2-(3-cyclopropyl-1,2,4-oxadiazol-5-yl)cyclohexyl)-6-(5-(difluoromethyl)-1,3,4-oxadiazol-2-yl)isoindolin-1-one A mixture of difluoroacetic anhydride (0.020 mL), DIPEA (0.027 mL), 2-((1RS,2RS)-2-(3-cyclopropyl-1,2,4-oxadiazol-5-yl)cyclohexyl)-3-oxoisoindoline-5-carbohydrazide (40 mg) and THF (2 mL) was stirred at room temperature for 2 hr. 4-Methylbenzenesulfonyl chloride (200 mg) and DIPEA (0.183 mL) were added thereto, and the mixture was stirred overnight at room temperature. The reaction mixture was concentrated under reduced pressure, and the residue was purified by silica gel column chromatography (ethyl acetate/hexane) to give the title compound (20 mg).

$^1$H NMR (300 MHz, DMSO-d$_6$) δ 0.23-0.39 (1H, m), 0.52-0.68 (1H, m), 0.72-0.92 (2H, m), 1.20-1.69 (2H, m), 1.72-1.97 (6H, m), 2.10 (1H, d, J=14.1 Hz), 3.39-3.53 (1H, m), 4.12-4.30 (1H, m), 4.48-4.73 (2H, m), 7.30-7.76 (1H, m), 7.90 (1H, d, J=8.0 Hz), 8.13 (1H, d, J=1.0 Hz), 8.29 (1H, dd, J=8.0, 1.7 Hz).

Example 563

2-((3S,4R)-3-(5-chloro-1H-benzotriazol-1-yl)tetrahydro-2H-pyran-4-yl)-6-(5-(difluoromethyl)-1,3,4-oxadiazol-2-yl)isoindolin-1-one A) tert-butyl ((3S,4R)-3-((4-chloro-2-nitrophenyl)amino)tetrahydro-2H-pyran-4-yl)carbamate A mixture of 4-chloro-1-fluoro-2-nitrobenzene (1.843 g), potassium carbonate (2.76 g), tert-butyl ((3S,4R)-3-aminotetrahydro-2H-pyran-4-yl)carbamate tetrahydrofuran-2-carboxylate (3.32 g) and DMF (35 mL) was stirred overnight at 80° C. To the reaction mixture was added water, and the resulting solid was collected by filtration to give the title compound (2.99 g).

$^1$H NMR (300 MHz, DMSO-d$_6$) δ 1.27 (9H, s), 1.52-1.69 (1H, m), 1.81 (1H, dd, J=13.5, 3.0 Hz), 3.24-3.31 (1H, m), 3.39-3.52 (1H, m), 3.52-3.79 (2H, m), 3.85 (1H, dt, J=11.5, 3.8 Hz), 3.93 (1H, dd, J=11.2, 3.9 Hz), 7.07 (1H, d, J=8.2 Hz), 7.30 (1H, d, J=9.4 Hz), 7.58 (1H, dd, J=9.3, 2.5 Hz), 7.97-8.07 (2H, m).

B) tert-butyl ((3S,4R)-3-((2-amino-4-chlorophenyl)amino)tetrahydro-2H-pyran-4-yl) carbamate A mixture of tert-butyl ((3S,4R)-3-((4-chloro-2-nitrophenyl)amino)tetrahydro-2H-pyran-4-yl)carbamate (2.99 g), zinc powder (5.26 g) and acetic acid (80 mL) was stirred at room temperature for 1 hr. The mixture was filtered through Celite, and the filtrate was concentrated. The residue was purified by silica gel column chromatography (ethyl acetate/hexane) to give the title compound (2.36 g). The obtained objective product was used in the next reaction without further purification.

MS: [M+H]$^+$ 342.0.

C) tert-butyl ((3S,4R)-3-(5-chloro-1H-benzotriazol-1-yl)tetrahydro-2H-pyran-4-yl)carbamate To a mixture of tert-butyl ((3S,4R)-3-((2-amino-4-chlorophenyl)amino)tetrahydro-2H-pyran-4-yl)carbamate (2.36 g), acetic acid (5 mL) and water (25 mL) was added a solution of sodium nitrite (0.524 g) in water (5 mL) at 0° C. The mixture was stirred at the same temperature for 1 hr, acetic acid (20 mL) was added thereto, and the mixture was stirred at 80° C. for 1 hr. The reaction mixture was concentrated under reduced pressure, and the residue was dissolved in ethyl acetate. The solution was added to 8M aqueous sodium hydroxide solution. The organic layer was separated, washed with water and saturated brine, dried over anhydrous sodium sulfate, and concentrated under reduced pressure. The residue was purified by silica gel column chromatography (ethyl acetate/hexane) to give the title compound (1.77 g).

MS: [M+H]$^+$ 353.1.

D) (3S,4R)-3-(5-chloro-1H-benzotriazol-1-yl)tetrahydro-2H-pyran-4-amine hydrochloride To a mixture of tert-butyl ((3S,4R)-3-(5-chloro-1H-benzotriazol-1-yl)tetrahydro-2H-pyran-4-yl)carbamate (1.77 g) and ethyl acetate (10 mL) was added 4M hydrogen chloride ethyl acetate (10 mL). The mixture was stirred at room temperature for 1 day. The mixture was concentrated under reduced pressure to give the title compound (1.451 g). The obtained objective product was used in the next reaction without further purification.

MS: [M+H]$^+$ 253.1.

E) methyl 2-((3S,4R)-3-(5-chloro-1H-benzotriazol-1-yl)tetrahydro-2H-pyran-4-yl)-3-oxoisoindoline-5-carboxylate A mixture of DIPEA (0.523 mL), dimethyl 4-(bromomethyl)isophthalate (0.287 g), (3S,4R)-3-(5-chloro-1H-benzotriazol-1-yl)tetrahydro-2H-pyran-4-amine hydrochloride (0.289 g) and DMF (2 mL) was stirred overnight at room temperature. The mixture was poured into water at room temperature, and extracted with ethyl acetate. The organic layer was separated, washed with water and saturated brine, dried over anhydrous sodium sulfate, and concentrated under reduced pressure. The residue was dissolved in acetic acid (2 mL), and the solution was stirred at 100° C. for 2 hr. The reaction mixture was concentrated under reduced pressure. The residue was purified by silica gel column chromatography (ethyl acetate/hexane) to give the title compound (0.25 g).

MS: [M+H]$^+$ 427.1.

F) 2-((3S,4R)-3-(5-chloro-1H-benzotriazol-1-yl)tetrahydro-2H-pyran-4-yl)-3-oxoisoindoline-5-carbohydrazide A mixture of methyl 2-((3S,4R)-3-(5-chloro-1H-benzotriazol-1-yl)tetrahydro-2H-pyran-4-yl)-3-oxoisoindoline-5-carboxylate (0.25 g), hydrazine monohydrate (0.568 mL) and methanol (6 mL) was stirred at 60° C. for 1 day. The reaction mixture was concentrated under reduced pressure to give the title compound (0.250 g). The obtained objective product was used in the next reaction without further purification.

MS: [M+H]$^+$ 427.1.

G) 2-((3S,4R)-3-(5-chloro-1H-benzotriazol-1-yl)tetrahydro-2H-pyran-4-yl)-6-(5-(difluoromethyl)-1,3,4-oxadiazol-2-yl)isoindolin-1-one A mixture of 2-((3S,4R)-3-(5-chloro-1H-benzotriazol-1-yl)tetrahydro-2H-pyran-4-yl)-3-oxoisoindoline-5-carbohydrazide (250 mg), difluoroacetic anhydride (0.109 mL), DIPEA (0.153 mL) and THF (5 mL) was stirred at room temperature for 2 hr. 4-Methylbenzenesulfonyl chloride (558 mg) and DIPEA (0.511 mL) were added thereto, and the mixture was stirred overnight at room temperature. The reaction mixture was concentrated under reduced pressure, and the residue was purified by silica gel column chromatography (ethyl acetate/hexane) to give the title compound (149 mg).

$^1$H NMR (300 MHz, DMSO-d$_6$) δ 2.06 (1H, d, J=8.9 Hz), 2.23-2.39 (1H, m), 3.84 (1H, t, J=11.4 Hz), 4.09-4.34 (3H, m), 4.48-4.79 (2H, m), 4.98 (1H, td, J=11.4, 4.3 Hz), 5.55

(1H, td, J=10.7, 4.8 Hz), 7.32-7.71 (2H, m), 7.76-7.82 (1H, m), 7.90 (1H, d, J=0.9 Hz), 8.00 (1H, d, J=8.9 Hz), 8.09 (1H, d, J=1.4 Hz), 8.20 (1H, dd, J=8.0, 1.7 Hz).

Example 564

1-(6-(5-(difluoromethyl)-1,3,4-oxadiazol-2-yl)-1-oxo-1,3-dihydro-2H-isoindol-2-yl)-4,4-difluoro-N-(2,2,2-trifluoroethyl)piperidine-2-carboxamide A) tert-butyl 2-(3-(methoxycarbonyl)-4-methylbenzoyl)hydrazinecarboxylate A mixture of methyl 5-bromo-2-methylbenzoate (12.11 g), tert-butyl hydrazinecarboxylate (8.29 g), bis(dibenzylideneacetone) palladium (0) (1.51 g), 4,5-bis(diphenylphosphino)-9,9-dimethylxanthene (alias: Xantophos) (1.51 g), N,N-dicyclohexylmethylamine (17.8 mL) and cyclopentyl methyl ether (300 mL) was stirred under carbon monoxide atmosphere (0.5 MPa) at 95° C. for 5 hr. The catalyst was removed by filtration, and the filtrate was concentrated under reduced pressure. The obtained residue was washed with diisopropyl ether, and the obtained residue was purified by silica gel column chromatography (NH, ethyl acetate), and washed with a mixed solvent of diisopropyl ether and hexane to give the title compound (13.4 g).
MS: [M−H]⁻ 306.9.

B) methyl 5-(hydrazinocarbonyl)-2-methylbenzoate hydrochloride

To tert-butyl 2-(3-(methoxycarbonyl)-4-methylbenzoyl)hydrazinecarboxylate (13.4 g) was added 4M hydrogen chloride cyclopentyl methyl ether (200 mL) at room temperature. The mixture was stirred at room temperature for 3 days. The obtained solid was collected by filtration, and dried to give the title compound (10.79 g).
MS: [M+H]⁺ 209.2.

C) methyl 5-(5-(difluoromethyl)-1,3,4-oxadiazol-2-yl)-2-methylbenzoate

To a mixture of methyl 5-(hydrazinocarbonyl)-2-methylbenzoate hydrochloride (1 g) and THF (40 mL) was added DIPEA (3.57 mL) at room temperature. To the reaction mixture was added dropwise difluoroacetic anhydride (0.762 mL) at 0° C. The mixture was stirred at room temperature for 1 hr. To the reaction solution was added 4-methylbenzenesulfonyl chloride (1.558 g) at room temperature, and the mixture was stirred overnight. To the mixture was added water at room temperature, and the mixture was extracted with ethyl acetate. The organic layer was separated, saturated aqueous sodium hydrogencarbonate solution washed with, dried over anhydrous magnesium sulfate, and concentrated under reduced pressure. The residue was purified by silica gel column chromatography (ethyl acetate/hexane) to give the title compound (1.02 g).
MS: [M+H]⁺ 269.1.

D) methyl 2-(bromomethyl)-5-(5-(difluoromethyl)-1,3,4-oxadiazol-2-yl)benzoate

To a mixture of methyl 5-(5-(difluoromethyl)-1,3,4-oxadiazol-2-yl)-2-methylbenzoate (2.8 g) and benzotrifluoride (100 mL) were added NBS (2.79 g) and AIBN (0.171 g) at room temperature. The mixture was stirred under argon atmosphere at 90° C. for 1 hr. To the mixture was added water at room temperature, and the mixture was extracted with ethyl acetate. The organic layer was separated, washed with saturated brine, dried over anhydrous sodium sulfate, and concentrated under reduced pressure. To a mixture of the obtained residue and THF (100 mL) was added DIPEA (2.0 mL). To the mixture was added dropwise diethyl phosphonate (1.48 mL) at 0° C., and the mixture was stirred overnight at room temperature. To the mixture was added water at room temperature, and the mixture was extracted with ethyl acetate. The organic layer was separated, washed with saturated aqueous ammonium chloride solution and saturated brine, dried over anhydrous magnesium sulfate, and concentrated under reduced pressure. The residue was purified by silica gel column chromatography (ethyl acetate/hexane) to give the title compound (3.19 g).
MS: [M+H]⁺ 347.1.

E) tert-butyl 4,4-difluoro-2-((2,2,2-trifluoroethyl)carbamoyl)piperidine-1-carboxylate A mixture of 1-(tert-butoxycarbonyl)-4,4-difluoropiperidine-2-carboxylic acid (400 mg), 2,2,2-trifluoroethanamine (299 mg), HATU (1147 mg), TEA (0.21 mL) and DMF (6.0 mL) was stirred at room temperature for 3 days. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (425 mg).
MS, found: 247.2.

F) 4,4-difluoro-N-(2,2,2-trifluoroethyl)piperidine-2-carboxamide hydrochloride

A mixture of tert-butyl 4,4-difluoro-2-((2,2,2-trifluoroethyl)carbamoyl)piperidine-1-carboxylate (453 mg), 4 N hydrogen chloride methanol solution (2 mL) and ethyl acetate (5.23 mL) was stirred at room temperature for 1 hr. The reaction solution was concentrated under reduced pressure to give the title compound (320 mg).
MS: [M+H]⁺ 247.1.

G) 4,4-difluoro-1-nitroso-N-(2,2,2-trifluoroethyl)piperidine-2-carboxamide

A mixture of 4,4-difluoro-N-(2,2,2-trifluoroethyl)piperidine-2-carboxamide hydrochloride (220 mg), sodium nitrite (161 mg), acetic acid (0.134 mL) and water (3.1 mL) was stirred overnight at room temperature. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (198 mg).
MS: [M+H]⁺ 276.0.

H) 1-amino-4,4-difluoro-N-(2,2,2-trifluoroethyl)piperidine-2-carboxamide

A mixture of 4,4-difluoro-1-nitroso-N-(2,2,2-trifluoroethyl)piperidine-2-carboxamide (198 mg), zinc (470 mg), 12N hydrochloric acid (60 μL) and ethanol (2.8 mL) was stirred at 0° C. for 10 hr, and the reaction solution was concentrated. The obtained residue was purified by silica gel column chromatography (NH, ethyl acetate/hexane) to give the title compound (168 mg).
MS: [M+H]$^+$ 262.2.

I) 1-(6-(5-(difluoromethyl)-1,3,4-oxadiazol-2-yl)-1-oxo-1,3-dihydro-2H-isoindol-2-yl)-4,4-difluoro-N-(2,2,2-trifluoroethyl)piperidine-2-carboxamide A mixture of methyl 2-(bromomethyl)-5-(5-(difluoromethyl)-1,3,4-oxadiazol-2-yl)benzoate (115 mg), 1-amino-4,4-difluoro-N-(2,2,2-trifluoroethyl)piperidine-2-carboxamide (100 mg), DIPEA (0.145 mL) and DMF (1.3 mL) was stirred overnight at room temperature. To the mixture was added saturated brine at room temperature, and the mixture was extracted with ethyl acetate. The organic layer was separated, washed with saturated brine, dried over anhydrous magnesium sulfate, and concentrated under reduced pressure. A mixture of the obtained residue and acetic acid (5 mL) was stirred at 80° C. for 3 hr. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (10 mg).
$^1$H NMR (400 MHz, DMSO-d$_6$) δ 2.08-2.25 (4H, m), 3.45-3.95 (4H, m), 4.40-4.79 (3H, m), 7.35-7.71 (1H, m), 7.81 (1H, d, J=8.1 Hz), 8.17 (1H, d, J=1.0 Hz), 8.28 (1H, dd, J=7.9, 1.6 Hz), 8.91 (1H, t, J=6.4 Hz).

Example 574 tert-butyl (2RS,3SR)-3-(6-(5-(difluoromethyl)-1,3,4-oxadiazol-2-yl)-1-oxo-1,3-dihydro-2H-isoindol-2-yl)-2-(4-fluorophenyl)piperidine-1-carboxylate A) methyl 2-(4-fluorophenyl)nicotinate To a mixture of methyl 2-chloronicotinate (13.20 g), DME (75 mL) and water (75 mL) were added (4-fluorophenyl)boronic acid (11.84 g) and potassium carbonate (21.26 g) at room temperature. To this mixture was added tetrakis(triphenylphosphine)palladium (0) (4.44 g), and the mixture was stirred at 85° C. for 3 hr. The mixture was cooled to room temperature, filtered through Celite, and washed with ethyl acetate, and the filtrate was partitioned. The aqueous layer was extracted three times with ethyl acetate, and the combined organic layers were washed with saturated brine, dried over anhydrous magnesium sulfate, and concentrated under reduced pressure. The residue was purified by silica gel column chromatography (ethyl acetate/hexane) to give the title compound (15.9 g).
MS: [M+H]$^+$ 231.9.

B) methyl (2SR,3RS)-2-(4-fluorophenyl)piperidine-3-carboxylate hydrochloride

To a mixture of methyl 2-(4-fluorophenyl)nicotinate (5.34 g), methanol (30 mL) and 6 N hydrochloric acid (8 mL) was added 5% platinum on carbon (1.24 g), and the mixture was subjected to hydrogenation at 50° C., 3 MPa for 3 hr, and filtered through Celite. The filtrate was concentrated under reduced pressure to give the title compound (6.57 g).
MS: [M+H]$^+$ 238.0.

C) 1-tert-butyl 3-methyl (2SR,3RS)-2-(4-fluorophenyl)piperidine-1,3-dicarboxylate To a mixture of methyl (2SR,3RS)-2-(4-fluorophenyl)piperidine-3-carboxylate hydrochloride (5.92 g), THF (20.0 mL) and water (20 mL) was added potassium carbonate (2.99 g) by a small amount at 0° C., and the mixture was stirred at the same temperature for 1 hr. To this mixture was added dropwise a solution of Boc$_2$O (5.66 g) in THF (5.0 mL) at 0° C., and the mixture was stirred at room temperature for 4 hr. The mixture was poured into water, and extracted with ethyl acetate. The extract was washed with water and saturated brine, dried over anhydrous sodium sulfate, and concentrated under reduced pressure. The residue was purified by silica gel column chromatography (ethyl acetate/hexane) to give the title compound (6.70 g).
MS, found: 238.1.

D) 1-tert-butyl 3-methyl (2SR,3SR)-2-(4-fluorophenyl)piperidine-1,3-dicarboxylate To a mixture of 1-tert-butyl 3-methyl (2SR,3RS)-2-(4-fluorophenyl)piperidine-1,3-dicarboxylate (6.15 g) and methanol (40.0 mL) was added sodium methoxide (28% methanol solution, 7.25 mL) at room temperature, and the mixture was stirred overnight at 60° C. The mixture was acidified with 1N hydrochloric acid (20 mL) at 0° C., and the methanol was evaporated under reduced pressure. The residue was partitioned between water and ethyl acetate. The separated organic layer was washed with saturated brine, dried over anhydrous sodium sulfate, and concentrated under reduced pressure to give the title compound (6.21 g). The obtained objective product was used in the next reaction without further purification.
MS, found: 238.1.

E) (2SR,3SR)-1-(tert-butoxycarbonyl)-2-(4-fluorophenyl)piperidine-3-carboxylic acid To a mixture of 1-tert-butyl 3-methyl (2SR,3SR)-2-(4-fluorophenyl)piperidine-1,3-dicarboxylate (6.20 g), THF (15 mL) and methanol (40 mL) was added dropwise 2N aqueous sodium hydroxide solution (18.4 mL) at room temperature, and the mixture was stirred overnight at 60° C. The mixture was acidified with 2N hydrochloric acid (20 mL) at 0° C., and the mixture was partitioned between water and ethyl acetate. The extract was washed with saturated brine, dried over anhydrous sodium sulfate, and concentrated under reduced pressure to give the title compound (5.90 g).
MS, found: 224.1.

F) tert-butyl (2RS,3SR)-3-(((benzyloxy)carbonyl)amino)-2-(4-fluorophenyl)piperidine-1-carboxylate To a mixture of (2SR,3SR)-1-(tert-butoxycarbonyl)-2-(4-fluorophenyl)piperidine-3-carboxylic acid (5.31 g), DPPA (4.24 mL) and toluene (50 mL) was added TEA (2.74 mL) at room temperature, and the mixture was stirred at 90° C. for 1.5 hr. To the mixture was added benzyl alcohol (3.40 mL), and the mixture was stirred overnight at 90° C. The mixture was poured into water, and extracted with ethyl acetate. The extract was washed with water and saturated brine, dried over anhydrous sodium sulfate, and concentrated under reduced pressure. The residue was purified by silica gel column chromatography (ethyl acetate/hexane) to give the title compound (4.558 g).

MS, found: 329.1.

G) tert-butyl (2RS,3SR)-3-amino-2-(4-fluorophenyl) piperidine-1-carboxylate

A mixture of tert-butyl (2RS,3SR)-3-(((benzyloxy)carbonyl)amino)-2-(4-fluorophenyl)piperidine-1-carboxylate (2.2 g), 20% palladium hydroxide on carbon (about 50% hydrous product, 0.200 g) and ethyl acetate (25 mL) was stirred under hydrogen atmosphere overnight at room temperature. The mixture was filtered through Celite, and the filtrate was concentrated under reduced pressure to give the title compound (1.51 g).

MS: [M+H]$^+$ 295.1.

H) methyl 2-((2RS,3SR)-1-(tert-butoxycarbonyl)-2-(4-fluorophenyl)piperidin-3-yl)-3-oxoisoindoline-5-carboxylate To a mixture of tert-butyl (2RS,3SR)-3-amino-2-(4-fluorophenyl)piperidine-1-carboxylate (1.51 g), dimethyl 4-(bromomethyl)isophthalate (1.52 g) and DMF (18 mL) was added TEA (1.43 mL) at room temperature, and the mixture was stirred overnight. The mixture was poured into water, and extracted with ethyl acetate. The extract was washed with water and saturated brine, dried over anhydrous sodium sulfate, and concentrated under reduced pressure. The residue was dissolved in acetic acid (18.0 mL), and the solution was stirred at 60° C. for 8 hr. The mixture was concentrated, and the residue was purified by silica gel column chromatography (ethyl acetate/hexane) to give the title compound (2.06 g).

MS, found: 413.1.

I) tert-butyl (2RS,3SR)-3-(6-(5-(difluoromethyl)-1,3,4-oxadiazol-2-yl)-1-oxo-1,3-dihydro-2H-isoindol-2-yl)-2-(4-fluorophenyl)piperidine-1-carboxylate A mixture of methyl 2-((2RS,3SR)-1-(tert-butoxycarbonyl)-2-(4-fluorophenyl)piperidin-3-yl)-3-oxoisoindoline-5-carboxylate (2.05 g), hydrazine monohydrate (2.12 mL), THF (2.0 mL) and methanol (18 mL) was stirred overnight at 60° C. The mixture was concentrated under reduced pressure. To a mixture of the obtained residue, TEA (1.22 mL) and THF (20 mL) was added dropwise difluoroacetic anhydride (0.817 mL) at room temperature, and the mixture was stirred for 1 hr. The mixture was concentrated under reduced pressure, and the residue was dissolved in THF (20 mL). To the solution were added TEA (4.87 mL) and 4-methylbenzenesulfonyl chloride (1.25 g) at room temperature, and the mixture was stirred for 3 hr. To this mixture was added 4-methylbenzenesulfonyl chloride (1.25 g) at room temperature, and the mixture was stirred overnight. The mixture was poured into water, and extracted twice with ethyl acetate. The extract was washed with water and saturated brine, dried over anhydrous sodium sulfate, and concentrated under reduced pressure. The residue was purified by silica gel column chromatography (NH, ethyl acetate/hexane) to give the title compound (1.59 g).

$^1$H NMR (300 MHz, DMSO-d$_6$) δ 1.26 (9H, s), 1.59-1.71 (1H, m), 1.81-2.06 (3H, m), 3.00-3.17 (1H, m), 3.94-4.10 (1H, m), 4.66-4.92 (3H, m), 5.20-5.38 (1H, m), 7.14-7.25 (2H, m), 7.35 (2H, dd, J=8.6, 5.4 Hz), 7.40-7.75 (1H, m), 7.90 (1H, d, J=8.3 Hz), 8.22 (1H, d, J=0.9 Hz), 8.31 (1H, dd, J=7.9, 1.7 Hz).

Example 575

6-(5-(difluoromethyl)-1,3,4-oxadiazol-2-yl)-2-((2RS,3SR)-2-(4-fluorophenyl)piperidin-3-yl)isoindolin-1-one A mixture of tert-butyl (2RS,3SR)-3-(6-(5-(difluoromethyl)-1,3,4-oxadiazol-2-yl)-1-oxo-1,3-dihydro-2H-isoindol-2-yl)-2-(4-fluorophenyl)piperidine-1-carboxylate (1.58 g) and TFA (8.0 mL) was stirred at room temperature for 3 hr. The mixture was concentrated under reduced pressure, and an excess amount of TFA was removed by azeotropic evaporation with ethyl acetate/toluene. The residue was solidified from ethyl acetate/diisopropyl ether to give the title compound (1.19 g).

$^1$H NMR (300 MHz, DMSO-d$_6$) δ 1.84-2.30 (4H, m), 3.13 (1H, d, J=10.7 Hz), 3.42 (1H, d, J=12.1 Hz), 4.40-4.61 (2H, m), 4.73 (2H, brs), 7.07-7.31 (2H, m), 7.35-7.74 (3H, m), 7.81 (1H, d, J=8.1 Hz), 8.06 (1H, d, J=0.9 Hz), 8.24 (1H, dd, J=8.0, 1.6 Hz), 9.11 (1H, d, J=9.0 Hz), 9.47 (1H, d, J=10.2 Hz).

Example 579

1-(6-(5-(difluoromethyl)-1,3,4-oxadiazol-2-yl)-1-oxo-1,3-dihydro-2H-isoindol-2-yl)-4,4-difluoro-N-(2,2,2-trifluoroethyl)piperidine-2-carboxamide (Optical Isomer)

1-(6-(5-(Difluoromethyl)-1,3,4-oxadiazol-2-yl)-1-oxo-1,3-dihydro-2H-isoindol-2-yl)-4,4-difluoro-N-(2,2,2-trifluoroethyl)piperidine-2-carboxamide (16.5 mg, racemate) was subjected to optical resolution using preparative HPLC (CHIRALCEL OJ-H (DAICEL), 20 mmID×250 mmL, mobile phase: hexane/ethanol=650/350) to give the title compound of Example 579 (7.8 mg, >99.9% ee, analytical column: CHIRALCEL OJ-H (DAICEL), 4.6 mmID×250 mmL, mobile phase: hexane/ethanol=650/350, retention time: 7.018 min) and the compound of Example 580 (8.8 mg, 99.7% ee, analytical column: CHIRALCEL OJ-H (DAICEL), 4.6 mmID×250 mmL, mobile phase: hexane/ethanol=650/350, retention time: 11.761 min).

$^1$H NMR (400 MHz, CDCl$_3$) δ2.08-2.60 (4H, m), 3.05-3.27 (1H, m), 3.34-4.31 (4H, m), 4.59 (2H, d, J=15.7 Hz), 6.70-7.14 (1H, m), 7.35-7.58 (1H, m), 7.65 (1H, d, J=8.1 Hz), 8.40 (1H, dd, J=8.1, 1.5 Hz), 8.52 (1H, s).

Example 581

N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2,3,3-tetrafluoropropanamide Oxalyl chloride (0.052 mL) and DMF (one drop) were added to a mixture of 2,2,3,3-tetrafluoropropanoic acid (87 mg) and THF (3 mL) at 0° C. The reaction mixture was stirred at room temperature for 30 min. A solution of 2-((1R,2S)-2-amino-3,3-difluorocyclohexyl)-6-(5-(difluoromethyl)-1,3,4-oxadiazol-2-yl)isoindolin-1-one (100 mg) and DIPEA (0.227 mL) in THF (1 mL) was added thereto at room temperature. The mixture was stirred overnight at room temperature. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (128 mg).

$^1$H NMR (300 MHz, DMSO-$d_6$) δ 1.42-1.65 (1H, m), 1.86 (2H, d, J=11.6 Hz), 1.95-2.26 (3H, m), 4.29-4.72 (3H, m), 4.75-4.97 (1H, m), 6.29-6.73 (1H, m), 7.34-7.77 (1H, m), 7.89 (1H, d, J=7.9 Hz), 8.20 (1H, d, J=0.9 Hz), 8.28 (1H, dd, J=8.0, 1.7 Hz), 9.67 (1H, d, J=8.9 Hz).

Example 584

2-((2RS,3SR)-1-(difluoroacetyl)-2-(4-fluorophenyl) piperidin-3-yl)-6-(5-(difluoromethyl)-1,3,4-oxadiazol-2-yl)isoindolin-1-one 6-(5-(Difluoromethyl)-1,3,4-oxadiazol-2-yl)-2-((2RS, 3SR)-2-(4-fluorophenyl)piperidin-3-yl)isoindolin-1-one trifluoroacetate (100 mg) was dissolved in methanol/ethyl acetate, and the solution was passed through NH silica gel short pad with methanol/ethyl acetate (1:4). The filtrate was concentrated under reduced pressure. To a mixture of the residue, TEA (0.077 mL) and THF (2.0 mL) was added dropwise difluoroacetic anhydride (0.034 mL) at 0° C., and the mixture was stirred overnight at room temperature. The mixture was filtered, and the filtrate was concentrated under reduced pressure. The residue was purified by silica gel column chromatography (ethyl acetate/hexane), and the crude product was solidified from ethyl acetate/hexane to give the title compound (70.9 mg).

$^1$H NMR (300 MHz, DMSO-$d_6$) δ 1.71-2.14 (4H, m), 3.35-3.56 (1H, m), 3.82-4.09 (1H, m), 4.76 (2H, s), 4.96 (1H, d, J=4.7 Hz), 5.57 (1H, brs), 6.65-7.09 (1H, m), 7.20 (2H, t, J=8.9 Hz), 7.37-7.78 (3H, m), 7.90 (1H, d, J=7.9 Hz), 8.21 (1H, s), 8.30 (1H, dd, J=8.0, 1.6 Hz)

Example 586

6-(5-(difluoromethyl)-1,3,4-oxadiazol-2-yl)-2-((1R*, 2R*)-4,4-difluoro-2-(pyridin-2-yl)cyclohexyl)isoindolin-1-one (Optical Isomer)

A) 4,4-difluoro-2-(pyridin-2-yl)cyclohexan-1-one

To a mixture of 4,4-difluorocyclohexan-1-one (5.00 g), 2-bromopyridine (5.90 g) and DMF (30 mL) was added sodium tert-butoxide (7.20 g) at room temperature. The mixture was stirred under nitrogen atmosphere at room temperature for 0.5 hr. Then, to the mixture were added palladium(II) acetate (1.30 g) and dicyclohexyl(2',6'-dimethoxy-2-biphenylyl)phosphine (4.60 g), and the mixture was stirred under nitrogen atmosphere at 80° C. for 19.5 hr. The mixture was diluted with water, and extracted with ethyl acetate. The organic layer was washed with saturated brine, dried over anhydrous sodium sulfate, and concentrated under reduced pressure. The residue was purified by silica gel column chromatography (ethyl acetate/petroleum ether) to give the title compound (2.00 g).

MS: [M+H]$^+$ 212.1.

B) N-[4,4-difluoro-2-(pyridin-2-yl)cyclohexylidene] hydroxylamine

To a mixture of 4,4-difluoro-2-(pyridin-2-yl)cyclohexan-1-one (2.00 g) and methanol (20 mL) were added hydroxylamine hydrochloride (724 mg) and sodium acetate (1.60 g), and the mixture was stirred at room temperature for 12 hr. The mixture was concentrated under reduced pressure, the residue was diluted with water, and the mixture was extracted with ethyl acetate. The organic layer was washed with saturated brine, dried over anhydrous sodium sulfate, and concentrated under reduced pressure to give the title compound (1.30 g).

MS: [M+H]$^+$ 227.1.

C) (1RS,2RS)-4,4-difluoro-2-(pyridin-2-yl)cyclohexan-1-amine

To a mixture of N-[4,4-difluoro-2-(pyridin-2-yl)cyclohexylidene]hydroxylamine (1.10 g) and methanol (20 mL) was added 10% palladium on carbon (50% hydrous product, 300 mg) under nitrogen atmosphere. The suspension was degassed under reduced pressure, and substituted several times with hydrogen. The mixture was stirred under hydrogen atmosphere (15 psi) at 50° C. for 20 hr. The mixture was filtered, and the filtrate was concentrated under reduced pressure. The residue was purified by preparative HPLC (column: C18, mobile phase: water (containing 0.05% (v/v) aqueous ammonia (25 w/w % aqueous solution))/acetonitrile) to give the title compound (150 mg) and (1RS,2SR)-4,4-difluoro-2-(pyridin-2-yl)cyclohexan-1-amine (160 mg).

$^1$H NMR (400 MHz, CD$_3$OD) δ1.55-1.72 (1H, m), 1.90-2.08 (2H, m), 2.10-2.29 (3H, m), 2.85 (1H, td, J=11.2, 4.8 Hz), 3.20 (1H, t, J=9.2 Hz), 7.27-7.41 (2H, m), 7.80 (1H, t, J=7.6 Hz), 8.55 (1H, d, J=4.4 Hz). (1RS,2SR)-4,4-difluoro-2-(pyridin-2-yl)cyclohexan-1-amine $^1$H NMR (400 MHz, CD$_3$OD) δ1.90-2.01 (2H, m), 2.03-2.32 (3H, m), 2.52-2.72 (1H, m), 3.27 (1H, d, J=15.2 Hz), 3.44 (1H, d, J=3.2 Hz), 7.24-7.39 (2H, m), 7.74-7.84 (1H, m), 8.47-8.56 (1H, m).

D) methyl 2-[(1RS,2RS)-4,4-difluoro-2-(pyridin-2-yl)cyclohexyl]-3-oxo-2,3-dihydro-1H-isoindole-5-carboxylate To a mixture of (1RS,2RS)-4,4-difluoro-2-(pyridin-2-yl)cyclohexan-1-amine (200 mg), DIPEA (582 μL) and DMF (6 mL) was added dimethyl 4-(bromomethyl)isophthalate (240 mg) at 0° C. The mixture was stirred at room temperature for 12 hr. The mixture was poured into water at room temperature, and extracted with ethyl acetate. The organic layer was separated, washed with water and saturated brine, dried over anhydrous sodium sulfate, and concentrated under reduced pressure. The residue was dissolved in acetic acid (5 mL), and the solution was stirred at 50° C. for 1 hr. The mixture was concentrated under reduced pressure, to the residue was added saturated aqueous sodium hydrogencarbonate solution, and the mixture was extracted with ethyl acetate. The organic layer was washed with saturated brine, dried over anhydrous sodium sulfate, and concentrated under reduced pressure to give the title compound (300 mg).

MS: [M+H]$^+$ 387.2.

E) 2-[(1RS,2RS)-4,4-difluoro-2-(pyridin-2-yl)cyclohexyl]-3-oxo-2,3-dihydro-1H-isoindole-5-carbohydrazide To a mixture of methyl 2-[(1RS,2RS)-4,4-difluoro-2-(pyridin-2-yl)cyclohexyl]-3-oxo-2,3-dihydro-1H-isoindole-5-carboxylate (300 mg) and ethanol (10 mL) was added hydrazine monohydrate (302 μL) at room temperature, and the mixture was stirred at 90° C. for 3 hr. The mixture was concentrated under reduced pressure to give the title compound (270 mg).

MS: [M+H]$^+$ 387.2.

F) 6-[5-(difluoromethyl)-1,3,4-oxadiazol-2-yl]-2-[(1RS,2RS)-4,4-difluoro-2-(pyridin-2-yl)cyclohexyl]-2,3-dihydro-1H-isoindol-1-one To a mixture of 2-[(1RS,2RS)-4,4-difluoro-2-(pyridin-2-yl)cyclohexyl]-3-oxo-2,3-dihydro-1H-isoindole-5-carbohydrazide (270 mg) and THF (10 mL) were added DIPEA (304 µL) and difluoroacetic anhydride (180 µL) at room temperature, and the mixture was stirred at room temperature for 12 hr. The mixture was diluted with water, and extracted with ethyl acetate. The organic layer was washed with saturated brine, dried over anhydrous sodium sulfate, and concentrated under reduced pressure. The residue was purified by silica gel column chromatography (ethyl acetate/petroleum ether) to give N'-(difluoroacetyl)-2-[(1RS,2RS)-4,4-difluoro-2-(pyridin-2-yl)cyclohexyl]-3-oxo-2,3-dihydro-1H-isoindole-5-carbohydrazide (300 mg). To a mixture of N'-(difluoroacetyl)-2-[(1RS,2RS)-4,4-difluoro-2-(pyridin-2-yl)cyclohexyl]-3-oxo-2,3-dihydro-1H-isoindole-5-carbohydrazide (300 mg) and THF (5 mL) were added DIPEA (225 µL) and 4-methylbenzenesulfonyl chloride (185 mg) at room temperature. The mixture was stirred at 50° C. for 12 hr. The mixture was concentrated under reduced pressure. The residue was diluted with water, and extracted with ethyl acetate. The organic layer was washed with saturated brine, dried over anhydrous sodium sulfate, and concentrated under reduced pressure. The residue was purified by preparative HPLC (column: C18, mobile phase: 10 mM aqueous ammonium hydrogencarbonate solution (containing 0.04% (v/v) aqueous ammonia (25 w/w % aqueous solution))/acetonitrile) to give the title compound (100 mg).

MS: [M+H]$^+$ 447.2.

G) 6-(5-(difluoromethyl)-1,3,4-oxadiazol-2-yl)-2-((1R*,2R*)-4,4-difluoro-2-(pyridin-2-yl)cyclohexyl)isoindolin-1-one (Optical Isomer)

6-[5-(Difluoromethyl)-1,3,4-oxadiazol-2-yl]-2-[(RS,2RS)-4,4-difluoro-2-(pyridin-2-yl)cyclohexyl]-2,3-dihydro-1H-isoindol-1-one (100 mg) was subjected to optical resolution using preparative SFC (column: CHIRALPAK AD (DAICEL), 50 mmID×250 mmL, mobile phase: 2-propanol (containing 0.1% (v/v) aqueous ammonia (25 w/w % aqueous solution))/CO$_2$) to give the title compound of Example 586 (21.4 mg, 99.9% ee, analysis SFC (column: Kromasil Amycoat (Eka Chemicals), 4.6 mmID×50 mmL, mobile phase: 2-propanol (containing 0.05% (v/v) diethylamine)/CO$_2$), retention time: 1.518 min) and the compound of Example 589 (16.7 mg, 99.9% ee, analysis SFC (column: Kromasil Amycoat (Eka Chemicals), 4.6 mmID×50 mmL, mobile phase: 2-propanol (containing 0.05% (v/v) diethylamine)/CO$_2$), retention time: 1.822 min).

$^1$H NMR (400 MHz, DMSO-d$_6$) δ1.90-1.93 (1H, m), 2.12-2.35 (4H, m), 2.52-2.64 (1H, m), 3.52 (1H, t, J=11.2 Hz), 4.44-4.66 (3H, m), 7.12 (1H, dd, J=6.8, 5.2 Hz), 7.34 (1H, d, J=7.6 Hz), 7.40-7.69 (2H, m), 7.78 (1H, d, J=8.0 Hz), 8.03 (1H, s), 8.20 (1H, dd, J=8.0, 1.6 Hz), 8.39 (1H, d, J=4.0 Hz).

Example 593

3-(5-(difluoromethyl)-1,3,4-oxadiazol-2-yl)-6-((1R,2R)-2-(pyridin-2-yloxy)cyclohexyl)-6,7-dihydro-5H-pyrrolo[3,4-b]pyridin-5-one

A) 2-((1R,2R)-2-((5-nitropyridin-2-yl)oxy)cyclohexyl)-1H-isoindole-1,3(2H)-dione To a mixture of 2-chloro-5-nitropyridine (1.189 g), 2-((1R,2R)-2-hydroxycyclohexyl)-1H-isoindole-1,3(2H)-dione (1.226 g) and THF (15 mL) was added 60% sodium hydride (0.21 g) at room temperature. The mixture was stirred at room temperature for 2 days. To the mixture was added water at room temperature, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (1.24 g).

MS: [M+H]$^+$ 368.1.

B) 2-((1R,2R)-2-((5-aminopyridin-2-yl)oxy)cyclohexyl)-1H-isoindole-1,3(2H)-dione A mixture of 2-((1R,2R)-2-((5-nitropyridin-2-yl)oxy)cyclohexyl)-1H-isoindole-1,3(2H)-dione (1.24 g), 10% palladium on carbon (0.180 g) and THF (35 mL) was hydrogenated under balloon pressure overnight at room temperature. The catalyst was removed by filtration, and the filtrate was concentrated under reduced pressure to give the title compound (1.05 g). The obtained objective product was used in the next reaction without further purification.

MS: [M+H]$^+$ 338.1.

C) 2-((1R,2R)-2-(pyridin-2-yloxy)cyclohexyl)-1H-isoindole-1,3(2H)-dione conc. Hydrochloric acid (0.209 mL) was added to a mixture of 2-((1R,2R)-2-((5-aminopyridin-2-yl)oxy)cyclohexyl)-1H-isoindole-1,3(2H)-dione (337 mg), acetic acid (4 mL) and water (1 mL) at 0° C. Sodium nitrite (103 mg) was added thereto at the same temperature, and then 50% aqueous hypophosphorous acid solution (2.072 mL) was added thereto. The mixture was stirred at room temperature for 3 days. To the mixture was added saturated aqueous sodium hydrogencarbonate solution at room temperature, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (296 mg).

MS: [M+H]$^+$ 323.1.

D) (1R,2R)-2-(pyridin-2-yloxy)cyclohexanamine

A mixture of 2-((1R,2R)-2-(pyridin-2-yloxy)cyclohexyl)-1H-isoindole-1,3(2H)-dione (296 mg), hydrazine monohydrate (0.445 mL) and ethanol (9 mL) was stirred at 70° C. for 2 hr. The reaction mixture was concentrated under reduced pressure. The residue was purified by silica gel column chromatography (NH, ethyl acetate/hexane) to give the title compound (153 mg).

MS: [M+H]$^+$ 193.2.

E) ethyl 5-oxo-6-((1R,2R)-2-(pyridin-2-yloxy)cyclohexyl)-6,7-dihydro-5H-pyrrolo[3,4-b]pyridine-3-carboxylate A mixture of diethyl 2-(bromomethyl)pyridine-3,5-dicarboxylate (302 mg), cesium carbonate (519 mg), (1R,2R)-2-(pyridin-2-yloxy)cyclohexanamine (153 mg) and DMF (8 mL) was stirred at room temperature for 3 hr. To the mixture was added water at room temperature, and the mixture was extracted with ethyl acetate. The organic layer was separated, washed with water and saturated brine, dried over anhydrous sodium sulfate, and concentrated under reduced pressure. The residue was dissolved in acetic acid (8.00 mL), and the solution was stirred at 100° C. for 2 hr. The reaction solution was concentrated under reduced pressure, and the residue was purified by silica gel column chromatography (ethyl acetate/hexane) to give the title compound (138 mg).
MS: [M+H]$^+$ 382.1.

F) 5-oxo-6-((1R,2R)-2-(pyridin-2-yloxy)cyclohexyl)-6,7-dihydro-5H-pyrrolo[3,4-b]pyridine-3-carbohydrazide A mixture of hydrazine monohydrate (0.351 mL), ethyl 5-oxo-6-((1R,2R)-2-(pyridin-2-yloxy)cyclohexyl)-6,7-dihydro-SH-pyrrolo[3,4-b]pyridine-3-carboxylate (138 mg) and methanol (4 mL) was stirred at 60° C. for 1 day. The reaction mixture was concentrated under reduced pressure to give the title compound (133 mg). The obtained objective product was used in the next reaction without further purification.
MS: [M+H]$^+$ 368.1.

G) 3-(5-(difluoromethyl)-1,3,4-oxadiazol-2-yl)-6-((1R,2R)-2-(pyridin-2-yloxy)cyclohexyl)-6,7-dihydro-5H-pyrrolo[3,4-b]pyridin-5-one Difluoroacetic anhydride (0.068 mL) was added to a mixture of DIPEA (0.190 mL), 5-oxo-6-((1R,2R)-2-(pyridin-2-yloxy)cyclohexyl)-6,7-dihydro-5H-pyrrolo[3,4-b]pyridine-3-carbohydrazide (133 mg) and THF (4 mL) at 0° C., and the mixture was stirred at room temperature for 1 hr. 4-Methylbenzenesulfonyl chloride (104 mg) and DIPEA (0.190 mL) were added thereto, and the mixture was stirred overnight at room temperature. The reaction mixture was concentrated under reduced pressure, and the residue was purified by silica gel column chromatography (ethyl acetate/hexane) to give the title compound (22 mg).
$^1$H NMR (300 MHz, DMSO-d$_6$) δ 1.38-1.61 (3H, m), 1.76-1.93 (4H, m), 2.18 (1H, d, J=10.9 Hz), 4.26-4.43 (1H, m), 4.47-4.77 (2H, m), 5.34-5.49 (1H, m), 6.58 (1H, dt, J=8.3, 0.8 Hz), 6.72 (1H, ddd, J=7.1, 5.1, 0.9 Hz), 7.37-7.77 (2H, m), 7.89-7.95 (1H, m), 8.38 (1H, d, J=2.1 Hz), 9.30 (1H, d, J=2.0 Hz).

Example 595

2-(4,4-difluoro-2-(5-fluoropyridin-2-yl)piperidin-1-yl)-6-(5-(difluoromethyl)-1,3,4-oxadiazol-2-yl)isoindolin-1-one A) benzyl 5-((tert-butoxycarbonyl)amino)-3-oxopentanoate To a mixture of 3-((tert-butoxycarbonyl)amino)propanoic acid (3.01 g) and THF (40 mL) was added CDI (3.22 g) at room temperature. The mixture was stirred at room temperature for 2 hr, magnesium chloride (powder, 1.52 g) and potassium 3-(benzyloxy)-3-oxopropanoate (5.48 g) were added thereto, and the obtained mixture was stirred at room temperature for 3 days. The reaction mixture was neutralized with 1N hydrochloric acid (33 mL) and water (50 mL) at room temperature, and extracted with ethyl acetate. The organic layer was separated, washed with IN hydrochloric acid and saturated brine, dried over anhydrous sodium sulfate, and concentrated under reduced pressure to give the title compound (5.08 g).
MS: [M−H]$^-$ 319.9.

B) a mixture of benzyl (2E)-5-((tert-butoxycarbonyl)amino)-2-((5-fluoropyridin-2-yl)methylene)-3-oxopentanoate and benzyl (2Z)-5-((tert-butoxycarbonyl)amino)-2-((5-fluoropyridin-2-yl)methylene)-3-oxopentanoate A mixture of benzyl 5-((tert-butoxycarbonyl)amino)-3-oxopentanoate (2.73 g), 5-fluoropyridine-2-carbaldehyde (1.04 g), piperidine (0.084 mL), acetic acid (0.048 mL) and toluene (150 mL) was refluxed under azeotropic condition using Dean-Stark trap for 3 hr. The reaction solution was concentrated under reduced pressure, and the obtained residue was purified by silica gel column chromatography (ethyl acetate/hexane) to give the title compound (2.553 g).
MS: [M−H]$^-$ 427.1.

C) 3-benzyl 1-tert-butyl 5'-fluoro-4-hydroxy-5,6-dihydro-2,2'-bipyridine-1,3(2H)-dicarboxylate To a mixture (2.46 g) of benzyl (2E)-5-((tert-butoxycarbonyl)amino)-2-((5-fluoropyridin-2-yl)methylene)-3-oxopentanoate and benzyl (2Z)-5-((tert-butoxycarbonyl)amino)-2-((5-fluoropyridin-2-yl)methylene)-3-oxopentanoate was added TFA (5 mL) at room temperature. The mixture was stirred at room temperature for 30 min, and the reaction solution was concentrated. To a mixture of the obtained residue and THF (15 mL) was added TEA (2.4 mL) at room temperature. The mixture was stirred at room temperature for 2 hr, and Boc$_2$O (2.0 mL) was added thereto at room temperature. The obtained mixture was stirred at room temperature for 3 days, and the reaction solution was concentrated. The obtained residue was partitioned between ethyl acetate and water. The organic layer was washed with saturated brine, dried over anhydrous magnesium sulfate, and concentrated under reduced pressure. The residue was purified by silica gel column chromatography (ethyl acetate/hexane) to give the title compound (1.73 g).
MS: [M+H]$^+$ 429.2.

D) tert-butyl 2-(5-fluoropyridin-2-yl)-4-oxopiperidine-1-carboxylate

A mixture of 3-benzyl 1-tert-butyl 5'-fluoro-4-hydroxy-5,6-dihydro-2,2'-bipyridine-1,3(2H)-dicarboxylate (1.73 g), 10% palladium on carbon (55% hydrous product, 0.39 g) and ethanol (68 mL) was hydrogenated under balloon pressure at room temperature for 15 hr. The catalyst was removed by filtration, and the filtrate was concentrated under reduced pressure. The residue was purified by silica gel column chromatography (ethyl acetate/hexane) to give the title compound (0.761 g).
MS: [M+H]$^+$ 295.2.

E) tert-butyl 4,4-difluoro-2-(5-fluoropyridin-2-yl)piperidine-1-carboxylate

To a mixture of tert-butyl 2-(5-fluoropyridin-2-yl)-4-oxopiperidine-1-carboxylate (0.731 g) and toluene (20 mL) was added bis(2-methoxyethyl)aminosulfur trifluoride (3.7 mL) at 0° C. The mixture was stirred under nitrogen atmosphere at room temperature for 3 days. To the mixture was added saturated aqueous ammonium chloride solution at 0° C., and the mixture was extracted with ethyl acetate. The organic layer was separated, washed with saturated aqueous sodium hydrogencarbonate solution and saturated brine, dried over anhydrous magnesium sulfate, and concentrated under reduced pressure. The residue was purified by silica gel column chromatography (NH ethyl acetate/hexane) to give the title compound (0.283 g).

MS: [M+H]$^+$ 317.2.

F) 1-oxa-2-azaspiro[2.5]octane

A mixture of cyclohexanone (11 mL), aqueous ammonia (25 w/w %, 2 mL), toluene (68 mL), water (42 mL) and ice (25 g) was vigorously shaken for 5 min in a separating funnel. To the obtained mixture was added aqueous sodium hypochlorite solution (35 mL), and the mixture was vigorously shaken for additional 5 min. The organic layer was separated, dried over anhydrous sodium sulfate, and filtered to give a toluene solution of the title compound. The obtained toluene solution was used as 0.28M solution without further purification.

G) 4,4-difluoro-2-(5-fluoropyridin-2-yl)piperidin-1-amine

A mixture of tert-butyl 4,4-difluoro-2-(5-fluoropyridin-2-yl)piperidine-1-carboxylate (281 mg) and 4N hydrogen chloride CPME solution (5 mL) was stirred at room temperature for 2 hr. To the reaction solution was added methanol (2 mL), the mixture was stirred at room temperature for additional 17 hr, and the reaction solution was concentrated. The residue was neutralized with saturated aqueous sodium hydrogencarbonate solution, and the mixture was extracted with ethyl acetate. The extract was washed with saturated brine, dried over anhydrous magnesium sulfate, and concentrated under reduced pressure. The residue was purified by silica gel column chromatography (methanol/ethyl acetate) to give 4,4-difluoro-2-(5-fluoropyridin-2-yl)piperidine (131 mg). To the obtained 4,4-difluoro-2-(5-fluoropyridin-2-yl)piperidine (128 mg) was added 0.28M toluene solution (3.0 mL) of 1-oxa-2-azaspiro[2.5]octane at room temperature. The mixture was stirred at room temperature for 3 days. The mixture was concentrated under reduced pressure, the residue was dissolved in methanol (2 mL), and 2N hydrochloric acid (2 mL) was added thereto at room temperature. The mixture was stirred at 55° C. for 17 hr. The mixture was concentrated under reduced pressure. To the residue were added THF (3 mL) and TEA (0.5 mL), and the mixture was supported on silica gel (NH, about 3.5 g), and purified by silica gel column chromatography (NH, ethyl acetate/hexane) to give the title compound (64.1 mg).

MS: [M+H]$^+$ 232.2.

H) 2-(4,4-difluoro-2-(5-fluoropyridin-2-yl)piperidin-1-yl)-6-(5-(difluoromethyl)-1,3,4-oxadiazol-2-yl)isoindolin-1-one To a mixture of 4,4-difluoro-2-(5-fluoropyridin-2-yl)piperidin-1-amine (64 mg), DIPEA (70 μL) and dimethylacetamide (1 mL) was added dropwise a mixture of methyl 2-(bromomethyl)-5-(5-(difluoromethyl)-1,3,4-oxadiazol-2-yl)benzoate (90 mg) and DMA (0.5 mL) at 0° C. The mixture was stirred under argon atmosphere at room temperature for 40 hr, and the reaction solution was partitioned between ethyl acetate and water. The organic layer was washed with saturated brine, dried over anhydrous magnesium sulfate, and concentrated under reduced pressure. The residue was dissolved in acetic acid (5 mL), the solution was stirred at 60° C. for 3 hr, and the reaction solution was concentrated. The obtained residue was partitioned between ethyl acetate and saturated aqueous sodium hydrogencarbonate solution. The organic layer was washed with saturated brine, dried over anhydrous magnesium sulfate, and concentrated under reduced pressure. The residue was purified by silica gel column chromatography (ethyl acetate/hexane) to give the title compound (72.4 mg).

$^1$H NMR (400 MHz, CDCl$_3$) δ 2.17-2.69 (2H, m), 2.28 (2H, t, J=12.0 Hz), 3.21-3.30 (1H, m), 3.38-4.96 (2H, m), 4.43 (1H, d, J=17.4 Hz), 4.97-5.63 (1H, m), 6.91 (1H, t, J=51.6 Hz), 7.17-7.59 (2.5H, m), 7.46 (1H, d, J=3.9 Hz), 8.18-8.55 (0.5H, m), 8.27 (1H, dd, J=7.8, 1.2 Hz), 8.41 (1H, s).

Example 598

N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2-difluoropropanamide

A) benzyl tert-butyl ((1R,2S)-3,3-difluorocyclohexane-1,2-diyl)biscarbamate

To a mixture of tert-butyl ((1R,2S)-2-amino-3,3-difluorocyclohexyl)carbamate (923 mg), potassium carbonate (1.53 g) and THF (10 mL) was added benzyl chloroformate (0.684 mL) at 0° C. The mixture was stirred overnight at room temperature. The precipitate was removed by filtration, the filtrate was concentrated under reduced pressure, and the residue was purified by silica gel column chromatography (ethyl acetate/hexane) to give the title compound (1.41 g).

MS, found: 285.1.

B) benzyl ((1S,6R)-6-amino-2,2-difluorocyclohexyl)carbamate

A mixture of benzyl tert-butyl ((1R,2S)-3,3-difluorocyclohexane-1,2-diyl)biscarbamate (1.41 g) and TFA (10 mL) was stirred at room temperature for 30 min. The mixture was concentrated under reduced pressure. The residue was purified by silica gel column chromatography (NH, ethyl acetate/hexane) to give the title compound (877 mg).

MS: [M+H]$^+$ 285.1.

C) ethyl 6-((1R,2S)-2-(((benzyloxy)carbonyl)amino)-3,3-difluorocyclohexyl)-5-oxo-6,7-dihydro-5H-pyrrolo[3,4-b]pyridine-3-carboxylate To a mixture of benzyl ((1S,6R)-6-amino-2,2-difluorocyclohexyl)carbamate (867 mg), cesium carbonate (1.99 g) and DMF (2 mL) was added diethyl 2-(bromomethyl)pyridine-3,5-dicarboxylate (1.01 g) at room temperature. The mixture was stirred at room temperature for 1 hr. To the mixture was added saturated aqueous sodium hydrogencarbonate solution at 0° C., and the mixture was extracted with ethyl acetate. The organic layer was separated, washed with water and saturated brine, dried over anhydrous magnesium sulfate, and concentrated under reduced pressure. The residue was dissolved in acetic acid (2.0 mL) at room temperature, and the mixture was stirred at 60° C. for 1 hr. The mixture was concentrated under reduced pressure, and the residue was purified by silica gel column chromatography (ethyl acetate/hexane) to give the title compound (850 mg).

MS: [M+H]$^+$ 474.1.

D) benzyl ((1S,6R)-2,2-difluoro-6-(3-(hydrazinocarbonyl)-5-oxo-5,7-dihydro-6H-pyrrolo[3,4-b]pyridin-6-yl)cyclohexyl)carbamate To a mixture of ethyl 6-((1R,2S)-2-(((benzyloxy)carbonyl)amino)-3,3-difluorocyclohexyl)-5-oxo-6,7-dihydro-5H-pyrrolo[3,4-b]pyridine-3-carboxylate (850 mg) and THF (10 mL)/methanol (10 mL) was added hydrazine monohydrate (1.75 mL) at room temperature. The mixture was stirred at 80° C. for 1 hr. The mixture was concentrated under reduced pressure, and azeotroped with toluene to give the title compound (754 mg).
MS: [M+H]$^+$ 460.2.

E) benzyl ((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)carbamate To a mixture of benzyl ((1S,6R)-2,2-difluoro-6-(3-(hydrazinocarbonyl)-5-oxo-5,7-dihydro-6H-pyrrolo[3,4-b]pyridin-6-yl)cyclohexyl)carbamate (754 mg), DIPEA (1.15 mL) and THF (15 mL) was added difluoroacetic anhydride (0.408 mL) at 0° C. The mixture was stirred at room temperature for 30 min. Then, to the reaction mixture were added DIPEA (1.15 mL) and 4-methylbenzenesulfonyl chloride (626 mg) at 0° C. The mixture was stirred at room temperature for 1 hr. To the mixture was added saturated aqueous sodium hydrogencarbonate solution at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (580 mg).
MS: [M+H]$^+$ 520.1.

F) 6-((1R,2S)-2-amino-3,3-difluorocyclohexyl)-3-(5-(difluoromethyl)-1,3,4-oxadiazol-2-yl)-6,7-dihydro-5H-pyrrolo[3,4-b]pyridin-5-one A mixture of benzyl ((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)carbamate (0.90 g), 10% palladium on carbon (0.184 g) and methanol (15 mL) was hydrogenated under balloon pressure at room temperature for 2 hr. The catalyst was removed by filtration, and the filtrate was concentrated under reduced pressure to give the title compound (586 mg).
MS: [M+H]$^+$ 386.1.

G) N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2-difluoropropanamide To a mixture of 2,2-difluoropropanoic acid (300 mg) and THF (15 mL) were added oxalyl chloride (0.239 mL) and DMF (one drop) at 0° C. The mixture was stirred at room temperature for 1 hr. Then, to the reaction mixture was added a mixture of 6-((1R,2S)-2-amino-3,3-difluorocyclohexyl)-3-(5-(difluoromethyl)-1,3,4-oxadiazol-2-yl)-6,7-dihydro-5H-pyrrolo[3,4-b]pyridin-5-one (350 mg), DIPEA (0.952 mL) and THF (5 mL) at 0° C. The mixture was stirred at room temperature for 1 hr. To the mixture was added saturated aqueous sodium hydrogencarbonate solution at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane), and the obtained solid was crystallized from ethyl acetate/hexane to give the title compound (121 mg).
$^1$H NMR (300 MHz, DMSO-d$_6$) δ 1.36-1.65 (4H, m), 1.80-1.94 (2H, m), 1.94-2.24 (3H, m), 4.40 (1H, td, J=11.8, 4.0 Hz), 4.52 (1H, d, J=18.4 Hz), 4.66-4.97 (2H, m), 7.59 (1H, t, J=51.6 Hz), 8.53 (1H, d, J=1.9 Hz), 8.94 (1H, d, J=9.4 Hz), 9.40 (1H, d, J=2.3 Hz).
powder X-RAY crystal diffraction pattern (diffraction angle 2θ): 11.7°, 12.5°, 14.3°, 16.1°, 18.1°, 18.4°, 21.1°, 21.6°, 26.1°

Example 601

N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2,3,3-tetrafluoropropanamide To a mixture of 2,2,3,3-tetrafluoropropanoic acid (87 mg) and THF (3 mL) were added oxalyl chloride (0.052 mL) and DMF (one drop) at 0° C. The reaction mixture was stirred at room temperature for 30 min, and a mixture of 6-((1R,2S)-2-amino-3,3-difluorocyclohexyl)-3-(5-(difluoromethyl)-1,3,4-oxadiazol-2-yl)-6,7-dihydro-5H-pyrrolo[3,4-b]pyridin-5-one (100 mg), DIPEA (0.227 mL) and THF (1 mL) was added thereto at room temperature. The mixture was stirred overnight at room temperature. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (124 mg).
$^1$H NMR (300 MHz, DMSO-d$_6$) δ 1.54 (1H, d, J=13.2 Hz), 1.80-1.95 (2H, m), 2.02 (1H, d, J=16.2 Hz), 2.10-2.27 (2H, m), 4.32-4.79 (3H, m), 4.79-5.01 (1H, m), 6.28-6.75 (1H, m), 7.38-7.79 (1H, m), 8.53 (1H, d, J=2.1 Hz), 9.39 (1H, d, J=2.1 Hz), 9.71 (1H, d, J=9.3 Hz).

Example 604 benzyl 1-(6-(5-(difluoromethyl)-1,3,4-oxadiazol-2-yl)-1-oxo-1,3-dihydro-2H-isoindol-2-yl)-4,4-difluoropiperidine-2-carboxylate

A) 2-benzyl 1-tert-butyl 4,4-difluoropiperidine-1,2-dicarboxylate

A mixture of 1-(tert-butoxycarbonyl)-4,4-difluoropiperidine-2-carboxylic acid (2.0 g), benzyl bromide (0.986 mL), cesium carbonate (3.69 g) and DMF (30 mL) was stirred overnight at room temperature. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (1.99 g).
MS, found: 256.2.

B) benzyl 4,4-difluoropiperidine-2-carboxylate hydrochloride

A mixture of 2-benzyl 1-tert-butyl 4,4-difluoropiperidine-1,2-dicarboxylate (1.99 g), 4M hydrogen chloride ethyl acetate solution (3 mL) and ethyl acetate (22.4 mL) was stirred at room temperature for 3 hr. The reaction solution was concentrated under reduced pressure to give the title compound (1.9 g).
MS: [M+H]$^+$ 256.2.

C) benzyl 4,4-difluoro-1-nitrosopiperidine-2-carboxylate

A mixture of benzyl 4,4-difluoropiperidine-2-carboxylate hydrochloride (359 mg), acetic acid (0.242 mL), sodium nitrite (291 mg) and water (5.6 mL) was stirred overnight at room temperature. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (361 mg).
MS: [M+H]$^+$ 285.2.

D) benzyl 1-amino-4,4-difluoropiperidine-2-carboxylate

A mixture of benzyl 4,4-difluoro-1-nitrosopiperidine-2-carboxylate (35 mg), zinc (40.3 mg), 12N hydrochloric acid (51 μL) and ethanol (10 mL) was stirred at 0° C. for 3 hr. The insoluble material was removed by filtration, and the filtrate was concentrated under reduced pressure. The residue was purified by silica gel column chromatography (NH, ethyl acetate/hexane) to give the title compound (30 mg).
MS: [M+H]$^+$ 271.2.

E) benzyl 1-(6-(5-(difluoromethyl)-1,3,4-oxadiazol-2-yl)-1-oxo-1,3-dihydro-2H-isoindol-2-yl)-4,4-difluoropiperidine-2-carboxylate A mixture of methyl 2-(bromomethyl)-5-(5-(difluoromethyl)-1,3,4-oxadiazol-2-yl)benzoate (411 mg), benzyl 1-amino-4,4-difluoropiperidine-2-carboxylate (320 mg), DIPEA (0.414 mL) and DMF (2 mL) was stirred overnight at room temperature. To the mixture was added saturated brine at room temperature, and the mixture was extracted with ethyl acetate. The organic layer was separated, washed with saturated brine, dried over anhydrous magnesium sulfate, and concentrated under reduced pressure. To the residue was added acetic acid (2 mL), and the mixture was stirred at 50° C. for 3 hr. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (318 mg).
MS: [M+H]$^+$ 505.2.

Example 610

2-(4,4-Difluoro-2-(5-fluoropyridin-2-yl)piperidin-1-yl)-6-(5-(difluoromethyl)-1,3,4-oxadiazol-2-yl)isoindolin-1-one (Optical Isomer)

2-(4,4-Difluoro-2-(5-fluoropyridin-2-yl)piperidin-1-yl)-6-(5-(difluoromethyl)-1,3,4-oxadiazol-2-yl)isoindolin-1-one (81.1 mg, racemate) was subjected to optical resolution using preparative HPLC (column: CHIRALPAK AS-H (VG001), 20 mmID×250 mmL, mobile phase: hexanes/ethanol/diethylamine (750/250/1)) to give the title compound of Example 610 (31.2 mg, >99.9% ee, analysis HPLC (column: CHIRALPAK AS-H (VG001), 4.6 mmID×250 mmL, mobile phase: hexanes/ethanol/diethylamine (750/250/1), retention time: 7.159 min) and the compound of Example 612 (27.4 mg, >99.9% ee, analysis HPLC (column: CHIRALPAK AS-H (VG001), 4.6 mmID×250 mmL, mobile phase: hexanes/ethanol/diethylamine (750/250/1), retention time: 16.296 min).
$^1$H NMR (400 MHz, CDCl$_3$) δ 1.09-1.38 (2H, m), 2.13-2.72 (3H, m), 3.21-3.33 (1H, m), 3.64-4.77 (1.5H, m), 4.44 (1H, d, J=16.9 Hz), 5.18-5.62 (0.5H, m), 6.91 (1H, t, J=51.7 Hz), 7.12-7.95 (2H, m), 7.47 (1H, brs), 8.18-8.57 (1H, m), 8.27 (1H, dd, J=7.8, 0.7 Hz), 8.41 (1H, d, J=1.0 Hz).

Example 618 tert-butyl (2RS,3RS)-3-(6-(5-(difluoromethyl)-1,3,4-oxadiazol-2-yl)-1-oxo-1,3-dihydro-2H-isoindol-2-yl)-2-(4-fluorophenyl)piperidine-1-carboxylate

A) (2SR,3RS)-1-(tert-butoxycarbonyl)-2-(4-fluorophenyl)piperidine-3-carboxylic acid A mixture of methyl (2SR,3RS)-2-(4-fluorophenyl)piperidine-3-carboxylate hydrochloride (1.03 g) and 6 N hydrochloric acid (20 mL) was stirred at 80° C. for 5 hr. The mixture was neutralized with 8N aqueous sodium hydroxide solution. To the reaction mixture were added THF (20 mL), DIPEA (1.97 mL) and Boc$_2$O (1.05 mL) at 0° C. The mixture was stirred overnight at room temperature. The pH of the mixture was adjusted with 2N hydrochloric acid to 3-4, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (798 mg).
$^1$H NMR (300 MHz, DMSO-d$_6$) δ 1.28-1.42 (9H, m), 1.57-1.96 (3H, m), 2.53-2.72 (1H, m), 2.78-3.02 (1H, m), 3.32 (1H, brs), 3.80 (1H, d, J=12.7 Hz), 5.68 (1H, brs), 7.00-7.46 (4H, m), 12.57 (1H, brs).

B) tert-butyl (2RS,3RS)-3-{[(benzyloxy)carbonyl]amino}-2-(4-fluorophenyl)piperidine-1-carboxylate To a mixture of (2SR,3RS)-1-(tert-butoxycarbonyl)-2-(4-fluorophenyl)piperidine-3-carboxylic acid (661 mg), TEA (0.341 mL) and toluene (20 mL) was added DPPA (0.527 mL) at room temperature. The mixture was stirred at 80° C. for 2 hr. Then, to the reaction mixture was added benzyl alcohol (0.423 mL) at room temperature. The mixture was stirred at 80° C. for 10 hr. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (596 mg).
MS, found: 329.1.

C) tert-butyl (2RS,3RS)-3-amino-2-(4-fluorophenyl)piperidine-1-carboxylate

A mixture of tert-butyl (2RS,3RS)-3-{[(benzyloxy)carbonyl]amino}-2-(4-fluorophenyl)piperidine-1-carboxylate (680 mg), 10% palladium on carbon (169 mg) and methanol (20 mL) was hydrogenated under balloon pressure at room temperature for 1 hr. The catalyst was removed by filtration, and the filtrate was concentrated under reduced pressure. The residue was purified by silica gel column chromatography (NH, ethyl acetate/hexane) to give the title compound (286 mg).

MS: [M+H]$^+$ 295.1.

D) methyl 2-[(2RS,3RS)-1-(tert-butoxycarbonyl)-2-(4-fluorophenyl)piperidin-3-yl]-3-oxo-2,3-dihydro-1H-isoindole-5-carboxylate To a mixture of tert-butyl (2RS,3RS)-3-amino-2-(4-fluorophenyl)piperidine-1-carboxylate (323 mg), DIPEA (0.522 mL) and DMF (20 mL) was added dimethyl 4-(bromomethyl)isophthalate (286 mg) at room temperature. The mixture was stirred overnight at room temperature. The reaction solution was concentrated under reduced pressure. The obtained residue was partitioned between ethyl acetate-saturated aqueous sodium hydrogencarbonate solution. The organic layer was washed with saturated brine, dried over anhydrous magnesium sulfate, and concentrated under reduced pressure. To the obtained residue was added acetic acid (10 mL). The mixture was stirred at 60° C. for 1 hr. The mixture was concentrated under reduced pressure, and the obtained residue was purified by silica gel column chromatography (ethyl acetate/hexane) to give the title compound (397 mg).

MS, found: 369.1.

E) tert-butyl (2RS,3RS)-2-(4-fluorophenyl)-3-[6-(hydrazinocarbonyl)-1-oxo-1,3-dihydro-2H-isoindol-2-yl]piperidine-1-carboxylate To a mixture of methyl 2-[(2RS,3RS)-1-(tert-butoxycarbonyl)-2-(4-fluorophenyl)piperidin-3-yl]-3-oxo-2,3-dihydro-1H-isoindole-5-carboxylate (397 mg) and THF (5 mL)/methanol (5 mL) was added hydrazine monohydrate (0.826 mL) at room temperature. The mixture was refluxed for 3 hr, and concentrated under reduced pressure. The obtained residue was subjected to azeotropic evaporation with toluene to give the title compound (375 mg).

MS, found: 369.1.

F) tert-butyl (2RS,3RS)-3-(6-(5-(difluoromethyl)-1,3,4-oxadiazol-2-yl)-1-oxo-1,3-dihydro-2H-isoindol-2-yl)-2-(4-fluorophenyl)piperidine-1-carboxylate To a mixture of tert-butyl (2RS,3RS)-2-(4-fluorophenyl)-3-[6-(hydrazinocarbonyl)-1-oxo-1,3-dihydro-2H-isoindol-2-yl]piperidine-1-carboxylate (375 mg), DIPEA (0.419 mL) and THF (10 mL) was added difluoroacetic anhydride (0.149 mL) at 0° C. The mixture was stirred at room temperature for 30 min. Then, to the reaction mixture were added DIPEA (0.419 mL) and 4-methylbenzenesulfonyl chloride (229 mg) at 0° C. The mixture was stirred overnight at room temperature. To the mixture was added saturated aqueous sodium hydrogencarbonate solution at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (314 mg).

$^1$H NMR (300 MHz, DMSO-d$_6$) δ 1.25 (9H, s), 1.94-2.13 (4H, m), 2.99 (1H, d, J=18.5 Hz), 3.35-3.53 (1H, m), 3.92-4.03 (1H, m), 4.30-4.60 (2H, m), 5.41 (1H, d, J=5.7 Hz), 7.02 (2H, t, J=8.8 Hz), 7.24 (2H, dd, J=8.7, 5.5 Hz), 7.39-7.78 (2H, m), 8.21 (1H, dd, J=7.9, 1.7 Hz), 8.25 (1H, d, J=0.8 Hz).

Example 619 benzyl ((1R,6R)-6-(6-(5-(difluoromethyl)-1,3,4-oxadiazol-2-yl)-1-oxo-1,3-dihydro-2H-isoindol-2-yl)-2,2-difluorocyclohexyl)carbamate A) benzyl tert-butyl ((1R,2R)-3,3-difluorocyclohexane-1,2-diyl)biscarbamate To a mixture of tert-butyl ((1R,2R)-2-amino-3,3-difluorocyclohexyl)carbamate (587 mg), potassium carbonate (972 mg) and THF (10 mL) was added benzyl chloroformate (0.402 mL) at 0° C. The reaction mixture was stirred overnight at room temperature. The insoluble material was removed by filtration, and the filtrate was concentrated under reduced pressure. The residue was purified by silica gel column chromatography (ethyl acetate/hexane) to give the title compound (701 mg).

$^1$H NMR (300 MHz, DMSO-d$_6$) δ1.28-1.68 (13H, m), 1.71-1.91 (1H, m), 2.00-2.22 (1H, m), 3.59 (1H, brs), 4.25 (1H, brs), 4.49 (1H, s), 4.76 (1H, s), 5.06 (2H, dd, J=19.0, 12.7 Hz), 7.35-7.40 (5H, m).

B) methyl 2-((1R,2R)-2-(((benzyloxy)carbonyl)amino)-3,3-difluorocyclohexyl)-3-oxoisoindoline-5-carboxylate To benzyl tert-butyl ((1R,2R)-3,3-difluorocyclohexane-1,2-diyl)biscarbamate (701 mg) was added 4M hydrogen chloride ethyl acetate solution (10 mL) at 0° C. The mixture was stirred at room temperature for 30 min, and concentrated under reduced pressure. To a mixture of the crude product and DMF (10 mL) were added DIPEA (1.27 mL) and dimethyl 4-(bromomethyl)isophthalate (576 mg) at room temperature. The mixture was stirred overnight at room temperature. The reaction solution was concentrated, and the obtained residue was partitioned between ethyl acetate-saturated aqueous sodium hydrogencarbonate solution. The organic layer was washed with saturated brine, dried over anhydrous magnesium sulfate, and concentrated under reduced pressure. The residue was purified by silica gel column chromatography (ethyl acetate/hexane) to give the title compound (728 mg).

MS: [M+H]$^+$ 459.1.

C) benzyl ((1R,6R)-2,2-difluoro-6-(6-(hydrazinocarbonyl)-1-oxo-1,3-dihydro-2H-isoindol-2-yl)cyclohexyl)carbamate To a mixture of methyl 2-((1R,2R)-2-(((benzyloxy)carbonyl)amino)-3,3-difluorocyclohexyl)-3-oxoisoindoline-5-carboxylate (728 mg) and THF (10 mL)/methanol (10 mL) was added hydrazine monohydrate (1.55 mL) at room temperature. The mixture was refluxed for 10 hr, and concentrated under reduced pressure. The obtained residue was subjected to azeotropic evaporation with toluene to give the title compound (698 mg).

MS: [M+H]$^+$ 459.2.

D) benzyl ((1R,6R)-6-(6-(5-(difluoromethyl)-1,3,4-oxadiazol-2-yl)-1-oxo-1,3-dihydro-2H-isoindol-2-yl)-2,2-difluorocyclohexyl)carbamate To a mixture of benzyl ((1R,6R)-2,2-difluoro-6-(6-(hydrazinocarbonyl)-1-oxo-1,3-dihydro-2H-isoindol-2-yl)cyclohexyl)carbamate (698 mg), DIPEA (0.798 mL) and THF (10 mL) was added difluoroacetic anhydride (0.284 mL) at 0° C. The mixture was stirred at 0° C. for 30 min. Then, to the reaction mixture were added DIPEA (0.798 mL) and 4-methylbenzenesulfonyl chloride (435 mg) at 0° C. The reaction mixture was refluxed for 5 hr, to the mixture was added saturated aqueous sodium hydrogencarbonate solution at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (533 mg).

$^1$H NMR (300 MHz, DMSO-$d_6$) δ 1.53 (1H, d, J=13.0 Hz), 1.73-2.31 (6H, m), 4.28-4.57 (3H, m), 4.61-4.78 (1H, m), 4.78-4.89 (1H, m), 4.93-5.07 (1H, m), 7.12-7.28 (4H, m), 7.39-7.78 (1H, m), 7.86 (1H, d, J=7.9 Hz), 8.01 (1H, d, J=10.2 Hz), 8.23 (1H, s), 8.32 (1H, d, J=7.9 Hz).

Example 620

6-(5-(difluoromethyl)-1,3,4-oxadiazol-2-yl)-2-((2RS,3RS)-2-(4-fluorophenyl)piperidin-3-yl)isoindolin-1-one A mixture of tert-butyl (2RS,3RS)-3-(6-(5-(difluoromethyl)-1,3,4-oxadiazol-2-yl)-1-oxoisoindolin-2-yl)-2-(4-fluorophenyl)piperidine-1-carboxylate (314 mg) and TFA (5 mL) was stirred at room temperature for 1 hr. The reaction mixture was concentrated under reduced pressure, and subjected to azeotropic evaporation with toluene. The residue was purified by silica gel column chromatography (NH, ethyl acetate/hexane) to give the title compound (193 mg).

$^1$H NMR (300 MHz, DMSO-$d_6$) δ 1.63 (1H, d, J=13.0 Hz), 1.93-2.13 (3H, m), 2.67-2.90 (2H, m), 3.21-3.30 (1H, m), 4.07 (1H, d, J=1.1 Hz), 4.66 (1H, brs), 4.91 (1H, d, J=19.4 Hz), 5.21 (1H, d, J=19.4 Hz), 6.86-7.00 (2H, m), 7.20-7.32 (2H, m), 7.35-7.75 (1H, m), 7.85 (1H, d, J=8.2 Hz), 7.98 (1H, d, J=0.9 Hz), 8.21 (1H, dd, J=7.9, 1.7 Hz).

Example 622

1-(6-(5-(difluoromethyl)-1,3,4-oxadiazol-2-yl)-1-oxo-1,3-dihydro-2H-isoindol-2-yl)-4,4-difluoro-N-(2,2,3,3,3-pentafluoropropyl)piperidine-2-carboxamide A) 1-(6-(5-(difluoromethyl)-1,3,4-oxadiazol-2-yl)-1-oxo-1,3-dihydro-2H-isoindol-2-yl)-4,4-difluoropiperidine-2-carboxylic acid A mixture of benzyl 1-(6-(5-(difluoromethyl)-1,3,4-oxadiazol-2-yl)-1-oxo-1,3-dihydro-2H-isoindol-2-yl)-4,4-difluoropiperidine-2-carboxylate (305 mg), 10% palladium on carbon (hydrous product, 32.2 mg) and ethanol (5 mL) was hydrogenated under balloon pressure at room temperature for 3 hr. The catalyst was removed by filtration, and the filtrate was concentrated under reduced pressure to give the title compound (251 mg).

MS: [M+H]$^+$ 415.2.

B) 1-(6-(5-(difluoromethyl)-1,3,4-oxadiazol-2-yl)-1-oxo-1,3-dihydro-2H-isoindol-2-yl)-4,4-difluoro-N-(2,2,3,3,3-pentafluoropropyl)piperidine-2-carboxamide A mixture of 1-(6-(5-(difluoromethyl)-1,3,4-oxadiazol-2-yl)-1-oxo-1,3-dihydro-2H-isoindol-2-yl)-4,4-difluoropiperi-dine-2-carboxylic acid (50 mg), HATU (59.7 mg), TEA (0.037 mL), 2,2,3,3,3-pentafluoropropan-1-amine (27.0 mg) and DMF (1.0 mL) was stirred overnight at room temperature. To the mixture was added saturated brine at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (21 mg).

$^1$H NMR (400 MHz, CDCl$_3$) δ 2.11-2.65 (4H, m), 3.08-3.25 (1H, m), 3.30-3.72 (3H, m), 3.88-4.09 (2H, m), 4.49-4.68 (2H, m), 6.79-7.09 (1H, m), 7.66 (1H, d, J=7.8 Hz), 8.31-8.45 (1H, m), 8.54 (1H, s).

Example 624

2-((2RS,3RS)-1-(difluoroacetyl)-2-(4-fluorophenyl)piperidin-3-yl)-6-(5-(difluoromethyl)-1,3,4-oxadiazol-2-yl)isoindolin-1-one To a mixture of 6-(5-(difluoromethyl)-1,3,4-oxadiazol-2-yl)-2-((2RS,3RS)-2-(4-fluorophenyl)piperidin-3-yl)isoindolin-1-one (70 mg), DIPEA (0.086 mL) and THF (2 mL) was added difluoroacetic anhydride (0.030 mL) at 0° C. The mixture was stirred at room temperature for 1 hr. To the mixture was added saturated aqueous sodium hydrogencarbonate solution at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (76.2 mg).

$^1$H NMR (300 MHz, DMSO-$d_6$) δ 1.85 (1H, d, J=12.9 Hz), 2.00-2.33 (3H, m), 3.02-3.30 (1H, m), 3.57-3.80 (1H, m), 3.85-4.03 (1H, m), 4.33-4.64 (2H, m), 5.86 (1H, d, J=6.6 Hz), 6.58-7.01 (1H, m), 7.01-7.16 (2H, m), 7.28-7.86 (4H, m), 8.08-8.32 (2H, m).

Example 628

N-((1R,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2,3,3-tetrafluoropropanamide To a mixture of 2,2,3,3-tetrafluoropropanoic acid (0.039 mL) and THF (2 mL) were added oxalyl chloride (0.036 mL) and DMF (one drop) at 0° C. The mixture was stirred at room temperature for 30 min. Then, to the reaction mixture was added a mixture of 2-((1R,2R)-2-amino-3,3-difluorocyclohexyl)-6-(5-(difluoromethyl)-1,3,4-oxadiazol-2-yl)isoindolin-1-one (80 mg), DIPEA (0.182 mL) and THF (2 mL) at 0° C. The mixture was stirred at room temperature for 1 hr. To the mixture was added saturated aqueous sodium hydrogencarbonate solution at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (67.4 mg).

$^1$H NMR (300 MHz, DMSO-$d_6$) δ 1.59 (1H, d, J=12.6 Hz), 1.79-1.98 (2H, m), 2.03 (1H, brs), 2.13-2.41 (2H, m), 4.35-4.53 (2H, m), 4.74 (1H, d, J=18.4 Hz), 4.93 (1H, brs), 6.38-6.82 (1H, m), 7.35-7.78 (1H, m), 7.90 (1H, d, J=7.9 Hz), 8.21 (1H, d, J=0.9 Hz), 8.29 (1H, dd, J=8.0, 1.7 Hz), 9.43 (1H, d, J=10.2 Hz).

Example 630

6-(5-(difluoromethyl)-1,3,4-oxadiazol-2-yl)-2-(2-(6-methylpyridin-3-yl)piperidin-1-yl)isoindolin-1-one A) benzyl 6-(((trifluoromethyl)sulfonyl)oxy)-3,4-dihydropyridine-1(2H)-carboxylate Under nitrogen atmosphere, to a mixture of 1M potassium bis(trimethylsilyl)amide THF solution (59.9 mL) and THF (300 mL) was added dropwise a mixture of benzyl 2-oxopiperidine-1-carboxylate (11.18 g) and THF (100 mL) at −60° C. The mixture was stirred at −60° C. for 90 min, and a mixture of 1,1,1-trifluoro-N-phenyl-N-((trifluoromethyl)sulfonyl)methanesulfonamide (21.40 g) and THF (80 mL) was added dropwise thereto. The mixture was stirred under nitrogen atmosphere at −60° C. for 1 hr, warmed to room temperature, and stirred overnight at room temperature. To the mixture was added 10% aqueous sodium hydroxide solution (200 mL), and the mixture was extracted three times with diethyl ether. The organic layer was separated, washed with water and saturated brine, dried over anhydrous sodium sulfate, and concentrated under reduced pressure. The residue was purified by silica gel column chromatography (NH, ethyl acetate/hexane) to give the title compound (11.81 g).
$^1$H NMR (400 MHz, CDCl$_3$) δ 1.74-1.81 (2H, m), 2.27 (2H, td, J=6.7, 3.9 Hz), 3.65-3.70 (2H, m), 5.21 (2H, s), 5.33 (1H, t, J=3.9 Hz), 7.31-7.40 (5H, m).

B) benzyl 6'-methyl-5,6-dihydro-2,3'-bipyridine-1(4H)-carboxylate

A mixture of benzyl 6-(((trifluoromethyl)sulfonyl)oxy)-3,4-dihydropyridine-1(2H)-carboxylate (3.09 g), 2-methyl-5-(4,4,5,5-tetramethyl-1,3,2-dioxaborolan-2-yl)pyridine (2.78 g), bis(di-tert-butyl(4-dimethylaminophenyl)phosphine)dichloropalladium(II) (0.599 g), 2 M sodium carbonate aqueous solution (10.57 mL) and DME (30 mL) was subjected to microwave irradiation at 100° C. for 1 hr. The reaction mixture was poured into water at room temperature, and the mixture was extracted with ethyl acetate. The organic layer was separated, washed with saturated brine, dried over magnesium sulfate, and concentrated under reduced pressure. The residue was purified by silica gel column chromatography (NH, ethyl acetate/hexane) to give the title compound (2.59 g).
MS: [M+H]$^+$ 309.2.

C) 2-methyl-5-(piperidin-2-yl)pyridine

A mixture of benzyl 6'-methyl-5,6-dihydro-2,3'-bipyridine-1(4H)-carboxylate (2.59 g), ammonium formate (2.65 g), 10% palladium on carbon (50% hydrous product, 300 mg) and ethanol (20 mL) was subjected to microwave irradiation at 60° C. for 2 hr. The catalyst was removed by filtration, and the filtrate was concentrated under reduced pressure to give the title compound (1.87 g). The obtained objective product was used in the next reaction without further purification.
MS: [M+H]$^+$ 177.2.

D) 2-(6-methylpyridin-3-yl)piperidin-1-amine dihydrochloride

A mixture of 2-methyl-5-(piperidin-2-yl)pyridine (900 mg) and 0.23 M 1-oxa-2-azaspiro[2.5]octane toluene solution (22.2 mL) was stirred at 80° C. for 1 hr. The reaction solution was concentrated under reduced pressure, and 1N hydrochloric acid (20 mL) was added thereto. The mixture was stirred at room temperature for 1 hr, and then at 60° C. for 3 hr. The mixture was concentrated under reduced pressure to give the title compound (955 mg). The obtained objective product was used in the next reaction without further purification.
MS: [M+H]$^+$ 192.2.

E) 6-(5-(difluoromethyl)-1,3,4-oxadiazol-2-yl)-2-(2-(6-methylpyridin-3-yl)piperidin-1-yl)isoindolin-1-one To a mixture of methyl 2-(bromomethyl)-5-(5-(difluoromethyl)-1,3,4-oxadiazol-2-yl)benzoate (188 mg), 2-(6-methylpyridin-3-yl)piperidin-1-amine dihydrochloride (478 mg) and N,N-dimethylacetamide (20 mL) was added DIPEA (0.946 mL) at room temperature, and the mixture was stirred at room temperature for 3 days. To the mixture was added N-(2-aminoethyl)ethane-1,2-diamine (0.236 mL) at room temperature, and the mixture was stirred at room temperature for 1 hr. The mixture was diluted with saturated brine/water, and extracted with ethyl acetate. The organic layer was separated, washed with saturated brine, dried over anhydrous magnesium sulfate, and concentrated under reduced pressure. To the residue was added acetic acid (15 mL), and the mixture was stirred at 80° C. for 1 hr. The mixture was concentrated, and the residue was purified by HPLC (column: C18, mobile phase: water (containing 0.1% (v/v) TFA)/acetonitrile (containing 0.1% TFA). The obtained fraction was filtered through StratoSpheres SPE (PL-HCO3 MP-Resin), and the filtrate was concentrated under reduced pressure to give the title compound (36 mg).
$^1$H NMR (400 MHz, DMSO-d$_6$, 363 K) δ 1.34-1.53 (1H, m), 1.57-1.72 (1H, m), 1.74-1.86 (4H, m), 2.30 (3H, s), 3.20 (1H, br d, J=10.5 Hz), 3.30-3.44 (1H, m), 4.14-4.30 (1H, m), 4.35-4.50 (2H, m), 7.05 (1H, d, J=7.8 Hz), 7.45 (1H, t, J=51.6 Hz), 7.65 (1H, d, J=8.1 Hz), 7.68 (1H, dd, J=8.1, 2.5 Hz), 8.09 (1H, d, J=1.0 Hz), 8.15 (1H, dd, J=8.0, 1.6 Hz), 8.40 (1H, d, J=2.0 Hz).

Example 633

1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(4-fluorophenyl)-threo-pentitol (Optical Isomer)

A) 2-amino-1,5-anhydro-2,4-dideoxy-3-O-(4-fluorophenyl)-DL-threo-pentitol

To a mixture of tert-butyl 3-oxa-7-azabicyclo[4.1.0]heptane-7-carboxylate (1.00 g), 4-fluorophenol (844 mg) and acetonitrile (20 mL) was added cesium carbonate (3.27 g) at room temperature. The mixture was stirred at 80° C. for 12 hr. The mixture was filtered through Celite, and the filtrate was concentrated under reduced pressure. The residue was dissolved in a mixture of ethyl acetate (15 mL) and 4M hydrogen chloride ethyl acetate solution (15 mL), and the solution was stirred at room temperature for 2 hr. The mixture was concentrated under reduced pressure, and the residue was purified by HPLC (column: C18, mobile phase: water (containing 0.05% (v/v) aqueous ammonia (25 w/w % aqueous solution))/acetonitrile) and silica gel column chromatography (dichloromethane/methanol) to give the title compound (540 mg).
MS: [M+H]+ 212.2.

B) 1,5-anhydro-2,4-dideoxy-2-[3-(ethoxycarbonyl)-5-oxo-5,7-dihydro-6H-pyrrolo[3,4-b]pyridin-6-yl]-3-O-(4-fluorophenyl)-DL-threo-pentitol To a mixture of 2-amino-1,5-anhydro-2,4-dideoxy-3-O-(4-fluorophenyl)-DL-threo-pentitol (490 mg), DIPEA (1.21 mL) and DMF (16 mL) was added diethyl 2-(bromomethyl)pyridine-3,5-dicarboxylate (587 mg) at 0° C., and the mixture was stirred at room temperature for 5 hr. To the mixture was added water at room temperature, and the mixture was extracted with ethyl acetate. The organic layer was separated, washed with saturated brine, dried over anhydrous sodium sulfate, and concentrated under reduced pressure. The residue was dissolved in acetic acid (20 mL), and the solution was stirred at 65° C. for 2 hr. The mixture was concentrated under reduced pressure. The residue was dissolved in ethyl acetate, and the solution was washed with 10% saturated aqueous sodium hydrogencarbonate solution, dried over anhydrous sodium sulfate, and concentrated under reduced pressure. The residue was purified by silica gel column chromatography (ethyl acetate/petroleum ether) to give the title compound (340 mg).
MS: [M+H]$^+$ 401.3.

C) 1,5-anhydro-2,4-dideoxy-3-O-(4-fluorophenyl)-2-[3-(hydrazinecarbonyl)-5-oxo-5,7-dihydro-6H-pyrrolo[3,4-b]pyridin-6-yl]-DL-threo-pentitol A mixture of 1,5-anhydro-2,4-dideoxy-2-[3-(ethoxycarbonyl)-5-oxo-5,7-dihydro-6H-pyrrolo[3,4-b]pyridin-6-yl]-3-O-(4-fluorophenyl)-DL-threo-pentitol (310 mg), hydrazine monohydrate (775 mg) and ethanol (20 mL) was stirred at 100° C. for 3 hr. The mixture was concentrated under reduced pressure, to the residue was added water, and the precipitated solid was collected by filtration to give the title compound (280 mg).
MS: [M+H]$^+$ 387.2.

D) 1,5-anhydro-2,4-dideoxy-2-{3-[5-(difluoromethyl)-1,3,4-oxadiazol-2-yl]-5-oxo-5,7-dihydro-6H-pyrrolo[3,4-b]pyridin-6-yl}-3-O-(4-fluorophenyl)-DL-threo-pentitol To a mixture of 1,5-anhydro-2,4-dideoxy-3-O-(4-fluorophenyl)-2-[3-(hydrazinecarbonyl)-5-oxo-5,7-dihydro-6H-pyrrolo[3,4-b]pyridin-6-yl]-DL-threo-pentitol (100 mg), DIPEA (0.14 mL) and THF (6 mL) was added dropwise difluoroacetic anhydride (65 μL) at 0° C. The mixture was stirred at room temperature for 12 hr. The mixture was concentrated under reduced pressure, and the residue was purified by preparative HPLC (column: C18, mobile phase: 10 mM aqueous ammonium hydrogencarbonate solution/acetonitrile) to give the title compound (100 mg).
MS: [M+H]$^+$ 447.2.

E) 1,5-anhydro-2,4-dideoxy-2-{3-[5-(difluoromethyl)-1,3,4-oxadiazol-2-yl]-5-oxo-5,7-dihydro-6H-pyrrolo[3,4-b]pyridin-6-yl}-3-O-(4-fluorophenyl)-threo-pentitol (Optical Isomer)

1,5-Anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(4-fluorophenyl)-DL-threo-pentitol (100 mg) was subjected to optical resolution using preparative SFC (column: CHIRALCEL OJ (DAICEL), 30 mmID×250 mmL, mobile phase: methanol (containing 0.1% (v/v) aqueous ammonia (25 w/w % aqueous solution))/CO$_2$) to give the title compound of Example 633 (40.3 mg, 98.1% ee, analysis SFC (column: CHIRALCEL OJ-3 (DAICEL), 4.6 mmID×50 mmL, mobile phase: methanol (containing 0.05% (v/v) diethylamine)/CO$_2$), retention time: 1.838 min) and the compound of Example 632 (30.4 mg, 99.9% ee, analysis SFC (column: CHIRALCEL OJ-3 (DAICEL), 4.6 mmID×50 mmL, mobile phase: methanol (containing 0.05% (v/v) diethylamine)/CO$_2$), retention time: 1.685 min).
$^1$H NMR (400 MHz, DMSO-d$_6$) δ 1.62-1.68 (1H, m), 2.17-2.22 (1H, m), 3.47-3.58 (1H, m), 3.64-3.72 (1H, m), 3.87-3.93 (2H, m), 4.23-4.27 (1H, m), 4.52 (1H, d, J=18.8 Hz), 4.74 (1H, d, J=18.8 Hz), 4.87-4.92 (1H, m), 6.95-7.02 (4H, m), 7.57 (1H, t, J=51.6 Hz), 8.50 (1H, d, J=2.0 Hz), 9.34 (1H, d, J=2.0 Hz).

Example 640

N-((1R,2R)-2-(3-(5-(difluoromethyl)-1,3,4-oxadiazol-2-yl)-5-oxo-5,7-dihydro-6H-pyrrolo[3,4-b]pyridin-6-yl)-5,5-difluorocyclohexyl)-2,2,3,3,3-pentafluoropropanamide To a mixture of 6-((1R,2R)-2-amino-4,4-difluorocyclohexyl)-3-(5-(difluoromethyl)-1,3,4-oxadiazol-2-yl)-6,7-dihydro-5H-pyrrolo[3,4-b]pyridin-5-one (70 mg), TEA (0.035 mL) and THF (2 mL) was added pentafluoropropanoic anhydride (0.036 mL) at 0° C. The mixture was stirred at 0° C. for 15 min. The mixture was extracted with ethyl acetate, washed with water and saturated brine, dried over anhydrous sodium sulfate, and concentrated under reduced pressure. The residue was purified by silica gel column chromatography (ethyl acetate/hexane) to give the title compound (52 mg).
$^1$H NMR (300 MHz, DMSO-d$_6$) δ 1.97 (1H, brs), 2.01-2.09 (1H, m), 2.16-2.29 (2H, m), 2.40 (2H, d, J=16.8 Hz), 4.26 (1H, brs), 4.35-4.47 (1H, m), 4.51-4.78 (2H, m), 7.36-7.80 (1H, m), 8.53 (1H, d, J=2.0 Hz), 9.40 (1H, d, J=2.0 Hz), 9.76 (1H, brs).

Example 649

1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(3,4-difluorophenyl)-threo-pentitol (Optical Isomer)

A) 2-amino-1,5-anhydro-2,4-dideoxy-3-O-(3,4-difluorophenyl)-DL-threo-pentitol

To a mixture of tert-butyl 3-oxa-7-azabicyclo[4.1.0]heptane-7-carboxylate (1.00 g), 3,4-difluorophenol (980 mg) and acetonitrile (20.0 mL) was added cesium carbonate (3.30 g) at room temperature. The mixture was stirred at 80° C. for 12 hr. The mixture was filtered, and the filtrate was concentrated under reduced pressure. A mixture of the residue and 4M hydrogen chloride ethyl acetate solution (20.0 mL) was stirred at room temperature for 2 hr. The mixture was concentrated under reduced pressure, and the residue was purified by HPLC (column: C18, mobile phase: water (containing 0.05% (v/v) aqueous ammonia (25 w/w % aqueous solution))/acetonitrile) to give the title compound (700 mg).
MS: [M+H]+ 230.1.
$^1$H NMR (400 MHz, CDCl$_3$) δ1.56-1.73 (1H, m), 2.04-2.13 (1H, m), 3.05 (1H, td, J=8.0, 4.4 Hz), 3.12-3.29 (1H, m), 3.40-3.55 (1H, m), 3.83-4.09 (3H, m), 6.60-6.70 (1H, m), 6.72-6.83 (1H, m), 6.99-7.10 (1H, m).

B) 1,5-anhydro-2,4-dideoxy-3-O-(3,4-difluorophenyl)-2-[3-(ethoxycarbonyl)-5-oxo-5,7-dihydro-6H-pyrrolo[3,4-b]pyridin-6-yl]-DL-threo-pentitol To a mixture of 2-amino-1,5-anhydro-2,4-dideoxy-3-O-(3,4-difluorophenyl)-DL-threo-pentitol (600 mg), DIPEA (1.40 mL) and DMF (10.0 mL) was added diethyl 2-(bromomethyl)pyridine-3,5-dicarboxylate (703 mg) at 0° C. The mixture was stirred at room temperature for 12 hr. The mixture was poured into water at room temperature, and extracted with ethyl acetate. The organic layer was separated, washed with saturated brine, dried over anhydrous sodium sulfate, and concentrated under reduced pressure. The residue was dissolved in acetic acid (10 mL), and the solution was stirred at 70° C. for 1 hr. The mixture was concentrated under reduced pressure, to the residue was added saturated aqueous sodium hydrogencarbonate solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (700 mg).
MS: [M+H]$^+$ 419.1.
$^1$H NMR (400 MHz, CDCl$_3$) δ1.43 (3H, t, J=7.2 Hz), 1.81-1.84 (1H, m), 2.17-2.23 (1H, m), 3.67-3.71 (1H, m), 3.94 (1H, dd, J=12.0, 8.0 Hz), 4.08-4.16 (2H, m), 4.24 (1H, td, J=7.6, 4.4 Hz), 4.44 (2H, m), 4.59-4.73 (2H, m), 4.87 (1H, td, J=8.0, 4.4 Hz), 6.71-6.78 (1H, m), 6.87-6.89 (1H, m), 7.00-7.03 (1H, m), 8.69 (1H, d, J=2.0 Hz), 9.35 (1H, d, J=2.0 Hz).

C) 1,5-anhydro-2,4-dideoxy-3-O-(3,4-difluorophenyl)-2-[3-(hydrazinocarbonyl)-5-oxo-5,7-dihydro-6H-pyrrolo[3,4-b]pyridin-6-yl]-DL-threo-pentitol To a mixture of 1,5-anhydro-2,4-dideoxy-3-O-(3,4-difluorophenyl)-2-[3-(ethoxycarbonyl)-5-oxo-5,7-dihydro-6H-pyrrolo[3,4-b]pyridin-6-yl]-DL-threo-pentitol (700 mg) and ethanol (10 mL) was added hydrazine monohydrate (651 μL), and the mixture was stirred at 90° C. for 3 hr. The mixture was concentrated under reduced pressure to give the title compound (600 mg).
MS: [M+H]$^+$ 405.2.

D) 1,5-anhydro-2,4-dideoxy-2-{3-[5-(difluoromethyl)-1,3,4-oxadiazol-2-yl]-5-oxo-5,7-dihydro-6H-pyrrolo[3,4-b]pyridin-6-yl}-3-O-(3,4-difluorophenyl)-DL-threo-pentitol To a mixture of 1,5-anhydro-2,4-dideoxy-3-O-(3,4-difluorophenyl)-2-[3-(hydrazinocarbonyl)-5-oxo-5,7-dihydro-6H-pyrrolo[3,4-b]pyridin-6-yl]-DL-threo-pentitol (540 mg) and THF (10 mL) were added DIPEA (698 μL) and difluoroacetic anhydride (465 mg) at room temperature, and the mixture was stirred at room temperature for 12 hr. The mixture was diluted with water, and extracted with ethyl acetate. The organic layer was washed with saturated brine, dried over anhydrous sodium sulfate, and concentrated under reduced pressure to give 1,5-anhydro-2,4-dideoxy-2-{3-[2-(difluoroacetyl)hydrazinocarbonyl]-5-oxo-5,7-dihydro-6H-pyrrolo[3,4-b]pyridin-6-yl}-3-O-(3,4-difluorophenyl)-DL-threo-pentitol (580 mg). To a mixture of 1,5-anhydro-2,4-dideoxy-2-{3-[2-(difluoroacetyl) hydrazinocarbonyl]-5-oxo-5,7-dihydro-6H-pyrrolo[3,4-b]pyridin-6-yl}-3-O-(3,4-difluorophenyl)-DL-threo-pentitol (530 mg) and THF (15 mL) were added DIPEA (478 μL) and 4-methylbenzenesulfonyl chloride (628 mg) at room temperature. The mixture was stirred at 50° C. for 3 hr. The mixture was concentrated under reduced pressure. The residue was diluted with water, and extracted with ethyl acetate. The organic layer was washed with saturated brine, dried over anhydrous sodium sulfate, and concentrated under reduced pressure. The residue was purified by preparative HPLC (column: C18, mobile phase: 10 mM aqueous ammonium hydrogencarbonate solution/acetonitrile) to give the title compound (290 mg).
MS: [M+H]$^+$ 465.2.

E) 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(3,4-difluorophenyl)-threo-pentitol (Optical Isomer)

1,5-Anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(3,4-difluorophenyl)-DL-threo-pentitol (200 mg) was subjected to optical resolution using preparative SFC (column: CHIRALCEL OJ (DAICEL), 30 mmID× 250 mmL, mobile phase: methanol (containing 0.1% (v/v) aqueous ammonia (25 w/w % aqueous solution))/CO$_2$) to give the title compound of Example 649 (97.6 mg, 99.9% ee, analysis SFC (column: CHIRALCEL OJ-3 (DAICEL), 4.6 mmID×50 mmL, mobile phase: methanol (containing 0.05% (v/v) diethylamine)/CO$_2$), retention time: 1.574 min) and the compound of Example 646 (90.3 mg, 99.9% ee, analysis SFC (column: CHIRALCEL OJ-3 (DAICEL), 4.6 mmID× 50 mmL, mobile phase: methanol (containing 0.05% (v/v) diethylamine)/CO$_2$), retention time: 1.382 min).
$^1$H NMR (400 MHz, DMSO-d$_6$) δ 1.62-1.72 (1H, m), 2.21-2.30 (1H, m), 3.58 (1H, td, J=11.2, 2.0 Hz), 3.71 (1H, dd, J=11.2, 10.0 Hz), 3.94 (2H, dd, J=11.2, 4.0 Hz), 4.29 (1H, td, J=9.2, 4.4 Hz), 4.56-4.64 (1H, m), 4.74-4.81 (1H, m), 4.99 (1H, td, J=9.2, 4.4 Hz), 6.82-6.89 (1H, m), 7.20-7.29 (2H, m), 7.47-7.74 (1H, m), 8.53 (1H, d, J=2.0 Hz), 9.38 (1H, d, J=2.0 Hz).

Example 654

3-[5-(difluoromethyl)-1,3,4-oxadiazol-2-yl]-6-[(1RS,2RS)-2-(1H-pyrazol-5-yl)cyclohexyl]-6,7-dihydro-5H-pyrrolo[3,4-b]pyridin-5-one A) (1RS,2SR)-2-[1-(oxan-2-yl)-1H-pyrazol-5-yl]cyclohexan-1-ol To a mixture of 1-(2-tetrahydropyranyl)-1H-pyrazole (18.0 g) and THF (200 mL) was added dropwise 1.3 M tert-butyllithium heptane solution (137 mL) at −78° C., and the mixture was stirred at −78° C. for 0.5 hr. To the mixture was added dropwise 7-oxabicyclo[4.1.0]heptane (13.9 g) at −78° C., and then, boron trifluoride diethyl ether complex (29.2 mL) was added dropwise thereto. The mixture was stirred under nitrogen atmosphere at −78° C. for 0.5 hr, and then at room temperature for 12 hr. To the mixture were added saturated aqueous ammonium chloride solution and water at room temperature, and the mixture was extracted with ethyl acetate. The organic layer was separated, washed with saturated brine, dried over anhydrous sodium sulfate, and concentrated under reduced pressure. The residue was purified by preparative HPLC (column: C18, mobile phase:

water (containing 0.05% (v/v) aqueous ammonia (25 w/w % aqueous solution))/acetonitrile) to give the title compound (5.74 g).
MS: [M+H]$^+$ 251.2.

B) 2-[1-(oxan-2-yl)-1H-pyrazol-5-yl]cyclohexan-1-one

To a mixture of oxalyl chloride (2.18 mL) and dichloromethane (100 mL) was added dropwise a solution of DMSO (1.79 g) in dichloromethane (20 mL) under nitrogen atmosphere at −78° C., and the mixture was stirred at −78° C. for 20 min. To the mixture was added dropwise a solution of (1RS,2SR)-2-[1-(oxan-2-yl)-1H-pyrazol-5-yl]cyclohexan-1-ol (2.60 g) in dichloromethane (40 mL) at −78° C. The mixture was stirred at −78° C. for 10 min, and TEA (14.5 mL) was added all at once at −78° C. The mixture was stirred at −78° C. for 20 min, and then at room temperature for 40 min. The mixture was concentrated, and the residue was purified by silica gel column chromatography (ethyl acetate/petroleum ether) to give the title compound (2.50 g).
MS, found: 271.1.
$^1$H NMR (400 MHz, CDCl$_3$) δ 1.62-1.85 (5H, m), 1.92-2.10 (6H, m), 2.23-2.45 (2H, m), 2.48-2.59 (1H, m), 3.58-3.71 (1H, m), 3.75-3.90 (1H, m), 3.98-4.08 (1H, m), 5.29-5.38 (1H, m), 6.08-6.23 (1H, m), 7.49-7.62 (1H, m).

C) N-{2-[1-(oxan-2-yl)-1H-pyrazol-5-yl]cyclohexylidene}hydroxylamine

To a mixture of 2-[1-(oxan-2-yl)-1H-pyrazol-5-yl]cyclohexan-1-one (2.50 g) and methanol (50 mL) were added hydroxylamine hydrochloride (1.05 g) and sodium acetate (2.48 g) at room temperature, and the mixture was stirred at room temperature for 7 hr. The mixture was concentrated under reduced pressure, and the residue was purified by silica gel column chromatography (ethyl acetate/petroleum ether) to give the title compound (1.89 g).
MS: [M+H]$^+$ 264.2.

D) 2-[1-(oxan-2-yl)-1H-pyrazol-5-yl]cyclohexan-1-amine

To a mixture of N-{2-[1-(oxan-2-yl)-1H-pyrazol-5-yl]cyclohexylidene}hydroxylamine (10.0 g), methanol (100 mL) and aqueous ammonia (25 w/w % aqueous solution, 20 mL) was added Raney nickel (W2 type, 0.33 g) at room temperature. The suspension was degassed under reduced pressure, and substituted several times with hydrogen. The mixture was stirred under hydrogen atmosphere (50 psi) at 60° C. for 6 hr. The mixture was passed through Celite, and the filtrate was dried over anhydrous sodium sulfate, and concentrated under reduced pressure. The residue was purified by silica gel column chromatography (ethyl acetate/petroleum ether) to give the title compound (3.00 g, a mixture of cis/trans).
MS: [M+H]$^+$ 250.2.

E) diethyl 2-[({2-[1-(oxan-2-yl)-1H-pyrazol-5-yl]cyclohexyl}amino)methyl]pyridine-3,5-dicarboxylate To a mixture of diethyl 2-(bromomethyl)pyridine-3,5-dicarboxylate (1.51 g), DMF (10 mL) and DIPEA (3.56 mL) was added 2-[1-(oxan-2-yl)-1H-pyrazol-5-yl]cyclohexan-1-amine (1.70 g) at 0° C., and the mixture was stirred at room temperature for 1 hr. The mixture was concentrated under reduced pressure, and the residue was purified by silica gel column chromatography (ethyl acetate/petroleum ether) to give the title compound (1.00 g, a mixture of cis/trans).
MS: [M+H]$^+$ 485.3.

F) ethyl 6-{(1RS,2RS)-2-[1-(oxan-2-yl)-1H-pyrazol-5-yl]cyclohexyl}-5-oxo-6,7-dihydro-5H-pyrrolo[3,4-b]pyridine-3-carboxylate A mixture of diethyl 2-[({2-[1-(oxan-2-yl)-1H-pyrazol-5-yl]cyclohexyl}amino)methyl]pyridine-3,5-dicarboxylate (600 mg) and acetic acid (10 mL) was stirred at 65° C. for 2 hr. The mixture was concentrated under reduced pressure, and the residue was purified by preparative HPLC (column: C18, mobile phase: water (containing 0.225% (v/v) formic acid)/acetonitrile) to give the title compound (100 mg).
MS: [M+H]$^+$ 439.2.
$^1$H NMR (400 MHz, CDCl$_3$) δ1.36-1.44 (5H, m), 1.55-1.75 (8H, m), 1.91-2.02 (2H, m), 2.04-2.15 (1H, m), 3.02-3.11 (1H, m), 3.46-3.54 (1H, m), 3.69-3.98 (1H, m), 4.32-4.49 (5H, m), 4.57-4.70 (1H, m), 4.98-5.10 (1H, m), 6.18 (1H, dd, J=9.2, 2.4 Hz), 7.35 (1H, dd, J=15.6, 2.4 Hz), 8.56 (1H, dd, J=4.4, 2.0 Hz), 9.27 (1H, d, J=2.0 Hz).

G) 6-{(1RS,2RS)-2-[1-(oxan-2-yl)-1H-pyrazol-5-yl]cyclohexyl}-5-oxo-6,7-dihydro-5H-pyrrolo[3,4-b]pyridine-3-carbohydrazide A mixture of ethyl 6-{(1RS,2RS)-2-[1-(oxan-2-yl)-1H-pyrazol-5-yl]cyclohexyl}-5-oxo-6,7-dihydro-5H-pyrrolo[3,4-b]pyridine-3-carboxylate (80.0 mg), hydrazine monohydrate (0.36 mL) and ethanol (2 mL) was stirred at 100° C. for 5 hr. The mixture was concentrated under reduced pressure to give the title compound (77 mg).
MS: [M+H]$^+$ 425.1.

H) 3-[5-(difluoromethyl)-1,3,4-oxadiazol-2-yl]-6-{(1RS,2RS)-2-[1-(oxan-2-yl)-1H-pyrazol-5-yl]cyclohexyl}-6,7-dihydro-5H-pyrrolo[3,4-b]pyridin-5-one To a mixture of difluoroacetic anhydride (947 mg), DIPEA (0.13 mL) and THF (5 mL) was added 6-{(1RS,2RS)-2-[1-(oxan-2-yl)-1H-pyrazol-5-yl]cyclohexyl}-5-oxo-6,7-dihydro-5H-pyrrolo[3,4-b]pyridine-3-carbohydrazide (77.0 mg) at 0° C. The mixture was stirred under nitrogen atmosphere at room temperature for 1 hr. The mixture was concentrated under reduced pressure, and the residue was purified by silica gel column chromatography (ethyl acetate/petroleum ether) to give the title compound (85.0 mg).
MS: [M+H]$^+$ 485.1.

I) 3-[5-(difluoromethyl)-1,3,4-oxadiazol-2-yl]-6-[(1RS,2RS)-2-(1H-pyrazol-5-yl)cyclohexyl]-6,7-dihydro-5H-pyrrolo[3,4-b]pyridin-5-one A mixture of 3-[5-(difluoromethyl)-1,3,4-oxadiazol-2-yl]-6-{(1RS,2RS)-2-[1-(oxan-2-yl)-1H-pyrazol-5-yl]cyclohexyl}-6,7-dihydro-5H-pyrrolo[3,4-b]pyridin-5-one (40.0 mg) and acetic acid (5 mL) was stirred at 80° C. for 5 hr. The mixture was concentrated under reduced pressure, and the residue was purified by preparative HPLC (column: C18, mobile phase: 10 mM aqueous ammonium hydrogencarbonate solution (containing 0.04% (v/v) aqueous ammonia (25 w/w % aqueous solution))/acetonitrile) to give the title compound (16.1 mg).
MS: [M+H]$^+$ 401.1.

$^1$H NMR (400 MHz, CD$_3$OD) δ 1.45-1.76 (3H, m), 1.83-2.02 (5H, m), 3.10-3.24 (1H, m), 4.39-4.52 (1H, m), 4.60 (2H, s), 6.17 (1H, d, J=1.6 Hz), 7.11-7.44 (2H, m), 8.58 (1H, d, J=2.0 Hz), 9.36 (1H, d, J=2.0 Hz).

Example 656

1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(2,4-difluorophenyl)-threo-pentitol (Optical Isomer)

A) 1,5-anhydro-2,4-dideoxy-3-O-(2,4-difluorophenyl)-2-[3-(ethoxycarbonyl)-5-oxo-5,7-dihydro-6H-pyrrolo[3,4-b]pyridin-6-yl]-DL-threo-pentitol To a mixture of tert-butyl 3-oxa-7-azabicyclo[4.1.0]heptane-7-carboxylate (1.00 g), 2,4-difluorophenol (979 mg) and acetonitrile (20 mL) was added cesium carbonate (3.27 g) at room temperature. The mixture was stirred under nitrogen atmosphere at 80° C. for 12 hr. To the mixture was added water at room temperature, and the mixture was extracted with ethyl acetate. The organic layer was separated, washed with saturated brine, dried over anhydrous sodium sulfate, and concentrated under reduced pressure to give a yellow oil (1.88 g). A mixture of the obtained oil (1.80 g) and 4M hydrogen chloride ethyl acetate solution (10 mL) was stirred at room temperature for 1 hr. The mixture was concentrated under reduced pressure, and the residue was purified by HPLC (column: C18, mobile phase: water (containing 0.05% (v/v) aqueous ammonia (25 w/w % aqueous solution))/acetonitrile) to give a yellow oil (710 mg). The obtained oil (370 mg) was added to a mixture of DIPEA (843 μL) and DMF (10 mL) at 0° C. To the mixture was added diethyl 2-(bromomethyl)pyridine-3,5-dicarboxylate (459 mg) at 0° C., and the mixture was stirred at room temperature for 12 hr. To the mixture was added water, and the mixture was extracted with ethyl acetate. The organic layer was separated, washed with saturated brine, dried over anhydrous sodium sulfate, and concentrated under reduced pressure. The residue was dissolved in acetic acid (10 mL), and the solution was stirred at 70° C. for 2 hr. The mixture was concentrated under reduced pressure, the residue was suspended in saturated aqueous sodium hydrogencarbonate solution, and the suspension was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (300 mg).
MS: [M+H]+ 419.1.

B) 1,5-anhydro-2,4-dideoxy-3-O-(2,4-difluorophenyl)-2-[3-(hydrazinocarbonyl)-5-oxo-5,7-dihydro-6H-pyrrolo[3,4-b]pyridin-6-yl]-DL-threo-pentitol To a mixture of 1,5-anhydro-2,4-dideoxy-3-O-(2,4-difluorophenyl)-2-[3-(ethoxycarbonyl)-5-oxo-5,7-dihydro-6H-pyrrolo[3,4-b]pyridin-6-yl]-DL-threo-pentitol (280 mg) and ethanol (20 mL) was added hydrazine monohydrate (664 μL) at room temperature, and the mixture was stirred under nitrogen atmosphere at 100° C. for 3 hr. The mixture was concentrated under reduced pressure to give the title compound (280 mg).
MS: [M+H]$^+$ 405.2.

C) 1,5-anhydro-2,4-dideoxy-2-{3-[5-(difluoromethyl)-1,3,4-oxadiazol-2-yl]-5-oxo-5,7-dihydro-6H-pyrrolo[3,4-b]pyridin-6-yl}-3-O-(2,4-difluorophenyl)-DL-threo-pentitol To a mixture of 1,5-anhydro-2,4-dideoxy-3-O-(2,4-difluorophenyl)-2-[3-(hydrazinocarbonyl)-5-oxo-5,7-dihydro-6H-pyrrolo[3,4-b]pyridin-6-yl]-DL-threo-pentitol (280 mg), DIPEA (362 μL) and THF (10 mL) was added difluoroacetic anhydride (259 μL) at 0° C., and the mixture was stirred under nitrogen atmosphere at room temperature for 2 hr. To the mixture was added water, and the mixture was extracted with ethyl acetate. The organic layer was separated, washed with saturated brine, dried over anhydrous sodium sulfate, and concentrated under reduced pressure to give 1,5-anhydro-2,4-dideoxy-2-{3-[2-(difluoroacetyl)hydrazinocarbonyl]-5-oxo-5,7-dihydro-6H-pyrrolo[3,4-b]pyridin-6-yl}-3-O-(2,4-difluorophenyl)-DL-threo-pentitol (340 mg). To a mixture of 1,5-anhydro-2,4-dideoxy-2-{3-[2-(difluoroacetyl)hydrazinocarbonyl]-5-oxo-5,7-dihydro-6H-pyrrolo[3,4-b]pyridin-6-yl}-3-O-(2,4-difluorophenyl)-DL-threo-pentitol (340 mg), DIPEA (368 μL) and THF (15 mL) was added 4-methylbenzenesulfonyl chloride (149 mg) at 0° C., and the mixture was stirred under nitrogen atmosphere at 50° C. for 6 hr. The mixture was concentrated under reduced pressure, and the residue was purified by preparative HPLC (column: C18, mobile phase: 10 mM aqueous ammonium hydrogencarbonate solution (containing 0.04% (v/v) aqueous ammonia (25 w/w % aqueous solution))/acetonitrile) to give the title compound (110 mg).
MS: [M+H]$^+$ 465.2.

D) 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(2,4-difluorophenyl)-threo-pentitol (optical isomer)

1,5-Anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(2,4-difluorophenyl)-DL-threo-pentitol (110 mg) was subjected to optical resolution using preparative SFC (column: CHIRALCEL OJ (DAICEL), 30 mmID×250 mmL, mobile phase: methanol (containing 0.1% (v/v) aqueous ammonia (25 w/w % aqueous solution))/CO$_2$) to give the title compound of Example 656 (34.3 mg, 98.7% ee, analysis SFC (column: CHIRALCEL OJ-3 (DAICEL), 4.6 mmID×50 mmL, mobile phase: methanol (containing 0.05% (v/v) diethylamine)/CO$_2$), retention time: 1.418 min) and the compound of Example 655 (35.7 mg, 99.9% ee, analysis SFC (column: CHIRALCEL OJ-3 (DAICEL), 4.6 mmID×50 mmL, mobile phase: methanol (containing 0.05% (v/v) diethylamine)/CO$_2$), retention time: 1.251 min).
$^1$H NMR (400 MHz, DMSO-d$_6$) δ 1.67-1.78 (1H, m), 2.17-2.24 (1H, m), 3.52 (1H, t, J=10.4 Hz), 3.71 (1H, t, J=10.6 Hz), 3.93 (2H, dd, J=11.2, 4.4 Hz), 4.27-4.36 (1H, m), 4.64 (1H, d, J=18.8 Hz), 4.77 (1H, d, J=18.8 Hz), 4.86-4.93 (1H, m), 6.91-6.97 (1H, m), 7.16-7.23 (1H, m), 7.32-7.39 (1H, m), 7.60 (1H, t, J=51.6 Hz), 8.53 (1H, d, J=2.0 Hz), 9.38 (1H, d, J=2.0 Hz).

The compounds of Examples are shown in the following Table 1-1 to Table 1-67. MS in the tables means actual measured value. The compounds of Examples 2, 7 to 9, 11 to 17, 19, 23 to 27, 29, 32 to 39, 41 to 52, 56, 58 to 61, 63 to 111, 113 to 117, 119, 121, 122, 126 to 134, 136 to 138, 140, 141, 143 to 148, 150 to 153, 155, 156, 158 to 166, 168 to 173, 175 to 177, 179 to 185, 189 to 195, 197 to 263, 265 to 267, 269 to 398, 400 to 405, 407 to 451, 453 to 468, 471 to 488, 490 to 501, 504 to 509, 515, 518 to 526, 528 to 534, 537 to 546, 548, 550, 551, 554 to 557, 559, 562, 565 to 573, 576 to 578, 580, 582, 583, 585, 587 to 592, 594, 596, 597, 599, 600, 602, 603, 605 to 609, 611 to 617, 621, 623, 625 to 627, 629, 631, 632, 634 to 639, 641 to 648, 650 to 653, 655, 657 to 661 in the following tables were synthesized according to the methods shown in the above-mentioned Examples or a method analogous thereto.

TABLE 1-1

| EXAMPLE | IUPAC NAME | Structure | ADDITIVE | MS |
|---|---|---|---|---|
| 1 | 6-(5-(difluoromethyl)-1,3,4-oxadiazol-2-yl)-2-((3S,4R)-3-(2-oxopyrrolidin-1-yl)tetrahydro-2H-pyran-4-yl)isoindolin-1-one | 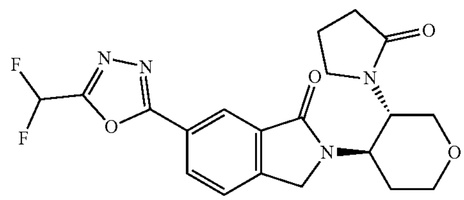 [SMILES: O=C1CCCN1[C@@H]1COCC[C@H]1N1Cc2ccc(-c3nnc(C(F)F)o3)cc2C1=O] | | 419.1 |
| 2 | 6-(5-(difluoromethyl)-1,3,4-oxadiazol-2-yl)-2-((1R,2R)-2-(2-oxopyrrolidin-1-yl)cyclohexyl)isoindolin-1-one | 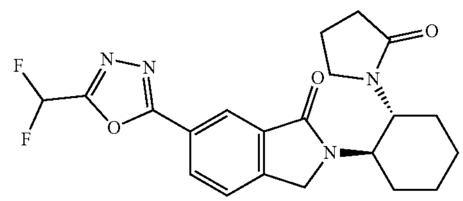 [SMILES: O=C1CCCN1[C@@H]1CCCC[C@H]1N1Cc2ccc(-c3nnc(C(F)F)o3)cc2C1=O] | | 417.1 |
| 3 | tert-butyl ((1R,2R)-2-(6-(5-(difluoromethyl)-1,3,4-oxadiazol-2-yl)-1-oxo-1,3-dihydro-2H-isoindol-2-yl)cyclohexyl)carbamate | 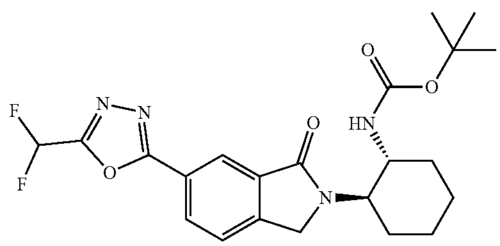 [SMILES: CC(C)(C)OC(=O)N[C@@H]1CCCC[C@H]1N1Cc2ccc(-c3nnc(C(F)F)o3)cc2C1=O] | | 449.1 |
| 4 | 6-(5-(difluoromethyl)-1,3,4-oxadiazol-2-yl)-2-((1R,2R)-2-(1,1-dioxido-1,2-thiazolidin-2-yl)cyclohexyl)isoindolin-1-one | 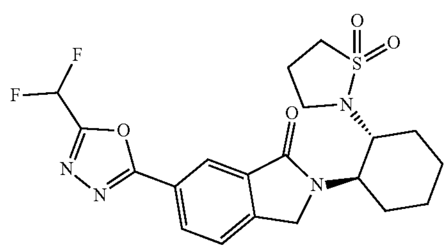 [SMILES: O=C1c2cc(-c3nnc(C(F)F)o3)ccc2CN1[C@@H]1CCCC[C@H]1N1CCCS1(=O)=O] | | 453.0 |
| 5 | N-((1R,2R)-2-(6-(5-(difluoromethyl)-1,3,4-oxadiazol-2-yl)-1-oxo-1,3-dihydro-2H-isoindol-2-yl)cyclohexyl)acetamide | 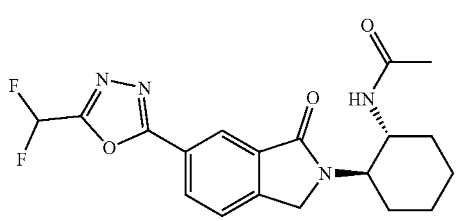 [SMILES: CC(=O)N[C@@H]1CCCC[C@H]1N1Cc2ccc(-c3nnc(C(F)F)o3)cc2C1=O] | | 391.1 |
| 6 | N-((1R,2R)-2-(6-(5-(difluoromethyl)-1,3,4-oxadiazol-2-yl)-1-oxo-1,3-dihydro-2H-isoindol-2-yl)cyclohexyl)-2,2,2-trifluoroacetamide | 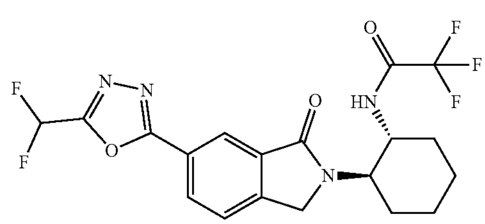 [SMILES: O=C1c2cc(-c3nnc(C(F)F)o3)ccc2CN1[C@@H]1CCCC[C@H]1NC(=O)C(F)(F)F] | | 445.0 |

TABLE 1-1-continued

| EXAMPLE | IUPAC NAME | Structure | ADDITIVE | MS |
|---|---|---|---|---|
| 7 | N-((1R,2R)-2-(6-(5-(difluoromethyl)-1,3,4-oxadiazol-2-yl)-1-oxo-1,3-dihydro-2H-isoindol-2-yl)cyclohexyl)propanamide | 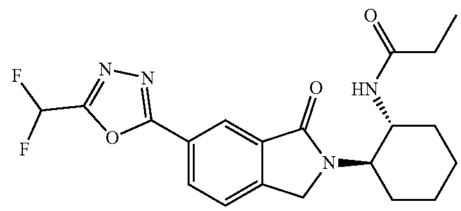 [SMILES: CCC(=O)N[C@@H]1CCCC[C@H]1N1Cc2ccc(-c3nnc(C(F)F)o3)cc2C1=O] | | 405.1 |
| 8 | cyclopropyl ((1R,2R)-2-(6-(5-(difluoromethyl)-1,3,4-oxadiazol-2-yl)-1-oxo-1,3-dihydro-2H-isoindol-2-yl)cyclohexyl)carbamate | 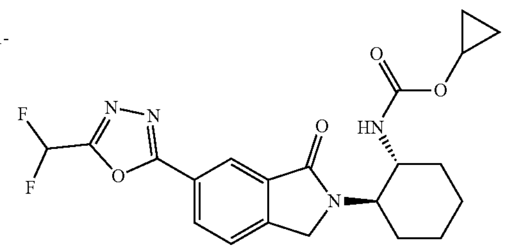 | | 433.1 |
| 9 | N-((1R,2R)-2-(6-(5-(difluoromethyl)-1,3,4-oxadiazol-2-yl)-1-oxo-1,3-dihydro-2H-isoindol-2-yl)cyclohexyl)-2-methylpropanamide | 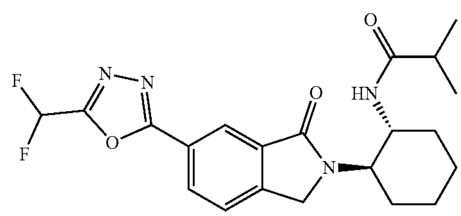 [SMILES: CC(C)C(=O)N[C@@H]1CCCC[C@H]1N1Cc2ccc(-c3nnc(C(F)F)o3)cc2C1=O] | | 419.3 |
| 10 | methyl ((1R,2R)-2-(6-(5-(difluoromethyl)-1,3,4-oxadiazol-2-yl)-1-oxo-1,3-dihydro-2H-isoindol-2-yl)cyclohexyl)carbamate | 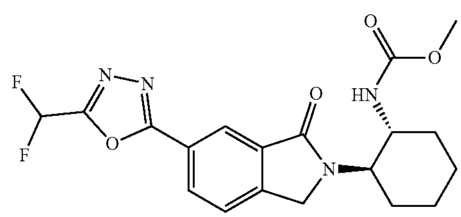 [SMILES: COC(=O)N[C@@H]1CCCC[C@H]1N1Cc2ccc(-c3nnc(C(F)F)o3)cc2C1=O] | | 407.1 |

TABLE 1-2

| EXAMPLE | IUPAC NAME | Structure | ADDITIVE | MS |
|---|---|---|---|---|
| 11 | N-((1R,2R)-2-(6-(5-(difluoromethyl)-1,3,4-oxadiazol-2-yl)-1-oxo-1,3-dihydro-2H-isoindol-2-yl)cyclohexyl)cyclopropanecarboxamide | 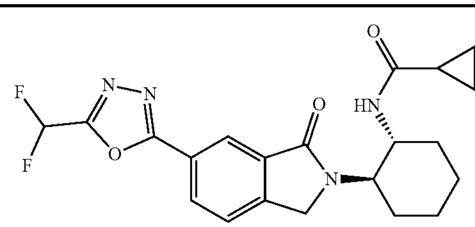 | | 417.1 |
| 12 | N-((1R,2R)-2-(6-(5-(difluoromethyl)-1,3,4-oxadiazol-2-yl)-1-oxo-1,3-dihydro-2H-isoindol-2-yl)cyclohexyl)cyclobutanecarboxamide | 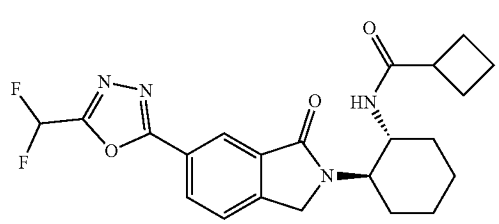 [SMILES: O=C(N[C@@H]1CCCC[C@H]1N1Cc2ccc(-c3nnc(C(F)F)o3)cc2C1=O)C1CCC1] | | 431.1 |

TABLE 1-2-continued

| EXAMPLE | IUPAC NAME | Structure | ADDITIVE | MS |
|---|---|---|---|---|
| 13 | N-((1R,2R)-2-(6-(5-(difluoromethyl)-1,3,4-oxadiazol-2-yl)-1-oxo-1,3-dihydro-2H-isoindol-2-yl)cyclohexyl)-3,3,3-trifluoropropanamide | 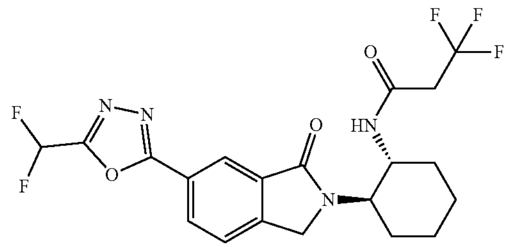 [SMILES: O=C(CC(F)(F)F)N[C@@H]1CCCC[C@H]1N1Cc2ccc(-c3nnc(C(F)F)o3)cc2C1=O] | | 459.1 |
| 14 | 6-(5-(difluoromethyl)-1,3,4-oxadiazol-2-yl)-2-((1R,2R)-2-(1-oxo-1,3-dihydro-2H-isoindol-2-yl)cyclohexyl)isoindolin-1-one | 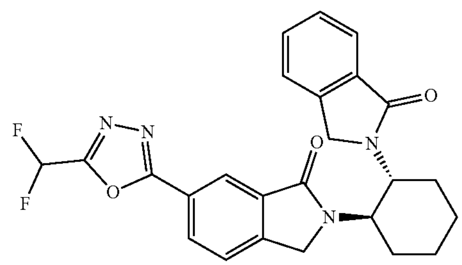 [SMILES: O=C1c2ccccc2CN1[C@@H]1CCCC[C@H]1N1Cc2ccc(-c3nnc(C(F)F)o3)cc2C1=O] | | 465.1 |
| 15 | N-((1R,2R)-2-(6-(5-(difluoromethyl)-1,3,4-oxadiazol-2-yl)-1-oxo-1,3-dihydro-2H-isoindol-2-yl)cyclohexyl)-1-methylcyclopropanecarboxamide | 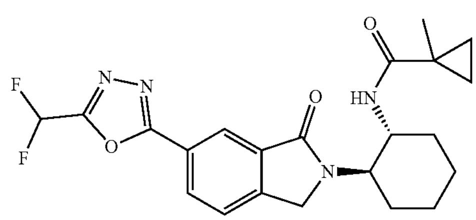 [SMILES: CC1(C(=O)N[C@@H]2CCCC[C@H]2N2Cc3ccc(-c4nnc(C(F)F)o4)cc3C2=O)CC1] | | 431.1 |
| 16 | N-((1R,2R)-2-(6-(5-(difluoromethyl)-1,3,4-oxadiazol-2-yl)-1-oxo-1,3-dihydro-2H-isoindol-2-yl)cyclohexyl)-3-methyloxetane-3-carboxamide | 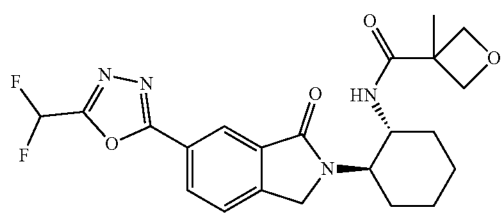 | | 447.1 |
| 17 | 1-cyano-N-((1R,2R)-2-(6-(5-(difluoromethyl)-1,3,4-oxadiazol-2-yl)-1-oxo-1,3-dihydro-2H-isoindol-2-yl)cyclohexyl)cyclopropanecarboxamide | 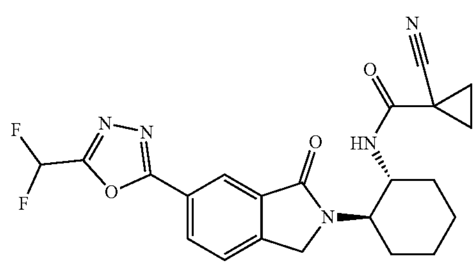 [SMILES: N#CC1(C(=O)N[C@@H]2CCCC[C@H]2N2Cc3ccc(-c4nnc(C(F)F)o4)cc3C2=O)CC1] | | 442.1 |
| 18 | (1S)-N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluorocyclopropanecarboxamide | 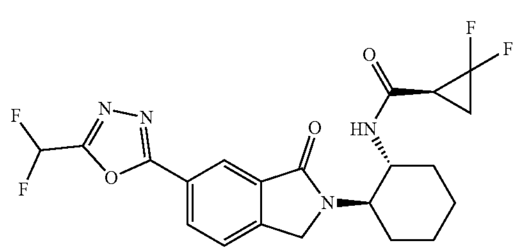 [SMILES: O=C(N[C@@H]1CCCC[C@H]1N1Cc2ccc(-c3nnc(C(F)F)o3)cc2C1=O)[C@@H]1CC1(F)F] | | 453.1 |

TABLE 1-2-continued

| EXAMPLE | IUPAC NAME | Structure | ADDITIVE | MS |
|---|---|---|---|---|
| 19 | N-((1R,2R)-2-(6-(5-(difluoromethyl)-1,3,4-oxadiazol-2-yl)-1-oxo-1,3-dihydro-2H-isoindol-2-yl)cyclohexyl)-1-fluorocyclopropanecarboxamide | 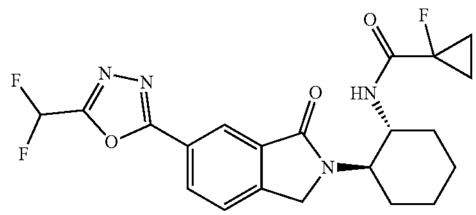 [SMILES: O=C1c2cc(-c3nnc(C(F)F)o3)ccc2CN1[C@@H]1CCCC[C@H]1NC(=O)C1(F)CC1] | | 435.1 |
| 20 | 6-(5-(difluoromethyl)-1,3,4-oxadiazol-2-yl)-2-((1R,2R)-2-(2-oxopiperidin-1-yl)cyclohexyl)isoindolin-1-one | 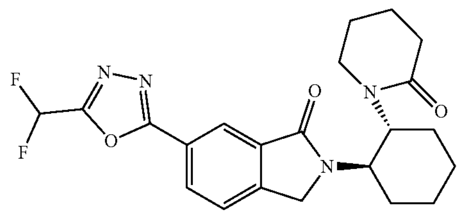 [SMILES: O=C1CCCCN1[C@@H]1CCCC[C@H]1N1Cc2ccc(-c3nnc(C(F)F)o3)cc2C1=O] | | 431.1 |

TABLE 1-3

| EXAMPLE | IUPAC NAME | Structure | ADDITIVE | MS |
|---|---|---|---|---|
| 21 | 6-(5-(difluoromethyl)-1,3,4-oxadiazol-2-yl)-2-((1R,2R)-2-(2-oxo-1,3-oxazinan-3-yl)cyclohexyl)isoindolin-1-one | 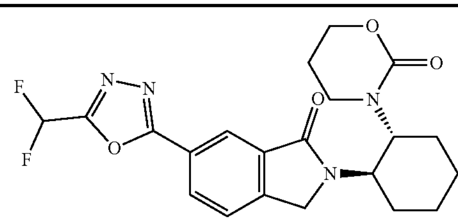 | | 433.1 |
| 22 | 6-(5-(difluoromethyl)-1,3,4-oxadiazol-2-yl)-2-((1R,2R)-2-(2-oxo-1,3-oxazolidin-3-yl)cyclohexyl)isoindolin-1-one | 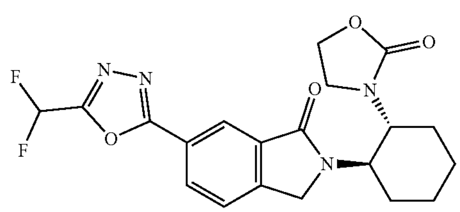 [SMILES: O=C1OCCN1[C@@H]1CCCC[C@H]1N1Cc2ccc(-c3nnc(C(F)F)o3)cc2C1=O] | | 419.1 |
| 23 | 1-(difluoromethyl)-N-((1R,2R)-2-(6-(5-(difluoromethyl)-1,3,4-oxadiazol-2-yl)-1-oxo-1,3-dihydro-2H-isoindol-2-yl)cyclohexyl)cyclopropanecarboxamide | 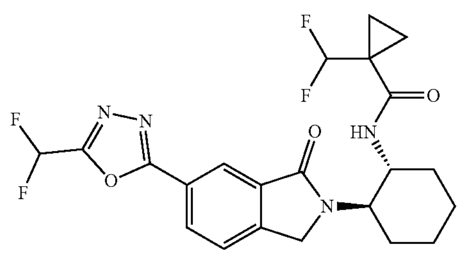 [SMILES: O=C1c2cc(-c3nnc(C(F)F)o3)ccc2CN1[C@@H]1CCCC[C@H]1NC(=O)C1(C(F)F)CC1] | | 467.1 |
| 24 | N-((1R,2R)-2-(6-(5-(difluoromethyl)-1,3,4-oxadiazol-2-yl)-1-oxo-1,3-dihydro-2H-isoindol-2-yl)cyclohexyl)-1-(trifluoromethyl)cyclobutanecarboxamide | 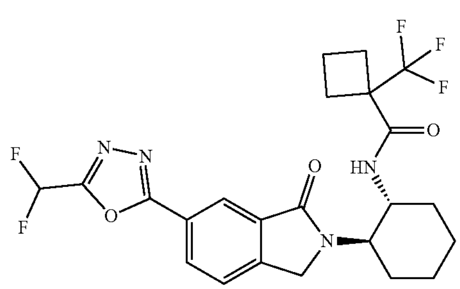 [SMILES: O=C1c2cc(-c3nnc(C(F)F)o3)ccc2CN1[C@@H]1CCCC[C@H]1NC(=O)C1(C(F)(F)F)CCC1] | | 499.1 |

TABLE 1-3-continued

| EXAMPLE | IUPAC NAME | Structure | ADDITIVE | MS |
|---|---|---|---|---|
| 25 | N-((1R,2R)-2-(6-(5-(difluoromethyl)-1,3,4-oxadiazol-2-yl)-1-oxo-1,3-dihydro-2H-isoindol-2-yl)cyclohexyl)-1-methoxycyclobutanecarboxamide | 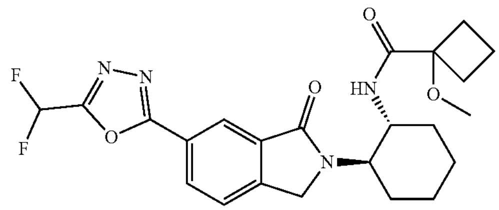 [SMILES: COC1(C(=O)N[C@@H]2CCCC[C@H]2N2Cc3ccc(-c4nnc(C(F)F)o4)cc3C2=O)CCC1] | | 461.2 |
| 26 | N-((1R,2R)-2-(6-(5-(difluoromethyl)-1,3,4-oxadiazol-2-yl)-1-oxo-1,3-dihydro-2H-isoindol-2-yl)cyclohexyl)-2-(1-hydroxycyclopentyl)acetamide | 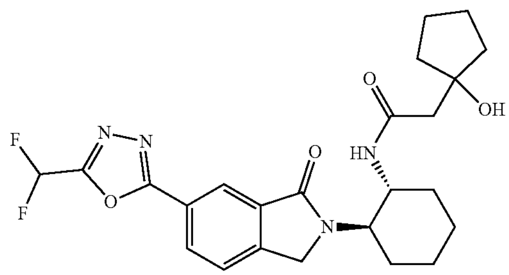 [SMILES: O=C(CC1(O)CCCC1)N[C@@H]1CCCC[C@H]1N1Cc2ccc(-c3nnc(C(F)F)o3)cc2C1=O] | | 475.2 |
| 27 | N-((1R,2R)-2-(6-(5-(difluoromethyl)-1,3,4-oxadiazol-2-yl)-1-oxo-1,3-dihydro-2H-isoindol-2-yl)cyclohexyl)-1,3-oxazole-4-carboxamide | 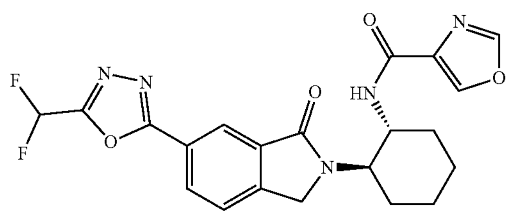 [SMILES: O=C(N[C@@H]1CCCC[C@H]1N1Cc2ccc(-c3nnc(C(F)F)o3)cc2C1=O)c1cocn1] | | 444.1 |
| 28 | N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluoroacetamide | 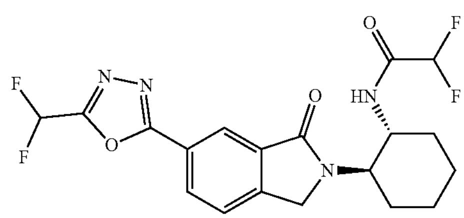 [SMILES: O=C(N[C@@H]1CCCC[C@H]1N1Cc2ccc(-c3nnc(C(F)F)o3)cc2C1=O)C(F)F] | | 427.1 |
| 29 | N-((1R,2R)-2-(6-(5-(difluoromethyl)-1,3,4-oxadiazol-2-yl)-1-oxo-1,3-dihydro-2H-isoindol-2-yl)cyclohexyl)-2,2,3,3,3-pentafluoropropanamide | 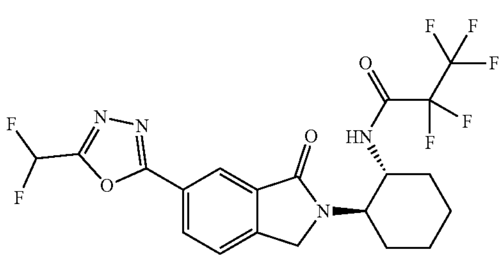 | | 495.0 |
| 30 | 6-(5-(difluoromethyl)-1,3,4-oxadiazol-2-yl)-2-((1R,2R)-2-(3-oxomorpholin-4-yl)cyclohexyl)isoindolin-1-one | 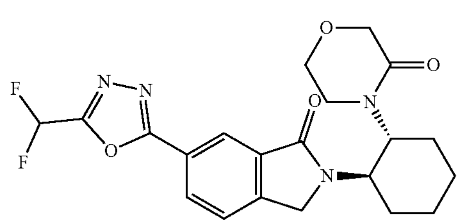 [SMILES: O=C1COCCN1[C@@H]1CCCC[C@H]1N1Cc2ccc(-c3nnc(C(F)F)o3)cc2C1=O] | | 433.1 |

TABLE 1-4

| EXAMPLE | IUPAC NAME | Structure | ADDITIVE | MS |
|---|---|---|---|---|
| 31 | 6-(5-(difluoromethyl)-1,3,4-oxadiazol-2-yl)-2-((1R,2R)-2-(2-oxotetrahydropyrimidin-1(2H)-yl)cyclohexyl)isoindolin-1-one | 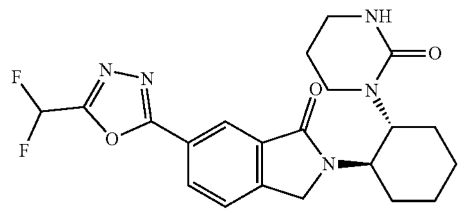 [SMILES: O=C1NCCCN1[C@@H]1CCCC[C@H]1N1Cc2ccc(-c3nnc(C(F)F)o3)cc2C1=O] | | 432.1 |
| 32 | N-((1R,2R)-2-(6-(5-(difluoromethyl)-1,3,4-oxadiazol-2-yl)-1-oxo-1,3-dihydro-2H-isoindol-2-yl)cyclohexyl)-1-(trifluoromethyl)cyclopropanecarboxamide | 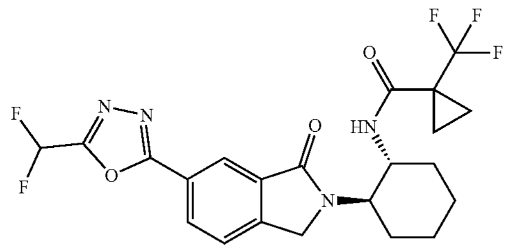 [SMILES: O=C1c2cc(-c3nnc(C(F)F)o3)ccc2CN1[C@@H]1CCCC[C@H]1NC(=O)C1(C(F)(F)F)CC1] | | 485.1 |
| 33 | N-((1R,2R)-2-(6-(5-(difluoromethyl)-1,3,4-oxadiazol-2-yl)-1-oxo-1,3-dihydro-2H-isoindol-2-yl)cyclohexyl)-3,3-difluorocyclobutanecarboxamide | 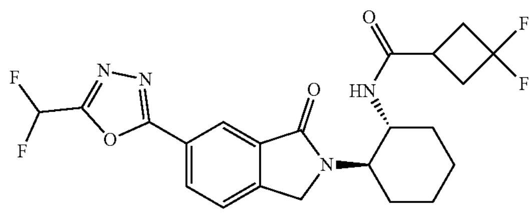 [SMILES: O=C(N[C@@H]1CCCC[C@H]1N1Cc2ccc(-c3nnc(C(F)F)o3)cc2C1=O)C1CC(F)(F)C1] | | 467.1 |
| 34 | tert-butyl (2R)-2-((6-(5-(difluoromethyl)-1,3,4-oxadiazol-2-yl)-1-oxo-1,3-dihydro-2H-isoindol-2-yl)methyl)piperidine-1-carboxylate | 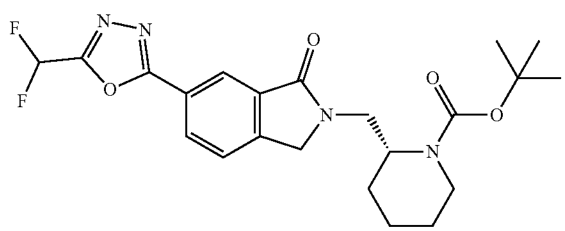 [SMILES: CC(C)(C)OC(=O)N1CCCC[C@@H]1CN1Cc2ccc(-c3nnc(C(F)F)o3)cc2C1=O] | | 449.1 |
| 35 | tert-butyl (3S)-3-((6-(5-(difluoromethyl)-1,3,4-oxadiazol-2-yl)-1-oxo-1,3-dihydro-2H-isoindol-2-yl)methyl)morpholine-4-carboxylate | 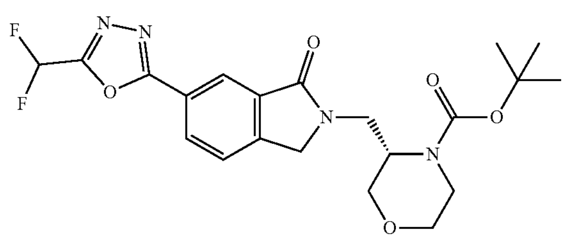 [SMILES: CC(C)(C)OC(=O)N1CCOC[C@@H]1CN1Cc2ccc(-c3nnc(C(F)F)o3)cc2C1=O] | | 451.1 |
| 36 | 6-(5-(difluoromethyl)-1,3,4-oxadiazol-2-yl)-2-((3S)-morpholin-3-ylmethyl)isoindolin-1-one | 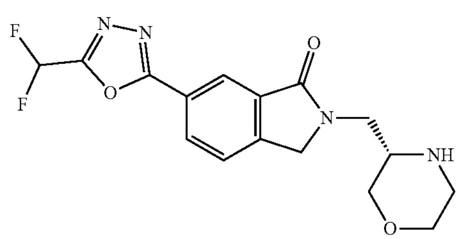 [SMILES: O=C1c2cc(-c3nnc(C(F)F)o3)ccc2CN1C[C@H]1COCCN1] | | 351.1 |
| 37 | 6-(5-(difluoromethyl)-1,3,4-oxadiazol-2-yl)-2-(2-(2-oxopyrrolidin-1-yl)phenyl)isoindolin-1-one | 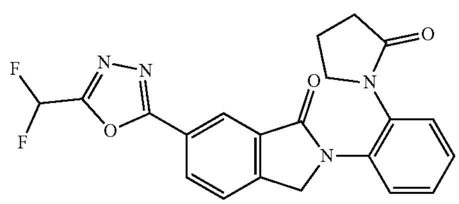 [SMILES: O=C1CCCN1c1ccccc1N1Cc2ccc(-c3nnc(C(F)F)o3)cc2C1=O] | | 411.1 |

TABLE 1-4-continued

| EXAMPLE | IUPAC NAME | Structure | ADDITIVE | MS |
|---|---|---|---|---|
| 38 | 2-((1R,2R)-2-aminocyclohexyl)-6-(5-(difluoromethyl)-1,3,4-oxadiazol-2-yl)isoindolin-1-one | 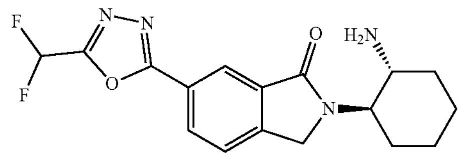 [SMILES: N[C@@H]1CCCC[C@H]1N1Cc2ccc(-c3nnc(C(F)F)o3)cc2C1=O] | | 349.1 |
| 39 | N-((1R,2R)-2-(6-(5-(difluoromethyl)-1,3,4-oxadiazol-2-yl)-1-oxo-1,3-dihydro-2H-isoindol-2-yl)cyclohexyl)pentanamide | 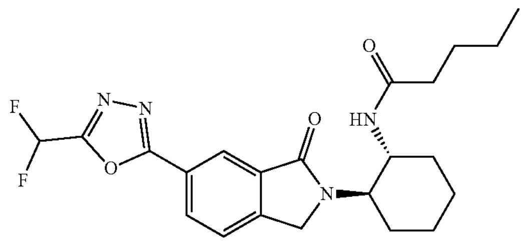 [SMILES: CCCCC(=O)N[C@@H]1CCCC[C@H]1N1Cc2ccc(-c3nnc(C(F)F)o3)cc2C1=O] | | 433.1 |
| 40 | N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluoropropanamide | 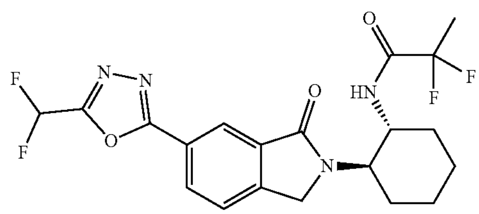 [SMILES: CC(F)(F)C(=O)N[C@@H]1CCCC[C@H]1N1Cc2ccc(-c3nnc(C(F)F)o3)cc2C1=O] | | 441.0 |

TABLE 1-5

| EXAMPLE | IUPAC NAME | Structure | ADDITIVE | MS |
|---|---|---|---|---|
| 41 | 2-(((2R)-1-(cyclopropylsulfonyl)piperidin-2-yl)methyl)-6-(5-(difluoromethyl)-1,3,4-oxadiazol-2-yl)isoindolin-1-one | 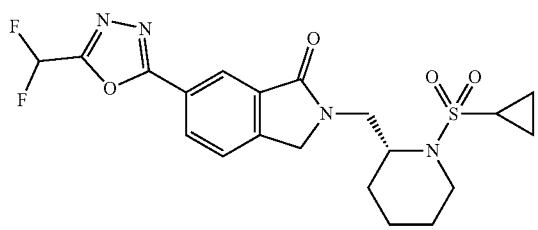 [SMILES: O=C1c2cc(-c3nnc(C(F)F)o3)ccc2CN1C[C@H]1CCCCN1S(=O)(=O)C1CC1] | | 453.1 |
| 42 | 2-(((2R)-1-(cyclopropylcarbonyl)piperidin-2-yl)methyl)-6-(5-(difluoromethyl)-1,3,4-oxadiazol-2-yl)isoindolin-1-one | 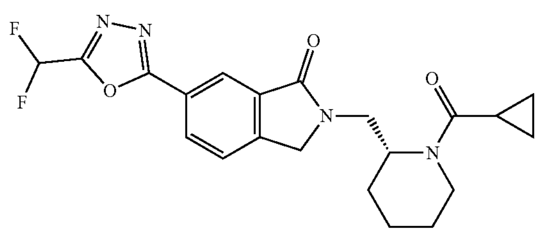 [SMILES: O=C1c2cc(-c3nnc(C(F)F)o3)ccc2CN1C[C@H]1CCCCN1C(=O)C1CC1] | | 417.1 |
| 43 | isopropyl (2R)-2-((6-(5-(difluoromethyl)-1,3,4-oxadiazol-2-yl)-1-oxo-1,3-dihydro-2H-isoindol-2-yl)methyl)piperidine-1-carboxylate | 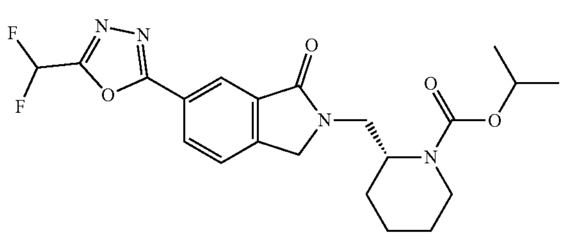 [SMILES: CC(C)OC(=O)N1CCCC[C@@H]1CN1Cc2ccc(-c3nnc(C(F)F)o3)cc2C1=O] | | 435.1 |

TABLE 1-5-continued

| EXAMPLE | IUPAC NAME | Structure | ADDITIVE | MS |
|---|---|---|---|---|
| 44 | 2-(((3S)-4-(cyclopropylsulfonyl)morpholin-3-yl)methyl)-6-(5-(difluoromethyl)-1,3,4-oxadiazol-2-yl)isoindolin-1-one | 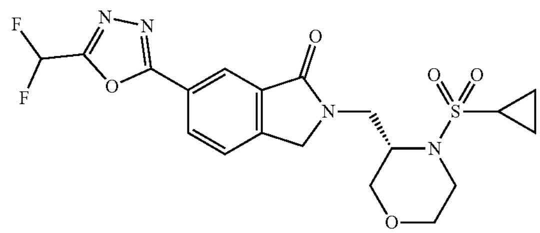 [SMILES: O=C1c2cc(-c3nnc(C(F)F)o3)ccc2CN1C[C@H]1COCCN1S(=O)(=O)C1CC1] | | 455.1 |
| 45 | 2-(((3S)-4-(cyclopropylcarbonyl)morpholin-3-yl)methyl)-6-(5-(difluoromethyl)-1,3,4-oxadiazol-2-yl)isoindolin-1-one | 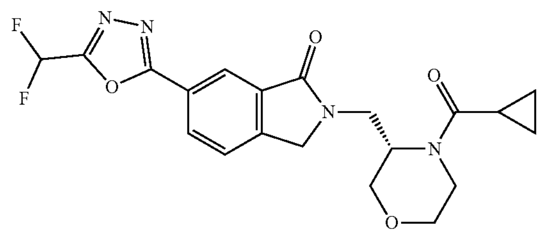 [SMILES: O=C1c2cc(-c3nnc(C(F)F)o3)ccc2CN1C[C@H]1COCCN1C(=O)C1CC1] | | 419.1 |
| 46 | isopropyl (3S)-3-((6-(5-(difluoromethyl)-1,3,4-oxadiazol-2-yl)-1-oxo-1,3-dihydro-2H-isoindol-2-yl)methyl)morpholine-4-carboxylate | 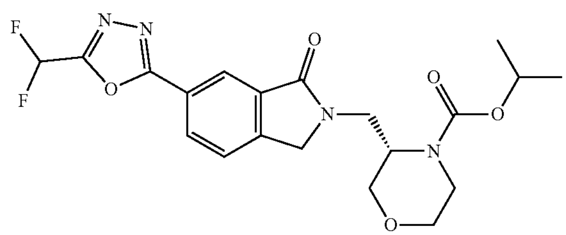 [SMILES: CC(C)OC(=O)N1CCOC[C@@H]1CN1Cc2ccc(-c3nnc(C(F)F)o3)cc2C1=O] | | 437.1 |
| 47 | 2-(((3S)-4-(cyclopentylcarbonyl)morpholin-3-yl)methyl)-6-(5-difluoromethyl)-1,3,4-oxadiazol-2-yl)isoindolin-1-one | 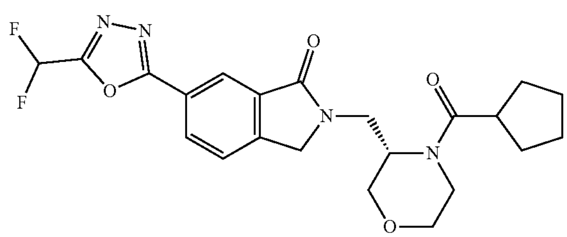 [SMILES: O=C1c2cc(-c3nnc(C(F)F)o3)ccc2CN1C[C@H]1COCCN1C(=O)C1CCCC1] | | 447.1 |
| 48 | methyl (3S)-3-((6-(5-(difluoromethyl)-1,3,4-oxadiazol-2-yl)-1-oxo-1,3-dihydro-2H-isoindol-2-yl)methyl)morpholine-4-carboxylate | 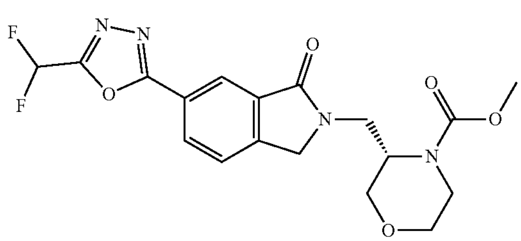 [SMILES: COC(=O)N1CCOC[C@@H]1CN1Cc2ccc(-c3nnc(C(F)F)o3)cc2C1=O] | | 409.0 |
| 49 | 6-(5-(difluoromethyl)-1,3,4-oxadiazol-2-yl)-2-(((3S)-4-((4-methylphenyl)sulfonyl)morpholin-3-yl)methyl)isoindolin-1-one | 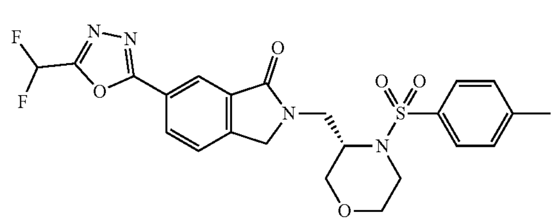 [SMILES: Cc1ccc(S(=O)(=O)N2CCOC[C@@H]2CN2Cc3ccc(-c4nnc(C(F)F)o4)cc3C2=O)cc1] | | 505.0 |

TABLE 1-5-continued

| EXAMPLE | IUPAC NAME | Structure | ADDITIVE | MS |
|---|---|---|---|---|
| 50 | N-((1R,2R)-2-(6-(5-(difluoromethyl)-1,3,4-oxadiazol-2-yl)-1-oxo-1,3-dihydro-2H-isoindol-2-yl)cyclohexyl)butanamide | 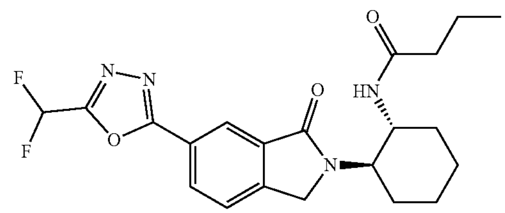 [SMILES: CCCC(=O)N[C@@H]1CCCC[C@H]1N1Cc2ccc(-c3nnc(C(F)F)o3)cc2C1=O] | | 419.1 |

TABLE 1-6

| EXAMPLE | IUPAC NAME | Structure | ADDITIVE | MS |
|---|---|---|---|---|
| 51 | N-((1R,2R)-2-(6-(5-(difluoromethyl)-1,3,4-oxadiazol-2-yl)-1-oxo-1,3-dihydro-2H-isoindol-2-yl)cyclohexyl)hexanamide | 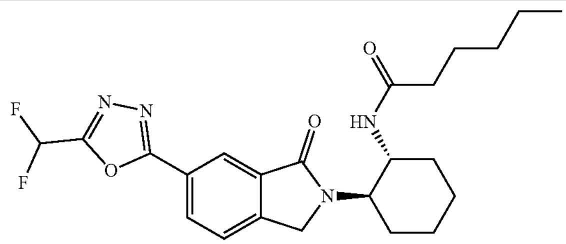 [SMILES: CCCCCC(=O)N[C@@H]1CCCC[C@H]1N1Cc2ccc(-c3nnc(C(F)F)o3)cc2C1=O] | | 447.1 |
| 52 | ethyl ((1R,2R)-2-(6-(5-(difluoromethyl)-1,3,4-oxadiazol-2-yl)-1-oxo-1,3-dihydro-2H-isoindol-2-yl)cyclohexyl)carbamate | 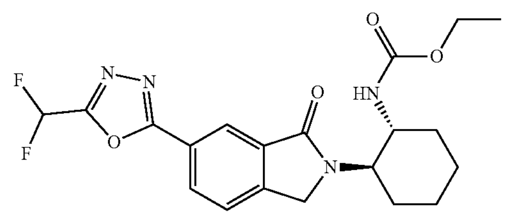 [SMILES: CCOC(=O)N[C@@H]1CCCC[C@H]1N1Cc2ccc(-c3nnc(C(F)F)o3)cc2C1=O] | | 421.1 |
| 53 | 6-(5-(difluoromethyl)-1,3,4-oxadiazol-2-yl)-2-((1R,2R)-2-(4-oxo-5-azaspiro[2.4]hept-5-yl)cyclohexyl)isoindolin-1-one | 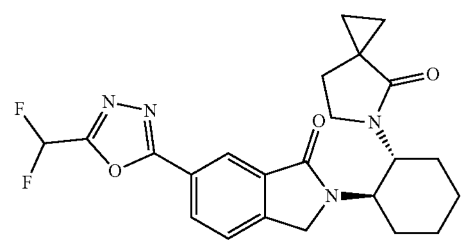 [SMILES: O=C1c2cc(-c3nnc(C(F)F)o3)ccc2CN1[C@@H]1CCCC[C@H]1N1CCC2(CC2)C1=O] | | 443.1 |
| 54 | 2-((1R,2R)-2-(3,5-diethyl-1H-pyrazol-1-yl)cyclohexyl)-6-(5-(difluoromethyl)-1,3,4-oxadiazol-2-yl)isoindolin-1-one | 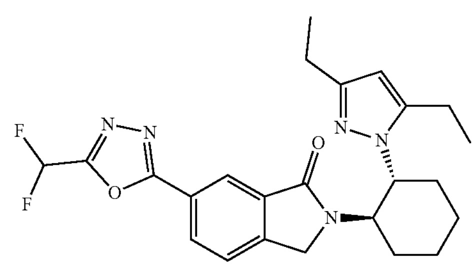 [SMILES: CCc1cc(CC)n([C@@H]2CCCC[C@H]2N2Cc3ccc(-c4nnc(C(F)F)o4)cc3C2=O)n1] | | 456.1 |
| 55 | 6-(5-(difluoromethyl)-1,3,4-oxadiazol-2-yl)-2-((1R,2R)-2-(2H-indazol-2-yl)cyclohexyl)isoindolin-1-one | 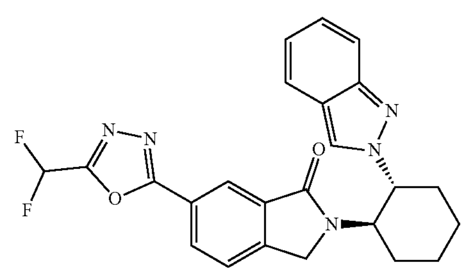 [SMILES: O=C1c2cc(-c3nnc(C(F)F)o3)ccc2CN1[C@@H]1CCCC[C@H]1n1cc2ccccc2n1] | | 450.1 |

TABLE 1-6-continued

| EXAMPLE | IUPAC NAME | Structure | ADDITIVE | MS |
|---|---|---|---|---|
| 56 | 2-(cyclopropylmethyl)-6-(5-(difluoromethyl)-1,3,4-oxadiazol-2-yl)isoindolin-1-one | 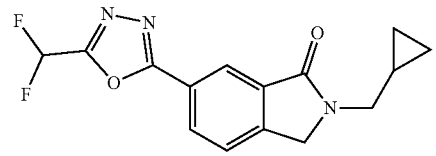 [SMILES: O=C1c2cc(-c3nnc(C(F)F)o3)ccc2CN1CC1CC1] | | 306.1 |
| 58 | 2-benzyl-6-(5-(difluoromethyl)-1,3,4-oxadiazol-2-yl)isoindolin-1-one | 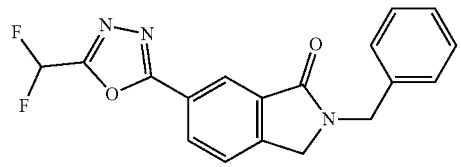 [SMILES: O=C1c2cc(-c3nnc(C(F)F)o3)ccc2CN1Cc1ccccc1] | | 342.0 |
| 59 | 6-(5-(difluoromethyl)-1,3,4-oxadiazol-2-yl)-2-(4-(trifluoromethyl)benzyl)isoindolin-1-one | 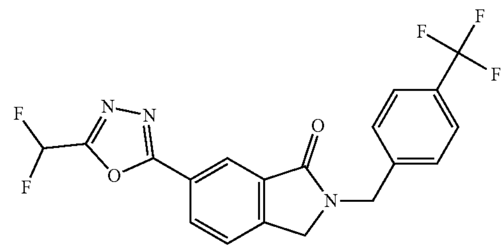 [SMILES: O=C1c2cc(-c3nnc(C(F)F)o3)ccc2CN1Cc1ccc(C(F)(F)F)cc1] | | 408.0 |
| 60 | 6-(5-(difluoromethyl)-1,3,4-oxadiazol-2-yl)-2-(pyridin-2-ylmethyl)isoindolin-1-one | 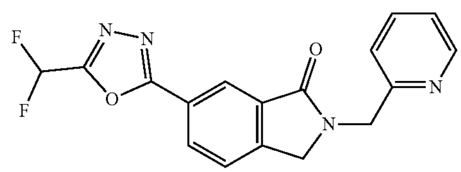 [SMILES: O=C1c2cc(-c3nnc(C(F)F)o3)ccc2CN1Cc1ccccn1] | | 343.1 |

TABLE 1-7

| EXAMPLE | IUPAC NAME | Structure | ADDITIVE | MS |
|---|---|---|---|---|
| 61 | 6-(5-(difluoromethyl)-1,3,4-oxadiazol-2-yl)-2-((1R,2R)-2-(3,5-dimethyl-1H-pyrazol-1-yl)cyclohexyl)isoindolin-1-one | 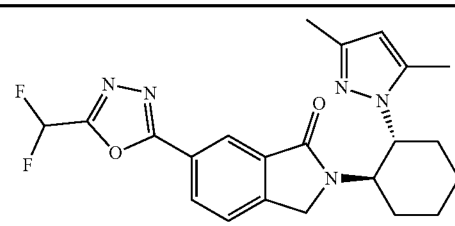 | | 428.2 |
| 62 | tert-butyl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate | 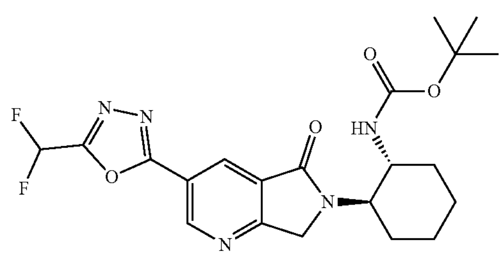 [SMILES: CC(C)(C)OC(=O)N[C@@H]1CCCC[C@H]1N1Cc2ncc(-c3nnc(C(F)F)o3)cc2C1=O] | | 448.1 |
| 63 | 2-cyclopropyl-N-((1R,2R)-2-(6-(5-(difluoromethyl)-1,3,4-oxadiazol-2-yl)-1-oxo-1,3-dihydro-2H-isoindol-2-yl)cyclohexyl)acetamide | 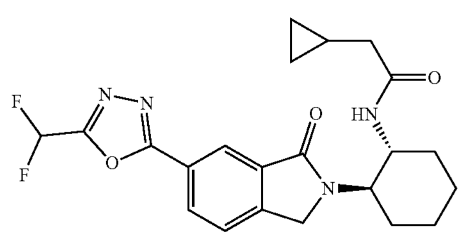 [SMILES: O=C(CC1CC1)N[C@@H]1CCCC[C@H]1N1Cc2ccc(-c3nnc(C(F)F)o3)cc2C1=O] | | 431.1 |

TABLE 1-7-continued

| EXAMPLE | IUPAC NAME | Structure | ADDITIVE | MS |
|---|---|---|---|---|
| 64 | N-((1R,2R)-2-(6-(5-(difluoromethyl)-1,3,4-oxadiazol-2-yl)-1-oxo-1,3-dihydro-2H-isoindol-2-yl)cyclohexyl)-4,4-difluorobutanamide | 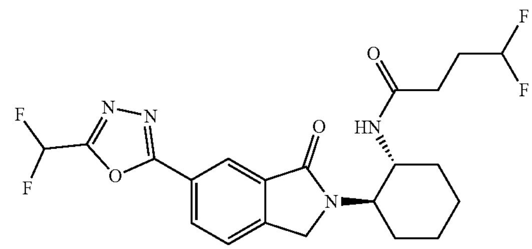 [SMILES: O=C(CCC(F)F)N[C@@H]1CCCC[C@H]1N1Cc2ccc(-c3nnc(C(F)F)o3)cc2C1=O] | | 455.1 |
| 65 | N-((1R,2R)-2-(6-(5-(difluoromethyl)-1,3,4-oxadiazol-2-yl)-1-oxo-1,3-dihydro-2H-isoindol-2-yl)cyclohexyl)-4,4,4-trifluorobutanamide | 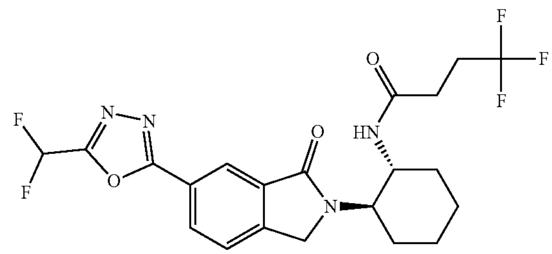 [SMILES: O=C(CCC(F)(F)F)N[C@@H]1CCCC[C@H]1N1Cc2ccc(-c3nnc(C(F)F)o3)cc2C1=O] | | 473.1 |
| 66 | N-((1R,2R)-2-(6-(5-(difluoromethyl)-1,3,4-oxadiazol-2-yl)-1-oxo-1,3-dihydro-2H-isoindol-2-yl)cyclohexyl)-2-fluoropropanamide | 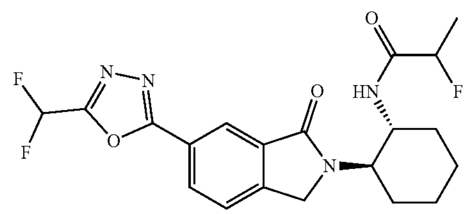 [SMILES: CC(F)C(=O)N[C@@H]1CCCC[C@H]1N1Cc2ccc(-c3nnc(C(F)F)o3)cc2C1=O] | | 423.1 |
| 67 | N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluorobutanamide | 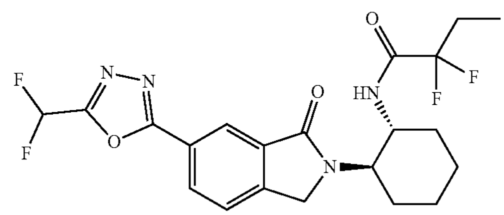 [SMILES: CCC(F)(F)C(=O)N[C@@H]1CCCC[C@H]1N1Cc2ccc(-c3nnc(C(F)F)o3)cc2C1=O] | | 455.1 |
| 68 | N-((1R,2R)-2-(6-(5-(difluoromethyl)-1,3,4-oxadiazol-2-yl)-1-oxo-1,3-dihydro-2H-isoindol-2-yl)cyclohexyl)-1-methoxycyclopropanecarboxamide | 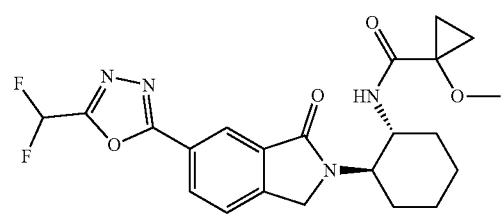 [SMILES: COC1(C(=O)N[C@@H]2CCCC[C@H]2N2Cc3ccc(-c4nnc(C(F)F)o4)cc3C2=O)CC1] | | 447.1 |
| 69 | (1SR,2RS)-N-((1R,2R)-2-(6-(5-(difluoromethyl)-1,3,4-oxadiazol-2--yl)-1-oxo-1,3-dihydro-2H-isoindol-2-yl)cyclohexyl)-2-fluorocyclopropanecarboxamide | 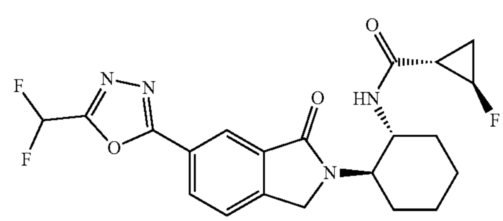 [SMILES: O=C(N[C@@H]1CCCC[C@H]1N1Cc2ccc(-c3nnc(C(F)F)o3)cc2C1=O)[C@@H]1C[C@H]1F] | | 435.1 |
| 70 | N-((1R,2R)-2-(6-(5-(difluoromethyl)-1,3,4-oxadiazol-2-yl)-1-oxo-1,3-dihydro-2H-isoindol-2-yl)cyclohexyl)-2-fluorocyclopropanecarboxamide | 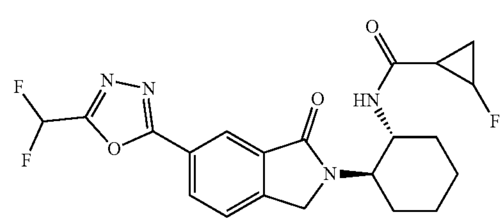 [SMILES: O=C(N[C@@H]1CCCC[C@H]1N1Cc2ccc(-c3nnc(C(F)F)o3)cc2C1=O)C1CC1F] | | 435.1 |

TABLE 1-8

| EXAMPLE | IUPAC NAME | Structure | ADDITIVE | MS |
|---|---|---|---|---|
| 71 | 2-(difluoromethyl)-N-((1R,2R)-2-(6-(5-(difluoromethyl)-1,3,4-oxadiazol-2-yl)-1-oxo-1,3-dihydro-2H-isoindol-2-yl)cyclohexyl)cyclopropanecarboxamide (optical isomer) | 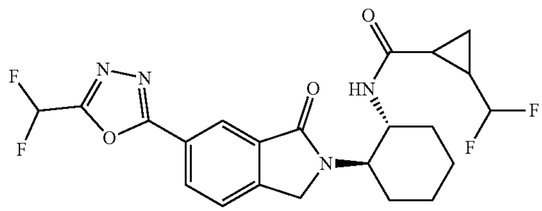 [SMILES: O=C(N[C@@H]1CCCC[C@H]1N1Cc2ccc(-c3nnc(C(F)F)o3)cc2C1=O)C1CC1C(F)F] | | 467.1 |
| 72 | N-((1R,2R)-2-(6-(5-(difluoromethyl)-1,3,4-oxadiazol-2-yl)-1-oxo-1,3-dihydro-2H-isoindol-2-yl)cyclohexyl)spiro[2.3]hexane-1-carboxamide (optical isomer) | 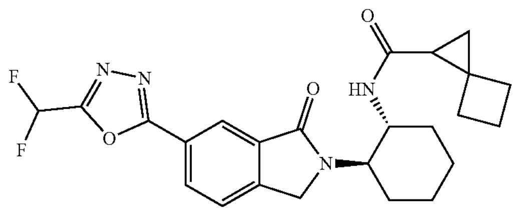 [SMILES: O=C(N[C@@H]1CCCC[C@H]1N1Cc2ccc(-c3nnc(C(F)F)o3)cc2C1=O)C1CC12CCC2] | | 457.2 |
| 73 | N-((1R,2R)-2-(6-(5-(difluoromethyl)-1,3,4-oxadiazol-2-yl)-1-oxo-1,3-dihydro-2H-isoindol-2-yl)cyclohexyl)-2-methylcyclopropanecarboxamide | 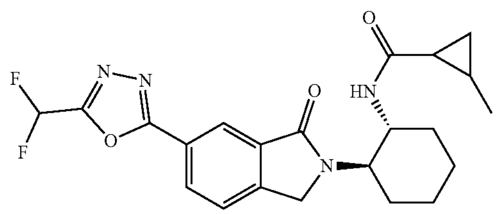 [SMILES: CC1CC1C(=O)N[C@@H]1CCCC[C@H]1N1Cc2ccc(-c3nnc(C(F)F)o3)cc2C1=O] | | 431.1 |
| 74 | N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluorocyclopropanecarboxamide (optical isomer) | 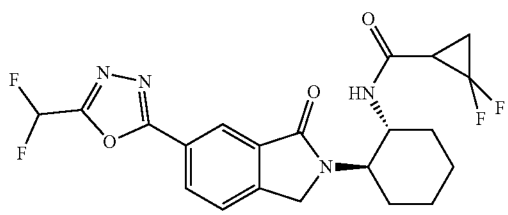 [SMILES: O=C(N[C@@H]1CCCC[C@H]1N1Cc2ccc(-c3nnc(C(F)F)o3)cc2C1=O)C1CC1(F)F] | | 453.1 |
| 75 | N-((1R,2R)-2-(6-(5-(difluoromethyl)-1,3,4-oxadiazol-2-yl)-1-oxo-1,3-dihydro-2H-isoindol-2-yl)cyclohexyl)-2,2-dimethylcyclopropanecarboxamide | 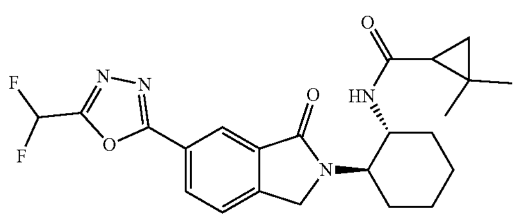 [SMILES: CC1(C)CC1C(=O)N[C@@H]1CCCC[C@H]1N1Cc2ccc(-c3nnc(C(F)F)o3)cc2C1=O] | | 445.2 |
| 76 | N-((1R,2R)-2-(6-(5-(difluoromethyl)-1,3,4-oxadiazol-2-yl)-1-oxo-1,3-dihydro-2H-isoindol-2-yl)cyclohexyl)-1-hydroxycyclobutanecarboxamide | 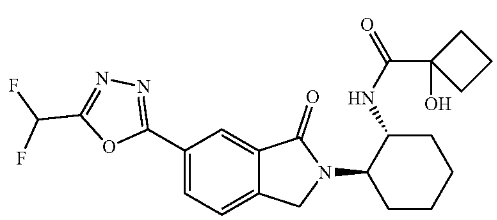 [SMILES: O=C1c2cc(-c3nnc(C(F)F)o3)ccc2CN1[C@@H]1CCCC[C@H]1NC(=O)C1(O)CCC1] | | 447.0 |
| 77 | N-((1R,2R)-2-(6-(5-(difluoromethyl)-1,3,4-oxadiazol-2-yl)-1-oxo-1,3-dihydro-2H-isoindol-2-yl)cyclohexyl)-1-fluorocyclobutanecarboxamide | 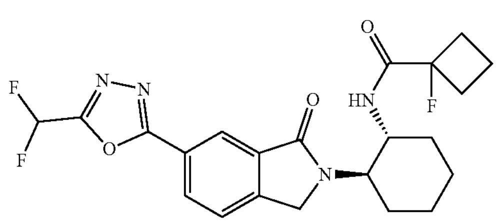 [SMILES: O=C1c2cc(-c3nnc(C(F)F)o3)ccc2CN1[C@@H]1CCCC[C@H]1NC(=O)C1(F)CCC1] | | 449.1 |

TABLE 1-8-continued

| EXAMPLE | IUPAC NAME | Structure | ADDITIVE | MS |
|---|---|---|---|---|
| 78 | 1-cyano-N-((1R,2R)-2-(6-(5-(difluoromethyl)-1,3,4-oxadiazol-2-yl)-1-oxo-1,3-dihydro-2H-isoindol-2-yl)cyclohexyl)cyclobutanecarboxamide | 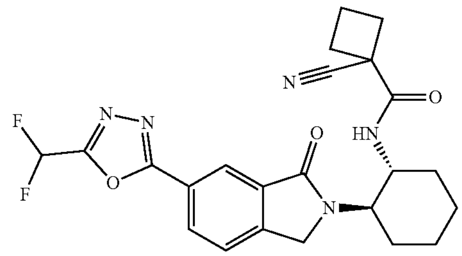 [SMILES: N#CC1(C(=O)N[C@@H]2CCCC[C@H]2N2Cc3ccc(-c4nnc(C(F)F)o4)cc3C2=O)CCC1] | | 456.1 |
| 79 | N-((1R,2R)-2-(6-(5-(difluoromethyl)-1,3,4-oxadiazol-2-yl)-1-oxo-1,3-dihydro-2H-isoindol-2-yl)cyclohexyl)spiro[3.3]heptane-2-carboxamide | 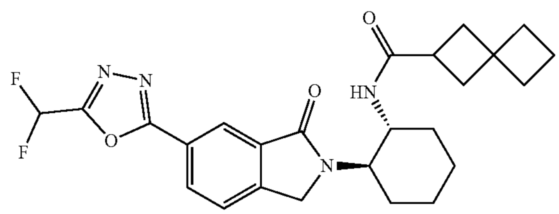 [SMILES: O=C(N[C@@H]1CCCC[C@H]1N1Cc2ccc(-c3nnc(C(F)F)o3)cc2C1=O)C1CC2(CCC2)C1] | | 471.1 |
| 80 | N-((1R,2R)-2-(6-(5-(difluoromethyl)-1,3,4-oxadiazol-2-yl)-1-oxo-1,3-dihydro-2H-isoindol-2-yl)cyclohexyl)-3-(trifluoromethyl)bicyclo[1.1.1]pentane-1-carboxamide | 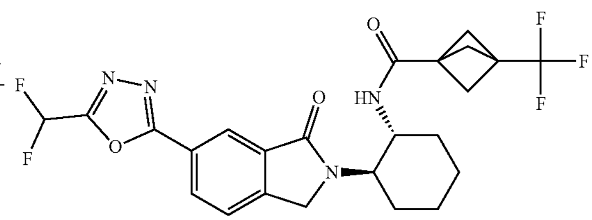 | | 511.1 |

TABLE 1-9

| EXAMPLE | IUPAC NAME | Structure | ADDITIVE | MS |
|---|---|---|---|---|
| 81 | N-((1R,2R)-2-(6-(5-(difluoromethyl)-1,3,4-oxadiazol-2-yl)-1-oxo-1,3-dihydro-2H-isoindol-2-yl)cyclohexyl)-2-hydroxy-2-methylpropanamide | 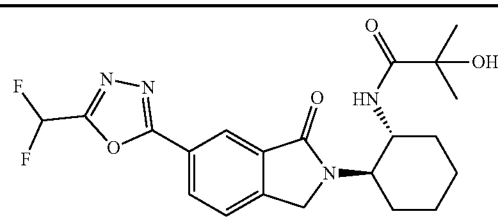 | | 435.1 |
| 82 | 2-cyano-N-((1R,2R)-2-(6-(5-(difluoromethyl)-1,3,4-oxadiazol-2-yl)-1-oxo-1,3-dihydro-2H-isoindol-2-yl)cyclohexyl)-2-methylpropanamide | 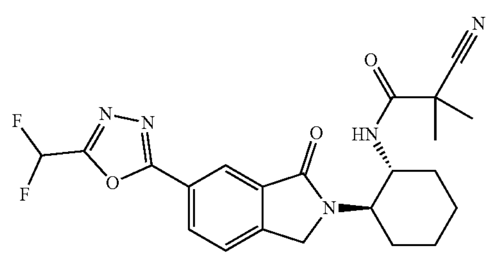 [SMILES: CC(C)(C#N)C(=O)N[C@@H]1CCCC[C@H]1N1Cc2ccc(-c3nnc(C(F)F)o3)cc2C1=O] | | 444.1 |
| 83 | N-((1R,2R)-2-(6-(5-(difluoromethyl)-1,3,4-oxadiazol-2-yl)-1-oxo-1,3-dihydro-2H-isoindol-2-yl)cyclohexyl)-3-hydroxy-3-methylbutanamide | 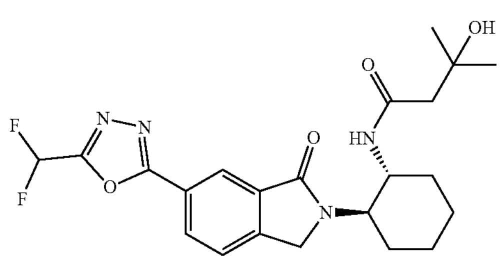 [SMILES: CC(C)(O)CC(=O)N[C@@H]1CCCC[C@H]1N1Cc2ccc(-c3nnc(C(F)F)o3)cc2C1=O] | | 449.1 |

TABLE 1-9-continued

| EXAMPLE | IUPAC NAME | Structure | ADDITIVE | MS |
|---|---|---|---|---|
| 84 | N-((1R,2R)-2-(6-(5-(difluoromethyl)-1,3,4-oxadiazol-2-yl)-1-oxo-1,3-dihydro-2H-isoindol-2-yl)cyclohexyl)-3,3,3-trifluoro-2,2-dimethylpropanamide | 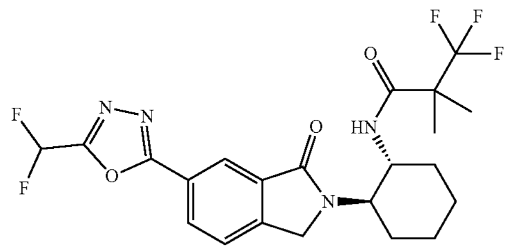 [SMILES: CC(C)(C(=O)N[C@@H]1CCCC[C@H]1N1Cc2ccc(-c3nnc(C(F)F)o3)cc2C1=O)C(F)(F)F] | | 487.1 |
| 85 | N-((1R,2R)-2-(6-(5-(difluoromethyl)-1,3,4-oxadiazol-2-yl)-1-oxo-1,3-dihydro-2H-isoindol-2-yl)cyclohexyl)-2-methoxy-2-methylpropanamide | 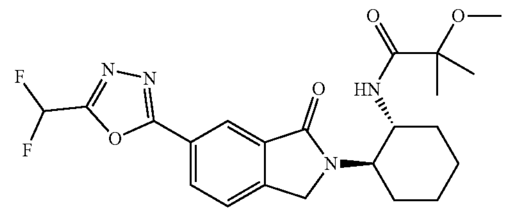 [SMILES: COC(C)(C)C(=O)N[C@@H]1CCCC[C@H]1N1Cc2ccc(-c3nnc(C(F)F)o3)cc2C1=O] | | 449.1 |
| 86 | 2-(1-cyanocyclopropyl)-N-((1R,2R)-2-(6-(5-(difluoromethyl)-1,3,4-oxadiazol-2-yl)-1-oxo-1,3-dihydro-2H-isoindol-2-yl)cyclohexyl)acetamide | 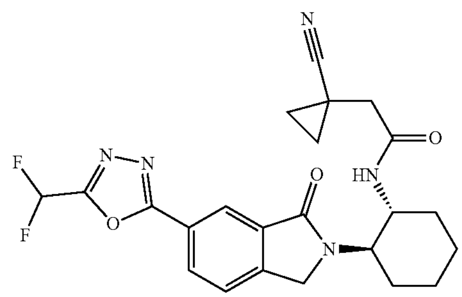 [SMILES: N#CC1(CC(=O)N[C@@H]2CCCC[C@H]2N2Cc3ccc(-c4nnc(C(F)F)o4)cc3C2=O)CC1] | | 456.1 |
| 87 | N-((1R,2R)-2-(6-(5-(difluoromethyl)-1,3,4-oxadiazol-2-yl)-1-oxo-1,3-dihydro-2H-isoindol-2-yl)cyclohexyl)-1-phenylcyclopropanecarboxamide | 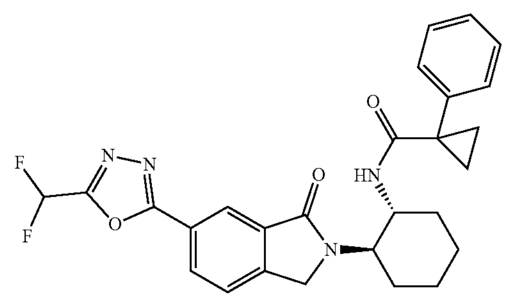 [SMILES: O=C1c2cc(-c3nnc(C(F)F)o3)ccc2CN1[C@@H]1CCCC[C@H]1NC(=O)C1(c2ccccc2)CC1] | | 493.2 |
| 88 | N-((1R,2R)-2-(6-(5-(difluoromethyl)-1,3,4-oxadiazol-2-yl)-1-oxo-1,3-dihydro-2H-isoindol-2-yl)cyclohexyl)-2-methyl-2-phenylpropanamide | 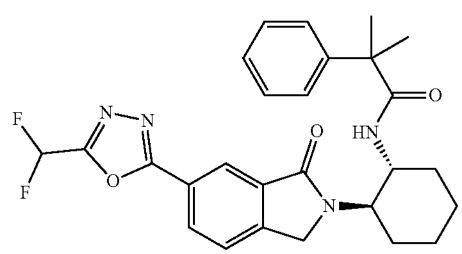 [SMILES: CC(C)(C(=O)N[C@@H]1CCCC[C@H]1N1Cc2ccc(-c3nnc(C(F)F)o3)cc2C1=O)c1ccccc1] | | 495.2 |
| 89 | N-((1R,2R)-2-(6-(5-(difluoromethyl)-1,3,4-oxadiazol-2-yl)-1-oxo-1,3-dihydro-2H-isoindol-2-yl)cyclohexyl)-1-phenylcyclobutanecarboxamide | 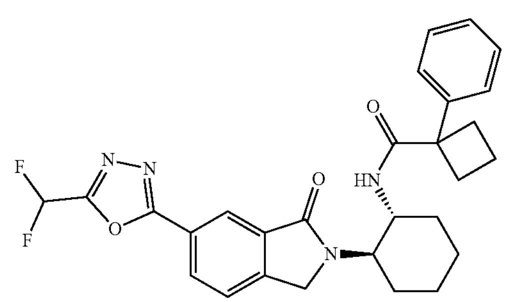 [SMILES: O=C1c2cc(-c3nnc(C(F)F)o3)ccc2CN1[C@@H]1CCCC[C@H]1NC(=O)C1(c2ccccc2)CCC1] | | 507.1 |

TABLE 1-9-continued

| EXAMPLE | IUPAC NAME | Structure | ADDITIVE | MS |
|---|---|---|---|---|
| 90 | N-((1R,2R)-2-(6-(5-(difluoromethyl)-1,3,4-oxadiazol-2-yl)-1-oxo-1,3-dihydro-2H-isoindol-2-yl)cyclohexyl)-3-phenyloxetane-3-carboxamide | 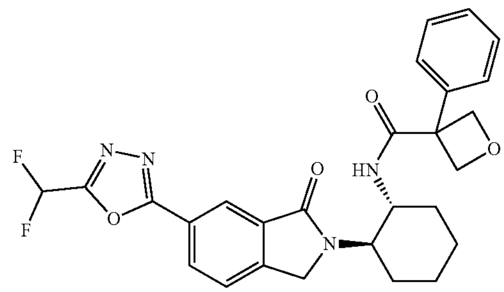 [SMILES: O=C1c2cc(-c3nnc(C(F)F)o3)ccc2CN1[C@@H]1CCCC[C@H]1NC(=O)C1(c2ccccc2)COC1] | | 509.2 |

TABLE 1-10

| EXAMPLE | IUPAC NAME | Structure | ADDITIVE | MS |
|---|---|---|---|---|
| 91 | N-((1R,2R)-2-(6-(5-(difluoromethyl)-1,3,4-oxadiazol-2-yl)-1-oxo-1,3-dihydro-2H-isoindol-2-yl)cyclohexyl)oxetane-3-carboxamide | 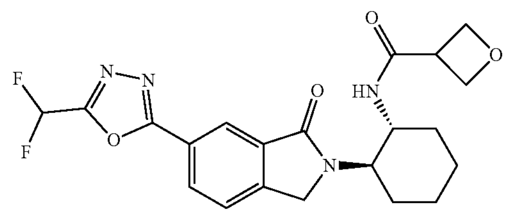 [SMILES: O=C(N[C@@H]1CCCC[C@H]1N1Cc2ccc(-c3nnc(C(F)F)o3)cc2C1=O)C1COC1] | | 433.1 |
| 92 | N-((1R,2R)-2-(6-(5-(difluoromethyl)-1,3,4-oxadiazol-2-yl)-1-oxo-1,3-dihydro-2H-isoindol-2-yl)cyclohexyl)-3-ethyloxetane-3-carboxamide | 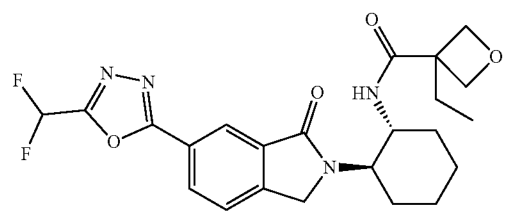 [SMILES: CCC1(C(=O)N[C@@H]2CCCC[C@H]2N2Cc3ccc(-c4nnc(C(F)F)o4)cc3C2=O)COC1] | | 461.2 |
| 93 | (2S)-N-((1R,2R)-2-(6-(5-(difluoromethyl)-1,3,4-oxadiazol-2-yl)-1-oxo-1,3-dihydro-2H-isoindol-2-yl)cyclohexyl)tetrahydrofuran-2-carboxamide | 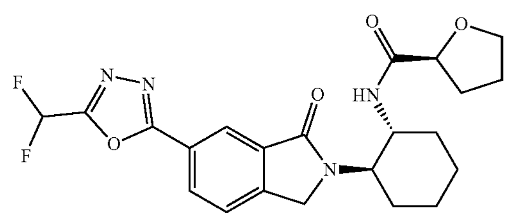 [SMILES: O=C(N[C@@H]1CCCC[C@H]1N1Cc2ccc(-c3nnc(C(F)F)o3)cc2C1=O)[C@@H]1CCCO1] | | 447.1 |
| 94 | (3R)-N-((1R,2R)-2-(6-(5-(difluoromethyl)-1,3,4-oxadiazol-2-yl)-1-oxo-1,3-dihydro-2H-isoindol-2-yl)cyclohexyl)tetrahydrofuran-2-carboxamide | 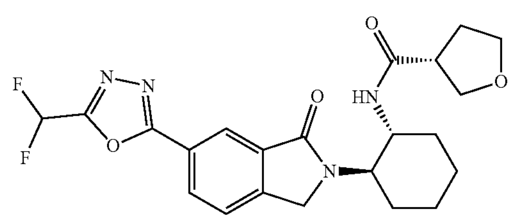 [SMILES: O=C(N[C@@H]1CCCC[C@H]1N1Cc2ccc(-c3nnc(C(F)F)o3)cc2C1=O)[C@@H]1CCOC1] | | 447.1 |
| 95 | N-((1R,2R)-2-(6-(5-(difluoromethyl)-1,3,4-oxadiazol-2-yl)-1-oxo-1,3-dihydro-2H-isoindol-2-yl)cyclohexyl)tetrahydro-2H-pyran-4-carboxamide | 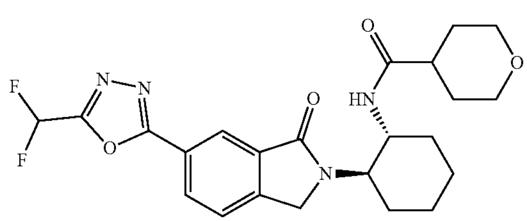 [SMILES: O=C(N[C@@H]1CCCC[C@H]1N1Cc2ccc(-c3nnc(C(F)F)o3)cc2C1=O)C1CCOCC1] | | 461.2 |

TABLE 1-10-continued

| EXAMPLE | IUPAC NAME | Structure | ADDITIVE | MS |
|---|---|---|---|---|
| 96 | N-((1R,2R)-2-(6-(5-(difluoromethyl)-1,3,4-oxadiazol-2-yl)-1-oxo-1,3-dihydro-2H-isoindol-2-yl)cyclohexyl)-1-methyl-1H-imidazole-5-carboxamide | 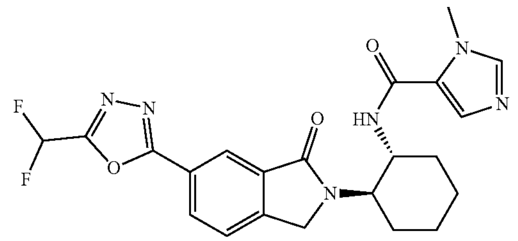 [SMILES: Cn1cncc1C(=O)N[C@@H]1CCCC[C@H]1N1Cc2ccc(-c3nnc(C(F)F)o3)cc2C1=O] | | 457.1 |
| 97 | N-((1R,2R)-2-(6-(5-(difluoromethyl)-1,3,4-oxadiazol-2-yl)-1-oxo-1,3-dihydro-2H-isoindol-2-yl)cyclohexyl)-1-methyl-1H-pyrazole-4-carboxamide | 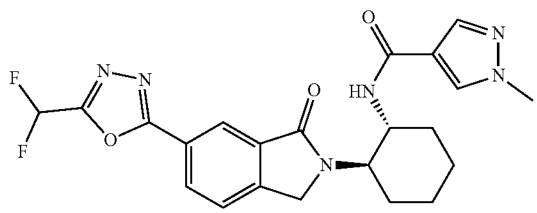 [SMILES: Cn1cc(C(=O)N[C@@H]2CCCC[C@H]2N2Cc3ccc(-c4nnc(C(F)F)o4)cc3C2=O)cn1] | | 457.1 |
| 98 | N-((1R,2R)-2-(6-(5-(difluoromethyl)-1,3,4-oxadiazol-2-yl)-1-oxo-1,3-dihydro-2H-isoindol-2-yl)cyclohexyl)benzamide | 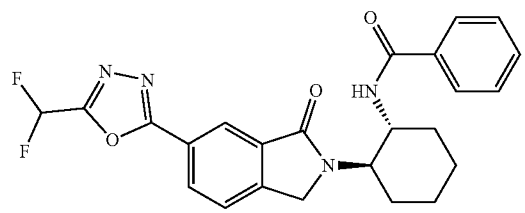 [SMILES: O=C(N[C@@H]1CCCC[C@H]1N1Cc2ccc(-c3nnc(C(F)F)o3)cc2C1=O)c1ccccc1] | | 453.1 |
| 99 | 2-chloro-N-((1R,2R)-2-(6-(5-(difluoromethyl)-1,3,4-oxadiazol-2-yl)-1-oxo-1,3-dihydro-2H-isoindol-2-yl)cyclohexyl)benzamide | 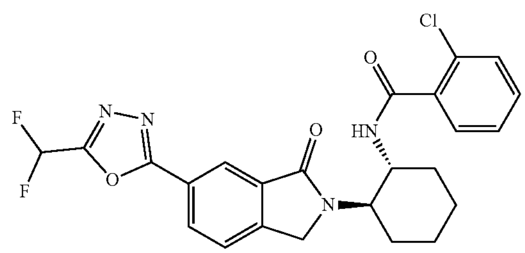 [SMILES: O=C(N[C@@H]1CCCC[C@H]1N1Cc2ccc(-c3nnc(C(F)F)o3)cc2C1=O)c1ccccc1Cl] | | 487.0 |
| 100 | 3-chloro-N-((1R,2R)-2-(6-(5-(difluoromethyl)-1,3,4-oxadiazol-2-yl)-1-oxo-1,3-dihydro-2H-isoindol-2-yl)cyclohexyl)benzamide | 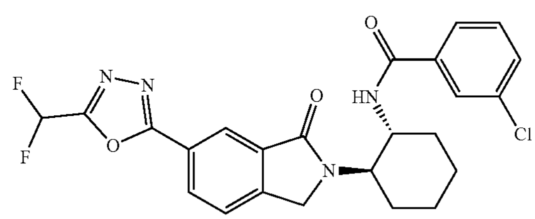 [SMILES: O=C(N[C@@H]1CCCC[C@H]1N1Cc2ccc(-c3nnc(C(F)F)o3)cc2C1=O)c1cccc(Cl)c1] | | 487.0 |

TABLE 1-11

| EXAMPLE | IUPAC NAME | Structure | ADDITIVE | MS |
|---|---|---|---|---|
| 101 | 4-chloro-N-((1R,2R)-2-(6-(5-(difluoromethyl)-1,3,4-oxadiazol-2-yl)-1-oxo-1,3-dihydro-2H-isoindol-2-yl)cyclohexyl)benzamide | 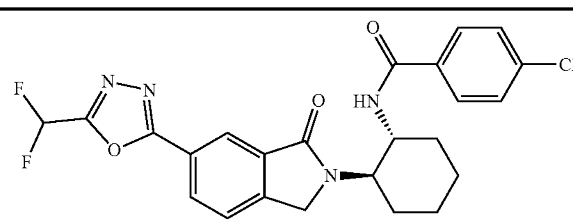 | | 487.0 |

TABLE 1-11-continued

| EXAMPLE | IUPAC NAME | Structure | ADDITIVE | MS |
|---|---|---|---|---|
| 102 | N-((1R,2R)-2-(6-(5-(difluoromethyl)-1,3,4-oxadiazol-2-yl)-1-oxo-1,3-dihydro-2H-isoindol-2-yl)cyclohexyl)-4,4-difluorocyclohexanecarboxamide | 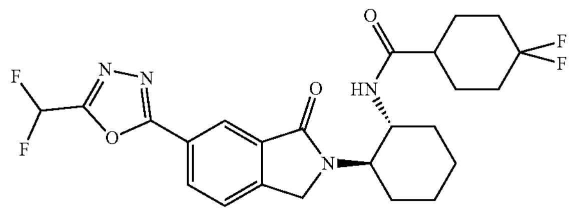 [SMILES: O=C(N[C@@H]1CCCC[C@H]1N1Cc2ccc(-c3nnc(C(F)F)o3)cc2C1=O)C1CCC(F)(F)CC1] | | 495.2 |
| 103 | (2S)-N-((1R,2R)-2-(6-(5-(difluoromethyl)-1,3,4-oxadiazol-2-yl)-1-oxo-1,3-dihydro-2H-isoindol-2-yl)cyclohexyl)-3,3,3-trifluoro-2-hydroxy-2-methylpropanamide | 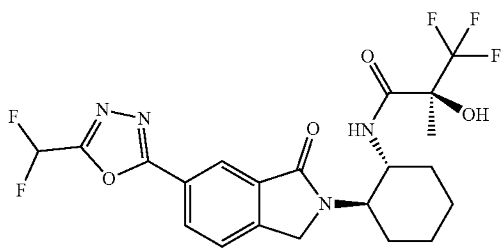 [SMILES: C[C@](O)(C(=O)N[C@@H]1CCCC[C@H]1N1Cc2ccc(-c3nnc(C(F)F)o3)cc2C1=O)C(F)(F)F] | | 487.1 |
| 104 | (2R)-N-((1R,2R)-2-(6-(5-(difluoromethyl)-1,3,4-oxadiazol-2-yl)-1-oxo-1,3-dihydro-2H-isoindol-2-yl)cyclohexyl)-3,3,3-trifluoro-2-hydroxy-2-methylpropanamide | 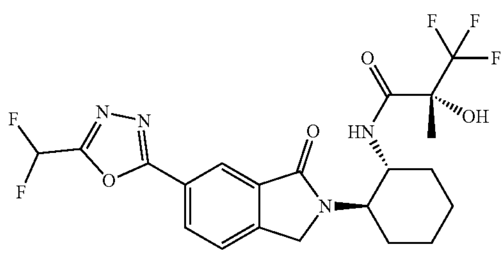 [SMILES: C[C@@](O)(C(=O)N[C@@H]1CCCC[C@H]1N1Cc2ccc(-c3nnc(C(F)F)o3)cc2C1=O)C(F)(F)F] | | 487.1 |
| 105 | N-((1R,2R)-2-(6-(5-(difluoromethyl)-1,3,4-oxadiazol-2-yl)-1-oxo-1,3-dihydro-2H-isoindol-2-yl)cyclohexyl)pyridine-2-carboxamide | 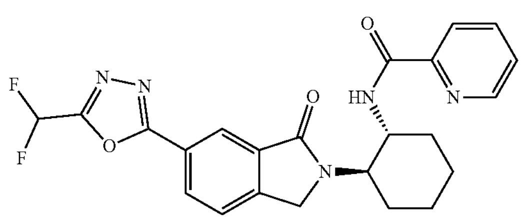 [SMILES: O=C(N[C@@H]1CCCC[C@H]1N1Cc2ccc(-c3nnc(C(F)F)o3)cc2C1=O)c1ccccn1] | | 454.1 |
| 106 | N-((1R,2R)-2-(6-(5-(difluoromethyl)-1,3,4-oxadiazol-2-yl)-1-oxo-1,3-dihydro-2H-isoindol-2-yl)cyclohexyl)-2-fluoro-2-methylpropanamide | 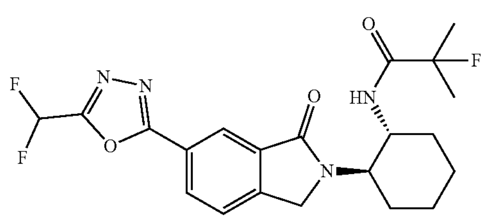 [SMILES: CC(C)(F)C(=O)N[C@@H]1CCCC[C@H]1N1Cc2ccc(-c3nnc(C(F)F)o3)cc2C1=O] | | 437.1 |
| 107 | N-((1R,2R)-2-(6-(5-(difluoromethyl)-1,3,4-oxadiazol-2-yl)-1-oxo-1,3-dihydro-2H-isoindol-2-yl)cyclohexyl)heptanamide | 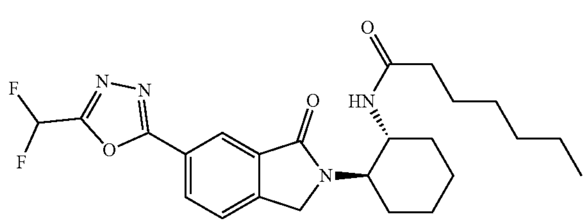 [SMILES: CCCCCCC(=O)N[C@@H]1CCCC[C@H]1N1Cc2ccc(-c3nnc(C(F)F)o3)cc2C1=O] | | 461.2 |

TABLE 1-11-continued

| EXAMPLE | IUPAC NAME | Structure | ADDITIVE | MS |
|---|---|---|---|---|
| 108 | N-((1R,2R)-2-(6-(5-(difluoromethyl)-1,3,4-oxadiazol-2-yl)-1-oxo-1,3-dihydro-2H-isoindol-2-yl)cyclohexyl)-1-(4-fluorophenyl)cyclopropanecarboxamide | 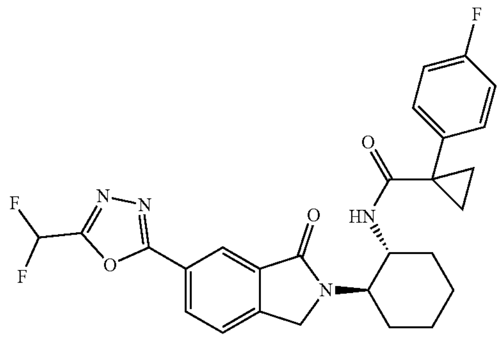 [SMILES: O=C1c2cc(-c3nnc(C(F)F)o3)ccc2CN1[C@@H]1CCCC[C@H]1NC(=O)C1(c2ccc(F)cc2)CC1] | | 511.1 |
| 109 | N-((1R,2R)-2-(6-(5-(difluoromethyl)-1,3,4-oxadiazol-2-yl)-1-oxo-1,3-dihydro-2H-isoindol-2-yl)cyclohexyl)-1-(4-fluorophenyl)cyclobutanecarboxamide | 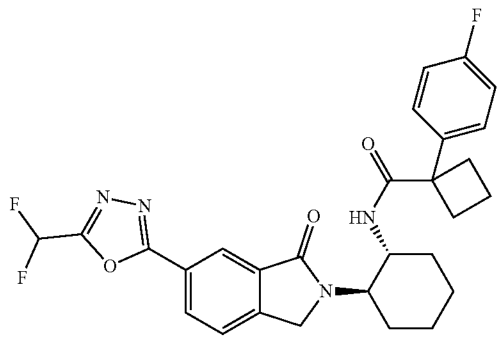 [SMILES: O=C1c2cc(-c3nnc(C(F)F)o3)ccc2CN1[C@@H]1CCCC[C@H]1NC(=O)C1(c2ccc(F)cc2)CCC1] | | 525.2 |
| 110 | 2-cyclobutyl-N-((1R,2R)-2-(6-(5-(difluoromethyl)-1,3,4-oxadiazol-2-yl)-1-oxo-1,3-dihydro-2H-isoindol-2-yl)cyclohexyl)acetamide | 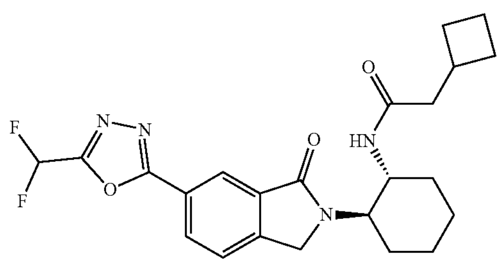 [SMILES: O=C(CC1CCC1)N[C@@H]1CCCC[C@H]1N1Cc2ccc(-c3nnc(C(F)F)o3)cc2C1=O] | | 445.1 |

TABLE 1-12

| EXAMPLE | IUPAC NAME | Structure | ADDITIVE | MS |
|---|---|---|---|---|
| 111 | (1RS,2RS)-N-((1R,2R)-2-(6-(5-(difluoromethyl)-1,3,4-oxadiazol-2-yl)-1-oxo-1,3-dihydro-2H-isoindol-2-yl)cyclohexyl)-2-fluorocyclopropanecarboxamide | 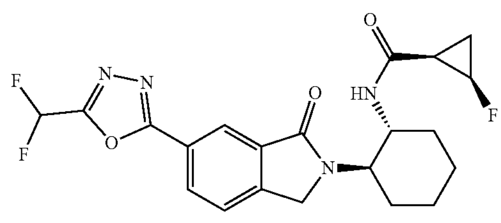 [SMILES: O=C(N[C@@H]1CCCC[C@H]1N1Cc2ccc(-c3nnc(C(F)F)o3)cc2C1=O)[C@H]1C[C@H]1F] | | 435.1 |
| 112 | 2-(2-bromophenyl)-6-(5-(difluoromethyl)-1,3,4-oxadiazol-2-yl)isoindolin-1-one | 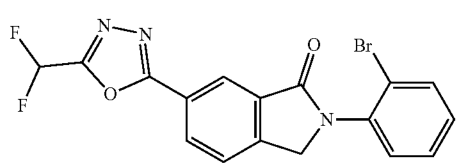 [SMILES: O=C1c2cc(-c3nnc(C(F)F)o3)ccc2CN1c1ccccc1Br] | | 406.0 |

TABLE 1-12-continued

| EXAMPLE | IUPAC NAME | Structure | ADDITIVE | MS |
|---|---|---|---|---|
| 113 | (2R)-N-((1R,2R)-2-(6-(5-(difluoromethyl)-1,3,4-oxadiazol-2-yl)-1-oxo-1,3-dihydro-2H-isoindol-2-yl)cyclohexyl)tetrahydrofuran-2-carboxamide | 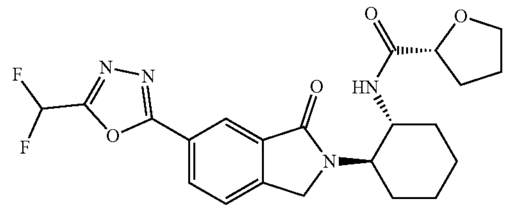 [SMILES: O=C(N[C@@H]1CCCC[C@H]1N1Cc2ccc(-c3nnc(C(F)F)o3)cc2C1=O)[C@H]1CCCO1] | | 447.1 |
| 114 | (3S)-N-((1R,2R)-2-(6-(5-(difluoromethyl)-1,3,4-oxadiazol-2-yl)-1-oxo-1,3-dihydro-2H-isoindol-2-yl)cyclohexyl)tetrahydrofuran-3-carboxamide | 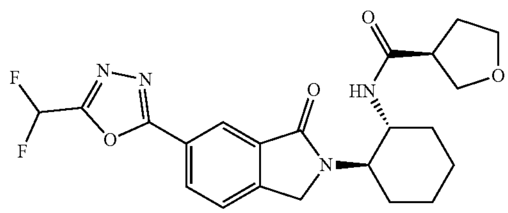 [SMILES: O=C(N[C@@H]1CCCC[C@H]1N1Cc2ccc(-c3nnc(C(F)F)o3)cc2C1=O)[C@H]1CCOC1] | | 447.1 |
| 115 | 2-((1R)-1-cyclopropylethyl)-6-(5-(difluoromethyl)-1,3,4-oxadiazol-2-yl)isoindolin-1-one | 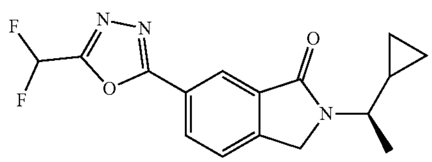 [SMILES: C[C@H](C1CC1)N1Cc2ccc(-c3nnc(C(F)F)o3)cc2C1=O] | | 320.1 |
| 116 | 2-((1S)-1-cyclopropylethyl)-6-(5-(difluoromethyl)-1,3,4-oxadiazol-2-yl)isoindolin-1-one | 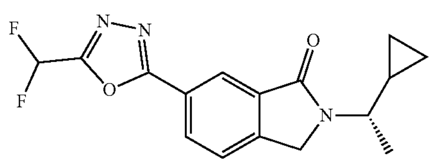 [SMILES: C[C@@H](C1CC1)N1Cc2ccc(-c3nnc(C(F)F)o3)cc2C1=O] | | 320.1 |
| 117 | 2-(trans-4-butoxycyclohexyl)-6-(5-(difluoromethyl)-1,3,4-oxadiazol-2-yl)isoindolin-1-one | 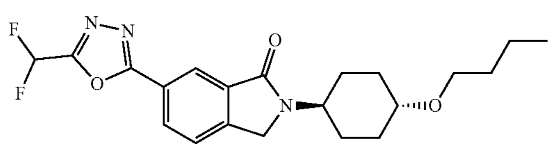 [SMILES: CCCCO[C@H]1CC[C@H](N2Cc3ccc(-c4nnc(C(F)F)o4)cc3C2=O)CC1] | | 406.1 |
| 119 | N-((1R,2R)-2-(6-(5-(difluoromethyl)-1,3,4-oxadiazol-2-yl)-1-oxo-1,3-dihydro-2H-isoindol-2-yl)cyclohexyl)spiro[2.3]hexane-1-carboxamide (optical isomer) | 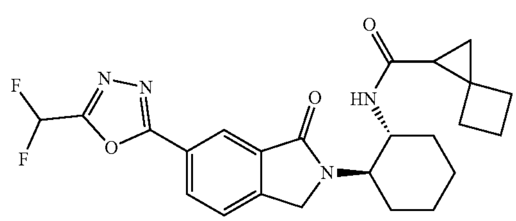 [SMILES: O=C(N[C@@H]1CCCC[C@H]1N1Cc2ccc(-c3nnc(C(F)F)o3)cc2C1=O)C1CC12CCC2] | | 457.2 |

TABLE 1-13

| EXAMPLE | IUPAC NAME | Structure | ADDITIVE | MS |
|---|---|---|---|---|
| 121 | N-((1R,2R)-2-(6-(5-(difluoromethyl)-1,3,4-oxadiazol-2-yl)-1-oxo-1,3-dihydro-2H-isoindol-2-yl)cyclohexyl)-2,2-difluorocyclopropanecarboxamide (optical isomer) | 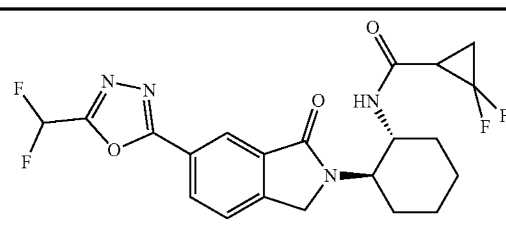 | | 453.1 |

TABLE 1-13-continued

| EXAMPLE | IUPAC NAME | Structure | ADDITIVE | MS |
|---|---|---|---|---|
| 122 | 6-(5-(difluoromethyl)-1,3,4-oxadiazol-2-yl)-2-(tetrahydro-2H-pyran-4-yl)isoindolin-1-one | 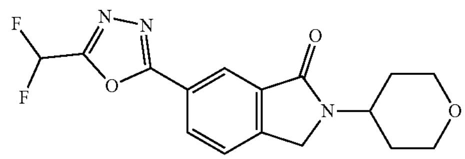 [SMILES: O=C1c2cc(-c3nnc(C(F)F)o3)ccc2CN1C1CCOCC1] | | 336.1 |
| 123 | 6-(5-(difluoromethyl)-1,3,4-oxadiazol-2-yl)-2-((1R,2R)-2-(1H-1,2,3-triazol-1-yl)cyclohexyl)isoindolin-1-one | 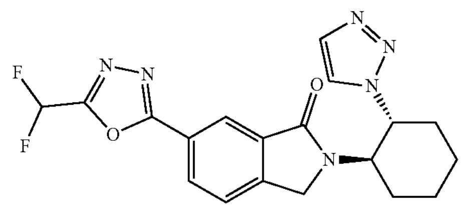 [SMILES: O=C1c2cc(-c3nnc(C(F)F)o3)ccc2CN1[C@@H]1CCCC[C@H]1n1ccnn1] | | 401.1 |
| 124 | 6-(5-(difluoromethyl)-1,3,4-oxadiazol-2-yl)-4-fluoro-2-((1R,2R)-2-(2-oxopyrrolidin-1-yl)cyclohexyl)isoindolin-1-one | 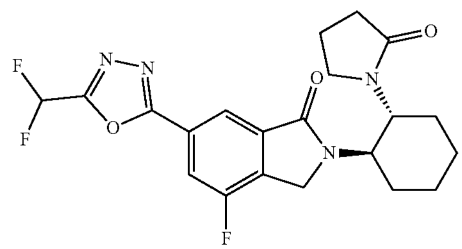 [SMILES: O=C1CCCN1[C@@H]1CCCC[C@H]1N1Cc2c(F)cc(-c3nnc(C(F)F)o3)cc2C1=O] | | 435.1 |
| 125 | tert-butyl (3S,4R)-4-(6-(5-(difluoromethyl)-1,3,4-oxadiazol-2-yl)-1-oxo-1,3-dihydro-2H-isoindol-2-yl)-3-phenylpiperidine-1-carboxylate | 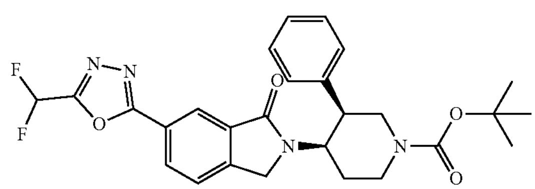 [SMILES: CC(C)(C)OC(=O)N1CC[C@@H](N2Cc3ccc(-c4nnc(C(F)F)o4)cc3C2=O)[C@@H](c2ccccc2)C1] | | 509.2 |
| 126 | 6-(5-(difluoromethyl)-1,3,4-oxadiazol-2-yl)-2-((3S,4R)-3-phenylpiperidin-4-yl)isoindolin-1-one | 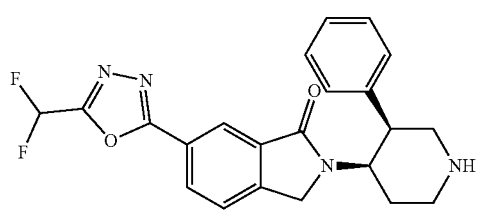 [SMILES: O=C1c2cc(-c3nnc(C(F)F)o3)ccc2CN1[C@@H]1CCNC[C@@H]1c1ccccc1] | | 411.2 |
| 127 | 2-((3S,4R)-1-acetyl-3-phenylpiperidin-4-yl)-6-(5-(difluoromethyl)-1,3,4-oxadiazol-2-yl)isoindolin-1-one | 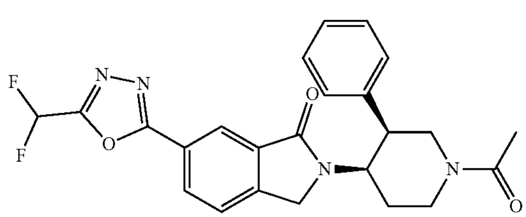 [SMILES: CC(=O)N1CC[C@@H](N2Cc3ccc(-c4nnc(C(F)F)o4)cc3C2=O)[C@@H](c2ccccc2)C1] | | 453.1 |
| 128 | methyl (3S,4R)-4-(6-(5-(difluoromethyl)-1,3,4-oxadiazol-2-yl)-1-oxo-1,3-dihydro-2H-isoindol-2-yl)-3-phenylpiperidine-1-carboxylate | 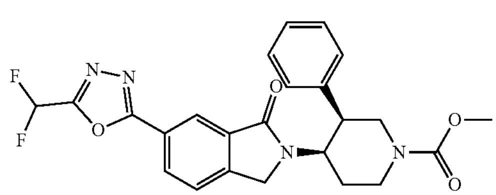 [SMILES: COC(=O)N1CC[C@@H](N2Cc3ccc(-c4nnc(C(F)F)o4)cc3C2=O)[C@@H](c2ccccc2)C1] | | 469.1 |

TABLE 1-13-continued

| EXAMPLE | IUPAC NAME | Structure | ADDITIVE | MS |
|---|---|---|---|---|
| 129 | 2-(biphenyl-2-yl)-6-(5-(difluoromethyl)-1,3,4-oxadiazol-2-yl)isoindolin-1-one | 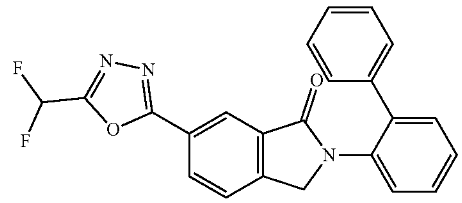 [SMILES: O=C1c2cc(-c3nnc(C(F)F)o3)ccc2CN1c1ccccc1-c1ccccc1] | | 404.1 |
| 130 | ethyl 4-(6-(5-(difluoromethyl)-1,3,4-oxadiazol-2-yl)-1-oxo-1,3-dihydro-2H-isoindol-2-yl)piperidine-1-carboxylate | 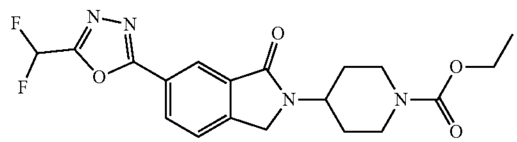 [SMILES: CCOC(=O)N1CCC(N2Cc3ccc(-c4nnc(C(F)F)o4)cc3C2=O)CC1] | | 407.1 |

TABLE 1-14

| EXAMPLE | IUPAC NAME | Structure | ADDITIVE | MS |
|---|---|---|---|---|
| 131 | 2,2-difluoroethyl ((1R,2R)-2-(6-(5-(difluoromethyl)-1,3,4-oxadiazol-2-yl)-1-oxo-1,3-dihydro-2H-isoindol-2-yl)cyclohexyl)carbamate | 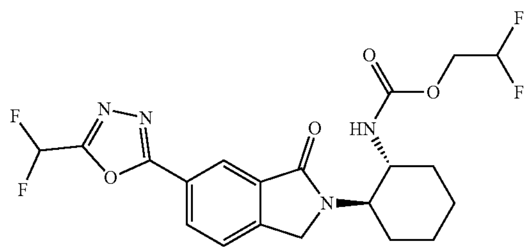 [SMILES: O=C(N[C@@H]1CCCC[C@H]1N1Cc2ccc(-c3nnc(C(F)F)o3)cc2C1=O)OCC(F)F] | | 457.1 |
| 132 | 3,3,3-trifluoropropyl ((1R,2R)-2-(6-(5-(difluoromethyl)-1,3,4-oxadiazol-2-yl)-1-oxo-1,3-dihydro-2H-isoindol-2-yl)cyclohexyl)carbamate | 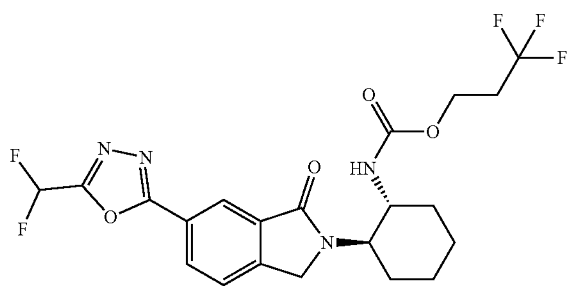 [SMILES: O=C(N[C@@H]1CCCC[C@H]1N1Cc2ccc(-c3nnc(C(F)F)o3)cc2C1=O)OCCC(F)(F)F] | | 489.1 |
| 133 | 6-(5-(difluoromethyl)-1,3,4-oxadiazol-2-yl)-2-(4'-(trifluoromethyl)biphenyl-2-yl)isoindolin-1-one | 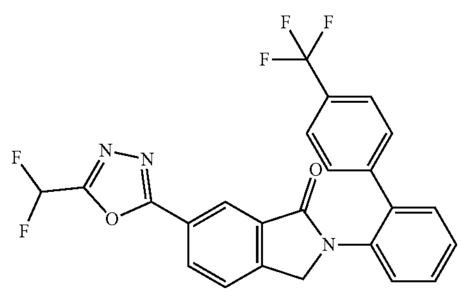 [SMILES: O=C1c2cc(-c3nnc(C(F)F)o3)ccc2CN1c1ccccc1-c1ccc(C(F)(F)F)cc1] | | 470.0 |
| 134 | 6-(5-(difluoromethyl)-1,3,4-oxadiazol-2-yl)-2-(4'-methoxybiphenyl-2-yl)isoindolin-1-one | 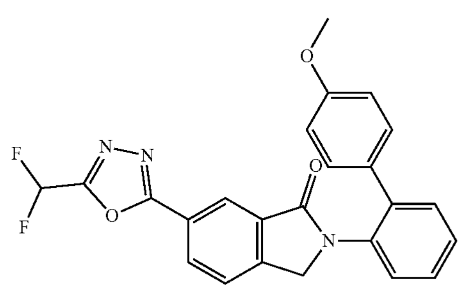 [SMILES: COc1ccc(-c2ccccc2N2Cc3ccc(-c4nnc(C(F)F)o4)cc3C2=O)cc1] | | 434.0 |

TABLE 1-14-continued

| EXAMPLE | IUPAC NAME | Structure | ADDITIVE | MS |
|---|---|---|---|---|
| 136 | 2-benzyl-6-(5-(difluoromethyl)-1,3,4-oxadiazol-2-yl)-4-fluoroisoindolin-1-one | 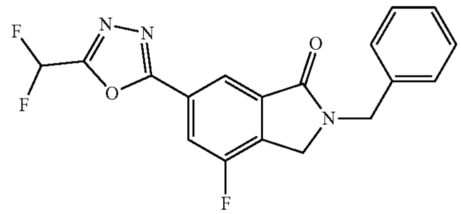 [SMILES: O=C1c2cc(-c3nnc(C(F)F)o3)cc(F)c2CN1Cc1ccccc1] | | 360.1 |
| 137 | 6-(5-(difluoromethyl)-1,3,4-oxadiazol-2-yl)-4-fluoro-2-((3S,4R)-3-(2-oxopiperidin-1-yl)tetrahydro-2H-pyran-4-yl)isoindolin-1-one | 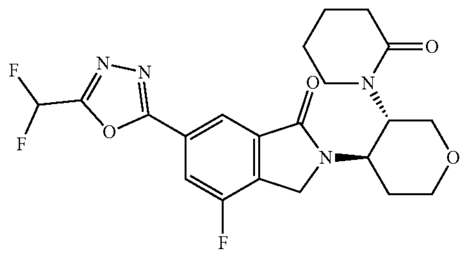 [SMILES: O=C1CCCCN1[C@@H]1COCC[C@H]1N1Cc2c(F)cc(-c3nnc(C(F)F)o3)cc2C1=O] | | 451.1 |
| 138 | 6-(5-(difluoromethyl)-1,3,4-oxadiazol-2-yl)-4-fluoro-2-((1R,2R)-2-(2-oxo-1,3-oxazolidin-3-yl)cyclohexyl)isoindolin-1-one | 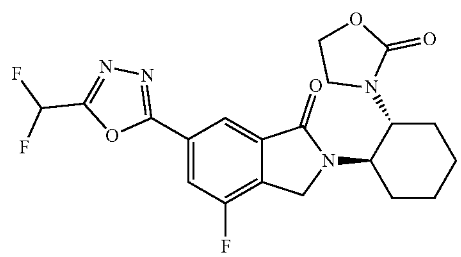 [SMILES: O=C1OCCN1[C@@H]1CCCC[C@H]1N1Cc2c(F)cc(-c3nnc(C(F)F)o3)cc2C1=O] | | 437.1 |
| 139 | 6-benzyl-3-(5-(difluoromethyl)-1,3,4-oxadiazol-2-yl)-6,7-dihydro-5H-pyrrolo[3,4-b]pyridin-5-one | 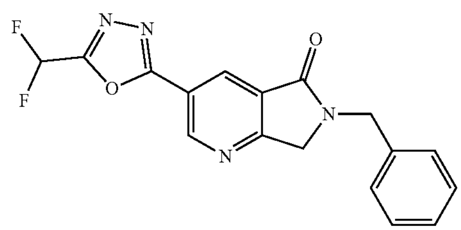 [SMILES: O=C1c2cc(-c3nnc(C(F)F)o3)cnc2CN1Cc1ccccc1] | | 343.1 |
| 140 | 3-(5-(difluoromethyl)-1,3,4-oxadiazol-2-yl)-6-((1R)-1-(4-fluorophenyl)ethyl)-6,7-dihydro-5H-pyrrolo[3,4-b]pyridin-5-one | 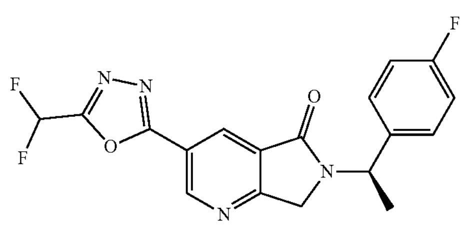 [SMILES: C[C@H](c1ccc(F)cc1)N1Cc2ncc(-c3nnc(C(F)F)o3)cc2C1=O] | | 373.0 |

TABLE 1-15

| EXAMPLE | IUPAC NAME | Structure | ADDITIVE | MS |
|---|---|---|---|---|
| 141 | 3-(5-(difluoromethyl)-1,3,4-oxadiazol-2-yl)-6-((1S)-1-(4-fluorophenyl)ethyl)-6,7-dihydro-5H-pyrrolo[3,4-b]pyridin-5-one | 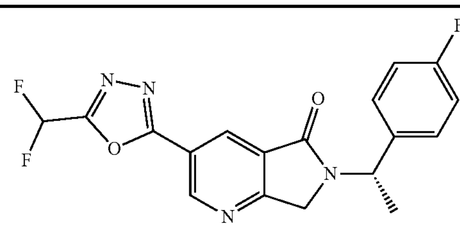 | | 373.0 |

TABLE 1-15-continued

| EXAMPLE | IUPAC NAME | Structure | ADDITIVE | MS |
| --- | --- | --- | --- | --- |
| 142 | benzyl ((1R,2R)-2-(5-(5-(difluoromethyl)-1,3,4-oxadiazol-2-yl)-1,3-dioxo-1,3-dihydro-2H-isoindol-2-yl)cyclohexyl)carbamate | 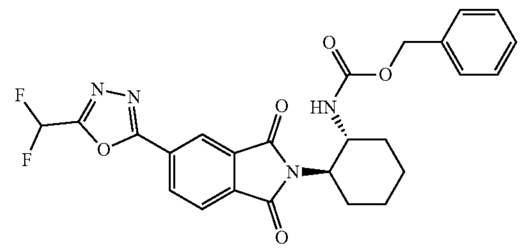 [SMILES: O=C(N[C@@H]1CCCC[C@H]1N1C(=O)c2ccc(-c3nnc(C(F)F)o3)cc2C1=O)OCc1ccccc1] | | 497.1 |
| 143 | 2-((3-chloropyridin-2-yl)methyl)-6-(5-(difluoromethyl)-1,3,4-oxadiazol-2-yl)isoindolin-1-one | 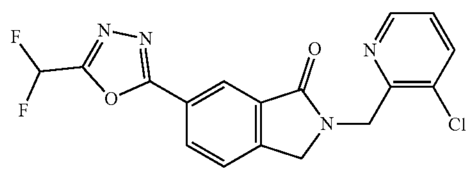 [SMILES: O=C1c2cc(-c3nnc(C(F)F)o3)ccc2CN1Cc1ncccc1Cl] | | 377.1 |
| 144 | 6-(5-(difluoromethyl)-1,3,4-oxadiazol-2-yl)-2-((5-(trifluoromethyl)pyridin-3-yl)methyl)isoindolin-1-one | 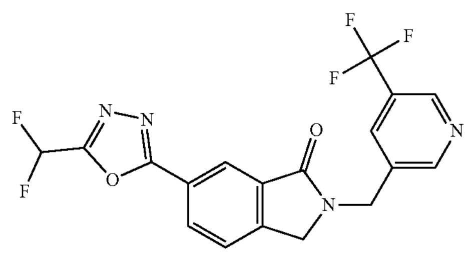 [SMILES: O=C1c2cc(-c3nnc(C(F)F)o3)ccc2CN1Cc1cncc(C(F)(F)F)c1] | | 411.1 |
| 145 | 6-(5-(difluoromethyl)-1,3,4-oxadiazol-2-yl)-2-(3-(methylsulfonyl)benzyl)isoindolin-1-one | 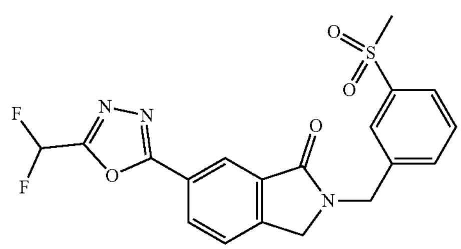 [SMILES: CS(=O)(=O)c1cccc(CN2Cc3ccc(-c4nnc(C(F)F)o4)cc3C2=O)c1] | | 420.0 |
| 146 | 2-((5-cyclopropyl-1,2-oxazol-3-yl)methyl)-6-(5-(difluoromethyl)-1,3,4-oxadiazol-2-yl)isoindolin-1-one | 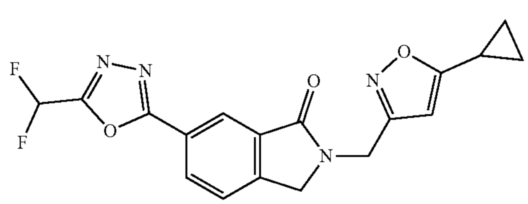 [SMILES: O=C1c2cc(-c3nnc(C(F)F)o3)ccc2CN1Cc1cc(C2CC2)on1] | | 373.1 |
| 147 | 6-(5-(difluoromethyl)-1,3,4-oxadiazol-2-yl)-2-((3,5-difluoropyridin-2-yl)methyl)isoindolin-1-one | 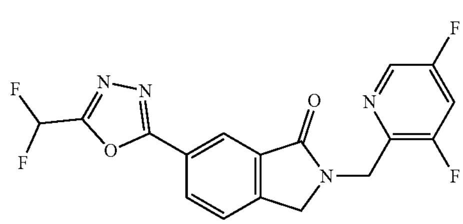 [SMILES: O=C1c2cc(-c3nnc(C(F)F)o3)ccc2CN1Cc1ncc(F)cc1F] | | 379.1 |

TABLE 1-15-continued

| EXAMPLE | IUPAC NAME | Structure | ADDITIVE | MS |
|---|---|---|---|---|
| 148 | tert-butyl ((1R,2R)-2-(6-(5-(difluoromethyl)-1,3,4-oxadiazol-2-yl)-4-fluoro-1-oxo-1,3-dihydro-2H-isoindol-2-yl)cyclohexyl)carbamate | 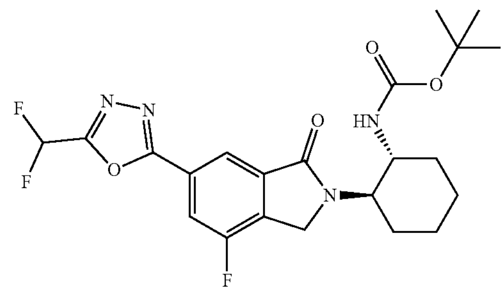 [SMILES: CC(C)(C)OC(=O)N[C@@H]1CCCC[C@H]1N1Cc2c(F)cc(-c3nnc(C(F)F)o3)cc2C1=O] | | 465.1 |
| 149 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-1-(trifluoromethyl)cyclopropanecarboxamide | 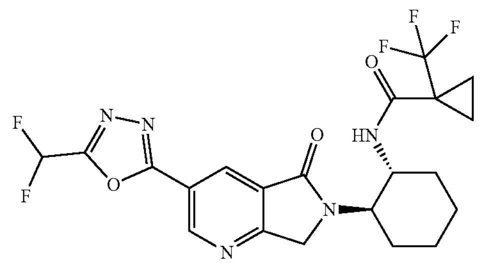 [SMILES: O=C1c2cc(-c3nnc(C(F)F)o3)cnc2CN1[C@@H]1CCCC[C@H]1NC(=O)C1(C(F)(F)F)CC1] | | 486.1 |
| 150 | cyclopropyl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate | 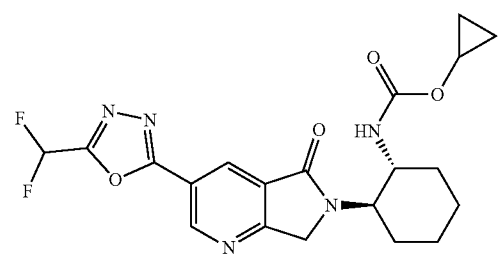 [SMILES: O=C(N[C@@H]1CCCC[C@H]1N1Cc2ncc(-c3nnc(C(F)F)o3)cc2C1=O)OC1CC1] | | 434.1 |

TABLE 1-16

| EXAMPLE | IUPAC NAME | Structure | ADDITIVE | MS |
|---|---|---|---|---|
| 151 | 6-(5-(difluoromethyl)-1,3,4-oxadiazol-2-yl)-2-(4-fluorobenzyl)isoindolin-1-one | 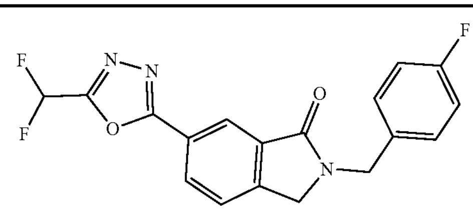 | | 360.0 |
| 152 | N-((1R,2R)-2-(6-(5-(difluoromethyl)-1,3,4-oxadiazol-2-yl)-4-fluoro-1-oxo-1,3-dihydro-2H-isoindol-2-yl)cyclohexyl)acetamide | 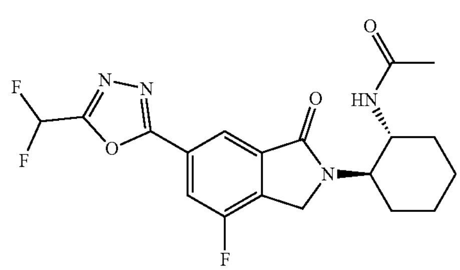 [SMILES: CC(=O)N[C@@H]1CCCC[C@H]1N1Cc2c(F)cc(-c3nnc(C(F)F)o3)cc2C1=O] | | 409.0 |

TABLE 1-16-continued

| EXAMPLE | IUPAC NAME | Structure | ADDITIVE | MS |
|---|---|---|---|---|
| 153 | methyl ((1R,2R)-2-(6-(5-(difluoromethyl)-1,3,4-oxadiazol-2-yl)-4-fluoro-1-oxo-1,3-dihydro-2H-isoindol-2-yl)cyclohexyl)carbamate | 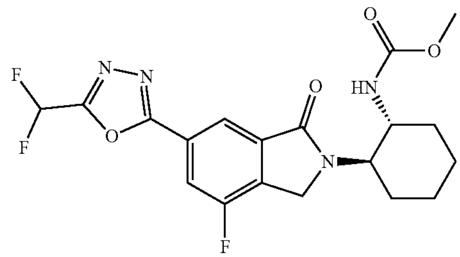 [SMILES: COC(=O)N[C@@H]1CCCC[C@H]1N1Cc2c(F)cc(-c3nnc(C(F)F)o3)cc2C1=O] | | 425.0 |
| 154 | (1R,2R)-2-(6-(5-(difluoromethyl)-1,3,4-oxadiazol-2-yl)-1-oxo-1,3-dihydro-2H-isoindol-2-yl)cyclohexyl methylcarbamate | 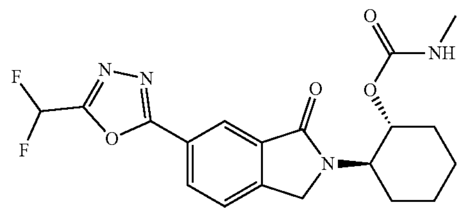 [SMILES: CNC(=O)O[C@@H]1CCCC[C@H]1N1Cc2ccc(-c3nnc(C(F)F)o3)cc2C1=O] | | 407.1 |
| 155 | 6-(5-(difluoromethyl)-1,3,4-oxadiazol-2-yl)-4-fluoro-2-(pyridin-2-ylmethyl)isoindolin-1-one | 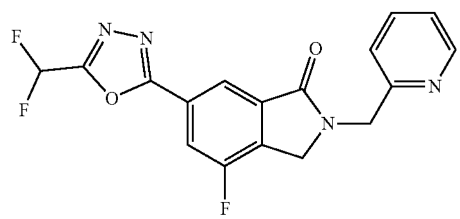 [SMILES: O=C1c2cc(-c3nnc(C(F)F)o3)cc(F)c2CN1Cc1ccccn1] | | 361.1 |
| 156 | 6-(5-(difluoromethyl)-1,3,4-oxadiazol-2-yl)-2-(2'-methoxybiphenyl-2-yl)isoindolin-1-one | 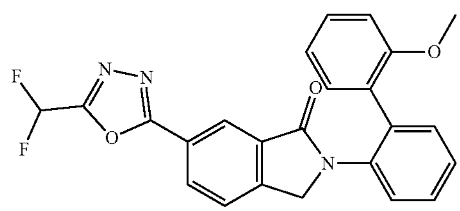 [SMILES: COc1ccccc1-c1ccccc1N1Cc2ccc(-c3nnc(C(F)F)o3)cc2C1=O] | | 434.0 |
| 157 | 6-(5-(difluoromethyl)-1,3,4-oxadiazol-2-yl)-2-((1R,2R)-2-(3-methyl-2-oxoimidazolidin-1-yl)cyclohexyl)isoindolin-1-one | 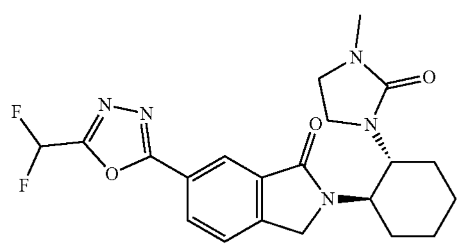 [SMILES: CN1CCN([C@@H]2CCCC[C@H]2N2Cc3ccc(-c4nnc(C(F)F)o4)cc3C2=O)C1=O] | | 432.1 |
| 158 | 6-(5-(difluoromethyl)-1,3,4-oxadiazol-2-yl)-2-(2-(1,3-dimethyl-1H-pyrazol-5-yl)phenyl)isoindolin-1-one | 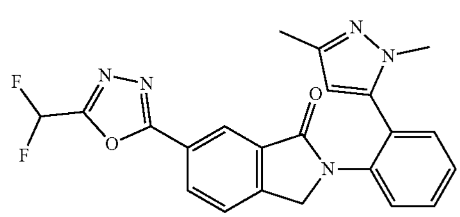 [SMILES: Cc1cc(-c2ccccc2N2Cc3ccc(-c4nnc(C(F)F)o4)cc3C2=O)n(C)n1] | | 422.1 |
| 159 | 6-(5-(difluoromethyl)-1,3,4-oxadiazol-2-yl)-2-(2-(1,3-dimethyl-1H-pyrazol-4-yl)phenyl)isoindolin-1-one | 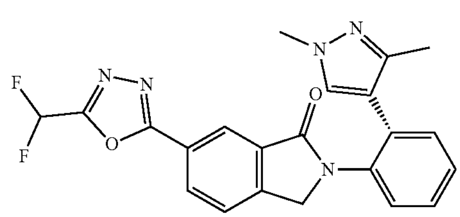 | | 422.1 |

TABLE 1-16-continued

| EXAMPLE | IUPAC NAME | Structure | ADDITIVE | MS |
|---|---|---|---|---|
| 160 | 6-(5-(difluoromethyl)-1,3,4-oxadiazol-2-yl)-2-(2-(1-methyl-1H-pyrazol-5-yl)phenyl)isoindolin-1-one | 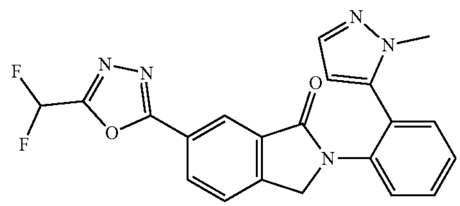 [SMILES: Cn1nccc1-c1ccccc1N1Cc2ccc(-c3nnc(C(F)F)o3)cc2C1=O] | | 408.0 |

TABLE 1-17

| EXAMPLE | IUPAC NAME | Structure | ADDITIVE | MS |
|---|---|---|---|---|
| 161 | methyl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate | 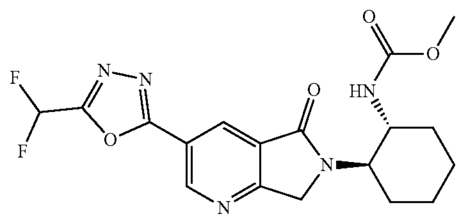 [SMILES: COC(=O)N[C@@H]1CCCC[C@H]1N1Cc2ncc(-c3nnc(C(F)F)o3)cc2C1=O] | | 408.1 |
| 162 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2-difluoropropanamide | 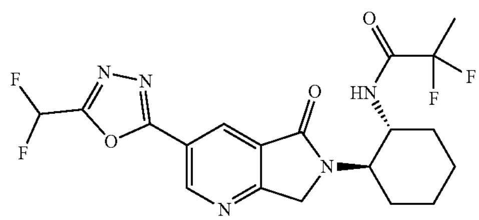 [SMILES: CC(F)(F)C(=O)N[C@@H]1CCCC[C@H]1N1Cc2ncc(-c3nnc(C(F)F)o3)cc2C1=O] | | 442.1 |
| 163 | 3-chloro-N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)benzamide | 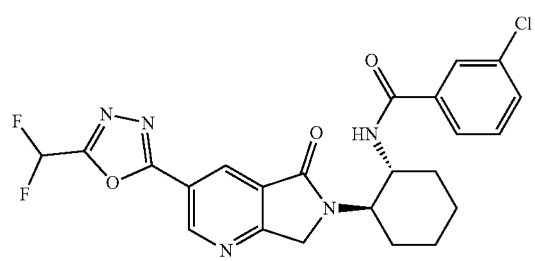 [SMILES: O=C(N[C@@H]1CCCC[C@H]1N1Cc2ncc(-c3nnc(C(F)F)o3)cc2C1=O)c1cccc(Cl)c1] | | 488.0 |
| 164 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)pyridine-2-carboxamide | 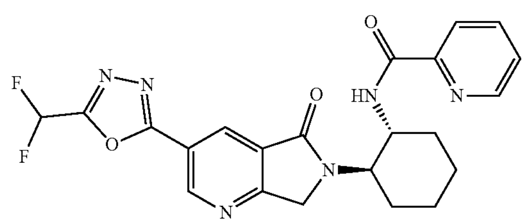 [SMILES: O=C(N[C@@H]1CCCC[C@H]1N1Cc2ncc(-c3nnc(C(F)F)o3)cc2C1=O)c1ccccn1] | | 455.1 |
| 165 | N-((1R,2R)-2-(6-(5-(difluoromethyl)-1,3,4-oxadiazol-2-yl)-4-fluoro-1-oxo-1,3-dihydro-2H-isoindol-2-yl)cyclohexyl)-2,2-difluoroacetamide | 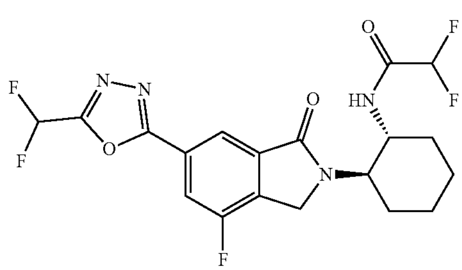 [SMILES: O=C(N[C@@H]1CCCC[C@H]1N1Cc2c(F)cc(-c3nnc(C(F)F)o3)cc2C1=O)C(F)F] | | 445.1 |

TABLE 1-17-continued

| EXAMPLE | IUPAC NAME | Structure | ADDITIVE | MS |
|---|---|---|---|---|
| 166 | N-((1R,2R)-2-(5-(5-(difluoromethyl)-1,3,4-oxadiazol-2-yl)-1,3-dioxo-1,3-dihydro-2H-isoindol-2-yl)cyclohexyl)propanamide | 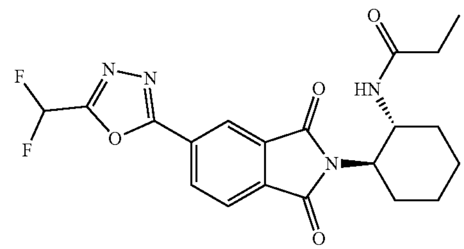 [SMILES: CCC(=O)N[C@@H]1CCCC[C@H]1N1C(=O)c2ccc(-c3nnc(C(F)F)o3)cc2C1=O] | | 419.1 |
| 167 | tert-butyl ((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)carbamate | 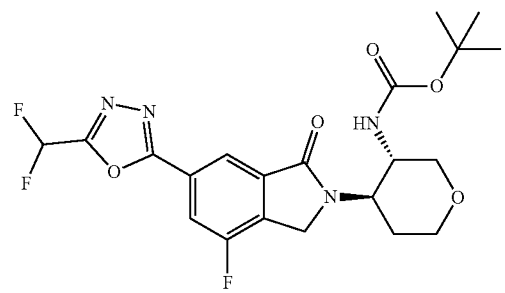 [SMILES: CC(C)(C)OC(=O)N[C@@H]1COCC[C@H]1N1Cc2c(F)cc(-c3nnc(C(F)F)o3)cc2C1=O] | | 467.1 |
| 168 | tert-butyl (3S)-3-((6-(5-(difluoromethyl)-1,3,4-oxadiazol-2-yl)-4-fluoro-1-oxo-1,3-dihydro-2H-isoindol-2-yl)methyl)morpholine-4-carboxylate | 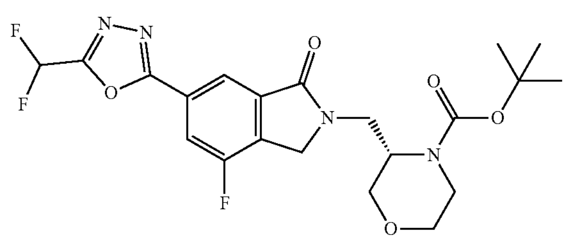 [SMILES: CC(C)(C)OC(=O)N1CCOC[C@@H]1CN1Cc2c(F)cc(-c3nnc(C(F)F)o3)cc2C1=O] | | 469.1 |
| 169 | 2'-(6-(5-(difluoromethyl)-1,3,4-oxadiazol-2-yl)-1-oxo-1,3-dihydro-2H-isoindol-2-yl)biphenyl-3-carbonitrile | 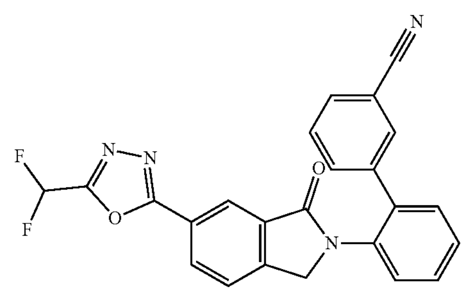 [SMILES: N#Cc1cccc(-c2ccccc2N2Cc3ccc(-c4nnc(C(F)F)o4)cc3C2=O)c1] | | 429.0 |
| 170 | 6-(5-(difluoromethyl)-1,3,4-oxadiazol-2-yl)-2-(3'-methoxybiphenyl-2-yl)isoindolin-1-one | 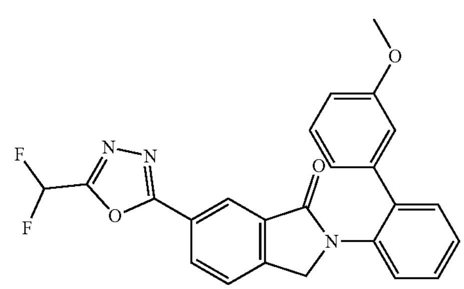 [SMILES: COc1cccc(-c2ccccc2N2Cc3ccc(-c4nnc(C(F)F)o4)cc3C2=O)c1] | | 434.0 |

TABLE 1-18

| EXAMPLE | IUPAC NAME | Structure | ADDITIVE | MS |
|---|---|---|---|---|
| 171 | 6-(5-(difluoromethyl)-1,3,4-oxadiazol-2-yl)-2-(3'-(trifluoromethyl)biphenyl-2-yl)isoindolin-1-one | 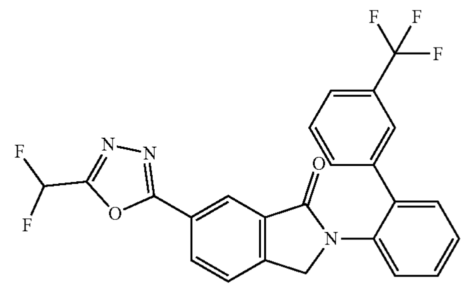 [SMILES: O=C1c2cc(-c3nnc(C(F)F)o3)ccc2CN1c1ccccc1-c1cccc(C(F)(F)F)c1] | | 472.0 |
| 172 | 6-(5-(difluoromethyl)-1,3,4-oxadiazol-2-yl)-2-(3'-(methylsulfonyl)biphenyl-2-yl)isoindolin-1-one | 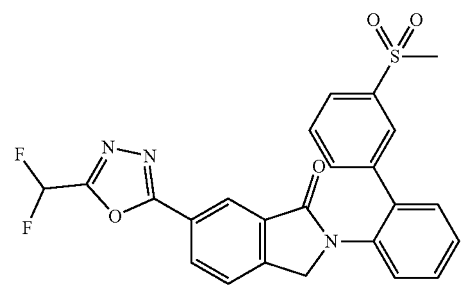 [SMILES: CS(=O)(=O)c1cccc(-c2ccccc2N2Cc3ccc(-c4nnc(C(F)F)o4)cc3C2=O)c1] | | 481.9 |
| 173 | 2-((1R,2R)-2-aminocyclohexyl)-6-(5-(difluoromethyl)-1,3,4-oxadiazol-2-yl)-4-fluoroisoindolin-1-one | 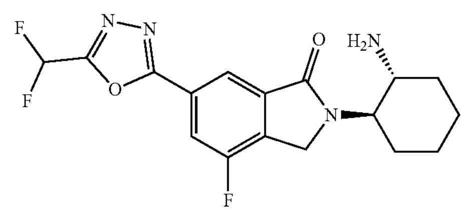 [SMILES: N[C@@H]1CCCC[C@H]1N1Cc2c(F)cc(-c3nnc(C(F)F)o3)cc2C1=O] | | 367.1 |
| 174 | N-((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-4-yl)-2,2,3,3,3-pentafluoropropanamide | 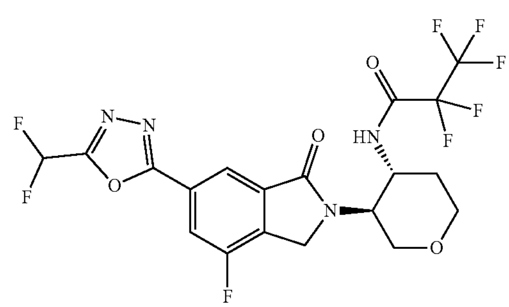 [SMILES: O=C1c2cc(-c3nnc(C(F)F)o3)cc(F)c2CN1[C@@H]1COCC[C@H]1NC(=O)C(F)(F)C(F)(F)F] | | 513.0 |
| 175 | N-((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-4-yl)-3,3,3-trifluoro-2,2-dimethylpropanamide | 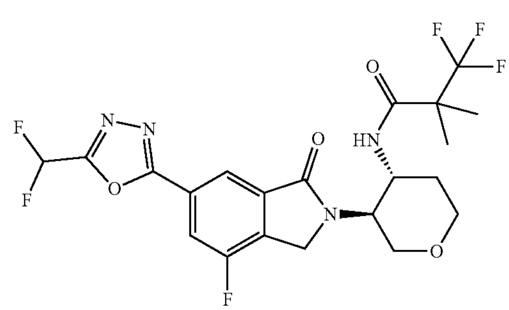 [SMILES: CC(C)(C(=O)N[C@@H]1CCOC[C@H]1N1Cc2c(F)cc(-c3nnc(C(F)F)o3)cc2C1=O)C(F)(F)F] | | 507.1 |

TABLE 1-18-continued

| EXAMPLE | IUPAC NAME | Structure | ADDITIVE | MS |
|---|---|---|---|---|
| 176 | N-((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-4-yl)-1-(trifluoromethyl)cyclopropanecarboxamide | 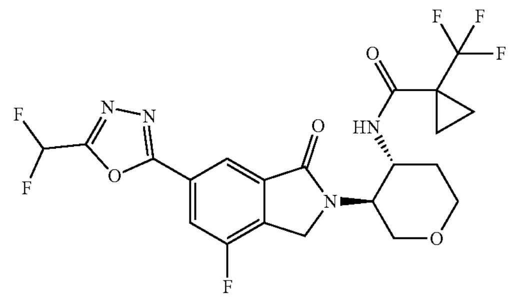 [SMILES: O=C1c2cc(-c3nnc(C(F)F)o3)cc(F)c2CN1[C@@H]1COCC[C@H]1NC(=O)C1(C(F)(F)F)CC1] | | 504.9 |
| 177 | 3-(5-(difluoromethyl)-1,3,4-oxadiazol-2-yl)-6-((1R,2R)-2-(2-oxopyrrolidin-1-yl)cyclohexyl)-6,7-dihydro-5H-pyrrolo[3,4-b]pyridin-5-one | 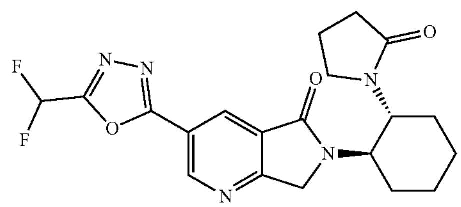 [SMILES: O=C1CCCN1[C@@H]1CCCC[C@H]1N1Cc2ncc(-c3nnc(C(F)F)o3)cc2C1=O] | | 418.0 |
| 178 | 6-(5-(difluoromethyl)-1,3,4-oxadiazol-2-yl)-2-(2-(4,4,5,5-tetramethyl-1,3,2-dioxaborolan-2-yl)phenyl)isoindolin-1-one | 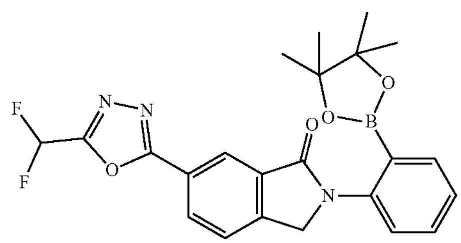 [SMILES: CC1(C)OB(c2ccccc2N2Cc3ccc(-c4nnc(C(F)F)o4)cc3C2=O)OC1(C)C] | | 454.1 |
| 179 | 3-(5-(difluoromethyl)-1,3,4-oxadiazol-2-yl)-6-((1R,2R)-2-(1-oxo-1,3-dihydro-2H-isoindol-2-yl)cyclohexyl)-6,7-dihydro-5H-pyrrolo[3,4-b]pyridin-5-one | 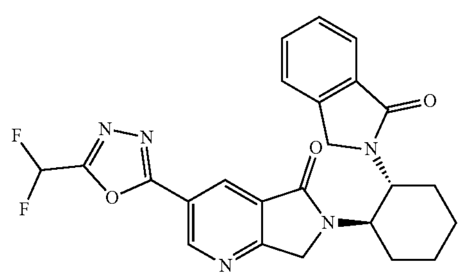 [SMILES: O=C1c2ccccc2CN1[C@@H]1CCCC[C@H]1N1Cc2ncc(-c3nnc(C(F)F)o3)cc2C1=O] | | 466.1 |
| 180 | 2-chloro-N-((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-4-yl)benzamide | 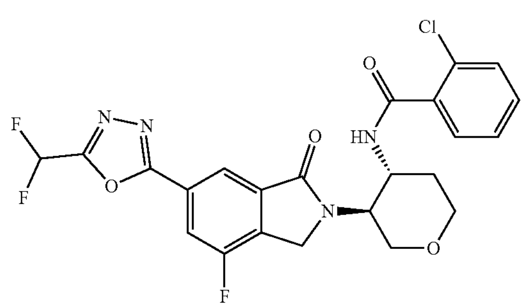 [SMILES: O=C(N[C@@H]1CCOC[C@H]1N1Cc2c(F)cc(-c3nnc(C(F)F)o3)cc2C1=O)c1ccccc1Cl] | | 507.0 |

TABLE 1-19

| EXAMPLE | IUPAC NAME | Structure | ADDITIVE | MS |
|---------|------------|-----------|----------|-----|
| 181 | 3-chloro-N-((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-4-yl)benzamide | 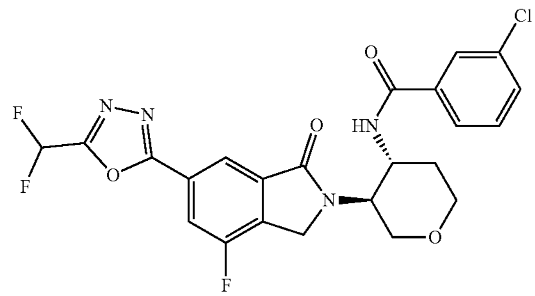 [SMILES: O=C(N[C@@H]1CCOC[C@H]1N1Cc2c(F)cc(-c3nnc(C(F)F)o3)cc2C1=O)c1cccc(Cl)c1] | | 507.0 |
| 182 | N-((1R,2R)-2-(6-(5-(difluoromethyl)-1,3,4-oxadiazol-2-yl)-4-fluoro-1-oxo-1,3-dihydro-2H-isoindol-2-yl)cyclohexyl)propanamide | 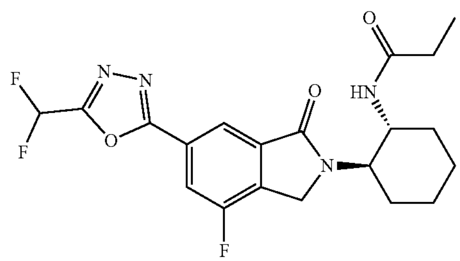 | | 423.1 |
| 183 | N-((1R,2R)-2-(6-(5-(difluoromethyl)-1,3,4-oxadiazol-2-yl)-4-fluoro-1-oxo-1,3-dihydro-2H-isoindol-2-yl)cyclohexyl)-2,2,2-trifluoroacetamide | 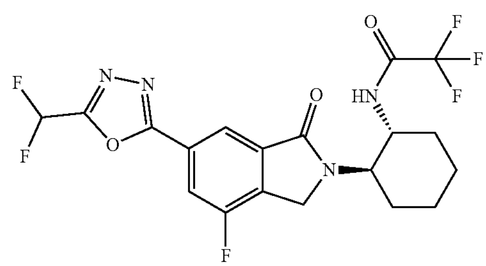 [SMILES: O=C1c2cc(-c3nnc(C(F)F)o3)cc(F)c2CN1[C@@H]1CCCC[C@H]1NC(=O)C(F)(F)F] | | 461.1 |
| 184 | N-((1R,2R)-2-(6-(5-(difluoromethyl)-1,3,4-oxadiazol-2-yl)-4-fluoro-1-oxo-1,3-dihydro-2H-isoindol-2-yl)cyclohexyl)-2,2-difluoropropanamide | 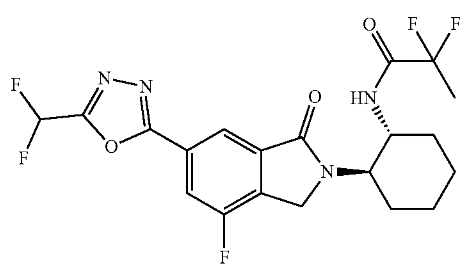 [SMILES: CC(F)(F)C(=O)N[C@@H]1CCCC[C@H]1N1Cc2c(F)cc(-c3nnc(C(F)F)o3)cc2C1=O] | | 459.1 |
| 185 | (1S)-N-((1R,2R)-2-(6-(5-(difluoromethyl)-1,3,4-oxadiazol-2-yl)-4-fluoro-1-oxo-1,3-dihydro-2H-isoindol-2-yl)cyclohexyl)-2,2-difluorocyclopropanecarboxamide | 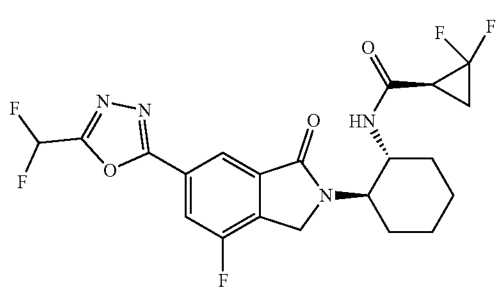 [SMILES: O=C(N[C@@H]1CCCC[C@H]1N1Cc2c(F)cc(-c3nnc(C(F)F)o3)cc2C1=O)[C@@H]1CC1(F)F] | | 471.0 |

TABLE 1-19-continued

| EXAMPLE | IUPAC NAME | Structure | ADDITIVE | MS |
|---|---|---|---|---|
| 186 | 2-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-1H-isoindole-1,3(2H)-dione | 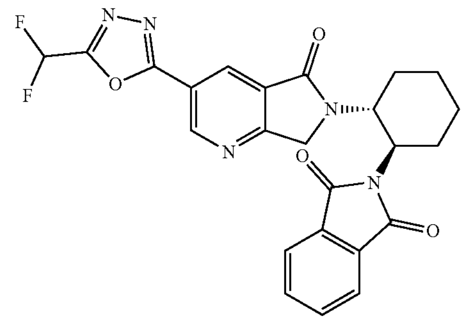 [SMILES: O=C1c2cc(-c3nnc(C(F)F)o3)cnc2CN1[C@@H]1CCCC[C@H]1N1C(=O)c2ccccc2C1=O] | | 480.0 |
| 187 | 1-(6-(5-(difluoromethyl)-1,3,4-oxadiazol-2-yl)-1-oxo-1,3-dihydro-2H-isoindol-2-yl)-N-(2,2,2-trifluoroethyl)cyclopropanecarboxamide | 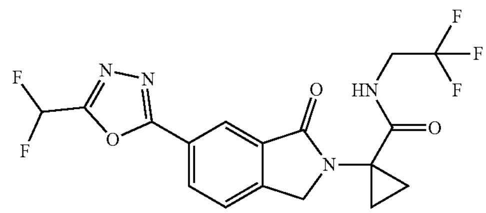 [SMILES: O=C1c2cc(-c3nnc(C(F)F)o3)ccc2CN1C1(C(=O)NCC(F)(F)F)CC1] | | 417.0 |
| 188 | 6-(5-(difluoromethyl)-1,3,4-oxadiazol-2-yl)-2-(1-methyl-4-phenyl-1H-pyrazol-3-yl)isoindolin-1-one | 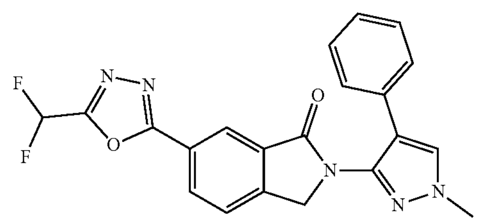 [SMILES: Cn1cc(-c2ccccc2)c(N2Cc3ccc(-c4nnc(C(F)F)o4)cc3C2=O)n1] | | 408.2 |

TABLE 1-20

| EXAMPLE | IUPAC NAME | Structure | ADDITIVE | MS |
|---|---|---|---|---|
| 189 | 2-chloro-N-((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)benzamide | 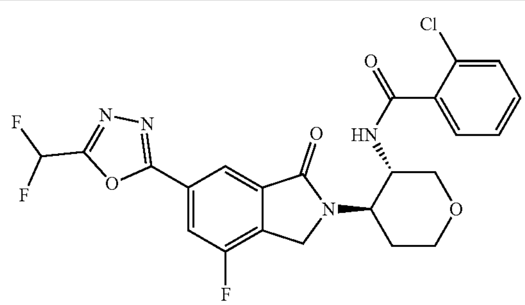 [SMILES: O=C(N[C@@H]1COCC[C@H]1N1Cc2c(F)cc(-c3nnc(C(F)F)o3)cc2C1=O)c1ccccc1Cl] | | 506.8 |
| 190 | 3-chloro-N-((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)benzamide | 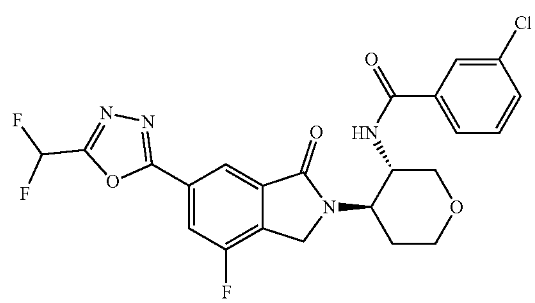 [SMILES: O=C(N[C@@H]1COCC[C@H]1N1Cc2c(F)cc(-c3nnc(C(F)F)o3)cc2C1=O)c1cccc(Cl)c1] | | 506.8 |

TABLE 1-20-continued

| EXAMPLE | IUPAC NAME | Structure | ADDITIVE | MS |
|---|---|---|---|---|
| 191 | N-((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)propanamide | 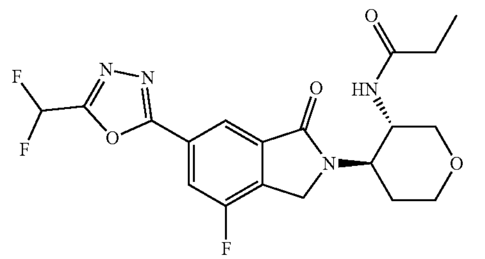 [SMILES: CCC(=O)N[C@@H]1COCC[C@H]1N1Cc2c(F)cc(-c3nnc(C(F)F)o3)cc2C1=O] | | 424.9 |
| 192 | tert-butyl (3S,4R)-4-(3-(5-(difluoromethyl)-1,3,4-oxadiazol-2-yl)-5-oxo-5,7-dihydro-6H-pyrrolo[3,4-b]pyridin-6-yl)-3-phenylpiperidine-1-carboxylate | 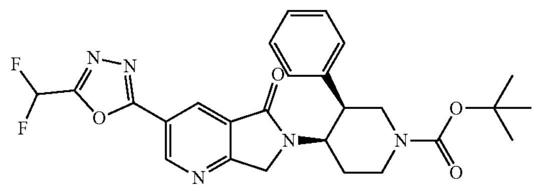 [SMILES: CC(C)(C)OC(=O)N1CC[C@@H](N2Cc3ncc(-c4nnc(C(F)F)o4)cc3C2=O)[C@@H](c2ccccc2)C1] | | 510.0 |
| 193 | 3-(5-(difluoromethyl)-1,3,4-oxadiazol-2-yl)-6-((3S,4R)-3-phenylpiperidin-4-yl)-6,7-dihydro-5H-pyrrolo[3,4-b]pyridin-5-one | 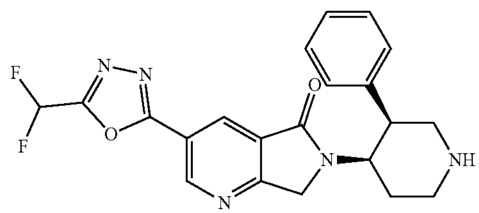 [SMILES: O=C1c2cc(-c3nnc(C(F)F)o3)cnc2CN1[C@@H]1CCNC[C@@H]1c1ccccc1] | | 412.0 |
| 194 | methyl (3S,4R)-4-(3-(5-(difluoromethyl)-1,3,4-oxadiazol-2-yl)-5-oxo-5,7-dihydro-6H-pyrrolo[3,4-b]pyridin-6-yl)-3-phenylpiperidine-carboxylate | 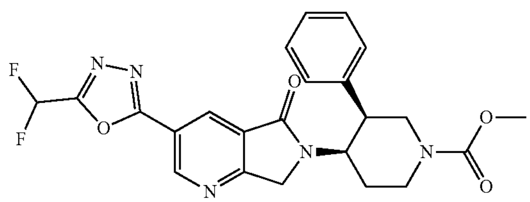 [SMILES: COC(=O)N1CC[C@@H](N2Cc3ncc(-c4nnc(C(F)F)o4)cc3C2=O)[C@@H](c2ccccc2)C1] | | 469.9 |
| 195 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2-difluorobutanamide | 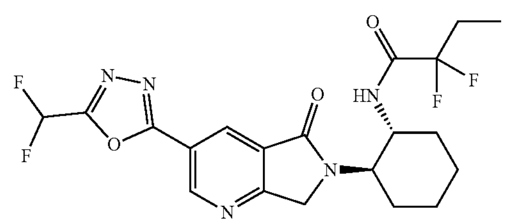 [SMILES: CCC(F)(F)C(=O)N[C@@H]1CCCC[C@H]1N1Cc2ncc(-c3nnc(C(F)F)o3)cc2C1=O] | | 456.0 |
| 196 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2,3,3,3-pentafluoropropanamide | 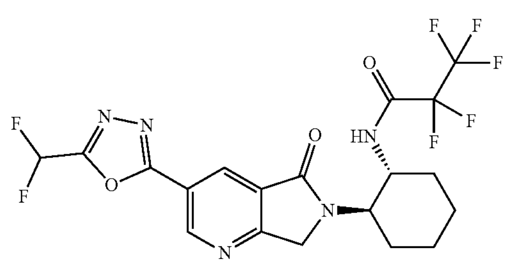 [SMILES: O=C1c2cc(-c3nnc(C(F)F)o3)cnc2CN1[C@@H]1CCCC[C@H]1NC(=O)C(F)(F)C(F)(F)F] | | 494.1 |
| 197 | 2-(((3S)-4-(cyclopropylsulfonyl)morpholin-3-yl)methyl)-6-(5-(difluoromethyl)-1,3,4-oxadiazol-2-yl)-4-fluoroisoindolin-1-one | 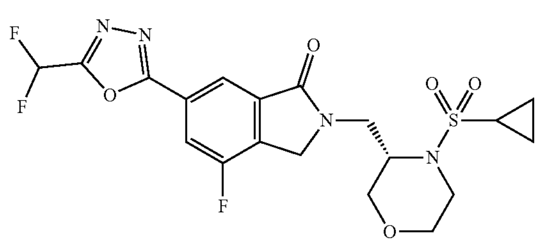 [SMILES: O=C1c2cc(-c3nnc(C(F)F)o3)cc(F)c2CN1C[C@H]1COCCN1S(=O)(=O)C1CC1] | | 472.9 |

TABLE 1-20-continued

| EXAMPLE | IUPAC NAME | Structure | ADDITIVE | MS |
|---|---|---|---|---|
| 198 | 6-(5-(difluoromethyl)-1,3,4-oxadiazol-2-yl)-4-fluoro-2-(((3S)-4-((4-methylphenyl)sulfonyl)morpholin-3-yl)methyl)isoindolin-1-one | 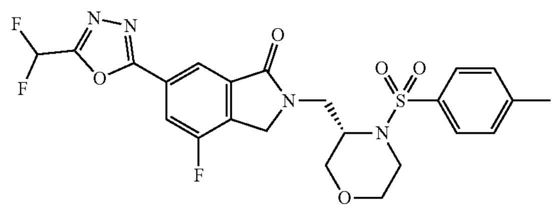 [SMILES: Cc1ccc(S(=O)(=O)N2CCOC[C@@H]2CN2Cc3c(F)cc(-c4nnc(C(F)F)o4)cc3C2=O)cc1] | | 522.8 |

TABLE 1-21

| EXAMPLE | IUPAC NAME | Structure | ADDITIVE | MS |
|---|---|---|---|---|
| 199 | 6-(5-(difluoromethyl)-1,3,4-oxadiazol-2-yl)-4-fluoro-2-(((3S)-4-((2,2,2-trifluoroethyl)sulfonyl)morpholin-3-yl)methyl)isoindolin-1-one | 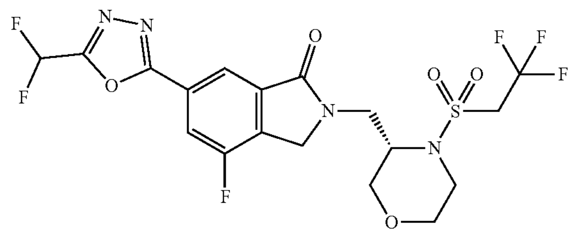 [SMILES: O=C1c2cc(-c3nnc(C(F)F)o3)cc(F)c2CN1C[C@H]1COCCN1S(=O)(=O)CC(F)(F)F] | | 514.8 |
| 200 | N-((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)-2,2,3,3,3-pentafluoropropanamide | 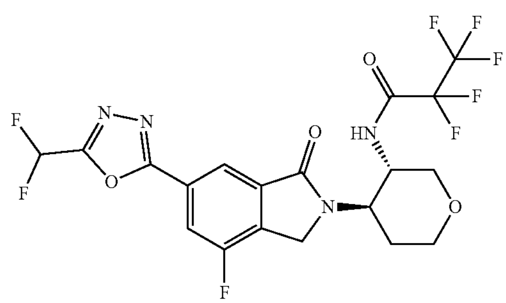 [SMILES: O=C1c2cc(-c3nnc(C(F)F)o3)cc(F)c2CN1[C@@H]1CCOC[C@H]1NC(=O)C(F)(F)C(F)(F)F] | | 513.1 |
| 201 | N-((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)-1-(trifluoromethyl)cyclopropanecarboxamide | 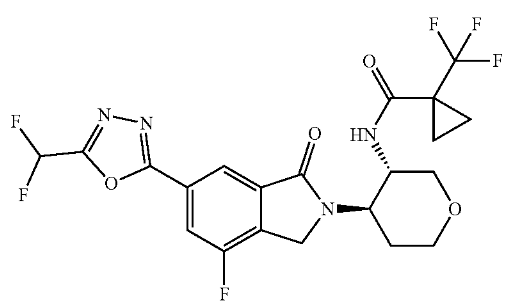 [SMILES: O=C1c2cc(-c3nnc(C(F)F)o3)cc(F)c2CN1[C@@H]1CCOC[C@H]1NC(=O)C1(C(F)(F)F)CC1] | | 504.8 |
| 202 | N-((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)-3,3,3-trifluoro-2,2-dimethylpropanamide | 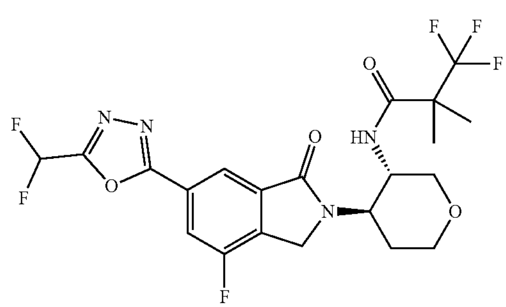 [SMILES: CC(C)(C(=O)N[C@@H]1COCC[C@H]1N1Cc2c(F)cc(-c3nnc(C(F)F)o3)cc2C1=O)C(F)(F)F] | | 506.8 |

TABLE 1-21-continued

| EXAMPLE | IUPAC NAME | Structure | ADDITIVE | MS |
|---|---|---|---|---|
| 203 | N-((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)-2,2-difluorobutanamide | 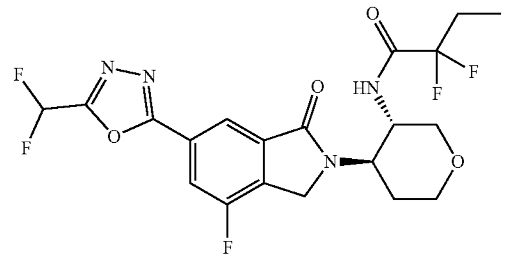 [SMILES: CCC(F)(F)C(=O)N[C@@H]1COCC[C@H]1N1Cc2c(F)cc(-c3nnc(C(F)F)o3)cc2C1=O] | | 474.9 |
| 204 | N-((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)-2,2-difluorobutanamide | 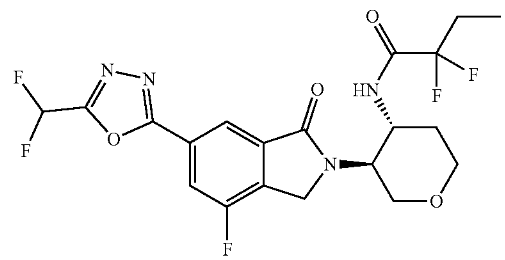 [SMILES: CCC(F)(F)C(=O)N[C@@H]1CCOC[C@H]1N1Cc2c(F)cc(-c3nnc(C(F)F)o3)cc2C1=O] | | 474.9 |
| 205 | N-((3S,4R)-3-(6-(5-(difluoromethyl)-1,3,4-oxadiazol-2-yl)-4-fluoro-1-oxo-1,3-dihydro-2H-isoindol-2-yl)tetrahydro-2H-pyran-4-yl)-1-(trifluoromethyl)cyclobutanecarboxamide | 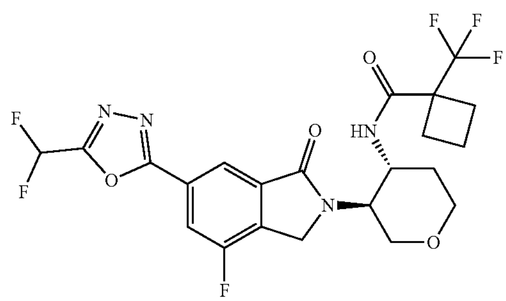 [SMILES: O=C1c2cc(-c3nnc(C(F)F)o3)cc(F)c2CN1[C@@H]1COCC[C@H]1NC(=O)C1(C(F)(F)F)CCC1] | | 518.9 |
| 206 | 6-(5-(difluoromethyl)-1,3,4-oxadiazol-2-yl)-2-(2-(1-methyl-1H-pyrazol-3-yl)phenyl)isoindolin-1-one | 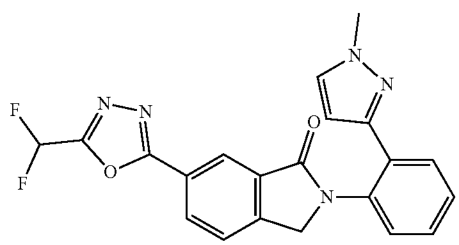 [SMILES: Cn1ccc(-c2ccccc2N2Cc3ccc(-c4nnc(C(F)F)o4)cc3C2=O)n1] | | 408.0 |
| 207 | 6-(5-(difluoromethyl)-1,3,4-oxadiazol-2-yl)-2-(2-(1-methyl-1H-pyrazol-4-yl)phenyl)isoindolin-1-one | 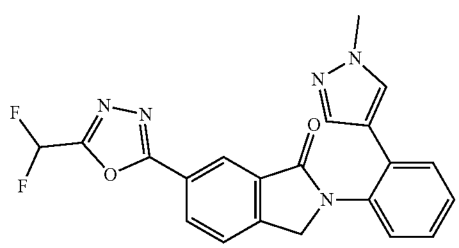 [SMILES: Cn1cc(-c2ccccc2N2Cc3ccc(-c4nnc(C(F)F)o4)cc3C2=O)cn1] | | 408.0 |
| 208 | 6-(5-(difluoromethyl)-1,3,4-oxadiazol-2-yl)-2-(2-(pyridin-3-yl)phenyl)isoindolin-1-one | 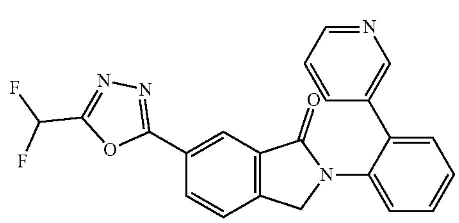 [SMILES: O=C1c2cc(-c3nnc(C(F)F)o3)ccc2CN1c1ccccc1-c1cccnc1] | | 405.0 |

TABLE 1-22

| EXAMPLE | IUPAC NAME | Structure | ADDITIVE | MS |
|---|---|---|---|---|
| 209 | 6-(5-(difluoromethyl)-1,3,4-oxadiazol-2-yl)-2-(2-phenoxyethyl)isoindolin-1-one | 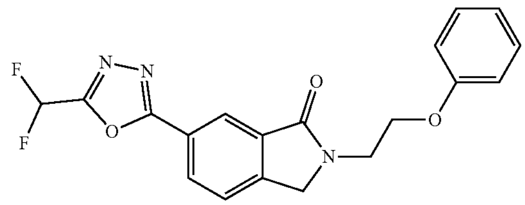 [SMILES: O=C1c2cc(-c3nnc(C(F)F)o3)ccc2CN1CCOc1ccccc1] | | 372.0 |
| 210 | N-((1R,2R)-2-(6-(5-(difluoromethyl)-1,3,4-oxadiazol-2-yl)-4-fluoro-1-oxo-1,3-dihydro-2H-isoindol-2-yl)cyclohexyl)-2,2-difluorobutanamide | 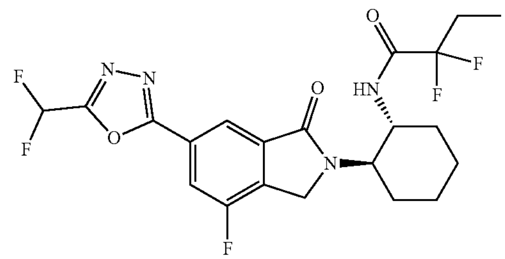 [SMILES: CCC(F)(F)C(=O)N[C@@H]1CCCC[C@H]1N1Cc2c(F)cc(-c3nnc(C(F)F)o3)cc2C1=O] | | 473.0 |
| 211 | N-((1R,2R)-2-(6-(5-(difluoromethyl)-1,3,4-oxadiazol-2-yl)-4-fluoro-1-oxo-1,3-dihydro-2H-isoindol-2-yl)cyclohexyl)-3-methyloxetane-3-carboxamide | 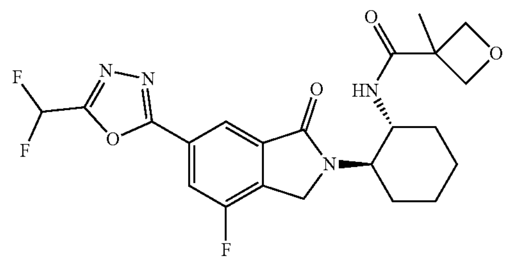 [SMILES: CC1(C(=O)N[C@@H]2CCCC[C@H]2N2Cc3c(F)cc(-c4nnc(C(F)F)o4)cc3C2=O)COC1] | | 464.9 |
| 212 | N-((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)-1-(trifluoromethyl)cyclobutanecarboxamide | 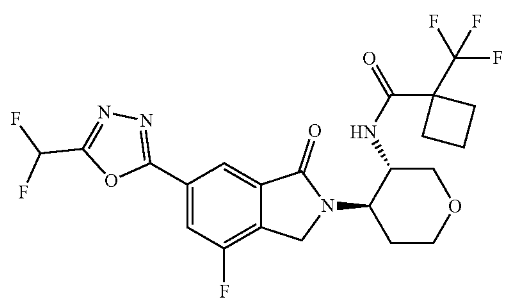 [SMILES: O=C1c2cc(-c3nnc(C(F)F)o3)cc(F)c2CN1[C@@H]1CCOC[C@H]1NC(=O)C1(C(F)(F)F)CCC1] | | 518.9 |
| 213 | 1,1,1-trifluoro-2-methylpropan-2-yl ((3S,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)carbamate | 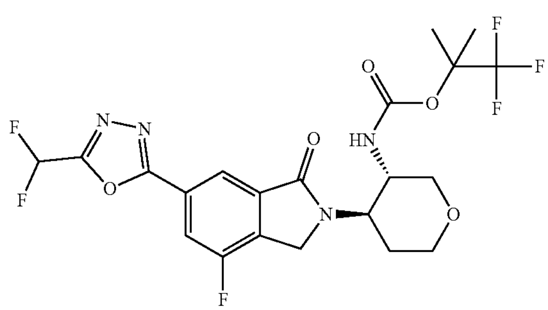 [SMILES: CC(C)(OC(=O)N[C@@H]1COCC[C@H]1N1Cc2c(F)cc(-c3nnc(C(F)F)o3)cc2C1=O)C(F)(F)F] | | 522.8 |
| 214 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2-fluoro-2-methylpropanamide | 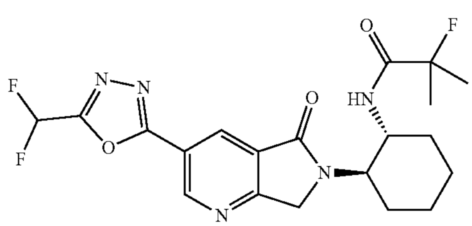 [SMILES: CC(C)(F)C(=O)N[C@@H]1CCCC[C@H]1N1Cc2ncc(-c3nnc(C(F)F)o3)cc2C1=O] | | 438.0 |

TABLE 1-22-continued

| EXAMPLE | IUPAC NAME | Structure | ADDITIVE | MS |
|---|---|---|---|---|
| 215 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2,2-trifluoroacetamide | 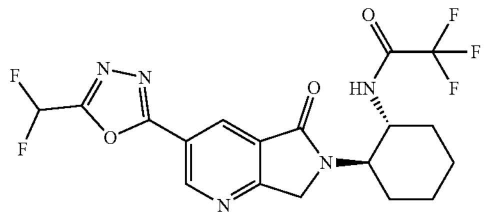 [SMILES: O=C1c2cc(-c3nnc(C(F)F)o3)cnc2CN1[C@@H]1CCCC[C@H]1NC(=O)C(F)(F)F] | | 445.9 |
| 216 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-1-fluorocyclopropanecarboxamide | 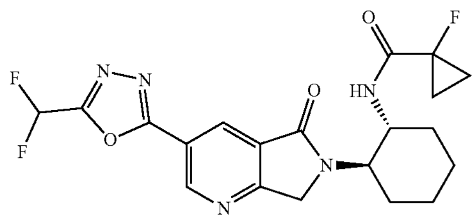 [SMILES: O=C1c2cc(-c3nnc(C(F)F)o3)cnc2CN1[C@@H]1CCCC[C@H]1NC(=O)C1(F)CC1] | | 436.0 |
| 217 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-3,3,3-trifluoro-2,2-dimethylpropanamide | 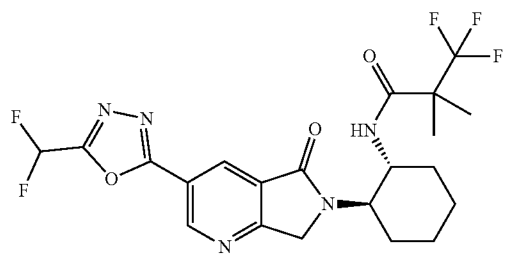 [SMILES: CC(C)(C(=O)N[C@@H]1CCCC[C@H]1N1Cc2ncc(-c3nnc(C(F)F)o3)cc2C1=O)C(F)(F)F] | | 488.0 |
| 218 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-1-fluorocyclobutanecarboxamide | 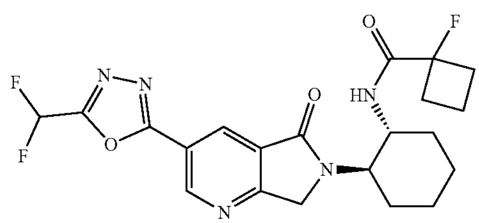 [SMILES: O=C1c2cc(-c3nnc(C(F)F)o3)cnc2CN1[C@@H]1CCCC[C@H]1NC(=O)C1(F)CCC1] | | 450.0 |

TABLE 1-23

| EXAMPLE | IUPAC NAME | Structure | ADDITIVE | MS |
|---|---|---|---|---|
| 219 | N-((1R(2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-1-(trifluoromethyl)-cyclobutanecarboxamide | 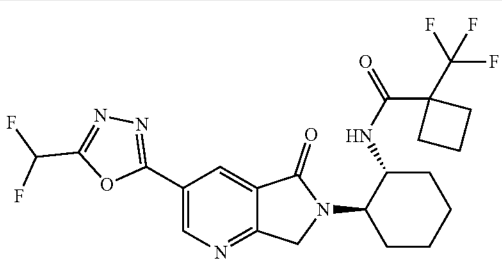 [SMILES: O=C1c2cc(-c3nnc(C(F)F)o3)cnc2CN1[C@@H]1CCCC[C@H]1NC(=O)C1(C(F)(F)F)CCC1] | | 499.9 |
| 220 | 6-(5-(difluoromethyl)-1,3,4-oxadiazol-2-yl)-2-((1R,2R)-2-hydroxycyclohexyl)-isoindolin-1-one | 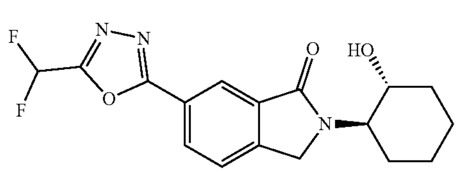 [SMILES: O=C1c2cc(-c3nnc(C(F)F)o3)ccc2CN1[C@@H]1CCCC[C@H]1O] | | 350.1 |

TABLE 1-23-continued

| EXAMPLE | IUPAC NAME | Structure | ADDITIVE | MS |
|---|---|---|---|---|
| 221 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-1-(4-fluorophenyl)-cyclopropanecarboxamide | 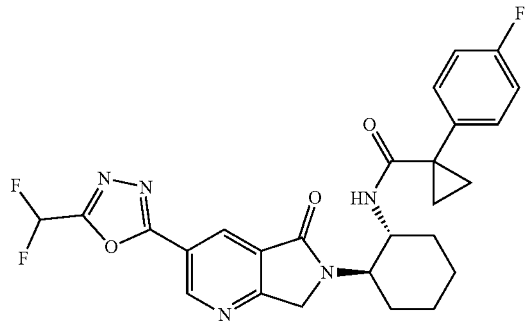 [SMILES: O=C1c2cc(-c3nnc(C(F)F)o3)cnc2CN1[C@@H]1CCCC[C@H]1NC(=O)C1(c2ccc(F)cc2)CC1] | | 511.9 |
| 222 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2-fluorobenzamide | 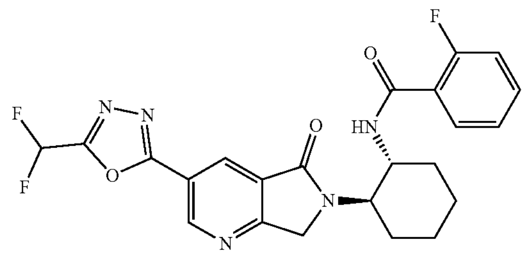 [SMILES: O=C(N[C@@H]1CCCC[C@H]1N1Cc2ncc(-c3nnc(C(F)F)o3)cc2C1=O)c1ccccc1F] | | 472.0 |
| 223 | 2-cyano-N-((1R,2R)-2-(3-(5-(difluoromethyl)-1,3,4-oxadiazol-2-yl)-5-oxo-5,7-dihydro-6H-pyrrolo[3,4-b]-pyridin-6-yl)cyclohexyl)benzamide | 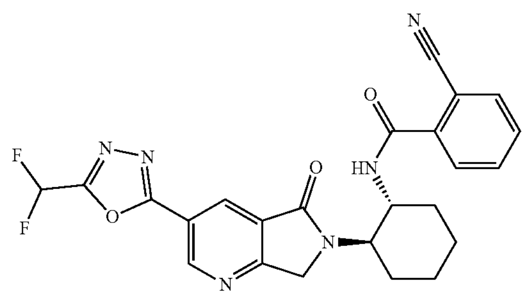 [SMILES: N#Cc1ccccc1C(=O)N[C@@H]1CCCC[C@H]1N1Cc2ncc(-c3nnc(C(F)F)o3)cc2C1=O] | | 478.9 |
| 224 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-3-fluorobenzamide | 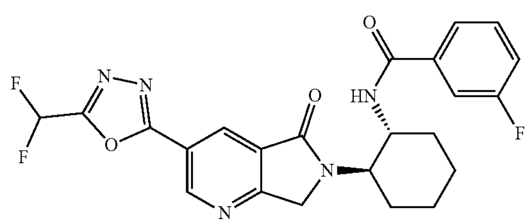 [SMILES: O=C(N[C@@H]1CCCC[C@H]1N1Cc2ncc(-c3nnc(C(F)F)o3)cc2C1=O)c1cccc(F)c1] | | 471.9 |
| 225 | 3-cyano-N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)benzamide | 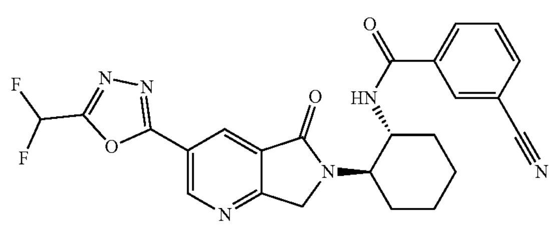 [SMILES: N#Cc1cccc(C(=O)N[C@@H]2CCCC[C@H]2N2Cc3ncc(-c4nnc(C(F)F)o4)cc3C2=O)c1] | | 479.0 |
| 226 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-3-(trifluoromethyl)-benzamide | 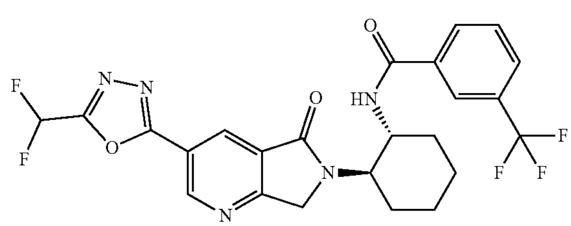 [SMILES: O=C(N[C@@H]1CCCC[C@H]1N1Cc2ncc(-c3nnc(C(F)F)o3)cc2C1=O)c1cccc(C(F)(F)F)c1] | | 521.8 |

TABLE 1-23-continued

| EXAMPLE | IUPAC NAME | Structure | ADDITIVE | MS |
|---|---|---|---|---|
| 227 | 6-(5-(difluoromethyl)-1,3,4-oxadiazol-2-yl)-4-fluoro-2-(((3S)-4-(2,2,3,3,3-pentafluoropropyl)morpholin-3-yl)methyl)isoindolin-1-one | 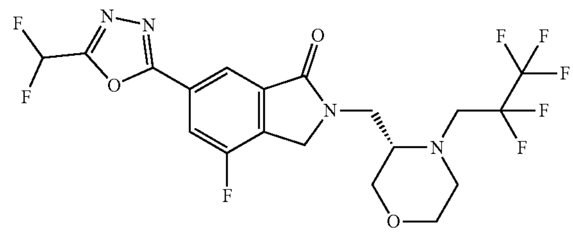 [SMILES: O=C1c2cc(-c3nnc(C(F)F)o3)cc(F)c2CN1C[C@H]1COCCN1CC(F)(F)C(F)(F)F] | | 500.9 |
| 228 | 6-(5-(difluoromethyl)-1,3,4-oxadiazol-2-yl)-4-fluoro-2-(((3S)-4-(2,2,3,3-tetrafluoropropyl)morpholin-3-yl)methyl)isoindolin-1-one | 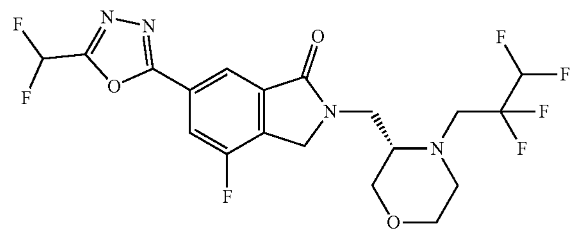 [SMILES: O=C1c2cc(-c3nnc(C(F)F)o3)cc(F)c2CN1C[C@H]1COCCN1CC(F)(F)C(F)F] | | 482.9 |

TABLE 1-24

| EXAMPLE | IUPAC NAME | Structure | ADDITIVE | MS |
|---|---|---|---|---|
| 229 | 6-(5-(difluoromethyl)-1,3,4-oxadiazol-2-yl)-4-fluoro-2-(((3S)-4-(2,2,3,3,4,4,4-heptafluorobutyl)morpholin-3-yl)methyl)isoindolin-1-one | 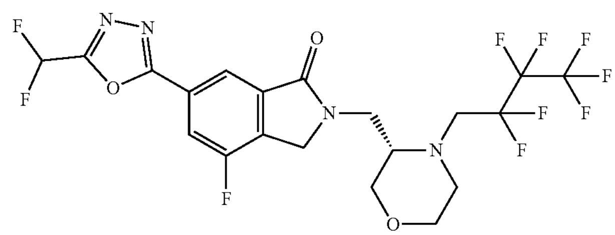 [SMILES: O=C1c2cc(-c3nnc(C(F)F)o3)cc(F)c2CN1C[C@H]1COCCN1CC(F)(F)C(F)(F)C(F)(F)F] | | 550.8 |
| 230 | 2'-(6-(5-(difluoromethyl)-1,3,4-oxadiazol-2-yl)-1-oxo-1,3-dihydro-2H-isoindol-2-yl)-biphenyl-2-carbonitrile | 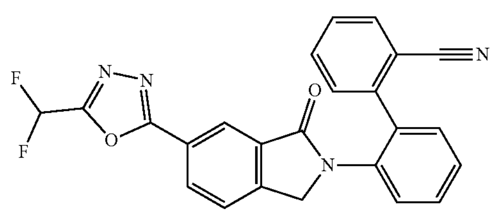 [SMILES: N#Cc1ccccc1-c1ccccc1N1Cc2ccc(-c3nnc(C(F)F)o3)cc2C1=O] | | 429.0 |
| 231 | 6-((1R,2R)-2-aminocyclohexyl)-3-(5-(difluoromethyl)-1,3,4-oxadiazol-2-yl)-6,7-dihydro-5H-pyrrolo[3,4-b]pyridin-5-one | 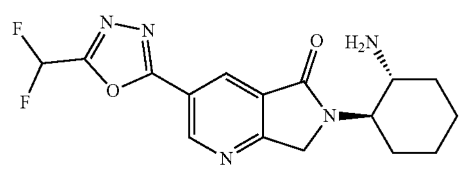 [SMILES: N[C@@H]1CCCC[C@H]1N1Cc2ncc(-c3nnc(C(F)F)o3)cc2C1=O] | | 350.1 |
| 232 | (1R,2R)-2-(6-(5-(difluoromethyl)-1,3,4-oxadiazol-2-yl)-1-oxo-1,3-dihydro-2H-isoindol-2-yl)-cyclohexyl azetidine-1-carboxylate | 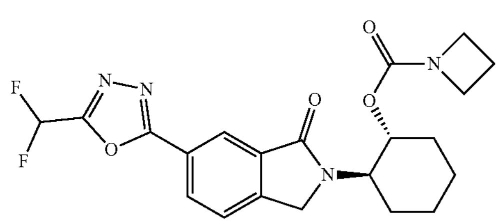 [SMILES: O=C(O[C@@H]1CCCC[C@H]1N1Cc2ccc(-c3nnc(C(F)F)o3)cc2C1=O)N1CCC1] | | 433.0 |

TABLE 1-24-continued

| EXAMPLE | IUPAC NAME | Structure | ADDITIVE | MS |
|---|---|---|---|---|
| 233 | (1R,2R)-2-(6-(5-(difluoromethyl)-1,3,4-oxadiazol-2-yl)-1-oxo-1,3-dihydro-2H-isoindol-2-yl)-cyclohexyl pyrrolidine-1-carboxylate | 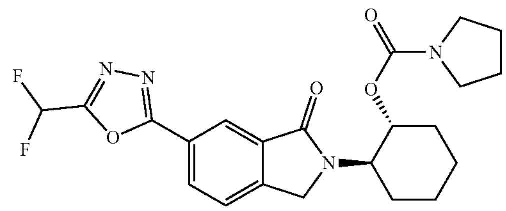 [SMILES: O=C(O[C@@H]1CCCC[C@H]1N1Cc2ccc(-c3nnc(C(F)F)o3)cc2C1=O)N1CCCC1] | | 447.0 |
| 234 | 2-(2-(benzyloxy)ethyl)-6-(5-(difluoromethyl)-1,3,4-oxadiazol-2-yl)isoindolin-1-one | 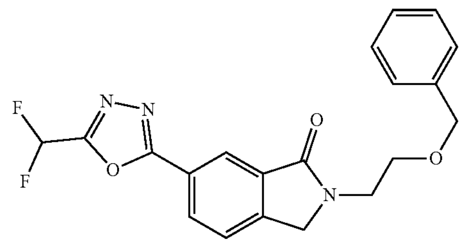 [SMILES: O=C1c2cc(-c3nnc(C(F)F)o3)ccc2CN1CCOCc1ccccc1] | | 386.1 |
| 235 | 1-(difluoromethyl)-N-((1R,2R)-2-(3-(5-(difluoromethyl)-1,3,4-oxadiazol-2-yl)-5-oxo-5,7-dihydro-6H-pyrrolo[3,4-b]pyridin-6-yl)-cyclohexyl)cyclopropane-carboxamide | 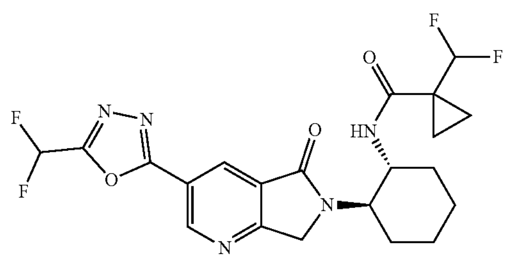 [SMILES: O=C1c2cc(-c3nnc(C(F)F)o3)cnc2CN1[C@@H]1CCCC[C@H]1NC(=O)C1(C(F)F)CC1] | | 467.9 |
| 236 | 1-(difluoromethyl)-N-((1R,2R)-2-(6-(5-(difluoromethyl)-1,3,4-oxadiazol-2-yl)-4-fluoro-1-oxo-1,3-dihydro-2H-isoindol-2-yl)-cyclohexyl)cyclopropanecarbox-amide | 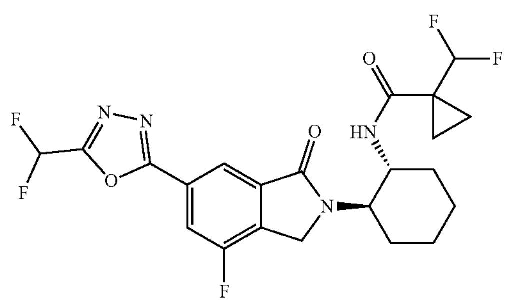 [SMILES: O=C1c2cc(-c3nnc(C(F)F)o3)cc(F)c2CN1[C@@H]1CCCC[C@H]1NC(=O)C1(C(F)F)CC1] | | 484.9 |
| 237 | 2-cyclopropyl-N-((1R,2R)-2-(3-(5-(difluoromethyl)-1,3,4-oxadiazol-2-yl)-5-oxo-5,7-dihydro-6H-pyrrolo[3,4-b]pyridin-5-yl)-cyclohexyl)-2,2-difluoroacetamide | 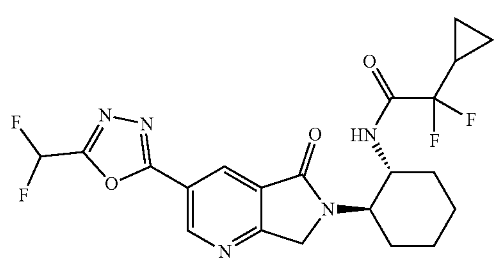 [SMILES: O=C1c2cc(-c3nnc(C(F)F)o3)cnc2CN1[C@@H]1CCCC[C@H]1NC(=O)C(F)(F)C1CC1] | | 467.9 |
| 238 | 6-(5-(difluoromethyl)-1,3,4-oxadiazol-2-yl)-2-(2-(pyridin-2-yl)phenyl)isoindolin-1-one | 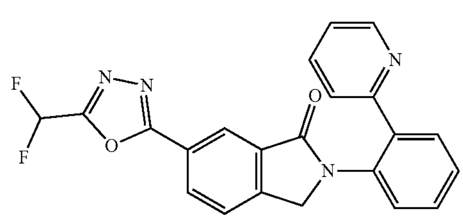 [SMILES: O=C1c2cc(-c3nnc(C(F)F)o3)ccc2CN1c1ccccc1-c1ccccn1] | | 404.9 |

TABLE 1-25

| EXAMPLE | IUPAC NAME | Structure | ADDITIVE | MS |
|---|---|---|---|---|
| 239 | 2-(((3S)-4-(cyclopropylsulfonyl)-morpholin-3-yl)methyl)-5-(5-(difluoromethyl)-1,3,4-oxadiazol-2-yl)-1H-isoindole-1,3(2H)-dione | 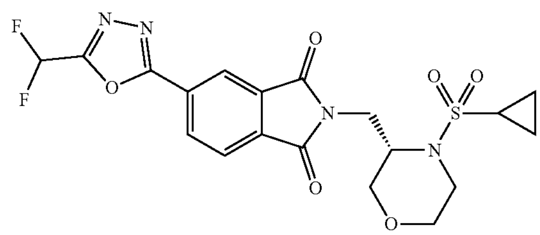 [SMILES: O=C1c2ccc(-c3nnc(C(F)F)o3)cc2C(=O)N1C[C@H]1COCCN1S(=O)(=O)C1CC1] | | 468.8 |
| 240 | 6-(2-bromophenyl)-3-(5-(difluoromethyl)-1,3,4-oxadiazol-2-yl)-6,7-dihydro-5H-pyrrolo[3,4-b]pyridin-5-one | 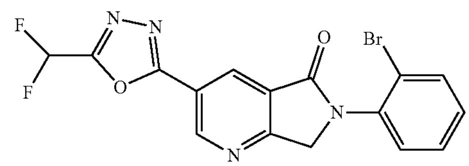 [SMILES: O=C1c2cc(-c3nnc(C(F)F)o3)cnc2CN1c1ccccc1Br] | | 406.8 |
| 241 | 2-(2-bromo-4-chlorophenyl)-6-(5-(difluoromethyl)-1,3,4-oxadiazol-2-yl)isoindolin-1-one | 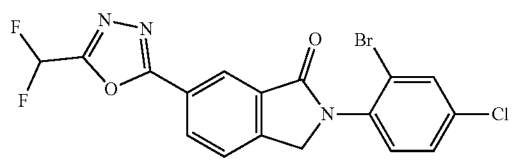 [SMILES: O=C1c2cc(-c3nnc(C(F)F)o3)ccc2CN1c1ccc(Cl)cc1Br] | | 439.7 |
| 242 | N-((1R,2R)-2-(6-(5-(difluoromethyl)-1,3,4-oxadiazol-2-yl)-4-fluoro-1-oxo-1,3-dihydro-2H-isoindol-2-yl)cyclohexyl)-cyclopropanesulfonamide | 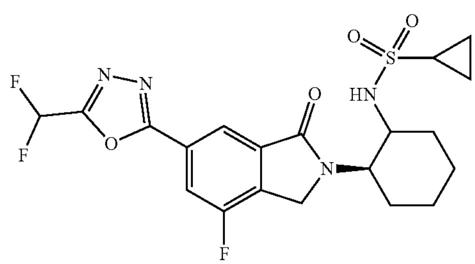 [SMILES: O=C1c2cc(-c3nnc(C(F)F)o3)cc(F)c2CN1[C@@H]1CCCCC1NS(=O)(=O)C1CC1] | | 470.9 |
| 243 | 2'-(3-(5-(difluoromethyl)-1,3,4-oxadiazol-2-yl)-5-oxo-5,7-dihydro-6H-pyrrolo[3,4-b]pyridin-6-yl)biphenyl-3-carbonitrile | 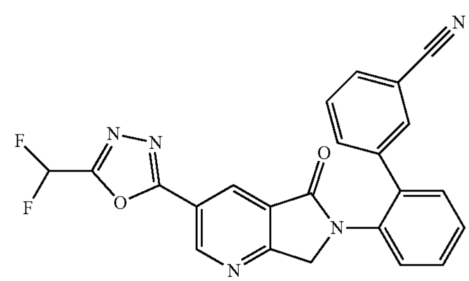 [SMILES: N#Cc1cccc(-c2ccccc2N2Cc3ncc(-c4nnc(C(F)F)o4)cc3C2=O)c1] | | 429.9 |
| 244 | N-((1R,2R)-2-(6-(5-(difluoromethyl)-1,3,4-oxadiazol-2-yl-4-fluoro-1-oxo-1,3-dihydro-2H-isoindol-2-yl)cyclohexyl)-2,2,2-trifluoroethanesulfonamide | 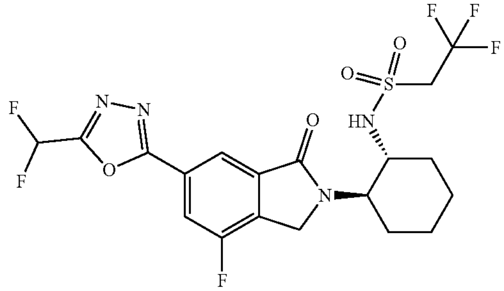 [SMILES: O=C1c2cc(-c3nnc(C(F)F)o3)cc(F)c2CN1[C@@H]1CCCC[C@H]1NS(=O)(=O)CC(F)(F)F] | | 512.8 |

TABLE 1-25-continued

| EXAMPLE | IUPAC NAME | Structure | ADDITIVE | MS |
|---|---|---|---|---|
| 245 | N-((1R,2R)-2-(6-(5-(difluoro-methyl)-1,3,4-oxadiazol-2-yl)-1-oxo-1,3-dihydro-2H-isoindol-2-yl)cyclohexyl)-2,2,2-trifluoro-ethanesulfonamide | 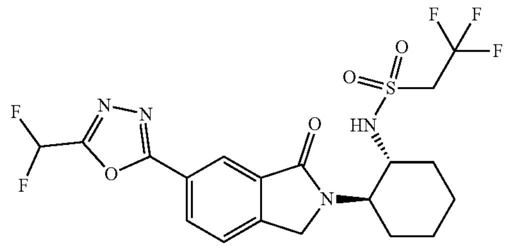 [SMILES: O=C1c2cc(-c3nnc(C(F)F)o3)ccc2CN1[C@@H]1CCCC[C@H]1NS(=O)(=O)CC(F)(F)F] | | 494.8 |
| 246 | N-((1R,2R)-2-(6-(5-(difluoro-methyl)-1,3,4-oxadiazol-2-yl)-1-oxo-1,3-dihydro-2H-isoindol-2-yl)cyclohexyl)cyclopropane-sulfonamide | 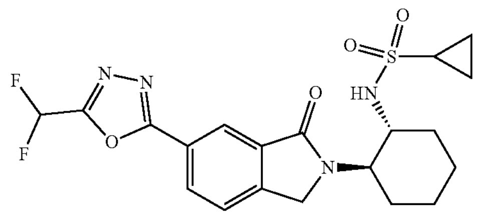 [SMILES: O=C1c2cc(-c3nnc(C(F)F)o3)ccc2CN1[C@@H]1CCCC[C@H]1NS(=O)(=O)C1CC1] | | 452.9 |
| 247 | 2-(2-bromo-4-fluorophenyl)-6-(5-(difluoromethyl)-1,3,4-oxadiazol-2-yl)isoindolin-1-one | 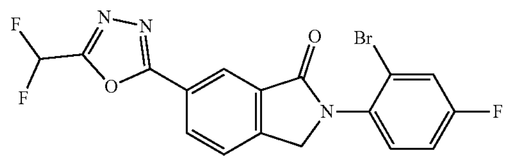 [SMILES: O=C1c2cc(-c3nnc(C(F)F)o3)ccc2CN1c1ccc(F)cc1Br] | | 423.8 |
| 248 | 5'-chloro-2'-(6-(5-(difluoro-methyl)-1,3,4-oxadiazol-2-yl)-1-oxo-1,3-dihydro-2H-isoindol-2-yl)biphenyl-3-carbonitrile | 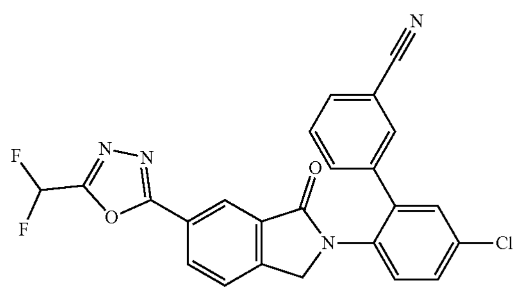 [SMILES: N#Cc1cccc(-c2cc(Cl)ccc2N2Cc3ccc(-c4nnc(C(F)F)o4)cc3C2=O)c1] | | 462.8 |

TABLE 1-26

| EXAMPLE | IUPAC NAME | Structure | ADDITIVE | MS |
|---|---|---|---|---|
| 249 | 2'-(6-(5-(difluoromethyl)-1,3,4-oxadiazol-2-yl)-1-oxo-1,3-dihydro-2H-isoindol-2-yl)-5'-fluorobiphenyl-3-carbonitrile | 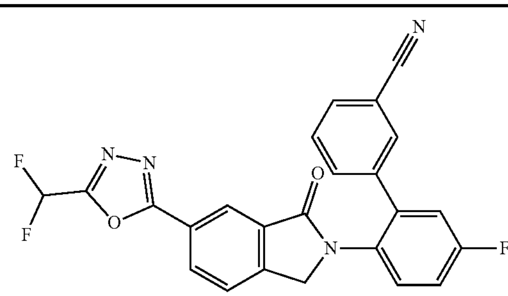 | | 446.9 |
| 250 | 2-(4-bromo-1-methyl-1H-pyrazol-3-yl)-6-(5-(difluoro-methyl)-1,3,4-oxadiazol-2-yl)isoindolin-1-one | 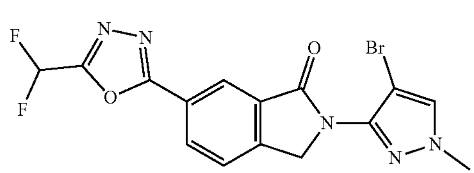 [SMILES: Cn1cc(Br)c(N2Cc3ccc(-c4nnc(C(F)F)o4)cc3C2=O)n1] | | 409.8 |

TABLE 1-26-continued

| EXAMPLE | IUPAC NAME | Structure | ADDITIVE | MS |
|---|---|---|---|---|
| 251 | 6-(5-(difluoromethyl)-1,3,4-oxadiazol-2-yl)-4-fluoro-2-(((3S)-4-((2-fluorophenyl)-sulfonyl)morpholin-3-yl)-methyl)isoindolin-1-one | 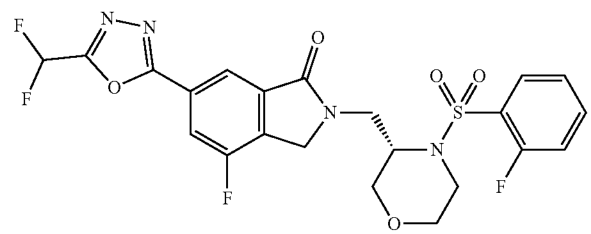 [SMILES: O=C1c2cc(-c3nnc(C(F)F)o3)cc(F)c2CN1C[C@H]1COCCN1S(=O)(=O)c1ccccc1F] | | 526.8 |
| 252 | 6-(5-(difluoromethyl)-1,3,4-oxadiazol-2-yl)-4-fluoro-2-(((3S)-4-((4-fluorophenyl)-sulfonyl)morpholin-3-yl)-methyl)isoindolin-1-one | 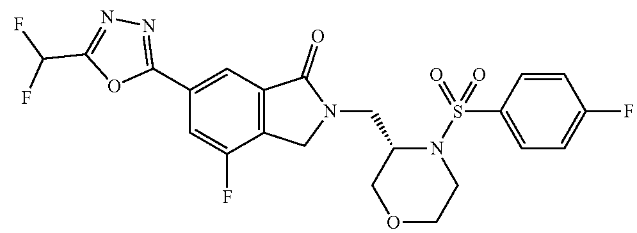 [SMILES: O=C1c2cc(-c3nnc(C(F)F)o3)cc(F)c2CN1C[C@H]1COCCN1S(=O)(=O)c1ccc(F)cc1] | | 526.8 |
| 253 | 2-(2-bromo-5-chlorophenyl)-6-(5-(difluoromethyl)-1,3,4-oxadiazol-2-yl)isoindolin-1-one | 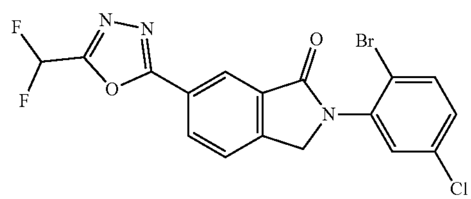 [SMILES: O=C1c2cc(-c3nnc(C(F)F)o3)ccc2CN1c1cc(Cl)ccc1Br] | | 439.8 |
| 254 | (1R,2R)-2-(6-(5-(difluoromethyl)-1,3,4-oxadiazol-2-yl)-1-oxo-1,3-dihydro-2H-isoindol-2-yl)cyclohexyl piperidine-1-carboxylate | 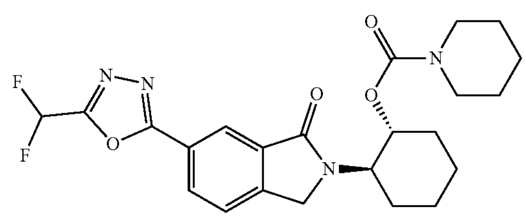 [SMILES: O=C(O[C@@H]1CCCC[C@H]1N1Cc2ccc(-c3nnc(C(F)F)o3)cc2C1=O)N1CCCCC1] | | 461.0 |
| 255 | tert-butyl ((1S,2R)-2-(6-(5-(difluoromethyl)-1,3,4-oxadiazol-2-yl)-1-oxo-1,3-dihydro-2H-isoindol-2-yl)cyclohexyl)carbamate | 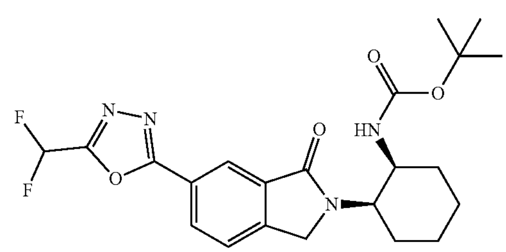 [SMILES: CC(C)(C)OC(=O)N[C@H]1CCCC[C@H]1N1Cc2ccc(-c3nnc(C(F)F)o3)cc2C1=O] | | 447.0 |
| 256 | 2-((1R,2S)-2-aminocyclohexyl)-6-(difluoromethyl)-1,3,4-oxadiazol-2-yl)isoindolin-1-one | 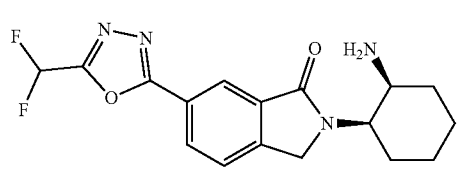 [SMILES: N[C@H]1CCCC[C@H]1N1Cc2ccc(-c3nnc(C(F)F)o3)cc2C1=O] | | 348.9 |
| 257 | 6-(5-(difluoromethyl)-1,3,4-oxadiazol-2-yl)-2-((1R,2R)-2-((2,2,2-trifluoroethyl)amino)-cyclohexyl)isoindolin-1-one | 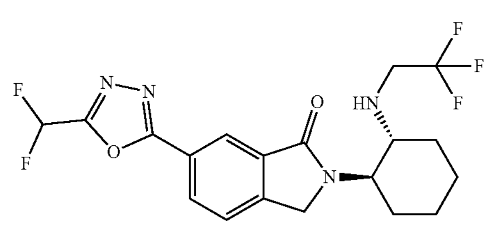 [SMILES: O=C1c2cc(-c3nnc(C(F)F)o3)ccc2CN1[C@@H]1CCCC[C@H]1NCC(F)(F)F] | | 431.0 |

TABLE 1-26-continued

| EXAMPLE | IUPAC NAME | Structure | ADDITIVE | MS |
|---|---|---|---|---|
| 258 | N-((1S,2R)-2-(6-(5-(difluoro-methyl)-1,3,4-oxadiazol-2-yl)-1-oxo-1,3-dihydro-2H-isoindol-2-yl)cyclohexyl)-2,2-difluoropropanamide | 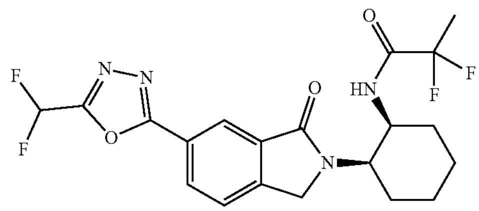 [SMILES: CC(F)(F)C(=O)N[C@H]1CCCC[C@H]1N1Cc2ccc(-c3nnc(C(F)F)o3)cc2C1=O] | | 441.0 |

TABLE 1-27

| EXAMPLE | IUPAC NAME | Structure | ADDITIVE | MS |
|---|---|---|---|---|
| 259 | N-((1S,2R)-2-(6-(5-(difluoro-methyl)-1,3,4-oxadiazol-2-yl)-1-oxo-1,3-dihydro-2H-isoindol-2-yl)cyclohexyl)-1-(trifluoromethyl)cyclopropanecarboxamide | 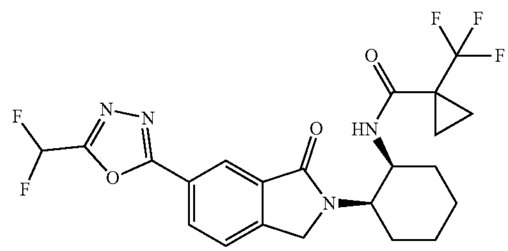 [SMILES: O=C1c2cc(-c3nnc(C(F)F)o3)ccc2CN1[C@@H]1CCCC[C@@H]1NC(=O)C1(C(F)(F)F)CC1] | | 484.9 |
| 260 | N-((1S,2R)-2-(6-(5-(difluoro-methyl)-1,3,4-oxadiazol-2-yl)-1-oxo-1,3-dihydro-2H-isoindol-2-yl)cyclohexyl)-3,3,3-trifluoro-2,2-dimethyl-propanamide | 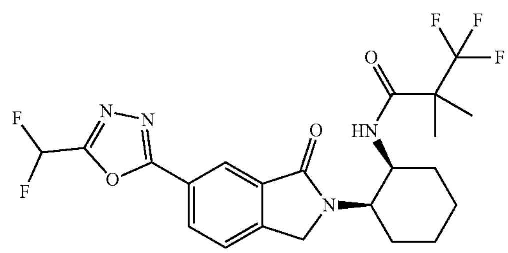 [SMILES: CC(C)(C(=O)N[C@H]1CCCC[C@H]1N1Cc2ccc(-c3nnc(C(F)F)o3)cc2C1=O)C(F)(F)F] | | 486.9 |
| 261 | N-((1S,2R)-2-(6-(5-(difluoro-methyl)-1,3,4-oxadiazol-2-yl)-1-oxo-1,3-dihydro-2H-isoindol-2-yl)cyclohexyl)-2,2,3,3,3-pentafluoropropan-amide | 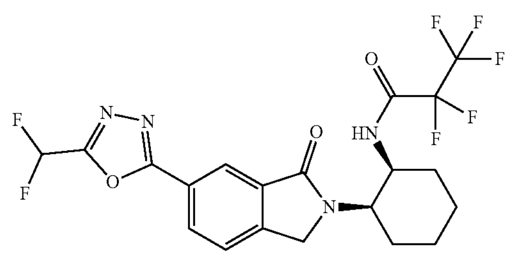 [SMILES: O=C1c2cc(-c3nnc(C(F)F)o3)ccc2CN1[C@@H]1CCCC[C@@H]1NC(=O)C(F)(F)C(F)(F)F] | | 494.9 |
| 262 | methyl ((1S,2R)-2-(6-(5-(difluoromethyl)-1,3,4-oxadiazol-2-yl)-1-oxo-1,3-dihydro-2H-isoindol-2-yl)cyclohexyl)carbamate | 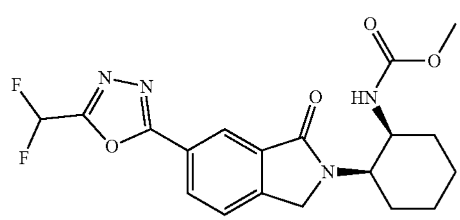 [SMILES: COC(=O)N[C@H]1CCCC[C@H]1N1Cc2ccc(-c3nnc(C(F)F)o3)cc2C1=O] | | 407.0 |
| 263 | tert-butyl (2R)-2-((6-(5-(difluoromethyl)-1,3,4-oxadiazol-2-yl)-4-fluoro-1-oxo-1,3-dihydro-2H-isoindol-2-yl)methyl)-pyrrolidine-1-carboxylate | 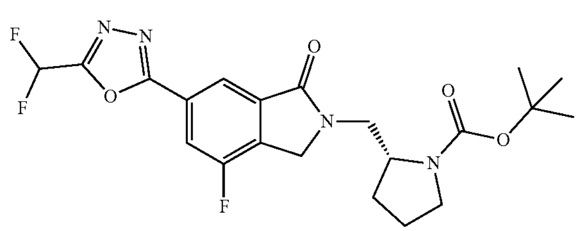 [SMILES: CC(C)(C)OC(=O)N1CCC[C@@H]1CN1Cc2c(F)cc(-c3nnc(C(F)F)o3)cc2C1=O] | | 451.0 |

TABLE 1-27-continued

| EXAMPLE | IUPAC NAME | Structure | ADDITIVE | MS |
|---|---|---|---|---|
| 264 | N-((1R,2R)-2-(6-(5-(difluoromethyl)-1,3,4-oxadiazol-2-yl)-1-oxo-1,3-dihydro-2H-isoindol-2-yl)cyclohexyl)-N-(pyridin-2-yl)acetamide | 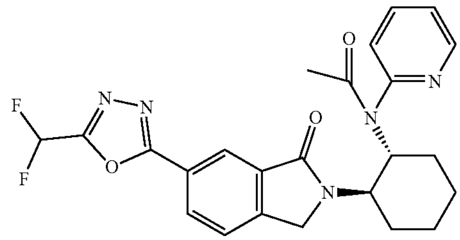 [SMILES: CC(=O)N(c1ccccn1)[C@@H]1CCCC[C@H]1N1Cc2ccc(-c3nnc(C(F)F)o3)cc2C1=O] | | 467.9 |
| 265 | 6-(5-(difluoromethyl)-1,3,4-oxadiazol-2-yl)-4-fluoro-2-(((3S)-4-((3-fluorophenyl)sulfonyl)morpholin-3-yl)methyl)isoindolin-1-one | 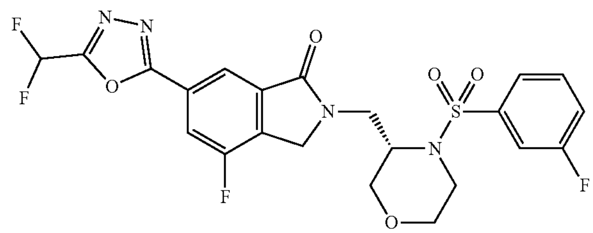 [SMILES: O=C1c2cc(-c3nnc(C(F)F)o3)cc(F)c2CN1C[C@H]1COCCN1S(=O)(=O)c1cccc(F)c1] | | 526.8 |
| 266 | 3-(5-(difluoromethyl)-1,3,4-oxadiazol-2-yl)-6-(3-methoxybenzyl)-6,7-dihydro-5H-pyrrolo[3,4-b]pyridin-5-one | 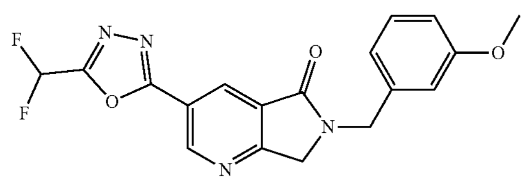 [SMILES: COc1cccc(CN2Cc3ncc(-c4nnc(C(F)F)o4)cc3C2=O)c1] | | 373.0 |
| 267 | 4'-chloro-2'-(6-(5-(difluoromethyl)-1,3,4-oxadiazol-2-yl)-1-oxo-1,3-dihydro-2H-isoindol-2-yl)biphenyl-3-carbonitrile | 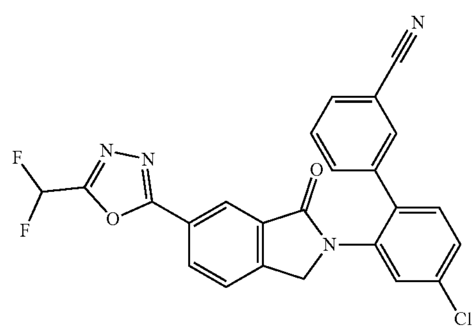 [SMILES: N#Cc1cccc(-c2ccc(Cl)cc2N2Cc3ccc(-c4nnc(C(F)F)o4)cc3C2=O)c1] | | 462.8 |
| 268 | 1,1,1-trifluoro-2-methylpropan-2-yl ((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)carbamate | 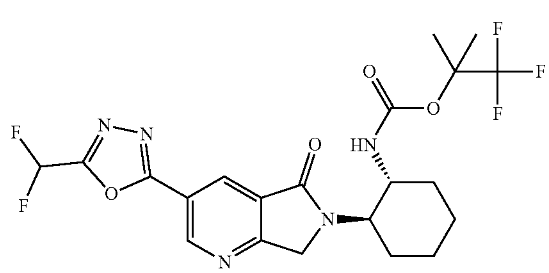 [SMILES: CC(C)(OC(=O)N[C@@H]1CCCC[C@H]1N1Cc2ncc(-c3nnc(C(F)F)o3)cc2C1=O)C(F)(F)F] | | 503.9 |

TABLE 1-28

| EXAMPLE | IUPAC NAME | Structure | ADDITIVE | MS |
|---|---|---|---|---|
| 269 | 3-(5-(difluoromethyl)-1,3,4-oxadiazol-2-yl)-6-(2-(2-oxopyrrolidin-1-yl)-1-phenylethyl)-6,7-dihydro-5H-pyrrolo[3,4-b]pyridin-5-one | 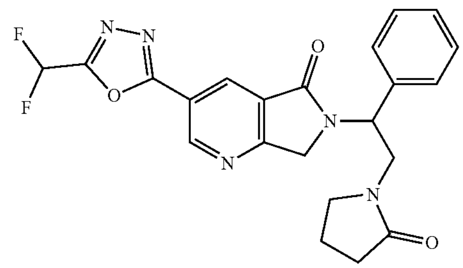 [SMILES: O=C1CCCN1CC(c1ccccc1)N1Cc2ncc(-c3nnc(C(F)F)o3)cc2C1=O] | | 440.0 |
| 270 | 2-(4-chloro-2-(1-methyl-1H-pyrazol-4-yl)phenyl)-6-(5-(difluoromethyl)-1,3,4-oxadiazol-2-yl)-isoindolin-1-one | 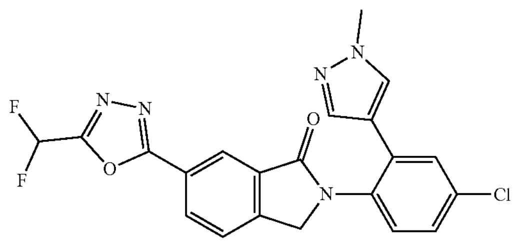 [SMILES: Cn1cc(-c2cc(Cl)ccc2N2Cc3ccc(-c4nnc(C(F)F)o4)cc3C2=O)cn1] | | 441.9 |
| 271 | 6-(5-(difluoromethyl)-1,3,4-oxadiazol-2-yl)-2-(4-fluoro-2-(1-methyl-1H-pyrazol-4-yl)phenyl)isoindolin-1-one | 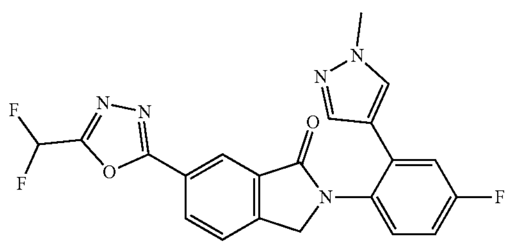 [SMILES: Cn1cc(-c2cc(F)ccc2N2Cc3ccc(-c4nnc(C(F)F)o4)cc3C2=O)cn1] | | 426.0 |
| 272 | 3-(5-(difluoromethyl)-1,3,4-oxadiazol-2-yl)-6-(2,4-dimethoxybenzyl)-6,7-dihydro-5H-pyrrolo-[3,4-b]pyridin-5-one | 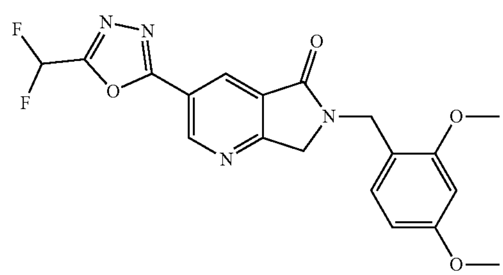 [SMILES: COc1ccc(CN2Cc3ncc(-c4nnc(C(F)F)o4)cc3C2=O)c(OC)c1] | | 403.0 |
| 273 | 3-(5-(difluoromethyl)-1,3,4-oxadiazol-2-yl)-6-(3-fluorobenzyl)-6,7-dihydro-5H-pyrrolo[3,4-b]pyridin-5-one | 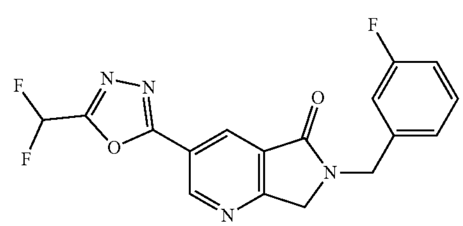 [SMILES: O=C1c2cc(-c3nnc(C(F)F)o3)cnc2CN1Cc1cccc(F)c1] | | 360.9 |
| 274 | 2-(((2R)-1-(cyclopropylsulfonyl)pyrrolidin-2-yl)methyl)-6-(5-(difluoromethyl)-1,3,4-oxadiazol-2-yl)-4-fluoroisoindolin-1-one | 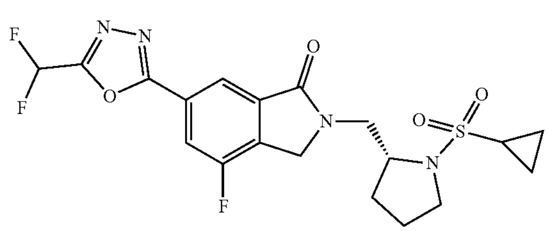 [SMILES: O=C1c2cc(-c3nnc(C(F)F)o3)cc(F)c2CN1C[C@H]1CCCN1S(=O)(=O)C1CC1] | | 457.0 |

TABLE 1-28-continued

| EXAMPLE | IUPAC NAME | Structure | ADDITIVE | MS |
|---|---|---|---|---|
| 275 | tert-butyl (2S)-2-((6-(5-(difluoromethyl)-1,3,4-oxadiazol-2-yl)-4-fluoro-1-oxo-1,3-dihydro-2H-isoindol-2-yl)methyl)-pyrrolidine-1-carboxylate | 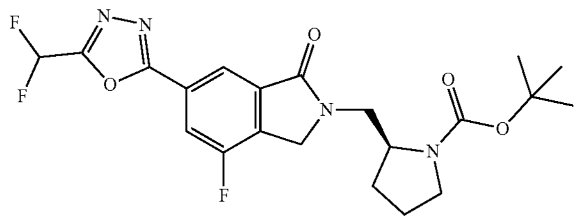 [SMILES: CC(C)(C)OC(=O)N1CCC[C@H]1CN1Cc2c(F)cc(-c3nnc(C(F)F)o3)cc2C1=O] | | 451.0 |
| 276 | 6-(5-(difluoromethyl)-1,3,4-oxadiazol-2-yl)-2-(4'-fluorobiphenyl-2-yl)-isoindolin-1-one | 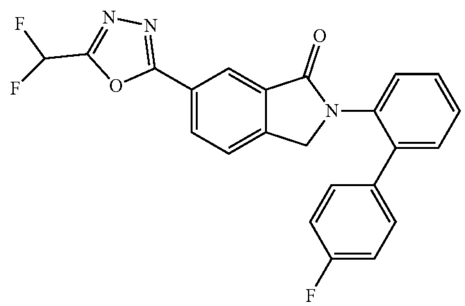 [SMILES: O=C1c2cc(-c3nnc(C(F)F)o3)ccc2CN1c1ccccc1-c1ccc(F)cc1] | | 422.0 |
| 277 | 6-(5-(difluoromethyl)-1,3,4-oxadiazol-2-yl)-2-(2'-fluorobiphenyl-2-yl)isoindolin-1-one | 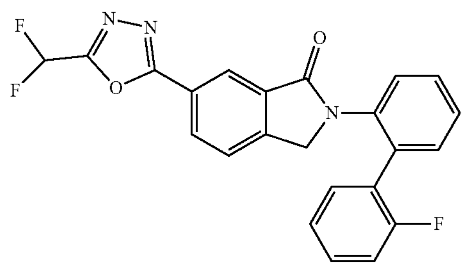 [SMILES: O=C1c2cc(-c3nnc(C(F)F)o3)ccc2CN1c1ccccc1-c1ccccc1F] | | 421.9 |
| 278 | 6-(5-(difluoromethyl)-1,3,4-oxadiazol-2-yl)-2-(3'-fluorobiphenyl-2-yl)-isoindolin-1-one | 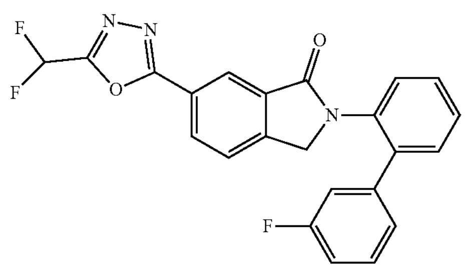 | | 421.9 |

TABLE 1-29

| EXAMPLE | IUPAC NAME | Structure | ADDITIVE | MS |
|---|---|---|---|---|
| 279 | 2'-(6-(5-(difluoromethyl)-1,3,4-oxadiazol-2-yl)-1-oxo-1,3-dihydro-2H-isoindol-2-yl)-biphenyl-4-carbonitrile | 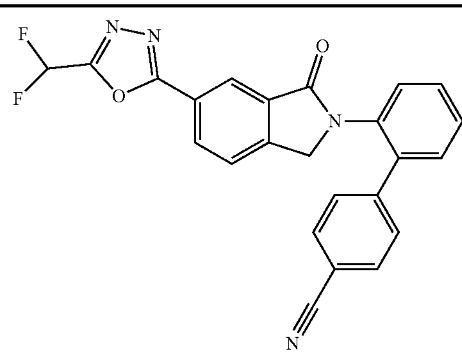 | | 429.0 |

TABLE 1-29-continued

| EXAMPLE | IUPAC NAME | Structure | ADDITIVE | MS |
|---|---|---|---|---|
| 280 | 6-(5-(difluoromethyl)-1,3,4-oxadiazol-2-yl)-2-(2-(2-ethylpyridin-3-yl)phenyl)-isoindolin-1-one | 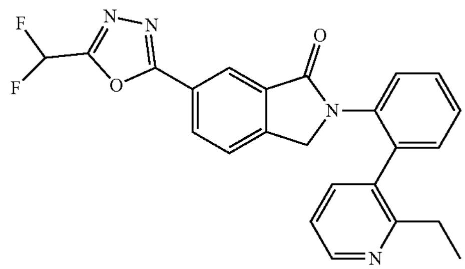 [SMILES: CCc1ncccc1-c1ccccc1N1Cc2ccc(-c3nnc(C(F)F)o3)cc2C1=O] | | 432.9 |
| 281 | 2-(2'-chlorobiphenyl-2-yl)-6-(5-(difluoromethyl)-1,3,4-oxadiazol-2-yl)isoindolin-1-one | 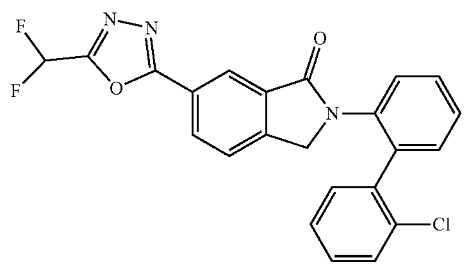 | | 438.0 |
| 282 | 2-(4'-chlorobiphenyl-2-yl)-6-(5-(difluoromethyl)-1,3,4-oxadiazol-2-yl)isoindolin-1-one | 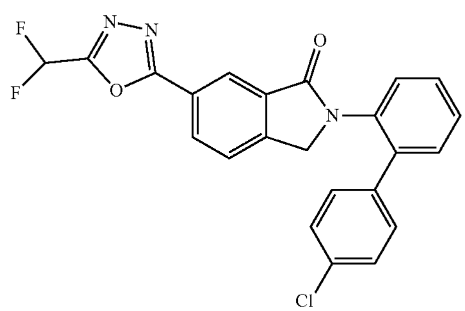 [SMILES: O=C1c2cc(-c3nnc(C(F)F)o3)ccc2CN1c1ccccc1-c1ccc(Cl)cc1] | | 437.9 |
| 283 | 2-(3'-chlorobiphenyl-2-yl)-6-(5-(difluoromethyl)-1,3,4-oxadiazol-2-yl)isoindolin-1-one | 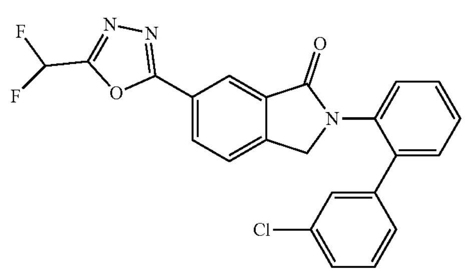 [SMILES: O=C1c2cc(-c3nnc(C(F)F)o3)ccc2CN1c1ccccc1-c1cccc(Cl)c1] | | 438.0 |
| 284 | 2-(3',5'-difluorobiphenyl-2-yl)-6-(5-(difluoromethyl)-1,3,4-oxadiazol-2-yl)isoindolin-1-one | 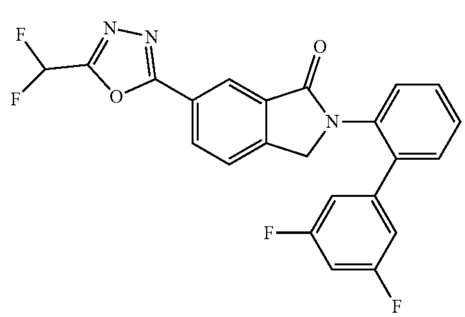 [SMILES: O=C1c2cc(-c3nnc(C(F)F)o3)ccc2CN1c1ccccc1-c1cc(F)cc(F)c1] | | 439.9 |

TABLE 1-29-continued

| EXAMPLE | IUPAC NAME | Structure | ADDITIVE | MS |
|---|---|---|---|---|
| 285 | 2-(4'-cyclopropylbiphenyl-2-yl)-6-(5-(difluoromethyl)-1,3,4-oxadiazol-2-yl)isoindolin-1-one | 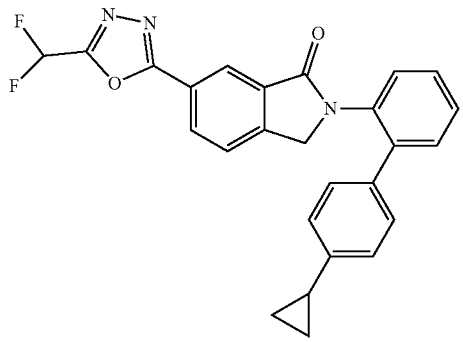 [SMILES: O=C1c2cc(-c3nnc(C(F)F)o3)ccc2CN1c1ccccc1-c1ccc(C2CC2)cc1] | | 444.0 |
| 286 | 2-(3'-cyclopropylbiphenyl-2-yl)-6-(5-(difluoromethyl)-1,3,4-oxadiazol-2-yl)isoindolin-1-one | 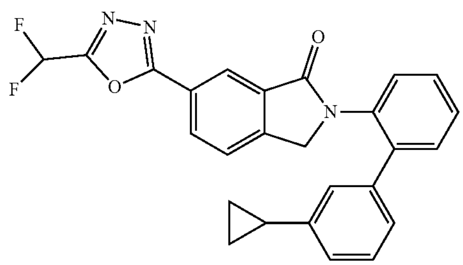 [SMILES: O=C1c2cc(-c3nnc(C(F)F)o3)ccc2CN1c1ccccc1-c1cccc(C2CC2)c1] | | 444.0 |
| 287 | 6-(5-(difluoromethyl)-1,3,4-oxadiazol-2-yl)-2-(2-(2,3-dihydro-1-benzofuran-5-yl)phenyl)isoindolin-1-one | 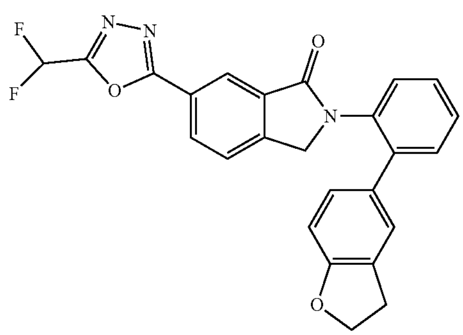 [SMILES: O=C1c2cc(-c3nnc(C(F)F)o3)ccc2CN1c1ccccc1-c1ccc2c(c1)CCO2] | | 445.9 |
| 288 | 6-(5-(difluoromethyl)-1,3,4-oxadiazol-2-yl)-2-(2-(2,3-dihydro-1-benzofuran-4-yl)phenyl)isoindolin-1-one | 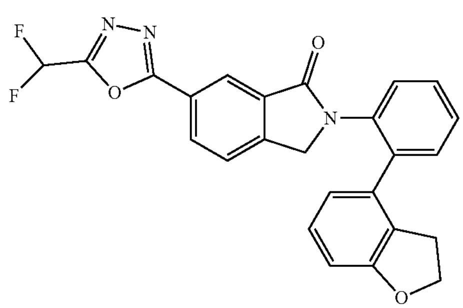 [SMILES: O=C1c2cc(-c3nnc(C(F)F)o3)ccc2CN1c1ccccc1-c1cccc2c1CCO2] | | 445.9 |

TABLE 1-30

| EXAMPLE | IUPAC NAME | Structure | ADDITIVE | MS |
|---|---|---|---|---|
| 289 | 6-(5-(difluoromethyl)-1,3,4-oxadiazol-2-yl)-2-(2-(2,3-dihydro-1-benzofuran-7-yl)phenyl)isoindolin-1-one | 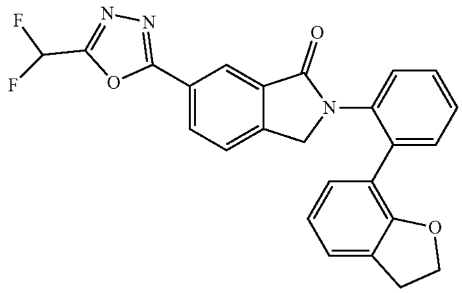 [SMILES: O=C1c2cc(-c3nnc(C(F)F)o3)ccc2CN1c1ccccc1-c1cccc2c1OCC2] | | 445.9 |
| 290 | 6-(5-(difluoromethyl)-1,3,4-oxadiazol-2-yl)-2-(2-(2-ethoxypyridin-4-yl)-phenyl)isoindolin-1-one | 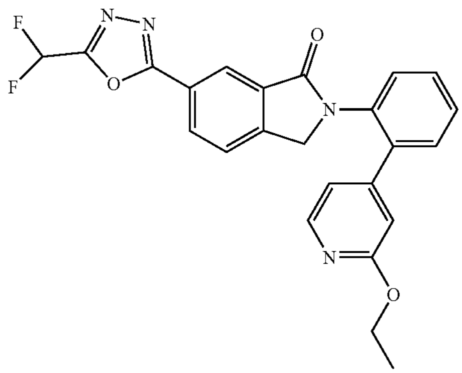 [SMILES: CCOc1cc(-c2ccccc2N2Cc3ccc(-c4nnc(C(F)F)o4)cc3C2=O)ccn1] | | 448.9 |
| 291 | 6-(5-(difluoromethyl)-1,3,4-oxadiazol-2-yl)-2-(2-(3-ethoxypyridin-4-yl)-phenyl)isoindolin-1-one | 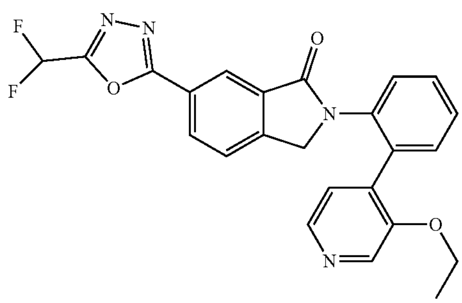 [SMILES: CCOc1cnccc1-c1ccccc1N1Cc2ccc(-c3nnc(C(F)F)o3)cc2C1=O] | | 448.9 |
| 292 | 2-(4'-(difluoromethyl)-biphenyl-2-yl)-6-(5-(difluoromethyl)-1,3,4-oxadiazol-2-yl)isoindolin-1-one | 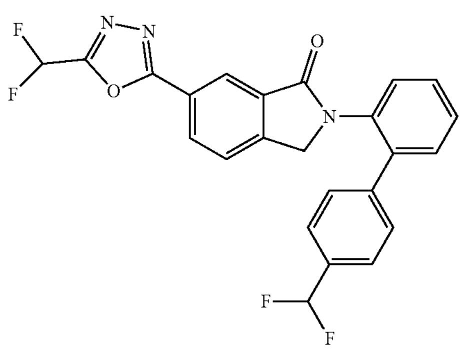 [SMILES: O=C1c2cc(-c3nnc(C(F)F)o3)ccc2CN1c1ccccc1-c1ccc(C(F)F)cc1] | | 453.9 |
| 293 | 2-(3'-(difluoromethyl)-biphenyl-2-yl)-6-(5-(difluoromethyl)-1,3,4-oxadiazol-2-yl)isoindolin-1-one | 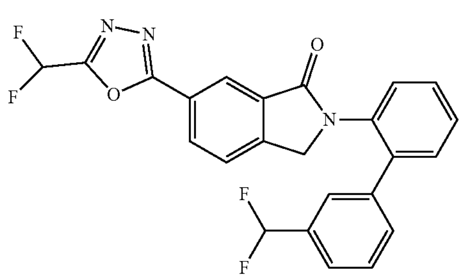 [SMILES: O=C1c2cc(-c3nnc(C(F)F)o3)ccc2CN1c1ccccc1-c1cccc(C(F)F)c1] | | 453.9 |

TABLE 1-30-continued

| EXAMPLE | IUPAC NAME | Structure | ADDITIVE | MS |
|---------|------------|-----------|----------|-----|
| 294 | 6-(5-(difluoromethyl)-1,3,4-oxadiazol-2-yl)-2-(2-(2-isopropoxypyridin-4-yl)phenyl)isoindolin-1-one | 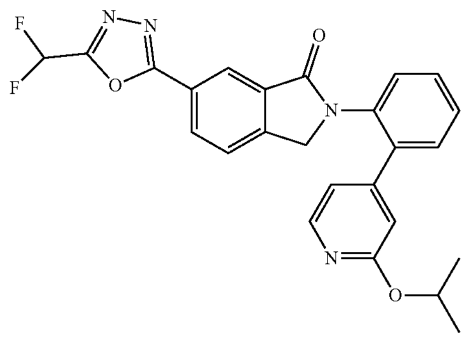 [SMILES: CC(C)Oc1cc(-c2ccccc2N2Cc3ccc(-c4nnc(C(F)F)o4)cc3C2=O)ccn1] | | 462.9 |
| 295 | 2-(2-(5-chloro-2-methoxy-pyridin-3-yl)phenyl)-6-(5-(difluoromethyl)-1,3,4-oxadiazol-2-yl)isoindolin-1-one | 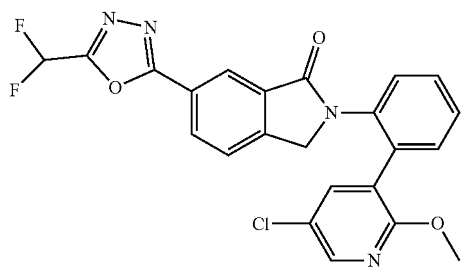 [SMILES: COc1ncc(Cl)cc1-c1ccccc1N1Cc2ccc(-c3nnc(C(F)F)o3)cc2C1=O] | | 468.8 |
| 296 | 2-(3'(difluoromethoxy)-biphenyl-2-yl)-6-(5-(difluoromethyl)-1,3,4-oxadiazol-2-yl)isoindolin-1-one | 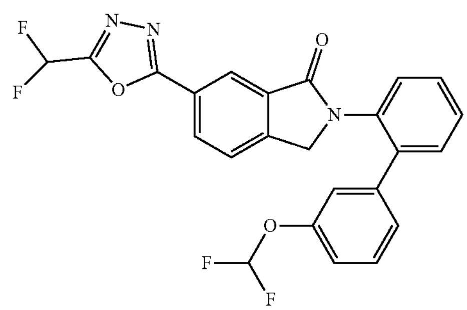 [SMILES: O=C1c2cc(-c3nnc(C(F)F)o3)ccc2CN1c1ccccc1-c1cccc(OC(F)F)c1] | | 469.9 |
| 297 | 6-(5-(difluoromethyl)-1,3,4-oxadiazol-2-yl)-2-(2-(5-(trifluoromethyl)pyridin-3-yl)phenyl)isoindolin-1-one | 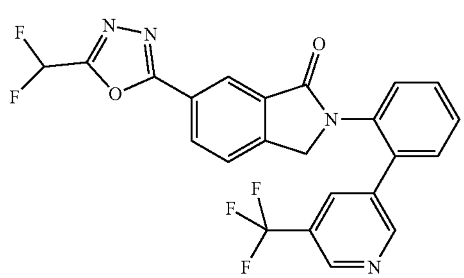 [SMILES: O=C1c2cc(-c3nnc(C(F)F)o3)ccc2CN1c1ccccc1-c1cncc(C(F)(F)F)c1] | | 472.9 |
| 298 | 6-(5-(difluoromethyl)-1,3,4-oxadiazol-2-yl)-2-(2'-(trifluoromethoxy)biphenyl-2-yl)isoindolin-1-one | 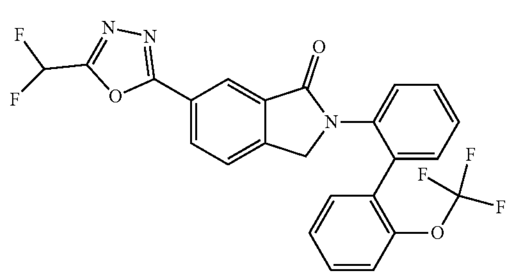 [SMILES: O=C1c2cc(-c3nnc(C(F)F)o3)ccc2CN1c1ccccc1-c1ccccc1OC(F)(F)F] | | 487.8 |

TABLE 1-31

| EXAMPLE | IUPAC NAME | Structure | ADDITIVE | MS |
|---|---|---|---|---|
| 299 | 6-(5-(difluoromethyl)-1,3,4-oxadiazol-2-yl)-2-(4'-(trifluoromethoxy)biphenyl-2-yl)isoindolin-1-one | 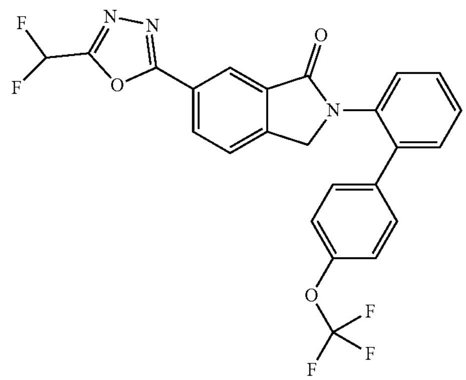 [SMILES: O=C1c2cc(-c3nnc(C(F)F)o3)ccc2CN1c1ccccc1-c1ccc(OC(F)(F)F)cc1] | | 487.9 |
| 300 | 6-(5-(difluoromethyl)-1,3,4-oxadiazol-2-yl)-2-(3'-(trifluoromethoxy)biphenyl-2-yl)isoindolin-1-one | 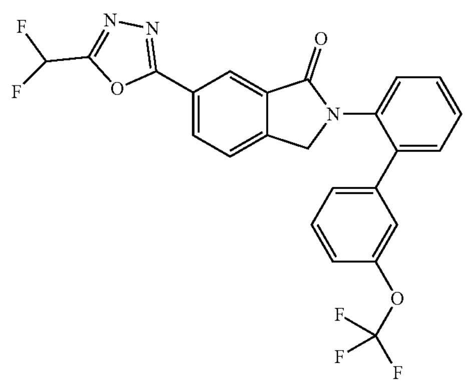 [SMILES: O=C1c2cc(-c3nnc(C(F)F)o3)ccc2CN1c1ccccc1-c1cccc(OC(F)(F)F)c1] | | 487.9 |
| 301 | 6-(5-(difluoromethyl)-1,3,4-oxadiazol-2-yl)-2-(2-(6-fluoropyridin-2-yl)phenyl)-isoindolin-1-one | 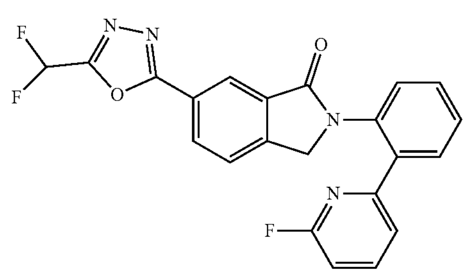 [SMILES: O=C1c2cc(-c3nnc(C(F)F)o3)ccc2CN1c1ccccc1-c1cccc(F)n1] | | 422.9 |
| 302 | 6-(5-(difluoromethyl)-1,3,4-oxadiazol-2-yl)-2-(2-(6-methoxypyridin-2-yl)-phenyl)isoindolin-1-one | 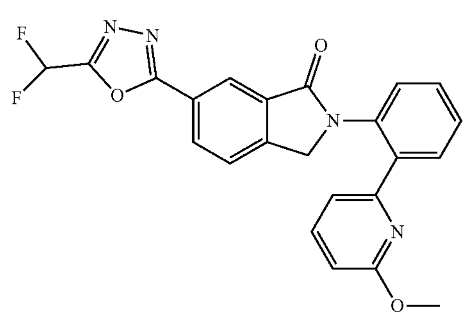 [SMILES: COc1cccc(-c2ccccc2N2Cc3ccc(-c4nnc(C(F)F)o4)cc3C2=O)n1] | | 435.0 |

TABLE 1-31-continued

| EXAMPLE | IUPAC NAME | Structure | ADDITIVE | MS |
|---|---|---|---|---|
| 303 | 6-(5-(difluoromethyl)-1,3,4-oxadiazol-2-yl)-2-(2-(furo[2,3-b]pyridin-5-yl)phenyl)-isoindolin-1-one | 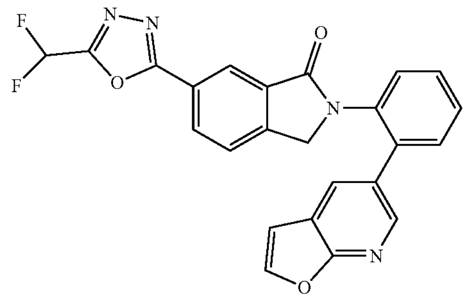 [SMILES: O=C1c2cc(-c3nnc(C(F)F)o3)ccc2CN1c1ccccc1-c1cnc2occc2c1] | | 444.9 |
| 304 | 6-(5-(difluoromethyl)-1,3,4-oxadiazol-2-yl)-2-(2-(2,3-dihydro-1-benzofuran-6-yl)phenyl)isoindolin-1-one | 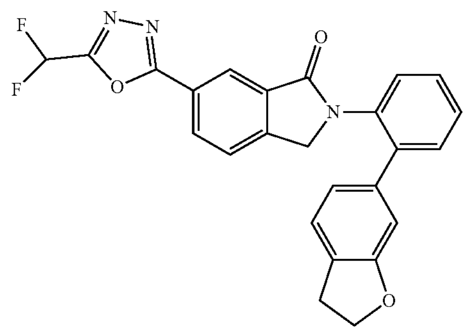 [SMILES: O=C1c2cc(-c3nnc(C(F)F)o3)ccc2CN1c1ccccc1-c1ccc2c(c1)OCC2] | | 445.9 |
| 305 | 2-(2-(6-chloropyridin-2-yl)-phenyl)-6-(5-(difluoromethyl)-1,3,4-oxadiazol-2-yl)isoindolin-1-one | 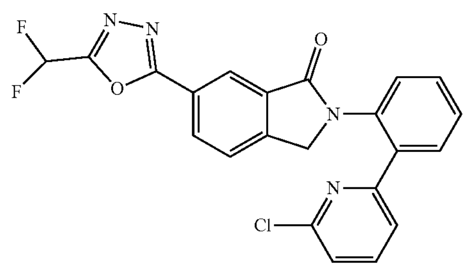 [SMILES: O=C1c2cc(-c3nnc(C(F)F)o3)ccc2CN1c1ccccc1-c1cccc(Cl)n1] | | 438.9 |
| 306 | 6-(5-(difluoromethyl)-1,3,4-oxadiazol-2-yl)-2-(2-(2-methylimidazo[1,2-a]pyridin-6-yl)phenyl)-isoindolin-1-one | 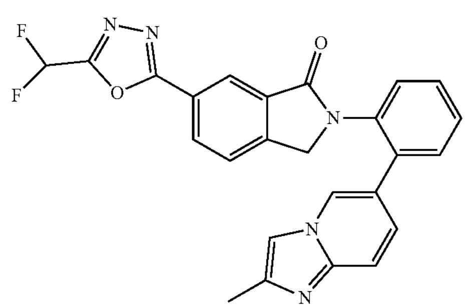 [SMILES: Cc1cn2cc(-c3ccccc3N3Cc4ccc(-c5nnc(C(F)F)o5)cc4C3=O)ccc2n1] | | 457.9 |
| 307 | 2-(3',4'-difluorobiphenyl-2-yl)-6-(5-(difluoromethyl)-1,3,4-oxadiazol-2-yl)-isoindolin-1-one | 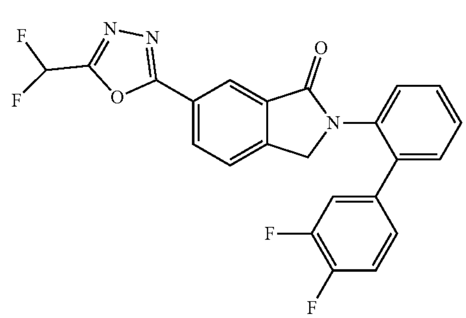 [SMILES: O=C1c2cc(-c3nnc(C(F)F)o3)ccc2CN1c1ccccc1-c1ccc(F)c(F)c1] | | 439.9 |

TABLE 1-31-continued

| EXAMPLE | IUPAC NAME | Structure | ADDITIVE | MS |
|---|---|---|---|---|
| 308 | 2-(2',3'-difluorobiphenyl-2-yl)-6-(5-(difluoromethyl)-1,3,4-oxadiazol-2-yl)-isoindolin-1-one | 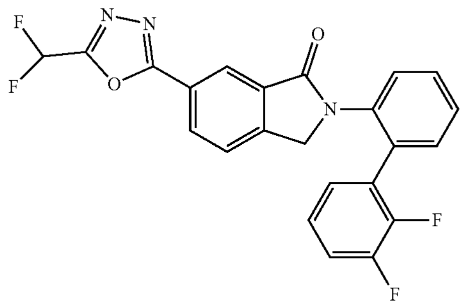 [SMILES: O=C1c2cc(-c3nnc(C(F)F)o3)ccc2CN1c1ccccc1-c1cccc(F)c1F] | | 439.9 |

TABLE 1-32

| EXAMPLE | IUPAC NAME | Structure | ADDITIVE | MS |
|---|---|---|---|---|
| 309 | 2-(2',5'-difluorobiphenyl-2-yl)-6-(5-(difluoromethyl)-1,3,4-oxadiazol-2-yl)isoindolin-1-one | 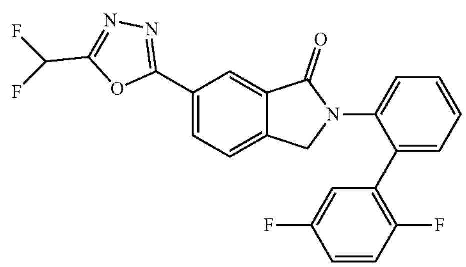 [SMILES: O=C1c2cc(-c3nnc(C(F)F)o3)ccc2CN1c1ccccc1-c1cc(F)ccc1F] | | 439.9 |
| 310 | 2-(2',4'-difluorobiphenyl-2-yl)-6-(5-(difluoromethyl)-1,3,4-oxadiazol-2-yl)isoindolin-1-one | 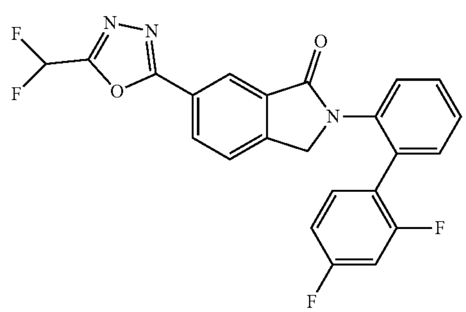 [SMILES: O=C1c2cc(-c3nnc(C(F)F)o3)ccc2CN1c1ccccc1-c1ccc(F)cc1F] | | 439.9 |
| 311 | 6-(5-(difluoromethyl)-1,3,4-oxadiazol-2-yl)-2-(2'-methyl-biphenyl-2-yl)isoindolin-1-one | 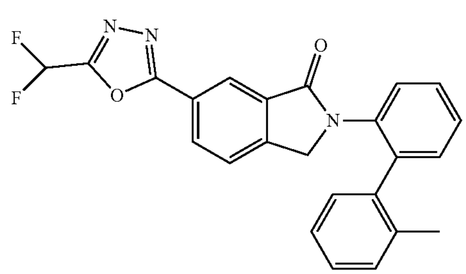 [SMILES: Cc1ccccc1-c1ccccc1N1Cc2ccc(-c3nnc(C(F)F)o3)cc2C1=O] | | 418.0 |
| 312 | 6-(5-(difluoromethyl)-1,3,4-oxadiazol-2-yl)-2-(3'-methyl-biphenyl-2-yl)isoindolin-1-one | 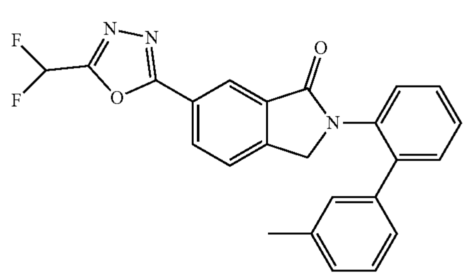 [SMILES: Cc1cccc(-c2ccccc2N2Cc3ccc(-c4nnc(C(F)F)o4)cc3C2=O)c1] | | 418.0 |

TABLE 1-32-continued

| EXAMPLE | IUPAC NAME | Structure | ADDITIVE | MS |
|---|---|---|---|---|
| 313 | 6-(5-(difluoromethyl)-1,3,4-oxadiazol-2-yl)-2-(4'-methyl-biphenyl-2-yl)isoindolin-1-one | 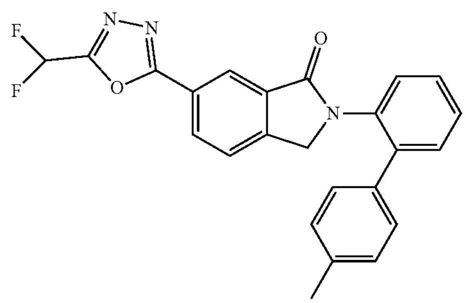 [SMILES: Cc1ccc(-c2ccccc2N2Cc3ccc(-c4nnc(C(F)F)o4)cc3C2=O)cc1] | | 418.0 |
| 314 | 6-(5-(difluoromethyl)-1,3,4-oxadiazol-2-yl)-2-(2-(5-(methylsulfonyl)pyridin-3-yl)phenyl)isoindolin-1-one | 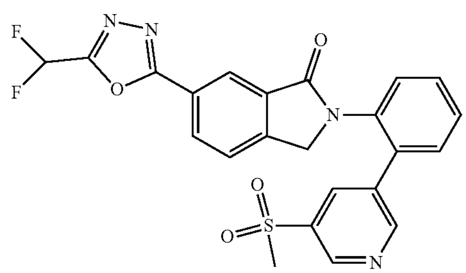 [SMILES: CS(=O)(=O)c1cncc(-c2ccccc2N2Cc3ccc(-c4nnc(C(F)F)o4)cc3C2=O)c1] | | 482.8 |
| 315 | 6-(5-(difluoromethyl)-1,3,4-oxadiazol-2-yl)-2-(3'-(2,2,2-trifluoroethoxy)biphenyl-2-yl)isoindolin-1-one | 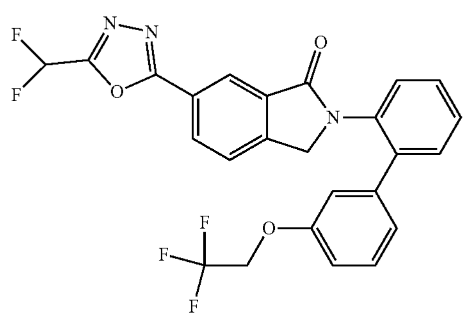 [SMILES: O=C1c2cc(-c3nnc(C(F)F)o3)ccc2CN1c1ccccc1-c1cccc(OCC(F)(F)F)c1] | | 501.9 |
| 316 | 1-(2'-(6-(5-(difluoromethyl)-1,3,4-oxadiazol-2-yl)-1-oxo-1,3-dihydro-2H-isoindol-2-yl)-biphenyl-4-yl)cyclopropane-carbonitrile | 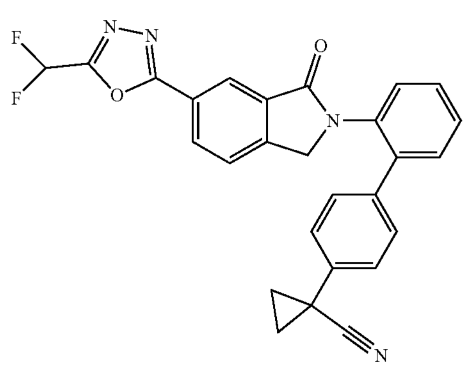 [SMILES: N#CC1(c2ccc(-c3ccccc3N3Cc4ccc(-c5nnc(C(F)F)o5)cc4C3=O)cc2)CC1] | | 468.9 |
| 317 | 6-(5-(difluoromethyl)-1,3,4-oxadiazol-2-yl)-2-(2'-(2-methoxyethoxy)biphenyl-2-yl)isoindolin-1-one | 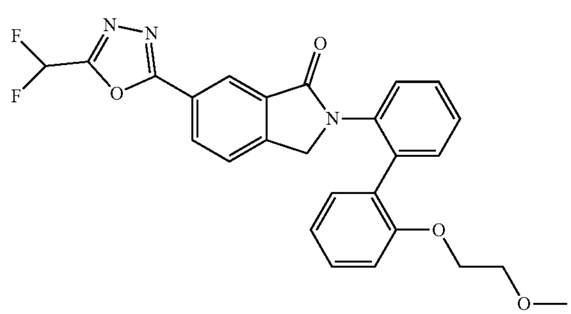 [SMILES: COCCOc1ccccc1-c1ccccc1N1Cc2ccc(-c3nnc(C(F)F)o3)cc2C1=O] | | 477.9 |

TABLE 1-32-continued

| EXAMPLE | IUPAC NAME | Structure | ADDITIVE | MS |
|---|---|---|---|---|
| 318 | 6-(5-(difluoromethyl)-1,3,4-oxadiazol-2-yl)-2-(2-(1-(difluoromethyl)-1H-pyrazol-4-yl)phenyl)isoindolin-1-one | 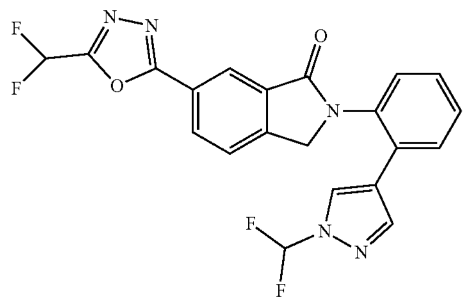 [SMILES: O=C1c2cc(-c3nnc(C(F)F)o3)ccc2CN1c1ccccc1-c1cnn(C(F)F)c1] | | 443.9 |

TABLE 1-33

| EXAMPLE | IUPAC NAME | Structure | ADDITIVE | MS |
|---|---|---|---|---|
| 319 | 6-(5-(difluoromethyl)-1,3,4-oxadiazol-2-yl)-2-(2-(1-(tetrahydro-2H-pyran-4-yl)-1H-pyrazol-4-yl)phenyl)-isoindolin-1-one | 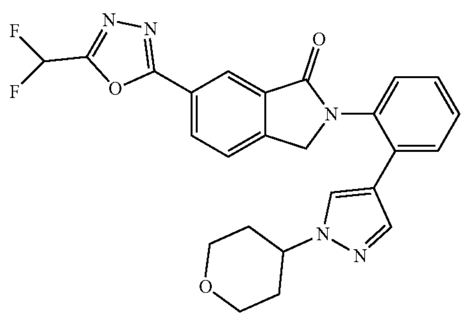 [SMILES: O=C1c2cc(-c3nnc(C(F)F)o3)ccc2CN1c1ccccc1-c1cnn(C2CCOCC2)c1] | | 477.9 |
| 320 | 6-(5-(difluoromethyl)-1,3,4-oxadiazol-2-yl)-2-(2-(1-methyl-3-(trifluoromethyl)-1H-pyrazol-5-yl)phenyl)-isoindolin-1-one | 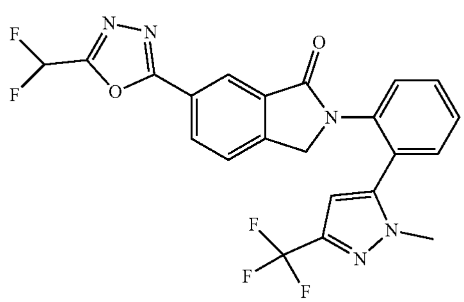 [SMILES: Cn1nc(C(F)(F)F)cc1-c1ccccc1N1Cc2ccc(-c3nnc(C(F)F)o3)cc2C1=O] | | 475.9 |
| 321 | 6-(5-(difluoromethyl)-1,3,4-oxadiazol-2-yl)-2-(4'-(2-methoxyethoxy)biphenyl-2-yl)isoindolin-1-one | 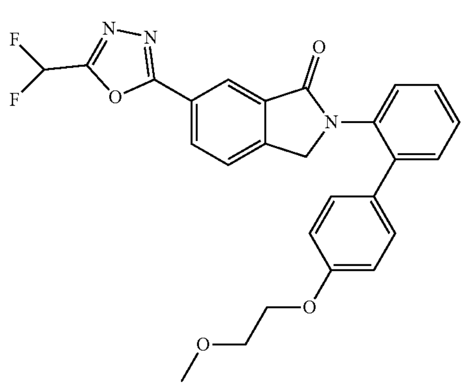 [SMILES: COCCOc1ccc(-c2ccccc2N2Cc3ccc(-c4nnc(C(F)F)o4)cc3C2=O)cc1] | | 477.9 |

| EXAMPLE | IUPAC NAME | Structure | ADDITIVE | MS |
|---|---|---|---|---|
| 322 | 6-(5-(difluoromethyl)-1,3,4-oxadiazol-2-yl)-2-(2-(2-(2,2,2-trifluoroethoxy)-pyrimidin-5-yl)phenyl)-isoindolin-1-one | 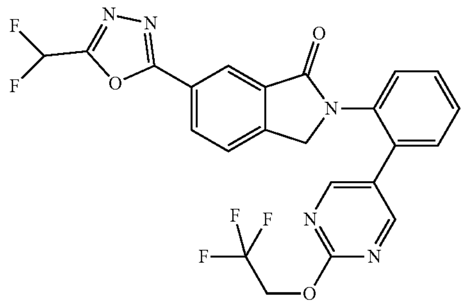 [SMILES: O=C1c2cc(-c3nnc(C(F)F)o3)ccc2CN1c1ccccc1-c1cnc(OCC(F)(F)F)nc1] | | 503.8 |
| 323 | 6-(5-(difluoromethyl)-1,3,4-oxadiazol-2-yl)-2-(2-(1-(pyridin-2-ylmethyl)-1H-pyrazol-4-yl)phenyl)-isoindolin-1-one | 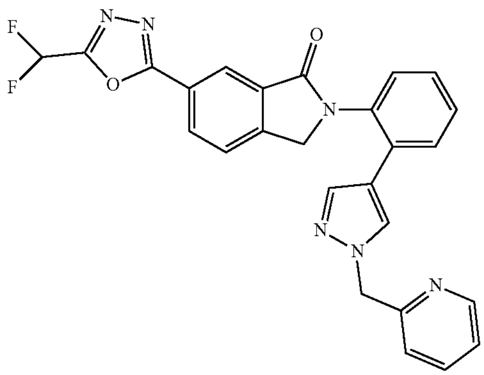 [SMILES: O=C1c2cc(-c3nnc(C(F)F)o3)ccc2CN1c1ccccc1-c1cnn(Cc2ccccn2)c1] | | 484.9 |
| 324 | ((2'-(6-(5-(difluoromethyl)-1,3,4-oxadiazol-2-yl)-1-oxo-1,3-dihydro-2H-isoindol-2-yl)biphenyl-3-yl)oxy)-acetonitrile | 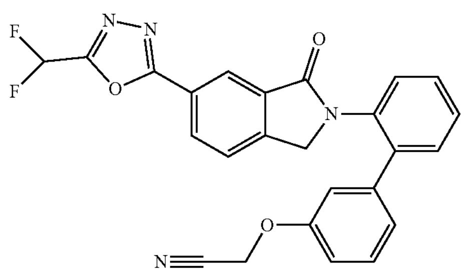 [SMILES: N#CCOc1cccc(-c2ccccc2N2Cc3ccc(-c4nnc(C(F)F)o4)cc3C2=O)c1] | | 458.9 |
| 325 | 6-(5-(difluoromethyl)-1,3,4-oxadiazol-2-yl)-2-(3'-(pyrrolidin-1-ylcarbonyl)-biphenyl-2-yl)isoindolin-1-one | 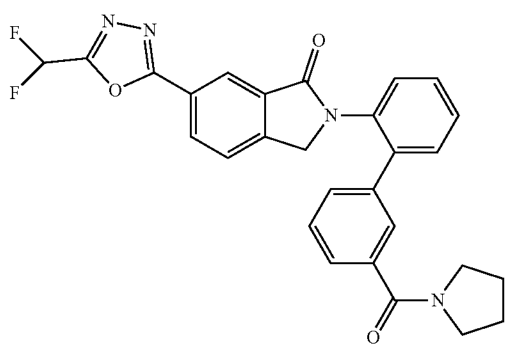 [SMILES: O=C(c1cccc(-c2ccccc2N2Cc3ccc(-c4nnc(C(F)F)o4)cc3C2=O)c1)N1CCCC1] | | 500.9 |
| 326 | 6-(5-(difluoromethyl)-1,3,4-oxadiazol-2-yl)-4-fluoro-2-((2S)-pyrrolidin-2-ylmethyl)-isoindolin-1-one | 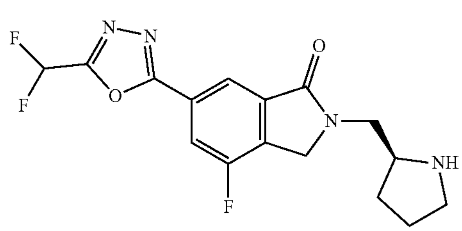 [SMILES: O=C1c2cc(-c3nnc(C(F)F)o3)cc(F)c2CN1C[C@@H]1CCCN1] | | 352.9 |

TABLE 1-33-continued

| EXAMPLE | IUPAC NAME | Structure | ADDITIVE | MS |
|---|---|---|---|---|
| 327 | 6-(2,3-difluorobenzyl)-3-(5-(difluoromethyl)-1,3,4-oxadiazol-2-yl)-6,7-dihydro-5H-pyrrolo[3,4-b]pyridin-5-one | 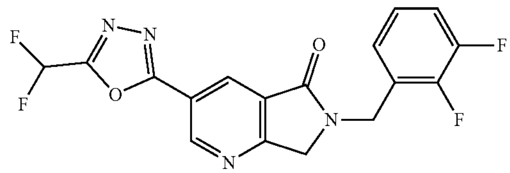 [SMILES: O=C1c2cc(-c3nnc(C(F)F)o3)cnc2CN1Cc1cccc(F)c1F] | | 378.9 |
| 328 | 3-(5-(difluoromethyl)-1,3,4-oxadiazol-2-yl)-6-(4-fluorobenzyl)-6,7-dihydro-5H-pyrrolo[3,4-b]pyridin-5-one | 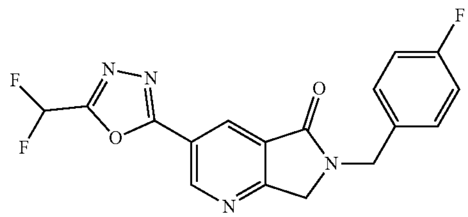 [SMILES: O=C1c2cc(-c3nnc(C(F)F)o3)cnc2CN1Cc1ccc(F)cc1] | | 358.9 |

TABLE 1-34

| EXAMPLE | IUPAC NAME | Structure | ADDITIVE | MS |
|---|---|---|---|---|
| 329 | 6-(2,6-difluorobenzyl)-3-(5-(difluoromethyl)-1,3,4-oxadiazol-2-yl)-6,7-dihydro-5H-pyrrolo[3,4-b]pyridin-5-one | 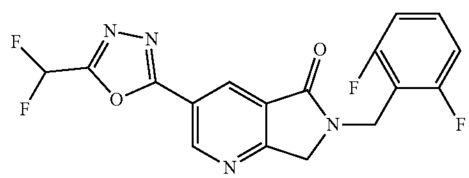 [SMILES: O=C1c2cc(-c3nnc(C(F)F)o3)cnc2CN1Cc1c(F)cccc1F] | | 378.9 |
| 330 | 6-(5-(difluoromethyl)-1,3,4-oxadiazol-2-yl)-2-(2-(1H-pyrazol-1-yl)phenyl)-isoindolin-1-one | 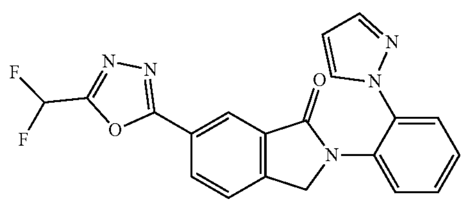 [SMILES: O=C1c2cc(-c3nnc(C(F)F)o3)ccc2CN1c1ccccc1-n1cccn1] | | 393.9 |
| 331 | tert-butyl (2S)-2-((6-(5-(difluoromethyl)-1,3,4-oxadiazol-2-yl)-4-fluoro-1-oxo-1,3-dihydro-2H-isoindol-2-yl)methyl)-4,4-difluoropyrrolidine-1-carboxylate | 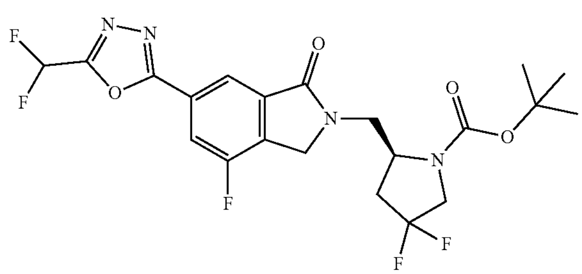 [SMILES: CC(C)(C)OC(=O)N1CC(F)(F)C[C@H]1CN1Cc2c(F)cc(-c3nnc(C(F)F)o3)cc2C1=O] | | 486.9 |
| 332 | 3-(5-(difluoromethyl)-1,3,4-oxadiazol-2-yl)-6-(4-methoxybenzyl)-6,7-dihydro-5H-pyrrolo[3,4-b]pyridin-5-one | 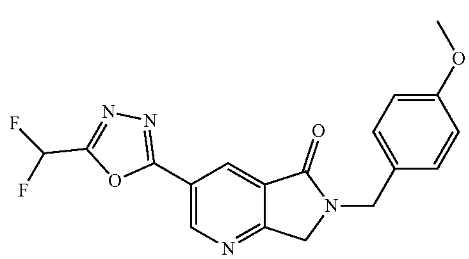 [SMILES: COc1ccc(CN2Cc3ncc(-c4nnc(C(F)F)o4)cc3C2=O)cc1] | | 372.9 |

TABLE 1-34-continued

| EXAMPLE | IUPAC NAME | Structure | ADDITIVE | MS |
|---|---|---|---|---|
| 333 | 6-(4-chlorobenzyl)-3-(5-(difluoromethyl)-1,3,4-oxadiazol-2-yl)-6,7-dihydro-5H-pyrrolo[3,4-b]pyridin-5-one | 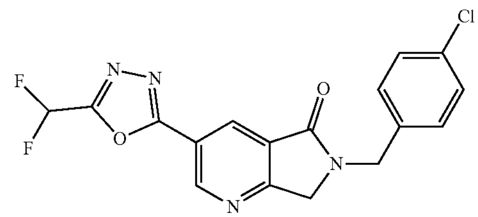 [SMILES: O=C1c2cc(-c3nnc(C(F)F)o3)cnc2CN1Cc1ccc(Cl)cc1] | | 374.9 |
| 334 | 3-(5-(difluoromethyl)-1,3,4-oxadiazol-2-yl)-6-(4-(trifluoromethyl)benzyl)-6,7-dihydro-5H-pyrrolo[3,4-b]pyridin-5-one | 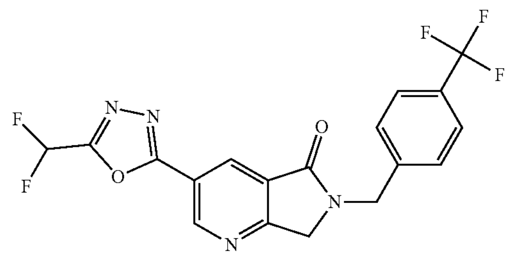 [SMILES: O=C1c2cc(-c3nnc(C(F)F)o3)cnc2CN1Cc1ccc(C(F)(F)F)cc1] | | 408.9 |
| 335 | 6-(4-difluoromethoxy)-benzyl)-3-(5-(difluoro-methyl)-1,3,4-oxadiazol-2-yl)-6,7-dihydro-5H-pyrrolo[3,4-b]pyridin-5-one | 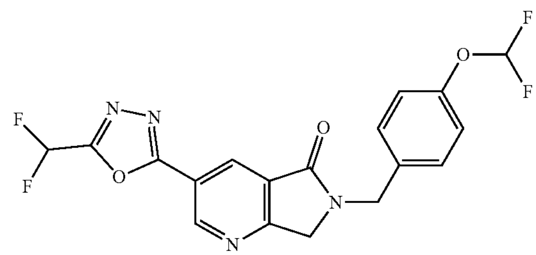 [SMILES: O=C1c2cc(-c3nnc(C(F)F)o3)cnc2CN1Cc1ccc(OC(F)F)cc1] | | 406.9 |
| 336 | 2-(((2S)-1-(cyclopropyl-sulfonyl)pyrrolidin-2-yl)methyl)-6-(5-(difluoromethyl)-1,3,4-oxadiazol-2-yl)-4-fluoroisoindolin-1-one | 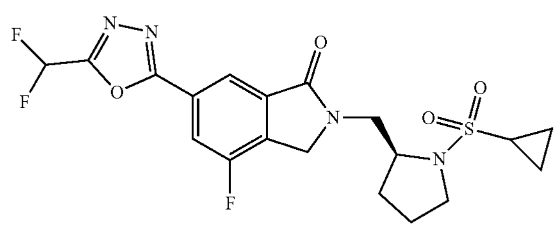 [SMILES: O=C1c2cc(-c3nnc(C(F)F)o3)cc(F)c2CN1C[C@@H]1CCCN1S(=O)(=O)C1CC1] | | 456.9 |
| 337 | N-((1R,2R)-2-(6-(5-(difluoromethyl)-1,3,4-oxadiazol-2-yl)-1-oxo-1,3-dihydro-2H-isoindol-2-yl)-cyclohexyl)-2,2-difluoro-N-(pyridin-2-yl)acetamide | 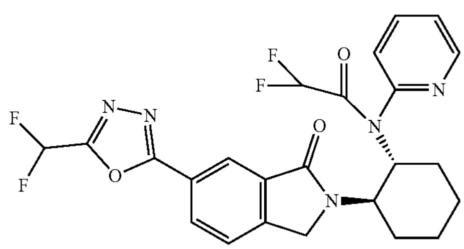 [SMILES: O=C1c2cc(-c3nnc(C(F)F)o3)ccc2CN1[C@@H]1CCCC[C@H]1N(C(=O)C(F)F)c1ccccn1] | | 503.9 |
| 338 | 6-(3,4-difluorobenzyl)-3-(5-(difluoromethyl)-1,3,4-oxadiazol-2-yl)-6,7-dihydro-5H-pyrrolo[3,4-b]pyridin-5-one | 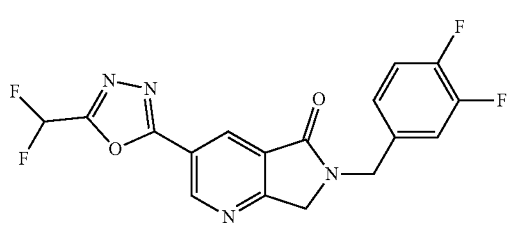 [SMILES: O=C1c2cc(-c3nnc(C(F)F)o3)cnc2CN1Cc1ccc(F)c(F)c1] | | 376.9 |

TABLE 1-35

| EXAMPLE | IUPAC NAME | Structure | ADDITIVE | MS |
|---|---|---|---|---|
| 339 | 3-(5-(difluoromethyl)-1,3,4-oxadiazol-2-yl)-6-(2-(trifluoromethyl)benzyl)-6,7-dihydro-5H-pyrrolo[3,4-b]-pyridin-5-one | 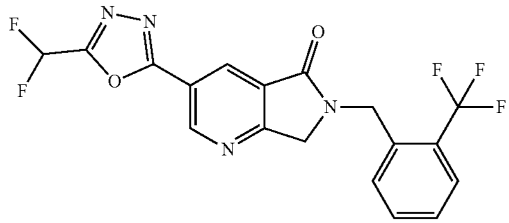 [SMILES: O=C1c2cc(-c3nnc(C(F)F)o3)cnc2CN1Cc1ccccc1C(F)(F)F] | | 410.9 |
| 340 | 6-(2-chlorobenzyl)-3-(5-(difluoromethyl)-1,3,4-oxadiazol-2-yl)-6,7-dihydro-5H-pyrrolo[3,4-b]pyridin-5-one | 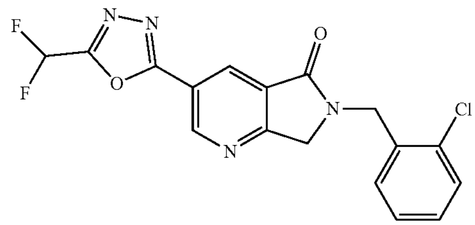 [SMILES: O=C1c2cc(-c3nnc(C(F)F)o3)cnc2CN1Cc1ccccc1Cl] | | 376.9 |
| 341 | tert-butyl ((1-(6-(5-(difluoromethyl)-1,3,4-oxadiazol-2-yl)-4-fluoro-1-oxo-1,3-dihydro-2H-isoindol-2-yl)cyclohexyl)methyl)carbamate | 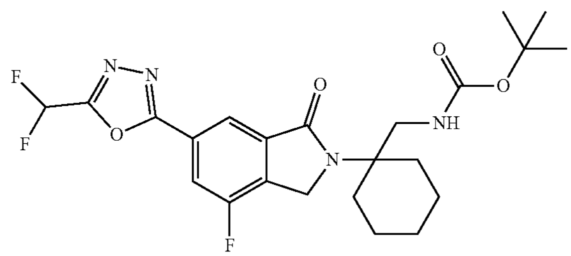 [SMILES: CC(C)(C)OC(=O)NCC1(N2Cc3c(F)cc(-c4nnc(C(F)F)o4)cc3C2=O)CCCCC1] | | 479.0 |
| 342 | 6-(3-chlorobenzyl)-3-(5-(difluoromethyl)-1,3,4,-oxadiazol-2-yl)-6,7-dihydro-5H-pyrrolo[3,4-b]pyridin-5-one | 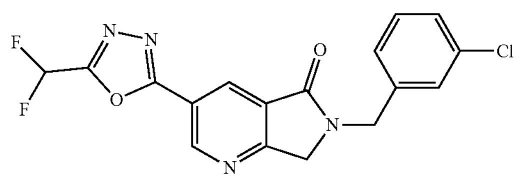 [SMILES: O=C1c2cc(-c3nnc(C(F)F)o3)cnc2CN1Cc1cccc(Cl)c1] | | 374.9 |
| 343 | 2-(((2S)-1-(cyclopropyl-sulfonyl)-4,4-difluoro-pyrrolidin-2-yl)methyl)-6-(5-(difluoromethyl)-1,3,4-oxadiazol-2-yl)-4-fluoroisoindolin-1-one | 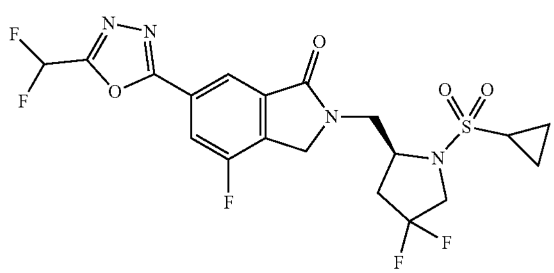 [SMILES: O=C1c2cc(-c3nnc(C(F)F)o3)cc(F)c2CN1C[C@@H]1CC(F)(F)CN1S(=O)(=O)C1CC1] | | 492.8 |
| 344 | 6-(5-(difluoromethyl)-1,3,4-oxadiazol-2-yl)-2-(((2S)-4,4-difluoro-1-((2,2,2-trifluoro-ethyl)sulfonyl)pyrrolidin-2-yl)methyl)-4-fluoroiso-indolin-1-one | 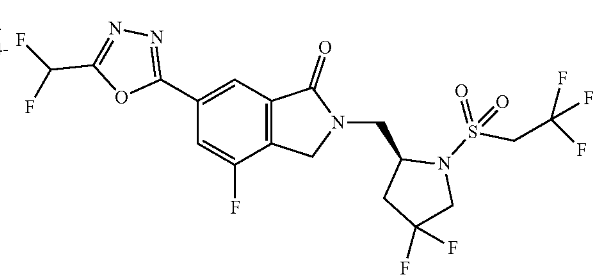 | | 534.8 |

TABLE 1-35-continued

| EXAMPLE | IUPAC NAME | Structure | ADDITIVE | MS |
|---|---|---|---|---|
| 345 | 2-(((2S)-4,4-difluoro-1-((3-fluorophenyl)sulfonyl)-pyrrolidin-2-yl)methyl)-6-(5-(difluoromethyl)-1,3,4-oxadiazol-2-yl)-4-fluoro-isoindolin-1-one | 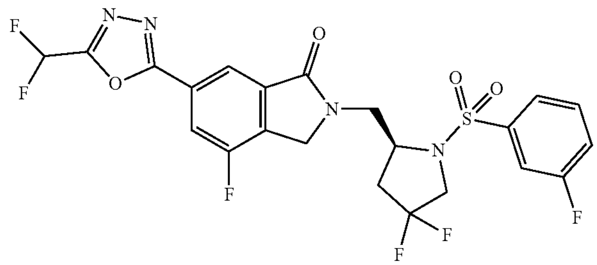 [SMILES: O=C1c2cc(-c3nnc(C(F)F)o3)cc(F)c2CN1C[C@@H]1CC(F)(F)CN1S(=O)(=O)c1cccc(F)c1] | | 546.7 |
| 346 | 3-(5-(difluoromethyl)-1,3,4-oxadiazol-2-yl)-6-(pyridin-4-ylmethyl)-6,7-dihydro-5H-pyrrolo[3,4-b]pyridin-5-one | 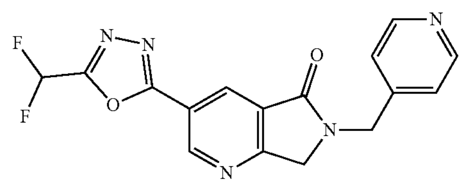 [SMILES: O=C1c2cc(-c3nnc(C(F)F)o3)cnc2CN1Cc1ccncc1] | | 343.9 |
| 347 | 3-(5-(difluoromethyl)-1,3,4-oxadiazol-2-yl)-6-(1-(4-fluorophenyl)cyclopropyl)-6,7-dihydro-5H-pyrrolo[3,4-b]pyridin-5-one | 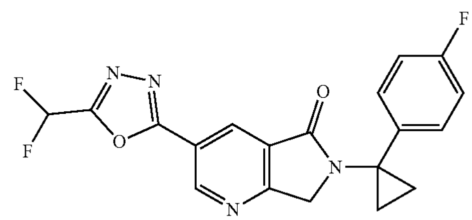 [SMILES: O=C1c2cc(-c3nnc(C(F)F)o3)cnc2CN1C1(c2ccc(F)cc2)CC1] | | 387.0 |
| 348 | 6-(2,4-difluorobenzyl)-3-(5-(difluoromethyl)-1,3,4-oxadiazol-2-yl)-6,7-dihydro-5H-pyrrolo-[3,4-b]pyridin-5-one | 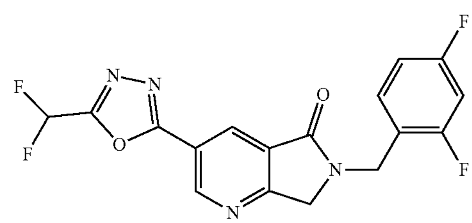 [SMILES: O=C1c2cc(-c3nnc(C(F)F)o3)cnc2CN1Cc1ccc(F)cc1F] | | 376.9 |

TABLE 1-36

| EXAMPLE | IUPAC NAME | Structure | ADDITIVE | MS |
|---|---|---|---|---|
| 349 | 3-(5-(difluoromethyl)-1,3,4-oxadiazol-2-yl)-6-((5-methyl-1,2-oxazol-3-yl)methyl)-6,7-dihydro-5H-pyrrolo[3,4-b]pyridin-5-one | 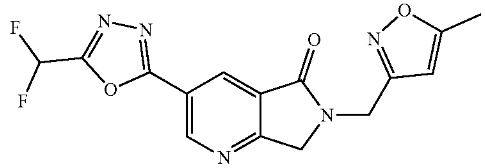 [SMILES: Cc1cc(CN2Cc3ncc(-c4nnc(C(F)F)o4)cc3C2=O)no1] | | 347.9 |
| 350 | 3-(5-(difluoromethyl)-1,3,4-oxadiazol-2-yl)-6-(1-(2-fluorophenyl)cyclopropyl)-6,7-dihydro-5H-pyrrolo[3,4-b]pyridin-5-one | 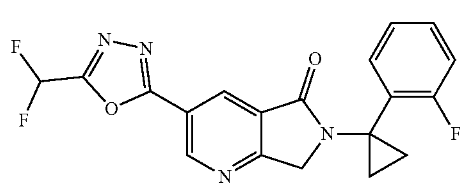 [SMILES: O=C1c2cc(-c3nnc(C(F)F)o3)cnc2CN1C1(c2ccccc2F)CC1] | | 386.9 |

TABLE 1-36-continued

| EXAMPLE | IUPAC NAME | Structure | ADDITIVE | MS |
|---|---|---|---|---|
| 351 | 3-(5-(difluoromethyl)-1,3,4-oxadiazol-2-yl)-6-(2-fluorobenzyl)-6,7-dihydro-5H-pyrrolo[3,4-b]pyridin-5-one | 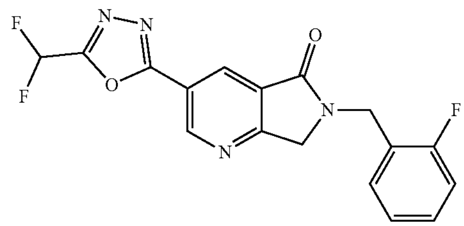 [SMILES: O=C1c2cc(-c3nnc(C(F)F)o3)cnc2CN1Cc1ccccc1F] | | 360.9 |
| 352 | tert-butyl (2R)-2-((6-(5-(difluoromethyl)-1,3,4-oxadiazol-2-yl)-4-fluoro-1-oxo-1,3-dihydro-2H-isoindol-2-yl)methyl)-4,4-difluoropyrrolidine-1-carboxylate | 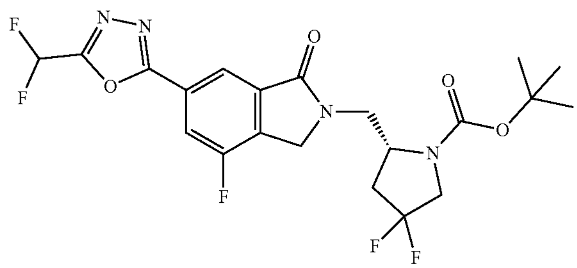 [SMILES: CC(C)(C)OC(=O)N1CC(F)(F)C[C@@H]1CN1Cc2c(F)cc(-c3nnc(C(F)F)o3)cc2C1=O] | | 486.9 |
| 353 | 6-(3,5-difluorobenzyl)-3-(5-(difluoromethyl)-1,3,4-oxadiazol-2-yl)-6,7-dihydro-5H-pyrrolo[3,4-b]pyridin-5-one | 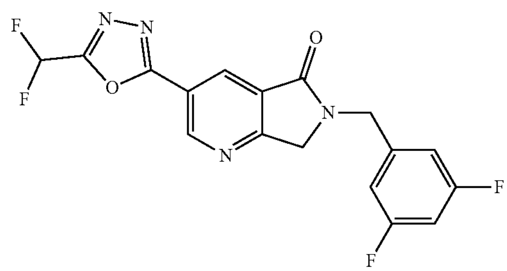 [SMILES: O=C1c2cc(-c3nnc(C(F)F)o3)cnc2CN1Cc1cc(F)cc(F)c1] | | 376.9 |
| 354 | 6-(5-(difluoromethyl)-1,3,4-oxadiazol-2-yl)-2-(((2R)-4,4-difluoropyrrolidin-2-yl)methyl)-4-fluoroisoindolin-1-one | 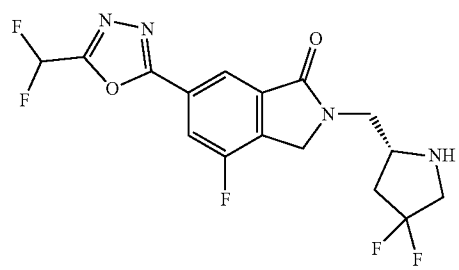 [SMILES: O=C1c2cc(-c3nnc(C(F)F)o3)cc(F)c2CN1C[C@H]1CC(F)(F)CN1] | | 388.9 |
| 355 | 3-(5-(difluoromethyl)-1,3,4-oxadiazol-2-yl)-6-(3-(trifluoromethyl)benzyl)-6,7-dihydro-5H-pyrrolo[3,4-b]-pyridin-5-one | 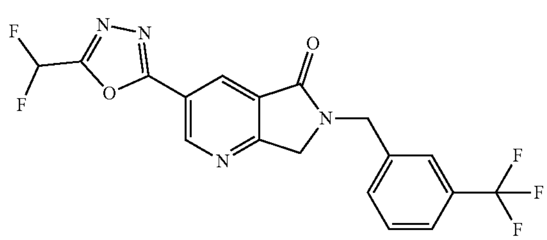 [SMILES: O=C1c2cc(-c3nnc(C(F)F)o3)cnc2CN1Cc1cccc(C(F)(F)F)c1] | | 408.9 |
| 356 | 2-(((2R)-1-(cyclopropylsulfonyl)-4,4-difluoropyrrolidin-2-yl)methyl)-6-(5-(difluoromethyl)-1,3,4-oxadiazol-2-yl)-4-fluoroisoindolin-1-one | 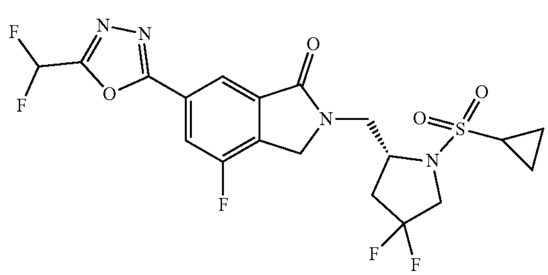 [SMILES: O=C1c2cc(-c3nnc(C(F)F)o3)cc(F)c2CN1C[C@H]1CC(F)(F)CN1S(=O)(=O)C1CC1] | | 492.8 |

TABLE 1-36-continued

| EXAMPLE | IUPAC NAME | Structure | ADDITIVE | MS |
|---|---|---|---|---|
| 357 | 3-(5-(difluoromethyl)-1,3,4-oxadiazol-2-yl)-6-(2-methoxybenzyl)-6,7-dihydro-5H-pyrrolo[3,4-b]-pyridin-5-one | 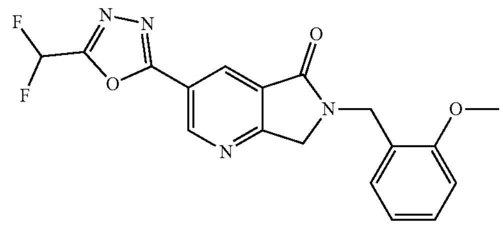 [SMILES: COc1ccccc1CN1Cc2ncc(-c3nnc(C(F)F)o3)cc2C1=O] | | 373.0 |
| 358 | 6-(2-(difluoromethoxy)-benzyl)-3-(5-(difluoro-methyl)-1,3,4-oxadiazol-2-yl)-6,7-dihydro-5H-pyrrolo-[3,4-b]pyridin-5-one | 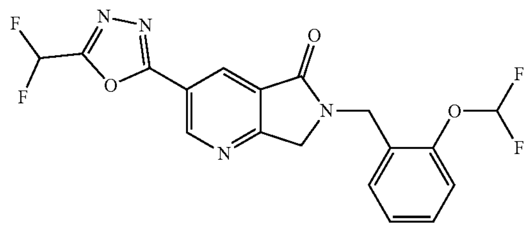 [SMILES: O=C1c2cc(-c3nnc(C(F)F)o3)cnc2CN1Cc1ccccc1OC(F)F] | | 408.9 |

TABLE 1-37

| EXAMPLE | IUPAC NAME | Structure | ADDITIVE | MS |
|---|---|---|---|---|
| 359 | 3-(5-(difluoromethyl)-1,3,4-oxadiazol-2-yl)-6-(pyridin-3-ylmethyl)-6,7-dihydro-5H-pyrrolo[3,4-b]pyridin-5-one | 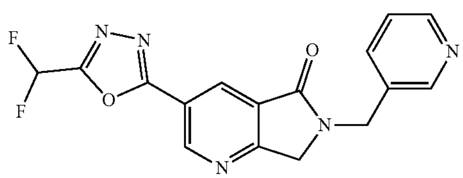 [SMILES: O=C1c2cc(-c3nnc(C(F)F)o3)cnc2CN1Cc1cccnc1] | | 343.9 |
| 360 | 6-(5-(difluoromethyl)-1,3,4-oxadiazol-2-yl)-4-fluoro-2-((3S,4R)-3-((2,2,2-trifluoro-ethyl)amino)tetrahydro-2H-pyran-4-yl)isoindolin-1-one | 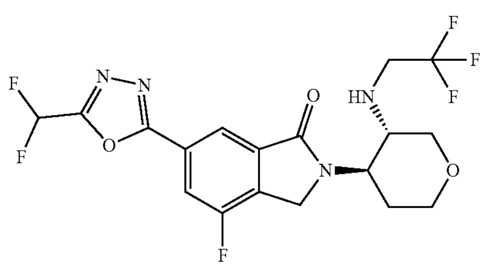 [SMILES: O=C1c2cc(-c3nnc(C(F)F)o3)cc(F)c2CN1[C@@H]1CCOC[C@H]1NCC(F)(F)F] | | 450.9 |
| 361 | 6-(5-(difluoromethyl)-1,3,4-oxadiazol-2-yl)-4-fluoro-2-((3S,4R)-4-((2,2,2-trifluoro-ethyl)amino)tetrahydro-2H-pyran-3-yl)isoindolin-1-one | 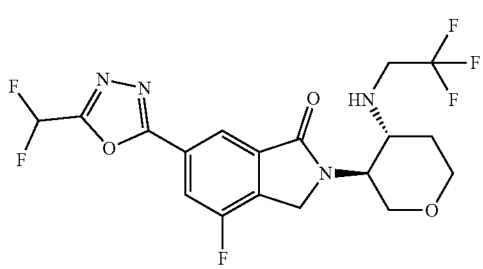 | | 450.9 |
| 362 | 3-(5-(difluoromethyl)-1,3,4-oxadiazol-2-yl)-6-(pyridin-2-yl-methyl)-6,7-dihydro-5H-pyrrolo[3,4-b]pyridin-5-one | 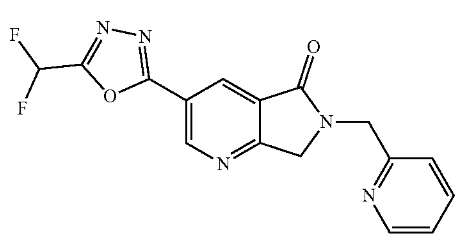 [SMILES: O=C1c2cc(-c3nnc(C(F)F)o3)cnc2CN1Cc1ccccn1] | | 344.0 |

TABLE 1-37-continued

| EXAMPLE | IUPAC NAME | Structure | ADDITIVE | MS |
|---|---|---|---|---|
| 363 | tert-butyl ((3R,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)carbamate | 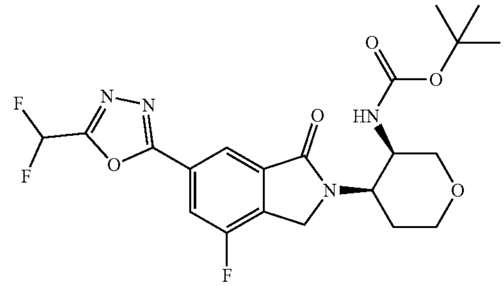 [SMILES: CC(C)(C)OC(=O)N[C@H]1COCC[C@H]1N1Cc2c(F)cc(-c3nnc(C(F)F)o3)cc2C1=O] | | 467.2 |
| 364 | 2-((3R,4R)-3-amino-tetrahydro-2H-pyran-4-yl)-6-(5-(difluoromethyl)-1,3,4-oxadiazol-2-yl)-4-fluoroisoindolin-1-one | 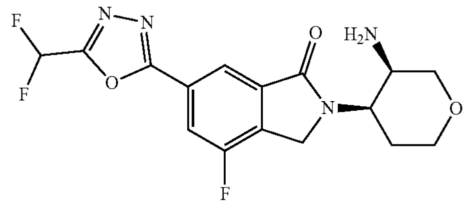 [SMILES: N[C@H]1COCC[C@H]1N1Cc2c(F)cc(-c3nnc(C(F)F)o3)cc2C1=O] | | 369.1 |
| 365 | N-((3R,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)-2,2,3,3,3-pentafluoropropanamide | 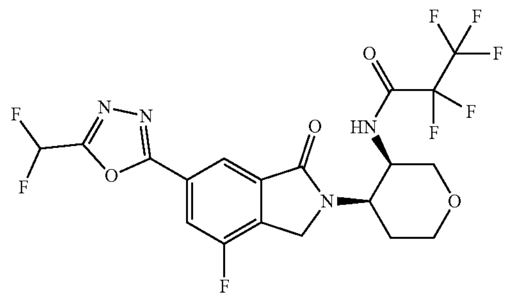 [SMILES: O=C1c2cc(-c3nnc(C(F)F)o3)cc(F)c2CN1[C@@H]1CCOC[C@@H]1NC(=O)C(F)(F)C(F)(F)F] | | 513.1 |
| 366 | N-((3R,4R)-4-(6-(5-(difluoromethyl)-1,3,4-oxadiazol-2-yl)-4-fluoro-1-oxo-1,3-dihydro-2H-isoindol-2-yl)tetrahydro-2H-pyran-3-yl)-2,2-difluoropropanamide | 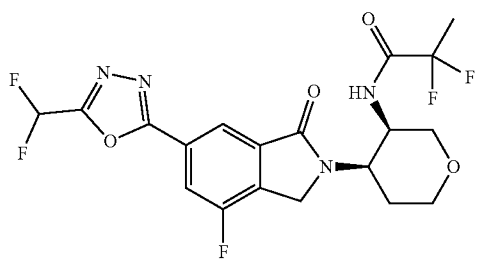 [SMILES: CC(F)(F)C(=O)N[C@H]1COCC[C@H]1N1Cc2c(F)cc(-c3nnc(C(F)F)o3)cc2C1=O] | | 461.1 |
| 367 | 3-(5-(difluoromethyl)-1,3,4-oxadiazol-2-yl)-6-((1R,2R)-2-((2,2,2-trifluoroethyl)amino)-cyclohexyl)-6,7-dihydro-5H-pyrrolo[3,4-b]pyridin-5-one | 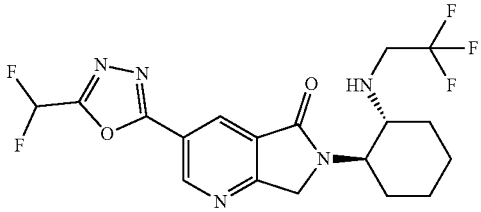 [SMILES: O=C1c2cc(-c3nnc(C(F)F)o3)cnc2CN1[C@@H]1CCCC[C@H]1NCC(F)(F)F] | | 432.2 |
| 368 | 3-(3-(6-(5-(difluoromethyl)-1,3,4-oxadiazol-2-yl)-1-oxo-1,3-dihydro-2H-isoindol-2-yl)-1-methyl-1H-pyrazol-4-yl)benzonitrile | 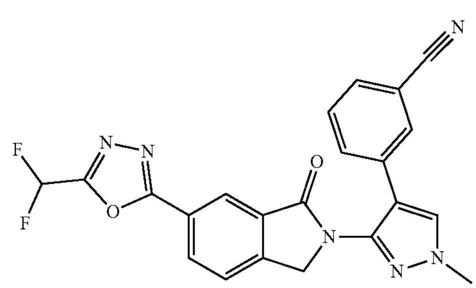 [SMILES: Cn1cc(-c2cccc(C#N)c2)c(N2Cc3ccc(-c4nnc(C(F)F)o4)cc3C2=O)n1] | | 433.1 |

TABLE 1-38

| EXAMPLE | IUPAC NAME | Structure | ADDITIVE | MS |
|---|---|---|---|---|
| 369 | 2-(4-(3-chlorophenyl)-1-methyl-1H-pyrazol-3-yl)-6-(5-(difluoromethyl)-1,3,4-oxadiazol-2-yl)isoindolin-1-one | 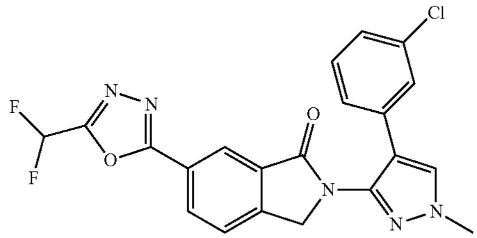 [SMILES: Cn1cc(-c2cccc(Cl)c2)c(N2Cc3ccc(-c4nnc(C(F)F)o4)cc3C2=O)n1] | | 442.0 |
| 370 | 6-(3-(difluoromethyl)benzyl)-3-(5-(difluoromethyl)-1,3,4-oxadiazol-2-yl)-6,7-dihydro-5H-pyrrolo[3,4-b]pyridin-5-one | 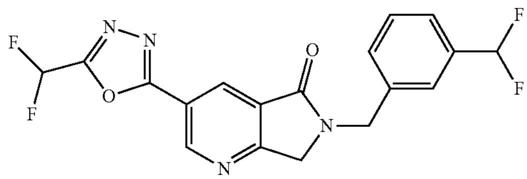 [SMILES: O=C1c2cc(-c3nnc(C(F)F)o3)cnc2CN1Cc1cccc(C(F)F)c1] | | 391.1 |
| 371 | N-((1-(6-(5-(difluoromethyl)-1,3,4-oxadiazol-2-yl)-4-fluoro-1-oxo-1,3-dihydro-2H-isoindol-2-yl)cyclohexyl)methyl)-2,2,2-trifluoroethanesulfonamide | 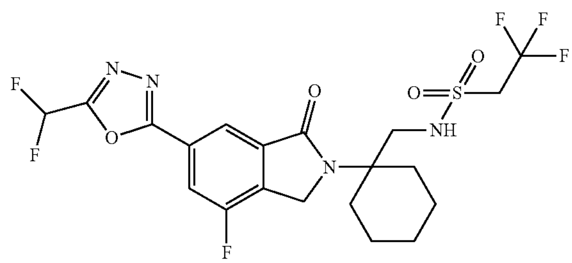 [SMILES: O=C1c2cc(-c3nnc(C(F)F)o3)cc(F)c2CN1C1(CNS(=O)(=O)CC(F)(F)F)CCCCC1] | | 527.0 |
| 372 | 2-(2-bromophenyl)-6-(5-(difluoromethyl)-1,3,4-oxadiazol-2-yl)-4-fluoroisoindolin-1-one | 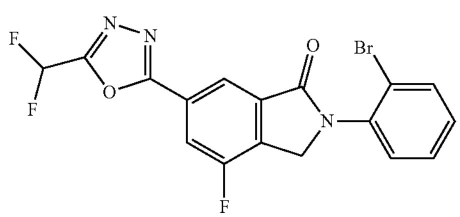 [SMILES: O=C1c2cc(-c3nnc(C(F)F)o3)cc(F)c2CN1c1ccccc1Br] | | 421.9 |
| 373 | 2-(2-bromo-3-fluorophenyl)-6-(5-(difluoromethyl)-1,3,4-oxadiazol-2-yl)isoindolin-1-one | 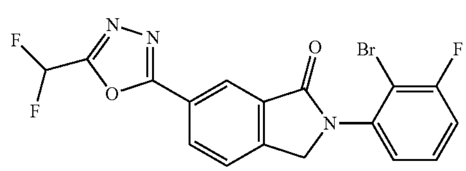 [SMILES: O=C1c2cc(-c3nnc(C(F)F)o3)ccc2CN1c1cccc(F)c1Br] | | 424.0 |
| 374 | 6-(5-(difluoromethyl)-1,3,4-oxadiazol-2-yl)-4-fluoro-2-((3R,4R)-3-((2,2,2-trifluoroethyl)amino)tetrahydro-2H-pyran-4-yl)isoindolin-1-one | 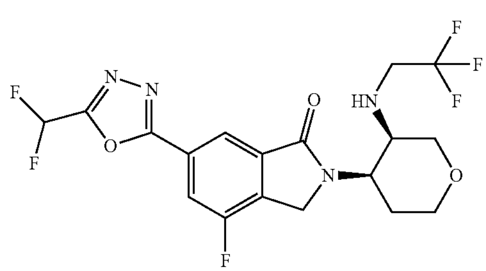 [SMILES: O=C1c2cc(-c3nnc(C(F)F)o3)cc(F)c2CN1[C@@H]1CCOC[C@@H]1NCC(F)(F)F] | | 451.1 |

TABLE 1-38-continued

| EXAMPLE | IUPAC NAME | Structure | ADDITIVE | MS |
|---|---|---|---|---|
| 375 | 6-(5-(difluoromethyl)-1,3,4-oxadiazol-2-yl)-4-fluoro-2-((3R,4R)-3-((2,2,3,3,3-pentafluoropropyl)amino)tetrahydro-2H-pyran-4-yl)isoindolin-1-one | 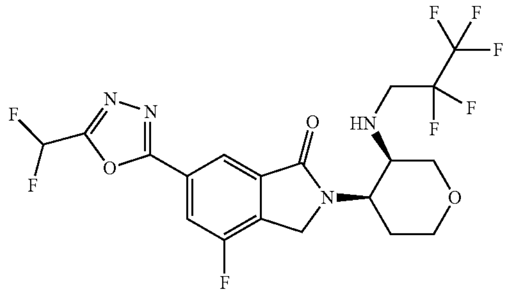 [SMILES: O=C1c2cc(-c3nnc(C(F)F)o3)cc(F)c2CN1[C@@H]1CCOC[C@@H]1NCC(F)(F)C(F)(F)F] | | 501.0 |
| 376 | 2'-(6-(5-(difluoromethyl)-1,3,4-oxadiazol-2-yl)-4-fluoro-1-oxo-1,3-dihydro-2H-isoindol-2-yl)biphenyl-3-carbonitrile | 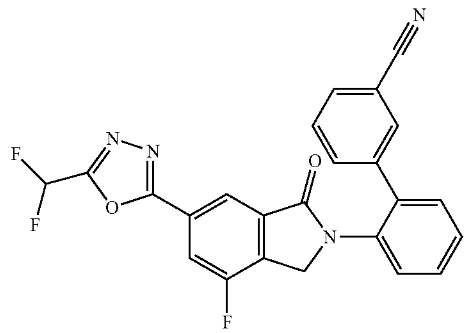 [SMILES: N#Cc1cccc(-c2ccccc2N2Cc3c(F)cc(-c4nnc(C(F)F)o4)cc3C2=O)c1] | | 446.9 |
| 377 | 2'-(6-(5-(difluoromethyl)-1,3,4-oxadiazol-2-yl)-1-oxo-1,3-dihydro-2H-isoindol-2-yl)-6'-fluorobiphenyl-3-carbonitrile | 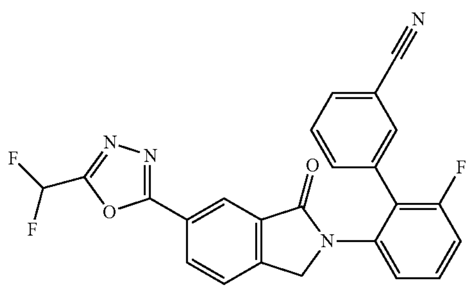 [SMILES: N#Cc1cccc(-c2c(F)cccc2N2Cc3ccc(-c4nnc(C(F)F)o4)cc3C2=O)c1] | | 446.9 |
| 378 | 2'-(6-(5-(difluoromethyl)-1,3,4-oxadiazol-2-yl)-4-fluoro-1-oxo-1,3-dihydro-2H-isoindol-2-yl)-5'-fluorobiphenyl-3-carbonitrile | 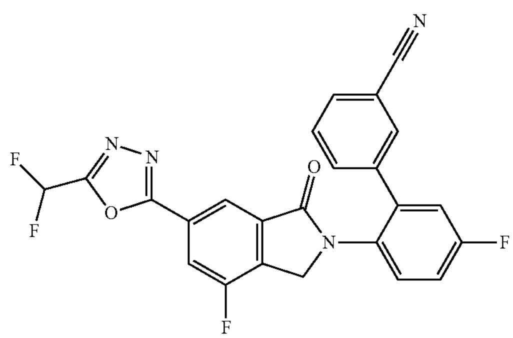 [SMILES: N#Cc1cccc(-c2cc(F)ccc2N2Cc3c(F)cc(-c4nnc(C(F)F)o4)cc3C2=O)c1] | | 464.9 |

TABLE 1-39

| EXAMPLE | IUPAC NAME | Structure | ADDITIVE | MS |
|---|---|---|---|---|
| 379 | 2-(((2S)-1-(cyclopropylcarbonyl)pyrrolidin-2-yl)methyl)-6-(5-(difluoromethyl)-1,3,4-oxadiazol-2-yl)-4-fluoroisoindolin-1-one | 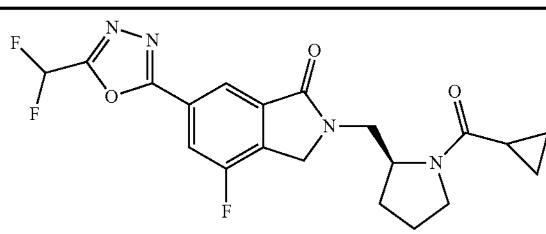 | | 421.0 |

TABLE 1-39-continued

| EXAMPLE | IUPAC NAME | Structure | ADDITIVE | MS |
|---|---|---|---|---|
| 380 | 6-(5-(difluoro-methyl)-1,3,4-oxadiazol-2-yl)-4-fluoro-2-(((2S)-1-((2,2,2-trifluoroethyl)sulfonyl)pyrrolidin-2-yl)methyl)isoindolin-1-one | 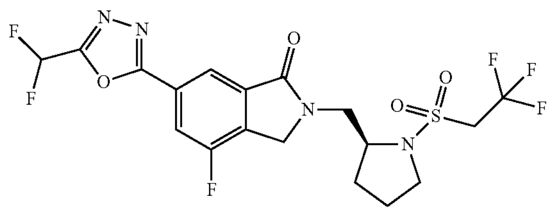 [SMILES: O=C1c2cc(-c3nnc(C(F)F)o3)cc(F)c2CN1C[C@@H]1CCCN1S(=O)(=O)CC(F)(F)F] | | 498.8 |
| 381 | 6-(5-(difluoro-methyl)-1,3,4-oxadiazol-2-yl)-2-(2-(1-(difluoro-methyl)-1H-pyrazol-4-yl)-4-fluorophenyl)-4-fluoroisoindolin-1-one | 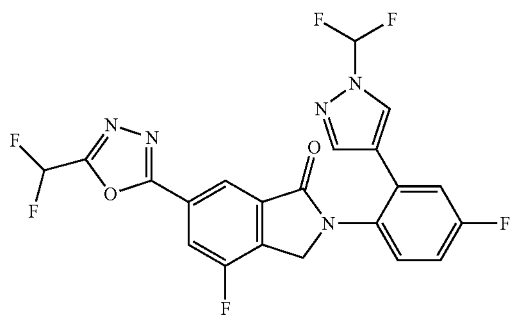 [SMILES: O=C1c2cc(-c3nnc(C(F)F)o3)cc(F)c2CN1c1ccc(F)cc1-c1cnn(C(F)F)c1] | | 477.9 |
| 382 | 6-(5-(difluoro-methyl)-1,3,4-oxadiazol-2-yl)-4-fluoro-2-(4-fluoro-2-(1-methyl-1H-pyrazol-4-yl)phenyl)isoindolin-1-one | 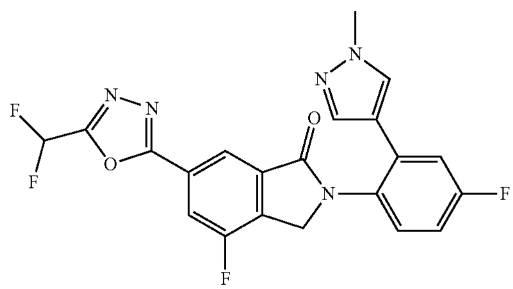 [SMILES: Cn1cc(-c2cc(F)ccc2N2Cc3c(F)cc(-c4nnc(C(F)F)o4)cc3C2=O)cn1] | | 443.9 |
| 383 | 2-(3',5-difluoro-biphenyl-2-yl)-6-(5-(difluoro-methyl)-1,3,4-oxadiazol-2-yl)-4-fluoroiso-indolin-1-one | 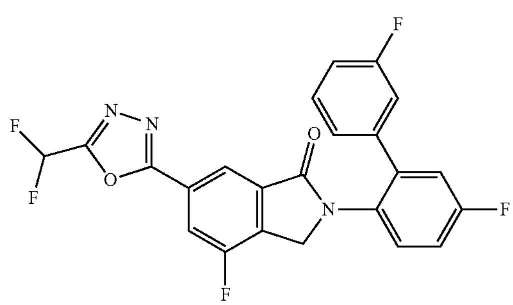 [SMILES: O=C1c2cc(-c3nnc(C(F)F)o3)cc(F)c2CN1c1ccc(F)cc1-c1cccc(F)c1] | | 457.9 |
| 384 | 6-(5-(difluoro-methyl)-1,3,4-oxadiazol-2-yl)-2-(4-(3-fluoro-phenyl)-1-methyl-1H-pyrazol-3-yl)isoindolin-1-one | 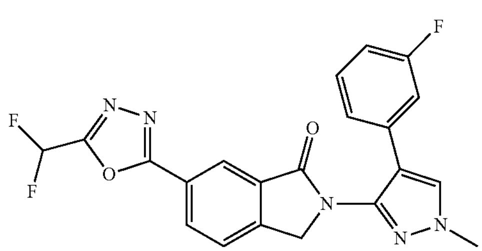 [SMILES: Cn1cc(-c2cccc(F)c2)c(N2Cc3ccc(-c4nnc(C(F)F)o4)cc3C2=O)n1] | | 425.9 |

TABLE 1-39-continued

| EXAMPLE | IUPAC NAME | Structure | ADDITIVE | MS |
|---|---|---|---|---|
| 385 | 6-(5-(difluoro-methyl)-1,3,4-oxadiazol-2-yl)-2-(2-(1-(difluoro-methyl)-1H-pyrazol-4-yl)-4-fluorophenyl)isoindolin-1-one | 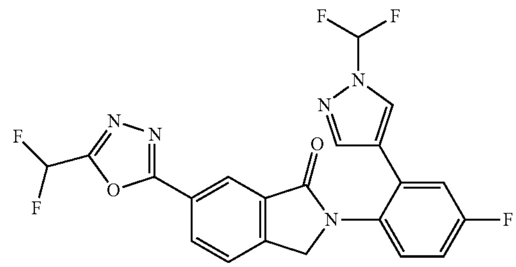 [SMILES: O=C1c2cc(-c3nnc(C(F)F)o3)ccc2CN1c1ccc(F)cc1-c1cnn(C(F)F)c1] | | 459.8 |
| 386 | 2-(3',5-difluoro-biphenyl-2-yl)-6-(5-(difluoro-methyl)-1,3,4-oxadiazol-2-yl)isoindolin-1-one | 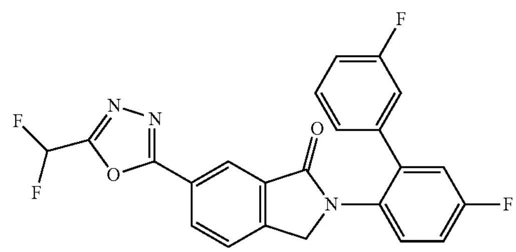 [SMILES: O=C1c2cc(-c3nnc(C(F)F)o3)ccc2CN1c1ccc(F)cc1-c1cccc(F)c1] | | 439.9 |
| 387 | 6-(5-(difluoro-methyl)-1,3,4-oxadiazol-2-yl)-2-(2-(1-(difluoro-methyl)-1H-pyrazol-4-yl)pyridin-3-yl)isoindolin-1-one | 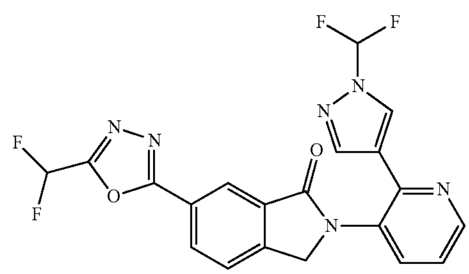 [SMILES: O=C1c2cc(-c3nnc(C(F)F)o3)ccc2CN1c1cccnc1-c1cnn(C(F)F)c1] | | 444.9 |
| 388 | 6-(5-(difluoro-methyl)-1,3,4-oxadiazol-2-yl)-4-fluoro-2-(4-fluoro-2-(1-methyl-3-(trifluoro-methyl)-1H-pyrazol-5-yl)phenyl)isoindolin-1-one | 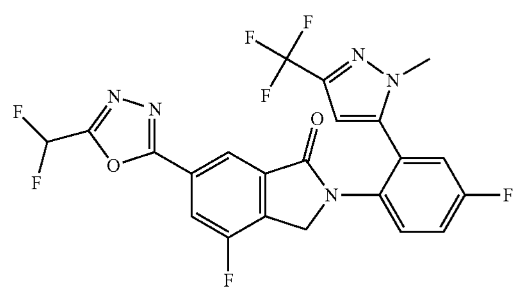 [SMILES: Cn1nc(C(F)(F)F)cc1-c1cc(F)ccc1N1Cc2c(F)cc(-c3nnc(C(F)F)o3)cc2C1=O] | | 509.8 |

TABLE 1-40

| EXAMPLE | IUPAC NAME | Structure | ADDITIVE | MS |
|---|---|---|---|---|
| 389 | 6-(5-(difluoro-methyl)-1,3,4-oxadiazol-2-yl)-2-(4-fluoro-2-(1-methyl-3-(trifluoro-methyl)-1H-pyrazol-5-yl)phenyl)isoindolin-1-one | 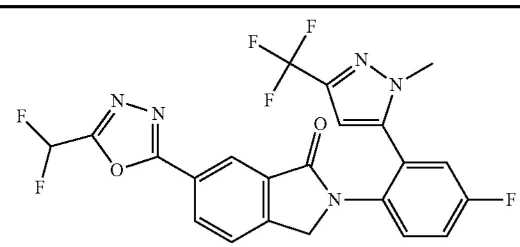 | | 493.8 |

TABLE 1-40-continued

| EXAMPLE | IUPAC NAME | Structure | ADDITIVE | MS |
|---|---|---|---|---|
| 390 | 6-(5-(difluoromethyl)-1,3,4-oxadiazol-2-yl)-2-(2-(1-(difluoromethyl)-1H-pyrazol-4-yl)phenyl)-4-fluoroisoindolin-1-one | 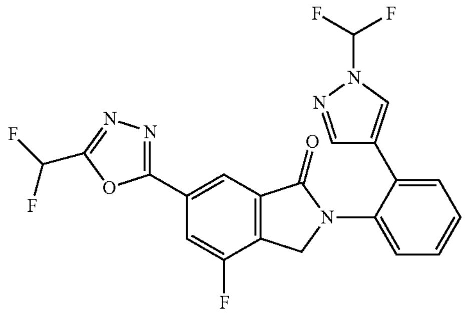 [SMILES: O=C1c2cc(-c3nnc(C(F)F)o3)cc(F)c2CN1c1ccccc1-c1cnn(C(F)F)c1] | | 461.9 |
| 391 | 3-(3-(6-(5-(difluoromethyl)-1,3,4-oxadiazol-2-yl)-1-oxo-1,3-dihydro-2H-isoindol-2-yl)pyridin-2-yl)benzonitrile | 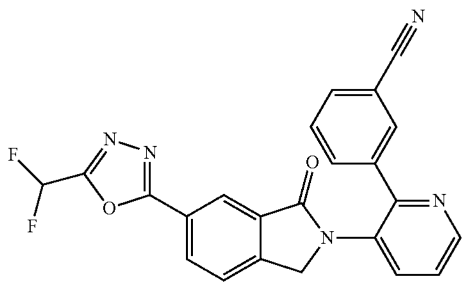 [SMILES: N#Cc1cccc(-c2ncccc2N2Cc3ccc(-c4nnc(C(F)F)o4)cc3C2=O)c1] | | 430.0 |
| 392 | 6-(5-(difluoromethyl)-1,3,4-oxadiazol-2-yl)-4-fluoro-2-(2-(1-methyl-1H-pyrazol-4-yl)phenyl)isoindolin-1-one | 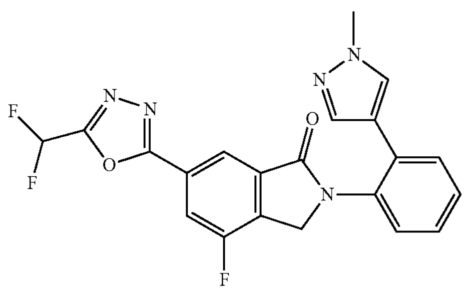 [SMILES: Cn1cc(-c2ccccc2N2Cc3c(F)cc(-c4nnc(C(F)F)o4)cc3C2=O)cn1] | | 426.0 |
| 393 | 6-(5-(difluoromethyl)-1,3,4-oxadiazol-2-yl)-4-fluoro-2-(3'-fluorobiphenyl-2-yl)isoindolin-1-one | 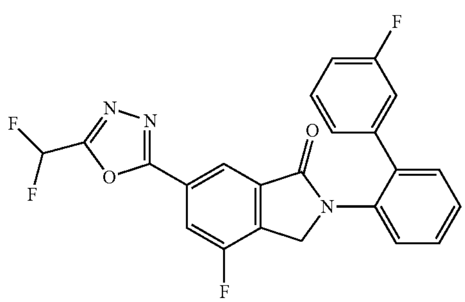 [SMILES: O=C1c2cc(-c3nnc(C(F)F)o3)cc(F)c2CN1c1ccccc1-c1cccc(F)c1] | | 439.9 |
| 394 | 6-(5-(difluoromethyl)-1,3,4-oxadiazol-2-yl)-4-fluoro-2-(2-(1-methyl-3-(trifluoromethyl)-1H-pyrazol-5-yl)phenyl)isoindolin-1-one | 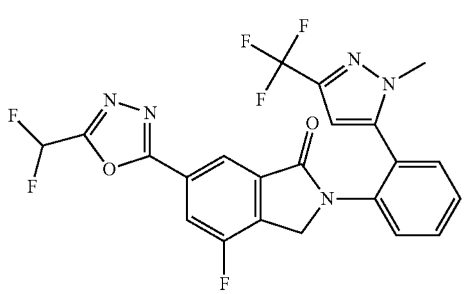 [SMILES: Cn1nc(C(F)(F)F)cc1-c1ccccc1N1Cc2c(F)cc(-c3nnc(C(F)F)o3)cc2C1=O] | | 493.8 |

TABLE 1-40-continued

| EXAMPLE | IUPAC NAME | Structure | ADDITIVE | MS |
|---------|------------|-----------|----------|-----|
| 395 | 6-(3-(difluoro-methoxy)benzyl)-3-(5-(difluoro-methyl)-1,3,4-oxadiazol-2-yl)-6,7-dihydro-5H-pyrrolo[3,4-b]pyridin-5-one | 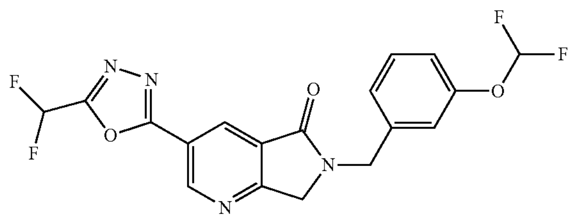 [SMILES: O=C1c2cc(-c3nnc(C(F)F)o3)cnc2CN1Cc1cccc(OC(F)F)c1] | | 406.9 |
| 396 | 6-(5-(difluoro-methyl)-1,3,4-oxadiazol-2-yl)-2-(2-(1-(difluoromethyl)-1H-pyrazol-4-yl)-3-fluorophenyl)isoindolin-1-one | 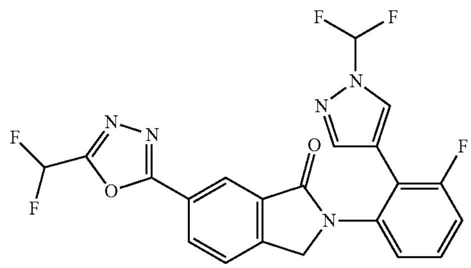 [SMILES: O=C1c2cc(-c3nnc(C(F)F)o3)ccc2CN1c1cccc(F)c1-c1cnn(C(F)F)c1] | | 461.9 |
| 397 | 2-(3'-chloro-6-fluorobiphenyl-2-yl)-6-(5-(difluoro-methyl)-1,3,4-oxadiazol-2-yl)isoindolin-1-one | 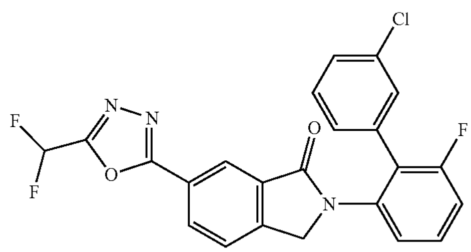 [SMILES: O=C1c2cc(-c3nnc(C(F)F)o3)ccc2CN1c1cccc(F)c1-c1cccc(F)c1] | | 455.9 |
| 398 | 2-(3',6-difluoro-biphenyl-2-yl)-6-(5-(difluoro-methyl)-1,3,4-oxadiazol-2-yl)isoindolin-1-one | 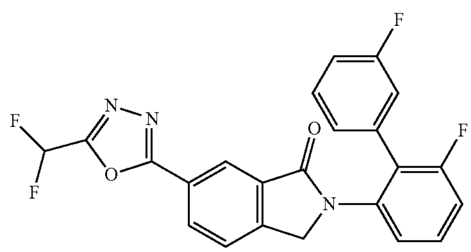 | | 439.9 |

TABLE 1-41

| EXAMPLE | IUPAC NAME | Structure | ADDITIVE | MS |
|---------|------------|-----------|----------|-----|
| 399 | 6-(5-(difluoro-methyl)-1,3,4-oxadiazol-2-yl)-2-((3S,4R)-3-((2,2,2-trifluoroethyl)amino)tetrahydro-2H-pyran-4-yl)isoindolin-1-one | 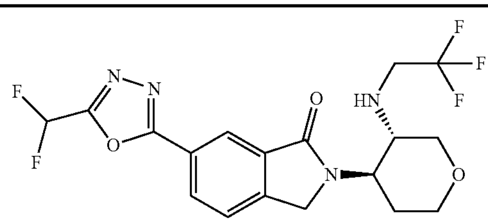 | | 432.9 |
| 400 | 3-(5-(difluoro-methyl)-1,3,4-oxadiazol-2-yl)-6-((3S,4R)-3-((2,2,2-trifluoroethyl)amino)tetrahydro-2H-pyran-4-yl)-6,7-dihydro-5H-pyrrolo[3,4-b]pyridin-5-one | 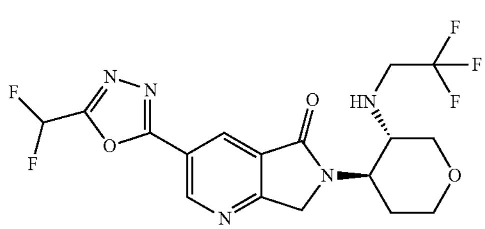 [SMILES: O=C1c2cc(-c3nnc(C(F)F)o3)cnc2CN1[C@@H]1CCOC[C@H]1NCC(F)(F)F] | | 433.9 |

TABLE 1-41-continued

| EXAMPLE | IUPAC NAME | Structure | ADDITIVE | MS |
|---|---|---|---|---|
| 401 | 2'-chloro-6'-(6-(5-(difluoro-methyl)-1,3,4-oxadiazol-2-yl)-1-oxo-1,3-dihydro-2H-isoindol-2-yl)biphenyl-3-carbonitrile | 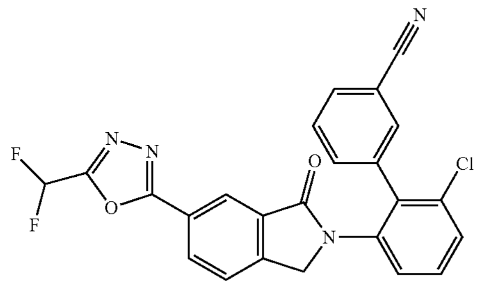 [SMILES: N#Cc1cccc(-c2c(Cl)cccc2N2Cc3ccc(-c4nnc(C(F)F)o4)cc3C2=O)c1] | | 462.8 |
| 402 | 2-(3-chloro-2-(1-(difluoro-methyl)-1H-pyrazol-4-yl)phenyl)-6-(5-(difluoro-methyl)-1,3,4-oxadiazol-2-yl)isoindolin-1-one | 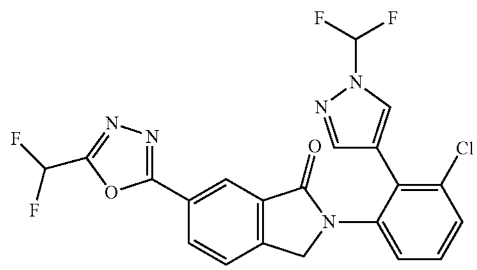 [SMILES: O=C1c2cc(-c3nnc(C(F)F)o3)ccc2CN1c1cccc(Cl)c1-c1cnn(C(F)F)c1] | | 477.8 |
| 403 | 2-(3-chloro-2-(1-methyl-1H-pyrazol-4-yl)phenyl)-6-(5-(difluoro-methyl)-1,3,4-oxadiazol-2-yl)isoindolin-1-one | 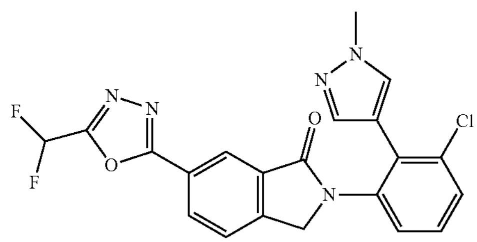 [SMILES: Cn1cc(-c2c(Cl)cccc2N2Cc3ccc(-c4nnc(C(F)F)o4)cc3C2=O)cn1] | | 441.9 |
| 404 | 2-(6-chloro-3'-fluoro-biphenyl-2-yl)-6-(5-(difluoro-methyl)-1,3,4-oxadiazol-2-yl)isoindolin-1-one | 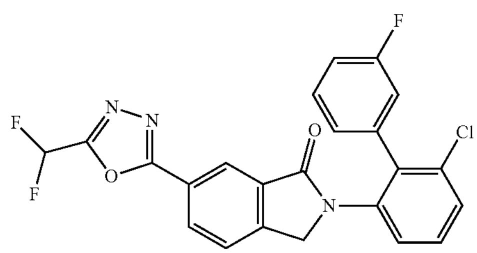 [SMILES: O=C1c2cc(-c3nnc(C(F)F)o3)ccc2CN1c1cccc(Cl)c1-c1cccc(F)c1] | | 455.8 |
| 405 | 2-(4-chloro-2-(1-(difluoro-methyl)-1H-pyrazol-4-yl)phenyl)-6-(5-(difluoro-methyl)-1,3,4-oxadiazol-2-yl)isoindolin-1-one | 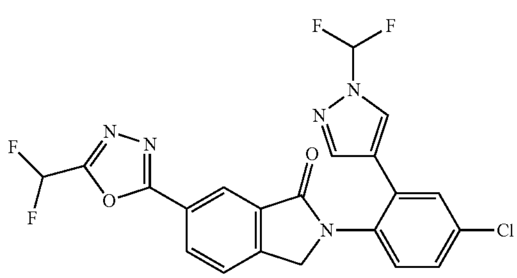 [SMILES: O=C1c2cc(-c3nnc(C(F)F)o3)ccc2CN1c1ccc(Cl)cc1-c1cnn(C(F)F)c1] | | 477.8 |
| 406 | 6-(2-bromo-4-fluorophenyl)-3-(5-(difluoro-methyl)-1,3,4-oxadiazol-2-yl)-6,7-dihydro-5H-pyrrolo[3,4-b]pyridin-5-one | 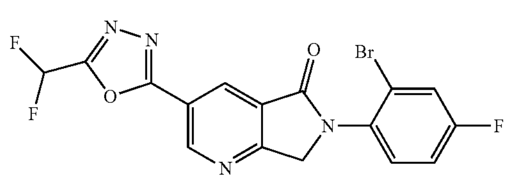 [SMILES: O=C1c2cc(-c3nnc(C(F)F)o3)cnc2CN1c1ccc(F)cc1Br] | | 422.8 |

TABLE 1-41-continued

| EXAMPLE | IUPAC NAME | Structure | ADDITIVE | MS |
|---|---|---|---|---|
| 407 | 2'-(3-(5-(difluoromethyl)-1,3,4-oxadiazol-2-yl)-5-oxo-5,7-dihydro-6H-pyrrolo[3,4-b]pyridin-6-yl)-5'-fluoro-biphenyl-3-carbonitrile | 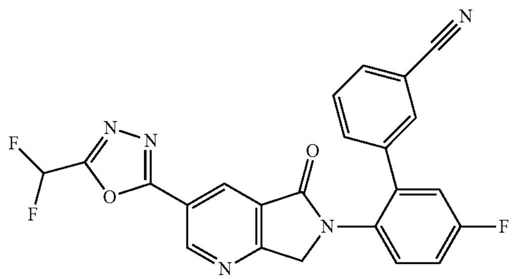 [SMILES: N#Cc1cccc(-c2cc(F)ccc2N2Cc3ncc(-c4nnc(C(F)F)o4)cc3C2=O)c1] | | 445.9 |
| 408 | 3-(5-(difluoromethyl)-1,3,4-oxadiazol-2-yl)-6-(2-(1-(difluoromethyl)-1H-pyrazol-4-yl)-4-fluorophenyl)-6,7-dihydro-5H-pyrrolo[3,4-b]pyridin-5-one | 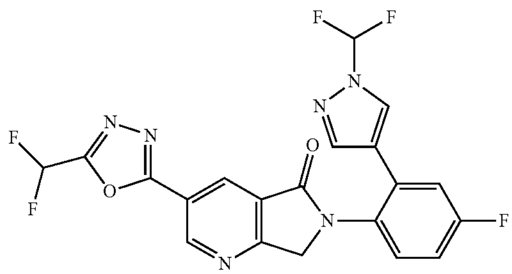 [SMILES: O=C1c2cc(-c3nnc(C(F)F)o3)cnc2CN1c1ccc(F)cc1-c1cnn(C(F)F)c1] | | 460.9 |

TABLE 1-42

| EXAMPLE | IUPAC NAME | Structure | ADDITIVE | MS |
|---|---|---|---|---|
| 409 | 6-(3',5-difluoro-biphenyl-2-yl)-3-(5-(difluoromethyl)-1,3,4-oxadiazol-2-yl)-6,7-dihydro-5H-pyrrolo[3,4-b]pyridin-5-one | 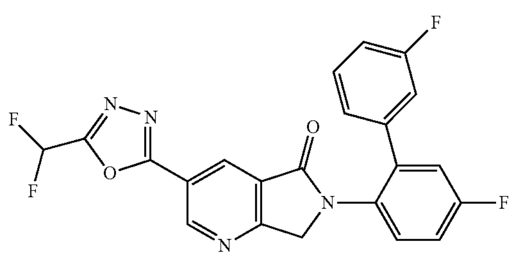 | | 440.8 |
| 410 | 6-(3'-chloro-5-fluoro-biphenyl-2-yl)-3-(5-(difluoromethyl)-1,3,4-oxadiazol-2-yl)-6,7-dihydro-5H-pyrrolo[3,4-b]pyridin-5-one | 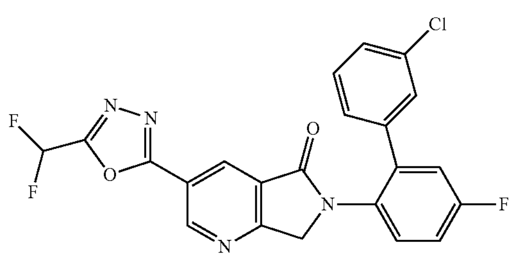 [SMILES: O=C1c2cc(-c3nnc(C(F)F)o3)cnc2CN1c1ccc(F)cc1-c1cccc(F)c1] | | 456.9 |
| 411 | 3-(5-(difluoromethyl)-1,3,4-oxadiazol-2-yl)-6-(4-fluoro-2-(1-methyl-1H-pyrazol-4-yl)phenyl)-6,7-dihydro-5H-pyrrolo[3,4-b]pyridin-5-one | 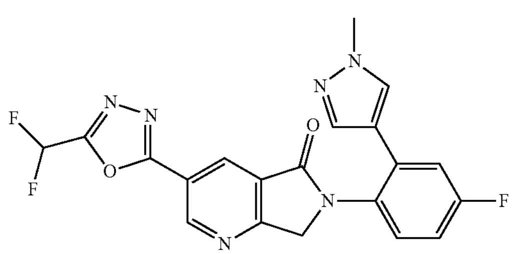 [SMILES: Cn1cc(-c2cc(F)ccc2N2Cc3ncc(-c4nnc(C(F)F)o4)cc3C2=O)cn1] | | 427.0 |

TABLE 1-42-continued

| EXAMPLE | IUPAC NAME | Structure | ADDITIVE | MS |
|---|---|---|---|---|
| 412 | 3-(5-(difluoro-methyl)-1,3,4-oxadiazol-2-yl)-6-(4-fluoro-2-(1-methyl-3-(trifluoro-methyl)-1H-pyrazol-5-yl)phenyl)-6,7-dihydro-5H-pyrrolo[3,4-b]pyridin-5-one | 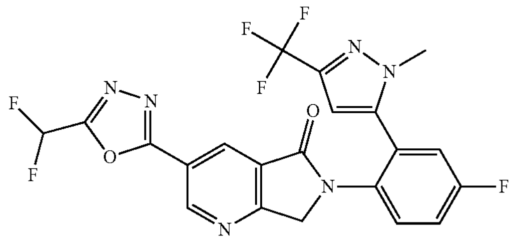 [SMILES: Cn1nc(C(F)(F)F)cc1-c1cc(F)ccc1N1Cc2ncc(-c3nnc(C(F)F)o3)cc2C1=O] | | 492.9 |
| 413 | tert-butyl ((3R,4R)-4-(6-(5-(difluoro-methyl)-1,3,4-oxadiazol-2-yl)-1-oxo-1,3-dihydro-2H-isoindol-2-yl)tetrahydro-2H-pyran-3-yl)carbamate | 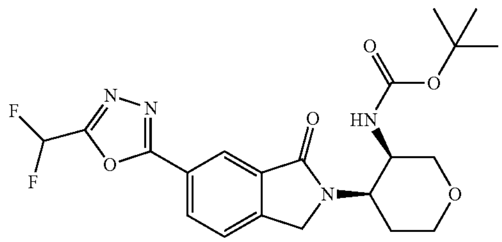 [SMILES: CC(C)(C)OC(=O)N[C@H]1COCC[C@H]1N1Cc2ccc(-c3nnc(C(F)F)o3)cc2C1=O] | | 449.0 |
| 414 | 2-((3R,4R)-3-aminotetra-hydro-2H-pyran-4-yl)-6-(5-(difluoro-methyl)-1,3,4-oxadiazol-2-yl)isoindolin-1-one | 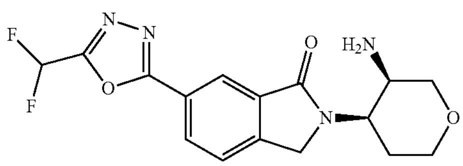 [SMILES: N[C@H]1COCC[C@H]1N1Cc2ccc(-c3nnc(C(F)F)o3)cc2C1=O] | | 350.9 |
| 415 | 6-(5-(difluoro-methyl)-1,3,4-oxadiazol-2-yl)-2-((3R,4R)-3-((2,2,2-trifluoro-ethyl)amino)tetrahydro-2H-pyran-4-yl)isoindolin-1-one | 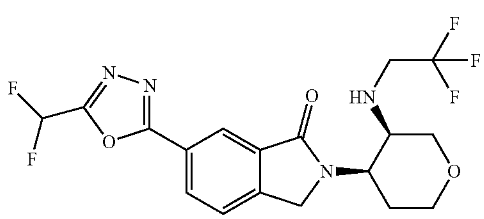 [SMILES: O=C1c2cc(-c3nnc(C(F)F)o3)ccc2CN1[C@@H]1CCOC[C@@H]1NCC(F)(F)F] | | 432.9 |
| 416 | 6-(5-(difluoro-methyl)-1,3,4-oxadiazol-2-yl)-2-((3R,4R)-3-((2,2,3,3,3-pentafluoro-propyl)amino)tetrahydro-2H-pyran-4-yl)isoindolin-1-one | 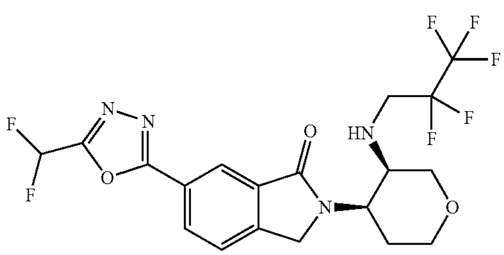 [SMILES: O=C1c2cc(-c3nnc(C(F)F)o3)ccc2CN1[C@@H]1CCOC[C@@H]1NCC(F)(F)C(F)(F)F] | | 482.9 |
| 417 | 6-(5-(difluoro-methyl)-1,3,4-oxadiazol-2-yl)-2-((3R,4R)-3-((2,2,3,3,4,4,4-heptafluoro-butyl)amino)tetrahydro-2H-pyran-4-yl)isoindolin-1-one | 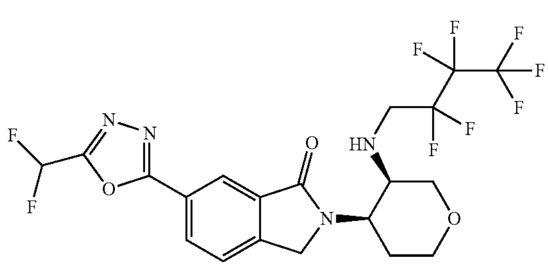 [SMILES: O=C1c2cc(-c3nnc(C(F)F)o3)ccc2CN1[C@@H]1CCOC[C@@H]1NCC(F)(F)C(F)(F)C(F)(F)F] | | 532.9 |

TABLE 1-42-continued

| EXAMPLE | IUPAC NAME | Structure | ADDITIVE | MS |
|---|---|---|---|---|
| 418 | N-((3R,4R)-4-(6-(5-(difluoromethyl)-1,3,4-oxadiazol-2-yl)-1-oxo-1,3-dihydro-2H-isoindol-2-yl)tetrahydro-2H-pyran-3-yl)-2,2,3,3,3-pentafluoropropanamide | 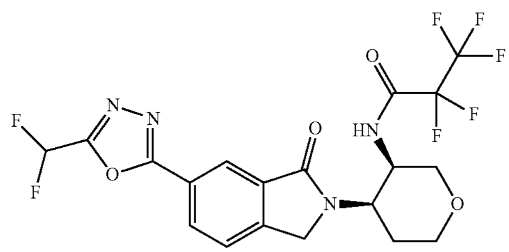 [SMILES: O=C1c2cc(-c3nnc(C(F)F)o3)ccc2CN1[C@@H]1CCOC[C@@H]1NC(=O)C(F)(F)C(F)(F)F] | | 496.8 |

TABLE 1-43

| EXAMPLE | IUPAC NAME | Structure | ADDITIVE | MS |
|---|---|---|---|---|
| 419 | 3-(5-(difluoromethyl)-1,3,4-oxadiazol-2-yl)-6-((1-methyl-1H-pyrazol-3-yl)methyl)-6,7-dihydro-5H-pyrrolo[3,4-b]pyridin-5-one | 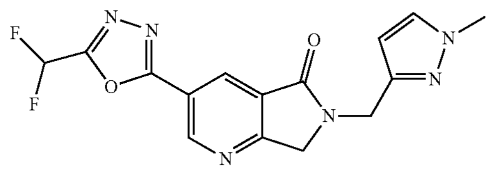 [SMILES: Cn1ccc(CN2Cc3ncc(-c4nnc(C(F)F)o4)cc3C2=O)n1] | | 347.0 |
| 420 | 2-(((2R)-4,4-difluoro-1-((3-fluorophenyl)sulfonyl)pyrrolidin-2-yl)methyl)-6-(5-(difluoromethyl)-1,3,4-oxadiazol-2-yl)-4-fluoroisoindolin-1-one | 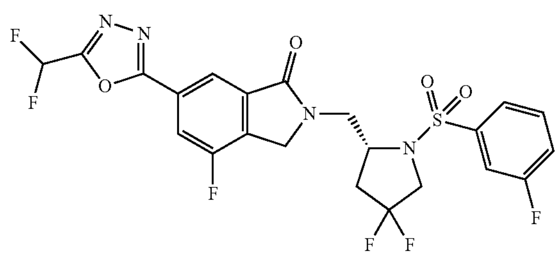 [SMILES: O=C1c2cc(-c3nnc(C(F)F)o3)cc(F)c2CN1C[C@H]1CC(F)(F)CN1S(=O)(=O)c1cccc(F)c1] | | 546.8 |
| 421 | 6-(5-(difluoromethyl)-1,3,4-oxadiazol-2-yl)-2-(((2R)-4,4-difluoro-1-((2,2,2-trifluoroethyl)sulfonyl)pyrrolidin-2-yl)methyl)-4-fluoroisoindolin-1-one | 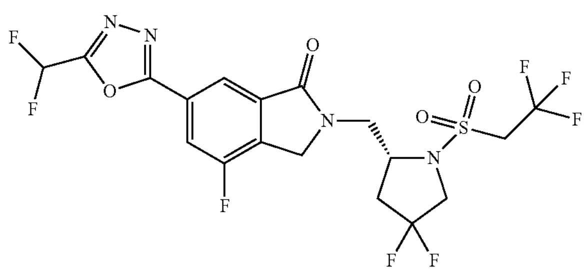 [SMILES: O=C1c2cc(-c3nnc(C(F)F)o3)cc(F)c2CN1C[C@H]1CC(F)(F)CN1S(=O)(=O)CC(F)(F)F] | | 534.8 |
| 422 | 2-(((2R)-1-(cyclopropylcarbonyl)-4,4-difluoropyrrolidin-2-yl)methyl)-6-(5-(difluoromethyl)-1,3,4-oxadiazol-2-yl)-4-fluoroisoindolin-1-one | 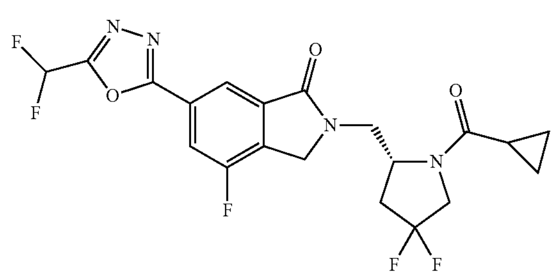 [SMILES: O=C1c2cc(-c3nnc(C(F)F)o3)cc(F)c2CN1C[C@H]1CC(F)(F)CN1C(=O)C1CC1] | | 456.9 |
| 423 | 3-(5-(difluoromethyl)-1,3,4-oxadiazol-2-yl)-6-((1-methyl-1H-pyrazol-4-yl)methyl)-6,7-dihydro-5H-pyrrolo[3,4-b]pyridin-5-one | 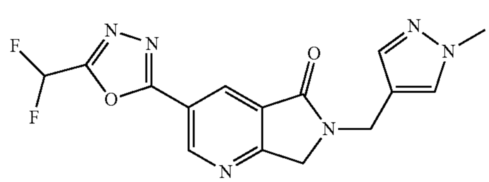 [SMILES: Cn1cc(CN2Cc3ncc(-c4nnc(C(F)F)o4)cc3C2=O)cn1] | | 346.9 |

TABLE 1-43-continued

| EXAMPLE | IUPAC NAME | Structure | ADDITIVE | MS |
|---|---|---|---|---|
| 424 | 3-(5-(difluoro-methyl)-1,3,4-oxadiazol-2-yl)-6-(2-(1-(difluoromethyl)-1H-pyrazol-4-yl)phenyl)-6,7-dihydro-5H-pyrrolo[3,4-b]pyridin-5-one | 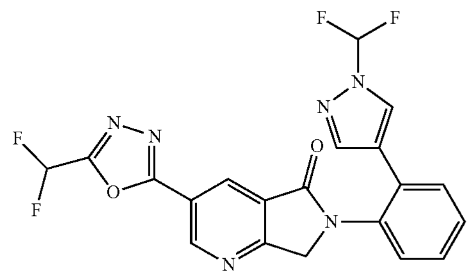 [SMILES: O=C1c2cc(-c3nnc(C(F)F)o3)cnc2CN1c1ccccc1-c1cnn(C(F)F)c1] | | 444.9 |
| 425 | 3-(5-(difluoro-methyl)-1,3,4-oxadiazol-2-yl)-6-((5-(trifluoromethyl)pyridin-3-yl)methyl)-6,7-dihydro-5H-pyrrolo[3,4-b]pyridin-5-one | 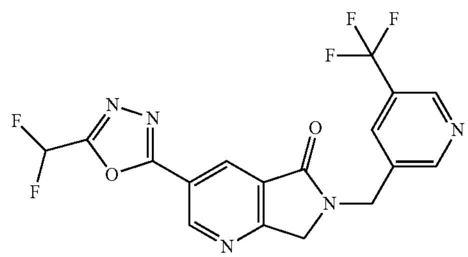 [SMILES: O=C1c2cc(-c3nnc(C(F)F)o3)cnc2CN1Cc1cncc(C(F)(F)F)c1] | | 411.9 |
| 426 | 2-(3-chloro-2-(1-methyl-3-(trifluoromethyl)-1H-pyrazol-5-yl)phenyl)-6-(5-(difluoromethyl)-1,3,4-oxadiazol-2-yl)isoindolin-1-one | 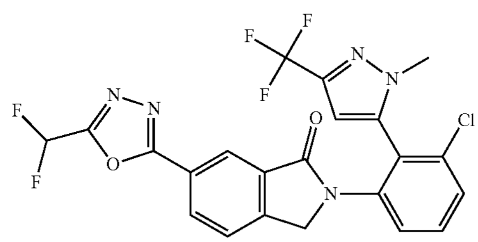 [SMILES: Cn1nc(C(F)(F)F)cc1-c1c(Cl)cccc1N1Cc2ccc(-c3nnc(C(F)F)o3)cc2C1=O] | | 509.8 |
| 427 | 6-(5-(difluoromethyl)-1,3,4-oxadiazol-2-yl)-4-fluoro-2-(((2R)-1-((3-fluorophenyl)sulfonyl)pyrrolidin-2-yl)methyl)isoindolin-1-one | 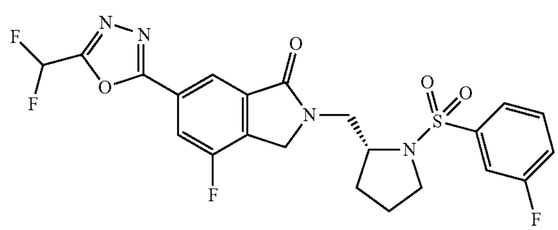 [SMILES: O=C1c2cc(-c3nnc(C(F)F)o3)cc(F)c2CN1C[C@H]1CCCN1S(=O)(=O)c1cccc(F)c1] | | 510.8 |
| 428 | 6-(3-bromo-benzyl)-3-(5-(difluoromethyl)-1,3,4-oxadiazol-2-yl)-6,7-dihydro-5H-pyrrolo[3,4-b]pyridin-5-one | 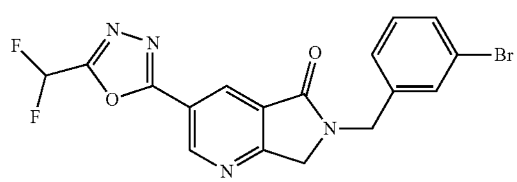 [SMILES: O=C1c2cc(-c3nnc(C(F)F)o3)cnc2CN1Cc1cccc(Br)c1] | | 418.8 |

TABLE 1-44

| EXAMPLE | IUPAC NAME | Structure | ADDITIVE | MS |
|---|---|---|---|---|
| 429 | 2-(((2R)-1-benzoyl-4,4-difluoropyrrolidin-2-yl)methyl)-6-(5-(difluoromethyl)-1,3,4-oxadiazol-2-yl)-4-fluoroisoindolin-1-one | 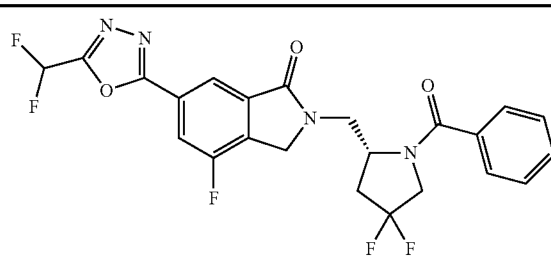 | | 493.0 |

TABLE 1-44-continued

| EXAMPLE | IUPAC NAME | Structure | ADDITIVE | MS |
|---|---|---|---|---|
| 430 | 6-(5-(difluoro-methyl)-1,3,4-oxadiazol-2-yl)-2-(((2R)-4,4-difluoro-1-(phenylsulfonyl)pyrrolidin-2-yl)methyl)-4-fluoroiso-indolin-1-one | 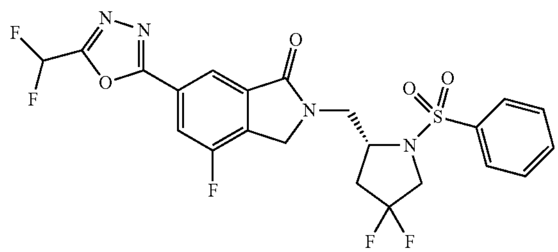 [SMILES: O=C1c2cc(-c3nnc(C(F)F)o3)cc(F)c2CN1C[C@H]1CC(F)(F)CN1S(=O)(=O)c1ccccc1] | | 528.9 |
| 431 | 6-(5-(difluoro-methyl)-1,3,4-oxadiazol-2-yl)-2-(3-fluoro-2-(1-methyl-3-(trifluoro-methyl)-1H-pyrazol-5-yl)phenyl)iso-indolin-1-one | 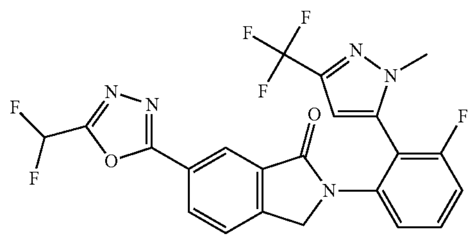 [SMILES: Cn1nc(C(F)(F)F)cc1-c1c(F)cccc1N1Cc2ccc(-c3nnc(C(F)F)o3)cc2C1=O] | | 494.0 |
| 432 | 3-(5-(difluoro-methyl)-1,3,4-oxadiazol-2-yl)-6-(3-(trifluoro-methoxy)benzyl)-6,7-dihydro-5H-pyrrolo[3,4-b]pyridin-5-one | 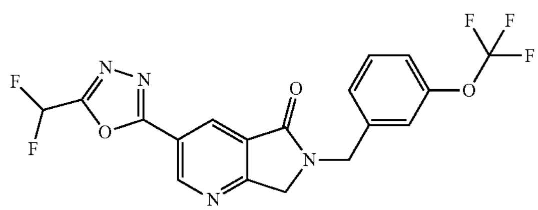 [SMILES: O=C1c2cc(-c3nnc(C(F)F)o3)cnc2CN1Cc1cccc(OC(F)(F)F)c1] | | 424.9 |
| 433 | 2-(4-benzyl-tetrahydro-2H-pyran-4-yl)-6-(5-(difluoro-methyl)-1,3,4-oxadiazol-2-yl)isoindolin-1-one | 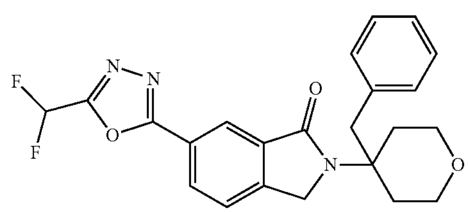 [SMILES: O=C1c2cc(-c3nnc(C(F)F)o3)ccc2CN1C1(Cc2ccccc2)CCOCC1] | | 426.1 |
| 434 | 6-(5-(difluoro-methyl)-1,3,4-oxadiazol-2-yl)-2-(1,1'-dimethyl-1H,1'H-4,4'-bipyrazol-3-yl)isoindolin-1-one | 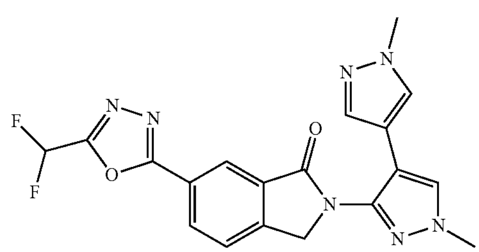 [SMILES: Cn1cc(-c2cn(C)nc2N2Cc3ccc(-c4nnc(C(F)F)o4)cc3C2=O)cn1] | | 412.0 |
| 435 | 6-(5-(difluoro-methyl)-1,3,4-oxadiazol-2-yl)-2-(1-phenyl-1H-pyrazol-5-yl)isoindolin-1-one | 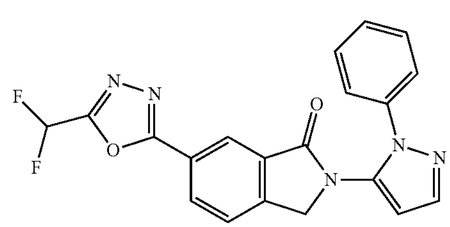 [SMILES: O=C1c2cc(-c3nnc(C(F)F)o3)ccc2CN1c1ccnn1-c1ccccc1] | | 394.1 |

TABLE 1-44-continued

| EXAMPLE | IUPAC NAME | Structure | ADDITIVE | MS |
|---|---|---|---|---|
| 436 | 6-(5-(difluoro-methyl)-1,3,4-oxadiazol-2-yl)-2-(3-fluoro-2-(1-methyl-1H-pyrazol-4-yl)phenyl)isoindolin-1-one | 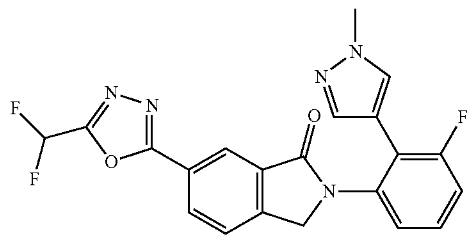 [SMILES: Cn1cc(-c2c(F)cccc2N2Cc3ccc(-c4nnc(C(F)F)o4)cc3C2=O)cn1] | | 426.0 |
| 437 | 3-(5-(difluoro-methyl)-1,3,4-oxadiazol-2-yl)-6-(2-(trifluoro-methoxy)benzyl)-6,7-dihydro-5H-pyrrolo[3,4-b]pyridin-5-one | 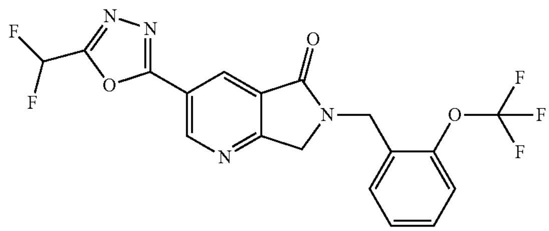 [SMILES: O=C1c2cc(-c3nnc(C(F)F)o3)cnc2CN1Cc1ccccc1OC(F)(F)F] | | 427.0 |
| 438 | 3-(5-(difluoro-methyl)-1,3,4-oxadiazol-2-yl)-6-((1-methyl-1H-pyrrol-2-yl)methyl)-6,7-dihydro-5H-pyrrolo[3,4-b]pyridin-5-one | 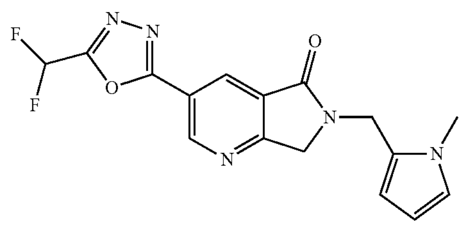 [SMILES: Cn1cccc1CN1Cc2ncc(-c3nnc(C(F)F)o3)cc2C1=O] | | 343.9 |

TABLE 1-45

| EXAMPLE | IUPAC NAME | Structure | ADDITIVE | MS |
|---|---|---|---|---|
| 439 | 6-(5-(difluoro-methyl)-1,3,4-oxadiazol-2-yl)-2-(4-fluoro-2-(2-oxo-pyrrolidin-1-yl)phenyl)isoindolin-1-one | 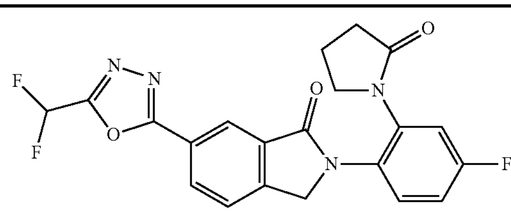 | | 429.0 |
| 440 | 3-(5-(difluoro-methyl)-1,3,4-oxadiazol-2-yl)-6-(1,3-thiazol-2-ylmethyl)-6,7-dihydro-5H-pyrrolo[3,4-b]pyridin-5-one | 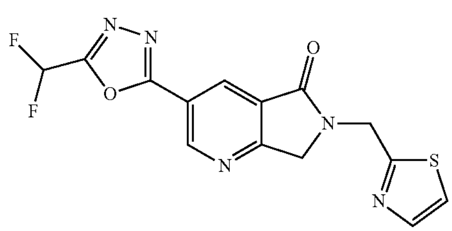 [SMILES: O=C1c2cc(-c3nnc(C(F)F)o3)cnc2CN1Cc1nccs1] | | 349.8 |
| 441 | 6-(2-bromo-benzyl)-3-(5-(difluoro-methyl)-1,3,4-oxadiazol-2-yl)-6,7-dihydro-5H-pyrrolo[3,4-b]pyridin-5-one | 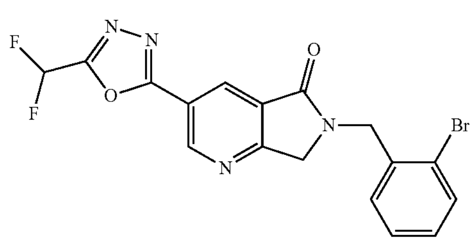 [SMILES: O=C1c2cc(-c3nnc(C(F)F)o3)cnc2CN1Cc1ccccc1Br] | | 421.0 |

TABLE 1-45-continued

| EXAMPLE | IUPAC NAME | Structure | ADDITIVE | MS |
|---|---|---|---|---|
| 442 | 6-(5-(difluoro-methyl)-1,3,4-oxadiazol-2-yl)-2-(1-methyl-1H-pyrazol-3-yl)isoindolin-1-one | 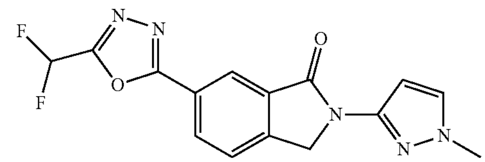 [SMILES: Cn1ccc(N2Cc3ccc(-c4nnc(C(F)F)o4)cc3C2=O)n1] | | 331.9 |
| 443 | 6-(6-(5-(difluoro-methyl)-1,3,4-oxadiazol-2-yl)-1-oxo-1,3-dihydro-2H-isoindol-2-yl)biphenyl-3-carbonitrile | 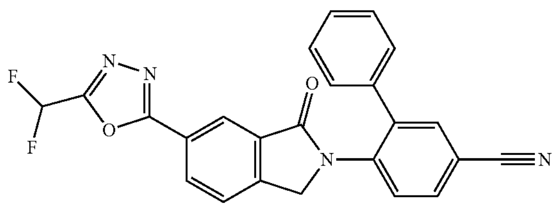 [SMILES: N#Cc1ccc(N2Cc3ccc(-c4nnc(C(F)F)o4)cc3C2=O)c(-c2ccccc2)c1] | | 426.9 |
| 444 | 4-(6-(5-(difluoro-methyl)-1,3,4-oxadiazol-2-yl)-1-oxo-1,3-dihydro-2H-isoindol-2-yl)-3-(1-(difluoro-methyl)-1H-pyrazol-4-yl)benzonitrile | 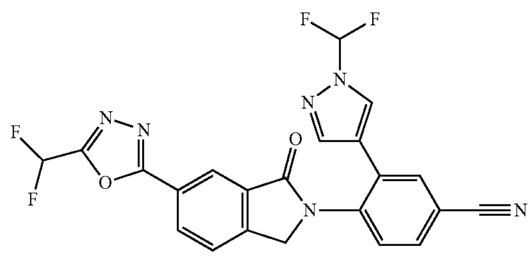 [SMILES: N#Cc1ccc(N2Cc3ccc(-c4nnc(C(F)F)o4)cc3C2=O)c(-c2cnn(C(F)F)c2)c1] | | 466.9 |
| 445 | 6-(6-(5-(difluoro-methyl)-1,3,4-oxadiazol-2-yl)-1-oxo-1,3-dihydro-2H-isoindol-2-yl)-3'-fluoro-biphenyl-3-carbonitrile | 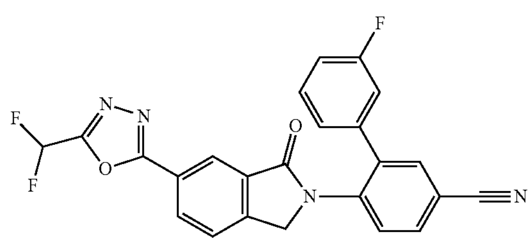 [SMILES: N#Cc1ccc(N2Cc3ccc(-c4nnc(C(F)F)o4)cc3C2=O)c(-c2cccc(F)c2)c1] | | 444.9 |
| 446 | 6-(5-(difluoro-methyl)-1,3,4-oxadiazol-2-yl)-2-(1-methyl-4-(tetrahydro-2H-pyran-4-yl)-1H-pyrazol-3-yl)isoindolin-1-one | 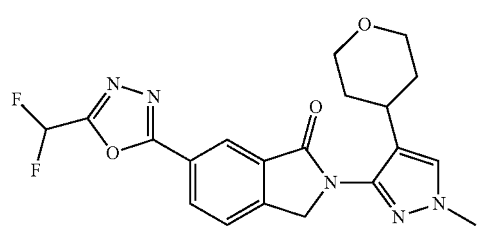 [SMILES: Cn1cc(C2CCOCC2)c(N2Cc3ccc(-c4nnc(C(F)F)o4)cc3C2=O)n1] | | 416.0 |
| 447 | 6-(5-(difluoro-methyl)-1,3,4-oxadiazol-2-yl)-2-(4-(3-methoxy-phenyl)-1-methyl-1H-pyrazol-3-yl)isoindolin-1-one | 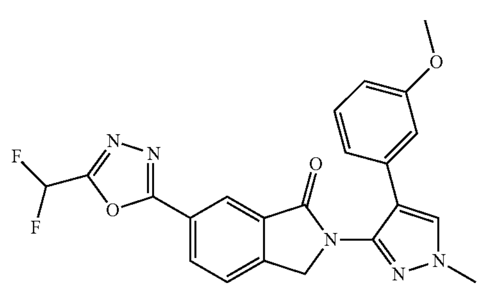 [SMILES: COc1cccc(-c2cn(C)nc2N2Cc3ccc(-c4nnc(C(F)F)o4)cc3C2=O)c1] | | 438.0 |

TABLE 1-45-continued

| EXAMPLE | IUPAC NAME | Structure | ADDITIVE | MS |
|---|---|---|---|---|
| 448 | 6-(5-(difluoromethyl)-1,3,4-oxadiazol-2-yl)-2-(4-(3,6-dihydro-2H-pyran-4-yl)-1-methyl-1H-pyrazol-3-yl)isoindolin-1-one | 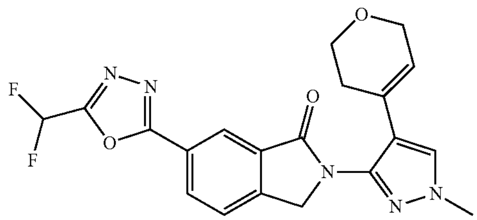 [SMILES: Cn1cc(C2=CCOCC2)c(N2Cc3ccc(-c4nnc(C(F)F)o4)cc3C2=O)n1] | | 412.0 |

TABLE 1-46

| EXAMPLE | IUPAC NAME | Structure | ADDITIVE | MS |
|---|---|---|---|---|
| 449 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)acetamide | 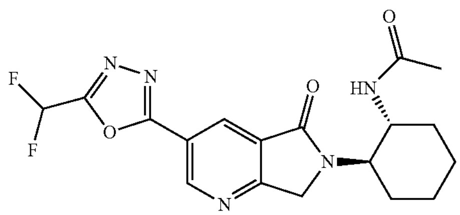 [SMILES: CC(=O)N[C@@H]1CCCC[C@H]1N1Cc2ncc(-c3nnc(C(F)F)o3)cc2C1=O] | | 391.9 |
| 450 | 6-(5-(difluoromethyl)-1,3,4-oxadiazol-2-yl)-2-(4-fluoro-2-(4-(trifluoromethyl)-1H-pyrazol-1-yl)phenyl)isoindolin-1-one | 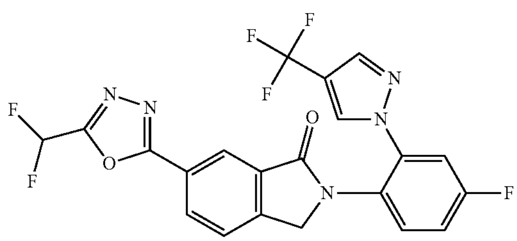 [SMILES: O=C1c2cc(-c3nnc(C(F)F)o3)ccc2CN1c1ccc(F)cc1-n1cc(C(F)(F)F)cn1] | | 480.0 |
| 451 | 2-(2-(4-chloro-1H-pyrazol-1-yl)-4-fluorophenyl)-6-(5-(difluoromethyl)-1,3,4-oxadiazol-2-yl)isoindolin-1-one | 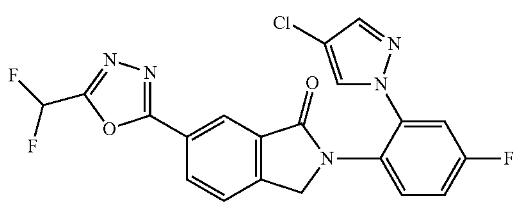 [SMILES: O=C1c2cc(-c3nnc(C(F)F)o3)ccc2CN1c1ccc(F)cc1-n1cc(F)cn1] | | 446.1 |
| 452 | 6-(5-(difluoromethyl)-1,3,4-oxadiazol-2-yl)-2-(4-fluoro-2-(4-fluoro-1H-pyrazol-1-yl)phenyl)isoindolin-1-one | 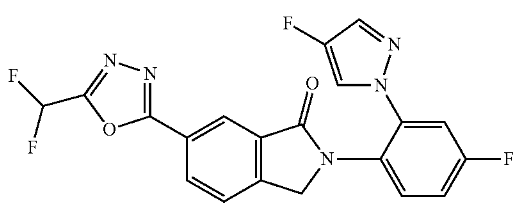 | | 430.1 |
| 453 | 6-(5-(difluoromethyl)-1,3,4-oxadiazol-2-yl)-2-(1-(3-fluorophenyl)-1H-pyrazol-5-yl)isoindolin-1-one | 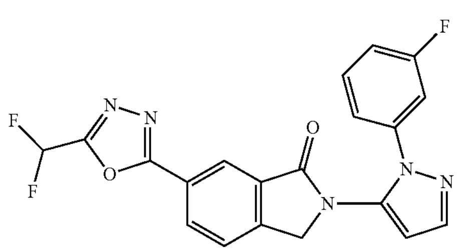 [SMILES: O=C1c2cc(-c3nnc(C(F)F)o3)ccc2CN1c1ccnn1-c1cccc(F)c1] | | 412.1 |

TABLE 1-46-continued

| EXAMPLE | IUPAC NAME | Structure | ADDITIVE | MS |
|---|---|---|---|---|
| 454 | 6-((5-chloro-2-thienyl)methyl)-3-(5-(difluoromethyl)-1,3,4-oxadiazol-2-yl)-6,7-dihydro-5H-pyrrolo[3,4-b]pyridin-5-one | 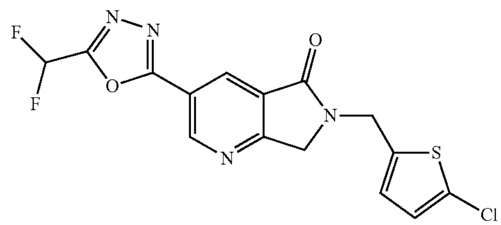 [SMILES: O=C1c2cc(-c3nnc(C(F)F)o3)cnc2CN1Cc1ccc(Cl)s1] | | 381.0 |
| 455 | 6-(5-(difluoromethyl)-1,3,4-oxadiazol-2-yl)-2-(4-(3,5-difluorophenyl)-1-methyl-1H-pyrazol-3-yl)isoindolin-1-one | 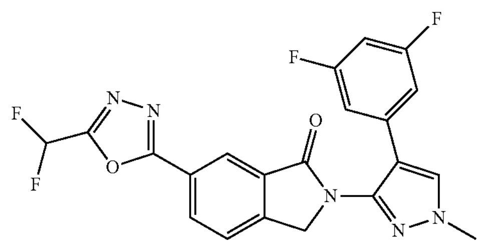 [SMILES: Cn1cc(-c2cc(F)cc(F)c2)c(N2Cc3ccc(-c4nnc(C(F)F)o4)cc3C2=O)n1] | | 444.1 |
| 456 | 3-(5-(difluoromethyl)-1,3,4-oxadiazol-2-yl)-6-(2-ethoxybenzyl)-6,7-dihydro-5H-pyrrolo[3,4-b]pyridin-5-one | 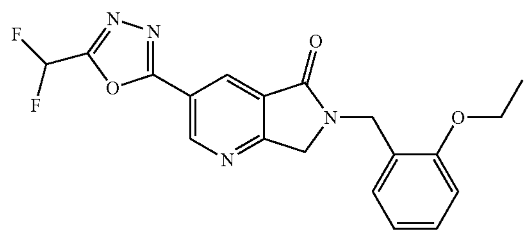 [SMILES: CCOc1ccccc1CN1Cc2ncc(-c3nnc(C(F)F)o3)cc2C1=O] | | 387.1 |
| 457 | 3-(5-(difluoromethyl)-1,3,4-oxadiazol-2-yl)-6-(pyrazolo[1,5-a]pyridin-2-ylmethyl)-6,7-dihydro-5H-pyrrolo[3,4-b]pyridin-5-one | 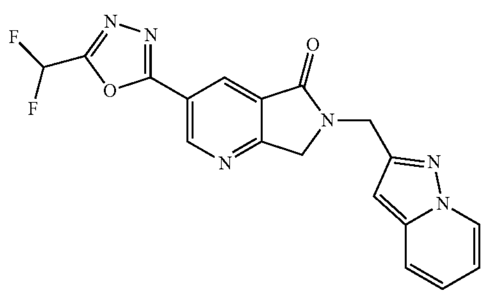 [SMILES: O=C1c2cc(-c3nnc(C(F)F)o3)cnc2CN1Cc1cc2ccccn2n1] | | 383.1 |
| 458 | 3-(5-(difluoromethyl)-1,3,4-oxadiazol-2-yl)-6-(pyrazolo[1,5-a]pyridin-3-ylmethyl)-6,7-dihydro-5H-pyrrolo[3,4-b]pyridin-5-one | 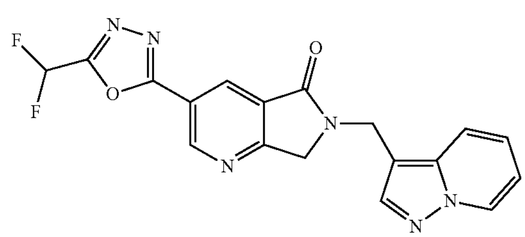 [SMILES: O=C1c2cc(-c3nnc(C(F)F)o3)cnc2CN1Cc1cnn2ccccc12] | | 383.1 |

TABLE 1-47

| EXAMPLE | IUPAC NAME | Structure | ADDITIVE | MS |
|---|---|---|---|---|
| 459 | 6-(5-(difluoromethyl)-1,3,4-oxadiazol-2-yl)-2-(4-(5-fluoropyridin-3-yl)-1-methyl-1H-pyrazol-3-yl)isoindolin-1-one | 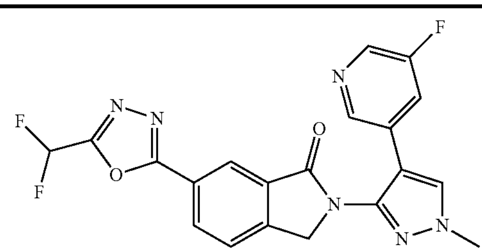 | | 427.1 |

TABLE 1-47-continued

| EXAMPLE | IUPAC NAME | Structure | ADDITIVE | MS |
|---|---|---|---|---|
| 460 | 6-(5-(difluoro-methyl)-1,3,4-oxadiazol-2-yl)-2-(4-(2-fluoro-phenyl)-1-methyl-1H-pyrazol-3-yl)isoindolin-1-one | 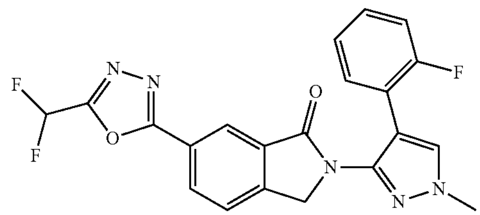 [SMILES: Cn1cc(-c2ccccc2F)c(N2Cc3ccc(-c4nnc(C(F)F)o4)cc3C2=O)n1] | | 426.1 |
| 461 | N-((1R,2R)-2-(3-(5-(difluoro-methyl)-1,3,4-oxadiazol-2-yl)-5-oxo-5,7-dihydro-6H-pyrrolo[3,4-b]pyridin-6-yl)cyclohexyl)propanamide | 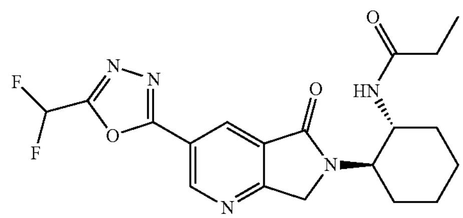 [SMILES: CCC(=O)N[C@@H]1CCCC[C@H]1N1Cc2ncc(-c3nnc(C(F)F)o3)cc2C1=O] | | 406.0 |
| 462 | N-((1R,2R)-2-(3-(5-(difluoro-methyl)-1,3,4-oxadiazol-2-yl)-5-oxo-5,7-dihydro-6H-pyrrolo[3,4-b]pyridin-6-yl)cyclohexyl)butanamide | 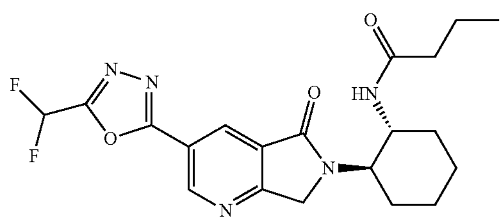 [SMILES: CCCC(=O)N[C@@H]1CCCC[C@H]1N1Cc2ncc(-c3nnc(C(F)F)o3)cc2C1=O] | | 420.0 |
| 463 | N-((1R,2R)-2-(3-(5-(difluoro-methyl)-1,3,4-oxadiazol-2-yl)-5-oxo-5,7-dihydro-6H-pyrrolo[3,4-b]pyridin-6-yl)cyclohexyl)cyclopropane-carboxamide | 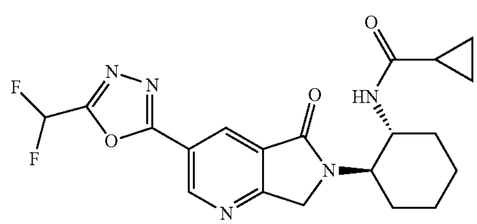 [SMILES: O=C(N[C@@H]1CCCC[C@H]1N1Cc2ncc(-c3nnc(C(F)F)o3)cc2C1=O)C1CC1] | | 418.0 |
| 464 | N-((1R,2R)-2-(3-(5-(difluoro-methyl)-1,3,4-oxadiazol-2-yl)-5-oxo-5,7-dihydro-6H-pyrrolo[3,4-b]pyridin-6-yl)cyclohexyl)cyclobutane-carboxamide | 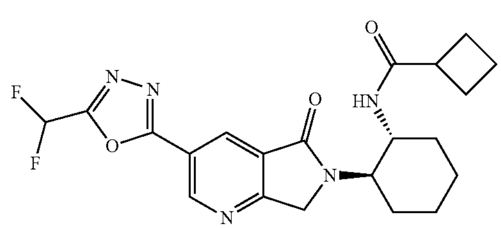 [SMILES: O=C(N[C@@H]1CCCC[C@H]1N1Cc2ncc(-c3nnc(C(F)F)o3)cc2C1=O)C1CCC1] | | 432.0 |
| 465 | N-((1R,2R)-2-(3-(5-(difluoro-methyl)-1,3,4-oxadiazol-2-yl)-5-oxo-5,7-dihydro-6H-pyrrolo[3,4-b]pyridin-6-yl)cyclohexyl)benzamide | 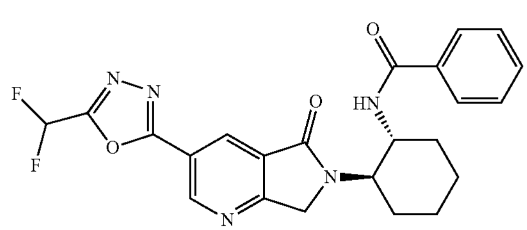 [SMILES: O=C(N[C@@H]1CCCC[C@H]1N1Cc2ncc(-c3nnc(C(F)F)o3)cc2C1=O)c1ccccc1] | | 454.0 |

TABLE 1-47-continued

| EXAMPLE | IUPAC NAME | Structure | ADDITIVE | MS |
|---|---|---|---|---|
| 466 | N-((1R,2R)-2-(3-(5-(difluoro-methyl)-1,3,4-oxadiazol-2-yl)-5-oxo-5,7-dihydro-6H-pyrrolo[3,4-b]pyridin-6-yl)cyclohexyl)-2-phenyl-acetamide | 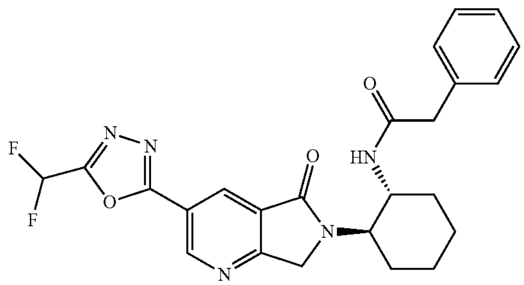 [SMILES: O=C(Cc1ccccc1)N[C@@H]1CCCC[C@H]1N1Cc2ncc(-c3nnc(C(F)F)o3)cc2C1=O] | | 468.0 |
| 467 | 6-(5-(difluoro-methyl)-1,3,4-oxadiazol-2-yl)-2-(4-fluoro-2-(1H-pyrazol-5-yl)phenyl)isoindolin-1-one | 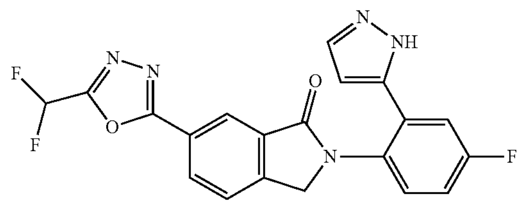 [SMILES: O=C1c2cc(-c3nnc(C(F)F)o3)ccc2CN1c1ccc(F)cc1-c1ccn[nH]1] | | 411.9 |
| 468 | 3-(3-(6-(5-(difluoro-methyl)-1,3,4-oxadiazol-2-yl)-1-oxo-1,3-dihydro-2H-isoindol-2-yl)-1-methyl-1H-pyrazol-4-yl)-5-fluoro-benzonitrile | 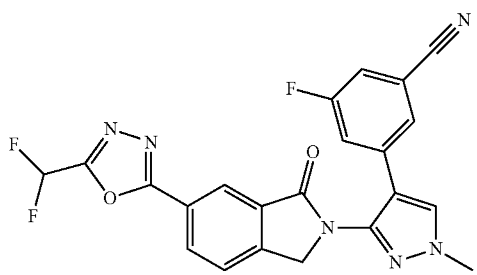 [SMILES: Cn1cc(-c2cc(F)cc(C#N)c2)c(N2Cc3ccc(-c4nnc(C(F)F)o4)cc3C2=O)n1] | | 450.9 |

TABLE 1-48

| EXAMPLE | IUPAC NAME | Structure | ADDITIVE | MS |
|---|---|---|---|---|
| 469 | N-((1R,2R)-2-(6-(5-(difluoro-methyl)-1,3,4-oxadiazol-2-yl)-1-oxo-1,3-dihydro-2H-isoindol-2-yl)-5,5-difluoro-cyclohexyl)-2,2,3,3,3-pentafluoro-propanamide | 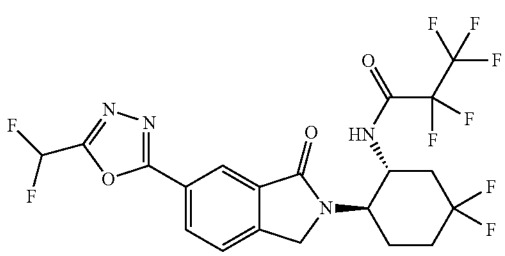 [SMILES: O=C1c2cc(-c3nnc(C(F)F)o3)ccc2CN1[C@@H]1CCC(F)(F)C[C@H]1NC(=O)C(F)(F)C(F)(F)F] | | 528.8 |
| 470 | N-((1R,2R)-2-(6-(5-(difluoro-methyl)-1,3,4-oxadiazol-2-yl)-1-oxo-1,3-dihydro-2H-isoindol-2-yl)-5,5-difluoro-cyclohexyl)-2,2-difluoro-propanamide | 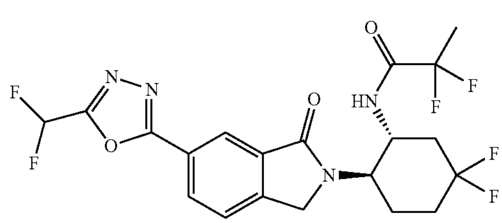 [SMILES: CC(F)(F)C(=O)N[C@@H]1CC(F)(F)CC[C@H]1N1Cc2ccc(-c3nnc(C(F)F)o3)cc2C1=O] | | 476.9 |

TABLE 1-48-continued

| EXAMPLE | IUPAC NAME | Structure | ADDITIVE | MS |
|---|---|---|---|---|
| 471 | 6-(5-(difluoro-methyl)-1,3,4-oxadiazol-2-yl)-2-(4-(2,6-difluoro-pyridin-4-yl)-1-methyl-1H-pyrazol-3-yl)isoindolin-1-one | 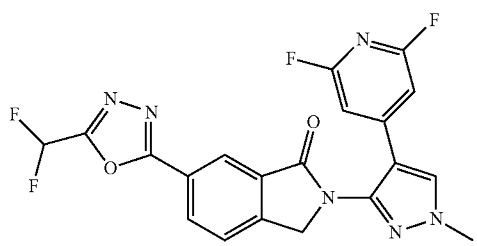 [SMILES: Cn1cc(-c2cc(F)nc(F)c2)c(N2Cc3ccc(-c4nnc(C(F)F)o4)cc3C2=O)n1] | | 444.9 |
| 472 | 2-(1-(3-chloro-phenyl)-1H-pyrazol-5-yl)-6-(5-(difluoro-methyl)-1,3,4-oxadiazol-2-yl)isoindolin-1-one | 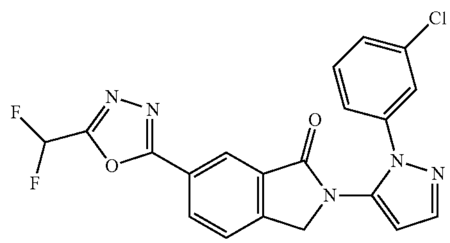 [SMILES: O=C1c2cc(-c3nnc(C(F)F)o3)ccc2CN1c1ccnn1-c1cccc(Cl)c1] | | 427.9 |
| 473 | 6-(5-(difluoro-methyl)-1,3,4-oxadiazol-2-yl)-2-(1-(4-fluoro-phenyl)-1H-pyrazol-5-yl)isoindolin-1-one | 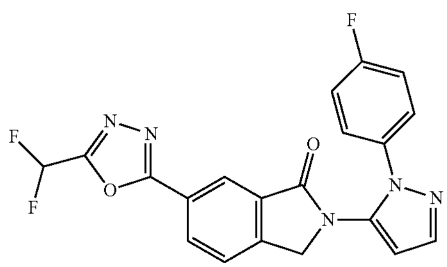 [SMILES: O=C1c2cc(-c3nnc(C(F)F)o3)ccc2CN1c1ccnn1-c1ccc(F)cc1] | | 411.9 |
| 474 | 2-(4-(4,4-difluorocyclo-hex-1-en-1-yl)-1-methyl-1H-pyrazol-3-yl)-6-(5-(difluoro-methyl)-1,3,4-oxadiazol-2-yl)isoindolin-1-one | 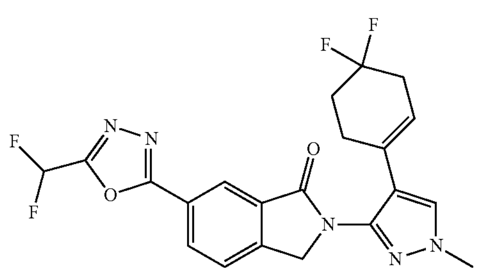 [SMILES: Cn1cc(C2=CCC(F)(F)CC2)c(N2Cc3ccc(-c4nnc(C(F)F)o4)cc3C2=O)n1] | | 447.9 |
| 475 | 3-(5-(difluoro-methyl)-1,3,4-oxadiazol-2-yl)-6-((1S)-1-phenylethyl)-6,7-dihydro-5H-pyrrolo[3,4-b]pyridin-5-one | 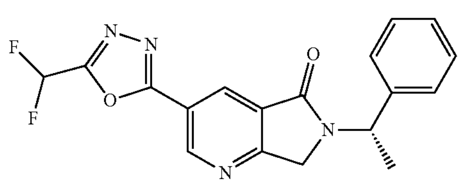 [SMILES: C[C@@H](c1ccccc1)N1Cc2ncc(-c3nnc(C(F)F)o3)cc2C1=O] | | 357.0 |
| 476 | 3-(5-(difluoro-methyl)-1,3,4-oxadiazol-2-yl)-6-((1R)-1-phenylethyl)-6,7-dihydro-5H-pyrrolo[3,4-b]pyridin-5-one | 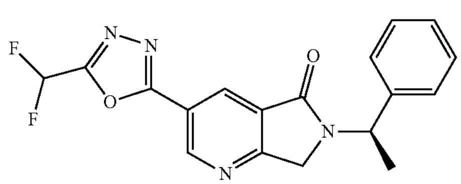 [SMILES: C[C@H](c1ccccc1)N1Cc2ncc(-c3nnc(C(F)F)o3)cc2C1=O] | | 357.0 |

TABLE 1-48-continued

| EXAMPLE | IUPAC NAME | Structure | ADDITIVE | MS |
|---|---|---|---|---|
| 477 | 2-(2-bromo-4-methoxy-phenyl)-6-(5-(difluoro-methyl)-1,3,4-oxadiazol-2-yl)isoindolin-1-one | 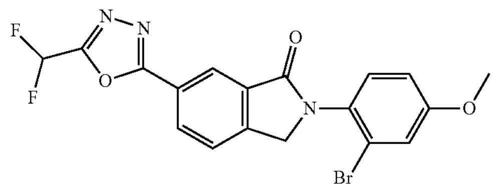 [SMILES: COc1ccc(N2Cc3ccc(-c4nnc(C(F)F)o4)cc3C2=O)c(Br)c1] | | 435.8 |
| 478 | 6-(2-(2,2-difluoroethoxy)benzyl)-3-(5-(difluoro-methyl)-1,3,4-oxadiazol-2-yl)-6,7-dihydro-5H-pyrrolo[3,4-b]pyridin-5-one | 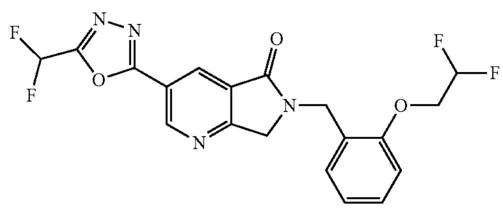 [SMILES: O=C1c2cc(-c3nnc(C(F)F)o3)cnc2CN1Cc1ccccc1OCC(F)F] | | 422.9 |

TABLE 1-49

| EXAMPLE | IUPAC NAME | Structure | ADDITIVE | MS |
|---|---|---|---|---|
| 479 | 3-(5-(difluoro-methyl)-1,3,4-oxadiazol-2-yl)-6-(3-(1-(difluoro-methyl)-1H-pyrazol-4-yl)benzyl)-6,7-dihydro-5H-pyrrolo[3,4-b]pyridin-5-one | 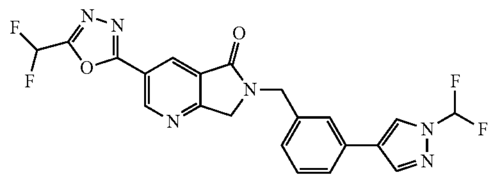 [SMILES: O=C1c2cc(-c3nnc(C(F)F)o3)cnc2CN1Cc1cccc(-c2cnn(C(F)F)c2)c1] | | 456.9 |
| 480 | 2-(4-(4,4-difluorocyclo-hexyl)-1-methyl-1H-pyrazol-3-yl)-6-(5-(difluoro-methyl)-1,3,4-oxadiazol-2-yl)isoindolin-1-one | 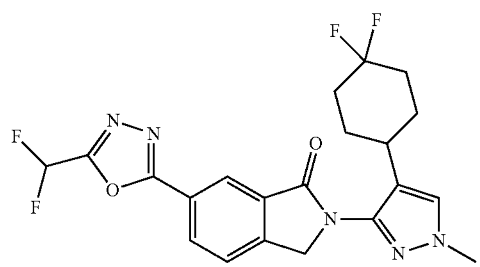 [SMILES: Cn1cc(C2CCC(F)(F)CC2)c(N2Cc3ccc(-c4nnc(C(F)F)o4)cc3C2=O)n1] | | 450.0 |
| 481 | 6-(5-(difluoro-methyl)-1,3,4-oxadiazol-2-yl)-2-(1-methyl-4-(pyrazolo[1,5-a]pyridin-7-yl)-1H-pyrazol-3-yl)isoindolin-1-one | 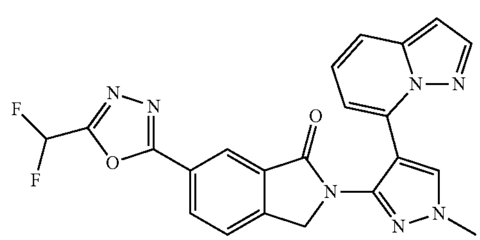 [SMILES: Cn1cc(-c2cccc3ccnn23)c(N2Cc3ccc(-c4nnc(C(F)F)o4)cc3C2=O)n1] | | 447.9 |
| 482 | 2-(2-(4-bromo-1H-pyrazol-1-yl)-4-fluoro-phenyl)-6-(5-(difluoro-methyl)-1,3,4-oxadiazol-2-yl)isoindolin-1-one | 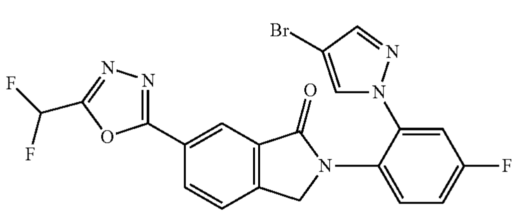 [SMILES: O=C1c2cc(-c3nnc(C(F)F)o3)ccc2CN1c1ccc(F)cc1-n1cc(Br)cn1] | | 490.0 |

TABLE 1-49-continued

| EXAMPLE | IUPAC NAME | Structure | ADDITIVE | MS |
|---|---|---|---|---|
| 483 | 2-(2-bromo-4-(trifluoromethoxy)phenyl)-6-(5-(difluoromethyl)-1,3,4-oxadiazol-2-yl)isoindolin-1-one | 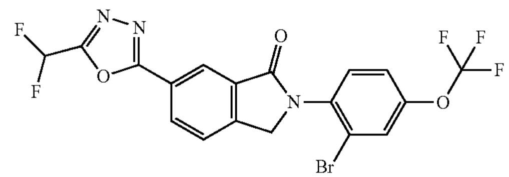 [SMILES: O=C1c2cc(-c3nnc(C(F)F)o3)ccc2CN1c1ccc(OC(F)(F)F)cc1Br] | | 489.9 |
| 484 | 6-(5-(difluoromethyl)-1,3,4-oxadiazol-2-yl)-2-(5-methoxybiphenyl-2-yl)isoindolin-1-one | 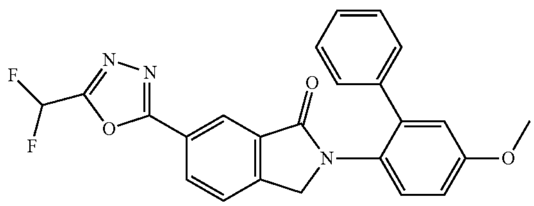 [SMILES: COc1ccc(N2Cc3ccc(-c4nnc(C(F)F)o4)cc3C2=O)c(-c2ccccc2)c1] | | 434.2 |
| 485 | 6-(5-(difluoromethyl)-1,3,4-oxadiazol-2-yl)-2-(5-(trifluoromethoxy)biphenyl-2-yl)isoindolin-1-one | 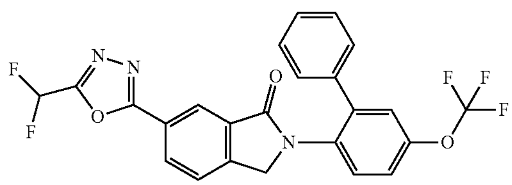 [SMILES: O=C1c2cc(-c3nnc(C(F)F)o3)ccc2CN1c1ccc(OC(F)(F)F)cc1-c1ccccc1] | | 488.1 |
| 486 | 2-(2-(4-cyclopropyl-1H-pyrazol-1-yl)-4-fluorophenyl)-6-(5-(difluoromethyl)-1,3,4-oxadiazol-2-yl)isoindolin-1-one | 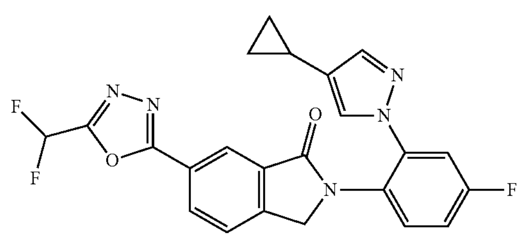 [SMILES: O=C1c2cc(-c3nnc(C(F)F)o3)ccc2CN1c1ccc(F)cc1-n1cc(C2CC2)cn1] | | 452.1 |
| 487 | 2-(2-benzylphenyl)-6-(5-(difluoromethyl)-1,3,4-oxadiazol-2-yl)isoindolin-1-one | 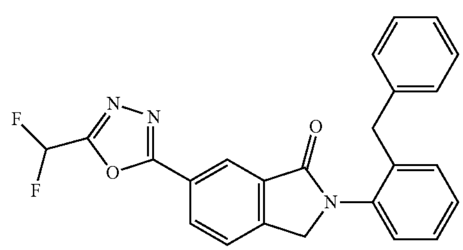 [SMILES: O=C1c2cc(-c3nnc(C(F)F)o3)ccc2CN1c1ccccc1Cc1ccccc1] | | 418.2 |
| 488 | 6-(5-(difluoromethyl)-1,3,4-oxadiazol-2-yl)-2-(2-(4-ethyl-1H-pyrazol-1-yl)-4-fluorophenyl)isoindolin-1-one | 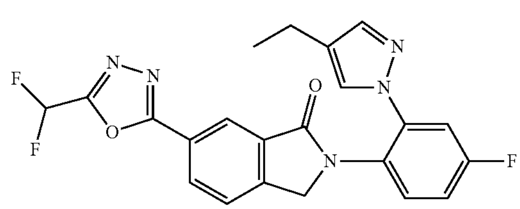 [SMILES: CCc1cnn(-c2cc(F)ccc2N2Cc3ccc(-c4nnc(C(F)F)o4)cc3C2=O)c1] | | 440.1 |

TABLE 1-50

| EXAMPLE | IUPAC NAME | Structure | ADDITIVE | MS |
|---|---|---|---|---|
| 489 | N-((1R,2R)-2-(3-(5-(difluoro-methyl)-1,3,4-oxadiazol-2-yl)-5-oxo-5,7-dihydro-6H-pyrrolo[3,4-b]pyridin-6-yl)cyclohexyl)-2,2,3,3,3-pentafluoro-propanamide | 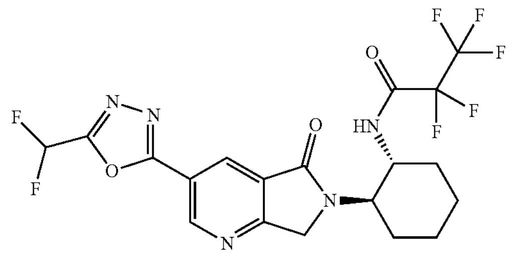 [SMILES: O=C1c2cc(-c3nnc(C(F)F)o3)cnc2CN1[C@@H]1CCCC[C@H]1NC(=O)C(F)(F)C(F)(F)F] | | 494.1 |
| 490 | 6-(5-(difluoro-methyl)-1,3,4-oxadiazol-2-yl)-2-(2-phenyl-piperidin-1-yl)isoindolin-1-one | 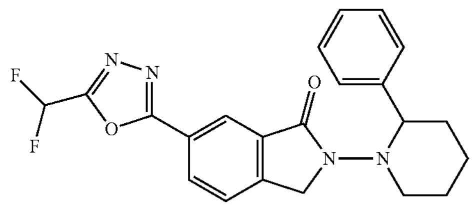 [SMILES: O=C1c2cc(-c3nnc(C(F)F)o3)ccc2CN1N1CCCCC1c1ccccc1] | | 411.0 |
| 491 | 6-(5-(difluoro-methyl)-1,3,4-oxadiazol-2-yl)-2-(2-phenyl-pyrrolidin-1-yl)isoindolin-1-one | 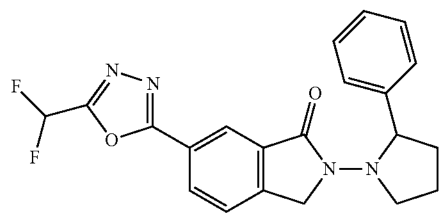 [SMILES: O=C1c2cc(-c3nnc(C(F)F)o3)ccc2CN1N1CCCC1c1ccccc1] | | 397.0 |
| 492 | 2-(3-bromo-1-methyl-1H-pyrazol-4-yl)-6-(5-(difluoro-methyl)-1,3,4-oxadiazol-2-yl)isoindolin-1-one | 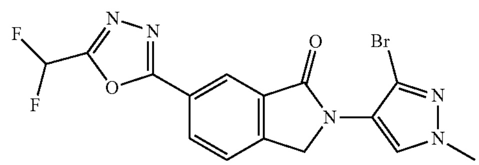 [SMILES: Cn1cc(N2Cc3ccc(-c4nnc(C(F)F)o4)cc3C2=O)c(Br)n1] | | 409.8 |
| 493 | 6-(5-(difluoro-methyl)-1,3,4-oxadiazol-2-yl)-2-(1-methyl-3-phenyl-1H-pyrazol-4-yl)isoindolin-1-one | 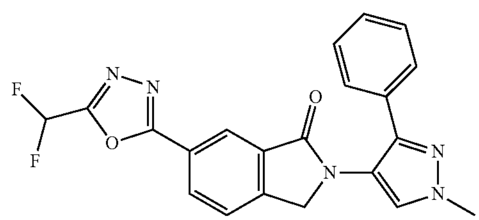 [SMILES: Cn1cc(N2Cc3ccc(-c4nnc(C(F)F)o4)cc3C2=O)c(-c2ccccc2)n1] | | 407.9 |
| 494 | methyl (3R,4R)-4-(3-(5-(difluoro-methyl)-1,3,4-oxadiazol-2-yl)-5-oxo-5,7-dihydro-6H-pyrrolo[3,4-b]pyridin-6-yl)-3-(4-fluoro-phenyl)piperidine-1-carboxylate | 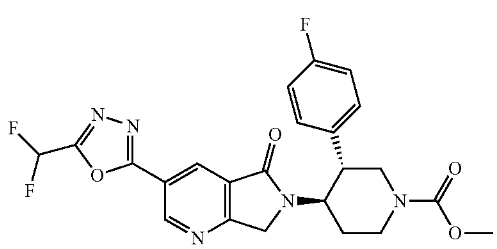 [SMILES: COC(=O)N1CC[C@@H](N2Cc3ncc(-c4nnc(C(F)F)o4)cc3C2=O)[C@H](c2ccc(F)cc2)C1] | | 486.1 |
| 495 | 6-((1S,6R)-6-amino-2,2-difluorocyclo-hexyl)-3-(5-(difluoro-methyl)-1,3,4-oxadiazol-2-yl)-6,7-dihydro-5H-pyrrolo[3,4-b]pyridin-5-one | 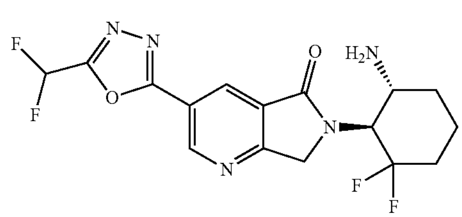 [SMILES: N[C@@H]1CCCC(F)(F)[C@H]1N1Cc2ncc(-c3nnc(C(F)F)o3)cc2C1=O] | CF3COOH | 384.1 |

TABLE 1-50-continued

| EXAMPLE | IUPAC NAME | Structure | ADDITIVE | MS |
|---|---|---|---|---|
| 496 | tert-butyl ((1R,2S)-2-(3-(5-(difluoromethyl)-1,3,4-oxadiazol-2-yl)-5-oxo-5,7-dihydro-6H-pyrrolo[3,4-b]pyridin-6-yl)-3,3-difluorocyclohexyl)carbamate | 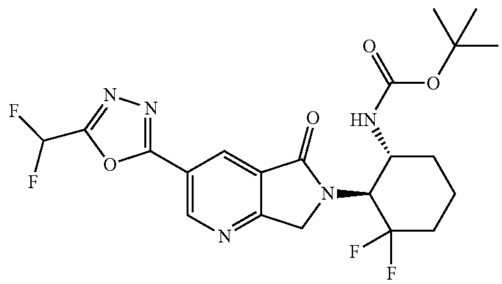 [SMILES: CC(C)(C)OC(=O)N[C@@H]1CCCC(F)(F)[C@H]1N1Cc2ncc(-c3nnc(C(F)F)o3)cc2C1=O] | | 484.1 |
| 497 | N-((1R,2S)-2-(3-(5-(difluoromethyl)-1,3,4-oxadiazol-2-yl)-5-oxo-5,7-dihydro-6H-pyrrolo[3,4-b]pyridin-6-yl)-3,3-difluorocyclohexyl)-2,2,3,3,3-pentafluoropropanamide | 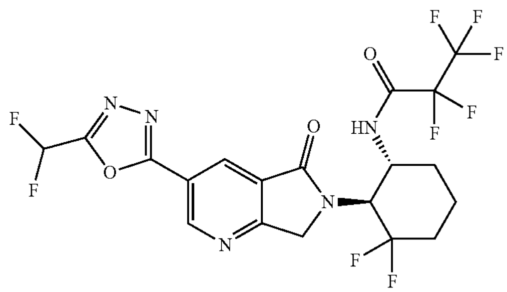 [SMILES: O=C1c2cc(-c3nnc(C(F)F)o3)cnc2CN1[C@H]1[C@H](NC(=O)C(F)(F)C(F)(F)F)CCCC1(F)F] | | 530.0 |
| 498 | 6-((3R,4R)-1-(cyclopropylcarbonyl)-3-(4-fluorophenyl)piperidin-4-yl)-3-(5-(difluoromethyl)-1,3,4-oxadiazol-2-yl)-6,7-dihydro-5H-pyrrolo[3,4-b]pyridin-5-one | 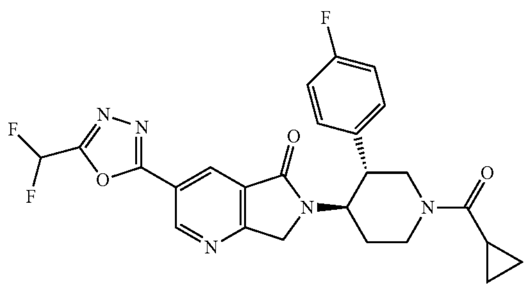 [SMILES: O=C(C1CC1)N1CC[C@@H](N2Cc3ncc(-c4nnc(C(F)F)o4)cc3C2=O)[C@H](c2ccc(F)cc2)C1] | | 498.1 |

TABLE 1-51

| EXAMPLE | IUPAC NAME | Structure | ADDITIVE | MS |
|---|---|---|---|---|
| 499 | methyl (3R,4R)-4-(3-(5-(difluoromethyl)-1,3,4-oxadiazol-2-yl)-5-oxo-5,7-dihydro-6H-pyrrolo[3,4-b]pyridin-6-yl)-3-(3,4-difluorophenyl)piperidine-1-carboxylate | 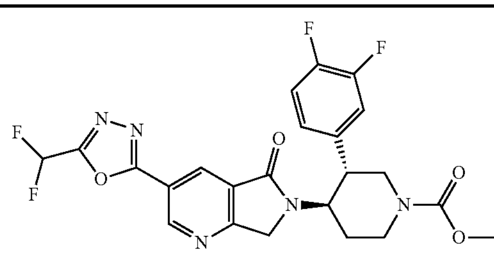 | | 504.1 |
| 500 | N-((1R,2S)-2-(3-(5-(difluoromethyl)-1,3,4-oxadiazol-2-yl)-5-oxo-5,7-dihydro-6H-pyrrolo[3,4-b]pyridin-6-yl)-3,3-difluorocyclohexyl)-2,2-difluoropropanamide | 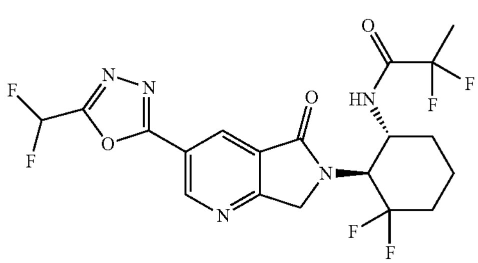 [SMILES: CC(F)(F)C(=O)N[C@@H]1CCCC(F)(F)[C@H]1N1Cc2ncc(-c3nnc(C(F)F)o3)cc2C1=O] | | 478.1 |

TABLE 1-51-continued

| EXAMPLE | IUPAC NAME | Structure | ADDITIVE | MS |
|---|---|---|---|---|
| 501 | 6-(5-(difluoro-methyl)-1,3,4-oxadiazol-2-yl)-2-(3-phenyl-morpholin-4-yl)isoindolin-1-one | 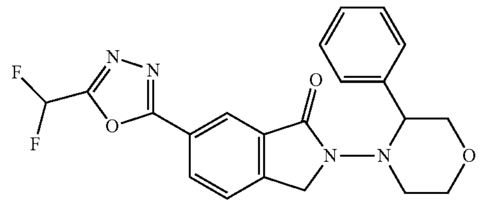 [SMILES: O=C1c2cc(-c3nnc(C(F)F)o3)ccc2CN1N1CCOCC1c1ccccc1] | | 413.2 |
| 502 | 6-((1R,2R)-2-(1H-benzimi-dazol-1-yl)cyclohexyl)-3-(5-(difluoro-methyl)-1,3,4-oxadiazol-2-yl)-6,7-dihydro-5H-pyrrolo[3,4-b]pyridin-5-one | 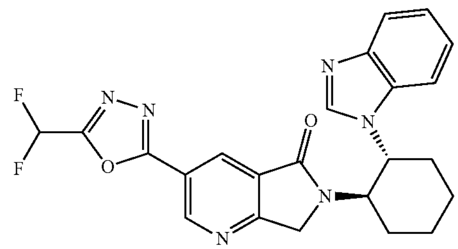 [SMILES: O=C1c2cc(-c3nnc(C(F)F)o3)cnc2CN1[C@@H]1CCCC[C@H]1n1cnc2ccccc21] | | 451.3 |
| 503 | 3-(5-(difluoro-methyl)-1,3,4-oxadiazol-2-yl)-6-((1R,2R)-2-(2-methyl-1H-benzimidazol-1-yl)cyclo-hexyl)-6,7-dihydro-5H-pyrrolo[3,4-b]pyridin-5-one | 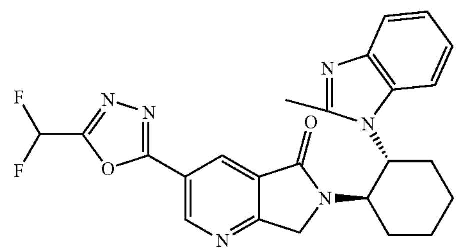 [SMILES: Cc1nc2ccccc2n1[C@@H]1CCCC[C@H]1N1Cc2ncc(-c3nnc(C(F)F)o3)cc2C1=O] | | 465.2 |
| 504 | methyl (3SR,4SR)-3-(6-(5-(difluoro-methyl)-1,3,4-oxadiazol-2-yl)-1-oxo-1,3-dihydro-2H-isoindol-2-yl)-4-(4-fluoro-phenyl)piperidine-1-carboxylate | 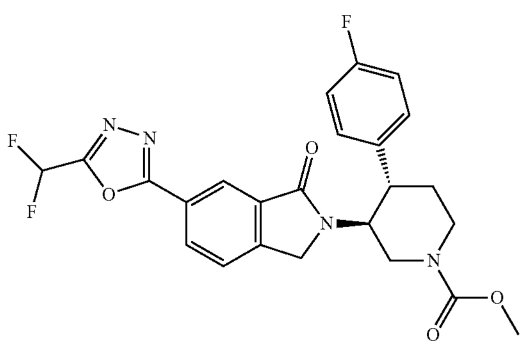 [SMILES: COC(=O)N1CC[C@@H](c2ccc(F)cc2)[C@H](N2Cc3ccc(-c4nnc(C(F)F)o4)cc3C2=O)C1] | | 487.2 |
| 505 | methyl (3R,4R)-4-(6-(5-(difluoro-methyl)-1,3,4-oxadiazol-2-yl)-1-oxo-1,3-dihydro-2H-isoindol-2-yl)-3-(4-fluoro-phenyl)piperidine-1-carboxylate | 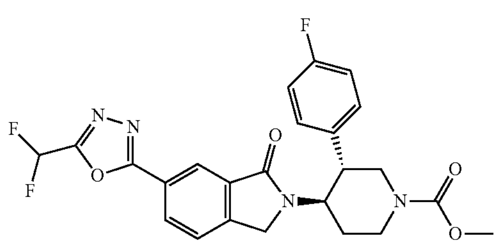 [SMILES: COC(=O)N1CC[C@@H](N2Cc3ccc(-c4nnc(C(F)F)o4)cc3C2=O)[C@H](c2ccc(F)cc2)C1] | | 487.2 |
| 506 | 6-(5-(difluoro-methyl)-1,3,4-oxadiazol-2-yl)-2-((3R,4R)-1-(2,2-difluoro-propanoyl)-3-(4-fluorophenyl)piperidin-4-yl)isoindolin-1-one | 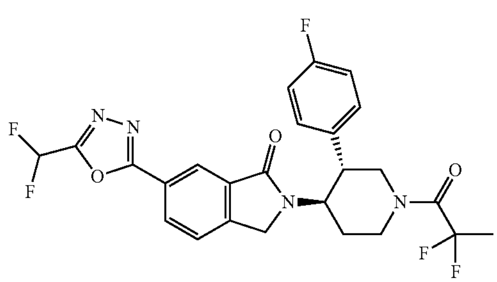 [SMILES: CC(F)(F)C(=O)N1CC[C@@H](N2Cc3ccc(-c4nnc(C(F)F)o4)cc3C2=O)[C@H](c2ccc(F)cc2)C1] | | 521.2 |

TABLE 1-51-continued

| EXAMPLE | IUPAC NAME | Structure | ADDITIVE | MS |
|---|---|---|---|---|
| 507 | 6-(5-(difluoro-methyl)-1,3,4-oxadiazol-2-yl)-2-((3R,4R)-1-((1-fluorocyclo-propyl)carbonyl)-3-(4-fluoro-phenyl)piperidin-4-yl)isoindolin-1-one | 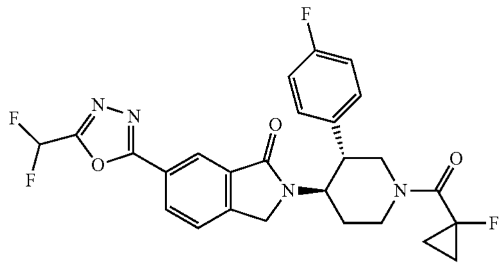 [SMILES: O=C1c2cc(-c3nnc(C(F)F)o3)ccc2CN1[C@@H]1CCN(C(=O)C2(F)CC2)C[C@H]1c1ccc(F)cc1] | | 515.2 |
| 508 | 6-(5-(difluoro-methyl)-1,3,4-oxadiazol-2-yl)-2-((3R,4R)-3-(4-fluorophenyl)-1-((1-(trifluoro-methyl)cyclo-propyl)carbonyl)pipeiridin-4-yl)isoindolin-1-one | 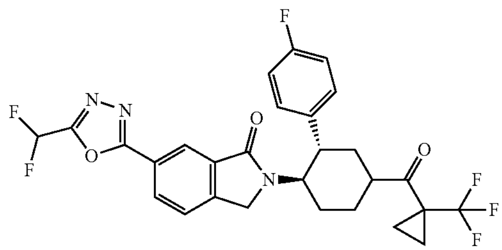 [SMILES: O=C1c2cc(-c3nnc(C(F)F)o3)ccc2CN1[C@@H]1CCC(C(=O)C2(C(F)(F)F)CC2)C[C@H]1c1ccc(F)cc1] | | 565.2 |

TABLE 1-52

| EXAMPLE | IUPAC NAME | Structure | ADDITIVE | MS |
|---|---|---|---|---|
| 509 | 2-((3R,4R)-1-acetyl-3-(4-fluorophenyl)piperidin-4-yl)-6-(5-(difluoro-methyl)-1,3,4-oxadiazol-2-yl)isoindolin-1-one | 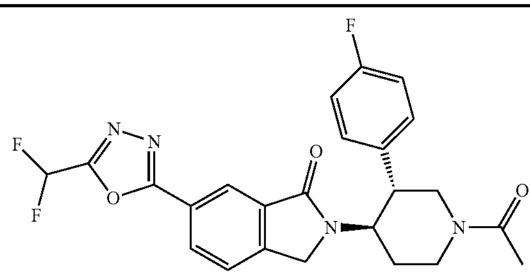 | | 471.2 |
| 510 | benzyl ((1S,6R)-6-(6-(5-(difluoro-methyl)-1,3,4-oxadiazol-2-yl)-1-oxo-1,3-dihydro-2H-isoindol-2-yl)-2,2-difluoro-cyclohexyl)carbamate | 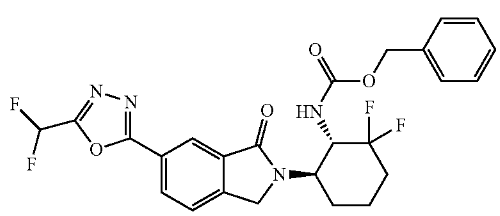 [SMILES: O=C(N[C@H]1[C@H](N2Cc3ccc(-c4nnc(C(F)F)o4)cc3C2=O)CCCC1(F)F)OCc1ccccc1] | | 519.2 |
| 511 | 2-((1R,2S)-2-amino-3,3-difluorocyclo-hexyl)-6-(5-(difluoro-methyl)-1,3,4-oxadiazol-2-yl)isoindolin-1-one | 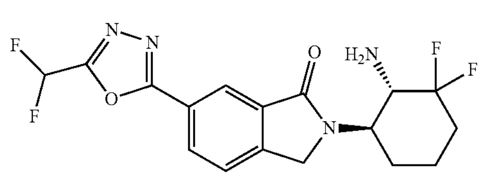 [SMILES: N[C@H]1[C@H](N2Cc3ccc(-c4nnc(C(F)F)o4)cc3C2=O)CCCC1(F)F] | | 385.2 |
| 512 | N-((1S,6R)-6-(6-(5-(difluoro-methyl)-1,3,4-oxadiazol-2-yl)-1-oxo-1,3-dihydro-2H-isoindol-2-yl)-2,2-difluoro-cyclohexyl)-2,2-difluoro-propanamide | 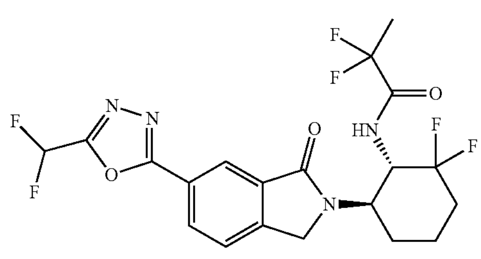 [SMILES: CC(F)(F)C(=O)N[C@H]1[C@H](N2Cc3ccc(-c4nnc(C(F)F)o4)cc3C2=O)CCCC1(F)F] | | 477.2 |

TABLE 1-52-continued

| EXAMPLE | IUPAC NAME | Structure | ADDITIVE | MS |
|---|---|---|---|---|
| 513 | N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2,3,3,3-pentafluoropropanamide | 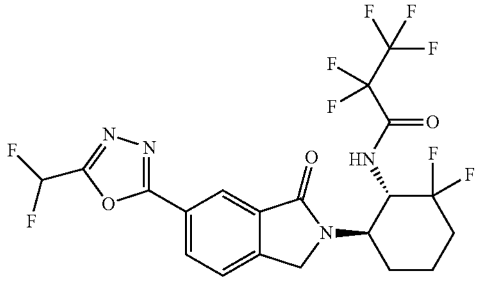 [SMILES: O=C1c2cc(-c3nnc(C(F)F)o3)ccc2CN1[C@@H]1CCCC(F)(F)[C@H]1NC(=O)C(F)(F)C(F)(F)F] | | 531.2 |
| 514 | 6-(5-(difluoromethyl)-1,3,4-oxadiazol-2-yl)-2-((1RS,2RS)-2-(1H-pyrazol-1-yl)cyclohexyl)isoindolin-1-one | 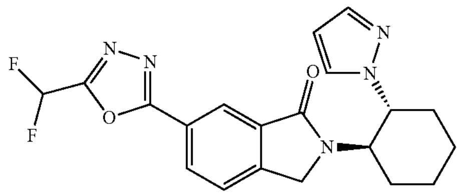 [SMILES: O=C1c2cc(-c3nnc(C(F)F)o3)ccc2CN1[C@@H]1CCCC[C@H]1n1cccn1] | | 400.2 |
| 515 | N-((1S,2R)-2-(6-(5-(difluoromethyl)-1,3,4-oxadiazol-2-yl)-1-oxo-1,3-dihydro-2H-isoindol-2-yl)-5,5-difluorocyclohexyl)-2,2,3,3,3-pentafluoropropanamide | 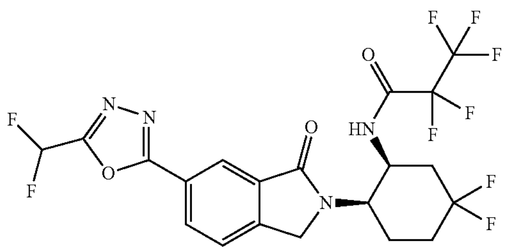 [SMILES: O=C1c2cc(-c3nnc(C(F)F)o3)ccc2CN1[C@@H]1CCC(F)(F)C[C@@H]1NC(=O)C(F)(F)C(F)(F)F] | | 529.1 |
| 516 | N-((1S,2R)-2-(6-(5-(difluoromethyl)-1,3,4-oxadiazol-2-yl)-1-oxo-1,3-dihydro-2H-isoindol-2-yl)-5,5-difluorocyclohexyl)-2,2-difluoropropanamide | 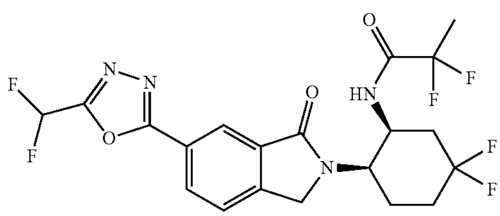 [SMILES: CC(F)(F)C(=O)N[C@H]1CC(F)(F)CC[C@H]1N1Cc2ccc(-c3nnc(C(F)F)o3)cc2C1=O] | | 477.2 |
| 517 | benzyl ((1S,2R)-2-(6-(5-(difluoromethyl)-1,3,4-oxadiazol-2-yl)-1-oxo-1,3-dihydro-2H-isoindol-2-yl)-5,5-difluorocyclohexyl)carbamate | 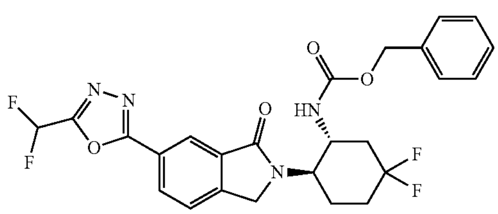 [SMILES: O=C(N[C@@H]1CC(F)(F)CC[C@H]1N1Cc2ccc(-c3nnc(C(F)F)o3)cc2C1=O)OCc1ccccc1] | | 519.2 |
| 518 | tert-butyl 4-(3-(6-(5-(difluoromethyl)-1,3,4-oxadiazol-2-yl)-1-oxo-1,3-dihydro-2H-isoindol-2-yl)-1-methyl-1H-pyrazol-4-yl)-3,6-dihydropyridine-1(2H)-carboxylate | 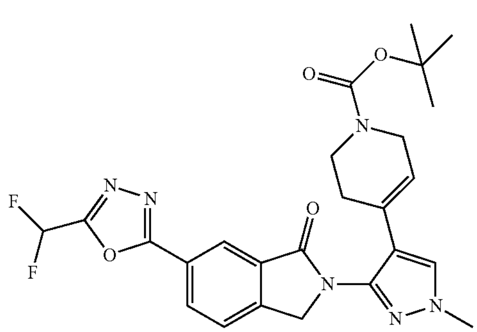 [SMILES: Cn1cc(C2=CCN(C(=O)OC(C)(C)C)CC2)c(N2Cc3ccc(-c4nnc(C(F)F)o4)cc3C2=O)n1] | | 511.2 |

TABLE 1-53

| EXAMPLE | IUPAC NAME | Structure | ADDITIVE | MS |
|---|---|---|---|---|
| 519 | tert-butyl (4-(3-(6-(5-(difluoromethyl)-1,3,4-oxadiazol-2-yl)-1-oxo-1,3-dihydro-2H-isoindol-2-yl)-1-methyl-1H-pyrazol-4-yl)cyclohex-3-en-1-yl)carbamate | 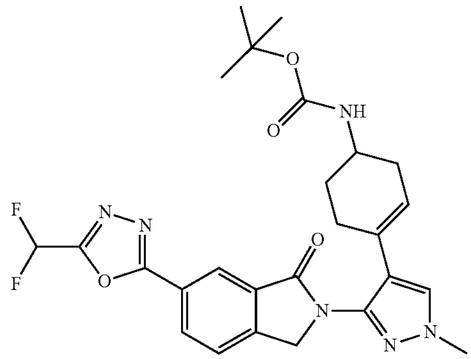 [SMILES: Cn1cc(C2=CCC(NC(=O)OC(C)(C)C)CC2)c(N2Cc3ccc(-c4nnc(C(F)F)o4)cc3C2=O)n1] | | 525.2 |
| 520 | tert-butyl (4-(2-(6-(5-(difluoromethyl)-1,3,4-oxadiazol-2-yl)-1-oxo-1,3-dihydro-2H-isoindol-2-yl)-5-fluorophenyl)cyclohex-3-en-1-yl)carbamate | 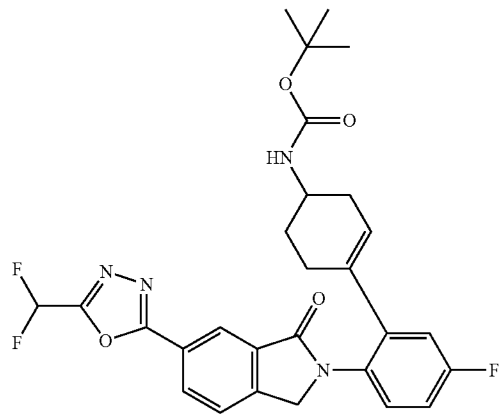 [SMILES: CC(C)(C)OC(=O)NC1CC=C(c2cc(F)ccc2N2Cc3ccc(-c4nnc(C(F)F)o4)cc3C2=O)CC1] | | 539.2 |
| 521 | 6-(5-(difluoromethyl)-1,3,4-oxadiazol-2-yl)-2-((1R,2R)-2-(pyridin-2-ylamino)cyclohexyl)isoindolin-1-one | 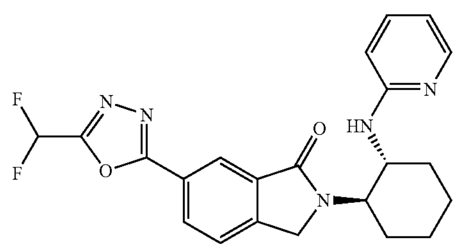 [SMILES: O=C1c2cc(-c3nnc(C(F)F)o3)ccc2CN1[C@@H]1CCCC[C@H]1Nc1ccccn1] | | 426.2 |
| 522 | tert-butyl 4-(3-(6-(5-(difluoromethyl)-1,3,4-oxadiazol-2-yl)-1-oxo-1,3-dihydro-2H-isoindol-2-yl)-1-methyl-1H-pyrazol-4-yl)piperidine-1-carboxylate | 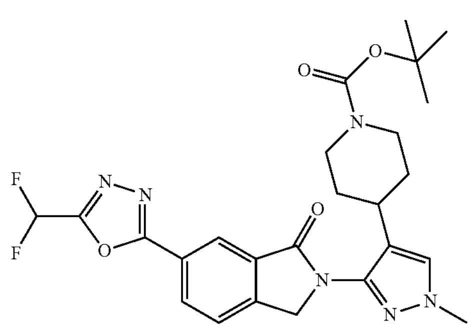 [SMILES: Cn1cc(C2CCN(C(=O)OC(C)(C)C)CC2)c(N2Cc3ccc(-c4nnc(C(F)F)o4)cc3C2=O)n1] | | 513.2 |

TABLE 1-53-continued

| EXAMPLE | IUPAC NAME | Structure | ADDITIVE | MS |
|---|---|---|---|---|
| 523 | tert-butyl (4-(3-(6-(5-(difluoromethyl)-1,3,4-oxadiazol-2-yl)-1-oxo-1,3-dihydro-2H-isoindol-2-yl)-1-methyl-1H-pyrazol-4-yl)cyclohexyl)carbamate | 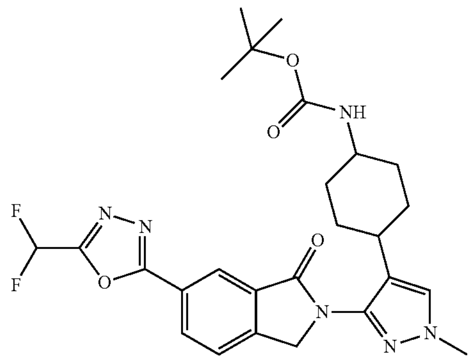 | | 527.1 |
| 524 | tert-butyl 4-(2-(6-(5-(difluoromethyl)-1,3,4-oxadiazol-2-yl)-1-oxo-1,3-dihydro-2H-isoindol-2-yl)-5-fluorophenyl)piperidine-1-carboxylate | 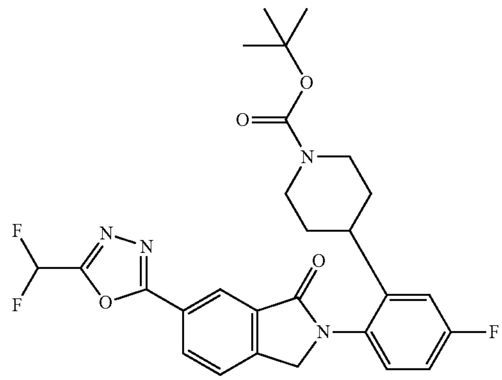 [SMILES: CC(C)(C)OC(=O)N1CCC(c2cc(F)ccc2N2Cc3ccc(-c4nnc(C(F)F)o4)cc3C2=O)CC1] | | 527.1 |
| 525 | tert-butyl (4-(2-(6-(5-(difluoromethyl)-1,3,4-oxadiazol-2-yl)-1-oxo-1,3-dihydro-2H-isoindol-2-yl)-5-fluorophenyl)cyclohexyl)carbamate | 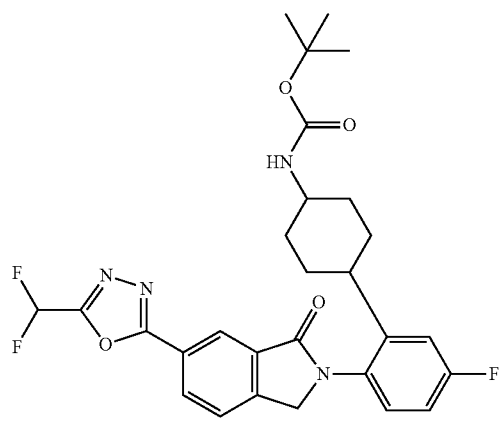 [SMILES: CC(C)(C)OC(=O)NC1CCC(c2cc(F)ccc2N2Cc3ccc(-c4nnc(C(F)F)o4)cc3C2=O)CC1] | | 541.3 |
| 526 | 3-(5-(difluoromethyl)-1,3,4-oxadiazol-2-yl)-6-((1RS,2RS)-2-(1H-pyrazol-1-yl)cyclohexyl)-6,7-dihydro-5H-pyrrolo[3,4-b]pyridin-5-one | 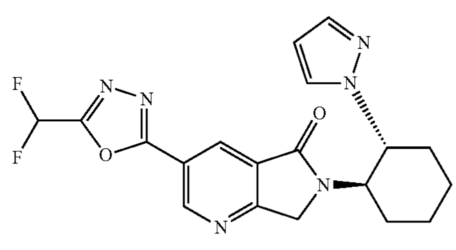 [SMILES: O=C1c2cc(-c3nnc(C(F)F)o3)cnc2CN1[C@@H]1CCCC[C@H]1n1cccn1] | | 401.1 |
| 527 | 6-(5-(difluoromethyl)-1,3,4-oxadiazol-2-yl)-2-((1SR,2RS)-2-(1H-pyrazol-1-yl)cyclohexyl)isoindolin-1-one | 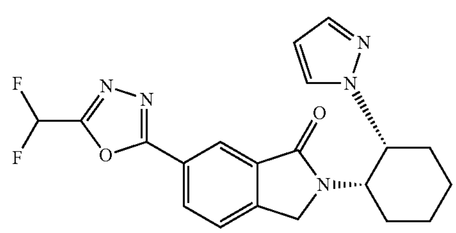 [SMILES: O=C1c2cc(-c3nnc(C(F)F)o3)ccc2CN1[C@H]1CCCC[C@H]1n1cccn1] | | 400.2 |

TABLE 1-53-continued

| EXAMPLE | IUPAC NAME | Structure | ADDITIVE | MS |
|---|---|---|---|---|
| 528 | 6-(5-(difluoromethyl)-1,3,4-oxadiazol-2-yl)-2-((1R*,2R*)-2-(1H-pyrazol-1-yl)cyclohexyl)isoindolin-1-one (optical isomer) | 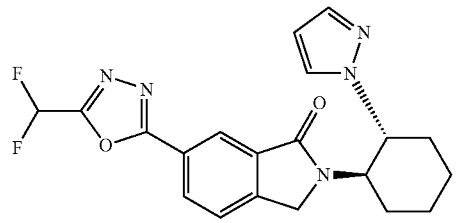 [SMILES: O=C1c2cc(-c3nnc(C(F)F)o3)ccc2CN1[C@@H]1CCCC[C@H]1n1cccn1] | | 400.2 |

TABLE 1-54

| EXAMPLE | IUPAC NAME | Structure | ADDITIVE | MS |
|---|---|---|---|---|
| 529 | 6-(5-(difluoromethyl)-1,3,4-oxadiazol-2-yl)-2-((1R*,2R*)-2-(1H-pyrazol-1-yl)cyclohexyl)isoindolin-1-one (optical isomer) | 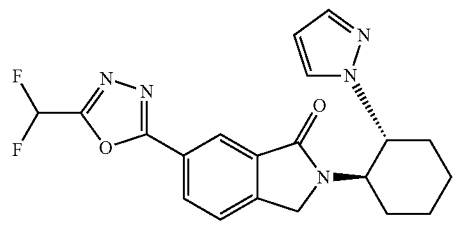 [SMILES: O=C1c2cc(-c3nnc(C(F)F)o3)ccc2CN1[C@@H]1CCCC[C@H]1n1cccn1] | | 400.2 |
| 530 | 6-(5-(difluoromethyl)-1,3,4-oxadiazol-2-yl)-2-(4,4-difluoro-2-phenylpiperidin-1-yl)isoindolin-1-one | 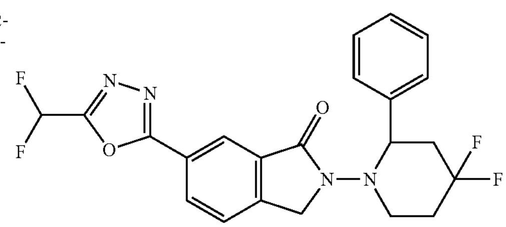 | | 445.1 |
| 531 | 6-(5-(difluoromethyl)-1,3,4-oxadiazol-2-yl)-2-((1R,2R)-2-(3,3,4,4,5,5-hexafluoropiperidin-1-yl)cyclohexyl)isoindolin-1-one | 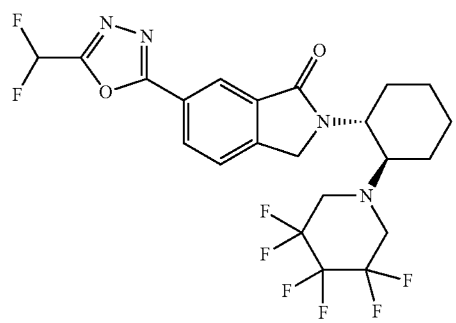 [SMILES: O=C1c2cc(-c3nnc(C(F)F)o3)ccc2CN1[C@@H]1CCCC[C@H]1N1CC(F)(F)C(F)(F)C(F)(F)C1] | | 523.1 |
| 532 | N-(4-(3-(6-(5-(difluoromethyl)-1,3,4-oxadiazol-2-yl)-1-oxo-1,3-dihydro-2H-isoindol-2-yl)-1-methyl-1H-pyrazol-4-yl)cyclohexyl)-2,2,3,3,3-pentafluoropropanamide | 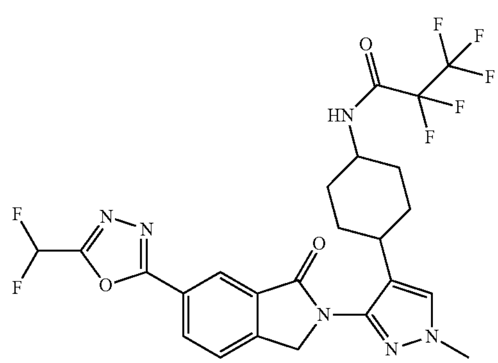 [SMILES: Cn1cc(C2CCC(NC(=O)C(F)(F)C(F)(F)F)CC2)c(N2Cc3ccc(-c4nnc(C(F)F)o4)cc3C2=O)n1] | | 575.2 |

TABLE 1-54-continued

| EXAMPLE | IUPAC NAME | Structure | ADDITIVE | MS |
|---|---|---|---|---|
| 533 | 6-(5-(difluoromethyl)-1,3,4-oxadiazol-2-yl)-2-(4-fluoro-2-(1-(2,2,3,3,3-pentafluoropropanoyl)piperidin-4-yl)phenyl)isoindolin-1-one | 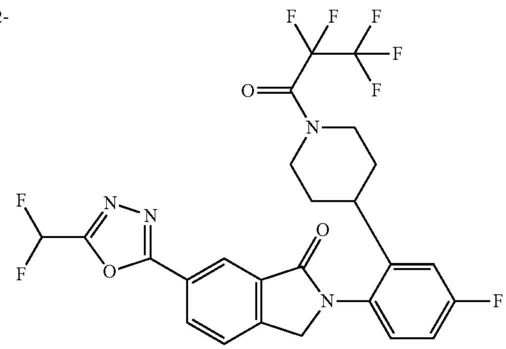 | | 573.0 |
| 534 | N-(4-(2-(6-(5-(difluoromethyl)-1,3,4-oxadiazol-2-yl)-1-oxo-1,3-dihydro-2H-isoindol-2-yl)-5-fluorophenyl)cyclohexyl)-2,2,3,3,3-pentafluoropropanamide | 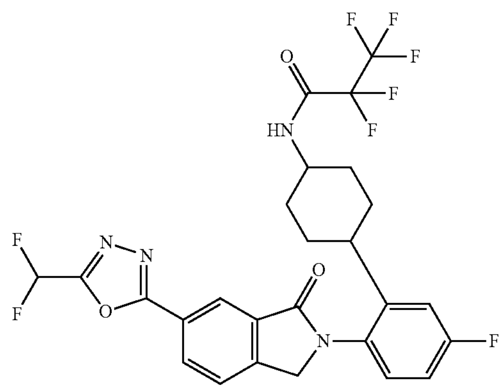 [SMILES: O=C1c2cc(-c3nnc(C(F)F)o3)ccc2CN1c1ccc(F)cc1C1CCC(NC(=O)C(F)(F)C(F)(F)F)CC1] | | 589.2 |
| 535 | 3-(5-(difluoromethyl)-1,3,4-oxadiazol-2-yl)-6-((1RS,2RS)-2-(4-fluorophenoxy)cyclohexyl)-6,7-dihydro-5H-pyrrolo[3,4-b]pyridin-5-one | 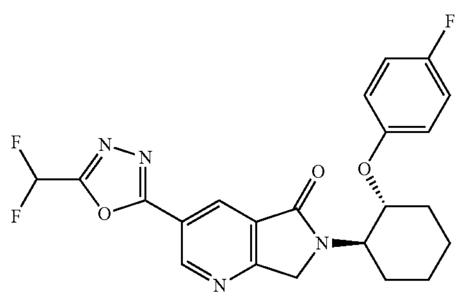 [SMILES: O=C1c2cc(-c3nnc(C(F)F)o3)cnc2CN1[C@@H]1CCCC[C@H]1Oc1ccc(F)cc1] | | 443.0 |
| 536 | 2-((1R,2R)-2-(1H-benzotriazol-1-yl)cyclohexyl)-6-(5-(difluoromethyl)-1,3,4-oxadiazol-2-yl)isoindolin-1-one | 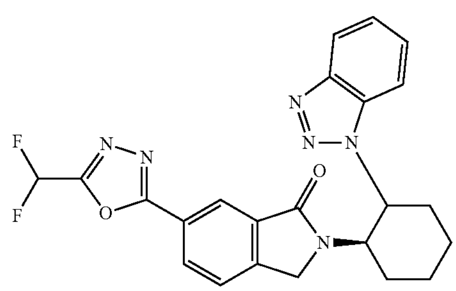 [SMILES: O=C1c2cc(-c3nnc(C(F)F)o3)ccc2CN1[C@@H]1CCCCC1n1nnc2ccccc21] | | 451.3 |
| 537 | 6-((1R,2R)-2-(1H-benzotriazol-1-yl)cyclohexyl)-3-(5-(difluoromethyl)-1,3,4-oxadiazol-2-yl)-6,7-dihydro-5H-pyrrolo[3,4-b]pyridin-5-one | 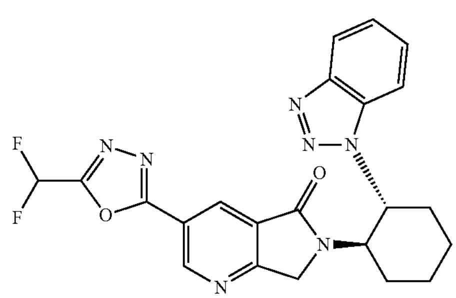 [SMILES: O=C1c2cc(-c3nnc(C(F)F)o3)cnc2CN1[C@@H]1CCCC[C@H]1n1nnc2ccccc21] | | 452.3 |

TABLE 1-54-continued

| EXAMPLE | IUPAC NAME | Structure | ADDITIVE | MS |
|---|---|---|---|---|
| 538 | 6-(5-(difluoromethyl)-1,3,4-oxadiazol-2-yl)-2-(1-methyl-4-(1-(2,2,3,3,3-pentafluoropropanoyl)piperidin-4-yl)-1H-pyrazol-3-yl)isoindolin-1-one | 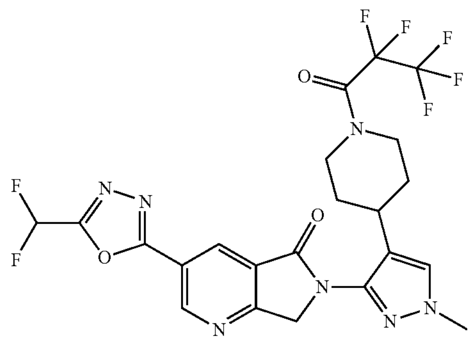 [SMILES: Cn1cc(C2CCN(C(=O)C(F)(F)C(F)(F)F)CC2)c(N2Cc3ncc(-c4nnc(C(F)F)o4)cc3C2=O)n1] | | 561.2 |

TABLE 1-55

| EXAMPLE | IUPAC NAME | Structure | ADDITIVE | MS |
|---|---|---|---|---|
| 539 | 3-(5-(difluoromethyl)-1,3,4-oxadiazol-2-yl)-6-((1R*,2R*)-2-(1H-pyrazol-1-yl)cyclohexyl)-6,7-dihydro-5H-pyrrolo[3,4-b]pyridin-5-one (optical isomer) | 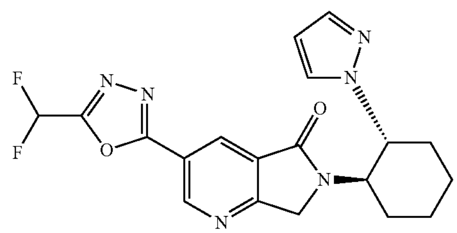 [SMILES: O=C1c2cc(-c3nnc(C(F)F)o3)cnc2CN1[C@@H]1CCCC[C@H]1n1cccn1] | | 401.3 |
| 540 | 3-(5-(difluoromethyl)-1,3,4-oxadiazol-2-yl)-6-((1R*,2R*)-2-(1H-pyrazol-1-yl)cyclohexyl)-6,7-dihydro-5H-pyrrolo[3,4-b]pyridin-5-one (optical isomer) | 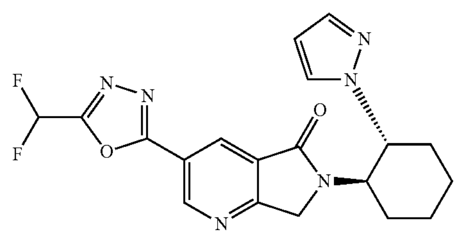 [SMILES: O=C1c2cc(-c3nnc(C(F)F)o3)cnc2CN1[C@@H]1CCCC[C@H]1n1cccn1] | | 401.3 |
| 541 | 3-(5-(difluoromethyl)-1,3,4-oxadiazol-2-yl)-6-((1SR,2RS)-2-(1H-pyrazol-1-yl)cyclohexyl)-6,7-dihydro-5H-pyrrolo[3,4-b]pyridin-5-one | 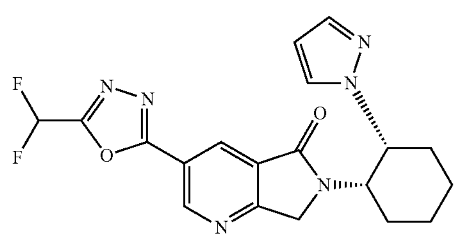 [SMILES: O=C1c2cc(-c3nnc(C(F)F)o3)cnc2CN1[C@H]1CCCC[C@H]1n1cccn1] | | 401.3 |
| 542 | 6-(5-(difluoromethyl)-1,3,4-oxadiazol-2-yl)-2-((1S*,2R*)-2-(1H-pyrazol-1-yl)cyclohexyl)isoindolin-1-one (optical isomer) | 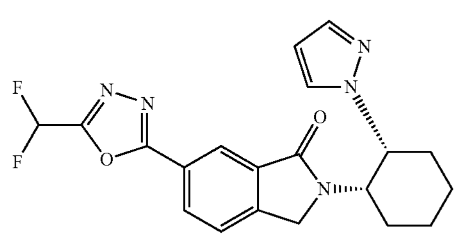 [SMILES: O=C1c2cc(-c3nnc(C(F)F)o3)ccc2CN1[C@H]1CCCC[C@H]1n1cccn1] | | 400.3 |

TABLE 1-55-continued

| EXAMPLE | IUPAC NAME | Structure | ADDITIVE | MS |
|---|---|---|---|---|
| 543 | 6-(5-(difluoromethyl)-1,3,4-oxadiazol-2-yl)-2-((1S*,2R*)-2-(1H-pyrazol-1-yl)cyclohexyl)isoindolin-1-one (optical isomer) | 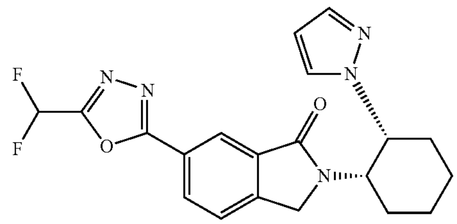 [SMILES: O=C1c2cc(-c3nnc(C(F)F)o3)ccc2CN1[C@H]1CCCC[C@H]1n1cccn1] | | 400.3 |
| 544 | methyl (3S*,4S*)-3-(6-(5-(difluoromethyl)-1,3,4-oxadiazol-2-yl)-1-oxo-1,3-dihydro-2H-isoindol-2-yl)-4-(4-fluorophenyl)piperidine-1-carboxylate (optical isomer) | 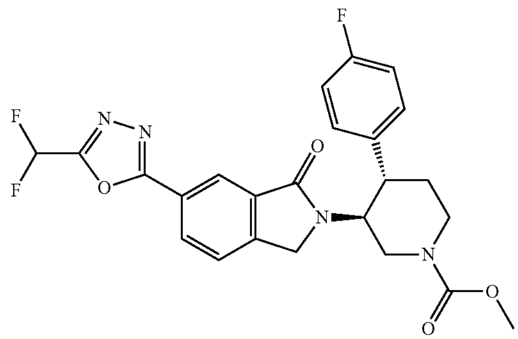 [SMILES: COC(=O)N1CC[C@@H](c2ccc(F)cc2)[C@H](N2Cc3ccc(-c4nnc(C(F)F)o4)cc3C2=O)C1] | | 487.2 |
| 545 | methyl (3S*,4S*)-3-(6-(5-(difluoromethyl)-1,3,4-oxadiazol-2-yl)-1-oxo-1,3-dihydro-2H-isoindol-2-yl)-4-(4-fluorophenyl)piperidine-1-carboxylate (optical isomer) | 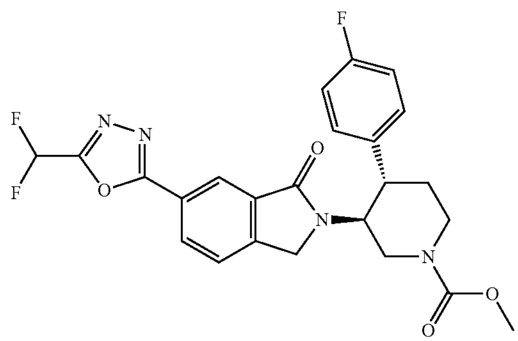 [SMILES: COC(=O)N1CC[C@@H](c2ccc(F)cc2)[C@H](N2Cc3ccc(-c4nnc(C(F)F)o4)cc3C2=O)C1] | | 487.2 |
| 546 | 2-((3SR,4SR)-1-(difluoroacetyl)-4-(4-fluorophenyl)piperidin-3-yl)-6-(5-(difluoromethyl)-1,3,4-oxadiazol-2-yl)isoindolin-1-one | 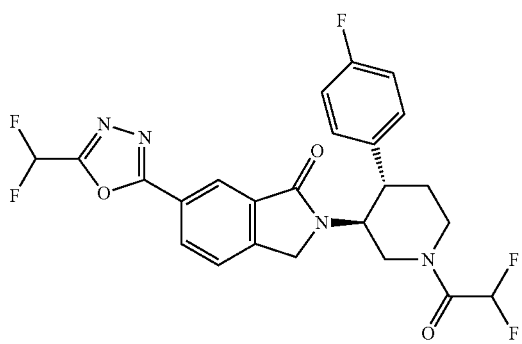 [SMILES: O=C(C(F)F)N1CC[C@@H](c2ccc(F)cc2)[C@H](N2Cc3ccc(-c4nnc(C(F)F)o4)cc3C2=O)C1] | | 505.1 |
| 547 | 6-(5-(difluoromethyl)-1,3,4-oxadiazol-2-yl)-2-((1R,2R)-2-([1,2,4]triazolo[4,3-a]pyridin-3-yl)cyclohexyl)isoindolin-1-one | 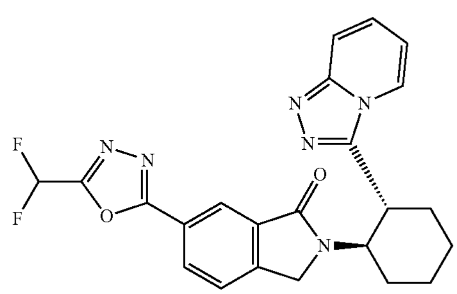 [SMILES: O=C1c2cc(-c3nnc(C(F)F)o3)ccc2CN1[C@@H]1CCCC[C@H]1c1nnc2ccccn12] | | 451.3 |

TABLE 1-55-continued

| EXAMPLE | IUPAC NAME | Structure | ADDITIVE | MS |
|---|---|---|---|---|
| 548 | 6-(5-(difluoromethyl)-1,3,4-oxadiazol-2-yl)-2-((3SR,4SR)-4-(4-fluorophenyl)-1-(2,2,3,3,3-pentafluoropropanoyl)piperidin-3-yl)isoindolin-1-one | 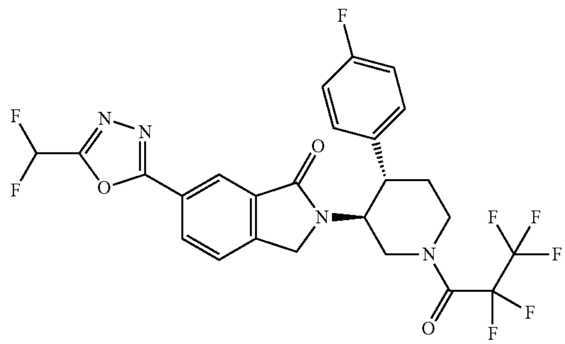 [SMILES: O=C1c2cc(-c3nnc(C(F)F)o3)ccc2CN1[C@@H]1CN(C(=O)C(F)(F)C(F)(F)F)CC[C@H]1c1ccc(F)cc1] | | 573.1 |

TABLE 1-56

| EXAMPLE | IUPAC NAME | Structure | ADDITIVE | MS |
|---|---|---|---|---|
| 549 | 6-(5-(difluoromethyl)-1,3,4-oxadiazol-2-yl)-2-((1RS,2RS)-2-(1,3-oxazol-2-yl)cyclohexyl)isoindolin-1-one | 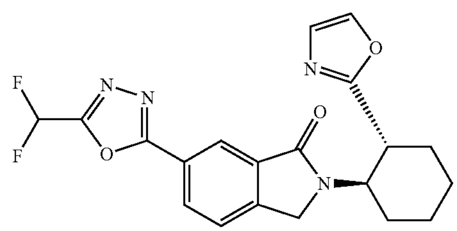 [SMILES: O=C1c2cc(-c3nnc(C(F)F)o3)ccc2CN1[C@@H]1CCCC[C@H]1c1ncco1] | | 401.3 |
| 550 | 6-(5-(difluoromethyl)-1,3,4-oxadiazol-2-yl)-2-(1-methyl-4-(1-(2,2,3,3,3-pentafluoropropyl)piperidin-4-yl)-1H-pyrazol-3-yl)isoindolin-1-one | 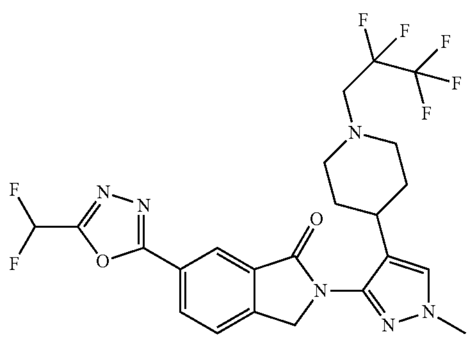 [SMILES: Cn1cc(C2CCN(CC(F)(F)C(F)(F)F)CC2)c(N2Cc3ccc(-c4nnc(C(F)F)o4)cc3C2=O)n1] | | 547.2 |
| 551 | 3-(5-(difluoromethyl)-1,3,4-oxadiazol-2-yl)-6-((1R*,2R*)-2-(4-fluorophenoxy)cyclohexyl)-6,7-dihydro-5H-pyrrolo[3,4-b]pyridin-5-one (optical isomer) | 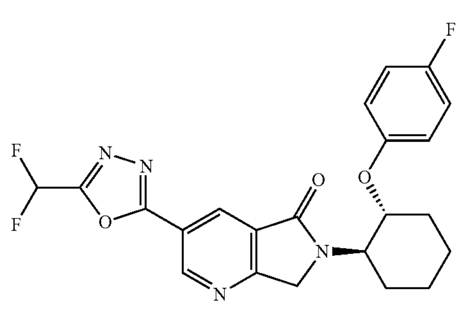 [SMILES: O=C1c2cc(-c3nnc(C(F)F)o3)cnc2CN1[C@@H]1CCCC[C@H]1Oc1ccc(F)cc1] | | 445.2 |

TABLE 1-56-continued

| EXAMPLE | IUPAC NAME | Structure | ADDITIVE | MS |
|---|---|---|---|---|
| 552 | 3-(5-(difluoromethyl)-1,3,4-oxadiazol-2-yl)-6-((1R*,2R*)-2-(4-fluorophenoxy)cyclohexyl)-6,7-dihydro-5H-pyrrolo[3,4-b]pyridin-5-one (optical isomer) | 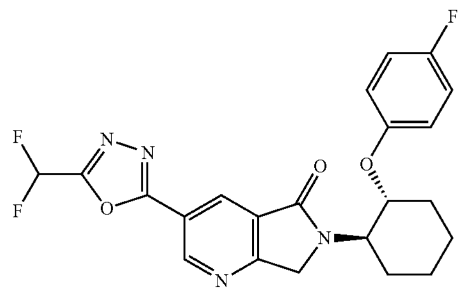 [SMILES: O=C1c2cc(-c3nnc(C(F)F)o3)cnc2CN1[C@@H]1CCCC[C@H]1Oc1ccc(F)cc1] | | 445.3 |
| 553 | 6-(5-(difluoromethyl)-1,3,4-oxadiazol-2-yl)-2-(2-(3-fluorophenyl)pyrrolidin-1-yl)isoindolin-1-one | 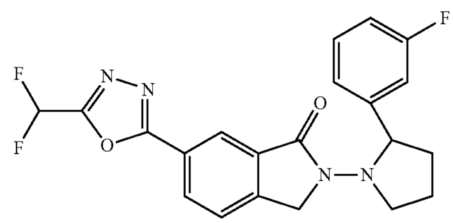 [SMILES: O=C1c2cc(-c3nnc(C(F)F)o3)ccc2CN1N1CCCC1c1cccc(F)c1] | | 415.2 |
| 554 | 6-(5-(difluoromethyl)-1,3,4-oxadiazol-2-yl)-2-(4,4-difluoro-2-phenylpiperidin-1-yl)isoindolin-1-one (optical isomer) | 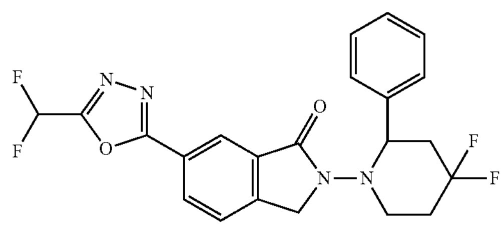 [SMILES: O=C1c2cc(-c3nnc(C(F)F)o3)ccc2CN1N1CCC(F)(F)CC1c1ccccc1] | | 447.2 |
| 555 | 6-(5-(difluoromethyl)-1,3,4-oxadiazol-2-yl)-2-(4,4-difluoro-2-phenylpiperidin-1-yl)isoindolin-1-one (optical isomer) | 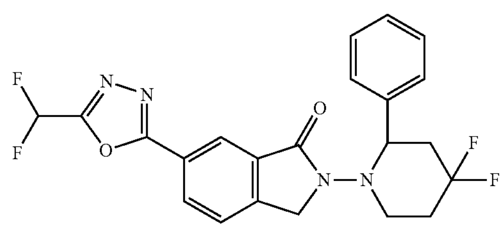 [SMILES: O=C1c2cc(-c3nnc(C(F)F)o3)ccc2CN1N1CCC(F)(F)CC1c1ccccc1] | | 447.2 |
| 556 | (1RS,2RS)-2-(6-(5-(difluoromethyl)-1,3,4-oxadiazol-2-yl)-1-oxo-1,3-dihydro-2H-isoindol-2-yl)cyclohexanecarbonitrile | 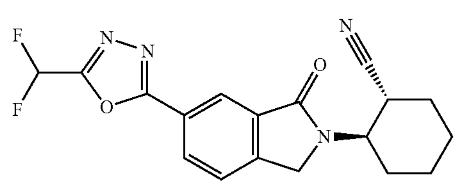 [SMILES: N#C[C@@H]1CCCC[C@H]1N1Cc2ccc(-c3nnc(C(F)F)o3)cc2C1=O] | | 359.0 |
| 557 | 6-(5-(difluoromethyl)-1,3,4-oxadiazol-2-yl)-2-(1-methyl-4-(4-((2,2,3,3,3-pentafluoropropyl)amino)cyclohexyl)-1H-pyrazol-3-yl)isoindolin-1-one | 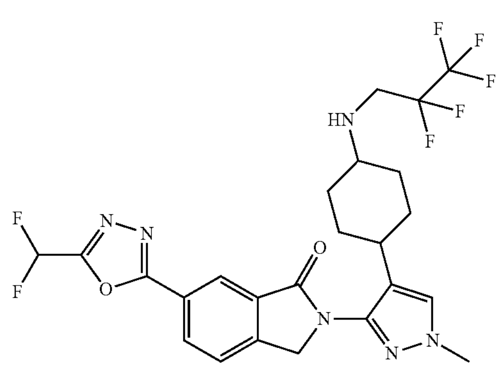 [SMILES: Cn1cc(C2CCC(NCC(F)(F)C(F)(F)F)CC2)c(N2Cc3ccc(-c4nnc(C(F)F)o4)cc3C2=O)n1] | | 561.0 |

TABLE 1-56-continued

| EXAMPLE | IUPAC NAME | Structure | ADDITIVE | MS |
|---|---|---|---|---|
| 558 | 2-((1RS,2RS)-2-(5-cyclopropyl-1,2,4-oxadiazol-3-yl)cyclohexyl)-6-(5-(difluoromethyl)-1,3,4-oxadiazol-2-yl)isoindolin-1-one | 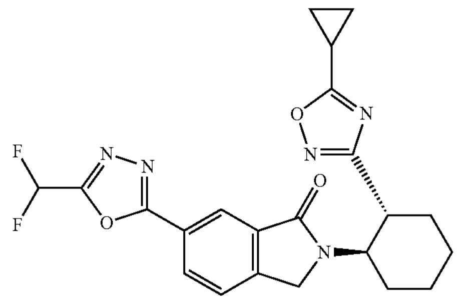 [SMILES: O=C1c2cc(-c3nnc(C(F)F)o3)ccc2CN1[C@@H]1CCCC[C@H]1c1noc(C2CC2)n1] | | 442.3 |

TABLE 1-57

| EXAMPLE | IUPAC NAME | Structure | ADDITIVE | MS |
|---|---|---|---|---|
| 559 | 6-(5-(difluoromethyl)-1,3,4-oxadiazol-2-yl)-2-((1RS,2RS)-2-((5-fluoropyridin-3-yl)oxy)cyclohexyl)isoindolin-1-one | 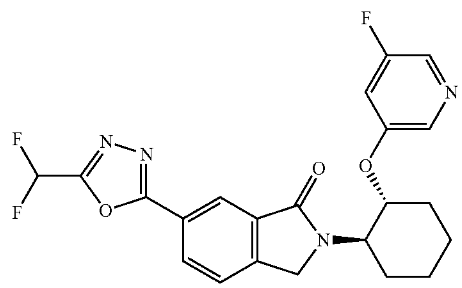 [SMILES: O=C1c2cc(-c3nnc(C(F)F)o3)ccc2CN1[C@@H]1CCCC[C@H]1Oc1cncc(F)c1] | | 445.2 |
| 560 | 2-(4,4-difluoro-2-(3-fluorophenyl)piperidin-1-yl)-6-(5-(difluoromethyl)-1,3,4-oxadiazol-2-yl)isoindolin-1-one | 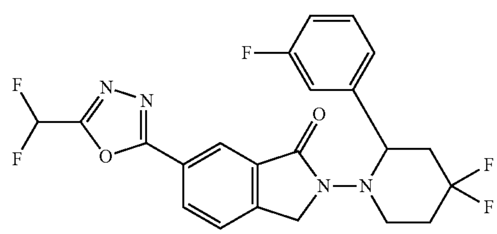 [SMILES: O=C1c2cc(-c3nnc(C(F)F)o3)ccc2CN1N1CCC(F)(F)CC1c1cccc(F)c1] | | 465.2 |
| 561 | 2-((1RS,2RS)-2-(3-cyclopropyl-1,2,4-oxadiazol-5-yl)cyclohexyl)-6-(5-(difluoromethyl)-1,3,4-oxadiazol-2-yl)isoindolin-1-one | 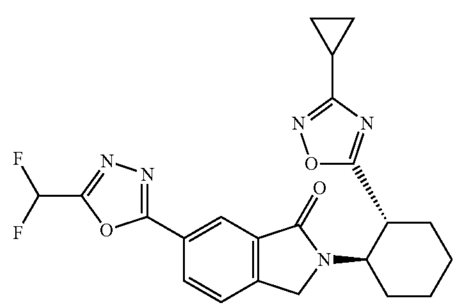 [SMILES: O=C1c2cc(-c3nnc(C(F)F)o3)ccc2CN1[C@@H]1CCCC[C@H]1c1nc(C2CC2)no1] | | 442.2 |
| 562 | 2-(4,4-difluoro-2-(3-fluorophenyl)piperidin-1-yl)-6-(5-(difluoromethyl)-1,3,4-oxadiazol-2-yl)isoindolin-1-one (optical isomer) | 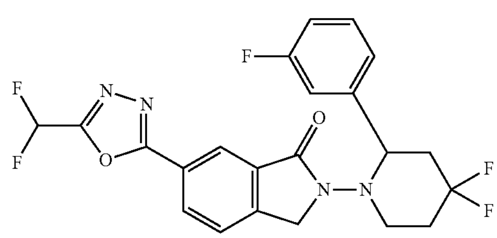 [SMILES: O=C1c2cc(-c3nnc(C(F)F)o3)ccc2CN1N1CCC(F)(F)CC1c1cccc(F)c1] | | 465.2 |

TABLE 1-57-continued

| EXAMPLE | IUPAC NAME | Structure | ADDITIVE | MS |
|---|---|---|---|---|
| 563 | 2-((3S,4R)-3-(5-chloro-1H-benzotriazol-1-yl)tetrahydro-2H-pyran-4-yl)-6-(5-(difluoromethyl)-1,3,4-oxadiazol-2-yl)isoindolin-1-one | 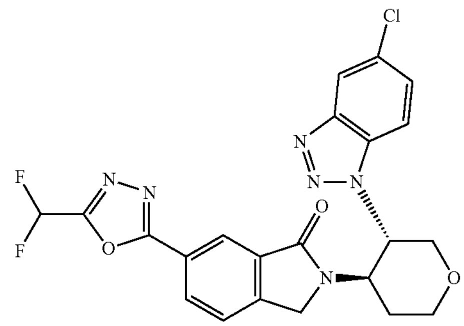 [SMILES: O=C1c2cc(-c3nnc(C(F)F)o3)ccc2CN1[C@@H]1CCOC[C@H]1n1nnc2cc(Cl)ccc21] | | 487.0 |
| 564 | 1-(6-(5-(difluoromethyl)-1,3,4-oxadiazol-2-yl)-1-oxo-1,3-dihydro-2H-isoindol-2-yl)-4,4-difluoro-N-(2,2,2-trifluoroethyl)piperidine-2-carboxamide | 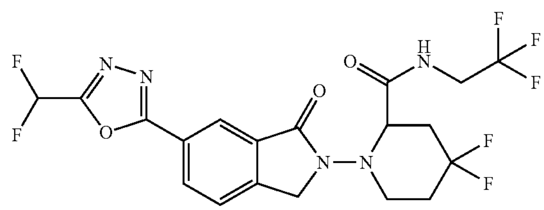 [SMILES: O=C(NCC(F)(F)F)C1CC(F)(F)CCN1N1Cc2ccc(-c3nnc(C(F)F)o3)cc2C1=O] | | 496.1 |
| 565 | 2-(4,4-difluoro-2-(3-fluorophenyl)piperidin-1-yl)-6-(5-(difluoromethyl)-1,3,4-oxadiazol-2-yl)isoindolin-1-one (optical isomer) | 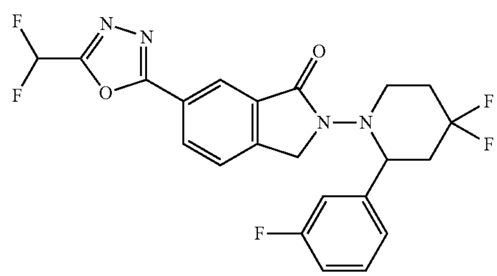 [SMILES: O=C1c2cc(-c3nnc(C(F)F)o3)ccc2CN1N1CCC(F)(F)CC1c1cccc(F)c1] | | 465.2 |
| 566 | 2-(4,4-difluoro-2-(4-fluorophenyl)piperidin-1-yl)-6-(5-(difluoromethyl)-1,3,4-oxadiazol-2-yl)isoindolin-1-one | 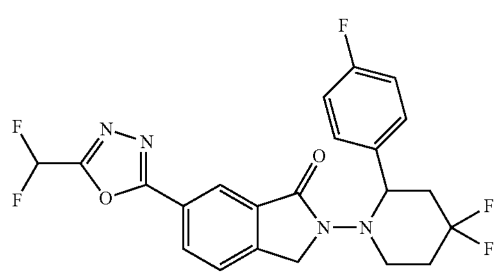 [SMILES: O=C1c2cc(-c3nnc(C(F)F)o3)ccc2CN1N1CCC(F)(F)CC1c1ccc(F)cc1] | | 463.2 |
| 567 | 3-(6-(5-(difluoromethyl)-1,3,4-oxadiazol-2-yl)-1-oxo-1,3-dihydro-2H-isoindol-2-yl)-1-methyl-N-(2,2,2-trifluoroethyl)-1H-pyrazole-4-carboxamide | 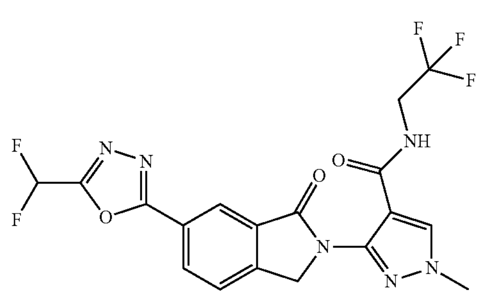 [SMILES: Cn1cc(C(=O)NCC(F)(F)F)c(N2Cc3ccc(-c4nnc(C(F)F)o4)cc3C2=O)n1] | | 457.2 |

TABLE 1-57-continued

| EXAMPLE | IUPAC NAME | Structure | ADDITIVE | MS |
|---|---|---|---|---|
| 568 | N-(cyclopropylmethyl)-3-(6-(5-(difluoromethyl)-1,3,4-oxadiazol-2-yl)-1-oxo-1,3-dihydro-2H-isoindol-2-yl)-1-methyl-1H-pyrazole-4-carboxamide | 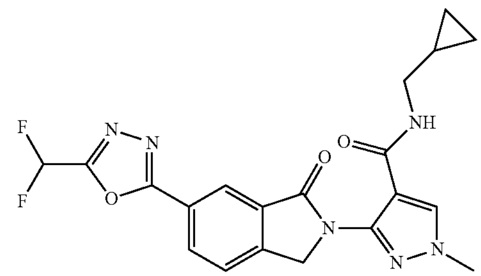 [SMILES: Cn1cc(C(=O)NCC2CC2)c(N2Cc3ccc(-c4nnc(C(F)F)o4)cc3C2=O)n1] | | 429.3 |

TABLE 1-58

| EXAMPLE | IUPAC NAME | Structure | ADDITIVE | MS |
|---|---|---|---|---|
| 569 | 6-(5-(difluoromethyl)-1,3,4-oxadiazol-2-yl)-2-(4-((4,4-difluoropiperidin-1-yl)carbonyl)-1-methyl-1H-pyrazol-3-yl)isoindolin-1-one | 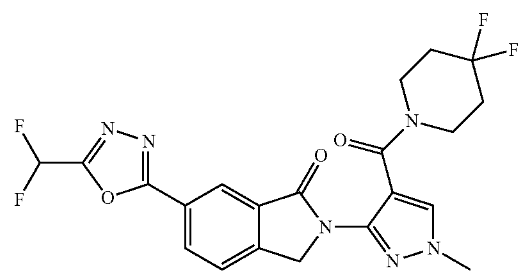 [SMILES: Cn1cc(C(=O)N2CCC(F)(F)CC2)c(N2Cc3ccc(-c4nnc(C(F)F)o4)cc3C2=O)n1] | | 479.2 |
| 570 | 6-(5-(difluoromethyl)-1,3,4-oxadiazol-2-yl)-2-(2-(pyridin-2-yl)pyrrolidin-1-yl)isoindolin-1-one | 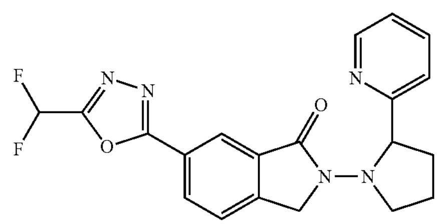 [SMILES: O=C1c2cc(-c3nnc(C(F)F)o3)ccc2CN1N1CCCC1c1ccccn1] | | 398.3 |
| 571 | 6-(5-(difluoromethyl)-1,3,4-oxadiazol-2-yl)-2-(2-(trifluoromethyl)imidazo[1,2-a]pyridin-8-yl)isoindolin-1-one | 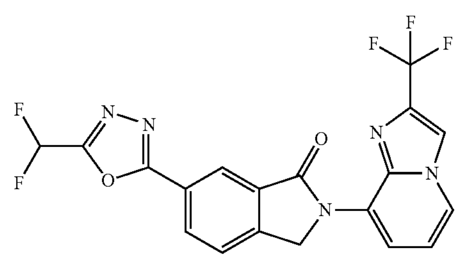 [SMILES: O=C1c2cc(-c3nnc(C(F)F)o3)ccc2CN1c1cccn2cc(C(F)(F)F)nc12] | | 436.2 |
| 572 | 2-(4,4-difluoro-2-(4-fluorophenyl)piperidin-1-yl)-6-(5-(difluoromethyl)-1,3,4-oxadiazol-2-yl)isoindolin-1-one (optical isomer) | 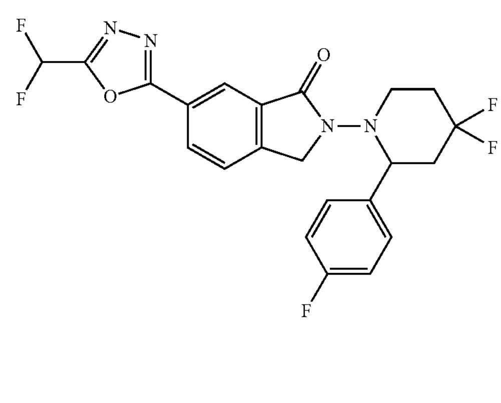 [SMILES: O=C1c2cc(-c3nnc(C(F)F)o3)ccc2CN1N1CCC(F)(F)CC1c1ccc(F)cc1] | | 565.2 |

TABLE 1-58-continued

| EXAMPLE | IUPAC NAME | Structure | ADDITIVE | MS |
|---|---|---|---|---|
| 573 | 2-(4,4-difluoro-2-(4-fluorophenyl)piperidin-1-yl)-6-(5-(difluoromethyl)-1,3,4-oxadiazol-2-yl)isoindolin-1-one (optical isomer) | 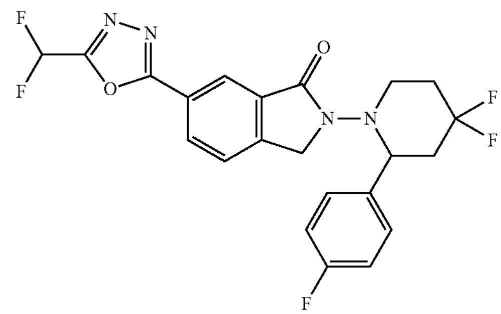 [SMILES: O=C1c2cc(-c3nnc(C(F)F)o3)ccc2CN1N1CCC(F)(F)CC1c1ccc(F)cc1] | | 465.2 |
| 574 | tert-butyl (2RS,3SR)-3-(6-(5-(difluoromethyl)-1,3,4-oxadiazol-2-yl)-1-oxo-1,3-dihydro-2H-isoindol-2-yl)-2-(4-fluorophenyl)piperidine-1-carboxylate | 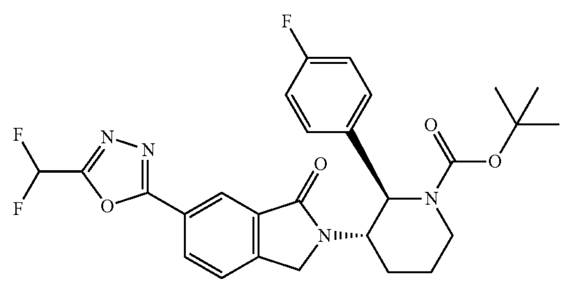 [SMILES: CC(C)(C)OC(=O)N1CCC[C@H](N2Cc3ccc(-c4nnc(C(F)F)o4)cc3C2=O)[C@H]1c1ccc(F)cc1] | | 527.2 |
| 575 | 6-(5-(difluoromethyl)-1,3,4-oxadiazol-2-yl)-2-((2RS,3SR)-2-(4-fluorophenyl)piperidin-3-yl)isoindolin-1-one | 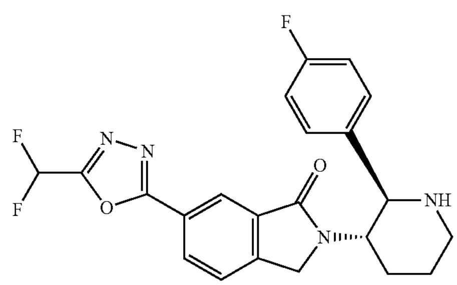 [SMILES: O=C1c2cc(-c3nnc(C(F)F)o3)ccc2CN1[C@H]1CCCN[C@@H]1c1ccc(F)cc1] | CF3COOH | 429.3 |
| 576 | 6-(5-(difluoromethyl)-1,3,4-oxadiazol-2-yl)-2-((2RS,3SR)-1-(2,2-difluoropropanoyl)-2-(4-fluorophenyl)piperidin-3-yl)isoindolin-1-one | 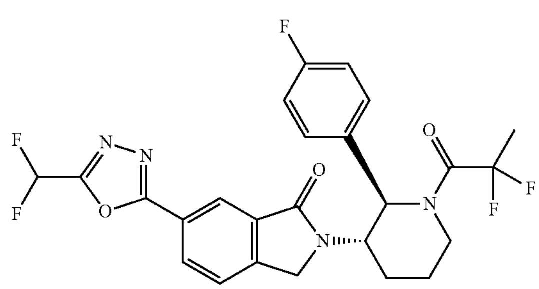 [SMILES: CC(F)(F)C(=O)N1CCC[C@H](N2Cc3ccc(-c4nnc(C(F)F)o4)cc3C2=O)[C@H]1c1ccc(F)cc1] | | 521.2 |
| 577 | 6-(5-(difluoromethyl)-1,3,4-oxadiazol-2-yl)-2-((2RS,3SR)-2-(4-fluorophenyl)-1-(2,2,3,3,3-pentafluoropropanoyl)piperidin-3-yl)isoindolin-1-one | 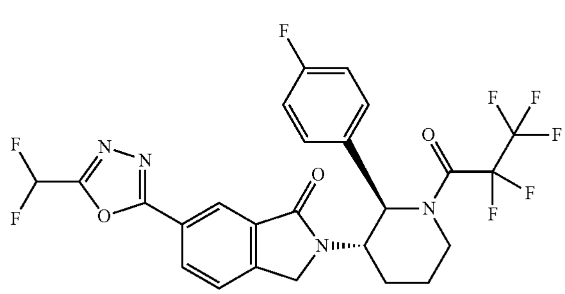 [SMILES: O=C1c2cc(-c3nnc(C(F)F)o3)ccc2CN1[C@H]1CCCN(C(=O)C(F)(F)C(F)(F)F)[C@@H]1c1ccc(F)cc1] | | 575.1 |

TABLE 1-58-continued

| EXAMPLE | IUPAC NAME | Structure | ADDITIVE | MS |
|---|---|---|---|---|
| 578 | methyl (2RS,3SR)-3-(6-(5-(difluoromethyl)-1,3,4-oxadiazol-2-yl)-1-oxo-1,3-dihydro-2H-isoindol-2-yl)-2-(4-fluorophenyl)piperidine-1-carboxylate | 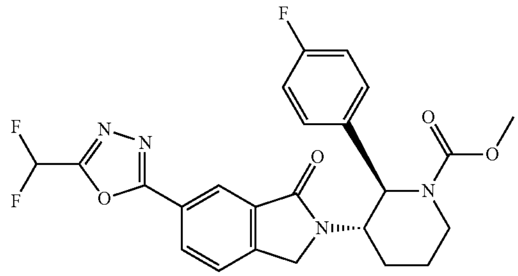 [SMILES: COC(=O)N1CCC[C@H](N2Cc3ccc(-c4nnc(C(F)F)o4)cc3C2=O)[C@H]1c1ccc(F)cc1] | | 487.2 |

TABLE 1-59

| EXAMPLE | IUPAC NAME | Structure | ADDITIVE | MS |
|---|---|---|---|---|
| 579 | 1-(6-(5-(difluoromethyl)-1,3,4-oxadiazol-2-yl)-1-oxo-1,3-dihydro-2H-isoindol-2-yl)-4,4-difluoro-N-(2,2,2-trifluoroethyl)piperidine-2-carboxamide (optical isomer) | 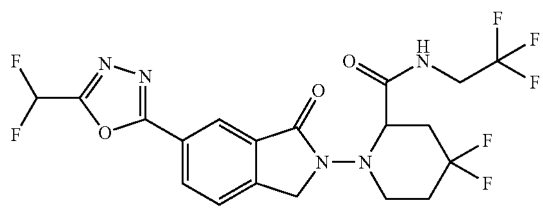 [SMILES: O=C(NCC(F)(F)F)C1CC(F)(F)CCN1N1Cc2ccc(-c3nnc(C(F)F)o3)cc2C1=O] | | 496.1 |
| 580 | 1-(6-(5-(difluoromethyl)-1,3,4-oxadiazol-2-yl)-1-oxo-1,3-dihydro-2H-isoindol-2-yl)-4,4-difluoro-N-(2,2,2-trifluoroethyl)piperidine-2-carboxamide (optical isomer) | 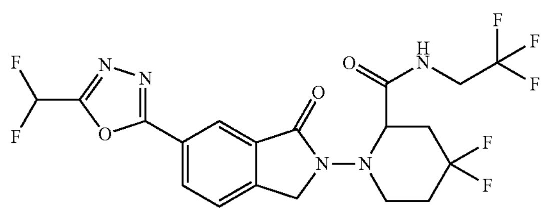 [SMILES: O=C(NCC(F)(F)F)C1CC(F)(F)CCN1N1Cc2ccc(-c3nnc(C(F)F)o3)cc2C1=O] | | 496.1 |
| 581 | N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2,3,3-tetrafluoropropanamide | 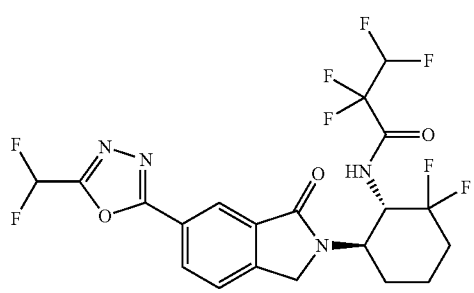 [SMILES: O=C1c2cc(-c3nnc(C(F)F)o3)ccc2CN1[C@@H]1CCCC(F)(F)[C@H]1NC(=O)C(F)(F)C(F)F] | | 513.1 |
| 582 | 1-fluoro-2-methylpropan-2-yl ((1S,6R)-6-(6-(5-(difluoromethyl)-1,3,4-oxadiazol-2-yl)-1-oxo-1,3-dihydro-2H-isoindol-2-yl)-2,2-difluorocyclohexyl)carbamate | 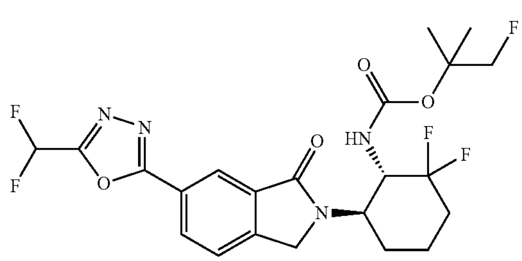 [SMILES: CC(C)(CF)OC(=O)N[C@H]1[C@H](N2Cc3ccc(-c4nnc(C(F)F)o4)cc3C2=O)CCCC1(F)F] | | 503.1 |

TABLE 1-59-continued

| EXAMPLE | IUPAC NAME | Structure | ADDITIVE | MS |
|---|---|---|---|---|
| 583 | 1,1-difluoro-2-methylpropan-2-yl ((1S,6R)-6-(6-(5-(difluoromethyl)-1,3,4-oxadiazol-2-yl)-1-oxo-1,3-dihydro-2H-isoindol-2-yl)-2,2-difluorocyclohexyl)carbamate | 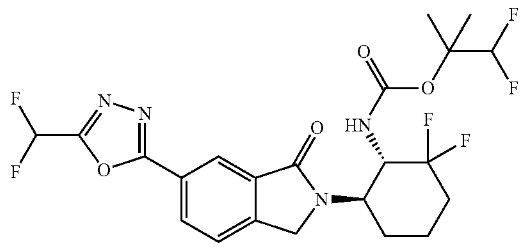 [SMILES: CC(C)(OC(=O)N[C@H]1[C@H](N2Cc3ccc(-c4nnc(C(F)F)o4)cc3C2=O)CCCC1(F)F)C(F)F] | | 521.2 |
| 584 | 2-((2RS,3SR)-1-(difluoroacetyl)-2-(4-fluorophenyl)piperidin-3-yl)-6-(5-(difluoromethyl)-1,3,4-oxadiazol-2-yl)isoindolin-1-one | 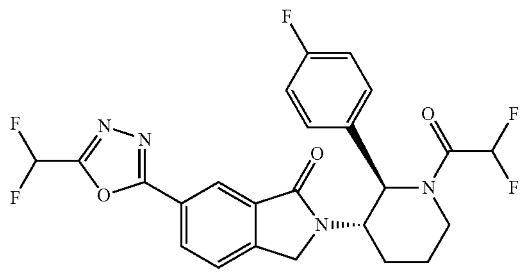 [SMILES: O=C(C(F)F)N1CCC[C@H](N2Cc3ccc(-c4nnc(C(F)F)o4)cc3C2=O)[C@H]1c1ccc(F)cc1] | | 507.1 |
| 585 | 3-(5-(difluoromethyl)-1,3,4-oxadiazol-2-yl)-6-((1RS,2RS)-2-((5-fluoropyridin-3-yl)oxy)cyclohexyl)-6,7-dihydro-5H-pyrrolo[3,4-b]pyridin-5-one | 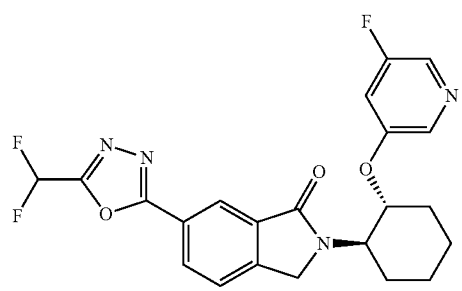 [SMILES: O=C1c2cc(-c3nnc(C(F)F)o3)ccc2CN1[C@@H]1CCCC[C@H]1Oc1cncc(F)c1] | | 446.2 |
| 586 | 6-(5-(difluoromethyl)-1,3,4-oxadiazol-2-yl)-2-((1R*,2R*)-4,4-difluoro-2-(pyridin-2-yl)cyclohexyl)isoindolin-1-one (optical isomer) | 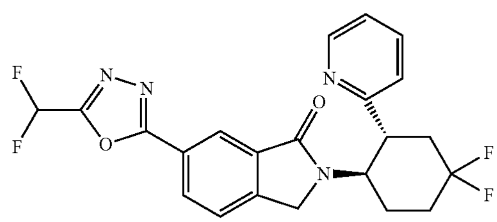 [SMILES: O=C1c2cc(-c3nnc(C(F)F)o3)ccc2CN1[C@@H]1CCC(F)(F)C[C@H]1c1ccccn1] | | 447.2 |
| 587 | 3-(5-(difluoromethyl)-1,3,4-oxadiazol-2-yl)-6-((1R*,2R*)-2-(pyridin-2-yl)cyclohexyl)-6,7-dihydro-5H-pyrrolo[3,4-b]pyridin-5-one (optical isomer) | 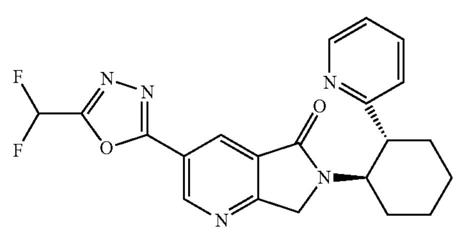 [SMILES: O=C1c2cc(-c3nnc(C(F)F)o3)cnc2CN1[C@@H]1CCCC[C@H]1c1ccccn1] | | 412.2 |
| 588 | 3-(5-(difluoromethyl)-1,3,4-oxadiazol-2-yl)-6-((1R*,2R*)-2-(pyridin-2-yl)cyclohexyl)-6,7-dihydro-5H-pyrrolo[3,4-b]pyridin-5-one (optical isomer) | 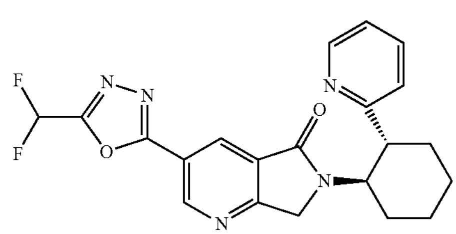 [SMILES: O=C1c2cc(-c3nnc(C(F)F)o3)cnc2CN1[C@@H]1CCCC[C@H]1c1ccccn1] | | 412.2 |

TABLE 1-60

| EXAMPLE | IUPAC NAME | Structure | ADDITIVE | MS |
|---|---|---|---|---|
| 589 | 6-(5-(difluoromethyl)-1,3,4-oxadiazol-2-yl)-2-((1R*,2R*)-4,4-difluoro-2-(pyridin-2-yl)cyclohexyl)isoindolin-1-one (optical isomer) | 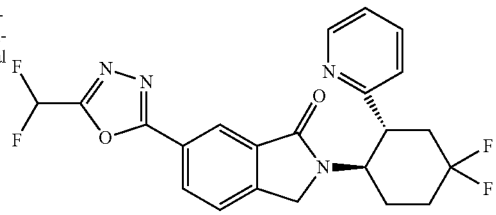 | | 447.2 |
| 590 | 6-(5-(difluooromethyl)-1,3,4-oxadiazol-2-yl)-2-((1R*,2S*)-4,4-difluoro-2-(pyridin-2-yl)cyclohexyl)isoindolin-1-one (optical isomer) | 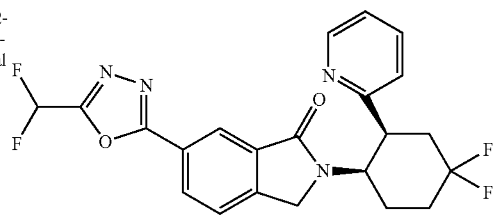 | | 447.2 |
| 591 | 6-(5-(difluoromethyl)-1,3,4-oxadiazol-2-yl)-2-((1R*,2S*)-4,4-difluoro-2-(pyridin-2-yl)cyclohexyl)isoindolin-1-one (optical isomer) | 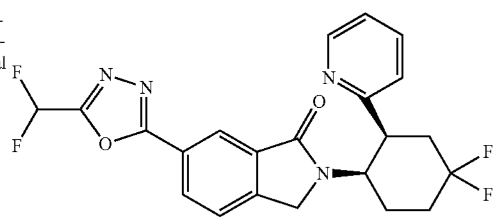 | | 447.2 |
| 592 | 2-(4-benzoyl-1-methyl-1H-pyrazol-3-yl)-6-(5-(difluoromethyl)-1,3,4-oxadiazol-2-yl)isoindolin-1-one | 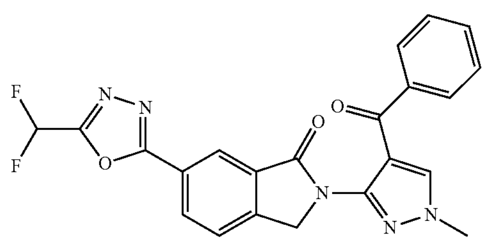 [SMILES: Cn1cc(C(=O)c2ccccc2)c(N2Cc3ccc(-c4nnc(C(F)F)o4)cc3C2=O)n1] | | 436.1 |
| 593 | 3-(5-(difluoromethyl)-1,3,4-oxadiazol-2-yl)-6-((1R,2R)-2-(pyridin-2-yloxy)cyclohexyl)-6,7-dihydro-5H-pyrrolo[3,4-b]pyridin-5-one | 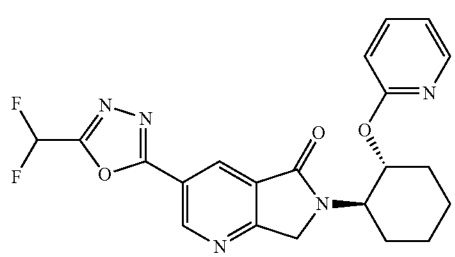 [SMILES: O=C1c2cc(-c3nnc(C(F)F)o3)cnc2CN1[C@@H]1CCCC[C@H]1Oc1ccccn1] | | 428.3 |
| 594 | 6-(5-(difluoromethyl)-1,3,4-oxadiazol-2-yl)-2-(2-(4-fluorophenyl)piperidin-1-yl)isoindolin-1-one | 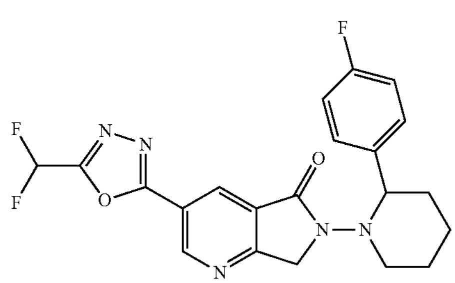 [SMILES: O=C1c2cc(-c3nnc(C(F)F)o3)cnc2CN1N1CCCCC1c1ccc(F)cc1] | | 429.3 |

TABLE 1-60-continued

| EXAMPLE | IUPAC NAME | Structure | ADDITIVE | MS |
|---|---|---|---|---|
| 595 | 2-(4,4-difluoro-2-(5-fluoropyridin-2-yl)piperidin-1-yl)-6-(5-(difluoromethyl)-1,3,4-oxadiazol-2-yl)isoindolin-1-one | 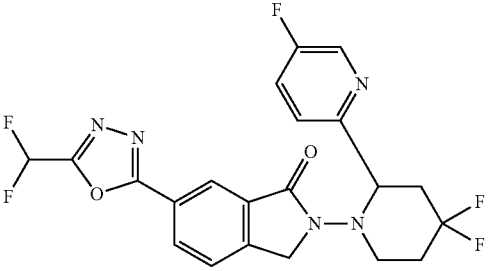 [SMILES: O=C1c2cc(-c3nnc(C(F)F)o3)ccc2CN1N1CCC(F)(F)CC1c1ccc(F)cn1] | | 466.2 |
| 596 | 6-(5-(difluoromethyl)-1,3,4-oxadiazol-2-yl)-2-(2-(pyridin-2-yl)pyrrolidin-1-yl)isoindolin-1-one (optical isomer) | 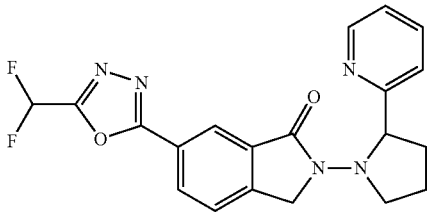 [SMILES: O=C1c2cc(-c3nnc(C(F)F)o3)ccc2CN1N1CCCC1c1ccccn1] | | 398.3 |
| 597 | 6-(5-(difluoromethyl)-1,3,4-oxadiazol-2-yl)-2-(2-(pyridin-2-yl)pyrrolidin-1-yl)isoindolin-1-one (optical isomer) | 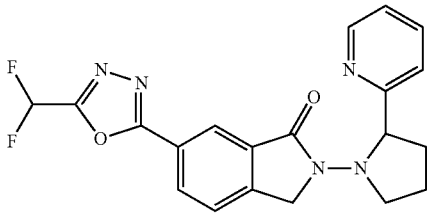 [SMILES: O=C1c2cc(-c3nnc(C(F)F)o3)ccc2CN1N1CCCC1c1ccccn1] | | 398.2 |
| 598 | N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2-difluoropropanamide | 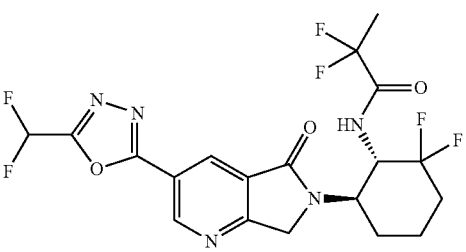 [SMILES: CC(F)(F)C(=O)N[C@H]1[C@H](N2Cc3ncc(-c4nnc(C(F)F)o4)cc3C2=O)CCCC1(F)F] | | 476.2 |

TABLE 1-61

| EXAMPLE | IUPAC NAME | Structure | ADDITIVE | MS |
|---|---|---|---|---|
| 599 | N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2,3,3,3-pentafluoropropanamide | 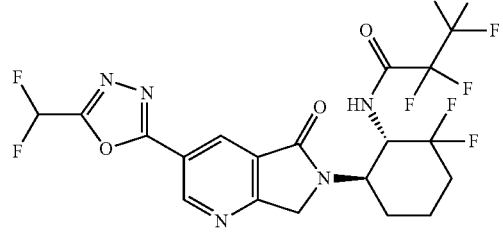 | | 530.1 |

TABLE 1-61-continued

| EXAMPLE | IUPAC NAME | Structure | ADDITIVE | MS |
|---|---|---|---|---|
| 600 | 6-(5-(difluoromethyl)-1,3,4-oxadiazol-2-yl)-2-(4,4-difluoro-2-(5-methylpyridin-2-yl)piperidin-1-yl)isoindolin-1-one | 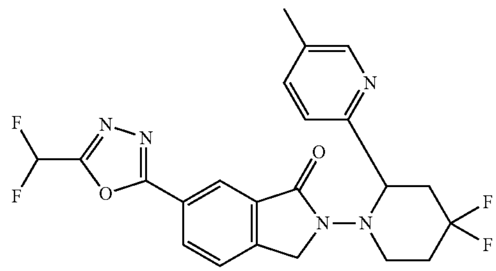 [SMILES: Cc1ccc(C2CC(F)(F)CCN2N2Cc3ccc(-c4nnc(C(F)F)o4)cc3C2=O)nc1] | | 462.1 |
| 601 | N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2,3,3-tetrafluoropropanamide | 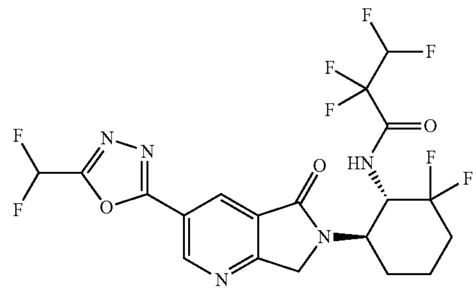 [SMILES: O=C1c2cc(-c3nnc(C(F)F)o3)cnc2CN1[C@@H]1CCCC(F)(F)[C@H]1NC(=O)C(F)(F)C(F)F] | | 512.1 |
| 602 | 6-(5-(difluoromethyl)-1,3,4-oxadiazol-2-yl)-2-(2-(5-fluoropyridin-3-yl)piperidin-1-yl)isoindolin-1-one | 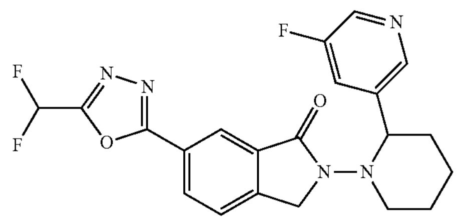 [SMILES: O=C1c2cc(-c3nnc(C(F)F)o3)ccc2CN1N1CCCCC1c1cncc(F)c1] | | 430.2 |
| 603 | 6-(5-(difluoromethyl)-1,3,4-oxadiazol-2-yl)-2-(2-(3-fluorophenyl)piperidin-1-yl)isoindolin-1-one | 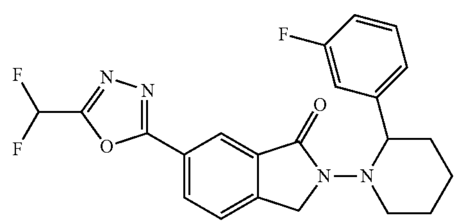 [SMILES: O=C1c2cc(-c3nnc(C(F)F)o3)ccc2CN1N1CCCCC1c1cccc(F)c1] | | 429.2 |
| 604 | benzyl 1-(6-(5-(difluoromethyl)-1,3,4-oxadiazol-2-yl)-1-oxo-1,3-dihydro-2H-isoindol-2-yl)-4,4-difluoropiperidine-2-carboxylate | 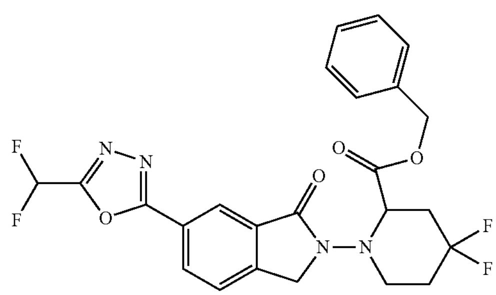 [SMILES: O=C(OCc1ccccc1)C1CC(F)(F)CCN1N1Cc2ccc(-c3nnc(C(F)F)o3)cc2C1=O] | | 505.1 |
| 605 | N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-3,3,3-trifluoro-2,2-dimethylpropanamide | 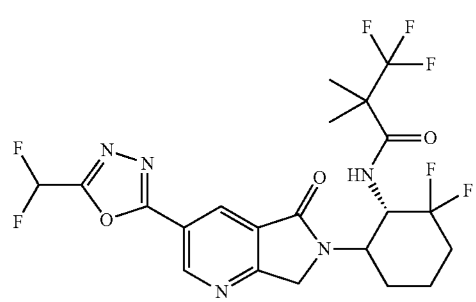 [SMILES: CC(C)(C(=O)N[C@H]1C(N2Cc3ncc(-c4nnc(C(F)F)o4)cc3C2=O)CCCC1(F)F)C(F)(F)F] | | 524.1 |

TABLE 1-61-continued

| EXAMPLE | IUPAC NAME | Structure | ADDITIVE | MS |
|---|---|---|---|---|
| 606 | N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl-1-(trifluoromethyl)cyclopropanecarboxamide | 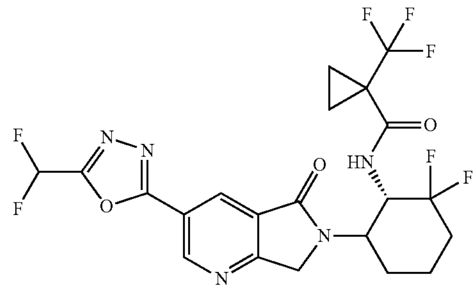 [SMILES: O=C1c2cc(-c3nnc(C(F)F)o3)cnc2CN1C1CCCC(F)(F)[C@H]1NC(=O)C1(C(F)(F)F)CC1] | | 522.1 |
| 607 | 1-fluoro-2-methylpropan-2-yl ((1S,6R)-6-(3-(5-(difluoromethyl)-1,3,4-oxadiazol-2-yl)-5-oxo-5,7-dihydro-6H-pyrrolo[3,4-b]pyridin-6-yl)2,2-difluorocyclohexyl)carbamate | 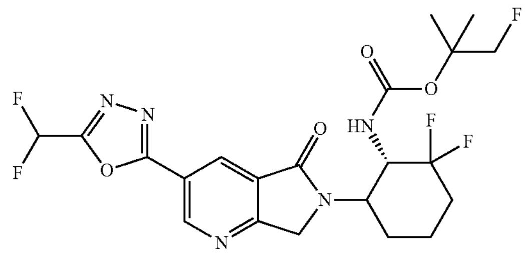 [SMILES: CC(C)(CF)OC(=O)N[C@H]1C(N2Cc3ncc(-c4nnc(C(F)F)o4)cc3C2=O)CCCC1(F)F] | | 502.2 |
| 608 | 1,1-difluoro-2-methylpropan-2-yl ((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)carbamate | 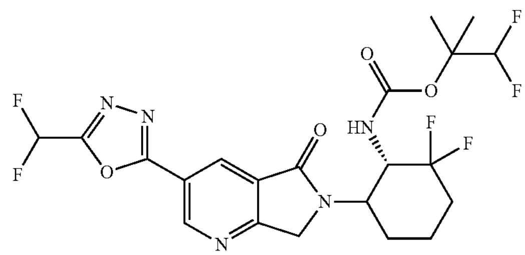 [SMILES: CC(C)(OC(=O)N[C@H]1C(N2Cc3ncc(-c4nnc(C(F)F)o4)cc3C2=O)CCCC1(F)F)C(F)F] | | 522.1 |

TABLE 1-62

| EXAMPLE | IUPAC NAME | Structure | ADDITIVE | MS |
|---|---|---|---|---|
| 609 | 6-(5-(difluoromethyl)-1,3,4-oxadiazol-2-yl)-2-(2-(1-methyl-1H-pyrazol-4-yl)piperidin-1-yl)isoindolin-1-one | 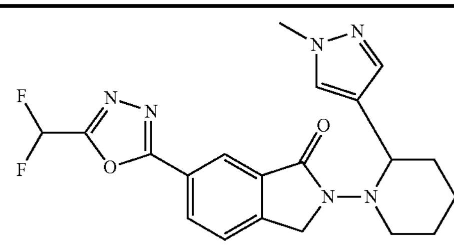 | | 415.2 |
| 610 | 2-(4,4-difluoro-2-(5-fluoropyridin-2-yl)piperidin-1-yl)-6-(5-(difluoromethyl)-1,3,4-oxadiazol-2-yl)isoindolin-1-one (optical isomer) | 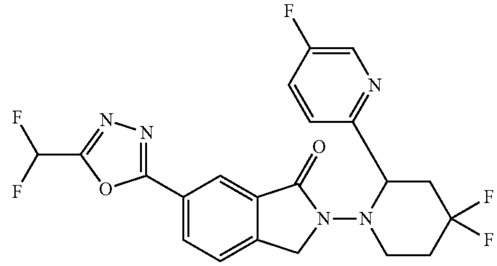 [SMILES: O=C1c2cc(-c3nnc(C(F)F)o3)ccc2CN1N1CCC(F)(F)CC1c1ccc(F)cn1] | | 466.1 |

TABLE 1-62-continued

| EXAMPLE | IUPAC NAME | Structure | ADDITIVE | MS |
|---|---|---|---|---|
| 611 | 2-(1'-acetyl-2,4'-bipiperidin-1-yl)-6-(5-(difluoromethyl)-1,3,4-oxadiazol-2-yl)isoindolin-1-one | 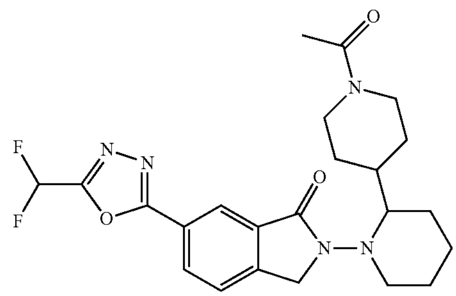 [SMILES: CC(=O)N1CCC(C2CCCCN2N2Cc3ccc(-c4nnc(C(F)F)o4)cc3C2=O)CC1] | | 460.2 |
| 612 | 2-(4,4-difluoro-2-(5-fluoropyridin-2-yl)piperidin-1-yl)-6-(5-(difluoromethyl)-1,3,4-oxadiazol-2-yl)isoindolin-1-one (optical isomer) | 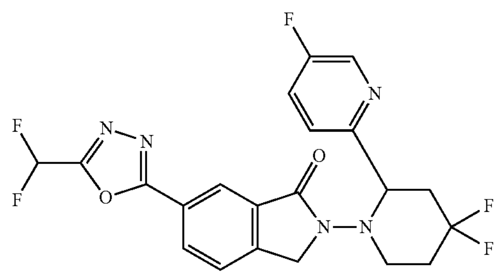 [SMILES: O=C1c2cc(-c3nnc(C(F)F)o3)ccc2CN1N1CCC(F)(F)CC1c1ccc(F)cn1] | | 466.1 |
| 613 | N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-3,3,3-trifluoro-2-(trifluoromethyl)propanamide | 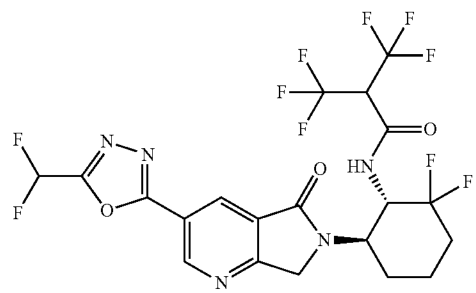 [SMILES: O=C(N[C@H]1[C@H](N2Cc3ncc(-c4nnc(C(F)F)o4)cc3C2=O)CCCC1(F)F)C(C(F)(F)F)C(F)(F)F] | | 562.1 |
| 614 | 6-(5-(difluoromethyl)-1,3,4-oxadiazol-2-yl)-2-(4,4-difluoro-2-(5-methylpyridin-2-yl)piperidin-1-yl)isoindolin-1-one (optical isomer) | 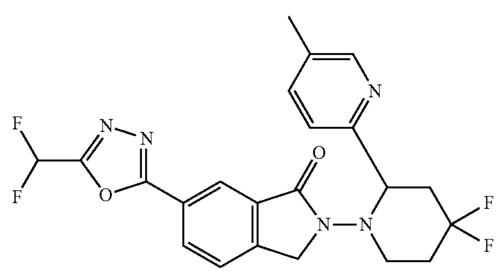 [SMILES: Cc1ccc(C2CC(F)(F)CCN2N2Cc3ccc(-c4nnc(C(F)F)o4)cc3C2=O)nc1] | | 462.1 |
| 615 | 6-(5-(difluoromethyl)-1,3,4-oxadiazol-2-yl)-2-(4,4-difluoro-2-(5-methylpyridin-2-yl)piperidin-1-yl)isoindolin-1-one (optical isomer) | 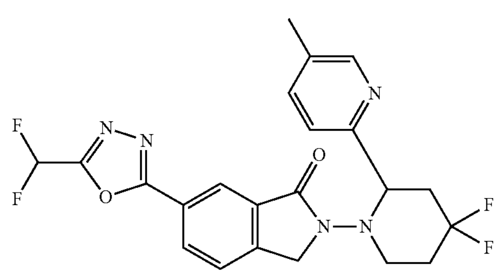 [SMILES: Cc1ccc(C2CC(F)(F)CCN2N2Cc3ccc(-c4nnc(C(F)F)o4)cc3C2=O)nc1] | | 462.1 |
| 616 | 6-(5-(difluoromethyl)-1,3,4-oxadiazol-2-yl)-2-(imidazo[1,2-a]pyridin-8-yl)isoindolin-1-one | 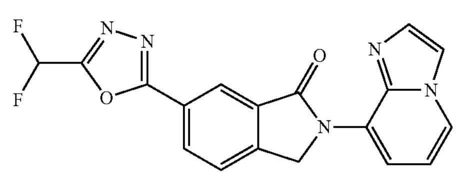 [SMILES: O=C1c2cc(-c3nnc(C(F)F)o3)ccc2CN1c1cccn2ccnc12] | | 368.2 |

TABLE 1-62-continued

| EXAMPLE | IUPAC NAME | Structure | ADDITIVE | MS |
|---|---|---|---|---|
| 617 | 6-(5-(difluoromethyl)-1,3,4-oxadiazol-2-yl)-2-(3-(4-fluorophenyl)morpholin-4-yl)isoindolin-1-one | 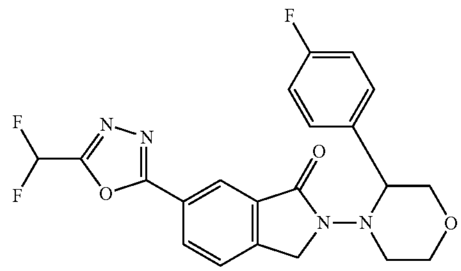 [SMILES: O=C1c2cc(-c3nnc(C(F)F)o3)ccc2CN1N1CCOCC1c1ccc(F)cc1] | | 431.2 |
| 618 | tert-butyl (2RS,3RS)-3-(6-(5-(difluoromethyl)-1,3,4-oxadiazol-2-yl)-1-oxo-1,3-dihydro-2H-isoindol-2-yl)-2-(4-fluorophenyl)piperidine-1-carboxylate | 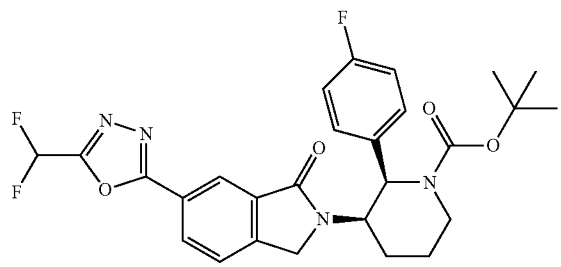 [SMILES: CC(C)(C)OC(=O)N1CCC[C@@H](N2Cc3ccc(-c4nnc(C(F)F)o4)cc3C2=O)[C@H]1c1ccc(F)cc1] | | 527.2 |

TABLE 1-63

| EXAMPLE | IUPAC NAME | Structure | ADDITIVE | MS |
|---|---|---|---|---|
| 619 | benzyl ((1R,6R)-6-(6-(5-(difluoromethyl)-1,3,4-oxadiazol-2-yl)-1-oxo-1,3-dihydro-2H-isoindol-2-yl)-2,2-difluorocyclohexyl)carbamate | 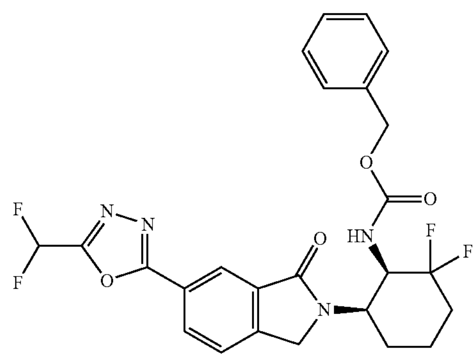 [SMILES: O=C(N[C@@H]1[C@H](N2Cc3ccc(-c4nnc(C(F)F)o4)cc3C2=O)CCCC1(F)F)OCc1ccccc1] | | 519.2 |
| 620 | 6-(5-(difluoromethyl)-1,3,4-oxadiazol-2-yl)-2-((2RS,3RS)-2-(4-fluorophenyl)piperidin-3-yl)isoindolin-1-one | 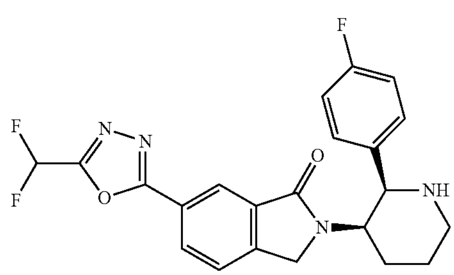 [SMILES: O=C1c2cc(-c3nnc(C(F)F)o3)ccc2CN1[C@@H]1CCCN[C@@H]1c1ccc(F)cc1] | | 429.3 |
| 621 | 2-((1R,2R)-2-amino-3,3-difluorocyclohexyl)-6-(5-(difluoromethyl)-1,3,4-oxadiazol-2-yl)isoindolin-1-one | 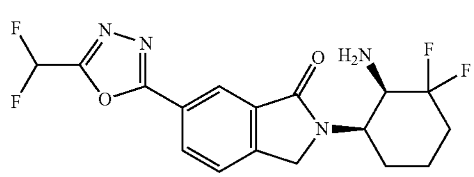 [SMILES: N[C@@H]1[C@H](N2Cc3ccc(-c4nnc(C(F)F)o4)cc3C2=O)CCCC1(F)F] | | 385.2 |

TABLE 1-63-continued

| EXAMPLE | IUPAC NAME | ADDITIVE | MS |
|---|---|---|---|
| 622 | 1-(6-(5-(difluoromethyl)-1,3,4-oxadiazol-2-yl)-1-oxo-1,3-dihydro-2H-isoindol-2-yl)-4,4-difluoro-N-(2,2,3,3,3-pentafluoropropyl)piperidine-2-carboxamide | | 546.1 |
| 623 | N-(2,2-difluoroethyl)-1-(6-(5-(difluoromethyl)-1,3,4-oxadiazol-2-yl)-1-oxo-1,3-dihydro-2H-isoindol-2-yl)-4,4-difluoropiperidine-2-carboxamide | | 478.1 |
| 624 | 2-((2RS,3RS)-1-(difluoroacetyl)-2-(4-fluorophenyl)piperidin-3-yl)-6-(5-(difluoromethyl)-1,3,4-oxadiazol-2-yl)isoindolin-1-one | | 507.2 |
| 625 | N-((1R,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2,3,3,3-pentafluoropropanamide | | 529.1 |
| 626 | N-((1R,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2-difluoropropanamide | | 477.1 |
| 627 | methyl (2R,3R)-3-(6-(5-(difluoromethyl)-1,3,4-oxadiazol-2-yl)-1-oxo-1,3-dihydro-2H-isoindol-2-yl)-2-(4-fluorophenyl)piperidine-1-carboxylate | | 487.1 |

TABLE 1-63-continued

| EXAMPLE | IUPAC NAME | Structure | ADDITIVE | MS |
|---|---|---|---|---|
| 628 | N-((1R,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2,3,3-tetrafluoropropanamide | 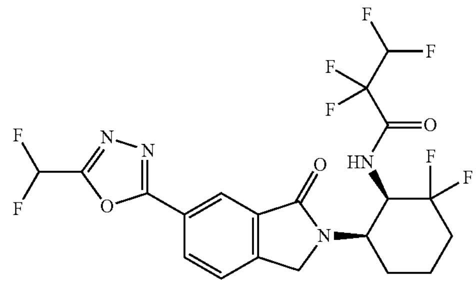 [SMILES: O=C1c2cc(-c3nnc(C(F)F)o3)ccc2CN1[C@@H]1CCCC(F)(F)[C@@H]1NC(=O)C(F)(F)C(F)F] | | 511.2 |

TABLE 1-64

| EXAMPLE | IUPAC NAME | Structure | ADDITIVE | MS |
|---|---|---|---|---|
| 629 | N-((1R,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2-difluoroacetamide | 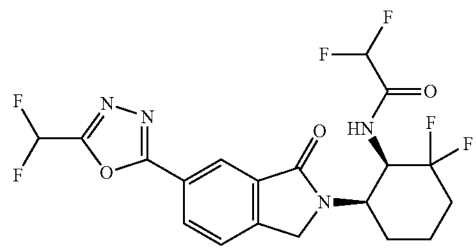 [SMILES: O=C(N[C@@H]1[C@H](N2Cc3ccc(-c4nnc(C(F)F)o4)cc3C2=O)CCCC1(F)F)C(F)F] | | 461.2 |
| 630 | 6-(5-(difluoromethyl)-1,3,4-oxadiazol-2-yl)-2-(2-(6-methylpyridin-3-yl)piperidin-1-yl)isoindolin-1-one | 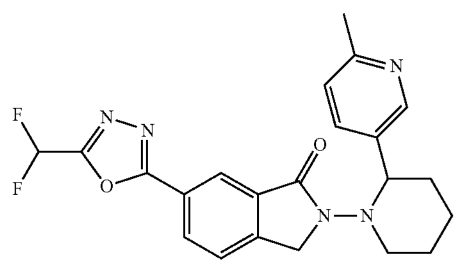 [SMILES: Cc1ccc(C2CCCCN2N2Cc3ccc(-c4nnc(C(F)F)o4)cc3C2=O)cn1] | | 426.2 |
| 631 | 6-(5-(difluoromethyl)-1,3,4-oxadiazol-2-yl)-2-(4-(2-hydroxypropan-2-yl)-1-methyl-1H-pyraozl-3-yl)isoindolin-1-one | 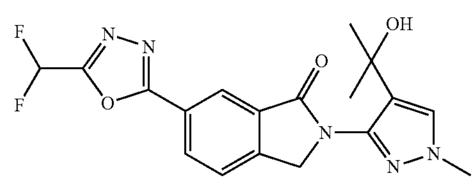 [SMILES: Cn1cc(C(C)(C)O)c(N2Cc3ccc(-c4nnc(C(F)F)o4)cc3C2=O)n1] | | 388.2 |
| 632 | 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(4-fluorophenyl)-threo-pentitiol (optical isomer) | 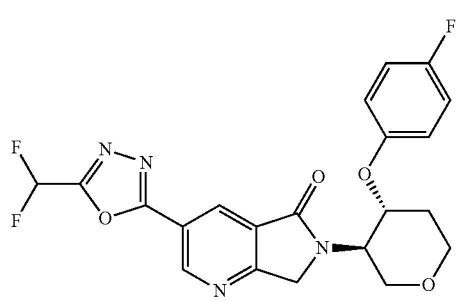 [SMILES: O=C1c2cc(-c3nnc(C(F)F)o3)cnc2CN1[C@@H]1COCC[C@H]1Oc1ccc(F)cc1] | | 445.2 |

TABLE 1-64-continued

| EXAMPLE | IUPAC NAME | Structure | ADDITIVE | MS |
|---|---|---|---|---|
| 633 | 1,5-anhydro-2,4-dideoxy-2-(3-(5-(difluoromethyl)-1,3,4-oxadiaol-2-yl)-5-oxo-5,7-dihydro-6H-pyrrolo[3,4-b]pyridin-6-yl)-3-O-(4-fluorophenyl)-threo-pentitol (optical isomer) | 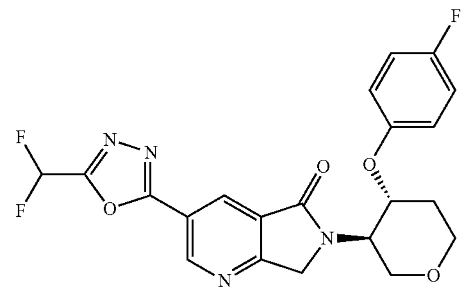 [SMILES: O=C1c2cc(-c3nnc(C(F)F)o3)cnc2CN1[C@@H]1COCC[C@H]1Oc1ccc(F)cc1] | | 445.2 |
| 634 | tert-butyl ((1R,2R)-2-(6-(5-(difluoromethyl)-1,3,4-oxadiazol-2-yl)-1-oxo-1,3-dihydro-2H-isoindol-2-yl)-4,4-difluorocyclohexyl)carbamate | 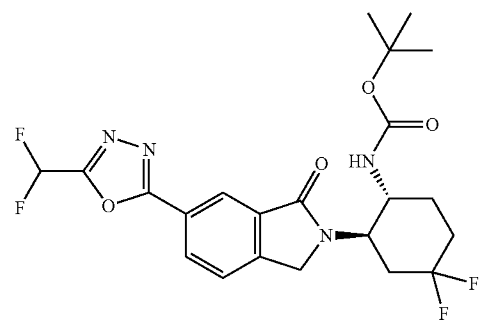 [SMILES: CC(C)(C)OC(=O)N[C@@H]1CCC(F)(F)C[C@H]1N1Cc2ccc(-c3nnc(C(F)F)o3)cc2C1=O] | | 483.2 |
| 635 | N-((1R,2R)-2-(6-(5-(difluoromethyl)-1,3,4-oxadiazol-2-yl)-1-oxo-1,3-dihydro-2H-isoindol-2-yl)-4,4-difluorocyclohexyl)-2,2,3,3,3-pentafluoropropanamide | 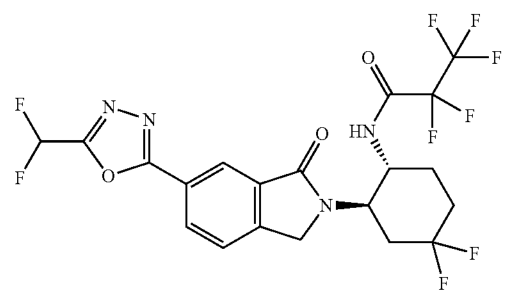 [SMILES: O=C1c2cc(-c3nnc(C(F)F)o3)ccc2CN1[C@@H]1CC(F)(F)CC[C@H]1NC(=O)C(F)(F)C(F)(F)F] | | 529.1 |
| 636 | N-((1R,2R)-2-(6-(5-(difluoromethyl)-1,3,4-oxadiazol-2-yl)-1-oxo-1,3-dihydro-2H-isoindol-2-yl)-4,4-difluorocyclohexyl)-2,2,3,3-tetrafluoropropanamide | 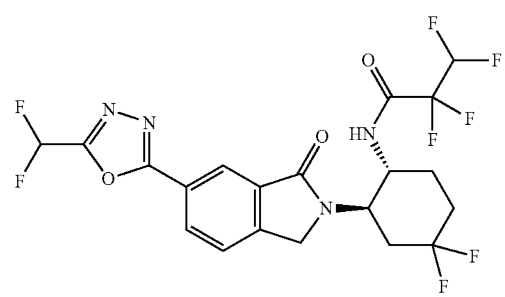 [SMILES: O=C1c2cc(-c3nnc(C(F)F)o3)ccc2CN1[C@@H]1CC(F)(F)CC[C@H]1NC(=O)C(F)(F)C(F)F] | | 511.1 |
| 637 | N-((1R,2R)-2-(6-(5-(difluoromethyl)-1,3,4-oxadiazol-2-yl)-1-oxo-1,3-dihydro-2H-isoindol-2-yl)-4,4-difluorocyclohexyl)-2,2-difluoropropanamide | 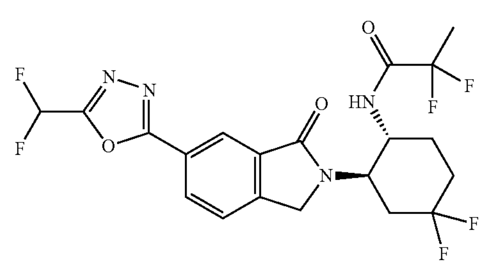 [SMILES: CC(F)(F)C(=O)N[C@@H]1CCC(F)(F)C[C@H]1N1Cc2ccc(-c3nnc(C(F)F)o3)cc2C1=O] | | 477.2 |

TABLE 1-64-continued

| EXAMPLE | IUPAC NAME | Structure | ADDITIVE | MS |
|---|---|---|---|---|
| 638 | 6-((1R,2R)-2-amino-5,5-difluorocyclohexyl)-3-(5-(difluoromethyl)-1,3,4-oxadiazol-2-yl)-6,7-dihydro-5H-pyrrollo[3,4-b]pyridin-5-one | 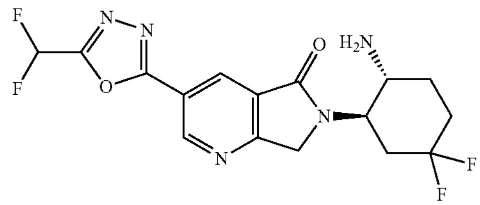 [SMILES: N[C@@H]1CCC(F)(F)C[C@H]1N1Cc2ncc(-c3nnc(C(F)F)o3)cc2C1=O] | | 386.2 |

TABLE 1-65

| EXAMPLE | IUPAC NAME | Structure | ADDITIVE | MS |
|---|---|---|---|---|
| 639 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)-5,5-difluorocyclohexyl)-2,2-difluoropropanamide | 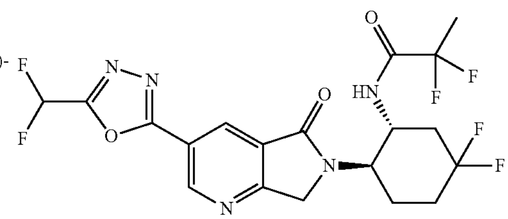 | | 476.1 |
| 640 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)-5,5-difluorocyclohexyl)-2,2,3,3,3-pentafluoropropanamide | 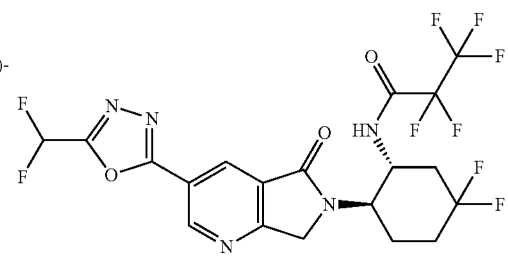 | | 530.1 |
| 641 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)-5,5-difluorocyclohexyl)-2,2,3,3-tetrafluoropropanamide | 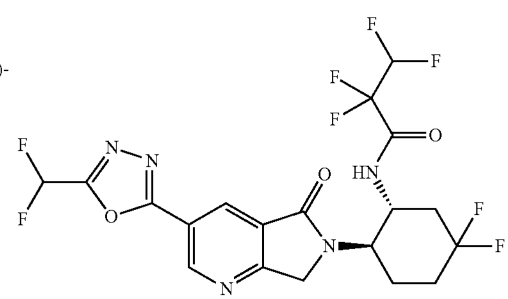 | | 512.1 |
| 642 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)-4,4-difluorocyclohexyl)-2,2,3,3,3-pentafluoropropanamide | 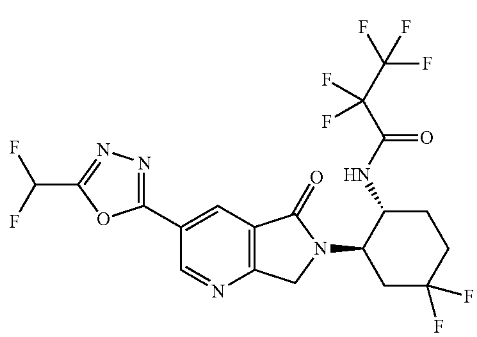 [SMILES: O=C1c2cc(-c3nnc(C(F)F)o3)cnc2CN1[C@@H]1CC(F)(F)CC[C@H]1NC(=O)C(F)(F)C(F)(F)F] | | 530.1 |

TABLE 1-65-continued

| EXAMPLE | IUPAC NAME | Structure | ADDITIVE | MS |
|---|---|---|---|---|
| 643 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)-4,4-difluorocyclohexyl)-2,2-difluoropropanamide | 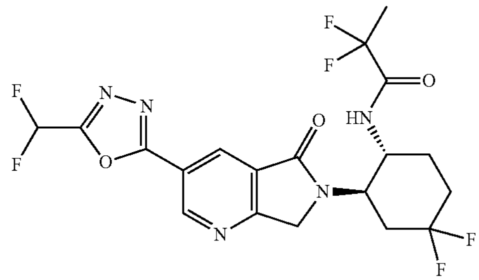 [SMILES: CC(F)(F)C(=O)N[C@@H]1CCC(F)(F)C[C@H]1N1Cc2ncc(-c3nnc(C(F)F)o3)cc2C1=O] | | 476.1 |
| 644 | N-((1R,2R)-2-(3-(5-(difluoromethyl)-1,3,4-oxadiazol-2-yl)-5-oxo-5,7-dihydro-6H-pyrrolo[3,4-b]pyridin-6-yl)-4,4-difluorocyclohexyl)-2,2,3,3-tetrafluoropropanamide | 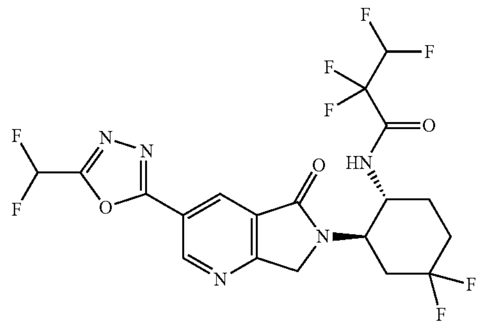 [SMILES: O=C1c2cc(-c3nnc(C(F)F)o3)cnc2CN1[C@@H]1CC(F)(F)CC[C@H]1NC(=O)C(F)(F)C(F)F] | | 512.1 |
| 645 | 1-(6-(5-(difluoromethyl)-1,3,4-oxadiazol-2-yl)-1-oxo-1,3-dihydro-2H-isoindol-2-yl)-N,N-diethyl-4,4-difluoropiperidine-2-carboxamide | 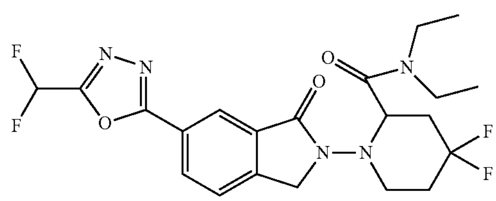 [SMILES: CCN(CC)C(=O)C1CC(F)(F)CCN1N1Cc2ccc(-c3nnc(C(F)F)o3)cc2C1=O] | | 470.1 |
| 646 | 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(3,4-difluorophenyl)-threo-pentitol (optical isomer) | 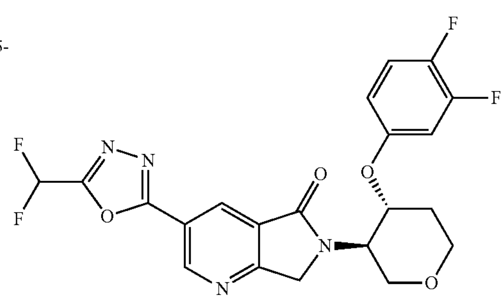 | | 463.2 |
| 647 | 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(2-fluorophenyl)-threo-pentitol (optical isomer) | 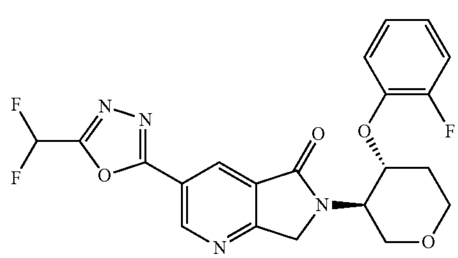 [SMILES: O=C1c2cc(-c3nnc(C(F)F)o3)cnc2CN1[C@@H]1COCC[C@H]1Oc1ccccc1F] | | 447.3 |

TABLE 1-65-continued

| EXAMPLE | IUPAC NAME | Structure | ADDITIVE | MS |
|---|---|---|---|---|
| 648 | 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(2-fluorophenyl)-threo-pentitol (optical isomer) | 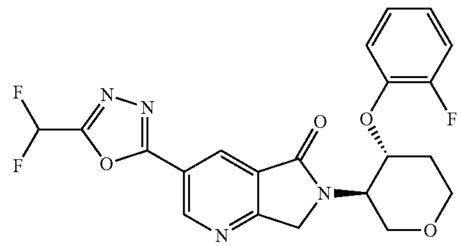 [SMILES: O=C1c2cc(-c3nnc(C(F)F)o3)cnc2CN1[C@@H]1COCC[C@H]1Oc1ccccc1F] | | 447.1 |

TABLE 1-66

| EXAMPLE | IUPAC NAME | Structure | ADDITIVE | MS |
|---|---|---|---|---|
| 649 | 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(3,4-difluorophenyl)-threo-pentitol (optical isomer) | 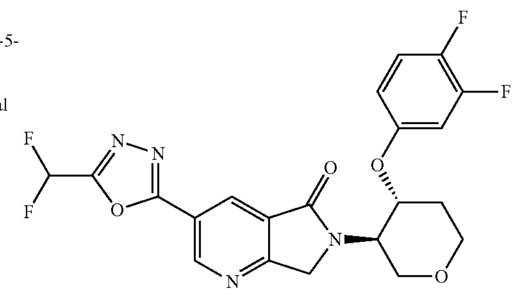 | | 463.2 |
| 650 | 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(3,5-difluorophenyl)-threo-pentitol (optical isomer) | 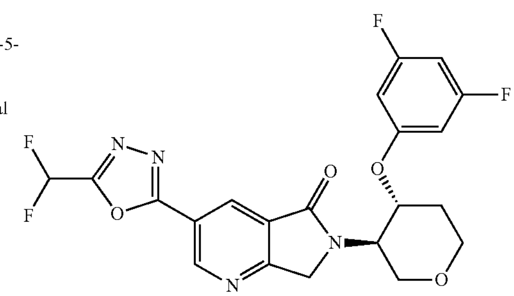 | | 463.2 |
| 651 | 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(3,5-difluorophenyl)-threo-pentitol (optical isomer) | 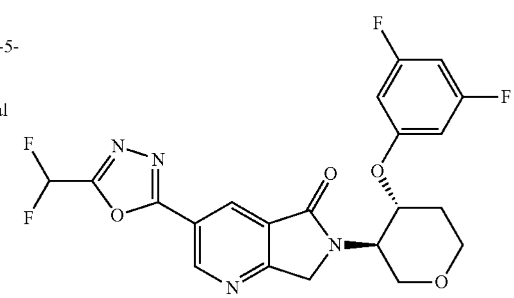 | | 463.2 |
| 652 | 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(3-fluorophenyl)-threo-pentitol (optical isomer) | 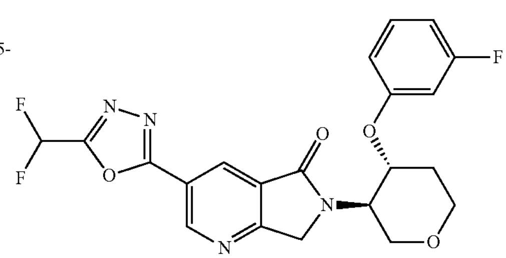 | | 445.2 |

TABLE 1-66-continued

| EXAMPLE | IUPAC NAME | Structure | ADDITIVE | MS |
|---|---|---|---|---|
| 653 | 1,5-anhydro-2,4-dideoxy-2-(3-(5-(difluoromethyl)-1,3,4-oxadiazol-2-yl)-5-oxo-5,7-dihydro-6H-pyrrolo[3,4-b]pyridin-6-yl)-3-O-(3-fluorophenyl)-threo-pentitol (optical isomer) | 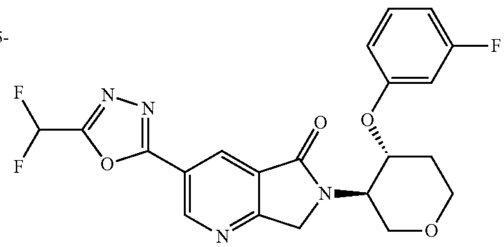 | | 445.2 |
| 654 | 3-[5-(difluoromethyl)-1,3,4-oxadiazol-2-yl]-6-[(1RS,2RS)-2-(1H-pyrazol-5-yl)cyclohexyl]-6,7-dihydro-5H-pyrrolo[3,4-b]pyridin-5-one | 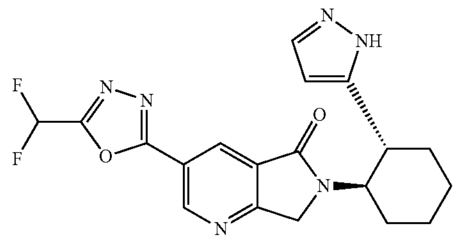 [SMILES: O=C1c2cc(-c3nnc(C(F)F)o3)cnc2CN1[C@@H]1CCCC[C@H]1c1ccn[nH]1] | | 401.2 |
| 655 | 1,5-anhydro-2,4-dideoxy-2-{3-[5-(difluoromethyl)-1,3,4-oxadiazol-2-yl]-5-oxo-5,7-dihydro-6H-pyrrolo[3,4-b]pyridin-6-yl}-3-O-(2,4-difluorophenyl)-threo-pentitol (optical isomer) | 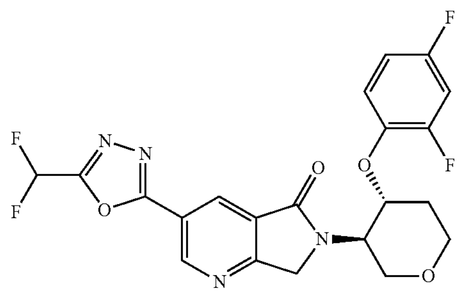 [SMILES: O=C1c2cc(-c3nnc(C(F)F)o3)cnc2CN1[C@@H]1COCC[C@H]1Oc1ccc(F)cc1F] | | 463.1 |
| 656 | 1,5-anhydro-2,4-dideoxy-2-{3-[5-(difluoromethyl)-1,3,4-oxadiazol-2-yl]-5-oxo-5,7-dihydro-6H-pyrrolo[3,4-b]pyridin-6-yl}-3-O-(2,4-difluorophenyl)-threo-pentitol (optical isomer) | 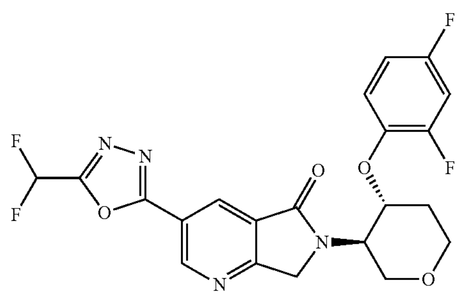 [SMILES: O=C1c2cc(-c3nnc(C(F)F)o3)cnc2CN1[C@@H]1COCC[C@H]1Oc1ccc(F)cc1F] | | 463.1 |
| 657 | 1,5-anhydro-2,4-dideoxy-2-{3-[5-(difluoromethyl)-1,3,4-oxadiazol-2-yl]-5-oxo-5,7-dihydro-6H-pyrrolo[3,4-b]pyridin-6-yl}-3-O-(2,3-difluorophenyl)-threo-pentitol (optical isomer) | 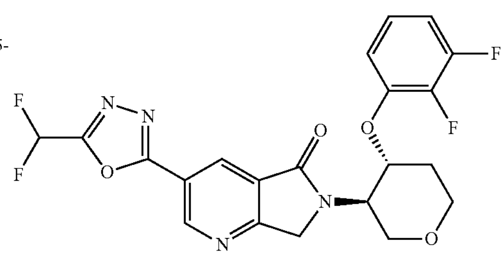 | | 463.2 |
| 658 | 1,5-anhydro-2,4-dideoxy-2-{3-[5-(difluoromethyl)-1,3,4-oxadiazol-2-yl]-5-oxo-5,7-dihydro-6H-pyrrolo[3,4-b]pyridin-6-yl}-3-O-(2,3-difluorophenyl)-threo-pentitol (optical isomer) | 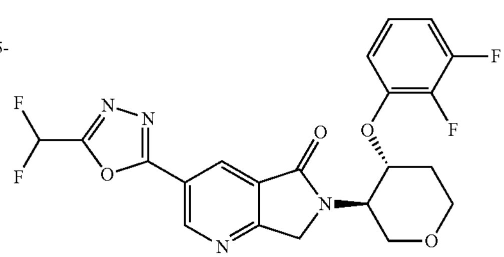 | | 463.2 |

TABLE 1-67

| EXAMPLE | IUPAC NAME | Structure | ADDITIVE | MS |
|---|---|---|---|---|
| 659 | 1,5-anhydro-2,4-dideoxy-2-{3-[5-(difluoromethyl)-1,3,4-oxadiazol-2-yl]-5-oxo-5,7-dihydro-6H-pyrrolo[3,4-b]pyridin-6-yl}-3-O-(2,6-difluorophenyl)-threo-pentitol (optical isomer) | 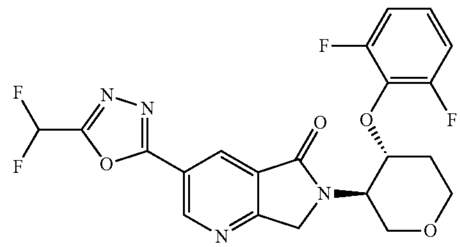 [SMILES: O=C1c2cc(-c3nnc(C(F)F)o3)cnc2CN1[C@@H]1COCC[C@H]1Oc1c(F)cccc1F] | | 465.1 |
| 660 | 1,5-anhydro-2,4-dideoxy-2-{3-[5-(difluoromethyl)-1,3,4-oxadiazol-2-yl]-5-oxo-5,7-dihydro-6H-pyrrolo[3,4-b]pyridin-6-yl}-3-O-(2,6-difluorophenyl)-threo-pentitol (optical isomer) | 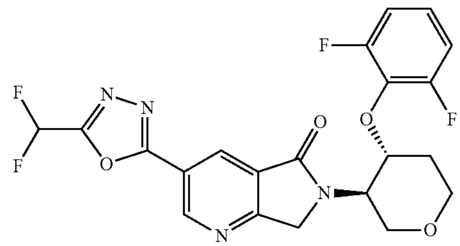 [SMILES: O=C1c2cc(-c3nnc(C(F)F)o3)cnc2CN1[C@@H]1COCC[C@H]1Oc1c(F)cccc1F] | | 465.1 |
| 661 | N-[(1S,2R)-2-{3-[5-(difluoromethyl)-1,3,4-oxadiazol-2-yl]-5-oxo-5,7-dihydro-6H-pyrrolo[3,4-b]pyridin-6-yl}cyclohexyl]-2,2,3,3,3-pentafluoropropanamide | 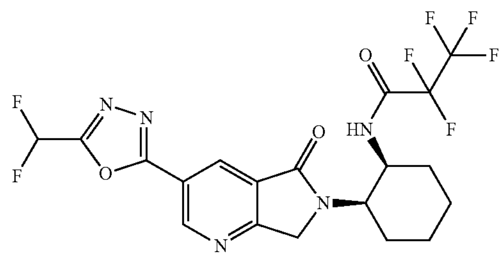 [SMILES: O=C1c2cc(-c3nnc(C(F)F)o3)cnc2CN1[C@@H]1CCCC[C@@H]1NC(=O)C(F)(F)C(F)(F)F] | | 494.2 |

Experimental Example 1

HDAC6 Enzyme Inhibitory Assay

HDAC6 enzyme prepared by transducing full length HDAC6 gene into Sf-9 insect cells and purifying by GST affinity column were purchased from SignalChem. Using this enzyme, HDAC6 enzyme inhibitory activities of the compound of the present invention were evaluated. Enzymes were used after preserved at −70° C. HDAC6 enzyme inhibitory activity of the compound of the present invention was measured using HDAC-Glo™ I/II Assay kit (Promega) according to the following experimental method. The test compound diluted with assay buffer (24 mM Tris-HCl (pH 7.5), 1 mM $MgCl_2$, 0.35 mM KCl, 135 mM NaCl, 0.6 mM Glutathione, 0.01% Tween-20) was added to a 384-well plate by each 2 μL. Then, HDAC6 enzyme solution diluted with assay buffer was added thereto by each 4 μL, and the plate was incubated at room temperature for 60 min. After incubated, HDAC substrate-Developer solution prepared according to Promega protocol attached to the assay kit was added to the 384-well plate by each 2 μL, and the enzyme reaction was started. After reacting at room temperature for 20 min, luminescence level was measured using plate reader Envision (PerkinElmer). The inhibitory activity of each compound of Example was calculated as a relative activity value when luminescence level in wells without enzyme is considered as 100% inhibition. The results are shown in Table 2-1 to 2-9.

TABLE 2-1

| Ex. No. | HDAC6 inhibitory rate (%) (10 μM) |
|---|---|
| 1 | 101 |
| 2 | 99 |
| 3 | 99 |
| 4 | 99 |
| 5 | 100 |
| 6 | 102 |
| 7 | 99 |
| 8 | 101 |
| 9 | 102 |
| 10 | 99 |
| 11 | 98 |
| 12 | 100 |
| 13 | 101 |
| 14 | 100 |
| 15 | 98 |
| 16 | 100 |
| 17 | 101 |
| 18 | 100 |
| 19 | 101 |
| 20 | 100 |
| 21 | 100 |
| 22 | 98 |
| 23 | 99 |
| 24 | 98 |
| 25 | 99 |
| 26 | 98 |
| 27 | 100 |
| 28 | 100 |
| 29 | 101 |
| 30 | 97 |

TABLE 2-1-continued

| Ex. No. | HDAC6 inhibitory rate (%) (10 μM) |
|---|---|
| 31 | 97 |
| 32 | 101 |
| 33 | 97 |
| 34 | 98 |
| 35 | 97 |
| 36 | 85 |
| 37 | 99 |
| 38 | 91 |
| 39 | 96 |
| 40 | 100 |
| 41 | 98 |
| 42 | 98 |
| 43 | 96 |
| 44 | 100 |
| 45 | 99 |
| 46 | 97 |
| 47 | 99 |
| 48 | 98 |
| 49 | 99 |
| 50 | 101 |
| 51 | 99 |
| 52 | 96 |
| 53 | 98 |
| 54 | 98 |
| 55 | 101 |
| 56 | 92 |
| 58 | 98 |
| 59 | 94 |
| 60 | 96 |
| 61 | 99 |
| 62 | 99 |
| 63 | 99 |
| 64 | 100 |
| 65 | 100 |
| 66 | 101 |
| 67 | 100 |
| 68 | 101 |
| 69 | 101 |
| 70 | 100 |
| 71 | 97 |
| 72 | 97 |
| 73 | 100 |
| 74 | 102 |
| 75 | 101 |
| 76 | 101 |
| 77 | 100 |
| 78 | 100 |
| 79 | 97 |
| 80 | 101 |
| 81 | 101 |
| 82 | 100 |
| 83 | 102 |
| 84 | 100 |
| 85 | 101 |
| 86 | 96 |
| 87 | 99 |
| 88 | 99 |
| 89 | 100 |
| 90 | 100 |
| 91 | 100 |

TABLE 2-2

| Ex. No. | HDAC6 inhibitory rate (%) (10 μM) |
|---|---|
| 92 | 101 |
| 93 | 100 |
| 94 | 100 |
| 95 | 96 |
| 96 | 98 |
| 97 | 100 |
| 98 | 101 |
| 99 | 100 |

TABLE 2-2-continued

| Ex. No. | HDAC6 inhibitory rate (%) (10 μM) |
|---|---|
| 100 | 100 |
| 101 | 99 |
| 102 | 96 |
| 103 | 98 |
| 104 | 97 |
| 105 | 98 |
| 106 | 99 |
| 107 | 102 |
| 108 | 100 |
| 109 | 97 |
| 110 | 98 |
| 111 | 101 |
| 112 | 95 |
| 113 | 102 |
| 114 | 100 |
| 115 | 96 |
| 116 | 98 |
| 117 | 96 |
| 119 | 100 |
| 121 | 100 |
| 122 | 95 |
| 123 | 101 |
| 124 | 99 |
| 125 | 98 |
| 126 | 100 |
| 127 | 100 |
| 128 | 100 |
| 129 | 100 |
| 130 | 93 |
| 131 | 99 |
| 132 | 94 |
| 133 | 93 |
| 134 | 101 |
| 136 | 99 |
| 137 | 98 |
| 138 | 98 |
| 139 | 100 |
| 140 | 100 |
| 141 | 100 |
| 142 | 99 |
| 143 | 95 |
| 144 | 97 |
| 145 | 100 |
| 146 | 94 |
| 147 | 93 |
| 148 | 99 |
| 149 | 102 |
| 150 | 97 |
| 151 | 98 |
| 152 | 99 |
| 153 | 100 |
| 154 | 98 |
| 155 | 95 |
| 156 | 100 |
| 157 | 98 |
| 158 | 100 |
| 159 | 100 |
| 160 | 101 |
| 161 | 99 |
| 162 | 97 |
| 163 | 98 |
| 164 | 99 |
| 165 | 99 |
| 166 | 97 |
| 167 | 100 |
| 168 | 100 |
| 169 | 101 |
| 170 | 102 |
| 171 | 101 |
| 172 | 100 |
| 173 | 91 |
| 174 | 102 |
| 175 | 100 |
| 176 | 100 |
| 177 | 97 |
| 178 | 41 |
| 179 | 100 |

TABLE 2-2-continued

| Ex. No. | HDAC6 inhibitory rate (%) (10 μM) |
|---|---|
| 180 | 100 |
| 181 | 97 |
| 182 | 99 |
| 183 | 99 |
| 184 | 102 |

TABLE 2-3

| Ex. No. | HDAC6 inhibitory rate (%) (10 μM) |
|---|---|
| 185 | 100 |
| 186 | 101 |
| 187 | 92 |
| 188 | 98 |

TABLE 2-4

| Ex. No. | HDAC6 inhibitory rate(%) (10 μM) |
|---|---|
| 189 | 100 |
| 190 | 100 |
| 191 | 101 |
| 192 | 100 |
| 193 | 102 |
| 194 | 100 |
| 195 | 100 |
| 196 | 100 |
| 197 | 100 |
| 198 | 99 |
| 199 | 100 |
| 200 | 100 |
| 201 | 101 |
| 202 | 101 |
| 203 | 100 |
| 204 | 100 |
| 205 | 101 |
| 206 | 100 |
| 207 | 100 |
| 208 | 100 |
| 209 | 107 |
| 210 | 101 |
| 211 | 100 |
| 212 | 101 |
| 213 | 100 |
| 214 | 100 |
| 215 | 101 |
| 216 | 100 |
| 217 | 98 |
| 218 | 100 |
| 219 | 100 |
| 220 | 94 |
| 221 | 101 |
| 222 | 99 |
| 223 | 99 |
| 224 | 100 |
| 225 | 98 |
| 226 | 99 |
| 227 | 100 |
| 228 | 98 |
| 229 | 100 |
| 230 | 100 |
| 231 | 98 |
| 232 | 98 |
| 233 | 100 |
| 234 | 98 |
| 235 | 99 |
| 236 | 98 |
| 237 | 100 |
| 238 | 100 |
| 239 | 99 |

TABLE 2-4-continued

| Ex. No. | HDAC6 inhibitory rate(%) (10 μM) |
|---|---|
| 240 | 98 |
| 241 | 91 |
| 242 | 101 |
| 243 | 99 |
| 244 | 101 |
| 245 | 101 |
| 246 | 100 |
| 247 | 94 |
| 248 | 100 |
| 249 | 100 |
| 250 | 95 |
| 251 | 100 |
| 252 | 99 |
| 253 | 72 |
| 254 | 102 |
| 255 | 100 |
| 256 | 91 |
| 257 | 101 |
| 258 | 101 |
| 259 | 101 |
| 260 | 98 |
| 261 | 99 |
| 262 | 98 |
| 263 | 99 |
| 264 | 101 |
| 265 | 98 |
| 266 | 99 |
| 267 | 100 |
| 268 | 100 |
| 269 | 99 |
| 270 | 99 |
| 271 | 100 |
| 272 | 100 |
| 273 | 97 |
| 274 | 99 |
| 275 | 98 |
| 276 | 98 |
| 277 | 97 |
| 278 | 99 |

TABLE 2-5

| Ex. No. | HDAC6 inhibitory rate(%) (10 μM) |
|---|---|
| 279 | 89 |
| 280 | 99 |
| 281 | 98 |
| 282 | 98 |
| 283 | 99 |
| 284 | 101 |
| 285 | 95 |
| 286 | 99 |
| 287 | 100 |
| 288 | 102 |
| 289 | 101 |
| 290 | 99 |
| 291 | 98 |
| 292 | 97 |
| 293 | 100 |
| 294 | 100 |
| 295 | 102 |
| 296 | 101 |
| 297 | 98 |
| 298 | 100 |
| 299 | 94 |
| 300 | 97 |
| 301 | 106 |
| 302 | 100 |
| 303 | 99 |
| 304 | 99 |
| 305 | 101 |
| 306 | 101 |
| 307 | 98 |

TABLE 2-5-continued

| Ex. No. | HDAC6 inhibitory rate(%) (10 μM) |
|---|---|
| 308 | 97 |
| 309 | 97 |
| 310 | 91 |
| 311 | 99 |
| 312 | 96 |
| 313 | 98 |
| 314 | 101 |
| 315 | 98 |
| 316 | 92 |
| 317 | 97 |
| 318 | 98 |
| 319 | 86 |
| 320 | 99 |
| 321 | 98 |
| 322 | 23 |
| 323 | 97 |
| 324 | 97 |
| 325 | 100 |
| 326 | 86 |
| 327 | 99 |
| 328 | 98 |
| 329 | 99 |
| 330 | 99 |
| 331 | 97 |
| 332 | 99 |
| 333 | 97 |
| 334 | 93 |
| 335 | 101 |
| 336 | 102 |
| 337 | 101 |
| 338 | 97 |
| 339 | 96 |
| 340 | 96 |
| 341 | 82 |
| 342 | 100 |
| 343 | 100 |
| 344 | 100 |
| 345 | 99 |
| 346 | 94 |
| 347 | 98 |
| 348 | 99 |
| 349 | 99 |
| 350 | 99 |
| 351 | 98 |
| 352 | 99 |
| 353 | 98 |
| 354 | 92 |
| 355 | 100 |
| 356 | 101 |
| 357 | 98 |
| 358 | 102 |
| 359 | 97 |
| 360 | 103 |
| 361 | 101 |
| 362 | 99 |
| 363 | 99 |
| 364 | 87 |
| 365 | 101 |
| 366 | 97 |
| 367 | 101 |
| 368 | 99 |

TABLE 2-6

| Ex. No. | HDAC6 inhibitory rate(%) (10 μM) |
|---|---|
| 369 | 99 |
| 370 | 101 |
| 371 | 99 |
| 372 | 92 |
| 373 | 97 |
| 374 | 99 |
| 375 | 101 |

TABLE 2-6-continued

| Ex. No. | HDAC6 inhibitory rate(%) (10 μM) |
|---|---|
| 376 | 101 |
| 377 | 101 |
| 378 | 99 |
| 379 | 97 |
| 380 | 99 |
| 381 | 100 |
| 382 | 98 |
| 383 | 95 |
| 384 | 99 |
| 385 | 101 |
| 386 | 101 |
| 387 | 101 |
| 388 | 101 |
| 389 | 101 |
| 390 | 100 |
| 391 | 100 |
| 392 | 99 |
| 393 | 99 |
| 394 | 99 |
| 395 | 99 |
| 396 | 101 |
| 397 | 100 |
| 398 | 102 |
| 399 | 101 |
| 400 | 99 |
| 401 | 99 |
| 402 | 100 |
| 403 | 102 |
| 404 | 100 |
| 405 | 101 |
| 406 | 100 |
| 407 | 99 |
| 408 | 99 |
| 409 | 99 |
| 410 | 101 |
| 411 | 100 |
| 412 | 100 |
| 413 | 98 |
| 414 | 87 |
| 415 | 101 |
| 416 | 101 |
| 417 | 101 |
| 418 | 99 |
| 419 | 99 |
| 420 | 99 |
| 421 | 98 |
| 422 | 98 |
| 423 | 99 |
| 424 | 101 |
| 425 | 99 |
| 426 | 99 |
| 427 | 100 |
| 428 | 99 |
| 429 | 97 |
| 430 | 101 |
| 431 | 100 |
| 432 | 94 |
| 433 | 101 |
| 434 | 98 |
| 435 | 99 |
| 436 | 98 |
| 437 | 101 |
| 438 | 97 |
| 439 | 99 |
| 440 | 97 |
| 441 | 99 |
| 442 | 94 |
| 443 | 100 |
| 444 | 100 |
| 445 | 100 |
| 446 | 100 |
| 447 | 100 |
| 448 | 100 |
| 449 | 100 |
| 450 | 100 |
| 451 | 98 |
| 452 | 99 |

TABLE 2-6-continued

| Ex. No. | HDAC6 inhibitory rate(%) (10 μM) |
|---|---|
| 453 | 99 |
| 454 | 101 |
| 455 | 102 |
| 456 | 100 |
| 457 | 97 |
| 458 | 100 |

TABLE 2-7

| Ex. No. | HDAC6 inhibitory rate(%) (10 μM) |
|---|---|
| 459 | 97 |
| 460 | 102 |
| 461 | 100 |
| 462 | 100 |
| 463 | 101 |
| 464 | 101 |
| 465 | 99 |
| 466 | 100 |
| 467 | 101 |
| 468 | 100 |
| 469 | 99 |
| 470 | 101 |
| 471 | 100 |
| 472 | 100 |
| 473 | 99 |
| 474 | 99 |
| 475 | 100 |
| 476 | 100 |
| 477 | 95 |
| 478 | 100 |
| 479 | 100 |
| 480 | 101 |
| 481 | 98 |
| 482 | 100 |
| 483 | 91 |
| 484 | 100 |
| 485 | 100 |
| 486 | 100 |
| 487 | 99 |
| 488 | 100 |

TABLE 2-8

| Ex. No. | HDAC6 inhibitory rate(%) (10 μM) |
|---|---|
| 489 | 99 |
| 490 | 98 |
| 491 | 99 |
| 492 | 91 |
| 493 | 99 |
| 494 | 100 |
| 495 | 89 |
| 496 | 100 |
| 497 | 101 |
| 498 | 100 |
| 499 | 99 |
| 500 | 99 |
| 501 | 98 |
| 502 | 100 |
| 503 | 99 |
| 504 | 100 |
| 505 | 100 |
| 506 | 99 |
| 507 | 100 |
| 508 | 100 |
| 509 | 99 |
| 510 | 100 |
| 511 | 95 |
| 512 | 99 |

TABLE 2-8-continued

| Ex. No. | HDAC6 inhibitory rate(%) (10 μM) |
|---|---|
| 513 | 99 |
| 514 | 99 |
| 515 | 99 |
| 516 | 100 |
| 517 | 100 |
| 518 | 99 |
| 519 | 99 |
| 520 | 99 |
| 521 | 99 |
| 522 | 99 |
| 523 | 99 |
| 524 | 99 |
| 525 | 100 |
| 526 | 101 |
| 527 | 99 |
| 528 | 99 |
| 529 | 100 |
| 530 | 100 |
| 531 | 100 |
| 532 | 99 |
| 533 | 98 |
| 534 | 100 |
| 535 | 99 |
| 536 | 100 |
| 537 | 100 |
| 538 | 99 |
| 539 | 99 |
| 540 | 99 |
| 541 | 99 |
| 542 | 90 |
| 543 | 100 |
| 544 | 99 |
| 545 | 100 |
| 546 | 100 |
| 547 | 100 |
| 548 | 100 |
| 549 | 100 |
| 550 | 99 |
| 551 | 99 |
| 552 | 100 |
| 553 | 100 |
| 554 | 100 |
| 555 | 100 |
| 556 | 97 |
| 557 | 99 |
| 558 | 99 |
| 559 | 100 |
| 560 | 100 |
| 561 | 100 |
| 562 | 99 |
| 563 | 100 |
| 564 | 100 |
| 565 | 100 |
| 566 | 100 |
| 567 | 95 |
| 568 | 96 |
| 569 | 99 |
| 570 | 100 |
| 571 | 73 |
| 572 | 100 |
| 573 | 99 |
| 574 | 100 |
| 575 | 100 |
| 576 | 99 |
| 577 | 97 |
| 578 | 100 |

TABLE 2-9

| Ex. No. | HDAC6 inhibitory rate(%) (10 μM) |
|---|---|
| 579 | 100 |
| 580 | 100 |

TABLE 2-9-continued

| Ex. No. | HDAC6 inhibitory rate(%) (10 µM) |
|---|---|
| 581 | 99 |
| 582 | 100 |
| 583 | 99 |
| 584 | 100 |
| 585 | 100 |
| 586 | 100 |
| 587 | 99 |
| 588 | 100 |
| 589 | 100 |
| 590 | 100 |
| 591 | 99 |
| 592 | 99 |
| 593 | 100 |
| 594 | 101 |
| 595 | 100 |
| 596 | 100 |
| 597 | 99 |
| 598 | 100 |
| 599 | 99 |
| 600 | 100 |
| 601 | 99 |
| 602 | 101 |
| 603 | 100 |
| 604 | 98 |
| 605 | 99 |
| 606 | 99 |
| 607 | 99 |
| 608 | 99 |
| 609 | 99 |
| 610 | 99 |
| 611 | 101 |
| 612 | 99 |
| 613 | 99 |
| 614 | 99 |
| 615 | 99 |
| 616 | 89 |
| 617 | 100 |
| 618 | 99 |
| 619 | 100 |
| 620 | 101 |
| 621 | 88 |
| 622 | 100 |
| 623 | 100 |
| 624 | 100 |
| 625 | 101 |
| 626 | 100 |
| 627 | 100 |
| 628 | 100 |
| 629 | 100 |
| 630 | 100 |
| 631 | 99 |
| 632 | 99 |
| 633 | 100 |
| 634 | 99 |
| 635 | 99 |
| 636 | 100 |
| 637 | 100 |
| 638 | 93 |
| 639 | 100 |
| 640 | 100 |
| 641 | 99 |
| 642 | 100 |
| 643 | 100 |
| 644 | 99 |
| 645 | 99 |
| 646 | 99 |
| 647 | 100 |
| 648 | 100 |
| 649 | 100 |
| 650 | 99 |
| 651 | 100 |
| 652 | 100 |
| 653 | 99 |
| 654 | 100 |
| 655 | 96 |
| 656 | 100 |
| 657 | 100 |
| 658 | 100 |
| 659 | 99 |
| 660 | 100 |
| 661 | 99 |

As is clear from Table 2-1 to Table 2-9, the compound of the present invention has an excellent HDAC6 inhibitory activity.

Experimental Example 2

Increase in Acetylated Tubulin in Brain

Figure 2:
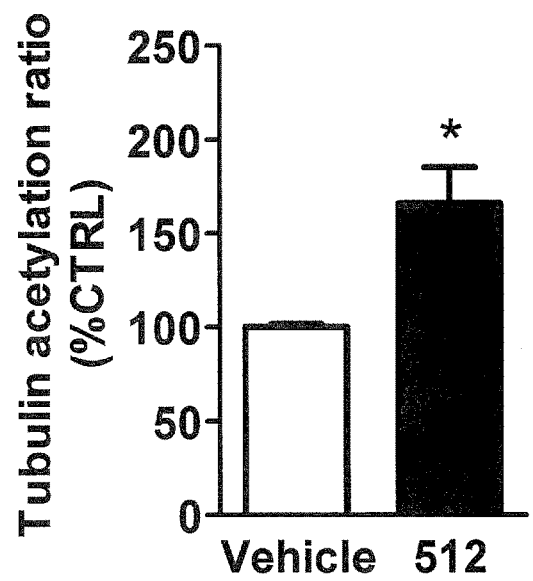
FIG. 2 shows relative tubulin acetylation level by the compound of Example 512.
Figure 3:
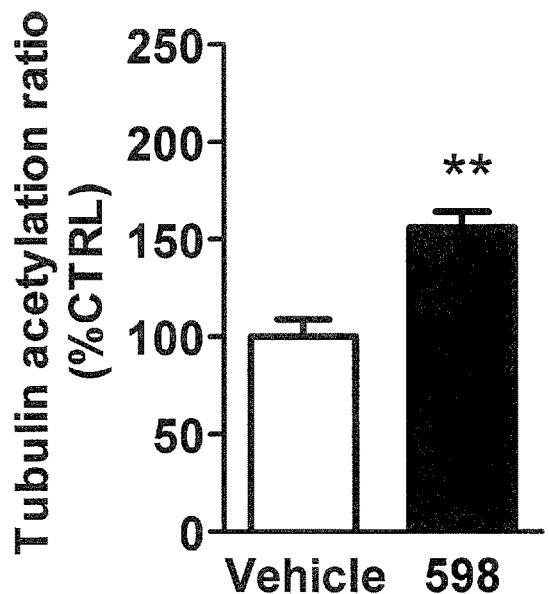
FIG. 3 shows relative tubulin acetylation level by the compound of Example 598.

A drug was suspended in 0.5% methyl cellulose to prepare a suspension for administration, having a concentration shown in Table 3. The suspension was orally administered into 8 to 10-old male C57BL/6J mouse, and after the passage of the time shown in Table 3, the brain was taken out, and hippocampus was obtained. The hippocampus was homogenized under RIPA extract (Wako) to which protease inhibitor (Thermo) and phosphatase inhibitor (Thermo) were added, and centrifuged in 15,000 g for 15 min to prepare a protein extract. The acetylated tubulin and total tubulin in the extract were detected by the following ELISA method. Tubulin antibody (Sigma) was immobilized on 96-well plate (Microlite2+, Thermo), and the plate was stored at 4° C. Next day, the plate was washed four times with PBS-T, and blocking buffer (1% BSA/PBS-T) was added thereto, and the reaction was carried out at 37° C. for 2 hr. The plate was washed four times with PBS-T, and the above-mentioned protein extract was added thereto to capture the tubulin on the antibody. The plate was stored at 37° C. for 2 hr, and washed four times with PBS-T. Anti-acetylated tubulin antibody or total tubulin antibody (Cell Signaling), each diluted with blocking buffer, was added thereto, and the reaction was carried out at 37° C. for 1 hr. Then, the plate was washed four times with PBS-T, and the reaction was carried out using anti-mouse HPR (Cell Signaling) at 37° C. for 30 min. The plate was washed, HRP substrate was added thereto, and the luminescence was measured using a plate reader. The acetylated tubulin and total tubulin were quantified from logistics curve based on dilution series using the mouse hippocampus tissue extract, and the acetylated tubulin relative to total tubulin was calculated, and evaluated as an relative tubulin acetylation level. The test was performed using SAS system 8. After F test for vehicle group and drug group, the significant difference between the two groups was analyzed by Student t-test or Welch test (indicated as * $p<0.05$, ** $p<0.01$). The graph was indicated by the mean±standard error. The results are shown in FIGS. 1 to 3. In the mouse into which the compound of Example 489, 512 or 598 was administered, increase in significant tubulin acetylation level was observed.

TABLE 3

| Ex. No. | concentration (mg/mL) | dose (mg/kg) | time (h) after administration of test compound | C57BL/6J old | C57BL/6J number |
|---|---|---|---|---|---|
| 489 | 1 | 10 | 4 | 8 | 6 |
| 512 | 0.3 | 3 | 1 | 10 | 5 |
| 598 | 0.3 | 3 | 1 | 8 | 5 |

Experimental Example 3

Cognitive Improvement Action in Neurodegenerative Disease Model Mouse

Figure 4:
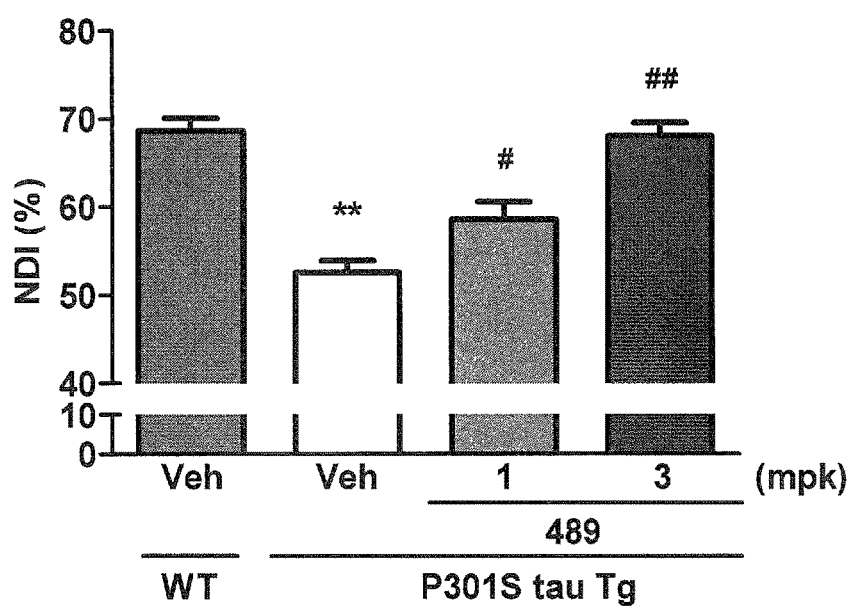
FIG. 4 shows novelty discrimination index (NDI) by the compound of Example 489.

A drug was suspended in 0.5% methyl cellulose to prepare a suspension for administration. The suspension was repeatedly administered into six month-old male P301S mutant human tau (4R1N) Tg mouse once a day for three months, and novel object recognition test was performed by the following method. The test is comprised of memory acquisition trial of object on the first day, and memory retention trial of familiar object and novel object on the second day. Drug was administered into the mouse 1 hr before the trials on both days. For acquisition trial, The mouse was put in a test box (30 cm×30 cm×25 cm) in which two identical objects were placed, and contact frequency and contact duration with the objects for 5 min were measured under 50 lux. Herein, the contact means a behavior getting a sniff of a object (Sniffing). Next day, one of the objects was replaced with new object, and contact frequency and contact duration with each object for 5 min were measured. Novelty Discrimination Index (NDI) as an index of cognitive function was calculated by novel object contact frequency/(novel object contact duration+familiar object contact duration)%. The test was performed using SAS system 8. After F test for vehicle administration wild-type group and vehicle administration Tg group, the significant difference between the two groups was analyzed by Student t-test or Welch test (indicated as  $p<0.01$). In addition, Bartlett test for homogeneity of variance was performed for vehicle administration or drug administration Tg group, and the significant difference was analyzed by one-tailed Williams test (indicated as # $p<0.025$, ## $p<0.005$). Each group consisted of 14 or 15 mice. The graph was indicated by the mean±standard error. The results are shown in FIG. 4**. In the mouse into which the compound of Example 489 was administered (1 mg/kg and 3 mg/kg), significant improvement in NDI was observed.

Experimental Example 4

γH2AX Assay Using TK6 Cells

Human lymphoblasts-derived TK6 cells were treated with the compounds of Examples 489, 512 or 519 at 0, 10, 30 or 100 μmol/L (final concentration) for 4 hr, and the presence or absence of DNA damage was evaluated by measuring phosphorylation of histone H2AX (γH2AX) as a marker. In addition, cytotoxicity after 24-hr treatment was also evaluated.

Figure 5:
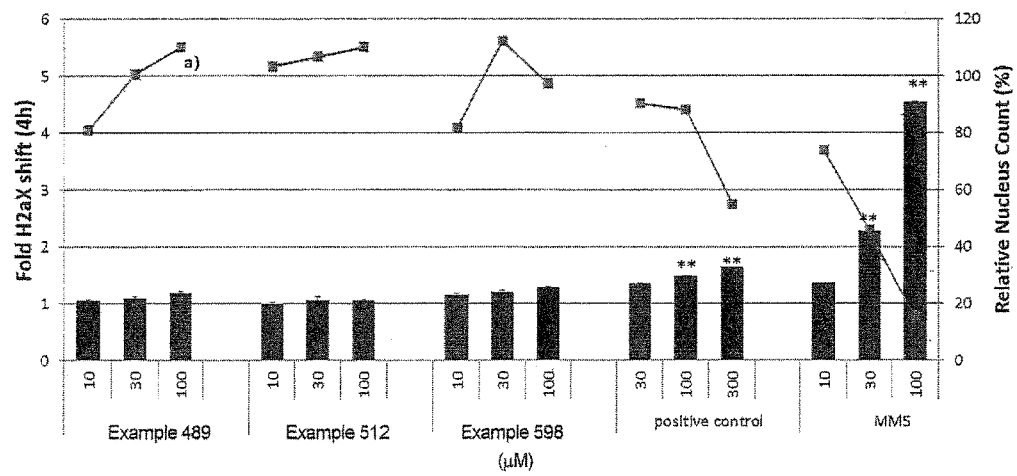
FIG. 5 shows variation in H2AX phosphorylation level by the compound of Example 489, the compound of Example 512 and the compound of Example 598.

Exponentially growing TK6 cells were prepared at the cell density of $4\times10^5$ cells/mL in a culture medium, and was added to a 96-well plate by 100 μL/well. A test compound solution (2% DMSO) prepared using a culture solution, having twice the concentration on the above-mentioned final concentrations, was added thereto by 100 μL/well. This plate was incubated at 37° C., the cell suspension after 4 hr was sampled, and stained using In Vitro MultiFlow™ DNA Damage Kit (Litron), and H2AX phosphorylation level in each nucleus was measured using a flow cytometer and average value was calculated. The H2AX phosphorylation level in the concurrent vehicle control group was also measured and average value was calculated. The rate of change in the H2AX phosphorylation level in the treatment groups relative to that in the control group was calculated, and Dunnett test (significance level: two-tailed 1%) was performed. In addition, the cell suspension after 24 hr treatment was sampled, and the nucleus number was measured, and variation in the nucleus number in the treatment groups relative to that in the concurrent vehicle control group was used as an indicator of cytotoxicity. The results are shown in FIG. 5. As in FIG. 5, the compounds of Example (the compounds of Example 489, 512 or 598) did not induce histone H2AX phosphorylation resulted from DNA strand breakage up to 100 μM compound concentration. Therefore, the potential of the compounds for DNA strand breakage was judged to be negative under this test condition.

Experimental Example 5

Combination Assay of Micronucleus Test and Comet Assay in Rats

The compound of Example 489 at doses of 1000 and 2000 mg/kg was orally administered to 8 to 9-week-old rats (Crl:CD(SD), five/group) once daily for 3 days, and micronucleus induction was evaluated in bone-marrow cells, and DNA damage was evaluated by DNA fragmentation of cell nucleus in the liver and glandular stomach.

Bone-marrow smear for micronucleus analysis was prepared as follows. Femur was cut at both ends, and washed with fetal bovine serum (FBS) in a centrifuging tube, and the obtained bone-marrow fluid was centrifuged for 5 min at room temperature. The supernatant was removed, and the cell sediment was suspended in the remaining small amount of the supernatant. A part of the suspension was dropped on a glass slide, and a cover glass was placed thereon to give a bone-marrow smear. The smear was dried well, and fixed with methanol for 5 min.

The bone-marrow smear of negative control, that of treatment groups as well as the previously prepared bone-marrow smear of positive control group were encoded, and observed by the blind method. An acridine orange solution (40 μg/mL) was dropped (several drops) to the smear just before observation, and a cover glass was placed thereon. A total of 4000 immature erythrocytes (IE) per individual were observed at 600-fold final magnification using a biological microscope with fluorescence attachment, and the frequency of micronucleated immature erythrocytes (MNIE %) in 4000 IE were calculated. In addition, as an index of growth inhibitory effect on bone-marrow cell, total of 500 erythrocytes [immature erythrocytes+mature erythrocytes (ME)] per individual were observed, and immature erythrocyte rate (IE %) relative to the total number of erythrocytes was calculated.

Sample for comet assay was obtained from liver and glandular stomach by the following procedures. A part of left lateral lobe of liver was washed well with a cooled mincing buffer solution (Hanks' balanced salt solution containing 20 mmol/L EDTA and 10 vol % DMSO, pH7.5), and minced finely with dissecting scissors. This sample was kept on ice for 15 to 30 seconds, the precipitated large cell mass was removed, and the obtained cell suspension was kept on ice. Glandular stomach was added to a cooled mincing buffer solution, and kept on ice for 15 to 30 min. Then, the surface epithelium was removed by scraping gently twice, the stomach mucosa was washed well with a cooled mincing buffer solution, and the mucosa surface was taken out by scraping carefully four times or five times. This was kept on ice for 15 to 30 seconds, the precipitated large cell mass was removed, and the obtained cell suspension was kept on ice.

The liver and glandular stomach cell suspensions prepared by the above-mentioned procedures were added to 0.5 w/v % low-melting agarose so that the concentration became 10 vol % or less, 40 μL of the suspension was dropped to MAS-coated slide (Matsunami Glass Ind., Ltd.), and fixed to give a slide sample. The slide sample was immersed in a cooled cell lysate [an aqueous solution containing 2.5 mol/L sodium chloride, 100 mmol/L EDTA, 10 mmol/L tris(hydroxymethyl)aminomethane, 10 vol % DMSO and 1 vol % Triton X-100, pH 10.0], and kept overnight under light shielding in a refrigerator (2 to 8° C.).

The slide sample was washed with ultrapure water, set at random into an electrophoresis apparatus filled with an alkali buffer solution (an aqueous solution containing 0.3 mol/L sodium hydroxide and 1 mmol/L EDTA, pH >13) for electrophoresis. After confirming that the sample was completely immersed, the sample was left for 20 min to unwind the strands. Next, electrophorese was performed at a constant voltage of 0.7 to 1 V/cm (current is set about 0.30 A) for 20 min (the electrophoresis apparatus was kept on ice so that the alkali buffer solution for electrophoresis was kept at a constant temperature of 10° C. or below, during from the dissociation of the strands to electrophoresis). After electrophoresis, the slide sample was immersed in a neutralizing solution [0.4 mol/L aqueous tris(hydroxymethyl)aminomethane solution, pH 7.5] for 5 min or longer. Then, the slide sample was immersed in ethanol for 5 min or longer, and air-dried. DNA stain solution (SYBR-Gold, Molecular Probes, Inc.) was dropped to the slide sample, and it was left for 10 min or longer. Next, the slide sample was washed for 5 min three times with ultrapure water, and air-dried. The slide samples for negative control, test compound and positive control groups were encoded, and analyzed by the blind method. In each individual animal, 150 of suitable cells were selected for observation using a biological microscope with fluorescence attachment at 200-fold final magnification, and analyzed by image analysis software (Comet Assay IV, Perceptive Instruments Ltd.). The degree of the DNA damage was evaluated by % tail intensity calculated automatically from image analysis software. The median of the % tail intensity was calculated in each slide sample, and the average of the median was calculated in each individual. The results are shown in Table 4 and Table 5. DNA strand breakage in liver and glandular stomach cells, and micronucleus formation in bone-marrow cell were not induced in rats by administration of the compound of Example 489 at doses of 1000 mg/kg and 2000 mg/kg once daily for 3 days. Therefore, the genotoxic potential of compound was judged to be negative under this assay condition.

TABLE 4

Micronucleus test result

| | Compound | | | | | |
|---|---|---|---|---|---|---|
| | Control | test article Dose (mg/kg/day) | | | | Posi. con.[a] |
| | 0 | 250 | 500 | 1000 | 2000 | 20 |
| Bone marrow[b] | 0.11 ± 0.07 | NE | NE | 0.10 ± 0.04 | 0.10 ± 0.03 | ↑2.77 ± 0.88[#] |

NE not examined, Control 0.5% methyl cellulose,
↑increased,
[a]cyclophosphamide,
[b]micronucleated immature erythrocytes incidences expressed as mean ± SD
[#]$p < 0.05$, one-tailed (Kastenbaum and Bowman's table)

TABLE 5

Comet assay result

| | Compound | | | | | |
|---|---|---|---|---|---|---|
| | Control | test article Dose (mg/kg/day) | | | | Posi. con.[a] |
| | 0 | 250 | 500 | 1000 | 2000 | 200 |
| Liver[b] | 0.08 ± 0.02 | NE | NE | 0.08 ± 0.03 | 0.11 ± 0.04 | ↑25.93 ± 6.20* |
| Stomach[b] | 0.40 ± 0.14 | | | 0.59 ± 0.22 | 0.48 ± 0.21 | ↑39.74 ± 4.71** |

NE not examined, Control 0.5% methyl cellulose,
↑increased
[a]ethyl methanesulfonate,
[b]% tail DNA values expressed as mean ± SD
**$p < 0.05$, two-tailed (Student's t-test)

Formulation Example 1

Production of Capsule

| | |
|---|---|
| 1) compound of Example 1 | 30 mg |
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has a HDAC inhibitory activity, and may be useful for the treatment of central nervous system diseases including neurodegenerative diseases (Alzheimer's disease, progressive supranuclear palsy, etc.) and the like.

This application is based on patent applications No. 2017-148649 filed on Jul. 31, 2017 and No. 2017-222301 filed on Nov. 17, 2017 in Japan, the contents of which are encompassed in full herein.

The invention claimed is:
1. A compound represented by the formula (I):

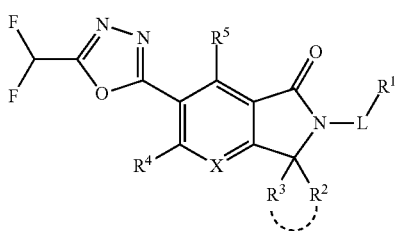

wherein
$R^1$ is
(1) a $C_{3-10}$ cycloalkyl group optionally substituted by 1 to 3 substituents selected from
  (a) an amino group,
  (b) a halogen atom,
  (c) a hydroxy group,
  (d) a $C_{1-6}$ alkyl group optionally substituted by 1 to 3 substituents selected from
    (i) a $C_{1-6}$ alkoxy-carbonylamino group, and
    (ii) a $C_{1-6}$ alkylsulfonylamino group optionally substituted by 1 to 3 halogen atoms,
  (e) a $C_{1-6}$ alkoxy group,
  (f) a $C_{1-6}$ alkyl-carbonylamino group optionally substituted by 1 to 6 substituents selected from
    (i) a halogen atom,
    (ii) a cyano group,
    (iii) a hydroxy group,
    (iv) a $C_{1-6}$ alkoxy group,
    (v) a $C_{3-10}$ cycloalkyl group optionally substituted by 1 to 3 substituents selected from a hydroxy group and a cyano group, and
    (vi) a $C_{6-14}$ aryl group,
  (g) a $C_{1-6}$ alkoxy-carbonylamino group optionally substituted by 1 to 3 halogen atoms,
  (h) a mono- or di-$C_{1-6}$ alkyl-carbamoyl group optionally substituted by 1 to 3 halogen atoms,
  (i) a mono- or di-$C_{1-6}$ alkyl-carbamoyloxy group,
  (j) a $C_{3-10}$ cycloalkyl-carbonylamino group optionally substituted by 1 to 3 substituents selected from
    (i) a halogen atom,
    (ii) a cyano group,
    (iii) a hydroxy group,
    (iv) an optionally halogenated $C_{1-6}$ alkyl group,
    (v) a $C_{1-6}$ alkoxy group, and
    (vi) a $C_{6-14}$ aryl group optionally substituted by 1 to 3 halogen atoms,
  (k) a $C_{3-10}$ cycloalkoxy-carbonylamino group,
  (l) a N-5- or 6-membered monocyclic aromatic heterocyclyl-N-$C_{1-6}$ alkyl-carbonyl-amino group optionally substituted by 1 to 3 halogen atoms,
  (m) a $C_{1-6}$ alkylsulfonylamino group optionally substituted by 1 to 3 halogen atoms,
  (n) a $C_{3-10}$ cycloalkylsulfonylamino group,
  (o) a $C_{1-6}$ alkylamino group optionally substituted by 1 to 3 halogen atoms,
  (p) a $C_{6-14}$ aryl group optionally substituted by 1 to 3 halogen atoms,
  (q) a $C_{6-14}$ aryl-carbonylamino group optionally substituted by 1 to 3 substituents selected from
    (i) a halogen atom,
    (ii) a cyano group, and
    (iii) an optionally halogenated $C_{1-6}$ alkyl group,
  (r) a $C_{7-16}$ aralkyl-carbonylamino group,
  (s) a $C_{7-16}$ aralkyl-oxycarbonylamino group,
  (t) a 5- to 14-membered aromatic heterocyclic group optionally substituted by 1 to 3 substituents selected from
    (i) a $C_{1-6}$ alkyl group, and
    (ii) a $C_{3-10}$ cycloalkyl group,
  (u) a 3-to 14-membered non-aromatic heterocyclic group optionally substituted by 1 to 6 substituents selected from
    (i) an oxo group,
    (ii) a $C_{1-6}$ alkyl group, and
    (iii) a halogen atom,
  (v) a 5- to 14-membered aromatic heterocyclylcarbonylamino group optionally substituted by 1 to 3 $C_{1-6}$ alkyl groups,
  (w) a 3- to 14-membered non-aromatic heterocyclylcarbonylamino group optionally substituted by 1 to 3 substituents selected from
    (i) a $C_{1-6}$ alkyl group, and
    (ii) a $C_{6-14}$ aryl group,
  (x) a 3- to 14-membered non-aromatic heterocyclylcarbonyloxy group,
  (y) a 5- to 14-membered aromatic heterocyclylamino group,
  (z) a $C_{6-14}$ aryloxy group optionally substituted by 1 to 3 halogen atoms,
  (aa) a cyano group, and
  (bb) a 5- to 14-membered aromatic heterocyclyloxy group optionally substituted by 1 to 3 halogen atoms,
(2) a $C_{6-14}$ aryl group optionally substituted by 1 to 3 substituents selected from
  (a) a halogen atom,
  (b) a cyano group,
  (c) an optionally halogenated $C_{1-6}$ alkyl group,
  (d) an optionally halogenated $C_{1-6}$ alkoxy group,
  (e) a $C_{1-6}$ alkylsulfonyl group,
  (f) a $C_{6-14}$ aryl group optionally substituted by 1 to 3 substituents selected from
    (i) a cyano group,
    (ii) an optionally halogenated $C_{1-6}$ alkyl group,
    (iii) a $C_{1-6}$ alkoxy group optionally substituted by 1 to 3 substituents selected from a halogen atom, a $C_{1-6}$alkoxy group and a cyano group,
    (iv) a $C_{1-6}$ alkylsulfonyl group,
    (v) a halogen atom,
    (vi) a $C_{3-10}$ cycloalkyl group optionally substituted by 1 to 3 cyano groups, and
    (vii) a 3- to 14-membered non-aromatic heterocylylcarbonyl group, (g) a $C_{7-16}$ aralkyl group,
(h) a 5- to 14-membered aromatic heterocyclic group optionally substituted by 1 to 3 substituents selected from
  (i) a halogen atom,
  (ii) a $C_{1-6}$ alkyl group optionally substituted by 1 to 3 substituents selected from a halogen atom and a pyridyl group,
  (iii) an optionally halogenated $C_{1-6}$ alkoxy group,
  (iv) a $C_{3-10}$ cycloalkyl group,
  (v) a $C_{1-6}$ alkylsulfonyl group, and
  (vi) a 3- to 14-membered non-aromatic heterocyclic group,
(i) a 3- to 14-membered non-aromatic heterocyclic group optionally substituted by 1 to 3 substituents selected from
  (i) an oxo group,
  (ii) a $C_{1-6}$ alkoxy-carbonyl group, and
  (iii) an optionally halogenated $C_{1-6}$ alkyl-carbonyl group,
(j) a 4,4,5,5-tetramethyl-1,3,2-dioxaborolan-2-yl group,
(k) a $C_{3-10}$ cycloalkenyl group optionally substituted by 1 to 3 $C_{1-6}$ alkoxy-carbonylamino groups, and
(l) a $C_{3-10}$ cycloalkyl group optionally substituted by 1 to 3 substituents selected from
  (i) a $C_{1-6}$ alkyl-carbonylamino group optionally substituted by 1 to 5 halogen atoms, and
  (ii) a $C_{1-6}$ alkoxy-carbonylamino group,
(3) a 5- to 14-membered aromatic heterocyclic group optionally substituted by 1 to 3 substituents selected from
  (a) a halogen atom,
  (b) a $C_{1-6}$ alkyl group optionally substituted by 1 to 3 substituents selected from
    (i) a halogen atom, and
    (ii) a hydroxy group,
  (c) a $C_{3-10}$ cycloalkyl group optionally substituted by 1 to 3 substituents selected from
    (i) a halogen atom,
    (ii) a $C_{1-6}$ alkoxy-carbonylamino group,
    (iii) a $C_{1-6}$ alkyl-carbonylamino group optionally substituted by 1 to 5 halogen atoms, and
    (iv) a mono- or di-$C_{1-6}$ alkylamino group optionally substituted by 1 to 5 halogen atoms,
  (d) a $C_{4-10}$ cycloalkenyl group optionally substituted by 1 to 3 substituents selected from
    (i) a halogen atom, and
    (ii) a $C_{1-6}$ alkoxy-carbonylamino group,
  (e) a $C_{6-14}$ aryl group optionally substituted by 1 to 3 substituents selected from
    (i) a cyano group,
    (ii) a halogen atom, and
    (iii) a $C_{1-6}$ alkoxy group,
  (f) a 5- to 14-membered aromatic heterocyclic group optionally substituted by 1 to 3 substituents selected from
    (i) a halogen atom, and
    (ii) an optionally halogenated $C_{1-6}$ alkyl group,
  (g) a 3- to 14-membered non-aromatic heterocyclic group optionally substituted by 1 to 3 substituents selected from
    (i) a $C_{1-6}$ alkoxy-carbonyl group,
    (ii) an optionally halogenated $C_{1-6}$ alkyl-carbonyl group, and
    (iii) an optionally halogenated $C_{1-6}$ alkyl group,
  (h) a mono- or di-$C_{1-6}$ alkyl-carbamoyl group optionally substituted by 1 to 3 substituents selected from
    (i) a halogen atom, and
    (ii) a $C_{3-10}$ cycloalkyl group,
  (i) a 3- to 14-membered non-aromatic heterocyclylcarbonyl group optionally substituted by 1 to 3 halogen atoms, and
  (j) a $C_{6-14}$ aryl-carbonyl group,
(4) a 3- to 14-membered non-aromatic heterocyclic group optionally substituted by 1 to 3 substituents selected from
  (a) a halogen atom,
  (b) an oxo group,
  (c) an amino group,
  (d) an optionally halogenated $C_{1-6}$ alkyl group,
  (e) a $C_{1-6}$ alkylamino group optionally substituted by 1 to 7 halogen atoms,
  (f) an optionally halogenated $C_{1-6}$ alkyl-carbonyl group,
  (g) a $C_{1-6}$ alkyl-carbonylamino group optionally substituted by 1 to 5 halogen atoms,
  (h) a $C_{1-6}$ alkoxy-carbonyl group,
  (i) a $C_{1-6}$ alkoxy-carbonylamino group optionally substituted by 1 to 3 halogen atoms,
  (j) a $C_{1-6}$ alkylsulfonyl group optionally substituted by 1 to 3 halogen atoms,
  (k) a $C_{3-10}$ cycloalkyl-carbonyl group optionally substituted by 1 to 3 substituents selected from
    (i) a halogen atom, and
    (ii) an optionally halogenated $C_{1-6}$ alkyl group,
  (l) a $C_{3-10}$ cycloalkyl-carbonylamino group optionally substituted by 1 to 3 optionally halogenated $C_{1-6}$ alkyl groups,
  (m) a $C_{3-10}$ cycloalkylsulfonyl group,
  (n) a $C_{6-14}$ aryl group optionally substituted by 1 to 3 halogen atoms,
  (o) a $C_{7-16}$ aralkyl group,
  (p) a $C_{6-14}$ aryl-carbonyl group,
  (q) a $C_{6-14}$ aryl-carbonylamino group optionally substituted by 1 to 3 halogen atoms,
  (r) a $C_{6-14}$ arylsulfonyl group optionally substituted by 1 to 3 substituents selected from
    (i) a $C_{1-6}$ alkyl group, and
    (ii) a halogen atom,
  (s) a 3- to 14-membered non-aromatic heterocyclic group optionally substituted by 1 to 3 substituents selected from
    (i) an oxo group, and
    (ii) a $C_{1-6}$ alkyl-carbonyl group,
  (t) a 5- to 14-membered aromatic heterocyclic group optionally substituted by 1 to 3 substituents selected from
    (i) a halogen atom, and
    (ii) a $C_{1-6}$ alkyl group,
  (u) a mono- or di-$C_{1-6}$ alkyl-carbamoyl group optionally substituted by 1 to 5 halogen atoms,
  (v) a $C_{7-16}$ aralkyloxy-carbonyl group, and
  (w) a $C_{6-14}$ aryloxy group optionally substituted by 1 to 3 halogen atoms, or
(5) a $C_{1-6}$ alkyl group optionally substituted by 1 to 3 substituents selected from
  (a) a $C_{6-14}$ aryloxy group, and
  (b) a $C_{7-16}$ aralkyloxy group,
$R^2$ and $R^3$ are each independently a hydrogen atom, a halogen atom or an optionally substituted $C_{1-6}$ alkyl group, or $R^2$ and $R^3$ in combination form an oxo group, R⁴ and R⁵ are each independently a hydrogen atom or a halogen atom, X is CR⁶ or N, R⁶ is a hydrogen atom or a halogen atom, L is a bond or an optionally substituted $C_{1-6}$ alkylene group, or a salt thereof.

2. The compound or salt according to claim 1, wherein R¹ is a cyclohexyl group optionally substituted by 1 to 3 substituents selected from
   (a) a halogen atom,
   (b) a $C_{1-6}$ alkyl-carbonylamino group optionally substituted by 1 to 5 halogen atoms,
   (c) a $C_{1-6}$ alkoxy-carbonylamino group optionally substituted by 1 to 3 halogen atoms, and
   (d) a $C_{3-10}$ cycloalkyl-carbonylamino group optionally substituted by 1 to 3 halogen atoms.

3. The compound or salt according to claim 1, wherein R² and R³ are both hydrogen atoms, or R² and R³ in combination form an oxo group.

4. The compound or salt according to claim 1, wherein R² and R³ are both hydrogen atoms.

5. The compound or salt according to claim 1, wherein R⁴ and R⁵ are both hydrogen atoms.

6. The compound or salt according to claim 1, wherein X is CH, CF or N.

7. The compound or salt according to claim 1, wherein X is CH or N.

8. The compound or salt according to claim 1, wherein L is
   (1) a bond, or
   (2) a $C_{1-6}$ alkylene group optionally substituted by 1 to 3 $C_{6-14}$aryl groups.

9. The compound or salt according to claim 1, wherein L is a bond.

10. The compound or salt according to claim 1, wherein R¹ is
    (1) a $C_{3-10}$ cycloalkyl group optionally substituted by 1 to 3 substituents selected from
        (a) an amino group,
        (b) a halogen atom,
        (c) a hydroxy group,
        (d) a $C_{1-6}$ alkyl group optionally substituted by 1 to 3 substituents selected from
            (i) a $C_{1-6}$ alkoxy-carbonylamino group, and
            (ii) a $C_{1-6}$ alkylsulfonylamino group optionally substituted by 1 to 3 halogen atoms,
        (e) a $C_{1-6}$ alkoxy group,
        (f) a $C_{1-6}$ alkyl-carbonylamino group optionally substituted by 1 to 6 substituents selected from
            (i) a halogen atom,
            (ii) a cyano group,
            (iii) a hydroxy group,
            (iv) a $C_{1-6}$ alkoxy group,
            (v) a $C_{3-10}$ cycloalkyl group optionally substituted by 1 to 3 substituents selected from a hydroxy group and a cyano group, and
            (vi) a $C_{6-14}$ aryl group,
        (g) a $C_{1-6}$ alkoxy-carbonylamino group optionally substituted by 1 to 3 halogen atoms,
        (h) a mono- or di-$C_{1-6}$ alkyl-carbamoyl group optionally substituted by 1 to 3 halogen atoms,
        (i) a mono- or di-$C_{1-6}$ alkyl-carbamoyloxy group,
        (j) a $C_{3-10}$ cycloalkyl-carbonylamino group optionally substituted by 1 to 3 substituents selected from
            (i) a halogen atom,
            (ii) a cyano group,
            (iii) a hydroxy group,
            (iv) an optionally halogenated $C_{1-6}$ alkyl group,
            (v) a $C_{1-6}$ alkoxy group, and
            (vi) a $C_{6-14}$ aryl group optionally substituted by 1 to 3 halogen atoms,
        (k) a $C_{3-10}$ cycloalkoxy-carbonylamino group,
        (l) a N-5- or 6-membered monocyclic aromatic heterocyclyl-N-$C_{1-6}$ alkyl-carbonyl-amino group optionally substituted by 1 to 3 halogen atoms,
        (m) a $C_{1-6}$ alkylsulfonylamino group optionally substituted by 1 to 3 halogen atoms,
        (n) a $C_{3-10}$ cycloalkylsulfonylamino group,
        (o) a $C_{1-6}$ alkylamino group optionally substituted by 1 to 3 halogen atoms,
        (p) a $C_{6-14}$ aryl group optionally substituted by 1 to 3 halogen atoms,
        (q) a $C_{6-14}$ aryl-carbonylamino group optionally substituted by 1 to 3 substituents selected from
            (i) a halogen atom,
            (ii) a cyano group, and
            (iii) an optionally halogenated $C_{1-6}$ alkyl group,
        (r) a $C_{7-16}$ aralkyl-carbonylamino group,
        (s) a $C_{7-16}$ aralkyl-oxycarbonylamino group,
        (t) a 5- to 14-membered aromatic heterocyclic group optionally substituted by 1 to 3 substituents selected from
            (i) a $C_{1-6}$ alkyl group, and
            (ii) a $C_{3-10}$ cycloalkyl group,
        (u) a 3- to 14-membered non-aromatic heterocyclic group optionally substituted by 1 to 6 substituents selected from
            (i) an oxo group,
            (ii) a $C_{1-6}$ alkyl group, and
            (iii) a halogen atom,
        (v) a 5- to 14-membered aromatic heterocyclylcarbonylamino group optionally substituted by 1 to 3 $C_{1-6}$ alkyl groups,
        (w) a 3- to 14-membered non-aromatic heterocyclyl-carbonylamino group optionally substituted by 1 to 3 substituents selected from
            (i) a $C_{1-6}$ alkyl group, and
            (ii) a $C_{6-14}$ aryl group,
        (x) a 3- to 14-membered non-aromatic heterocyclylcarbonyloxy group,
        (y) a 5- to 14-membered aromatic heterocyclylamino group,
        (z) a $C_{6-14}$ aryloxy group optionally substituted by 1 to 3 halogen atoms,
        (aa) a cyano group, and
        (bb) a 5- to 14-membered aromatic heterocyclyloxy group optionally substituted by 1 to 3 halogen atoms,
    (2) a $C_{6-14}$ aryl group optionally substituted by 1 to 3 substituents selected from
        (a) a halogen atom,
        (b) a cyano group,
        (c) an optionally halogenated $C_{1-6}$ alkyl group,
        (d) an optionally halogenated $C_{1-6}$ alkoxy group,
        (e) a $C_{1-6}$ alkylsulfonyl group,
        (f) a $C_{6-14}$ aryl group optionally substituted by 1 to 3 substituents selected from
            (i) a cyano group,
            (ii) an optionally halogenated $C_{1-6}$ alkyl group,
            (iii) a $C_{1-6}$ alkoxy group optionally substituted by 1 to 3 substituents selected from a halogen atom, a $C_{1-6}$alkoxy group and a cyano group, (iv) a $C_{1-6}$ alkylsulfonyl group,
(v) a halogen atom,
(vi) a $C_{3-10}$ cycloalkyl group optionally substituted by 1 to 3 cyano groups, and
(vii) a 3- to 14-membered non-aromatic heterocyclylcarbonyl group,
(g) a $C_{7-16}$ aralkyl group,
(h) a 5- to 14-membered aromatic heterocyclic group optionally substituted by 1 to 3 substituents selected from
(i) a halogen atom,
(ii) a $C_{1-6}$ alkyl group optionally substituted by 1 to 3 substituents selected from a halogen atom and a pyridyl group,
(iii) an optionally halogenated $C_{1-6}$ alkoxy group,
(iv) a $C_{3-10}$ cycloalkyl group,
(v) a $C_{1-6}$ alkylsulfonyl group, and
(vi) a 3- to 14-membered non-aromatic heterocyclic group,
(i) a 3- to 14-membered non-aromatic heterocyclic group optionally substituted by 1 to 3 substituents selected from
(i) an oxo group,
(ii) a $C_{1-6}$ alkoxy-carbonyl group, and
(iii) an optionally halogenated $C_{1-6}$ alkyl-carbonyl group,
(j) a 4,4,5,5-tetramethyl-1,3,2-dioxaborolan-2-yl group,
(k) a $C_{3-10}$ cycloalkenyl group optionally substituted by 1 to 3 $C_{1-6}$ alkoxy-carbonylamino groups, and
(l) a $C_{3-10}$ cycloalkyl group optionally substituted by 1 to 3 substituents selected from
(i) a $C_{1-6}$ alkyl-carbonylamino group optionally substituted by 1 to 5 halogen atoms, and
(ii) a $C_{1-6}$ alkoxy-carbonylamino group,
(3) a 5- to 14-membered aromatic heterocyclic group optionally substituted by 1 to 3 substituents selected from
(a) a halogen atom,
(b) a $C_{1-6}$ alkyl group optionally substituted by 1 to 3 substituents selected from
(i) a halogen atom, and
(ii) a hydroxy group,
(c) a $C_{3-10}$ cycloalkyl group optionally substituted by 1 to 3 substituents selected from
(i) a halogen atom,
(ii) a $C_{1-6}$ alkoxy-carbonylamino group,
(iii) a $C_{1-6}$ alkyl-carbonylamino group optionally substituted by 1 to 5 halogen atoms, and
(iv) a mono- or di-$C_{1-6}$ alkylamino group optionally substituted by 1 to 5 halogen atoms,
(d) a $C_{4-10}$ cycloalkenyl group optionally substituted by 1 to 3 substituents selected from
(i) a halogen atom, and
(ii) a $C_{1-6}$ alkoxy-carbonylamino group,
(e) a $C_{6-14}$ aryl group optionally substituted by 1 to 3 substituents selected from
(i) a cyano group,
(ii) a halogen atom, and
(iii) a $C_{1-6}$ alkoxy group,
(f) a 5- to 14-membered aromatic heterocyclic group optionally substituted by 1 to 3 substituents selected from
(i) a halogen atom, and
(ii) an optionally halogenated $C_{1-6}$ alkyl group,
(g) a 3- to 14-membered non-aromatic heterocyclic group optionally substituted by 1 to 3 substituents selected from
(i) a $C_{1-6}$ alkoxy-carbonyl group,
(ii) an optionally halogenated $C_{1-6}$ alkyl-carbonyl group, and
(iii) an optionally halogenated $C_{1-6}$ alkyl group,
(h) a mono- or di-$C_{1-6}$ alkyl-carbamoyl group optionally substituted by 1 to 3 substituents selected from
(i) a halogen atom, and
(ii) a $C_{3-10}$ cycloalkyl group,
(i) a 3- to 14-membered non-aromatic heterocyclylcarbonyl group optionally substituted by 1 to 3 halogen atoms, and
(j) a $C_{6-14}$ aryl-carbonyl group,
(4) a 3- to 14-membered non-aromatic heterocyclic group optionally substituted by 1 to 3 substituents selected from
(a) a halogen atom,
(b) an oxo group,
(c) an amino group,
(d) an optionally halogenated $C_{1-6}$ alkyl group,
(e) a $C_{1-6}$ alkylamino group optionally substituted by 1 to 7 halogen atoms,
(f) an optionally halogenated $C_{1-6}$ alkyl-carbonyl group,
(g) a $C_{1-6}$ alkyl-carbonylamino group optionally substituted by 1 to 5 halogen atoms,
(h) a $C_{1-6}$ alkoxy-carbonyl group,
(i) a $C_{1-6}$ alkoxy-carbonylamino group optionally substituted by 1 to 3 halogen atoms,
(j) a $C_{1-6}$ alkylsulfonyl group optionally substituted by 1 to 3 halogen atoms,
(k) a $C_{3-10}$ cycloalkyl-carbonyl group optionally substituted by 1 to 3 substituents selected from
(i) a halogen atom, and
(ii) an optionally halogenated $C_{1-6}$ alkyl group,
(l) a $C_{3-10}$ cycloalkyl-carbonylamino group optionally substituted by 1 to 3 optionally halogenated $C_{1-6}$ alkyl groups,
(m) a $C_{3-10}$ cycloalkylsulfonyl group,
(n) a $C_{6-14}$ aryl group optionally substituted by 1 to 3 halogen atoms,
(o) a $C_{7-16}$ aralkyl group,
(p) a $C_{6-14}$ aryl-carbonyl group,
(q) a $C_{6-14}$ aryl-carbonylamino group optionally substituted by 1 to 3 halogen atoms,
(r) a $C_{6-14}$ arylsulfonyl group optionally substituted by 1 to 3 substituents selected from
(i) a $C_{1-6}$ alkyl group, and
(ii) a halogen atom,
(s) a 3- to 14-membered non-aromatic heterocyclic group optionally substituted by 1 to 3 substituents selected from
(i) an oxo group, and
(ii) a $C_{1-6}$ alkyl-carbonyl group,
(t) a 5- to 14-membered aromatic heterocyclic group optionally substituted by 1 to 3 substituents selected from
(i) a halogen atom, and
(ii) a $C_{1-6}$ alkyl group,
(u) a mono- or di-$C_{1-6}$ alkyl-carbamoyl group optionally substituted by 1 to 5 halogen atoms,
(v) a $C_{7-16}$ aralkyloxy-carbonyl group, and
(w) a $C_{6-14}$ aryloxy group optionally substituted by 1 to 3 halogen atoms, or (5) a $C_{1-6}$ alkyl group optionally substituted by 1 to 3 substituents selected from
  (a) a $C_{6-14}$ aryloxy group, and
  (b) a $C_{7-16}$ aralkyloxy group;
$R^2$ and $R^3$ are both hydrogen atoms, or $R^2$ and $R^3$ in combination form an oxo group;
$R^4$ and $R^5$ are both hydrogen atoms;
X is $CR^6$ or N;
$R^6$ is a hydrogen atom or a halogen atom ; and
L is
(1) a bond, or
(2) a $C_{1-6}$ alkylene group optionally substituted by 1 to 3 $C_{6-14}$aryl groups.

11. The compound or salt according to claim 1, wherein $R^1$ is a cyclohexyl group optionally substituted by 1 to 3 substituents selected from
  (a) a halogen atom,
  (b) a $C_{1-6}$ alkyl-carbonylamino group optionally substituted by 1 to 5 halogen atoms,
  (c) a $C_{1-6}$ alkoxy-carbonylamino group optionally substituted by 1 to 3 halogen atoms, and
  (d) a $C_{3-10}$ cycloalkyl-carbonylamino group optionally substituted by 1 to 3 halogen atoms;
$R^2$ and $R^3$ are both hydrogen atoms;
$R^4$ and $R^5$ are both hydrogen atoms;
X is CH or N; and
L is a bond.

12. N-((1R,2R)-2-(3-(5-(difluoromethyl)-1,3,4-oxadiazol-2-yl)-5-oxo-5,7-dihydro-6H-pyrrolo[3,4-b]pyridin-6-yl)cyclohexyl)-2,2,3,3,3-pentafluoropropanamide or a salt thereof.

13. N-((1S,6R)-6-(6-(5-(difluoromethyl)-1,3,4-oxadiazol-2-yl)-1-oxo-1,3-dihydro-2H-isoindol-2-yl)-2,2-difluorocyclohexyl)-2,2-difluoropropanamide or a salt thereof.

14. N-((1S,6R)-6-(3-(5-(difluoromethyl)-1,3,4-oxadiazol-2-yl)-5-oxo-5,7-dihydro-6H-pyrrolo[3,4-b]pyridin-6-yl)-2,2-difluorocyclohexyl)-2,2-difluoropropanamide or a salt thereof.

15. A medicament comprising the compound or salt according to claim 1 and a pharmacologically acceptable carrier.

16. A method of inhibiting histone deacetylase (HDAC6) in a mammal, which comprises administering an effective amount of the compound or salt according to claim 1 to the mammal.

17. A method for the treatment of Alzheimer's disease in a mammal, which comprises administering an effective amount of the compound or salt according to claim 1 to the mammal.

* * * * *